(12) United States Patent
Bissantz et al.

(10) Patent No.: US 8,765,730 B2
(45) Date of Patent: Jul. 1, 2014

(54) 1-HYDROXYIMINO-3-PHENYL-PROPANES

(75) Inventors: Caterina Bissantz, Village-Neuf (FR); Henrietta Dehmlow, Loerrach (DE); Shawn David Erickson, Leonia, NJ (US); Kyungjin Kim, Livingston, NJ (US); Rainer E. Martin, Basel (CH); Patrizio Mattei, Riehen (CH); Ulrike Obst Sander, Reinach BL (CH); Sherrie Lynn Pietranico-Cole, Montclair, NJ (US); Hans Richter, Grenzach-Wyhlen (DE); Christoph Ullmer, Fischingen (DE)

(73) Assignee: Hoffmann-La Roche Inc, Nutley, NJ (US)

( * ) Notice: Subject to any disclaimer, the term of this patent is extended or adjusted under 35 U.S.C. 154(b) by 168 days.

(21) Appl. No.: 13/180,574

(22) Filed: Jul. 12, 2011

(65) Prior Publication Data

US 2012/0010190 A1 Jan. 12, 2012

(30) Foreign Application Priority Data

Jul. 12, 2010 (EP) .................................. 10169293

(51) Int. Cl.
*A61K 31/4409* (2006.01)
*C07D 401/10* (2006.01)

(52) U.S. Cl.
USPC ................ 514/210.18; 514/210.2; 514/235.5; 514/256; 514/357; 544/58.2; 544/124; 544/131; 544/333; 546/338

(58) Field of Classification Search
USPC ............. 514/210.2, 210.18, 235.5, 256, 357; 544/58.2, 124, 131, 333; 546/338
See application file for complete search history.

(56) References Cited

U.S. PATENT DOCUMENTS 5,516,785 A * 5/1996 Zoltewicz et al. ............. 514/334
5,741,802 A * 4/1998 Kem et al. ..................... 514/334

FOREIGN PATENT DOCUMENTS

| EP | 0009740 | 4/1980 |
|----|---------|--------|
| EP | 2172448 | 4/2010 |
| WO | 00/58293 | 10/2000 |
| WO | 2004/005243 | 1/2004 |
| WO | 2008/122375 | 10/2008 |

OTHER PUBLICATIONS

Abdel-Latif et al. "Synthesis . . . " CA148:538212 (2007).*
Arena et al. "Isoxazoles . . . " CA83:114266 (1975).*
Betal Nut from internet p. 1-4 (1985).*
Bieganowska et al. "Ion-pair . . . " CA117:198620 (1992).*
Delhomel et al. "Preparation of substituted . . . " CA149:128726 (2008).*
Durinda et al. "Suprarenal gland . . . " CA78:29576 (1973).*
Improper Markush "supplemental training" p. 1, 64-67 (2011).*
Kuchkova et al. "Carbolines . . . " CA72:121397 (1970).*
Rentzea et al. "Triazolyloximes" CA93:114537 (1980).*
Samula "Oximation of . . . " CA76:153509 (1972).*
Waksmundzka-Hajnos "Thin-Layer Chromatograph in phtochemistry" vo. 99, p. 63-64 (2008).*
Yamamoto et al. "Nicotinoid insecticids . . . " p. 1-41 (1999).*
Johnston et al. "Reactions of . . . " CA68:21649 (1968).*
XP002629759 (Chem Abstracts Database Access No. 1970:1213971970).
Evans, Karen et al., J. Med. Chem. (XP002629762), 52(10):7962-7965 (Nov. 10, 2009).
(International Search Report for PCT/EP2011/061577 Dec. 6, 2011).
(Chem Abstract Access No. 1962:73267 XP0026297611962).
Database CA Online Chemical Abstracts Service Accession No. 1978:152191 XP002629758.
Maksoud, A. et al., Revue Roumaine de Chimie 23(11-12):1541-1542 ( 1978).
Beam, C. et al., Journal of Chemical and Engineering Data (XP002629758), 23(2):183-184 ( 1978).
Johnston, K.M. et al., Journal of the Chemical Society (XP002629760 Chem Abstract Access No. 1968:21649), 23:2476-2478 ( 1967).
Lutz, Robert E. et al., Journal of Organic Chemistry (XP002629761 Chem Abstract Assec No. 1962:73267), 26:4888-4893 ( 1961).
(Chem Abstract Access No. 1968:21649 XP00026297601968).
Database CA; Chem Abstract Service Accession No. 1979:439067 XP002629757—relates to Maksoud, A.
Keitel et al., "Hepatology" 45(3):695-704 ( 2007).
Katsuma et al., "Biochem. Biophys. Res. Commun." 329(1):386-390 ( 2005).
Hosomi et al., "Tetrahedron Letters" 21:955-958 ( 1980).
Plaisancie et al., "Journal of Endocrinology" 145(3):521-526 ( 1995).
Keitel et al., "Hepatology" 50(3):861-870 ( 2009).

(Continued)

*Primary Examiner* — Celia Chang

(57) ABSTRACT

This invention relates to novel 1-hydroxyimino-3-phenyl-propanes of the formula

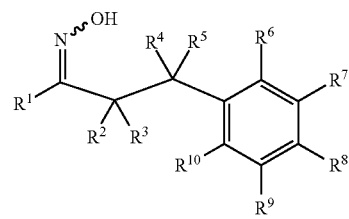

wherein $R^1$ to $R^{10}$ are as defined in the description and in the claims, as well as pharmaceutically acceptable salts thereof. These compounds are GPBAR1 agonists and may be used as medicaments for the treatment of diseases such as type II diabetes.

14 Claims, No Drawings

(56) References Cited

OTHER PUBLICATIONS

Maiti et al., "Synthetic Communications" 37:2309-2316 (2007).
Eberlein et al., "Peptides" 10:797-803 (1989).
Keitel et al., "Biophys. Res. Comm." 372:78-84 (2008).
Kawamata et al., "Journal of Biological Chemistry" 278:9435-9440 (2003).
Bojanowska et al., "Medical Science Monitor" 8:RA271-278 (2005).
Watanabe et al., "Nature" 439:484-489 (2006).
Yoshinaga et al., "American Journal Physiology" 263:G695-701 (1992).
Kreymann et al., "Lancet" 2:1300-1304 (1987).
Cave et al., "Journal Chemical Society Perkin Transactions" 1:3258-3264 (2001).
Pellicciari et al., "Journal of Medicinal Chemistry" 52(24):7958-7961 (2009).
Meier et al., "Diabetes Metabolism Research Reviews" 2:91-117 (2005).
Itooka et al., "Chemistry Letters" :722-723 (2001).
Batterham et al., "Nature" 2002:650-654 (2002).
Grandt et al., "Regulatory Peptides" 51:151-159 (1994).
Perry et al., "Current Alzheimer Res." 3:377-385 (2005).
Adrian et al., "Gut" 34:1219-1224 (1993).
Malmberg et al., "Tetrahedron" 38:1509-1510 (1982).
Dong et al., "Synthesis" :1057-1061 (2004).
Maruyama et al., "Biochemical & Biophysical Research Communications" 298:714-719 (2002).
Savage et al., "Gut" 28:166-170 (1987).
Thomas et al., "Cell Metabolism" 10(3):167-177 (2009).
Skytte et al., "Journal of Medicinal Chemistry" 49:436-440 (2006).
Berger et al., "Synthesis" :3106-3110 (2006).
The Chinese Office Action, issued on Jan. 6, 2014, in the corresponding Chinese application No. 201180031913.4.
Arena et al., "Isoxazoles substituted with 4-pyridyl and o-chlorophenyl radicals," Il Farmaco; edizione scientifica (Farmaco Sci), vol. 30, Issue 5, pp. 380-390 (May 1975).
Bieganowska et al., "Ion Pair, Reversed Phase Thin Layer Chromatography of Some Basic Drugs and Related Pyridine Derivatives," Journal of Planar Chromatography, 1992, 5(3), pp. 184-191.
Abdel-Latif et al., "Synthesis, Analgesic, and Antiparkinsonian Profiles of Some Pyridine, Pyrazoline, and Thiopyrimidine Derivatives," Monatshefte für Chemie—Chemical Monthly, Jul. 2007, vol. 138, Issue 7, pp. 715-724.

\* cited by examiner

1-HYDROXYIMINO-3-PHENYL-PROPANES

PRIORITY TO RELATED APPLICATION(S)

This application claims the benefit of European Patent Application No. 10169293.7, filed Jul. 12, 2010, which is hereby incorporated by reference in its entirety.

FIELD OF THE INVENTION

The present invention relates to novel 1-hydroxyimino-3-phenyl-propanes having pharmaceutical activity, their manufacture, pharmaceutical compositions containing them and their potential use as medicaments.

The compounds are modulators or ligands of the GPBAR1 receptor. More particularly, the compounds are potent GPBAR1 agonists and may be useful for the treatment and prevention of metabolic and inflammatory diseases, in particular type II diabetes.

BACKGROUND OF THE INVENTION

Diabetes mellitus is an ever-increasing threat to human health. For example, in the United States current estimates maintain that about 16 million people suffer from diabetes mellitus. Type II diabetes also known as non-insulin-dependent diabetes mellitus accounts for approximately 90-95% of diabetes cases, killing about 193,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary lifestyle, diet, and obesity now prevalent in developed countries. About 80% of diabetics with type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature on set, can develop at any age, but most commonly becomes apparent during adulthood. However, the incidence of type II diabetes in children is rising. In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulfonylureas, which increase insulin production from pancreatic β-cells; glucose-lowering effectors, such as metformin which reduce glucose production from the liver; activators of the peroxisome proliferator-activated receptor γ (PPARγ), such as the thiazolidinediones, which enhances insulin action; and α-glucosidase inhibitors which interfere with gut glucose production. There are, however, deficiencies associated with currently available treatments. For example sulfonylureas and insulin injections can be associated with hypoglycemic episodes and weight gain. Furthermore, patients often lose responsiveness to sulfonylureas over time. Metformin and α-glucosidase inhibitors often lead to gastrointestinal problems and PPARγ agonists tend to cause increased weight gain and edema.

Bile acids (BA) are amphipathic molecules which are synthesized in the liver from cholesterol and stored in the gall bladder until secretion to the duodenum and intestine to play an important role in the solubilization and absorption of dietary fat and lipid-soluble vitamins. Approx. 99% of BA are absorbed again by passive diffusion and active transport in the terminal ileum and transported back to the liver via the portal vein (enterohepatic circulation). In the liver, BA decrease their own biosynthesis from cholesterol through the activation of the farnesoid X receptor alpha (FXRα) and small heterodimer partner (SHP), leading to the transcriptional repression of cholesterol 7α-hydroxylase, the rate-limiting step of BA biosynthesis from cholesterol.

GPBAR1, in the literature termed TGR5, M-BAR or BG37 as well, was recently identified as a G-protein coupled receptor (GPCR) responsive to BA (Kawamata et al., *J. Biol. Chem.* 2003, 278, 9435-9440; Maruyama et al., *Biochem. Biophys. Res. Commun.* 2002, 298, 714-719). GPBAR1 is a G(alpha)s-coupled GPCR and stimulation by ligand binding causes activation of adenylyl cyclase which leads to the elevation of intracellular cAMP and subsequent activation of downstream signaling pathways. The human receptor shares 86, 90, 82, and 83% amino acid identity to bovine, rabbit, rat, and mouse receptor, respectively. GPBAR1 is abundantly expressed in the intestinal tract, monocytes and macrophages, lung, spleen, placenta (Kawamata et al., *J. Biol. Chem.* 2003, 278, 9435-9440). BA induced receptor internalization, intracellular cAMP production and activation of extracellular signal-regulated kinase in GPBAR1-expressing HEK293 and CHO cells.

GPBAR1 was found to be abundantly expressed in monocytes/macrophages from humans and rabbits (Kawamata et al., *J. Biol. Chem.* 2003, 278, 9435-9440), and BA treatment suppressed LPS-induced cytokine production in rabbit alveolar macrophages and human THP-1 cells expressing GPBAR1. These data suggest that bile acids can suppress the macrophage function via activation of GPBAR1. In the liver functional GPBAR1 was found in the plasma membranes of Kupffer cells, mediating inhibition of LPS-induced cytokine expression (Keitel, *Biochem. Biophys. Res. Commun.* 2008, 372, 78-84), and of sinusoidal endothelial cells, where bile salts led to an increase in intracellular cAMP and to the activation and enhanced expression of the endothelial nitric oxide (NO) synthase (Keitel, *Hepatology* 2007, 45, 695-704). Furthermore, GPBAR1 has been detected in cholangiocytes of rat liver (Keitel, *Biochem. Biophys. Res. Commun.* 2008, 372, 78-84). Hydrophobic bile acids, such as taurolithocholic acid, increase cAMP in cholangiocytes suggesting that GPBAR1 may modulate ductal secretion and bile flow. Indeed, GPBAR1 staining colocalized with the cyclic adenosine monophosphate regulated chloride channel cystic fibrosis transmembrane conductance regulator (CFTR) and the apical sodium-dependent bile salt uptake transporter (ASBT). A functional coupling of GPBAR1 to chloride secretion and bile flow has been shown using GPBAR1 agonists (Keitel et al., *Hepatology* 2009 50, 861-870; Pellicciari et al., *J Med Chem* 2009, 52(24), 7958-7961). In summary, GPBAR1 agonists may trigger a protective as well as medicative mechanism in cholestatic livers.

GPBAR1 is expressed in intestinal enteroendocrine cell lines from human (NCI-H716) and murine (STC-1, GLUTag) origin (Maruyama et al., *Biochem. Biophys. Res. Commun.* 2002, 298, 714-719). Stimulation of GPBAR1 by BA stimulated cAMP production in NCI-H716 cells. Intracellular increases in cAMP suggested that BA may induce the secretion of glucagon-like peptide-1 (GLP-1). Indeed, activation of GPBAR1 by BA promoted GLP-1 secretion in STC-1 cells (Katsuma et al., *Biochem. Biophys. Res. Commun.* 2005, 329, 386-390). Receptor-specificity has been demonstrated by RNA interference experiments which revealed that reduced expression of GPBAR1 resulted in diminished secretion of GLP-1. There is compelling evidence that GPBAR1-mediated GLP-1 and PYY release from intestinal L-cells extends to in vivo. In the isolated vascularly perfused rat colon, BAs have been shown to trigger GLP-1 secretion (Plaisancie et al., *J. Endocrin.* 1995, 145, 521-526). Using a combination of pharmacological and genetic gain- and loss-of-function studies in vivo, GPBAR1 signaling was shown to induce GLP-1 release, leading to improved liver and pancreatic function and enhanced glucose tolerance in obese mice (Thomas et al., *Cell Metabolism,* 2009, 10, 167-177). In humans, intracolonic administration of deoxycholate showed marked increases in plasma levels of GLP-1 and the co-secreted PYY (Adrian et al., *Gut* 1993, 34, 1219-1224).

GLP-1 is a peptide secreted from enteroendocrine L cells has been shown to stimulate insulin release in glucose dependent manner in humans (Kreymann et al., *Lancet* 1987, 2, 1300-1304) and studies in experimental animals demonstrated that this incretin hormone is necessary for normal glucose homeostasis. In addition, GLP-1 can exert several beneficial effects in diabetes and obesity, including 1) increased glucose disposal, 2) suppression in glucose production, 3) reduced gastric emptying, 4) reduction in food intake and 5) weight loss. More recently, much research has been focused on the use of GLP-1 in the treatment of conditions and disorders such as diabetes mellitus, stress, obesity, appetite control and satiety, Alzheimer disease, inflammation, and diseases of the central nervous system. (see, for example, Bojanowska et al., *Med. Sci. Monit.* 2005, 8, RA271-8; Perry et al., *Current Alzheimer Res.* 2005, 3, 377-385; and Meier et al., *Diabetes Metab. Res. Rev.* 2005, 2, 91-117). However, the use of a peptide in clinical treatment is limited due to difficult administration, and in vivo stability. Therefore, a small molecule that either mimics the effects of GLP-1 directly, or increases GLP-1 secretion, may be useful in treatment of the variety of conditions or disorders described above, namely diabetes mellitus.

PYY is co-secreted with GLP-1 from intestinal L-cells following a meal. An dipeptidyl peptidase-IV (DPP4) cleavage product of PYY is PYY[3-36] (Eberlein et al. *Peptides* 1989, 10, 797-803) (Grandt et al. *Regul Pept* 1994, 51, 151-159). This fragment constitutes approximately 40% of total PYY-like immunoreactivity in human and canine intestinal extracts and about 36% of total plasma PYY immunoreactivity in a fasting state to slightly over 50% following a meal. PYY[3-36] is reportedly a selective ligand at the Y2 and Y5 receptors. Peripheral administration of PYY reportedly reduces gastric acid secretion, gastric motility, exocrine pancreatic secretion (Yoshinaga et al. *Am J Physiol* 1992, 263, G695-701), gallbladder contraction and intestinal motility (Savage et al. *Gut* 1987, 28, 166-170). It has been demonstrated that intra-arcuate (IC) or intra-peritoneal (IP) injection of PYY3-36 reduced feeding in rats and, as a chronic treatment, reduced body weight gain. Intra-venous (IV) infusion (0.8 μmol/kg/min) for 90 min of PYY3-36 reduced food intake in obese and normal human subjects 33% over 24 hours. These finding suggest that the PYY system may be a therapeutic target for the treatment of obesity (Bloom et. al. *Nature* 2002, 418, 650-654).

Furthermore, activation of GPBAR1 might be beneficial for the treatment of obesity and metabolic syndrome. Mice fed a high fat diet (HFD) containing 0.5% cholic acid gained less weight than control mice on HFD alone independent of food intake (Watanabe et al., *Nature* 2006, 439, 484-489). These effects were independent of FXR-alpha, and are likely to results from the binding of BA to GPBAR1. The proposed GPBAR1-mediated mechanism is leading to the subsequent induction of the cAMP-dependent thyroid hormone activating enzyme type 2 (D2) which converts the inactive T3 into the active T4, resulting in the stimulation of the thyroid hormone receptor and promoting energy expenditure. Mice lacking the D2 gene were resistant to cholic acid-induced weight loss. In both rodents and humans, the most thermogenically important tissues (the brown adipose and skeletal muscle) are specifically targeted by this mechanism because they co-express D2 and GPBAR1. The BA-GPBAR1-cAMP-D2 signalling pathway is therefore a crucial mechanism for fine-tuning energy homeostasis that can be targeted to improve metabolic control.

It is therefore an object of the present invention to provide selective, directly acting GPBAR1 agonists. Such agonists are useful as therapeutically active substances, particularly in the treatment and/or prevention of diseases which are associated with the activation of GPBAR1.

The novel compounds of the present invention exceed the compounds known in the art, inasmuch as they are small molecules and they bind to and selectively activate GPBAR1 very efficiently. They are expected to have an enhanced therapeutic potential compared to the compounds already known in the art and can be used for the treatment of diabetes, obesity, metabolic syndrome, hypercholesterolemia, dyslipidemia and a wide range of acute and chronic inflammatory diseases.

SUMMARY OF THE INVENTION

The present invention relates to 1-hydroxyimino-3-phenyl-propanes of the formula

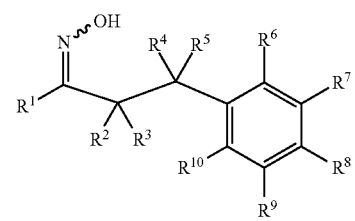

wherein
R$^1$ is —(CH$_2$)$_m$-phenyl, wherein m is 0 or 1 and said phenyl is substituted by one, two or three groups independently selected from the group consisting of C$_{1-7}$-alkyl, hydroxy and halogen, or —(CH$_2$)$_n$-heteroaryl, wherein n is 0 or 1 and said heteroaryl is selected from the group consisting of pyridine, 1H-pyridin-2-one, 1-oxy-pyridine, 1H-pyrimidin-2-one, quinoline and pyrazine, and is unsubstituted or substituted by one, two or three groups independently selected from the group consisting of C$_{1-7}$-alkyl, halogen, halogen-C$_{1-7}$-alkyl, hydroxy, hydroxy-C$_{1-7}$-alkyl, C$_{1-7}$-alkoxy, C$_{1-7}$-alkoxy-C$_{1-7}$-alkyl, C$_{1-7}$-alkoxy-C$_{1-7}$-alkoxy-C$_{1-7}$-alkyl, C$_{3-7}$-cyloalkyl, C$_{3-7}$-cycloalkyl-C$_{1-7}$-alkyl, carboxyl-C$_{1-7}$-alkyl and aminocarbonyl-C$_{1-7}$-alkyl;

R$^2$ is hydrogen or C$_{1-7}$-alkyl, or, in case R$^4$ is hydrogen, R$^2$ is unsubstituted phenyl or phenyl substituted by C$_{1-7}$-alkyl;

R$^3$ is hydrogen;

R$^5$ is hydrogen or hydroxy;

or R$^3$ and R$^5$ are replaced by a double bond;

R$^4$ is selected from the group consisting of: hydrogen; C$_{1-7}$-alkyl;
  C$_{3-7}$-cycloalkyl; C$_{2-7}$-alkenyl; halogen-C$_{1-7}$-alkyl;
  unsubstituted phenyl or phenyl substituted by one, two or three groups independently selected from the group consisting of C$_{1-7}$-alkyl, halogen, halogen-C$_{1-7}$-alkyl, halogen-C$_{1-7}$-alkoxy and C$_{1-7}$-alkylsulfonyl;
  phenyl-C$_{1-7}$-alkyl, wherein said phenyl is unsubstituted or substituted by one, two or three groups independently selected from the group consisting of C$_{1-7}$-alkyl, halogen, halogen-C$_{1-7}$-alkyl and halogen-C$_{1-7}$-alkoxy;
  heteroaryl, said heteroaryl being unsubstituted or substituted by C$_{1-7}$-alkyl or oxo; and
  heterocyclyl, said heterocyclyl being selected from morpholinyl, piperazinyl and piperidinyl and being unsubstituted or substituted by C$_{1-7}$-alkyl, oxo or C$_{1-7}$-alkylcarbonyl;

or R$^4$ and R$^5$ together with the carbon atom to which they are attached form a C$_{3-7}$-cycloalkyl ring;

R$^6$ is selected from the group consisting of hydrogen, halogen and C$_{1-7}$-alkyl;

or R$^4$ and R$^6$ together with the carbon atoms to which they are attached form a cyclic group

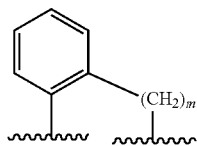

G wherein m is 0 or 2;

R$^7$ and R$^9$ are independently selected from the group consisting of
  hydrogen;
  halogen; halogen-C$_{1-7}$-alkyl;
  cyano; cyano-C$_{1-7}$-alkyl;
  C$_{1-7}$-alkyl; C$_{3-7}$-alkenyl; C$_{1-7}$-alkinyl;
  C$_{1-7}$-alkoxy; C$_{1-7}$-alkoxy-C$_{1-7}$-alkyl;
  hydroxy; hydroxy-C$_{1-7}$-alkyl; hydroxy-C$_{3-7}$-alkenyl; hydroxy-C$_{3-7}$-alkinyl;
  hydroxy-C$_{1-7}$-alkoxy;
  carboxyl; carboxyl-C$_{1-7}$-alkyl; carboxyl-C$_{3-7}$-alkenyl; carboxyl-C$_{1-7}$-alkinyl;
  carboxyl-C$_{1-7}$-alkoxy;
  tetrazolyl;
  C$_{1-7}$-alkoxycarbonyl;
  C$_{1-7}$-alkylsulfonyl; C$_{1-7}$-alkylsulfonyloxy;
  C$_{1-7}$-alkylsulfonylamino; C$_{3-7}$-cycloalkylsulfonylamino;
  aminosulfonyl; (C$_{1-7}$-alkyl)-aminosulfonyl; di-(C$_{1-7}$-alkyl)-aminosulfonyl;
  heterocyclylsulfonyl; C$_{1-7}$-alkyl-amino; di-(C$_{1-7}$-alkyl)-amino; C$_{1-7}$-alkoxy-C$_{1-7}$-alkyl-amino; C$_{1-7}$-alkoxy-C$_{1-7}$-alkyl-C$_{1-7}$-alkyl-amino; C$_{1-7}$-alkoxy-halogen-C$_{1-7}$-alkyl-aminohydroxy-C$_{1-7}$-alkyl-C$_{1-7}$-alkyl-amino;
  an amino acid attached through the amino group of the amino acid;
  C$_{3-7}$-cycloalkyl-amino, wherein said C$_{3-7}$-cycloalkyl is unsubstituted or substituted by hydroxy, hydroxy-C$_{1-7}$-alkyl or carboxyl;
  carboxyl-C$_{1-7}$-alkyl-aminocarbonyl; carboxyl-C$_{1-7}$-alkyl-(C$_{1-7}$-alkyl)-aminocarbonyl; C$_{1-7}$-alkoxycarbonyl-C$_{1-7}$-alkyl-aminocarbonyl;
  C$_{1-7}$-alkyl-aminocarbonyl; di-(C$_{1-7}$-alkyl)-aminocarbonyl;
  C$_{1-7}$-alkylsulfonyl-C$_{1-7}$-alkyl-aminocarbonyl;
  halogen-C$_{1-7}$-alkyl-aminocarbonyl; hydroxy-C$_{1-7}$-alkyl-aminocarbonyl;
  hydroxy-C$_{1-7}$-alkyl-C$_{1-7}$-alkyl-aminocarbonyl; halogen-hydroxy-C$_{1-7}$-alkyl-aminocarbonyl;
  C$_{1-7}$-alkoxy-C$_{1-7}$-alkyl-aminocarbonyl;
  C$_{3-7}$-cycloalkylaminocarbonyl, wherein said C$_{3-7}$-cycloalkyl is unsubstituted or substituted by hydroxy, hydroxy-C$_{1-7}$-alkyl or carboxyl;
  heterocyclyl-aminocarbonyl, wherein said heterocyclyl is unsubstituted or substituted by C$_{1-7}$-alkyl or oxo;
  heterocyclyl-C$_{1-7}$-alkyl-aminocarbonyl, wherein said heterocyclyl is unsubstituted or substituted by C$_{1-7}$-alkyl or oxo;
  hydroxy-C$_{1-7}$-alkyl-aminocarbonyl-C$_{1-7}$-alkyl;
  C$_{1-7}$-alkoxycarbonyl-C$_{1-7}$-alkyl;
  di-(C$_{1-7}$-alkoxycarbonyl)-C$_{1-7}$-alkyl;
  C$_{1-7}$-alkylcarbonylamino-C$_{1-7}$-alkylaminocarbonyl;
  C$_{1-7}$-alkylcarbonylamino, carboxyl-C$_{1-7}$-alkylcarbonylamino;
  C$_{1-7}$-alkoxycarbonyl-C$_{1-7}$-alkylcarbonylamino;
  C$_{3-7}$-cycloalkyl, wherein said C$_{3-7}$-cycloalkyl is unsubstituted or substituted by hydroxy, hydroxy-C$_{1-7}$-alkyl or carboxyl;
  C$_{3-7}$-cycloalkyl-C$_{1-7}$-alkyl, wherein said C$_{3-7}$-cycloalkyl is unsubstituted or substituted by hydroxy, hydroxy-C$_{1-7}$-alkyl or carboxyl;
  heterocyclyl, said heterocyclyl being unsubstituted or substituted by C$_{1-7}$-alkyl, halogen, hydroxy, hydroxy-C$_{1-7}$-alkyl, C$_{1-7}$-alkoxy, oxo, carboxyl, carboxyl-C$_{1-7}$-alkyl, C$_{1-7}$-alkoxycarbonyl, aminocarbonyl, C$_{1-7}$-alkylsulfonyl, aminosulfonyl, C$_{1-7}$-alkylcarbonyl, carboxyl-C$_{1-7}$-alkyl-aminocarbonyl or hydroxysulfonyl-C$_{1-7}$-alkyl-aminocarbonyl;
  heterocyclylcarbonyl, said heterocyclyl being unsubstituted or substituted by C$_{1-7}$-alkyl, halogen, hydroxy, hydroxy-C$_{1-7}$-alkyl, C$_{1-7}$-alkoxy, oxo, carboxyl, carboxyl-C$_{1-7}$-alkyl or C$_{1-7}$-alkylsulfonyl;
  heteroaryl, said heteroaryl being unsubstituted or substituted by C$_{1-7}$-alkyl, C$_{3-7}$-cycloalkyl, tetrahydropyranyl, carboxyl, carboxyl-C$_{1-7}$-alkyl, C$_{1-7}$-alkoxy-C$_{1-7}$-alkyl or C$_{1-7}$-alkoxycarbonyl;
  phenyloxy, wherein said phenyl is unsubstituted or substituted by one to three groups selected from halogen or carboxyl; and
  phenyl, said phenyl being unsubstituted or substituted by one to three groups selected from the group consisting of halogen, C$_{1-7}$-alkyl, hydroxy, hydroxy-C$_{1-7}$-alkyl, cyano, cyano-C$_{1-7}$-alkyl, amino, C$_{1-7}$-alkoxy, carboxyl, carboxyl-C$_{1-7}$-alkyl, C$_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;

$R^8$ is selected from the group consisting of:
hydrogen;
halogen; halogen-$C_{1-7}$-alkyl;
cyano; cyano-$C_{1-7}$-alkyl;
$C_{1-7}$-alkyl; $C_{3-7}$-alkenyl; $C_{1-7}$-alkinyl;
$C_{1-7}$-alkoxy; $C_{1-7}$-alkoxy-$C_{1-7}$-alkyl;
hydroxy; hydroxy-$C_{1-7}$-alkyl; hydroxy-$C_{3-7}$-alkenyl; hydroxy-$C_{3-7}$-alkinyl;
hydroxy-$C_{1-7}$-alkoxy;
carboxyl; carboxyl-$C_{1-7}$-alkyl; carboxyl-$C_{3-7}$-alkenyl; carboxyl-$C_{1-7}$-alkinyl;
carboxyl-$C_{1-7}$-alkoxy;
tetrazolyl;
$C_{1-7}$-alkoxycarbonyl;
$C_{1-7}$-alkylsulfonyl; $C_{1-7}$-alkylsulfonyloxy;
$C_{1-7}$-alkylsulfonylamino; $C_{3-7}$-cycloalkylsulfonylamino;
aminosulfonyl; ($C_{1-7}$-alkyl)-aminosulfonyl; di-($C_{1-7}$-alkyl)-aminosulfonyl;
heterocyclylsulfonyl; $C_{1-7}$-alkyl-amino; di-($C_{1-7}$-alkyl)-amino; $C_{1-7}$-alkoxy-$C_{1-7}$-alkyl-amino;
$C_{1-7}$-alkoxy-$C_{1-7}$-alkyl-$C_{1-7}$-alkyl-amino; $C_{1-7}$-alkoxy-halogen-$C_{1-7}$-alkyl-amino;
hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl;
$C_{1-7}$-alkoxycarbonyl-$C_{1-7}$-alkyl-aminocarbonyl;
$C_{1-7}$-alkyl-aminocarbonyl; di-($C_{1-7}$-alkyl)-aminocarbonyl;
$C_{1-7}$-alkylsulfonyl-$C_{1-7}$-alkyl-aminocarbonyl;
halogen-$C_{1-7}$-alkyl-aminocarbonyl; hydroxy-$C_{1-7}$-alkyl-aminocarbonyl;
hydroxy-$C_{1-7}$-alkyl-$C_{1-7}$-alkyl-aminocarbonyl; halogen-hydroxy-$C_{1-7}$-alkyl-aminocarbonyl;
$C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl;
$C_{1-7}$-alkoxycarbonyl-$C_{1-7}$-alkyl;
di-($C_{1-7}$-alkoxycarbonyl)-$C_{1-7}$-alkyl;
$C_{1-7}$-alkylcarbonylamino-$C_{1-7}$-alkylaminocarbonyl;
$C_{1-7}$-alkylcarbonylamino; carboxyl-$C_{1-7}$-alkylcarbonylamino;
$C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;
phenyloxy, wherein said phenyl is unsubstituted or substituted by one to three groups selected from halogen or carboxyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl; and $R^{10}$ is selected from the group consisting of hydrogen, halogen and $C_{1-7}$-alkyl;
or pharmaceutically acceptable salts thereof.

The invention is also concerned with processes for the manufacture of compounds of formula I.

The invention also relates to pharmaceutical compositions comprising a compound as described above and a pharmaceutically acceptable carrier and/or adjuvant.

A further aspect of the invention is the use of compounds of formula I as therapeutic active substances for the treatment of diseases which are associated with the modulation of GPBAR1 activity. The invention thus relates to a method for the treatment of a disease associated with the modulation of GPBAR1 activity such as for example diabetes, particularly type II diabetes or gestational diabetes.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this Application is based on IUPAC systematic nomenclature, unless indicated otherwise.

The term "compound(s) of this invention" and "compound(s) of the present invention" refers to compounds of formula I and stereoisomers, solvates or salts thereof (e.g., pharmaceutically acceptable salts).

The term "substituent" denotes an atom or a group of atoms replacing a hydrogen atom on the parent molecule.

The term "halogen" refers to fluoro, chloro, bromo and iodo, with fluoro, chloro and bromo being of particular interest. More particularly, halogen refers to fluoro and chloro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. The term "$C_{1-10}$-alkyl" refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. More particularly, the term "alkyl" also embraces lower alkyl groups as described below.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl, in particular 2-propenyl (allyl).

The term "lower alkinyl" or "$C_{2-7}$-alkinyl" signifies a straight-chain or branched chain hydrocarbon residue comprising a triple bond and 2 to 7 carbon atoms. Examples of lower alkinyl groups are ethinyl and 1-propinyl (—C≡C—CH$_2$).

The term "cycloalkyl" or "$C_{3-7}$-cycloalkyl" denotes a saturated moncyclic hydrocarbon group containing from 3 to 7 carbon atoms, such as cyclopropyl, cyclobutyl, cyclopentyl, cyclohexyl or cycloheptyl, more particularly cyclopropyl. In addition, the term "cycloalkyl" also embraces bicyclic hydrocarbon groups containing from 3 to 10 carbon atoms. Bicyclic means consisting of two saturated carbocycles having one or more carbon atoms in common. Examples for bicyclic cycloalkyl are bicyclo[2.2.1]heptanyl or bicyclo[2.2.2]octanyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl and 2-methoxyethyl.

The term "lower alkoxyalkoxyalkyl" or "$C_{1-7}$-alkoxy-$C_{1-7}$-alkoxy-$C_{1-7}$-alkyl" refers to lower alkyl groups as defined above wherein at least one of the hydrogen atoms of the lower alkyl group is replaced by a lower alkoxy group which itself is also substituted by a further lower alkoxy group. Among the lower alkoxyalkoxyalkyl groups of particular interest is —(CH$_2$)$_2$—O—(CH$_2$)$_2$—O—CH$_3$.

The term hydroxy means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower hydroxyalkenyl" or "hydroxy-$C_{1-7}$-alkenyl" refers to lower alkenyl groups as defined above wherein at least one of the hydrogen atoms of the lower alkenyl group is replaced by a hydroxy group. Among the particular interesting lower hydroxyalkenyl groups is 3-hydroxy-propenyl.

The term "lower hydroxyalkinyl" or "hydroxy-$C_{1-7}$-alkinyl" refers to lower alkinyl groups as defined above wherein at least one of the hydrogen atoms of the lower alkinyl group is replaced by a hydroxy group. Among the particular interesting lower hydroxyalkinyl groups is 3-hydroxy-propinyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl or difluoromethyl being especially interesting.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the lower halogenalkoxy groups of particular interest are trifluoromethoxy, difluoromethoxy, fluormethoxy and chloromethoxy, more particularly trifluoromethoxy.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxylalkyl groups or particular interest are carboxylmethyl (—CH$_2$—COOH) and carboxylethyl (—CH$_2$—CH$_2$—COOH).

The term "lower carboxylalkenyl" or "carboxyl-$C_{1-7}$-alkenyl" refers to lower alkenyl groups as defined above wherein at least one of the hydrogen atoms of the lower alkenyl group is replaced by a carboxyl group. Among the particular interesting lower carboxylalkenyl groups is 3-carboxyl-prop enyl (—CH═CH—CH$_2$—COOH).

The term "lower carboxylalkinyl" or "carboxyl-$C_{1-7}$-alkinyl" refers to lower alkinyl groups as defined above wherein at least one of the hydrogen atoms of the lower alkinyl group is replaced by a carboxyl group. Among the particular interesting lower carboxylalkinyl groups is 3-carboxyl-propinyl.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. A lower carboxylalkoxy group of particular interest is carboxylmethoxy (—O—CH$_2$—COOH).

The term "lower carboxylalkylaminocarbonyl" or "carboxyl-$C_{1-7}$-alkylaminocarbonyl" refers to aminocarbonyl as defined above wherein one of the hydrogen atoms of the amino group is replaced by carboxyl-$C_{1-7}$-alkyl. Preferred lower carboxylalkylaminocarbonyl group is —CO—NH—$CH_2$—COOH.

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A particular lower alkoxycarbonylalkyl group is —$CH_2$—$COOCH_3$.

The term "di-(lower alkoxycarbonyl)-alkyl" or "di-($C_{1-7}$-alkoxycarbonyl)-$C_{1-7}$-alkyl" means lower alkyl groups as defined above wherein two of the hydrogen atoms of the lower alkyl group are replaced by $C_{1-7}$-alkoxycarbonyl. A particular di-(lower alkoxycarbonyl)-alkyl group is —CH—$(COOCH_3)_2$.

The term "lower alkoxycarbonylalkoxy" or "$C_{1-7}$-alkoxycarbonyl-$C_{1-7}$-alkoxy" means a lower alkoxy group as defined above wherein one of the hydrogen atoms of the lower alkoxy group is replaced by $C_{1-7}$-alkoxycarbonyl. An example for a lower alkoxycarbonylalkoxy group is —O—$CH_2$—$COOCH_3$.

The term "lower alkoxycarbonylalkylaminocarbonyl" or "$C_{1-7}$-alkoxycarbonyl-$C_{1-7}$-alkylaminocarbonyl" refers to aminocarbonyl as defined above wherein one of the hydrogen atoms of the amino group is replaced by $C_{1-7}$-alkoxycarbonyl-$C_{1-7}$-alkyl. Preferred lower alkoxycarbonylalkylaminocarbonyl group is —CO—NH—$CH_2$—$COOCH_3$.

The term "lower alkylsulfonyl" or "$C_{1-7}$-alkylsulfonyl" means the group —$S(O)_2$—R, wherein R is a lower alkyl group as defined above. A lower alkylsulfonyl group of particular interest is methylsulfonyl.

The term "lower alkylcarbonyl" or "$C_{1-7}$-alkylcarbonyl" means the group —C(O)—R, wherein R is a lower alkyl group as defined above. A lower alkylcarbonyl group of particular interest is methylcarbonyl or acetyl.

The term "$C_{1-7}$-alkylsulfonyloxy" means the group —O—$S(O)_2$—R, wherein R is a lower alkyl group as defined above.

The term "aminosulfonyl" means the group —$S(O)_2$—$NH_2$.

The term "lower alkylaminosulfonyl" or "$C_{1-7}$-alkyl-aminosulfonyl" defines the group —$S(O)_2$—NH—R, wherein R is lower alkyl and the term "lower alkyl" has the previously given meaning. An example of a lower alkylaminosulfonyl group is methylaminosulfonyl.

The term "di-lower alkylaminosulfonyl" or "di-($C_{1-7}$-alkyl)-aminosulfonyl" defines the group —$S(O)_2$—NRR', wherein R and R' are lower alkyl groups as defined above. An example of a di-lower alkylaminosulfonyl group is dimethylaminosulfonyl.

The term "heterocyclylsulfonyl" defines a group —$S(O)_2$-Het, wherein Het is a heterocyclyl group as defined herein below.

"Amino" refers to the group —$NH_2$. The term "$C_{1-7}$-alkylamino" means a group —NHR, wherein R is lower alkyl and the term "lower alkyl" has the previously given significance. The term "di-($C_{1-7}$-alkyl)-amino" means a group —NRR', wherein R and R' are lower alkyl groups as defined above.

The term "$C_{1-7}$-alkoxy-$C_{1-7}$-alkyl-$C_{1-7}$-alkylamino" refers to a group —NRR", wherein R is a lower alkyl group as defined above and R" is a lower alkoxyalkyl group as defined herein.

The term "$C_{1-7}$-hydroxyalkyl-$C_{1-7}$-alkylamino" refers to a group —NRR''', wherein R is a lower alkyl group as defined above and R''' is a lower hydroxyalkyl group as defined herein.

The term "$C_{1-7}$-alkoxy-halogen-$C_{1-7}$-alkyl-amino" refers to a group —$NR^xR^y$, wherein $R^x$ is a lower alkyl group as defined above and $R^y$ is a lower halogenalkyl group as defined herein.

The term "cycloalkyl-amino" or "$C_{3-7}$-cycloalkyl-amino" means a group —NH—$R^C$, wherein $R^C$ is a cycloalkyl group as defined above.

The term "carboxylalkyl-alkylamino" or "carboxyl-$C_{1-7}$-alkyl-$C_{1-7}$-alkyl-amino" defines the group —NR—$R^B$, wherein R is lower alkyl as defined above and $R^B$ is lower carboxylalkyl and has the previously given meaning The term "lower alkylsulfonylamino" or "$C_{1-7}$-alkylsulfonylamino" defines the group —NH—$S(O)_2$—R, wherein R is lower alkyl and the term "lower alkyl" has the previously given meaning The term "cycloalkylsulfonylamino" or "$C_{3-7}$-cycloalkylsulfonylamino" defines the group —NH—$S(O)_2$—$R^C$, wherein $R^C$ is cycloalkyl and has the previously given meaning. An example is cyclopropylsulfonylamino.

The term "lower alkylcarbonylamino" or "$C_{1-7}$-alkylcarbonylamino" defines the group —NH—CO—R, wherein R is lower alkyl and the term "lower alkyl" has the previously given meaning The term "lower carboxylalkylcarbonylamino" or "carboxyl-$C_{1-7}$-alkylcarbonylamino" defines the group —NH—CO—$R^B$, wherein $R^B$ is lower carboxylalkyl and has the previously given meaning.

The term "lower alkoxycarbonyl-carbonylamino" or "$C_{1-7}$-alkoxycarbonyl-carbonylamino" defines the group —NH—CO—$R^E$, wherein $R^E$ is lower alkoxycarbonyl and has the previously given meaning The term "lower alkoxycarbonyl-alkylcarbonylamino" or "$C_{1-7}$-alkoxycarbonyl-$C_{1-7}$-alkylcarbonylamino" defines the group —NH—CO—R—$R^E$, wherein R is a lower alkyl group as defined above and at least one of the hydrogen atoms of the lower alkyl group is replaced by a lower alkoxycarbonyl group $R^E$ as defined above.

The term "lower alkoxycarbonyl-alkylcarbonylamino-alkylsulfonyl" or "$C_{1-7}$-alkoxycarbonyl-$C_{1-7}$-alkyl-carbonylamino-$C_{1-7}$-alkylsulfonyl" refers to the group —$S(O)_2$—R—NH—CO—R'—$R^E$, wherein R and R' are lower alkyl groups as defined above and at least one of the hydrogen atoms of the lower alkyl group R' is replaced by a lower alkoxycarbonyl group $R^E$ as defined above.

The term "an amino acid attached through the amino group of the amino acid" means the substituent —NR—$CHR^A$—COOH, wherein R is hydrogen or lower alkyl as defined above and $R^A$ is the side chain of an amino acid, in particular the side chain of a natural amino acid, but $R^A$ denotes also other organic substituents such as chloromethyl.

The term "aminocarbonyl" refers to the group —CO—$NH_2$.

The term "lower alkylaminocarbonyl" or "$C_{1-7}$-alkyl-aminocarbonyl" refers to a group —CONH—R, wherein R is lower alkyl as defined herein before.

The term "lower dialkylaminocarbonyl" or "di-($C_{1-7}$-alkyl)-aminocarbonyl" refers to a group —CONRR', wherein R and R' are lower alkyl groups as defined above.

The term "lower alkylsulfonyl-lower alkylaminocarbonyl" or "$C_{1-7}$-alkylsulfonyl-$C_{1-7}$-alkyl-aminocarbonyl" refers to a group —CONR—$R^S$, wherein R is lower alkyl as defined herein before and $R^S$ is a lower alkylsulfonyl group as defined above.

The term "hydroxysulfonyl" means the group —S(O)$_2$—OH.

The term "lower hydroxysulfonylalkyl-aminocarbonyl" or "hydroxysulfonyl-C$_{1-7}$-alkyl-aminocarbonyl" means a group —CONH—R$^W$, wherein R$^W$ is a lower alkyl group as defined above and wherein one of the hydrogen atoms of the lower alkyl group is replaced by —S(O)$_2$—OH. An example is —CONH—CH$_2$—CH$_2$—S(O)$_2$—OH.

The term "lower aminocarbonylalkyl" or "aminocarbonyl-C$_{1-7}$-alkyl" means lower alkyl groups as defined above wherein one of the hydrogen atoms of the lower alkyl group is replaced by aminocarbonyl. A lower aminoarbonylalkyl group of particular interest is —CH$_2$—CONH$_2$.

The term "lower halogenalkyl-aminocarbonyl" or "halogen-C$_{1-7}$-alkyl-aminocarbonyl" refers to a group —CONH—R$^y$, wherein R$^y$ is a lower halogenalkyl group as defined above.

The term "lower hydroxyalkyl-aminocarbonyl" or "hydroxy-C$_{1-7}$-alkyl-aminocarbonyl" means a group —CONH—R'", wherein R'" is a lower hydroxyalkyl group as defined above.

The term "lower hydroxyalkyl-aminocarbonylalkyl" or "hydroxy-C$_{1-7}$-alkyl-aminocarbonyl-C$_{1-7}$-alkyl" denotes a lower alkyl group as defined above wherein one of the hydrogen atoms of the lower alkyl group is replaced by a group —CONH—R'", wherein R'" is a lower hydroxyalkyl group as defined above.

The term "lower halogenhydroxyalkyl-aminocarbonyl" or "halogen-hydroxy-C$_{1-7}$-alkyl-aminocarbonyl" means a group —CONH—R$^N$, wherein R$^N$ is a lower hydroxyalkyl group as defined above and wherein at least one of the hydrogen atoms of the lower hydroxyalkyl group is replaced by a halogen atom, particularly fluoro or chloro.

The term "(lower hydroxyalkyl)-lower alkylaminocarbonyl" or "hydroxy-C$_{1-7}$-alkyl-C$_{1-7}$-alkylaminocarbonyl" means a group —CONR—R'", wherein R is a lower alkyl group as defined herein before, in particular methyl, and R'" is a lower hydroxyalkyl group as defined above.

The term "lower alkoxyalkyl-aminocarbonyl" or "(C$_{1-7}$-alkoxy-C$_{1-7}$-alkyl)-aminocarbonyl" means a group —CONH—R$^Z$, wherein R$^Z$ is a lower alkoxyalkyl group as defined above.

The term "cycloalkyl-aminocarbonyl" or "C$_{3-7}$-cycloalkyl-aminocarbonyl" means a group —CONH—R$^C$, wherein R$^C$ is a cycloalkyl group as defined above.

The term "lower carboxylalkyl-aminocarbonyl" or "carboxyl-C$_{1-7}$-alkyl-aminocarbonyl" means a group —CONH—R$^D$, wherein R$^D$ is a lower carboxylalkyl group as defined above, for example —CONH—CH$_2$—COOH.

The term "lower alkoxycarbonyl-alkyl-aminocarbonyl" or "C$_{1-7}$-alkoxycarbonyl-C$_{1-7}$-alkyl-aminocarbonyl" defines the group —CO—NH—R—R$^E$, wherein R is a lower alkyl group as defined above and at least one of the hydrogen atoms of the lower alkyl group is replaced by a lower alkoxycarbonyl group as defined above.

The term "heterocyclyl-aminocarbonyl" means a group —CONH-Het, wherein Het is a heterocyclyl group as defined herein below.

The term "lower heterocyclylalkyl-aminocarbonyl" or "heterocyclyl-C$_{1-7}$-alkyl-aminocarbonyl" refers to a group —CONH—R$^H$, wherein R$^H$ is a lower alkyl group as defined above wherein at least one of the hydrogen atoms of the lower alkyl group is replaced by a heterocyclyl group as defined herein below.

The term "lower alkylcarbonylamino-alkylaminocarbonyl" or "C$_{1-7}$-alkylcarbonylamino-C$_{1-7}$-alkylaminocarbonyl" refers to aminocarbonyl as defined above wherein one of the hydrogen atoms of the amino group is replaced by C$_{1-7}$-alkylcarbonylamino-C$_{1-7}$-alkyl. An example for a lower alkylcarbonylamino-alkylaminocarbonyl group is —CO—NH—CH$_2$—NH—CO—CH$_3$.

The term "phenyloxy" refers to the group —O-Ph wherein Ph is phenyl.

The term "lower phenylalkyl" or "phenyl-C$_{1-7}$-alkyl" means lower alkyl groups as defined above wherein one of the hydrogen atoms of the lower alkyl group is replaced by an optionally substituted phenyl group.

The term "lower phenylalkyl-aminocarbonyl" or "(phenyl-C$_{1-7}$-alkyl)-aminocarbonyl" means a group —CONH—R$^V$, wherein R$^V$ is a lower phenylalkyl group as defined above.

The term "heterocyclyl" refers to a saturated or partly unsaturated monocyclic or bicyclic ring containing from 3 to 10 ring atoms which can comprise one, two or three atoms selected from nitrogen, oxygen and/or sulfur. Bicyclic means consisting of two cycles having two ring atoms in common, i.e. the bridge separating the two rings is either a single bond or a chain of one or two ring atoms. Examples of moncyclic heterocyclyl rings include azirinyl, azetidinyl, oxetanyl, piperidinyl, piperazinyl, azepinyl, diazepanyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolidinyl, dihydrofuryl, tetrahydrofuryl, dihydropyranyl, tetrahydropyranyl, thiomorpholinyl and 1,1-dioxo-1λ6-thiomorpholinyl. Examples of bicyclic heterocyclyl rings are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, or dihydropyranyl.

The term "lower heterocyclylalkyl" or "heterocyclyl-C$_{1-7}$-alkyl" refers to lower alkyl groups as defined above wherein at least one of the hydrogen atoms of the lower alkyl group is replaced by a heterocyclyl group as defined above.

The term "heterocyclylcarbonyl" refers to the group —CO-Het wherein Het is a heterocyclyl group as defined above.

The term "heteroaryl" in general refers to an aromatic 5- or 6-membered ring which comprises one, two, three or four atoms selected from nitrogen, oxygen and/or sulfur, such as pyridyl, pyrazinyl, pyrimidinyl, 2,4-dioxo-1H-pyrimidinyl, pyridazinyl, 2-oxo-1,2-dihydropyridinyl, pyrrolyl, oxazolyl, oxadiazolyl, isoxazolyl, thiadiazolyl, tetrazolyl, pyrazolyl, imidazolyl, furanyl, thiazolyl, isothiazolyl, triazolyl, tetrazolyl, thienyl, azepinyl, diazepinyl. The term "heteroaryl" further refers to bicyclic aromatic groups comprising from 5 to 12 ring atoms, in which one or both rings can contain one, two or three atoms selected from nitrogen, oxygen or sulfur, such as quinolinyl, isoquinolinyl, cinnolinyl, quinazolinyl, pyrazolo[1,5-a]pyridyl, imidazo[1,2-a]pyridyl, quinoxalinyl, benzofuranyl, benzothienyl, benzothiazolyl, benzotriazolyl, indolyl and indazolyl.

The term "lower heteroarylalkyl" or "heteroaryl-C$_{1-7}$-alkyl" refers to lower alkyl groups as defined above wherein at least one of the hydrogen atoms of the lower alkyl group is replaced by a heteroaryl group as defined above. A specific example of a lower heteroarylalkyl group is tetrazolyl-C$_{1-7}$-alkyl.

The term "heteroaryl-aminocarbonyl" means a group —CONH—R$^U$, wherein R$^U$ is a heteroaryl group as defined above. A specific example of a heteroaryl-aminocarbonyl group is tetrazolylaminocarbonyl.

The term "oxo" means that a C-atom of the heterocyclyl or heteroaryl ring may be substituted by =O, thus meaning that the heterocyclyl or heteroaryl ring may contain one or more carbonyl (—CO—) groups.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers". Diastereomers have two or more chiral centers and are characterized by different physical properties, e.g. melting points, boiling points, spectral properties, and reactivities. Stereoisomers that are non-superimposable mirror images are termed "enantiomers", or sometimes optical isomers. A carbon atom bonded to four non-identical substituents is termed a "chiral center".

The term "modulator" denotes a molecule that interacts with a target. The interactions include e.g. agonistic, antagonistic, or inverse agonistic activity.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

In detail, the present invention relates to compounds of the formula

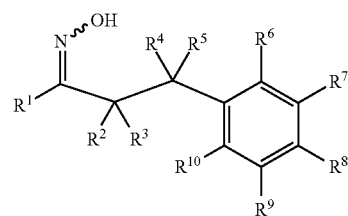

I wherein $R^1$ is —$(CH_2)_m$-phenyl, wherein m is 0 or 1 and said phenyl is substituted by one, two or three groups independently selected from the group consisting of $C_{1-7}$-alkyl, hydroxy and halogen, or —$(CH_2)_n$-heteroaryl, wherein n is 0 or 1 and said heteroaryl is selected from the group consisting of pyridine, 1H-pyridin-2-one, 1-oxy-pyridine, 1H-pyrimidin-2-one, quinoline and pyrazine, and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl;

$R^2$ is hydrogen or $C_{1-7}$-alkyl;

or, in case $R^4$ is hydrogen, $R^2$ is unsubstituted phenyl or phenyl substituted by $C_{1-7}$-alkyl;

$R^3$ is hydrogen;

$R^5$ is hydrogen or hydroxy;

or $R^3$ and $R^5$ are replaced by a double bond;

R⁴ is selected from the group consisting of: hydrogen; $C_{1-7}$-alkyl;
$C_{3-7}$-cycloalkyl; $C_{2-7}$-alkenyl; halogen-$C_{1-7}$-alkyl;
unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl;
phenyl-$C_{1-7}$-alkyl, wherein said phenyl is unsubstituted or substituted by one, two or three groups independently selected from the group consisting of $C_{1-7}$-alkyl, halogen, halogen-$C_{1-7}$-alkyl and halogen-$C_{1-7}$-alkoxy;
heteroaryl, said heteroaryl being unsubstituted or substituted by $C_{1-7}$-alkyl or oxo; and
heterocyclyl, said heterocyclyl being selected from morpholinyl, piperazinyl and piperidinyl and being unsubstituted or substituted by $C_{1-7}$-alkyl, oxo or $C_{1-7}$-alkylcarbonyl;
or R⁴ and R⁵ together with the carbon atom to which they are attached form a $C_{3-7}$-cycloalkyl ring;
R⁶ is selected from the group consisting of hydrogen, halogen and $C_{1-7}$-alkyl;
or R⁴ and R⁶ together with the carbon atoms to which they are attached form a cyclic group

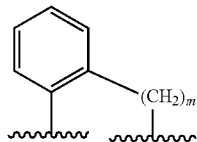

G wherein m is 0 or 2;
R⁷ and R⁹ are independently selected from the group consisting of:
hydrogen;
halogen; halogen-$C_{1-7}$-alkyl;
cyano; cyano-$C_{1-7}$-alkyl;
$C_{1-7}$-alkyl; $C_{3-7}$-alkenyl; $C_{1-7}$-alkinyl;
$C_{1-7}$-alkoxy; $C_{1-7}$-alkoxy-$C_{1-7}$-alkyl;
hydroxy; hydroxy-$C_{1-7}$-alkyl; hydroxy-$C_{3-7}$-alkenyl; hydroxy-$C_{3-7}$-alkinyl;
hydroxy-$C_{1-7}$-alkoxy;
carboxyl; carboxyl-$C_{1-7}$-alkyl; carboxyl-$C_{3-7}$-alkenyl; carboxyl-$C_{1-7}$-alkinyl;
carboxyl-$C_{1-7}$-alkoxy;
tetrazolyl;
$C_{1-7}$-alkoxycarbonyl;
$C_{1-7}$-alkylsulfonyl; $C_{1-7}$-alkylsulfonyloxy;
$C_{1-7}$-alkylsulfonylamino; $C_{3-7}$-cycloalkylsulfonylamino; aminosulfonyl; ($C_{1-7}$-alkyl)-aminosulfonyl; di-($C_{1-7}$-alkyl)-aminosulfonyl;
heterocyclylsulfonyl; $C_{1-7}$-alkyl-amino, di-($C_{1-7}$-alkyl)-amino; $C_{1-7}$-alkoxy-$C_{1-7}$-alkyl-amino;
$C_{1-7}$-alkoxy-$C_{1-7}$-alkyl-$C_{1-7}$-alkyl-amino; $C_{1-7}$-alkoxy-halogen-$C_{1-7}$-alkyl-amino;
hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl;
$C_{1-7}$-alkoxycarbonyl-$C_{1-7}$-alkyl-aminocarbonyl;
$C_{1-7}$-alkyl-aminocarbonyl; di-($C_{1-7}$-alkyl)-aminocarbonyl;
$C_{1-7}$-alkylsulfonyl-$C_{1-7}$-alkyl-aminocarbonyl;
halogen-$C_{1-7}$-alkyl-aminocarbonyl; hydroxy-$C_{1-7}$-alkyl-aminocarbonyl;
hydroxy-$C_{1-7}$-alkyl-$C_{1-7}$-alkyl-aminocarbonyl; halogen-hydroxy-$C_{1-7}$-alkyl-aminocarbonyl;
$C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl;
$C_{1-7}$-alkoxycarbonyl-$C_{1-7}$-alkyl;
di-($C_{1-7}$-alkoxycarbonyl)-$C_{1-7}$-alkyl;
$C_{1-7}$-alkylcarbonylamino-$C_{1-7}$-alkylaminocarbonyl;
$C_{1-7}$-alkylcarbonylamino; carboxyl-$C_{1-7}$-alkylcarbonylamino;
$C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;
phenyloxy, wherein said phenyl is unsubstituted or substituted by one to three groups selected from halogen or carboxyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;
R⁸ is selected from the group consisting of: hydrogen;
halogen; halogen-$C_{1-7}$-alkyl;
cyano; cyano-$C_{1-7}$-alkyl;
$C_{1-7}$-alkyl; $C_{3-7}$-alkenyl; $C_{1-7}$-alkinyl;
$C_{1-7}$-alkoxy; $C_{1-7}$-alkoxy-$C_{1-7}$-alkyl;

hydroxy; hydroxy-$C_{1-7}$-alkyl; hydroxy-$C_{3-7}$-alkenyl; hydroxy-$C_{3-7}$-alkinyl;
hydroxy-$C_{1-7}$-alkoxy;
carboxyl; carboxyl-$C_{1-7}$-alkyl; carboxyl-$C_{3-7}$-alkenyl; carboxyl-$C_{1-7}$-alkinyl;
carboxyl-$C_{1-7}$-alkoxy;
tetrazolyl;
$C_{1-7}$-alkoxycarbonyl;
$C_{1-7}$-alkylsulfonyl; $C_{1-7}$-alkylsulfonyloxy;
$C_{1-7}$-alkylsulfonylamino; $C_{3-7}$-cycloalkylsulfonylamino;
aminosulfonyl; ($C_{1-7}$-alkyl)-aminosulfonyl; di-($C_{1-7}$-alkyl)-aminosulfonyl;
heterocyclylsulfonyl; $C_{1-7}$-alkyl-amino; di-($C_{1-7}$-alkyl)-amino; $C_{1-7}$-alkoxy-$C_{1-7}$-alkyl-amino;
$C_{1-7}$-alkoxy-$C_{1-7}$-alkyl-$C_{1-7}$-alkyl-amino; $C_{1-7}$-alkoxy-halogen-$C_{1-7}$-alkyl-amino hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl;
$C_{1-7}$-alkoxycarbonyl-$C_{1-7}$-alkyl-aminocarbonyl;
$C_{1-7}$-alkyl-aminocarbonyl; di-($C_{1-7}$-alkyl)-aminocarbonyl;
$C_{1-7}$-alkylsulfonyl-$C_{1-7}$-alkyl-aminocarbonyl;
halogen-$C_{1-7}$-alkyl-aminocarbonyl; hydroxy-$C_{1-7}$-alkyl-aminocarbonyl;
hydroxy-$C_{1-7}$-alkyl-$C_{1-7}$-alkyl-aminocarbonyl; halogen-hydroxy-$C_{1-7}$-alkyl-aminocarbonyl;
$C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl;
$C_{1-7}$-alkoxycarbonyl-$C_{1-7}$-alkyl;
di-($C_{1-7}$-alkoxycarbonyl)-$C_{1-7}$-alkyl;
$C_{1-7}$-alkylcarbonylamino-$C_{1-7}$-alkylaminocarbonyl;
$C_{1-7}$-alkylcarbonylamino; carboxyl-$C_{1-7}$-alkylcarbonylamino;
$C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminosulfonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;
phenyloxy, wherein said phenyl is unsubstituted or substituted by one to three groups selected from halogen or carboxyl, and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl; and
$R^{10}$ is selected from the group consisting of hydrogen, halogen and $C_{1-7}$-alkyl;
or pharmaceutically acceptable salts thereof.

One group of compounds of formula I according to the invention are those, wherein $R^1$ is —$(CH_2)_n$-heteroaryl, wherein n is 0 or 1 and said heteroaryl is selected from the group consisting of pyridine, 1H-pyridin-2-one, 1-oxy-pyridine, 1H-pyrimidin-2-one, quinoline and pyrazine, and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl.

In particular, the invention relates to compounds of formula I according to the invention, wherein $R^1$ is —$(CH_2)_n$-heteroaryl, wherein n is 0 or 1 and said heteroaryl is selected from the group consisting of pyridine, 1H-pyridin-2-one, 1-oxy-pyridine, quinoline and pyrazine, and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl.

In particular, the invention relates to compounds of formula I as shown above, wherein $R^1$ is —$(CH_2)_n$-heteroaryl, wherein n is 0 or 1 and said heteroaryl is pyridine or 1-oxy-pyridine, and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl.

Furthermore, the invention relates to compounds of formula I as shown above, wherein $R^1$ is —$(CH_2)_n$-heteroaryl, wherein n is 0 or 1 and said heteroaryl is 1H-pyridin-2-one, which is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$- alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl.

More particularly, the invention relates to compounds of formula I according to the invention, wherein $R^1$ is —$(CH_2)_n$-heteroaryl, wherein n is 0 and said heteroaryl is pyridine or 1H-pyridin-2-one, and is unsubstituted or substituted by $C_{1-7}$-alkyl.

The invention also relates to compounds of formula I as shown above, wherein $R^1$ is —$(CH_2)_m$-phenyl, wherein m is 0 or 1 and said phenyl is substituted by one, two or three groups independently selected from the group consisting of $C_{1-7}$-alkyl, hydroxy and halogen.

Compounds of formula I according to the present invention are further those, wherein $R^2$ and $R^3$ are hydrogen.

In particular, the present invention also relates to compounds of formula I, wherein $R^5$ is hydrogen.

One group of compounds of formula I are those, wherein $R^4$ is selected from the group consisting of $C_{1-7}$-alkyl, $C_{3-7}$-cycloalkyl, $C_{2-7}$-alkenyl and halogen-$C_{1-7}$-alkyl.

Another group of compounds of formula I according to the present invention are in particular those, wherein $R^4$ is selected from the group consisting of: unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl;
phenyl-$C_{1-7}$-alkyl, wherein said phenyl is unsubstituted or substituted by one, two or three groups independently selected from the group consisting of $C_{1-7}$-alkyl, halogen, halogen-$C_{1-7}$-alkyl and halogen-$C_{1-7}$-alkoxy;
heteroaryl, said heteroaryl being unsubstituted or substituted by $C_{1-7}$-alkyl or oxo; and
heterocyclyl, said heterocyclyl being selected from morpholinyl, piperazinyl and piperidinyl and being unsubstituted or substituted by $C_{1-7}$-alkyl, oxo or $C_{1-7}$-alkylcarbonyl.

The invention also relates to compounds of formula I, wherein $R^4$ is selected from the group consisting of:
unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl;
phenyl-$C_{1-7}$-alkyl, wherein said phenyl is unsubstituted or substituted by one, two or three groups independently selected from the group consisting of $C_{1-7}$-alkyl, halogen, halogen-$C_{1-7}$-alkyl and halogen-$C_{1-7}$-alkoxy;
heteroaryl, said heteroaryl being unsubstituted or substituted by $C_{1-7}$-alkyl or oxo;
piperidinyl and 1,1-dimethylpiperidinium.

More particularly, the present invention relates to compounds of formula I, wherein $R^4$ is selected from the group consisting of:
unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl; and
and phenyl-$C_{1-7}$-alkyl, wherein phenyl is unsubstituted or substituted by one, two or three groups independently selected from the group consisting of $C_{1-7}$-alkyl, halogen, halogen-$C_{1-7}$-alkyl and halogen-$C_{1-7}$-alkoxy.

Even more particularly, $R^4$ is unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl.

The invention also relates to compounds of formula I, wherein $R^4$ is heteroaryl, said heteroaryl being unsubstituted or substituted by $C_{1-7}$-alkyl or oxo. In particular, $R^4$ is heteroaryl selected from the group consisting of pyridyl, indolyl and thiazolyl, most particularly pyridyl, said heteroaryl being unsubstituted or substituted by $C_{1-7}$-alkyl or oxo.

The invention further relates to compounds of formula I, wherein $R^4$ is heterocyclyl, said heterocyclyl being selected from the group consisting of morpholinyl, piperazinyl and piperidinyl and being unsubstituted or substituted by $C_{1-7}$-alkyl, oxo or $C_{1-7}$-alkylcarbonyl. More particularly, $R^4$ is heterocyclyl selected from piperidinyl and 1,1-dimethylpiperidinium.

A further group of compounds of formula I according to present invention are those, wherein
$R^7$ and $R^9$ are hydrogen and
$R^8$ is selected from the group consisting of:
halogen; halogen-$C_{1-7}$-alkyl;
cyano; cyano-$C_{1-7}$-alkyl;
$C_{1-7}$-alkyl; $C_{3-7}$-alkenyl; $C_{1-7}$-alkinyl;
$C_{1-7}$-alkoxy; $C_{1-7}$-alkoxy-$C_{1-7}$-alkyl;
hydroxy; hydroxy-$C_{1-7}$-alkyl; hydroxy-$C_{3-7}$-alkenyl; hydroxy-$C_{3-7}$-alkinyl;
hydroxy-$C_{1-7}$-alkoxy;
carboxyl; carboxyl-$C_{1-7}$-alkyl; carboxyl-$C_{3-7}$-alkenyl; carboxyl-$C_{1-7}$-alkinyl;
carboxyl-$C_{1-7}$-alkoxy;
tetrazolyl;
$C_{1-7}$-alkoxycarbonyl;
$C_{1-7}$-alkylsulfonyl; $C_{1-7}$-alkylsulfonyloxy;
$C_{1-7}$-alkylsulfonylamino, $C_{3-7}$-cycloalkylsulfonylamino;
Aminosulfonyl; ($C_{1-7}$-alkyl)-aminosulfonyl; di-($C_{1-7}$-alkyl)-aminosulfonyl; heterocyclylsulfonyl;
$C_{1-7}$-alkyl-amino, di-($C_{1-7}$-alkyl)-amino; $C_{1-7}$-alkoxy-$C_{1-7}$-alkyl-amino;
$C_{1-7}$-alkoxy-$C_{1-7}$-alkyl-$C_{1-7}$-alkyl-amino; $C_{1-7}$-alkoxy-halogen-$C_{1-7}$-alkyl-amino;
hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl;
$C_{1-7}$-alkoxycarbonyl-$C_{1-7}$-alkyl-aminocarbonyl;
$C_{1-7}$-alkyl-aminocarbonyl; di-($C_{1-7}$-alkyl)-aminocarbonyl;
$C_{1-7}$-alkylsulfonyl-$C_{1-7}$-alkyl-aminocarbonyl;
halogen-$C_{1-7}$-alkyl-aminocarbonyl; hydroxy-$C_{1-7}$-alkyl-aminocarbonyl;
hydroxy-$C_{1-7}$-alkyl-$C_{1-7}$-alkyl-aminocarbonyl; halogen-hydroxy-$C_{1-7}$-alkyl-aminocarbonyl;
$C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by
hydroxy, hydroxy-$C_{1-7}$-alkyl or carboxyl;
heterocyclyl-aminocarbonyl, wherein said heterocyclyl is unsubstituted or substituted by
$C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl;
$C_{1-7}$-alkoxycarbonyl-$C_{1-7}$-alkyl;
di-($C_{1-7}$-alkoxycarbonyl)-$C_{1-7}$-alkyl;
$C_{1-7}$-alkylcarbonylamino-$C_{1-7}$-alkylaminocarbonyl;
$C_{1-7}$-alkylcarbonylamino; carboxyl-$C_{1-7}$-alkylcarbonylamino;

$C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy,
hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by
hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;
phenyloxy, wherein said phenyl is unsubstituted or substituted by one to three groups selected from halogen or carboxyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

More specifically, the invention relates to compounds of formula I, wherein $R^8$ is phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

The invention also relates to compounds of formula I, wherein $R^8$ is selected from the group consisting of:
halogen; halogen-$C_{1-7}$-alkyl;
cyano; cyano-$C_{1-7}$-alkyl;
$C_{1-7}$-alkyl; $C_{3-7}$-alkenyl; $C_{1-7}$-alkinyl;
$C_{1-7}$-alkoxy; $C_{1-7}$-alkoxy-$C_{1-7}$-alkyl;
hydroxy; hydroxy-$C_{1-7}$-alkyl; hydroxy-$C_{3-7}$-alkenyl; hydroxy-$C_{3-7}$-alkinyl;
hydroxy-$C_{1-7}$-alkoxy;
carboxyl; carboxyl-$C_{1-7}$-alkyl; carboxyl-$C_{3-7}$-alkenyl; carboxyl-$C_{1-7}$-alkinyl;
carboxyl-$C_{1-7}$-alkoxy;
tetrazolyl;
$C_{1-7}$-alkoxycarbonyl;
$C_{1-7}$-alkylsulfonyl; $C_{1-7}$-alkylsulfonyloxy;
$C_{1-7}$-alkylsulfonylamino; $C_{3-7}$-cycloalkylsulfonylamino;
aminosulfonyl; ($C_{1-7}$-alkyl)-aminosulfonyl; di-($C_{1-7}$-alkyl)-aminosulfonyl; heterocyclylsulfonyl;
$C_{1-7}$-alkyl-amino, di-($C_{1-7}$-alkyl)-amino; $C_{1-7}$-alkoxy-$C_{1-7}$-alkyl-amino;
$C_{1-7}$-alkoxy-$C_{1-7}$-alkyl-$C_{1-7}$-alkyl-amino; $C_{1-7}$-alkoxy-halogen-$C_{1-7}$-alkyl-amino;
hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl;
$C_{1-7}$-alkoxycarbonyl-$C_{1-7}$-alkyl-aminocarbonyl;
$C_{1-7}$-alkyl-aminocarbonyl; di-($C_{1-7}$-alkyl)-aminocarbonyl;
$C_{1-7}$-alkylsulfonyl-$C_{1-7}$-alkyl-aminocarbonyl;
halogen-$C_{1-7}$-alkyl-aminocarbonyl; hydroxy-$C_{1-7}$-alkyl-aminocarbonyl;
hydroxy-$C_{1-7}$-alkyl-$C_{1-7}$-alkyl-aminocarbonyl; halogen-hydroxy-$C_{1-7}$-alkyl-aminocarbonyl;
$C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl;
$C_{1-7}$-alkoxycarbonyl-$C_{1-7}$-alkyl;
di-($C_{1-7}$-alkoxycarbonyl)-$C_{1-7}$-alkyl;
$C_{1-7}$-alkylcarbonylamino-$C_{1-7}$-alkylaminocarbonyl;
$C_{1-7}$-alkylcarbonylamino; carboxyl-$C_{1-7}$-alkylcarbonylamino;
$C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl; and
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl.

The invention further relates to compounds of formula I, wherein $R^8$ is selected from the group consisting of:
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl; and
phenyloxy, wherein phenyl is unsubstituted or substituted by one to three groups selected from halogen or carboxyl.

More particularly, the invention relates to compounds of formula I, wherein $R^8$ is heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxy-carbonyl, aminocarbonyl, $C_{1-7}$- alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl. Most particularly, said heterocyclyl is selected from the group consisting of azetidinyl, pyrrolidinyl, piperidinyl, tetrahydropyridinyl, morpholinyl, piperazinyl, tetrahydropyrimidinyl, thiomorpholinyl and 2-thia-6-aza-spiro[3.3]heptane-yl.

Also more particularly, the invention relates to compounds of formula I, wherein $R^8$ is heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl. Most particularly, said heteroaryl is selected from the group consisting of pyridyl, pyrimidinyl, thienyl and thiazolyl.

Most particularly, $R^8$ is selected from the group consisting of:
halogen; hydroxy-$C_{1-7}$-alkyl;
carboxyl; carboxyl-$C_{1-7}$-alkyl; $C_{1-7}$-alkylsulfonyl;
$C_{3-7}$-cycloalkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl, phenyloxy, wherein phenyl is unsubstituted or substituted by one to three groups selected from halogen or carboxyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

Another group of compounds of formula I according to the invention are those, wherein $R^7$ and $R^8$ are hydrogen and $R^9$ is selected from the group consisting of:
halogen; halogen-$C_{1-7}$-alkyl;
cyano; cyano-$C_{1-7}$-alkyl;
$C_{1-7}$-alkyl; $C_{3-7}$-alkenyl; $C_{1-7}$-alkinyl;
$C_{1-7}$-alkoxy; $C_{1-7}$-alkoxy-$C_{1-7}$-alkyl;
hydroxy; hydroxy-$C_{1-7}$-alkyl; hydroxy-$C_{3-7}$-alkenyl; hydroxy-$C_{3-7}$-alkinyl;
hydroxy-$C_{1-7}$-alkoxy;
carboxyl; carboxyl-$C_{1-7}$-alkyl; carboxyl-$C_{3-7}$-alkenyl; carboxyl-$C_{1-7}$-alkinyl;
carboxyl-$C_{1-7}$-alkoxy;
tetrazolyl;
$C_{1-7}$-alkoxycarbonyl;
$C_{1-7}$-alkylsulfonyl; $C_{1-7}$-alkylsulfonyloxy;
$C_{1-7}$-alkylsulfonylamino; $C_{3-7}$-cycloalkylsulfonylamino;
aminosulfonyl; ($C_{1-7}$-alkyl)-aminosulfonyl; di-($C_{1-7}$-alkyl)-aminosulfonyl; heterocyclylsulfonyl;

$C_{1-7}$-alkyl-amino; di-($C_{1-7}$-alkyl)-amino; $C_{1-7}$-alkoxy-$C_{1-7}$-alkyl-amino;
$C_{1-7}$-alkoxy-$C_{1-7}$-alkyl-$C_{1-7}$-alkyl-amino; $C_{1-7}$-alkoxy-halogen-$C_{1-7}$-alkyl-amino;
hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl;
$C_{1-7}$-alkoxycarbonyl-$C_{1-7}$-alkyl-aminocarbonyl;
$C_{1-7}$-alkyl-aminocarbonyl; di-($C_{1-7}$-alkyl)-aminocarbonyl; $C_{1-7}$-alkylsulfonyl-$C_{1-7}$-alkyl-aminocarbonyl;
halogen-$C_{1-7}$-alkyl-aminocarbonyl; hydroxy-$C_{1-7}$-alkyl-aminocarbonyl;
hydroxy-$C_{1-7}$-alkyl-$C_{1-7}$-alkyl-aminocarbonyl; halogen-hydroxy-$C_{1-7}$-alkyl-aminocarbonyl;
$C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl;
$C_{1-7}$-alkoxycarbonyl-$C_{1-7}$-alkyl;
di-($C_{1-7}$-alkoxycarbonyl)-$C_{1-7}$-alkyl;
$C_{1-7}$-alkylcarbonylamino-$C_{1-7}$-alkylaminocarbonyl;
$C_{1-7}$-alkylcarbonylamino; carboxyl-$C_{1-7}$-alkylcarbonylamino;
$C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;
phenyloxy, wherein said phenyl is unsubstituted or substituted by one to three groups selected from halogen or carboxyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkylcarbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

In particular, the invention relates to those compounds of formula I, wherein
$R^7$ and $R^8$ are hydrogen and
$R^9$ is selected from the group consisting of:
halogen; hydroxy-$C_{1-7}$-alkyl; hydroxy-$C_{3-7}$-alkinyl; carboxyl; carboxyl-$C_{1-7}$-alkyl; hydroxy-$C_{1-7}$-alkyl-aminocarbonyl;
hydroxy-$C_{1-7}$-alkyl-$C_{1-7}$-alkyl-aminocarbonyl;
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

More particularly, the invention relates to compounds of formula I, wherein said $R^9$ is phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

In one aspect, the invention relates to compounds of the formula

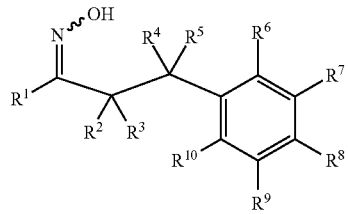

I wherein
$R^1$ is —$(CH_2)_m$-phenyl, wherein m is 0 or 1 and said phenyl is substituted by one, two or three groups independently selected from the group consisting of $C_{1-7}$-alkyl, hydroxy and halogen, or
—$(CH_2)_n$-heteroaryl, wherein n is 0 or 1 and said heteroaryl is selected from the group consisting of pyridine, 1H-pyridin-2-one, 1-oxy-pyridine, quinoline and pyrazine, and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl,
$C_{1-7}$-alkoxy, $C_{1-7}$-alkoxy-$C_{1-7}$-alkyl,
$C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl;
$R^2$ is hydrogen or $C_{1-7}$-alkyl,
or in case $R^4$ is hydrogen, $R^2$ is unsubstituted phenyl or phenyl substituted by $C_{1-7}$-alkyl;
$R^3$ is hydrogen,
$R^5$ is hydrogen or hydroxy,
or $R^3$ and $R^5$ are replaced by a double bond;
$R^4$ is selected from the group consisting of: hydrogen; $C_{1-7}$-alkyl;
$C_{3-7}$-cycloalkyl; $C_{2-7}$-alkenyl; halogen-$C_{1-7}$-alkyl;
unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl;
phenyl-$C_{1-7}$-alkyl, wherein said phenyl is unsubstituted or substituted by one, two or three groups independently selected from the group consisting of $C_{1-7}$-alkyl, halogen, halogen-$C_{1-7}$-alkyl and halogen-$C_{1-7}$-alkoxy; and
heteroaryl, said heteroaryl being unsubstituted or substituted by $C_{1-7}$-alkyl or oxo, piperidinyl and 1,1-dimethylpiperidinium;
or $R^4$ and $R^5$ together with the carbon atom to which they are attached form a $C_{3-7}$-cycloalkyl ring;
$R^6$ is selected from the group consisting of hydrogen, halogen and $C_{1-7}$-alkyl;
or $R^4$ and $R^6$ together with the carbon atoms to which they are attached form a cyclic group

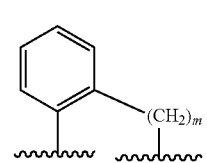

G wherein m is 0 or 2;
$R^7$ and $R^9$ are independently selected from the group consisting of: hydrogen;
halogen; halogen-$C_{1-7}$-alkyl; cyano; cyano-$C_{1-7}$-alkyl; $C_{1-7}$-alkyl; $C_{1-7}$-alkoxy;
$C_{1-7}$-alkoxy-$C_{1-7}$-alkyl; hydroxy; hydroxy-$C_{1-7}$-alkyl; hydroxy-$C_{3-7}$-alkenyl;
hydroxy-$C_{3-7}$-alkinyl; hydroxy-$C_{1-7}$-alkoxy; carboxyl; carboxyl-$C_{1-7}$-alkyl;
carboxyl-$C_{3-7}$-alkenyl; carboxyl-$C_{1-7}$-alkinyl; carboxyl-$C_{1-7}$-alkoxy;
tetrazolyl; $C_{1-7}$-alkoxycarbonyl; $C_{1-7}$-alkylsulfonyl; $C_{1-7}$-alkylsulfonyloxy;
$C_{1-7}$-alkylsulfonylamino; $C_{3-7}$-cycloalkylsulfonylamino; aminosulfonyl; $C_{1-7}$-alkylaminosulfonyl; di-$C_{1-7}$-alkylaminosulfonyl;
heterocyclylsulfonyl; $C_{1-7}$-alkylamino; di-$C_{1-7}$-alkylamino; $C_{1-7}$-alkoxy-$C_{1-7}$-alkylamino;
$C_{1-7}$-hydroxyalkyl-$C_{1-7}$-alkylamino; an amino acid attached through the amino group of the amino acid; carboxyl-$C_{1-7}$-alkylaminocarbonyl; $C_{1-7}$-alkoxycarbonyl-$C_{1-7}$-alkylaminocarbonyl; $C_{1-7}$-alkylaminocarbonyl; $C_{1-7}$-alkylsulfonyl-$C_{1-7}$-alkylaminocarbonyl; halogen-$C_{1-7}$-alkylaminocarbonyl; hydroxy-$C_{1-7}$-alkylaminocarbonyl; hydroxy-$C_{1-7}$-alkyl-$C_{1-7}$-alkylaminocarbonyl; $C_{1-7}$-alkoxy-$C_{1-7}$-alkylaminocarbonyl;

$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;

heterocyclylaminocarbonyl, wherein said heterocyclyl is unsubstituted or substituted by $C_{1-7}$-alkyl;

heterocyclyl-$C_{1-7}$-alkylaminocarbonyl;

$C_{1-7}$-alkylcarbonylamino-$C_{1-7}$-alkylaminocarbonyl;

$C_{1-7}$-alkylcarbonylamino; carboxyl-$C_{1-7}$-alkylcarbonylamino;

$C_{1-7}$-alkoxycarbonyl-$C_{1-7}$-alkylcarbonylamino;

$C_{3-7}$-cycloalkyl; $C_{3-7}$-cycloalkyl-$C_{1-7}$-alkyl;

heterocyclyl, said heterocyclyl being unsubstituted or substituted by $C_{1-7}$-alkyl, hydroxy, hydroxy-$C_{1-7}$-alkyl, $C_{1-7}$-alkoxy, carboxyl, carboxyl-$C_{1-7}$-alkyl, $C_{1-7}$-alkoxycarbonyl or $C_{1-7}$-alkylsulfonyl;

heterocyclylcarbonyl;

heteroaryl, said heteroaryl being unsubstituted or substituted by $C_{1-7}$-alkyl, carboxyl or carboxyl-$C_{1-7}$-alkyl;

phenyloxy, wherein said phenyl is unsubstituted or substituted by one to three groups selected from halogen or carboxyl; and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkylsulfonyl, aminosulfonyl, $C_{1-7}$-alkylaminosulfonyl, di-$C_{1-7}$-alkylaminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;

$R^8$ is selected from the group consisting of: hydrogen; halogen; halogen-$C_{1-7}$-alkyl; cyano; cyano-$C_{1-7}$-alkyl; $C_{1-7}$-alkyl; $C_{1-7}$-alkoxy;

$C_{1-7}$-alkoxy-$C_{1-7}$-alkyl; hydroxy; hydroxy-$C_{1-7}$-alkyl; hydroxy-$C_{3-7}$-alkenyl;

hydroxy-$C_{3-7}$-alkinyl; hydroxy-$C_{1-7}$-alkoxy; carboxyl; carboxyl-$C_{1-7}$-alkyl;

carboxyl-$C_{3-7}$-alkenyl; carboxyl-$C_{1-7}$-alkinyl; carboxyl-$C_{1-7}$-alkoxy;

tetrazolyl; $C_{1-7}$-alkoxycarbonyl; $C_{1-7}$-alkylsulfonyl; $C_{1-7}$-alkylsulfonyloxy;

$C_{1-7}$-alkylsulfonylamino; $C_{3-7}$-cycloalkylsulfonylamino;

aminosulfonyl; $C_{1-7}$-alkylaminosulfonyl; di-$C_{1-7}$-alkylaminosulfonyl;

heterocyclylsulfonyl; $C_{1-7}$-alkylamino; di-$C_{1-7}$-alkylamino; $C_{1-7}$-alkoxy-$C_{1-7}$-alkylamino;

$C_{1-7}$-hydroxyalkyl-$C_{1-7}$-alkylamino; an amino acid attached through the amino group of the amino acid; carboxyl-$C_{1-7}$-alkylaminocarbonyl; $C_{1-7}$-alkoxycarbonyl-$C_{1-7}$-alkylaminocarbonyl; $C_{1-7}$-alkylaminocarbonyl; $C_{1-7}$-alkylsulfonyl-$C_{1-7}$-alkylaminocarbonyl; halogen-$C_{1-7}$-alkylaminocarbonyl; hydroxy-$C_{1-7}$-alkylaminocarbonyl; hydroxy-$C_{1-7}$-alkyl-$C_{1-7}$-alkylaminocarbonyl; $C_{1-7}$-alkoxy-$C_{1-7}$-alkylaminocarbonyl;

$C_{3-7}$-cycloalkylaminocarbonyl, wherein $C_{3-7}$-cycloalkyl is unsubstituted or substituted by hydroxy, hydroxy-$C_{1-7}$-alkyl or carboxyl;

heterocyclylaminocarbonyl, wherein said heterocyclyl is unsubstituted or substituted by $C_{1-7}$-alkyl;

heterocyclyl-$C_{1-7}$-alkylaminocarbonyl;

$C_{1-7}$-alkylcarbonylamino-$C_{1-7}$-alkylaminocarbonyl;

$C_{1-7}$-alkylcarbonylamino; carboxyl-$C_{1-7}$-alkylcarbonylamino;

$C_{1-7}$-alkoxycarbonyl-$C_{1-7}$-alkylcarbonylamino;

$C_{3-7}$-cycloalkyl; $C_{3-7}$-cycloalkyl-$C_{1-7}$-alkyl;

heterocyclyl, said heterocyclyl being unsubstituted or substituted by $C_{1-7}$-alkyl, hydroxy, hydroxy-$C_{1-7}$-alkyl, $C_{1-7}$-alkoxy, carboxyl, carboxyl-$C_{1-7}$-alkyl, $C_{1-7}$-alkoxycarbonyl or $C_{1-7}$-alkylsulfonyl;

heterocyclylcarbonyl;

heteroaryl, said heteroaryl being unsubstituted or substituted by $C_{1-7}$-alkyl, carboxyl or carboxyl-$C_{1-7}$-alkyl;

phenyloxy, wherein phenyl is unsubstituted or substituted by one to three groups selected from halogen or carboxyl; and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkylsulfonyl, aminosulfonyl, $C_{1-7}$-alkylaminosulfonyl, di-$C_{1-7}$-alkylaminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl; and $R^{10}$ is selected from the group consisting of hydrogen, halogen and $C_{1-7}$-alkyl;

or pharmaceutically acceptable salts thereof.

Particular compounds of formula I are the following:

(E)-3-(4-dimethylamino-phenyl)-3-phenyl-1-pyridin-4-yl-propan-1-one oxime, (Z)-3-(4-dimethylamino-phenyl)-3-phenyl-1-pyridin-4-yl-propan-1-one oxime, (+)-(E)-3-(4-dimethylamino-phenyl)-3-phenyl-1-pyridin-4-yl-propan-1-one oxime, (−)-(E)-3-(4-dimethylamino-phenyl)-3-phenyl-1-pyridin-4-yl-propan-1-one oxime, (E)-3-(4-bromo-phenyl)-3-phenyl-1-pyridin-4-yl-propan-1-one oxime, (E)-3-(4-dimethylamino-phenyl)-1-pyridin-4-yl-3-o-tolyl-propan-1-one oxime, 3-(4-dimethylamino-phenyl)-1-pyridin-4-yl-3-m-tolyl-propan-1-one oxime, (+)-(E)-3-(4-dimethylamino-phenyl)-1-pyridin-4-yl-3-p-tolyl-propan-1-one oxime, (−)-(E)-3-(4-dimethylamino-phenyl)-1-pyridin-4-yl-3-p-tolyl-propan-1-one oxime, (Z)-3-(4-dimethylamino-phenyl)-1-pyridin-4-yl-3-p-tolyl-propan-1-one oxime, 3-(3-bromo-phenyl)-1-pyridin-4-yl-3-o-tolyl-propan-1-one oxime, (E)-3-(3-bromo-phenyl)-3-phenyl-1-pyridin-4-yl-propan-1-one oxime, 3-(3-bromo-phenyl)-1-pyridin-4-yl-pentan-1-one oxime, (E)-3,3-diphenyl-1-pyridin-4-yl-propan-1-one oxime, (E)-3-(4-bromo-phenyl)-1-(1-oxy-pyridin-4-yl)-3-phenyl-propan-1-one oxime, (E)-3-(4-cyclopropyl-phenyl)-3-phenyl-1-pyridin-4-yl-propan-1-one oxime, 3-(4-dimethylamino-phenyl)-3-(3,4-dimethyl-phenyl)-1-pyridin-4-yl-propan-1-one oxime, 3-(4-dimethylamino-phenyl)-3-(3,5-dimethyl-phenyl)-1-pyridin-4-yl-propan-1-one oxime,
(E)-3-(3'-methanesulfonyl-biphenyl-4-yl)-3-phenyl-1-pyridin-4-yl-propan-1-one oxime,
(E)-3-(4'-methanesulfonyl-biphenyl-4-yl)-3-phenyl-1-pyridin-4-yl-propan-1-one oxime,
4'-{3-[(E)-hydroxyimino]-1-phenyl-3-pyridin-4-yl-propyl}-biphenyl-4-sulfonic acid methylamide,
(E)-3-phenyl-1-pyridin-4-yl-3-(4-pyrimidin-5-yl-phenyl)-propan-1-one oxime,
(E)-3-(3'-methanesulfonyl-biphenyl-3-yl)-3-phenyl-1-pyridin-4-yl-propan-1-one oxime,
(E)-3-(4'-methanesulfonyl-biphenyl-3-yl)-3-phenyl-1-pyridin-4-yl-propan-1-one oxime,
(E)-3-[4-(6-methyl-pyridin-3-yl)-phenyl]-3-phenyl-1-pyridin-4-yl-propan-1-one oxime,
(E)-3-(4'-ethanesulfonyl-biphenyl-4-yl)-3-phenyl-1-pyridin-4-yl-propan-1-one oxime,
(E)-3-(4'-hydroxymethyl-biphenyl-4-yl)-3-phenyl-1-pyridin-4-yl-propan-1-one oxime,
(4'-{3-[(E)-hydroxyimino]-1-phenyl-3-pyridin-4-yl-propyl}-biphenyl-3-yloxy)-acetic acid ethyl ester,
3-(4'-methanesulfonyl-biphenyl-3-yl)-1-pyridin-4-yl-3-o-tolyl-propan-1-one oxime,
3-(3'-methanesulfonyl-biphenyl-3-yl)-1-pyridin-4-yl-3-o-tolyl-propan-1-one oxime,
3-(4-bromo-phenyl)-1-pyridin-4-yl-3-o-tolyl-propan-1-one oxime,
3-(3'-methanesulfonyl-biphenyl-4-yl)-1-pyridin-4-yl-3-o-tolyl-propan-1-one oxime,
3-(4'-methanesulfonyl-biphenyl-4-yl)-1-pyridin-4-yl-3-o-tolyl-propan-1-one oxime,
1-pyridin-4-yl-3-(4-pyrimidin-5-yl-phenyl)-3-o-tolyl-propan-1-one oxime,
(+)-(E)-1-pyridin-4-yl-3-(4-pyrimidin-5-yl-phenyl)-3-o-tolyl-propan-1-one oxime,
(−)-(E)-1-pyridin-4-yl-3-(4-pyrimidin-5-yl-phenyl)-3-o-tolyl-propan-1-one oxime,
(−)-(Z)-1-pyridin-4-yl-3-(4-pyrimidin-5-yl-phenyl)-3-o-tolyl-propan-1-one oxime,
(+)-(Z)-1-pyridin-4-yl-3-(4-pyrimidin-5-yl-phenyl)-3-o-tolyl-propan-1-one oxime,
(E)-3-{4-[(2-methoxy-ethyl)-methyl-amino]-phenyl}-1-pyridin-4-yl-3-o-tolyl-propan-1-one oxime,
3-(4-piperidin-1-yl-phenyl)-1-pyridin-4-yl-3-o-tolyl-propan-1-one oxime,
3-(4-morpholin-4-yl-phenyl)-1-pyridin-4-yl-3-o-tolyl-propan-1-one oxime,
3-(4-diethylamino-phenyl)-1-pyridin-4-yl-3-o-tolyl-propan-1-one oxime,
(Z)-3-(4-bromo-phenyl)-1-pyridin-4-yl-2-o-tolyl-propan-1-one oxime,
(E)-3-(4-bromo-phenyl)-1-pyridin-4-yl-2-o-tolyl-propan-1-one oxime,
3-(4-bromo-phenyl)-1-(2,6-dimethyl-pyridin-4-yl)-2-phenyl-propan-1-one oxime,
3-(4-bromo-phenyl)-1-(2-chloro-pyridin-4-yl)-3-phenyl-propan-1-one oxime,
(E)-3-(4-bromo-phenyl)-1-(2,6-dichloro-pyridin-4-yl)-3-phenyl-propan-1-one oxime,
(E)-3-(4-bromo-phenyl)-3-o-tolyl-1-(2,3,5-trifluoro-phenyl)-propan-1-one oxime,
3-(4-bromo-phenyl)-1-(2,5-dichloro-phenyl)-3-o-tolyl-propan-1-one oxime,
(+)-(E)-3-(4-bromo-phenyl)-1-(2,5-dichloro-phenyl)-3-o-tolyl-propan-1-one oxime,
(−)-(−E)-3-(4-bromo-phenyl)-1-(2,5-dichloro-phenyl)-3-o-tolyl-propan-1-one oxime,
(E)-3-(4-bromo-phenyl)-1-(2,5-difluoro-phenyl)-3-o-tolyl-propan-1-one oxime,
(E)-3-(4-bromo-phenyl)-1-(3,5-difluoro-phenyl)-3-o-tolyl-propan-1-one oxime,
(E)-1-(3,5-difluoro-phenyl)-3-(4-pyrimidin-5-yl-phenyl)-3-o-tolyl-propan-1-one oxime,
1-(2-chloro-5-fluoro-pyridin-4-yl)-3,3-diphenyl-propan-1-one oxime,
(E)-1-(2-fluoro-6-methyl-pyridin-4-yl)-3,3-diphenyl-propan-1-one oxime,
1-(2-methyl-pyridin-4-yl)-3,3-diphenyl-propan-1-one oxime,
1-(5-chloro-2-fluoro-pyridin-4-yl)-3,3-diphenyl-propan-1-one oxime,
1-(2-fluoro-5-methyl-pyridin-4-yl)-3,3-diphenyl-propan-1-one oxime,
(E)-2-(10,11-dihydro-5H-dibenzo[a,d]cyclohepten-5-yl)-1-pyridin-4-yl-ethanone oxime,
2-(9H-fluoren-9-yl)-1-pyridin-4-yl-ethanone oxime,
3-(4-dimethylamino-phenyl)-3-(1H-indol-3-yl)-1-pyridin-4-yl-propan-1-one oxime,
3-(4-dimethylamino-phenyl)-3-(2-methyl-1H-indol-3-yl)-1-pyridin-4-yl-propan-1-one oxime,
(E)-3-(4-dimethylamino-phenyl)-3-pyridin-2-yl-1-pyridin-4-yl-propan-1-one oxime,
(E)-3-(4-dimethylamino-phenyl)-3-(3-methyl-pyridin-2-yl)-1-pyridin-4-yl-propan-1-one oxime,
1-(2,6-dimethyl-pyridin-4-yl)-3,3-diphenyl-propenone oxime,
1-(2,6-dimethyl-pyridin-4-yl)-3,3-diphenyl-propan-1-one oxime,
(E)-1-(2,6-dimethyl-pyridin-4-yl)-3-phenyl-3-pyridin-2-yl-propan-1-one oxime,
3-{3-[(E)-hydroxyimino]-1-phenyl-3-pyridin-4-yl-propyl}-benzoic acid,
4-{3-[hydroxyimino]-3-pyridin-4-yl-1-o-tolyl-propyl}-benzoic acid,
3-{3-[hydroxyimino]-3-pyridin-4-yl-1-o-tolyl-propyl}-benzoic acid,
(E)-1-(2,6-dichloro-pyridin-4-yl)-3,3-diphenyl-propan-1-one oxime,
(Z)-1-(2,6-dichloro-pyridin-4-yl)-3,3-diphenyl-propan-1-one oxime,
4'-[3-[hydroxyimino]-3-(2-methyl-pyridin-4-yl)-1-o-tolyl-propyl]-biphenyl-4-carboxylic acid methyl ester,
4'-[3-[hydroxyimino]-3-(2-methyl-pyridin-4-yl)-1-o-tolyl-propyl]-biphenyl-4-carboxylic acid,
4'-{3-[(E)-hydroxyimino]-1-phenyl-3-pyridin-4-yl-propyl}-biphenyl-3-carboxylic acid,
4'-{3-[(E)-hydroxyimino]-1-phenyl-3-pyridin-4-yl-propyl}-biphenyl-4-carboxylic acid,
4'-[3-[hydroxyimino]-3-(2-methyl-pyridin-4-yl)-1-o-tolyl-propyl]-biphenyl-3-carboxylic acid ethyl ester,
4'-[3-[hydroxyimino]-3-(2-methyl-pyridin-4-yl)-1-o-tolyl-propyl]-biphenyl-3-carboxylic acid,
{4-[3-[hydroxyimino]-3-(2-methyl-pyridin-4-yl)-1-o-tolyl-propyl]-phenyl}-acetic acid,
2-fluoro-4'-[3-[hydroxyimino]-3-(2-methyl-pyridin-4-yl)-1-o-tolyl-propyl]-biphenyl-4-carboxylic acid methyl ester,
2-fluoro-4'-[3-[hydroxyimino]-3-(2-methyl-pyridin-4-yl)-1-o-tolyl-propyl]-biphenyl-4-carboxylic acid,
3-chloro-4'-[3-[hydroxyimino]-3-(2-methyl-pyridin-4-yl)-1-o-tolyl-propyl]-biphenyl-4-carboxylic acid methyl ester,
3-chloro-4'-[3-[hydroxyimino]-3-(2-methyl-pyridin-4-yl)-1-o-tolyl-propyl]-biphenyl-4-carboxylic acid, 3-[4-(3-hydroxy-prop-1-ynyl)-phenyl]-1-(2-methyl-pyridin-4-yl)-3-o-tolyl-propan-1-one oxime,
4-[3-[hydroxyimino]-3-(2-methyl-pyridin-4-yl)-1-o-tolyl-propyl]-benzoic acid,
3-{4-[3-[hydroxyimino]-3-(2-methyl-pyridin-4-yl)-1-o-tolyl-propyl]-phenyl}-acrylic acid,
3-[4-(3-hydroxy-propyl)-phenyl]-1-(2-methyl-pyridin-4-yl)-3-o-tolyl-propan-1-one oxime,
3-({4'-[3-[hydroxyimino]-3-(2-methyl-pyridin-4-yl)-1-o-tolyl-propyl]-biphenyl-4-carbonyl}-amino)-propionic acid,
({4'-[3-[hydroxyimino]-3-(2-methyl-pyridin-4-yl)-1-o-tolyl-propyl]-biphenyl-4-carbonyl}-amino)-acetic acid,
4'-[(S)-3-[(E)-hydroxyimino]-3-(2-methyl-pyridin-4-yl)-1-o-tolyl-propyl]-biphenyl-4-carboxylic acid,
4'-[(S)-3-[(Z)-hydroxyimino]-3-(2-methyl-pyridin-4-yl)-1-o-tolyl-propyl]-biphenyl-4-carboxylic acid,
4'-[(R)-3-[(E)-hydroxyimino]-3-(2-methyl-pyridin-4-yl)-1-o-tolyl-propyl]-biphenyl-4-carboxylic acid,
4'-[(R)-3-[(Z)-hydroxyimino]-3-(2-methyl-pyridin-4-yl)-1-o-tolyl-propyl]-biphenyl-4-carboxylic acid,
(S)-2-({4'-[(S)-3-[hydroxyimino]-3-(2-methyl-pyridin-4-yl)-1-o-tolyl-propyl]-biphenyl-4-carbonyl}-amino)-propionic acid,
({4'-[(R)-3-[(E)-hydroxyimino]-3-(2-methyl-pyridin-4-yl)-1-o-tolyl-propyl]-biphenyl-4-carbonyl}-amino)-acetic acid,
4'-[(S)-3-[hydroxyimino]-3-(2-methyl-pyridin-4-yl)-1-o-tolyl-propyl]-biphenyl-4-carboxylic acid ((R)-1-phenyl-ethyl)-amide,
3-(3-bromo-phenyl)-1-(2-methyl-pyridin-4-yl)-3-o-tolyl-propan-1-one oxime,
5-{3-[3-[hydroxyimino]-3-(2-methyl-pyridin-4-yl)-1-o-tolyl-propyl]-phenyl}-pyridine-2-carboxylic acid,
3-fluoro-3'-[3-[hydroxyimino]-3-(2-methyl-pyridin-4-yl)-1-o-tolyl-propyl]-biphenyl-4-carboxylic acid methyl ester,
3-fluoro-3'-[3-[(E)-hydroxyimino]-3-(2-methyl-pyridin-4-yl)-1-o-tolyl-propyl]-biphenyl-4-carboxylic acid,
3'-[3-[hydroxyimino]-3-(2-methyl-pyridin-4-yl)-1-o-tolyl-propyl]-biphenyl-3-carboxylic acid,
(E)-3'-[3-[hydroxyimino]-3-(2-methyl-pyridin-4-yl)-1-o-tolyl-propyl]-biphenyl-4-carboxylic acid,
3-(4'-methanesulfonyl-biphenyl-3-yl)-1-(2-methyl-pyridin-4-yl)-3-o-tolyl-propan-1-one oxime,
{3-[3-[(E)-hydroxyimino]-3-(2-methyl-pyridin-4-yl)-1-o-tolyl-propyl]-phenyl}-acetic acid,
3-[3-(3-hydroxy-prop-1-ynyl)-phenyl]-1-(2-methyl-pyridin-4-yl)-3-o-tolyl-propan-1-one oxime,
3-[3-(3-hydroxy-propyl)-phenyl]-1-(2-methyl-pyridin-4-yl)-3-o-tolyl-propan-1-one oxime,
({3'-[3-[(E)-hydroxyimino]-3-(2-methyl-pyridin-4-yl)-1-o-tolyl-propyl]-biphenyl-3-carbonyl}-amino)-acetic acid,
3-(4-bromo-phenyl)-1-(2-methoxy-pyridin-4-yl)-3-o-tolyl-propan-1-one oxime,
4-{3-(4-bromo-phenyl)-1-[(E)-hydroxyimino]-3-o-tolyl-propyl}-1-methyl-1H-pyridin-2-one,
5-{-4-[3-[hydroxyimino]-3-(2-methyl-pyridin-4-yl)-1-o-tolyl-propyl]-phenyl}-pent-4-ynoic acid,
3-fluoro-4'-[3-[hydroxyimino]-3-(2-methyl-pyridin-4-yl)-1-o-tolyl-propyl]-biphenyl-4-carboxylic acid,
4-fluoro-4'-[3-[hydroxyimino]-3-(2-methyl-pyridin-4-yl)-1-o-tolyl-propyl]-biphenyl-3-carboxylic acid,
3-(4-bromo-phenyl)-5-methyl-1-pyridin-4-yl-hexan-1-one oxime,
5-{4-[3-[hydroxyimino]-3-(2-methyl-pyridin-4-yl)-1-o-tolyl-propyl]-phenyl}-pentanoic acid,
(E)-3-(4-bromo-phenyl)-3-(3-methyl-pyridin-2-yl)-1-(2-methyl-pyridin-4-yl)-propan-1-one oxime,
(E)-4'-[3-[hydroxyimino]-3-(2-methyl-pyridin-4-yl)-1-(3-methyl-pyridin-2-yl)-propyl]-biphenyl-4-carboxylic acid,
3-(4-bromo-phenyl)-1-(2-methyl-pyridin-4-yl)-3-o-tolyl-propan-1-one oxime,
3-(4-bromo-phenyl)-1-(2-chloro-pyridin-4-yl)-3-o-tolyl-propan-1-one oxime,
(E)-3-(4-bromo-phenyl)-1-(2,6-dichloro-pyridin-4-yl)-3-o-tolyl-propan-1-one oxime,
3-(4-bromo-phenyl)-1-(5-chloro-2-fluoro-pyridin-4-yl)-3-o-tolyl-propan-1-one oxime,
(E)-3-(3-bromo-phenyl)-1-(2-fluoro-6-methyl-pyridin-4-yl)-3-o-tolyl-propan-1-one oxime,
(E)-3-(3-bromo-phenyl)-1-(5-bromo-pyridin-3-yl)-3-o-tolyl-propan-1-one oxime,
3-(4-bromo-phenyl)-1-(2-fluoro-5-methyl-pyridin-4-yl)-3-o-tolyl-propan-1-one oxime,
3-(4-bromo-phenyl)-1-quinolin-6-yl-3-o-tolyl-propan-1-one oxime,
3-(4-bromo-phenyl)-1-(2-fluoro-6-methyl-pyridin-4-yl)-3-o-tolyl-propan-1-one oxime,
3-(4-bromo-phenyl)-1-(2-chloro-5-fluoro-pyridin-4-yl)-3-o-tolyl-propan-1-one oxime,
(E)-3-(4-bromo-phenyl)-1-(2-fluoro-5-methyl-pyridin-3-yl)-3-o-tolyl-propan-1-one oxime,
3-(4-bromo-phenyl)-4,4-dimethyl-1-(2-methyl-pyridin-4-yl)-pentan-1-one oxime,
4'-{3-(2-fluoro-5-methyl-pyridin-4-yl)-3-[hydroxyimino]-1-o-tolyl-propyl}-biphenyl-4-carboxylic acid,
3-fluoro-4'-[3-[(E)-hydroxyimino]-3-(2-methyl-pyridin-4-yl)-1-o-tolyl-propyl]-biphenyl-4-carboxylic acid,
(E)-3-(4-bromo-phenyl)-1-(2-methyl-pyridin-4-yl)-3-(2-trifluoromethyl-phenyl)-propan-1-one oxime,
(E)-3-(4'-methanesulfonyl-biphenyl-4-yl)-1-(2-methyl-pyridin-4-yl)-3-(2-trifluoromethyl-phenyl)-propan-1-one oxime,
4'-[3-[(E)-hydroxyimino]-3-(2-methyl-pyridin-4-yl)-1-(2-trifluoromethyl-phenyl)-propyl]-biphenyl-4-carboxylic acid,
3-fluoro-4'-[3-[(E)-hydroxyimino]-3-(2-methyl-pyridin-4-yl)-1-(2-trifluoromethyl-phenyl)-propyl]-biphenyl-4-carboxylic acid,
(E)-3-[4-(4-methanesulfonyl-piperazin-1-yl)-phenyl]-1-pyridin-4-yl-3-o-tolyl-propan-1-one oxime,
(E)-3-[4-(4-methanesulfonyl-piperazin-1-yl)-phenyl]-1-(2-methyl-pyridin-4-yl)-3-(2-trifluoromethyl-phenyl)-propan-1-one oxime,
(E)-3-(4-bromophenyl)-3-(4-chloro-2-methylphenyl)-1-(2-methylpyridin-4-yl)propan-1-one oxime,
(E)-4'-(1-(4-chloro-2-methylphenyl)-3-(hydroxyimino)-3-(2-methylpyridin-4-yl)propyl)biphenyl-4-carboxylic acid,
(E)-3-(4-bromophenyl)-3-(4-fluoro-2-methylphenyl)-1-(2-methylpyridin-4-yl)propan-1-one oxime,
(E)-4'-(1-(4-fluoro-2-methylphenyl)-3-(hydroxyimino)-3-(2-methylpyridin-4-yl)propyl)biphenyl-4-carboxylic acid,
(E,R)-3-(4-bromophenyl)-1-(2-methylpyridin-4-yl)-3-o-tolylpropan-1-one oxime,
(E,R)-1-(2-methylpyridin-4-yl)-3-(4-pyrimidin-5-yl-phenyl)-3-o-tolyl-propan-1-one oxime,
(E,R)-1-(2-methylpyridin-4-yl)-3-(4-(4-(methylsulfonyl)piperazin-1-yl)phenyl)-3-o-tolylpropan-1-one oxime,
(E,R)-3-(4-(4-hydroxypiperidin-1-yl)phenyl)-1-(2-methylpyridin-4-yl)-3-o-tolylpropan-1-one oxime,
(E,R)-4'-(3-(2,6-dichloropyridin-4-yl)-3-(hydroxyimino)-1-o-tolylpropyl)biphenyl-4-carboxylic acid, (E)-3-(4-bromo-phenyl)-3-(4-chloro-2-fluoro-phenyl)-1-(2-methyl-pyridin-4-yl)-propan-1-one oxime, 4'-[1-(4-chloro-2-fluoro-phenyl)-3-[(E)-hydroxyimino]-3-(2-methyl-pyridin-4-yl)-propyl]-biphenyl-4-carboxylic acid, 4-{4-[1-(4-chloro-2-fluoro-phenyl)-3-[(E)-hydroxyimino]-3-(2-methyl-pyridin-4-yl)-propyl]-phenyl}-thiophene-2-carboxylic acid ethyl ester, 4-{4-[1-(4-chloro-2-fluoro-phenyl)-3-[(E)-hydroxyimino]-3-(2-methyl-pyridin-4-yl)-propyl]-phenyl}-thiophene-2-carboxylic acid, (E)-3-(4-bromo-phenyl)-1-(4-hydroxy-phenyl)-3-o-tolyl-propan-1-one oxime, (E)-3-(4-bromo-phenyl)-1-(4-hydroxy-3,5-dimethyl-phenyl)-3-o-tolyl-propan-1-one oxime, (E)-2-methyl-3,3-diphenyl-1-pyridin-4-yl-propan-1-one oxime, (E)-3-hydroxy-3,3-diphenyl-1-pyridin-4-yl-propan-1-one oxime, (Z)-3-hydroxy-3,3-diphenyl-1-pyridin-4-yl-propan-1-one oxime, (E)-3-(4-bromo-phenyl)-1-pyrazin-2-yl-3-o-tolyl-propan-1-one oxime, 3-(4-bromo-phenyl)-1-(7-chloro-quinolin-4-yl)-3-o-tolyl-propan-1-one oxime, (E)-2-[1-(4-methoxy-phenyl)-cyclohexyl]-1-(2-methyl-pyridin-4-yl)-ethanone oxime, (Z)-2-[1-(4-methoxy-phenyl)-cyclohexyl]-1-(2-methyl-pyridin-4-yl)-ethanone oxime, 5-{1-[(E)-hydroxyimino]-3,3-diphenyl-propyl}-1H-pyridin-2-one, 5-{1-[(E)-hydroxyimino]-3,3-diphenyl-propyl}-1-methyl-1H-pyridin-2-one, 5-{3-(4-bromo-phenyl)-1-[(E)-hydroxyimino]-3-o-tolyl-propyl}-1-methyl-1H-pyridin-2-one, 5-{3-(4-bromo-phenyl)-1-[(Z)-hydroxyimino]-3-o-tolyl-propyl}-1-methyl-1H-pyridin-2-one, 5-{3-(4-bromo-phenyl)-1-[(E)-hydroxyimino]-3-o-tolyl-propyl}-1-ethyl-1H-pyridin-2-one, 5-{3-(4-bromo-phenyl)-1-[(Z)-hydroxyimino]-3-o-tolyl-propyl}-1-ethyl-1H-pyridin-2-one, 4'-[3-[(E)-hydroxyimino]-3-(1-methyl-6-oxo-1,6-dihydro-pyridin-3-yl)-1-o-tolyl-propyl]-biphenyl-4-carboxylic acid, 4'-[(S)-3-[(E)-hydroxyimino]-3-(1-methyl-6-oxo-1,6-dihydro-pyridin-3-yl)-1-o-tolyl-propyl]-biphenyl-4-carboxylic acid, 4'-[(R)-3-[(E)-hydroxyimino]-3-(1-methyl-6-oxo-1,6-dihydro-pyridin-3-yl)-1-o-tolyl-propyl]-biphenyl-4-carboxylic acid, 3-fluoro-4'-[3-[(E)-hydroxyimino]-3-(1-methyl-6-oxo-1,6-dihydro-pyridin-3-yl)-1-o-tolyl-propyl]-biphenyl-4-carboxylic acid, 5-{3-(4-bromo-phenyl)-1-[(E)-hydroxyimino]-5-methyl-hexyl}-1-methyl-1H-pyridin-2-one, 5-{3-(4-bromo-phenyl)-1-[(Z)-hydroxyimino]-5-methyl-hexyl}-1-methyl-1H-pyridin-2-one, 5-{3-(4-bromo-phenyl)-3-cyclopentyl-1-[(E)-hydroxyimino]-propyl}-1-methyl-1H-pyridin-2-one, 5-{3-(4-bromo-phenyl)-3-cyclopentyl-1-[(Z)-hydroxyimino]-propyl}-1-methyl-1H-pyridin-2-one, 5-{3-(4-bromo-phenyl)-1-[(E)-hydroxyimino]-hexyl}-1-methyl-1H-pyridin-2-one, 5-{3-(4-bromo-phenyl)-7,7,7-trifluoro-1-[(E)-hydroxyimino]-heptyl}-1-methyl-1H-pyridin-2-one, 5-{3-(4-bromo-phenyl)-1-[(E)-hydroxyimino]-hex-5-enyl}-1-methyl-1H-pyridin-2-one, 5-{3-(4-bromo-phenyl)-1-[(E)-hydroxyimino]-heptyl}-1-methyl-1H-pyridin-2-one, 5-{3-(4-bromo-phenyl)-3-cyclohexyl-1-[(E)-hydroxyimino]-propyl}-1-methyl-1H-pyridin-2-one, 5-{3-(4-bromo-phenyl)-3-cyclobutyl-1-[(E)-hydroxyimino]-propyl}-1-methyl-1H-pyridin-2-one, 5-[3-(4-bromo-phenyl)-1-[(E)-hydroxyimino]-4-(4-trifluoromethoxy-phenyl)-butyl]-1-methyl-1H-pyridin-2-one, 5-{3-(4-bromo-phenyl)-1-[(E)-hydroxyimino]-3-o-tolyl-propyl}-1-isopropyl-1H-pyridin-2-one, 5-{3-(4-bromo-phenyl)-1-[(Z)-hydroxyimino]-3-o-tolyl-propyl}-1-isopropyl-1H-pyridin-2-one, 5-{3-(4-bromo-phenyl)-1-[(E)-hydroxyimino]-3-o-tolyl-propyl}-1-cyclopropylmethyl-1H-pyridin-2-one, 5-{3-(4-bromo-phenyl)-1-[(Z)-hydroxyimino]-3-o-tolyl-propyl}-1-cyclopropylmethyl-1H-pyridin-2-one, 5-{3-(4-bromo-phenyl)-1-[(E)-hydroxyimino]-3-o-tolyl-propyl}-1-(2-methoxy-ethyl)-1H-pyridin-2-one, 2-(5-{3-(4-bromo-phenyl)-1-[(E)-hydroxyimino]-3-o-tolyl-propyl}-2-oxo-2H-pyridin-1-yl)-acetamide, 5-{3-(4-bromo-phenyl)-1-[(E)-hydroxyimino]-3-o-tolyl-propyl}-1-cyclobutyl-1H-pyridin-2-one, 5-{3-(4-bromo-phenyl)-1-[(Z)-hydroxyimino]-3-o-tolyl-propyl}-1-cyclobutyl-1H-pyridin-2-one, 3-(5-{3-(4-bromo-phenyl)-1-[(E)-hydroxyimino]-3-o-tolyl-propyl}-2-oxo-2H-pyridin-1-yl)-propionic acid, 4-(5-{3-(4-bromo-phenyl)-1-[(E)-hydroxyimino]-3-o-tolyl-propyl}-2-oxo-2H-pyridin-1-yl)-butyric acid, 5-{3-(4-bromo-2-fluoro-phenyl)-1-[(E)-hydroxyimino]-hexyl}-1-methyl-1H-pyridin-2-one, 5-{3-(4-bromo-2-fluoro-phenyl)-3-cyclopentyl-1-[(E)-hydroxyimino]-propyl}-1-methyl-1H-pyridin-2-one, 5-{3-(4-bromo-2-fluoro-phenyl)-1-[(E)-hydroxyimino]-3-o-tolyl-propyl}-1-methyl-1H-pyridin-2-one, 3'-fluoro-4'-[3-[(E)-hydroxyimino]-3-(1-methyl-6-oxo-1,6-dihydro-pyridin-3-yl)-1-o-tolyl-propyl]-biphenyl-4-carboxylic acid, 3,3'-difluoro-4'-[3-[(E)-hydroxyimino]-3-(1-methyl-6-oxo-1,6-dihydro-pyridin-3-yl)-1-o-tolyl-propyl]-biphenyl-4-carboxylic acid methyl ester, 3,3'-difluoro-4'-[3-[(E)-hydroxyimino]-3-(1-methyl-6-oxo-1,6-dihydro-pyridin-3-yl)-1-o-tolyl-propyl]-biphenyl-4-carboxylic acid, 5-{3-(2-chloro-phenyl)-3-cyclopentyl-1-[(E)-hydroxyimino]-propyl}-1-methyl-1H-pyridin-2-one, 4-[1-(2-chloro-phenyl)-3-[(E)-hydroxyimino]-3-(1-methyl-6-oxo-1,6-dihydro-pyridin-3-yl)-propyl]-1,1-dimethyl-piperidinium iodide, 5-{3-(4-bromo-phenyl)-1-[(E)-hydroxyimino]-3-o-tolyl-propyl}-1,4-dimethyl-1H-pyridin-2-one, 5-{3-(4-bromo-phenyl)-1-[(Z)-hydroxyimino]-3-o-tolyl-propyl}-1,4-dimethyl-1H-pyridin-2-one, 4'-[3-[(E)-hydroxyimino]-3-(1-methyl-6-oxo-1,6-dihydro-pyridin-3-yl)-1-o-tolyl-propyl]-biphenyl-3-carboxylic acid, 3-{4'-[3-[(E)-hydroxyimino]-3-(1-methyl-6-oxo-1,6-dihydro-pyridin-3-yl)-1-o-tolyl-propyl]-biphenyl-4-yl}-propionic acid, 5-{3-(4-bromo-phenyl)-3-(2-chloro-phenyl)-1-[(E)-hydroxyimino]-propyl}-1-methyl-1H-pyridin-2-one, 4'-[1-(2-chloro-phenyl)-3-[(E)-hydroxyimino]-3-(1-methyl-6-oxo-1,6-dihydro-pyridin-3-yl)-propyl]-biphenyl-4-carboxylic acid, 4'-[1-(2-chloro-phenyl)-3-[(E)-hydroxyimino]-3-(1-methyl-6-oxo-1,6-dihydro-pyridin-3-yl)-propyl]-3-fluoro-biphenyl-4-carboxylic acid methyl ester, 4'-[1-(2-chloro-phenyl)-3-[(E)-hydroxyimino]-3-(1-methyl-6-oxo-1,6-dihydro-pyridin-3-yl)-propyl]-3-fluoro-biphenyl-4-carboxylic acid, 5-{1-[(E)-hydroxyimino]-3-[4-(morpholine-4-carbonyl)-phenyl]-3-o-tolyl-propyl}-1-methyl-1H-pyridin-2-one, N-(2-hydroxy-ethyl)-4-[3-[(E)-hydroxyimino]-3-(1-methyl-6-oxo-1,6-dihydro-pyridin-3-yl)-1-o-tolyl-propyl]-benzamide, N-(2-hydroxy-ethyl)-4-[3-[(E)-hydroxyimino]-3-(1-methyl-6-oxo-1,6-dihydro-pyridin-3-yl)-1-O— tolyl-propyl]-N-methyl-benzamide, (1-{4-[3-[(E)-hydroxyimino]-3-(1-methyl-6-oxo-1,6-dihydro-pyridin-3-yl)-1-o-tolyl-propyl]-benzoyl}-piperidin-4-yl)-acetic acid, ({4-[3-[(E)-hydroxyimino]-3-(1-methyl-6-oxo-1,6-dihydro-pyridin-3-yl)-1-o-tolyl-propyl]-benzoyl}-methyl-amino)-acetic acid, 4-{4-[3-[(E)-hydroxyimino]-3-(1-methyl-6-oxo-1,6-dihydro-pyridin-3-yl)-1-o-tolyl-propyl]-benzoylamino}-butyric acid ethyl ester, 4-{4-[3-[(E)-hydroxyimino]-3-(1-methyl-6-oxo-1,6-dihydro-pyridin-3-yl)-1-o-tolyl-propyl]-benzoylamino}-butyric acid, 3-{4-[3-[(E)-hydroxyimino]-3-(1-methyl-6-oxo-1,6-dihydro-pyridin-3-yl)-1-o-tolyl-propyl]-benzoylamino}-propionic acid, {4-[3-[(E)-hydroxyimino]-3-(1-methyl-6-oxo-1,6-dihydro-pyridin-3-yl)-1-o-tolyl-propyl]-benzoylamino}-acetic acid, (E/Z)-4-(1-(2-chlorophenyl)-3-(hydroxyimino)-3-(1-methyl-6-oxo-1,6-dihydropyridin-3-yl)propyl)-2-fluoro-N-(2-hydroxyethyl)benzamide, trans-4-[1-(2-chloro-phenyl)-3-[(E)-hydroxyimino]-3-(1-methyl-6-oxo-1,6-dihydro-pyridin-3-yl)-propyl]-2-fluoro-N-(4-hydroxy-cyclohexyl)-benzamide, (E)-4-(1-(2-chlorophenyl)-3-(hydroxyimino)-3-(1-methyl-6-oxo-1,6-dihydropyridin-3-yl)propyl)-2-fluoro-N-methyl-N-(1-methylpiperidin-4-yl)benzamide, (E)-4-(1-(2-chlorophenyl)-3-(hydroxyimino)-3-(1-methyl-6-oxo-1,6-dihydropyridin-3-yl)propyl)-2-fluoro-N-(tetrahydro-2H-pyran-4-yl)benzamide, (E)-4-(1-(2-chlorophenyl)-3-(hydroxyimino)-3-(1-methyl-6-oxo-1,6-dihydropyridin-3-yl)propyl)-2-fluoro-N-(oxetan-3-yl)benzamide, {3-fluoro-4-[3-[(E)-hydroxyimino]-3-(1-methyl-6-oxo-1,6-dihydro-pyridin-3-yl)-1-o-tolyl-propyl]-phenoxy}-acetic acid, 2-fluoro-4-{3-fluoro-4-[3-[(E)-hydroxyimino]-3-(1-methyl-6-oxo-1,6-dihydro-pyridin-3-yl)-1-o-tolyl-propyl]-phenoxy}-benzoic acid, 5-{(R)-3-(4-bromo-phenyl)-1-[(E)-hydroxyimino]-3-o-tolyl-propyl}-1-methyl-1H-pyridin-2-one, (E)-5-(3-(4-bromophenyl)-3-(4-fluoro-2-methylphenyl)-1-(hydroxyimino)propyl)-1-methylpyridin-2(1H)-one, (E)-4'-(1-(4-fluoro-2-methylphenyl)-3-(hydroxyimino)-3-(1-methyl-6-oxo-1,6-dihydropyridin-3-yl)propyl)biphenyl-4-carboxylic acid, 5-{3-(4-bromo-phenyl)-3-(4-chloro-2-methyl-phenyl)-1-[(E)-hydroxyimino]-propyl}-1-methyl-1H-pyridin-2-one, (E)-4'-(1-(4-chloro-2-methylphenyl)-3-(hydroxyimino)-3-(1-methyl-6-oxo-1,6-dihydropyridin-3-yl)propyl)biphenyl-4-carboxylic acid, (E)-methyl 2-(4'-(1-(4-chloro-2-methylphenyl)-3-(hydroxyimino)-3-(1-methyl-6-oxo-1,6-dihydropyridin-3-yl)propyl)biphenyl-4-ylcarboxamido)acetate, (E)-2-(4'-(1-(4-chloro-2-methylphenyl)-3-(hydroxyimino)-3-(1-methyl-6-oxo-1,6-dihydropyridin-3-yl)propyl)biphenyl-4-ylcarboxamido)acetic acid, (E)-N-((1H-tetrazol-5-yl)methyl)-4'-(1-(4-chloro-2-methylphenyl)-3-(hydroxyimino)-3-(1-methyl-6-oxo-1,6-dihydropyridin-3-yl)propyl)biphenyl-4-carboxamide, trans-4-{4-[1-(2-chloro-phenyl)-3-[(E)-hydroxyimino]-3-(1-methyl-6-oxo-1,6-dihydro-pyridin-3-yl)-propyl]-2-fluoro-benzoylamino}-cyclohexanecarboxylic acid, (E)-4-(1-(2-chlorophenyl)-3-(hydroxyimino)-3-(1-methyl-6-oxo-1,6-dihydropyridin-3-yl)propyl)-2-fluoro-N-(2-methoxyethyl)benzamide, (E)-4-(1-(2-chlorophenyl)-3-(hydroxyimino)-3-(1-methyl-6-oxo-1,6-dihydropyridin-3-yl)propyl)-N-cyclopropyl-2-fluorobenzamide, (E)-4-(1-(2-chlorophenyl)-3-(hydroxyimino)-3-(1-methyl-6-oxo-1,6-dihydropyridin-3-yl)propyl)-2-fluoro-N-(2,2,2-trifluoroethyl)benzamide, 3-{3-fluoro-4-[3-[(E)-hydroxyimino]-3-(1-methyl-6-oxo-1,6-dihydro-pyridin-3-yl)-1-o-tolyl-propyl]-phenoxy}-benzoic acid, 3'-fluoro-4'-[3-[(E)-hydroxyimino]-3-(1-methyl-6-oxo-1,6-dihydro-pyridin-3-yl)-1-o-tolyl-propyl]-biphenyl-2-carboxylic acid, 5-{3-(4-bromo-phenyl)-3-(4-chloro-2-fluoro-phenyl)-1-[(E)-hydroxyimino]-propyl}-1-methyl-1H-pyridin-2-one, 4'-[1-(4-chloro-2-fluoro-phenyl)-3-[(E)-hydroxyimino]-3-(1-methyl-6-oxo-1,6-dihydro-pyridin-3-yl)-propyl]-biphenyl-4-carboxylic acid, (+)-5-{3-(4-bromo-phenyl)-3-(4-chloro-2-fluoro-phenyl)-1-[(E)-hydroxyimino]-propyl}-1-methyl-1H-pyridin-2-one, (−)-5-{3-(4-bromo-phenyl)-3-(4-chloro-2-fluoro-phenyl)-1-[(E)-hydroxyimino]-propyl}-1-methyl-1H-pyridin-2-one, (+)-4'-[1-(4-chloro-2-fluoro-phenyl)-3-[(E)-hydroxyimino]-3-(1-methyl-6-oxo-1,6-dihydro-pyridin-3-yl)-propyl]-biphenyl-4-carboxylic acid, (−)-4'-[1-(4-chloro-2-fluoro-phenyl)-3-[(E)-hydroxyimino]-3-(1-methyl-6-oxo-1,6-dihydro-pyridin-3-yl)-propyl]-biphenyl-4-carboxylic acid, (E)-5-(3-(4-bromophenyl)-3-(2-fluorophenyl)-1-(hydroxyimino)propyl)-1-methylpyridin-2(1H)-one, (E)-4'-(1-(2-fluorophenyl)-3-(hydroxyimino)-3-(1-methyl-6-oxo-1,6-dihydropyridin-3-yl)propyl)biphenyl-4-carboxylic acid, (E)-4-(1-(2-chlorophenyl)-3-(hydroxyimino)-3-(1-methyl-6-oxo-1,6-dihydropyridin-3-yl)propyl)-N-ethyl-2-fluorobenzamide, (E)-N-(2-acetamidoethyl)-4-(3-(hydroxyimino)-3-(1-methyl-6-oxo-1,6-dihydropyridin-3-yl)-1-o-tolylpropyl)benzamide, 4-((E)-3-(hydroxyimino)-3-(1-methyl-6-oxo-1,6-dihydropyridin-3-yl)-1-o-tolylpropyl)-N—((S)-2-hydroxypropyl)benzamide, 4-((E)-3-(hydroxyimino)-3-(1-methyl-6-oxo-1,6-dihydropyridin-3-yl)-1-o-tolylpropyl)-N—((R)-2-hydroxypropyl)benzamide, (E)-5-(3-(2-chlorophenyl)-1-(hydroxyimino)-3-(4-(methylsulfonyl)phenyl)propyl)-1-methylpyridin-2(1H)-one, (E)-5,5'-(1-(2-chlorophenyl)-3-(hydroxyimino)propane-1,3-diyl)bis(1-methylpyridin-2(1H)-one), (E)-4'-(1-(4-chloro-2-methylphenyl)-3-(hydroxyimino)-3-(1-methyl-6-oxo-1,6-dihydropyridin-3-yl)propyl)biphenyl-4-carbonitrile, 3-bromo-5-{(R)-3-(4-bromo-phenyl)-1-[(E)-hydroxyimino]-3-o-tolyl-propyl}-1-methyl-1H-pyridin-2-one, (−)-({4'-[1-(4-chloro-2-methyl-phenyl)-3-[(E)-hydroxy-imino]-3-(1-methyl-6-oxo-1,6-dihydro-pyridin-3-yl)-propyl]-biphenyl-4-carbonyl}-amino)-acetic acid methyl ester,
(+)-({4'-[1-(4-chloro-2-methyl-phenyl)-3-[(E)-hydroxy-imino]-3-(1-methyl-6-oxo-1,6-dihydro-pyridin-3-yl)-propyl]-biphenyl-4-carbonyl}-amino)-acetic acid methyl ester,
(−)-({4'-[1-(4-chloro-2-methyl-phenyl)-3-[(E)-hydroxy-imino]-3-(1-methyl-6-oxo-1,6-dihydro-pyridin-3-yl)-propyl]-biphenyl-4-carbonyl}-amino)-acetic acid,
(+)-({4'-[1-(4-chloro-2-methyl-phenyl)-3-[(E)-hydroxy-imino]-3-(1-methyl-6-oxo-1,6-dihydro-pyridin-3-yl)-propyl]-biphenyl-4-carbonyl}-amino)-acetic acid,
({4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester,
({4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid,
5-{3-(4'-amino-biphenyl-4-yl)-3-(4-fluoro-2-methyl-phenyl)-1-[(E)-hydroxyimino]-propyl}-1-methyl-1H-pyridin-2-one,
5-{3-(4-fluoro-2-methyl-phenyl)-1-[(E)-hydroxyimino]-3-[4'-(1H-tetrazol-5-yl)-biphenyl-4-yl]-propyl}-1-methyl-1H-pyridin-2-one,
(E,R)-4-(4-bromophenyl)-1-(pyridin-4-yl)-4-o-tolylbutan-2-one oxime,
(Z,R)-4-(4-bromophenyl)-1-(pyridin-4-yl)-4-o-tolylbutan-2-one oxime,
(E,R)-4-(4-bromophenyl)-1-(pyridin-2-yl)-4-o-tolylbutan-2-one oxime,
(E,R)-1-(2-methyl-pyridin-4-yl)-3-(4-morpholin-4-yl-phenyl)-3-o-tolyl-propan-1-one oxime,
1-{4-[(R)-3-[(E)-hydroxyimino]-3-(2-methyl-pyridin-4-yl)-1-o-tolyl-propyl]-phenyl}-piperidine-4-carboxylic acid ethyl ester,
1-{4-[(R)-3-[(E)-hydroxyimino]-3-(2-methyl-pyridin-4-yl)-1-o-tolyl-propyl]-phenyl}-piperidine-4-carboxylic acid,
(E,R)-3-{4-[(2-methoxy-ethyl)-methyl-amino]-phenyl}-1-(2-methyl-pyridin-4-yl)-3-o-tolyl-propan-1-one oxime,
(E,R)-3-{4-[(2-hydroxy-ethyl)-methyl-amino]-phenyl}-1-(2-methyl-pyridin-4-yl)-3-o-tolyl-propan-1-one oxime,
(E,R)-3-[4-(4-hydroxymethyl-piperidin-1-yl)-phenyl]-1-(2-methyl-pyridin-4-yl)-3-o-tolyl-propan-1-one oxime,
(E,R)-3-[4-(3-methoxy-azetidin-1-yl)-phenyl]-1-(2-methyl-pyridin-4-yl)-3-o-tolyl-propan-1-one oxime,
(E,R)-3-[4-(1,1-dioxo-1×6-thiomorpholin-4-yl)-phenyl]-1-(2-methyl-pyridin-4-yl)-3-o-tolyl-propan-1-one oxime,
or pharmaceutically acceptable salts thereof.
Further particular compounds of formula I are the following:
(R,E)-4-(3-(hydroxyimino)-3-(2-methylpyridin-4-yl)-1-o-tolylpropyl)benzoic acid,
(R,E)-N-(2-hydroxyethyl)-4-(3-(hydroxyimino)-3-(2-methylpyridin-4-yl)-1-O— tolylpropyl)benzamide,
(R,E)-N-(2-hydroxyethyl)-4-(3-(hydroxyimino)-3-(2-methylpyridin-4-yl)-1-o-tolylpropyl)-N-methylbenzamide,
4-((R,E)-3-(hydroxyimino)-3-(2-methylpyridin-4-yl)-1-o-tolylpropyl)-N—((S)-2-hydroxypropyl)benzamide,
trans-4-(4-((R,E)-3-(hydroxyimino)-3-(2-methylpyridin-4-yl)-1-o-tolylpropyl)benzamido)-cyclohexanecarboxylic acid,
(R,E)-4-(3-(hydroxyimino)-3-(2-methylpyridin-4-yl)-1-o-tolylpropyl)-N,N-dimethylbenzamide,
(R,E)-4-(3-(hydroxyimino)-3-(2-methylpyridin-4-yl)-1-o-tolylpropyl)-N-methylbenzamide,
(R,E)-1-(4-(3-(hydroxyimino)-3-(2-methylpyridin-4-yl)-1-o-tolylpropyl)phenyl)azetidine-3-carboxylic acid,
3-chloro-2-((4-((R,E)-3-(hydroxyimino)-3-(2-methylpyridin-4-yl)-1-o-tolylpropyl)phenyl-amino)methyl)propanoic acid,
(S,E)-1-(4-(3-(hydroxyimino)-3-(2-methylpyridin-4-yl)-1-o-tolylpropyl)phenyl)piperidine-4-carboxylic acid,
4-[(S)-1-(4-chloro-2-methyl-phenyl)-3-[(E)-hydroxy-imino]-3-(2-methyl-pyridin-4-yl)-propyl]-benzoic acid,
4-[(S)-1-(4-chloro-2-methyl-phenyl)-3-[(E)-hydroxy-imino]-3-(2-methyl-pyridin-4-yl)-propyl]-N,N-dimethyl-benzamide,
1-{4-[(R)-1-(4-chloro-2-methyl-phenyl)-3-[(E)-hydroxy-imino]-3-(2-methyl-pyridin-4-yl)-propyl]-phenyl}-piperidine-4-carboxylic acid,
1-{4-[(S)-1-(4-chloro-2-methyl-phenyl)-3-[(E)-hydroxy-imino]-3-(2-methyl-pyridin-4-yl)-propyl]-phenyl}-piperidine-4-carboxylic acid,
(S,E)-diethyl 2-(4-(3-(hydroxyimino)-3-(2-methylpyridin-4-yl)-1-o-tolylpropyl)phenyl)malonate,
(R,E)-3-(4-ethynylphenyl)-1-(2-methylpyridin-4-yl)-3-o-tolylpropan-1-one oxime,
(R,E)-2-(4-(3-(hydroxyimino)-3-(2-methylpyridin-4-yl)-1-o-tolylpropyl)phenyl)acetic acid,
(R,E)-N-(2-hydroxyethyl)-2-(4-(3-(hydroxyimino)-3-(2-methylpyridin-4-yl)-1-o-tolylpropyl)phenyl)acetamide,
(R,E)-4'-(3-(2-chloropyridin-4-yl)-3-(hydroxyimino)-1-o-tolylpropyl)biphenyl-4-carboxylic acid,
(R,E)-4'-(3-(hydroxyimino)-1-o-tolyl-3-(2-(trifluoromethyl)pyridin-4-yl)propyl)biphenyl-4-carboxylic acid,
(R)-4'-(3-(2-chloro-5-fluoropyridin-4-yl)-3-(hydroxy-imino)-1-o-tolylpropyl)biphenyl-4-carboxylic acid,
(R)-4'-(3-(5-chloro-2-fluoropyridin-4-yl)-3-(hydroxy-imino)-1-o-tolylpropyl)biphenyl-4-carboxylic acid,
(R,E)-4'-(3-(2,6-dimethylpyridin-4-yl)-3-(hydroxyimino)-1-o-tolylpropyl)biphenyl-4-carboxylic acid,
3-(4-bromo-phenyl)-1-pyridin-4-yl-3-o-tolyl-propan-1-one oxime,
(+)4'-[(S)-1-(4-chloro-2-methyl-phenyl)-3-[(E)-hydroxy-imino]-3-(2-methyl-pyridin-4-yl)-propyl]-biphenyl-4-carboxylic acid,
(−)-4'-[(R)-1-(4-chloro-2-methyl-phenyl)-3-[(E)-hydroxy-imino]-3-(2-methyl-pyridin-4-yl)-propyl]-biphenyl-4-carboxylic acid,
(R,E)-4'-(3-(hydroxyimino)-4-(pyridin-4-yl)-1-o-tolylbutyl)biphenyl-4-carboxylic acid,
(R,E)-1-(4-(3-(hydroxyimino)-3-(2-methylpyridin-4-yl)-1-o-tolylpropyl)phenyl)pyrrolidin-2-one
(1S,3s)-3-(4-((R,E)-3-(hydroxyimino)-3-(2-methylpyridin-4-yl)-1-o-tolylpropyl)phenyl-amino)cyclobutanecarboxylic acid,
4-((E)-3-(hydroxyimino)-3-(1-methyl-6-oxo-1,6-dihydropyridin-3-yl)-1-o-tolylpropyl)-N—((R)-1-hydroxypropan-2-yl)benzamide,
4-((E)-3-(hydroxyimino)-3-(1-methyl-6-oxo-1,6-dihydropyridin-3-yl)-1-o-tolylpropyl)-N—((S)-1-hydroxypropan-2-yl)benzamide,
(E)-N-(1-hydroxy-2-methylpropan-2-yl)-4-(3-(hydroxy-imino)-3-(1-methyl-6-oxo-1,6-dihydropyridin-3-yl)-1-o-tolylpropyl)benzamide,
(E)-N-(1,3-dihydroxypropan-2-yl)-4-(3-(hydroxyimino)-3-(1-methyl-6-oxo-1,6-dihydropyridin-3-yl)-1-o-tolylpropyl)benzamide,
N—((R)-1-hydroxy-3-methylbutan-2-yl)-4-((E)-3-(hydroxyimino)-3-(1-methyl-6-oxo-1,6-dihydropyridin-3-yl)-1-o-tolylpropyl)benzamide, N—((S)-1-hydroxy-3-methylbutan-2-yl)-4-((E)-3-(hydroxyimino)-3-(1-methyl-6-oxo-1,6-dihydropyridin-3-yl)-1-o-tolylpropyl)benzamide, N—((R)-2,3-dihydroxypropyl)-4-((E)-3-(hydroxyimino)-3-(1-methyl-6-oxo-1,6-dihydropyridin-3-yl)-1-o-tolylpropyl)benzamide, (E)-4-(3-(hydroxyimino)-3-(1-methyl-6-oxo-1,6-dihydropyridin-3-yl)-1-o-tolylpropyl)-N-(1-(hydroxymethyl)cyclopropyl)benzamide, (E)-4-(3-(hydroxyimino)-3-(1-methyl-6-oxo-1,6-dihydropyridin-3-yl)-1-o-tolylpropyl)-N-(3,3,3-trifluoro-2-hydroxypropyl)benzamide, (E)-4-(3-(hydroxyimino)-3-(1-methyl-6-oxo-1,6-dihydropyridin-3-yl)-1-o-tolylpropyl)-N-(2-(methylsulfonyl)ethyl)benzamide, (RS)-4-[1-(4-chloro-2-fluoro-phenyl)-3-[(E)-hydroxyimino]-3-(1-methyl-6-oxo-1,6-dihydro-pyridin-3-yl)-propyl]-N-(2-hydroxy-ethyl)-benzamide, 4-((E)-1-(4-chloro-2-fluorophenyl)-3-(hydroxyimino)-3-(1-methyl-6-oxo-1,6-dihydropyridin-3-yl)propyl)-N—((R)-2,3-dihydroxypropyl)benzamide, (RS)-4-[1-(4-chloro-2-fluoro-phenyl)-3-[(E)-hydroxyimino]-3-(1-methyl-6-oxo-1,6-dihydro-pyridin-3-yl)-propyl]-N-(2-methanesulfonyl-ethyl)-benzamide, (E)-5-(3-(4-chloro-2-fluorophenyl)-1-(hydroxyimino)-3-(4-(methylsulfonyl)phenyl)propyl)-1-methylpyridin-2(1H)-one, (E)-5-(3-(4-chloro-2-fluorophenyl)-1-(hydroxyimino)-3-(3-(methylsulfonyl)phenyl)propyl)-1-methylpyridin-2(1H)-one, (E)-5-(3-(4-chloro-2-fluorophenyl)-3-(4-(ethylsulfonyl)phenyl)-1-(hydroxyimino)propyl)-1-methylpyridin-2(1H)-one, (E)-5-(3-(4-chloro-2-fluorophenyl)-1-(hydroxyimino)-3-(4-(hydroxymethyl)phenyl)propyl)-1-methylpyridin-2(1H)-one, (E)-5-(3-(4-chloro-2-fluorophenyl)-1-(hydroxyimino)-3-(4-hydroxyphenyl)propyl)-1-methylpyridin-2(1H)-one, (E)-N-(3-(1-(4-chloro-2-fluorophenyl)-3-(hydroxyimino)-3-(1-methyl-6-oxo-1,6-dihydropyridin-3-yl)propyl)phenyl)acetamide, (E)-3-(1-(4-chloro-2-fluorophenyl)-3-(hydroxyimino)-3-(1-methyl-6-oxo-1,6-dihydropyridin-3-yl)propyl)-N-(2-hydroxyethyl)benzamide, (E)-3-(1-(4-chloro-2-fluorophenyl)-3-(hydroxyimino)-3-(1-methyl-6-oxo-1,6-dihydropyridin-3-yl)propyl)-N-(2-hydroxyethyl)-N-methylbenzamide, (E)-5-(3-(4-chloro-2-fluorophenyl)-1-(hydroxyimino)-3-(3-(morpholine-4-carbonyl)phenyl)propyl)-1-methylpyridin-2(1H)-one, (RS)-5-{3-(4-chloro-2-methyl-phenyl)-3-(3-fluoro-4-isopropoxy-phenyl)-1-[(E)-hydroxyimino]-propyl}-1-methyl-1H-pyridin-2-one, (RS)-5-{3-(4-chloro-2-methyl-phenyl)-3-(3-fluoro-4-hydroxy-phenyl)-1-[(E)-hydroxyimino]-propyl}-1-methyl-1H-pyridin-2-one, (RS)-3-{4-[1-(4-chloro-2-methyl-phenyl)-3-[(E)-hydroxyimino]-3-(1-methyl-6-oxo-1,6-dihydro-pyridin-3-yl)-propyl]-2-fluoro-phenoxy}-benzoic acid, (RS)-2-chloro-5-{4-[1-(4-chloro-2-methyl-phenyl)-3-[(E)-hydroxyimino]-3-(1-methyl-6-oxo-1,6-dihydro-pyridin-3-yl)-propyl]-2-fluoro-phenoxy}-benzoic acid, (RS)-4-{4-[1-(4-chloro-2-methyl-phenyl)-3-[(E)-hydroxyimino]-3-(1-methyl-6-oxo-1,6-dihydro-pyridin-3-yl)-propyl]-2-fluoro-phenoxy}-butyric acid, (RS)-5-{3-(4-chloro-2-methyl-phenyl)-3-[3-fluoro-4-(2-hydroxy-ethoxy)-phenyl]-1-[(E)-hydroxyimino]-propyl}-1-methyl-1H-pyridin-2-one, (RS)-methanesulfonic acid 4-[1-(4-chloro-2-methyl-phenyl)-3-[(E)-hydroxyimino]-3-(1-methyl-6-oxo-1,6-dihydro-pyridin-3-yl)-propyl]-2-fluoro-phenyl ester, (E)-5-(3-(4-bromophenyl)-1-(hydroxyimino)-3-(4-methylthiazol-5-yl)propyl)-1-methylpyridin-2(1H)-one, (E)-5-(3-(4-chloro-2-methylphenyl)-1-(hydroxyimino)-3-(4-(methylsulfonyl)phenyl)propyl)-1-methylpyridin-2(1H)-one, (E)-4-(1-(4-chloro-2-methylphenyl)-3-(hydroxyimino)-3-(1-methyl-6-oxo-1,6-dihydropyridin-3-yl)propyl)-N-(2-hydroxyethyl)benzamide, (R,E)-5-(3-(4-chloro-2-methylphenyl)-1-(hydroxyimino)-3-(4-(methylsulfonyl)phenyl)propyl)-1-methylpyridin-2(1H)-one, (S,E)-5-(3-(4-chloro-2-methylphenyl)-1-(hydroxyimino)-3-(4-(methylsulfonyl)phenyl)propyl)-1-methylpyridin-2(1H)-one, 4-((E)-1-(4-chloro-2-methylphenyl)-3-(hydroxyimino)-3-(1-methyl-6-oxo-1,6-dihydropyridin-3-yl)propyl)-N—((R)-2,3-dihydroxypropyl)benzamide, (E)-4-(1-(4-chloro-2-methylphenyl)-3-(hydroxyimino)-3-(1-methyl-6-oxo-1,6-dihydropyridin-3-yl)propyl)-N-(2-(methylsulfonyl)ethyl)benzamide, (E)-5-(3-(4-chloro-2-methylphenyl)-1-(hydroxyimino)-3-(4-(hydroxymethyl)phenyl)propyl)-1-methylpyridin-2(1H)-one, (E)-4-(1-(4-chloro-2-methylphenyl)-3-(hydroxyimino)-3-(1-methyl-6-oxo-1,6-dihydropyridin-3-yl)propyl)benzenesulfonamide, (E)-5-(3-(4-chloro-2-methylphenyl)-1-(hydroxyimino)-3-(4-(methylsulfonyl)phenyl)propyl)-1-(2-(2-methoxyethoxy)ethyl)pyridin-2(1H)-one, (E)-5-(3-(4-chloro-2-methylphenyl)-1-(hydroxyimino)-3-(4-(methylsulfonyl)phenyl)propyl)-1-(2-ethoxyethyl)pyridin-2(1H)-one, (E)-5-(3-(4-chloro-2-methylphenyl)-1-(hydroxyimino)-3-(4-(methylsulfonyl)phenyl)propyl)-1-(2-methoxyethyl)pyridin-2(1H)-one, (E)-5-(3-(4-chloro-2-methylphenyl)-1-(hydroxyimino)-3-(4-(methylsulfonyl)phenyl)propyl)-1-(2-hydroxyethyl)pyridin-2(1H)-one, (E)-2-(5-(3-(4-chloro-2-methylphenyl)-1-(hydroxyimino)-3-(4-(methylsulfonyl)phenyl)propyl)-2-oxopyridin-1(2H)-yl)acetamide, (E)-3-(5-(3-(4-chloro-2-methylphenyl)-1-(hydroxyimino)-3-(4-(methylsulfonyl)phenyl)propyl)-2-oxopyridin-1(2H)-yl)propanamide, (E)-3-(5-(3-(4-chloro-2-methylphenyl)-1-(hydroxyimino)-3-(4-(methylsulfonyl)phenyl)propyl)-2-oxopyridin-1(2H)-yl)propanoic acid, (RS)-3-{4-[1-(4-chloro-2-methyl-phenyl)-3-[(E)-hydroxyimino]-3-(1-methyl-6-oxo-1,6-dihydro-pyridin-3-yl)-propyl]-phenoxy}-benzoic acid, (RS)-2-chloro-5-{4-[1-(4-chloro-2-methyl-phenyl)-3-[(E)-hydroxyimino]-3-(1-methyl-6-oxo-1,6-dihydro-pyridin-3-yl)-propyl]-phenoxy}-benzoic acid, (RS)-5-{4-[1-(4-chloro-2-methyl-phenyl)-3-[(E)-hydroxyimino]-3-(1-methyl-6-oxo-1,6-dihydro-pyridin-3-yl)-propyl]-phenoxy}-2-fluoro-benzoic acid, (RS)-4-{4-[1-(4-chloro-2-methyl-phenyl)-3-[(E)-hydroxyimino]-3-(1-methyl-6-oxo-1,6-dihydro-pyridin-3-yl)-propyl]-phenoxy}-butyric acid, (E)-5-(3-(2,5-dichlorophenyl)-1-(hydroxyimino)-3-(4-(methylsulfonyl)phenyl)propyl)-1-methylpyridin-2(1H)-one, (E)-5-(3-(3,5-difluorophenyl)-1-(hydroxyimino)-3-(4-(methylsulfonyl)phenyl)propyl)-1-methylpyridin-2(1H)-one,
(E)-5-(3-(3,5-dichlorophenyl)-1-(hydroxyimino)-3-(4-(methylsulfonyl)phenyl)propyl)-1-methylpyridin-2(1H)-one,
(RS)—N-{4-[1-(4-chloro-2-methyl-phenyl)-3-[(E)-hydroxyimino]-3-(1-methyl-6-oxo-1,6-dihydro-pyridin-3-yl)-propyl]-phenyl}-methanesulfonamide,
(RS)-cyclopropanesulfonic acid {4-[1-(4-chloro-2-methyl-phenyl)-3-[(E)-hydroxyimino]-3-(1-methyl-6-oxo-1,6-dihydro-pyridin-3-yl)-propyl]-phenyl}-amide,
(RS)-5-{3-(4-chloro-2-methyl-phenyl)-1-[(E)-hydroxyimino]-3-[4-(2-oxo-pyrrolidin-1-yl)-phenyl]-propyl}-1-methyl-1H-pyridin-2-one,
(1R,3r)-3-(4-((R,E)-3-(hydroxyimino)-3-(2-methylpyridin-4-yl)-1-o-tolylpropyl)phenylamino)cyclobutanecarboxylic acid,
(3R,E)-3-(4-(3-chloro-2-methoxypropylamino)phenyl)-1-(2-methylpyridin-4-yl)-3-o-tolylpropan-1-one oxime,
(R,E)-1-(2-methylpyridin-4-yl)-3-(4-(methylsulfonyl)phenyl)-3-o-tolylpropan-1-one oxime,
(R,E)-3-(4-chloro-2-methylphenyl)-1-(2-methylpyridin-4-yl)-3-(4-(methylsulfonyl)phenyl)-propan-1-one oxime,
(E)-4-(3-(hydroxyimino)-3-(1-methyl-6-oxo-1,6-dihydro-pyridin-3-yl)-1-o-tolylpropyl)benzoic acid,
(E)-4-(1-(4-chloro-2-methylphenyl)-3-(hydroxyimino)-3-(1-methyl-6-oxo-1,6-dihydropyridin-3-yl)propyl)benzoic acid,
(R,E)-4-(4-bromophenyl)-4-(4-chloro-2-methylphenyl)-1-(pyridin-2-yl)butan-2-one oxime,
(R,E)-3-(4-hydroxyphenyl)-1-(2-methylpyridin-4-yl)-3-o-tolylpropan-1-one oxime,
(R,E)-3-(4-ethoxyphenyl)-1-(2-methylpyridin-4-yl)-3-o-tolylpropan-1-one oxime,
(S,E)-3-(4-chloro-2-methylphenyl)-3-(4-hydroxyphenyl)-1-(2-methylpyridin-4-yl)propan-1-one oxime,
(S,E)-3-(4-chloro-2-methylphenyl)-3-(4-ethoxyphenyl)-1-(2-methylpyridin-4-yl)propan-1-one oxime,
(R,E)-1-(4-(3-(hydroxyimino)-3-(2-methylpyridin-4-yl)-1-o-tolylpropyl)phenyl)piperidine-4-carboxamide,
(R,E)-1-(2-methylpyridin-4-yl)-3-phenyl-3-o-tolylpropan-1-one oxime,
(R,E)-2-(1-(4-(3-(hydroxyimino)-3-(2-methylpyridin-4-yl)-1-o-tolylpropyl)phenyl)piperidine-4-carboxamido)acetic acid,
(R,E)-2-(1-(4-(3-(hydroxyimino)-3-(2-methylpyridin-4-yl)-1-o-tolylpropyl)phenyl)piperidine-4-carboxamido)ethanesulfonic acid,
(3R,E)-3-(4-(2-thia-6-azaspiro[3.3]heptan-6-yl)phenyl)-1-(2-methylpyridin-4-yl)-3-o-tolylpropan-1-one oxime,
(R)-tert-butyl 4-(4-(3-(hydroxyimino)-3-(2-methylpyridin-4-yl)-1-o-tolylpropyl)phenyl)-5,6-dihydropyridine-1(2H)-carboxylate,
(R,E)-4-(3-(4-(4-carboxypiperidin-1-yl)phenyl)-1-(hydroxyimino)-3-o-tolylpropyl)-2-methylpyridine 1-oxide,
(R,E)-1-(4-(3-(hydroxyimino)-3-(2-(hydroxymethyl)pyridin-4-yl)-1-o-tolylpropyl)phenyl)piperidine-4-carboxylic acid,
(R,E)-1-(2-methylpyridin-4-yl)-3-(4-(1,2,3,6-tetrahydropyridin-4-yl)phenyl)-3-o-tolylpropan-1-one oxime,
(R,E)-1-(2-methylpyridin-4-yl)-3-(4-(1-(methylsulfonyl)-1,2,3,6-tetrahydropyridin-4-yl)phenyl)-3-o-tolylpropan-1-one oxime,
(R,E)-4-(4-(3-(hydroxyimino)-3-(2-methylpyridin-4-yl)-1-o-tolylpropyl)phenyl)-5,6-dihydropyridin-2(1H)-one,
(R,E)-1-(2-methylpyridin-4-yl)-3-(4-(piperidin-4-yl)phenyl)-3-o-tolylpropan-1-one oxime,
(R,E)-1-(2-methylpyridin-4-yl)-3-(4-(1-(methylsulfonyl)piperidin-4-yl)phenyl)-3-o-tolylpropan-1-one oxime,
(S,E)-2-(4-(3-(hydroxyimino)-3-(2-methylpyridin-4-yl)-1-o-tolylpropyl)phenyl)acetic acid,
(S,E)-1-(2-methylpyridin-4-yl)-3-(4-morpholinophenyl)-3-o-tolylpropan-1-one oxime,
{4-[(R)-1-(4-chloro-2-methyl-phenyl)-3-[(E)-hydroxyimino]-3-(2-methyl-pyridin-4-yl)-propyl]-phenyl}-acetic acid,
(R,E)-3-(4-bromophenyl)-3-(4-chloro-2-methylphenyl)-1-(2-(hydroxymethyl)pyridin-4-yl)propan-1-one oxime,
(R,E)-4-(3-(4-bromophenyl)-3-(4-chloro-2-methylphenyl)-1-(hydroxyimino)propyl)-2-methylpyridine 1-oxide,
(3R,E)-3-(4-bromophenyl)-3-(4-chloro-2-methylphenyl)-2-methyl-1-(2-methylpyridin-4-yl)propan-1-one oxime,
(R,E)-3-(4-bromophenyl)-3-(4-chloro-2-methylphenyl)-1-(2-methylpyridin-4-yl)propan-1-one oxime,
(R,E)-tert-butyl 4-(4-(1-(4-chloro-2-methylphenyl)-3-(hydroxyimino)-3-(2-methylpyridin-4-yl)propyl)phenyl)piperidine-1-carboxylate,
(R,E)-3-(4-chloro-2-methylphenyl)-1-(2-methylpyridin-4-yl)-3-(4-(piperidin-4-yl)phenyl)-propan-1-one oxime,
(R,E)-3-(4-chloro-2-methylphenyl)-1-(2-methylpyridin-4-yl)-3-(4-(1-(methylsulfonyl)piperidin-4-yl)phenyl)propan-1-one oxime,
(S)-3-(4-chloro-2-methyl-phenyl)-1-(2-methyl-pyridin-4-yl)-3-phenyl-propan-1-one oxime,
(E)-1-(2-methylpyridin-4-yl)-3-(3-(methylsulfonyl)phenyl)-3-o-tolylpropan-1-one oxime,
N-{4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-yl}-succinamic acid,
(+)-4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carboxylic acid,
(−)-4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carboxylic acid,
(+)-4'-[1-(4-chloro-2-methyl-phenyl)-3-[(E)-hydroxyimino]-3-(2-methyl-pyridin-4-yl)-propyl]-biphenyl-4-carboxylic acid,
(−)4'-[1-(4-chloro-2-methyl-phenyl)-3-[(E)-hydroxyimino]-3-(2-methyl-pyridin-4-yl)-propyl]-biphenyl-4-carboxylic acid,
(+)-4'-[1-(4-fluoro-2-methyl-phenyl)-3-[(E)-hydroxyimino]-3-(2-methyl-pyridin-4-yl)-propyl]-biphenyl-4-carboxylic acid,
(−)-4'-[1-(4-fluoro-2-methyl-phenyl)-3-[(E)-hydroxyimino]-3-(2-methyl-pyridin-4-yl)-propyl]-biphenyl-4-carboxylic acid,
N-{4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-yl}-malonamic acid methyl ester,
N-{4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-yl}-malonamic acid,
4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-sulfonic acid amide,
5-{3-(4-bromo-phenyl)-3-(2,4-difluoro-phenyl)-1-[(E)-hydroxyimino]-propyl}-1-methyl-1H-pyridin-2-one,
4'-[1-(2,4-difluoro-phenyl)-3-[(E)-hydroxyimino]-3-(1-methyl-6-oxo-1,6-dihydro-pyridin-3-yl)-propyl]-biphenyl-4-carboxylic acid,
5-{(R)-3-(4-bromo-phenyl)-3-(4-fluoro-2-methyl-phenyl)-1-[(E)-hydroxyimino]-propyl}-1-methyl-1H-pyridin-2-one, 5-{(S)-3-(4-bromo-phenyl)-3-(4-fluoro-2-methyl-phenyl)-1-[(E)-hydroxyimino]-propyl}-1-methyl-1H-pyridin-2-one, 4'-[(R)-1-(4-fluoro-2-methyl-phenyl)-3-[(E)-hydroxyimino]-3-(1-methyl-6-oxo-1,6-dihydro-pyridin-3-yl)-propyl]-biphenyl-4-sulfonic acid amide, 4'-[(S)-1-(4-fluoro-2-methyl-phenyl)-3-[(E)-hydroxyimino]-3-(1-methyl-6-oxo-1,6-dihydro-pyridin-3-yl)-propyl]-biphenyl-4-sulfonic acid amide, (E)-5-(3-(4-bromophenyl)-3-(2-fluoro-4-methylphenyl)-1-(hydroxyimino)propyl)-1-methylpyridin-2(1H)-one, 5-{3-(4-bromo-phenyl)-3-(4-fluoro-2-methanesulfonyl-phenyl)-1-[(E)-hydroxyimino]-propyl}-1-methyl-1H-pyridin-2-one, (E)-5-(3-(4-bromophenyl)-3-(2-chloro-4-fluorophenyl)-1-(hydroxyimino)propyl)-1-methylpyridin-2(1H)-one, (E)-4'-(1-(2-fluoro-4-methylphenyl)-3-(hydroxyimino)-3-(1-methyl-6-oxo-1,6-dihydropyridin-3-yl)propyl)biphenyl-4-carboxylic acid (E)-4'-(1-(2-chloro-4-fluorophenyl)-3-(hydroxyimino)-3-(1-methyl-6-oxo-1,6-dihydropyridin-3-yl)propyl)biphenyl-4-carboxylic acid 4'-[(R or S)-1-(4-chloro-2-methyl-phenyl)-3-[(E)-hydroxyimino]-3-(1-methyl-6-oxo-1,6-dihydro-pyridin-3-yl)-propyl]-biphenyl-4-sulfonic acid amide, 4'-[(R or S)-1-(4-chloro-2-methyl-phenyl)-3-[(E)-hydroxyimino]-3-(1-methyl-6-oxo-1,6-dihydro-pyridin-3-yl)-propyl]-biphenyl-4-sulfonic acid amide, 5-{(R or S)-3-(4-bromo-phenyl)-3-(4-chloro-2-methyl-phenyl)-1-[(E)-hydroxyimino]-propyl}-1-methyl-1H-pyridin-2-one, N-{4'-[(R or S)-1-(4-chloro-2-methyl-phenyl)-3-[(E)-hydroxyimino]-3-(1-methyl-6-oxo-1,6-dihydro-pyridin-3-yl)-propyl]-biphenyl-4-yl}-methanesulfonamide, (R,E)-3-(4-(5-methyl-1,3,4-oxadiazol-2-yl)phenyl)-1-(2-methylpyridin-4-yl)-3-o-tolylpropan-1-one oxime, (R,E)-3-(4-(5-cyclopropyl-1,3,4-oxadiazol-2-yl)phenyl)-1-(2-methylpyridin-4-yl)-3-o-tolylpropan-1-one oxime, (R,E)-3-(4-(5-(methoxymethyl)-1,3,4-oxadiazol-2-yl)phenyl)-1-(2-methylpyridin-4-yl)-3-o-tolylpropan-1-one oxime, (R,E)-3-(4-(5-(2-methoxyethyl)-1,3,4-oxadiazol-2-yl)phenyl)-1-(2-methylpyridin-4-yl)-3-o-tolylpropan-1-one oxime, (R,E)-1-(2-methylpyridin-4-yl)-3-(4-(5-(tetrahydro-2H-pyran-4-yl)-1,3,4-oxadiazol-2-yl)phenyl)-3-o-tolylpropan-1-one oxime, (R,E)-2-(5-(4-(3-(hydroxyimino)-3-(2-methylpyridin-4-yl)-1-o-tolylpropyl)phenyl)-1,3,4-oxadiazol-2-yl)acetic acid, (R,E)-1-(2-methylpyridin-4-yl)-3-(4-(oxazol-2-yl)phenyl)-3-o-tolylpropan-1-one oxime, (R,E)-3-(4-(1-methyl-1H-1,2,3-triazol-4-yl)phenyl)-1-(2-methylpyridin-4-yl)-3-o-tolylpropan-1-one oxime, (R,E)-2-(4-(4-(3-(hydroxyimino)-3-(2-methylpyridin-4-yl)-1-o-tolylpropyl)phenyl)-1H-1,2,3-triazol-1-yl)acetic acid, (+)-(R,E)-3-(4-bromophenyl)-3-(2,4-difluorophenyl)-1-(2-methylpyridin-4-yl)propan-1-one oxime, (−)-(R,E)-1-(4-(1-(2,4-difluorophenyl)-3-(hydroxyimino)-3-(2-methylpyridin-4-yl)propyl)phenyl)piperidine-4-carboxylic acid, (S,E)-1-(4-(1-(2,4-difluorophenyl)-3-(hydroxyimino)-3-(2-methylpyridin-4-yl)propyl)phenyl)piperidine-4-carboxylic acid, (1R,5S)-3-(4-((R,E)-1-(2,4-difluorophenyl)-3-(hydroxyimino)-3-(2-methylpyridin-4-yl)propyl)phenyl)-3-azabicyclo[3.1.0]hexane-6-carboxylic acid, (1-{4-[(S)-1-(2,4-difluoro-phenyl)-3-[(E)-hydroxyimino]-3-(2-methyl-pyridin-4-yl)-propyl]-phenyl}-piperidin-4-yl)-acetic acid, (E)-4-(1-(2,4-difluorophenyl)-3-(hydroxyimino)-3-(2-methylpyridin-4-yl)propyl)benzoic acid, (E)-N-cyclopropyl-4-(1-(2,4-difluorophenyl)-3-(hydroxyimino)-3-(2-methylpyridin-4-yl)propyl)benzamide, (E)-4-(1-(2,4-difluorophenyl)-3-(hydroxyimino)-3-(2-methylpyridin-4-yl)propyl)-N-(2-hydroxyethyl)benzamide, 4-[1-(2,4-difluoro-phenyl)-3-[(E)-hydroxyimino]-3-(2-methyl-pyridin-4-yl)-propyl]-N—((R)-2-hydroxy-propyl)-benzamide, (E)-4-(1-(2,4-difluorophenyl)-3-(hydroxyimino)-3-(2-methylpyridin-4-yl)propyl)-N-(1-hydroxy-2-methylpropan-2-yl)benzamide, (E)-N-cyclohexyl-4-(1-(2,4-difluorophenyl)-3-(hydroxyimino)-3-(2-methylpyridin-4-yl)propyl)benzamide, (E)-(4-(1-(2,4-difluorophenyl)-3-(hydroxyimino)-3-(2-methylpyridin-4-yl)propyl)phenyl)(4,4-difluoropiperidin-1-yl)methanone, (E)-(4-(1-(2,4-difluorophenyl)-3-(hydroxyimino)-3-(2-methylpyridin-4-yl)propyl)phenyl)-(morpholino)methanone, (E)-(4-(1-(2,4-difluorophenyl)-3-(hydroxyimino)-3-(2-methylpyridin-4-yl)propyl)phenyl)(4-(methylsulfonyl)piperazin-1-yl)methanone, 4-[1-(2,4-difluoro-phenyl)-3-[(E)-hydroxyimino]-3-(2-methyl-pyridin-4-yl)-propyl]-N-(1,1-dioxo-hexahydro-1$\lambda^6$-thiopyran-4-yl)-benzamide, 4-[1-(2,4-difluoro-phenyl)-3-[(E)-hydroxyimino]-3-(2-methyl-pyridin-4-yl)-propyl]-N-[2-(1,1-dioxo-1$\lambda^6$-thiomorpholin-4-yl)-ethyl]-benzamide, (E)-3-(2,4-difluorophenyl)-1-(2-methylpyridin-4-yl)-3-(4-(trifluoromethyl)phenyl)propan-1-one oxime, (E)-3-(2,4-difluorophenyl)-1-(2-methylpyridin-4-yl)-3-(6-morpholinopyridin-3-yl)propan-1-one oxime, (E)-1-(4-(5-(1-(2,4-difluorophenyl)-3-(hydroxyimino)-3-(2-methylpyridin-4-yl)propyl)pyridin-2-yl)piperazin-1-yl)ethanone, (E)-3-(4-bromophenyl)-3-(3,5-difluorophenyl)-1-(2-methylpyridin-4-yl)propan-1-one oxime, (E)-methyl 4'-(1-(4-chloro-2-fluorophenyl)-3-(hydroxyimino)-3-(2-methylpyridin-4-yl)propyl)-3-fluorobiphenyl-4-carboxylate, (rac)-(E)-4'-(1-(4-chloro-2-fluorophenyl)-3-(hydroxyimino)-3-(2-methylpyridin-4-yl)propyl)-3-fluorobiphenyl-4-carboxylic acid, (−)-4'-[(R)-1-(4-chloro-2-fluoro-phenyl)-3-[(E)-hydroxyimino]-3-(2-methyl-pyridin-4-yl)-propyl]-3-fluoro-biphenyl-4-carboxylic acid, (+)-4'-[(S)-1-(4-chloro-2-fluoro-phenyl)-3-[(E)-hydroxyimino]-3-(2-methyl-pyridin-4-yl)-propyl]-3-fluoro-biphenyl-4-carboxylic acid, (E)-methyl 3-chloro-4'-(1-(4-chloro-2-fluorophenyl)-3-(hydroxyimino)-3-(2-methylpyridin-4-yl)propyl)biphenyl-4-carboxylate, (rac)-(E)-3-chloro-4'-(1-(4-chloro-2-fluorophenyl)-3-(hydroxyimino)-3-(2-methylpyridin-4-yl)propyl)biphenyl-4-carboxylic acid, (−)-3-chloro-4'-[(R)-1-(4-chloro-2-fluoro-phenyl)-3-[(E)-hydroxyimino]-3-(2-methyl-pyridin-4-yl)-propyl]-biphenyl-4-carboxylic acid, (+)-3-chloro-4'-[(S)-1-(4-chloro-2-fluoro-phenyl)-3-[(E)-hydroxyimino]-3-(2-methyl-pyridin-4-yl)-propyl]-biphenyl-4-carboxylic acid, (E)-methyl 4'-(1-(4-chloro-2-fluorophenyl)-3-(hydroxyimino)-3-(2-methylpyridin-4-yl)propyl)-3-methoxybiphenyl-4-carboxylate, (rac)-(E)-4'-(1-(4-chloro-2-fluorophenyl)-3-(hydroxyimino)-3-(2-methylpyridin-4-yl)propyl)-3-methoxybiphenyl-4-carboxylic acid, (E)-4'-(1-(4-chloro-2-fluorophenyl)-3-(hydroxyimino)-3-(2-methylpyridin-4-yl)propyl)-2-methylbiphenyl-4-carboxylic acid, (E)-5-(4-(1-(4-chloro-2-fluorophenyl)-3-(hydroxyimino)-3-(2-methylpyridin-4-yl)propyl)phenyl)thiophene-2-carboxylic acid, (E)-5-(4-(1-(4-chloro-2-fluorophenyl)-3-(hydroxyimino)-3-(2-methylpyridin-4-yl)propyl)phenyl)pyrimidine-2,4(1H,3H)-dione, (E)-2-(4'-(1-(4-chloro-2-fluorophenyl)-3-(hydroxyimino)-3-(1-methyl-6-oxo-1,6-dihydropyridin-3-yl)propyl)biphenyl-4-yl)acetonitrile, (E)-2-(4'-(1-(4-chloro-2-fluorophenyl)-3-(hydroxyimino)-3-(1-methyl-6-oxo-1,6-dihydropyridin-3-yl)propyl)biphenyl-4-yl)acetic acid, (−)-(R,E)-2-(4'-(1-(4-chloro-2-fluorophenyl)-3-(hydroxyimino)-3-(1-methyl-6-oxo-1,6-dihydropyridin-3-yl)propyl)biphenyl-4-yl)acetic acid, (+)-(S,E)-2-(4'-(1-(4-chloro-2-fluorophenyl)-3-(hydroxyimino)-3-(1-methyl-6-oxo-1,6-dihydropyridin-3-yl)propyl)biphenyl-4-yl)acetic acid, (−)-(R,E)-4'-(1-(4-chloro-2-fluorophenyl)-3-(hydroxyimino)-3-(1-methyl-6-oxo-1,6-dihydropyridin-3-yl)propyl)-3-fluorobiphenyl-4-carboxylic acid, (+)-(S,E)-4'-(1-(4-chloro-2-fluorophenyl)-3-(hydroxyimino)-3-(1-methyl-6-oxo-1,6-dihydropyridin-3-yl)propyl)-3-fluorobiphenyl-4-carboxylic acid, (−)-(R,E)-4'-(1-(4-chloro-2-fluorophenyl)-3-(hydroxyimino)-3-(1-methyl-6-oxo-1,6-dihydropyridin-3-yl)propyl)-2-methylbiphenyl-4-carboxylic acid, (+)-(S,E)-4'-(1-(4-chloro-2-fluorophenyl)-3-(hydroxyimino)-3-(1-methyl-6-oxo-1,6-dihydropyridin-3-yl)propyl)-2-methylbiphenyl-4-carboxylic acid, (−)-(R,E)-ethyl 4-(4-(1-(4-chloro-2-fluorophenyl)-3-(hydroxyimino)-3-(1-methyl-6-oxo-1,6-dihydropyridin-3-yl)propyl)phenyl)thiophene-2-carboxylate, (−)-(R,E)-4-(4-(1-(4-chloro-2-fluorophenyl)-3-(hydroxyimino)-3-(1-methyl-6-oxo-1,6-dihydropyridin-3-yl)propyl)phenyl)thiophene-2-carboxylic acid, (+)-(S,E)-ethyl 4-(4-(1-(4-chloro-2-fluorophenyl)-3-(hydroxyimino)-3-(1-methyl-6-oxo-1,6-dihydropyridin-3-yl)propyl)phenyl)thiophene-2-carboxylate, (+)-(S,E)-4-(4-(1-(4-chloro-2-fluorophenyl)-3-(hydroxyimino)-3-(1-methyl-6-oxo-1,6-dihydropyridin-3-yl)propyl)phenyl)thiophene-2-carboxylic acid, (E)-5-(4-(1-(4-chloro-2-fluorophenyl)-3-(hydroxyimino)-3-(1-methyl-6-oxo-1,6-dihydropyridin-3-yl)propyl)phenyl)pyrimidine-2,4(1H,3H)-dione, (E)-5-(3-(4-bromophenyl)-3-(2,4-dichlorophenyl)-1-(hydroxyimino)propyl)-1-methylpyridin-2(1H)-one, (E)-4'-(1-(2,4-dichlorophenyl)-3-(hydroxyimino)-3-(1-methyl-6-oxo-1,6-dihydropyridin-3-yl)propyl)-3-fluorobiphenyl-4-carboxylic acid, (−)-4'-[(R)-1-(2,4-Dichloro-phenyl)-3-[(E)-hydroxyimino]-3-(1-methyl-6-oxo-1,6-dihydro-pyridin-3-yl)-propyl]-3-fluoro-biphenyl-4-carboxylic acid, (+)-4'-[(S)-1-(2,4-Dichloro-phenyl)-3-[(E)-hydroxyimino]-3-(1-methyl-6-oxo-1,6-dihydro-pyridin-3-yl)-propyl]-3-fluoro-biphenyl-4-carboxylic acid, (E)-4'-(1-(2,4-dichlorophenyl)-3-(hydroxyimino)-3-(1-methyl-6-oxo-1,6-dihydropyridin-3-yl)propyl)-2-methylbiphenyl-4-carboxylic acid, (−)-4'-[(R)-1-(2,4-Dichloro-phenyl)-3-[(E)-hydroxyimino]-3-(1-methyl-6-oxo-1,6-dihydro-pyridin-3-yl)-propyl]-2-methyl-biphenyl-4-carboxylic acid, (+)-4'-[(S)-1-(2,4-Dichloro-phenyl)-3-[(E)-hydroxyimino]-3-(1-methyl-6-oxo-1,6-dihydro-pyridin-3-yl)-propyl]-2-methyl-biphenyl-4-carboxylic acid, (E)-5-(3-(4-bromophenyl)-3-(4-fluorophenyl)-1-(hydroxyimino)propyl)-1-methylpyridin-2(1H)-one, (R,E)-4-(4-(1-(4-chloro-2-methylphenyl)-3-(hydroxyimino)-3-(2-methylpyridin-4-yl)propyl)phenyl)piperidine-1-sulfonamide, (R,E)-tert-butyl 3-(4-(3-(hydroxyimino)-3-(2-methylpyridin-4-yl)-1-o-tolylpropyl)phenyl)azetidine-1-carboxylate, (R,E)-3-(4-(azetidin-3-yl)phenyl)-1-(2-methylpyridin-4-yl)-3-o-tolylpropan-1-one oxime, (R,E)-1-(3-(4-(3-(hydroxyimino)-3-(2-methylpyridin-4-yl)-1-o-tolylpropyl)phenyl)azetidin-1-yl)ethanone, (R,E)-1-(2-methylpyridin-4-yl)-3-(4-(1-(methylsulfonyl)azetidin-3-yl)phenyl)-3-o-tolylpropan-1-one oxime, (R,E)-3-(4-(3-(hydroxyimino)-3-(2-methylpyridin-4-yl)-1-o-tolylpropyl)phenyl)azetidine-1-sulfonamide, (S,E)-5-(3-(4-bromophenyl)-1-(hydroxyimino)-3-o-tolylpropyl)-1-methylpyridin-2(1H)-one, (S,E)-4-(4-(3-(hydroxyimino)-3-(1-methyl-6-oxo-1,6-dihydropyridin-3-yl)-1-o-tolylpropyl)phenyl)cyclohexanecarboxylic acid, (1R,4s)-4-(4-((S,E)-3-(hydroxyimino)-3-(1-methyl-6-oxo-1,6-dihydropyridin-3-yl)-1-O—tolylpropyl)phenyl)cyclohexanecarboxylic acid, (1S,4r)-4-(4-((S,E)-3-(hydroxyimino)-3-(1-methyl-6-oxo-1,6-dihydropyridin-3-yl)-1-o-tolylpropyl)phenyl)cyclohexanecarboxylic acid, (R,E)-4-(4-(3-(hydroxyimino)-3-(2-methylpyridin-4-yl)-1-o-tolylpropyl)phenyl)cyclohexanecarboxylic acid, 4-{4-[(R)-3-[(E)-hydroxyimino]-3-(2-methyl-pyridin-4-yl)-1-o-tolyl-propyl]-phenyl}-cyclohexanecarboxylic acid, 4-{4-[(R)-3-[(E)-hydroxyimino]-3-(2-methyl-pyridin-4-yl)-1-o-tolyl-propyl]-phenyl}-cyclohexanecarboxylic acid, (R,E)-2-(4-(3-(hydroxyimino)-3-(1-methyl-6-oxo-1,6-dihydropyridin-3-yl)-1-o-tolylpropyl)phenyl)acetic acid, (R,E)-5-(1-(hydroxyimino)-3-(4-(methylsulfonyl)phenyl)-3-o-tolylpropyl)-1-methylpyridin-2(1H)-one, (R,Z)-5-(1-(hydroxyimino)-3-(4-(methylsulfonyl)phenyl)-3-o-tolylpropyl)-1-methylpyridin-2(1H)-one, 5-[(S)-1-[(E)-hydroxyimino]-3-(4-methanesulfonyl-phenyl)-3-o-tolyl-propyl]-1-methyl-1H-pyridin-2-one, sodium (R,E)-1-(4-(3-(hydroxyimino)-3-(1-methyl-6-oxo-1,6-dihydropyridin-3-yl)-1-O-tolylpropyl)phenyl)piperidine-4-carboxylate, (R,E)-4-(3-(hydroxyimino)-3-(1-methyl-6-oxo-1,6-dihydropyridin-3-yl)-1-o-tolylpropyl)-benzonitrile, (R,Z)-4-(3-(hydroxyimino)-3-(1-methyl-6-oxo-1,6-dihydropyridin-3-yl)-1-o-tolylpropyl)-benzonitrile (R,E)-5-(3-(4-(1H-tetrazol-5-yl)phenyl)-1-(hydroxyimino)-3-o-tolylpropyl)-1-methylpyridin-2(1H)-one, (S,E)-5-(3-(4-bromophenyl)-1-(hydroxyimino)-3-o-tolylpropyl)-1-methylpyrimidin-2(1H)-one, (S,E)-5-(1-(hydroxyimino)-3-(4-(methylsulfonyl)phenyl)-3-o-tolylpropyl)-1-methylpyrimidin-2(1H)-one, (R,E)-4-(4-(1-(4-chloro-2-methylphenyl)-3-(hydroxyimino)-3-(2-methylpyridin-4-yl)propyl)phenyl)cyclohexanecarboxylic acid, (1R,4r)-4-(4-((R,E)-1-(4-chloro-2-methylphenyl)-3-(hydroxyimino)-3-(2-methylpyridin-4-yl)propyl)phenyl)cyclohexanecarboxylic acid, (1S,4s)-4-(4-((R,E)-1-(4-chloro-2-methylphenyl)-3-(hydroxyimino)-3-(2-methylpyridin-4-yl)propyl)phenyl)cyclohexanecarboxylic acid, (R,E)-tert-butyl 4-(4-(3-(hydroxyimino)-3-(1-methyl-6-oxo-1,6-dihydropyridin-3-yl)-1-o-tolylpropyl)phenyl)piperidine-1-carboxylate, (R,E)-5-(1-(hydroxyimino)-3-(4-(piperidin-4-yl)phenyl)-3-o-tolylpropyl)-1-methylpyridin-2(1H)-one, (R,E)-5-(3-(4-(1-acetylpiperidin-4-yl)phenyl)-1-(hydroxyimino)-3-o-tolylpropyl)-1-methylpyridin-2(1H)-one, (R,E)-5-(1-(hydroxyimino)-3-(4-(1-(methylsulfonyl)piperidin-4-yl)phenyl)-3-o-tolylpropyl)-1-methylpyridin-2(1H)-one, (R,E)-4-(4-(3-(hydroxyimino)-3-(1-methyl-6-oxo-1,6-dihydropyridin-3-yl)-1-o-tolylpropyl)phenyl)piperidine-1-sulfonamide, (R,E)-1-(4-(4-(1-(4-chloro-2-methylphenyl)-3-(hydroxyimino)-3-(2-methylpyridin-4-yl)propyl)phenyl)piperidin-1-yl)ethanone, or pharmaceutically acceptable salts thereof.

More particularly, the invention relates to the following compounds of formula I:

{4-[3-[hydroxyimino]-3-(2-methyl-pyridin-4-yl)-1-o-tolyl-propyl]-phenyl}-acetic acid, 3-[4-(3-hydroxy-propyl)-phenyl]-1-(2-methyl-pyridin-4-yl)-3-o-tolyl-propan-1-one oxime, ({4'-[3-[hydroxyimino]-3-(2-methyl-pyridin-4-yl)-1-o-tolyl-propyl]-biphenyl-4-carbonyl}-amino)-acetic acid, 4'-[(S)-3-[(E)-hydroxyimino]-3-(2-methyl-pyridin-4-yl)-1-o-tolyl-propyl]-biphenyl-4-carboxylic acid, 4'-[(R)-3-[(E)-hydroxyimino]-3-(2-methyl-pyridin-4-yl)-1-o-tolyl-propyl]-biphenyl-4-carboxylic acid, (E)-4'-[3-[hydroxyimino]-3-(2-methyl-pyridin-4-yl)-1-(3-methyl-pyridin-2-yl)-propyl]-biphenyl-4-carboxylic acid, 3-(4-bromo-phenyl)-1-(2-methyl-pyridin-4-yl)-3-o-tolyl-propan-1-one oxime, 3-fluoro-4'-[3-[(E)-hydroxyimino]-3-(2-methyl-pyridin-4-yl)-1-o-tolyl-propyl]-biphenyl-4-carboxylic acid, (E,R)-1-(2-methyl-pyridin-4-yl)-3-(4-pyrimidin-5-yl-phenyl)-3-o-tolyl-propan-1-one oxime (E,R)-1-(2-methylpyridin-4-yl)-3-(4-(4-(methylsulfonyl)piperazin-1-yl)phenyl)-3-o-tolylpropan-1-one oxime, (E,R)-3-(4-(4-hydroxypiperidin-1-yl)phenyl)-1-(2-methylpyridin-4-yl)-3-o-tolylpropan-1-one oxime, 4'-[1-(4-chloro-2-fluoro-phenyl)-3-[(E)-hydroxyimino]-3-(2-methyl-pyridin-4-yl)-propyl]-biphenyl-4-carboxylic acid 4'-[(R)-3-[(E)-hydroxyimino]-3-(1-methyl-6-oxo-1,6-dihydro-pyridin-3-yl)-1-o-tolyl-propyl]-biphenyl-4-carboxylic acid, 3,3'-difluoro-4'-[3-[(E)-hydroxyimino]-3-(1-methyl-6-oxo-1,6-dihydro-pyridin-3-yl)-1-o-tolyl-propyl]-biphenyl-4-carboxylic acid, 4'-[1-(2-chloro-phenyl)-3-[(E)-hydroxyimino]-3-(1-methyl-6-oxo-1,6-dihydro-pyridin-3-yl)-propyl]-biphenyl-4-carboxylic acid, N-(2-hydroxy-ethyl)-4-[3-[(E)-hydroxyimino]-3-(1-methyl-6-oxo-1,6-dihydro-pyridin-3-yl)-1-o-tolyl-propyl]-benzamide, (E)-4'-(1-(4-chloro-2-methylphenyl)-3-(hydroxyimino)-3-(1-methyl-6-oxo-1,6-dihydropyridin-3-yl)propyl)biphenyl-4-carboxylic acid, 3-{3-fluoro-4-[3-[(E)-hydroxyimino]-3-(1-methyl-6-oxo-1,6-dihydro-pyridin-3-yl)-1-o-tolyl-propyl]-phenoxy}-benzoic acid, 4'-[1-(4-chloro-2-fluoro-phenyl)-3-[(E)-hydroxyimino]-3-(1-methyl-6-oxo-1,6-dihydro-pyridin-3-yl)-propyl]-biphenyl-4-carboxylic acid, (E)-5-(3-(2-chlorophenyl)-1-(hydroxyimino)-3-(4-(methylsulfonyl)phenyl)propyl)-1-methylpyridin-2(1H)-one, 1-{4-[(R)-3-[(E)-hydroxyimino]-3-(2-methyl-pyridin-4-yl)-1-o-tolyl-propyl]-phenyl}-piperidine-4-carboxylic acid, or pharmaceutically acceptable salts thereof.

More particularly, the invention also relates to the following compounds of formula I:

1-{4-[(R)-1-(4-chloro-2-methyl-phenyl)-3-[(E)-hydroxyimino]-3-(2-methyl-pyridin-4-yl)-propyl]-phenyl}-piperidine-4-carboxylic acid, (R,E)-2-(4-(3-(hydroxyimino)-3-(2-methylpyridin-4-yl)-1-o-tolylpropyl)phenyl)acetic acid, (R,E)-2-(1-(4-(3-(hydroxyimino)-3-(2-methylpyridin-4-yl)-1-o-tolylpropyl)phenyl)piperidine-4-carboxamido)acetic acid, (R,E)-2-(1-(4-(3-(hydroxyimino)-3-(2-methylpyridin-4-yl)-1-o-tolylpropyl)phenyl)piperidine-4-carboxamido)ethanesulfonic acid, 4-{4-[(R)-3-[(E)-hydroxyimino]-3-(2-methyl-pyridin-4-yl)-1-o-tolyl-propyl]-phenyl}-cyclohexanecarboxylic acid, (R,E)-5-(1-(hydroxyimino)-3-(4-(methylsulfonyl)phenyl)-3-o-tolylpropyl)-1-methylpyridin-2(1H)-one, or pharmaceutically acceptable salts thereof.

The pharmaceutically acceptable salts of the compounds of formula I also individually constitute compounds of the present invention of particular interest.

Examples thereof are the following:

(R,E)-5-(3-(4-(1H-tetrazol-5-yl)phenyl)-1-(hydroxyimino)-3-o-tolylpropyl)-1-methylpyridin-2(1H)-one, sodium salt, (+)-4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carboxylic acid; compound with triethyl-amine 1:0.9, (−)-4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carboxylic acid; compound with triethyl-amine 1:0.85, (+)-4'-[1-(4-chloro-2-methyl-phenyl)-3-[(E)-hydroxyimino]-3-(2-methyl-pyridin-4-yl)-propyl]-biphenyl-4-carboxylic acid; compound with triethyl-amine 1:1, (−)4'-[1-(4-chloro-2-methyl-phenyl)-3-[(E)-hydroxyimino]-3-(2-methyl-pyridin-4-yl)-propyl]-biphenyl-4-carboxylic acid; compound with triethyl-amine 1:0.7, (+)-4'-[1-(4-fluoro-2-methyl-phenyl)-3-[(E)-hydroxyimino]-3-(2-methyl-pyridin-4-yl)-propyl]-biphenyl-4-carboxylic acid; compound with triethyl-amine 1:0.75, and (−)-4'-[1-(4-fluoro-2-methyl-phenyl)-3-[(E)-hydroxyimino]-3-(2-methyl-pyridin-4-yl)-propyl]-biphenyl-4-carboxylic acid; compound with triethyl-amine 1:0.75.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

In particular, the compounds of formula I of the present invention are oximes and thus can exist in two isomeric forms at the C=N—OH double bond, i.e the E- (or anti) and the Z- (or syn) isomer.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a ketone of the formula II

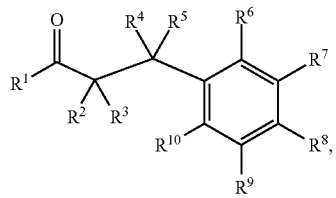

wherein $R^1$ to $R^{12}$ are as defined above, with hydroxylamine hydrochloride in the presence of a base to obtain a compound of the formula I

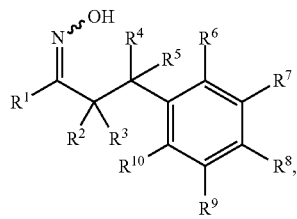

wherein $R^1$ to $R^{12}$ are as defined above, and, if desired, converting the compound obtained into a pharmaceutically acceptable salt.

Appropriate bases are for example are for example sodium hydroxide, sodium hydrogen carbonate or sodium acetate. The reaction is carried out in a suitable solvent such as for example ethanol or methanol, at temperatures between room temperature and reflux of the solvent.

Optionally, the ratio of E and Z isomers of the compound of formula I can be modified by treating the obtained oxime of formula I with acids such as hydrochloric acid in solvents such as ethanol, DME and dioxane or in mixtures thereof at temperatures between room temperature and reflux of the solvent. The E and Z isomers can separated by column chromatography or by HPLC.

The invention further relates to compounds of formula I as defined above obtainable according to a process as defined above.

In more detail, the compounds of formula I can be prepared as described below in schemes 1 to 12, or in analogy to the methods described below with methods known in the art. All starting materials are either commercially available, described in the literature or can be prepared by methods well known in the art or by methods in analogy to those described below. Unless otherwise indicated, $R^1$, $R^2$, $R^3$, $R^4$, $R^5$, $R^6$, $R^7$, $R^8$, $R^9$, $R^{10}$ are as defined above.

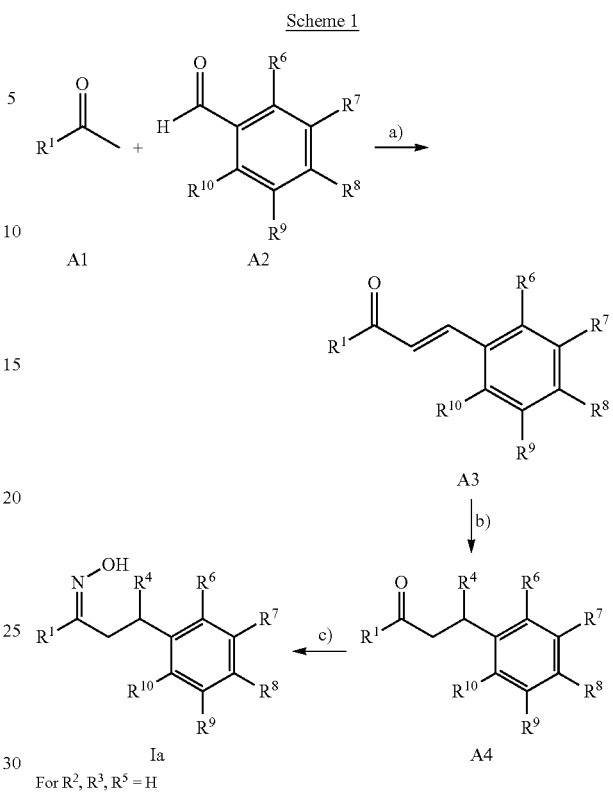

In Scheme 1 the synthesis of compounds of the general formula Ia, wherein $R^2$, $R^3$ and $R^5$ are hydrogen, is described. The synthesis starts from ketone A1 and aldehyde A2 which are transformed into the corresponding enones (chalcones) A3 by treatment with a base such as sodium or potassium hydroxide or piperidine in a solvent such as methanol or ethanol at room temperature up to reflux (step a). Alternatively, microwave conditions can be employed. In some cases, the conversion of the starting materials under solvent free conditions in the presence of sodium hydroxide can be used (e.g. Cave, G. W. V.; Raston, C. L. *J. Chem. Soc., Perkin Trans.* 1, 2001, 3258-3264). Conjugate addition to the enone A3 can be achieved using zinc organic reagents, which are either commercially available or can be generated in situ from the corresponding aryl boronic acids and diethyl zinc (e.g. Dong, L.; Xu, Y.-J.; Gong, L.-Z.; Mi, A.-Q.; Jiang, Y.-Z. *Synthesis* 2004, 1057-1061), in a solvent such as toluene at elevated temperature to yield ketone A4 (step b). Alternatively, the rhodium catalyzed reaction with an aryl boronic acid in a mixture of dioxane and water at elevated temperature in the presence of a catalyst such as chloro(1,5-cyclooctadiene)rhodium(I) dimer provides ketone A4 (Itooka, R.; Iguchi, Y.; Miyaura, N. *Chemistry Letters,* 2001, 722-723). Yet another method uses Grignard reagents $R^4$MgX (with X=Br, Cl) in the presence of copper iodide in a solvent such as diethyl ether or THF at 0° C. (Skytte, D. M.; Nielsen, S. F.; Chen, M.; Zhai, L.; Olsen, C. E.; Christensen, S. B. *Journal of Medicinal Chemistry,* 2006, 49, 436-440). Furthermore organo cuprates can be used for the conjugate addition to enone A3 which can be prepared for example from CuBr DMS and $R^4$Li in a solvent such as diethyl ether or THF at temperatures between −78° C. and room temperature (e.g. Malmberg, H.; Nilsson, M. *Tetrahedron* 1982, 38, 1509-1510). Another method is the addition of allylsilanes to enone A3 catalyzed by Lewis acids such as TiCl$_4$ in solvents such as dichloromethane (Hosomi, A.; Kobayashi, H.; Sakurai, H.; *Tetrahedron Letters,* 1980, 21, 955-958).

In the case that R$^4$ is a 3-substituted indole residue, the conjugate addition can be achieved using indoles in the presence of a catalytic amount of antimony trichloride in a solvent such as acetonitrile under refluxing conditions to give compounds A4 (e.g. Maiti, G.; Kundu, P. *Synthetic Communications* 2007, 37, 2309-2316). The conversion of the ketone A4 to the compounds of formula Ia is achieved using hydroxylamine hydrochloride in the presence of a base such as sodium hydroxide, sodium hydrogen carbonate or sodium acetate in a solvent such as ethanol, methanol or water (or mixtures thereof) at room temperature up to 200° C. (step c), optionally under microwave irridation. If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC. Compounds of the general formula Ia in addition can contain one or more stereocenters and can optionally be separated into optically pure enantiomers or diastereomers by methods well known in the art, e.g. by HPLC chromatography, chromatography on a chiral HPLC column or chromatography with a chiral eluant. Racemic compounds carrying a carboxylate or tetrazole group can also be separated into their antipodes for example via diastereomeric salts by crystallization with optically pure amines, those carrying an amine moiety can also be separated into their antipodes for example via diastereomeric salts by crystallization with optically pure chiral acids. This chiral separation can be accomplished either on the final product of formula Ia or on the chiral intermediate A4.

If R$^1$ is a pyridine moiety, this can be further transformed into the corresponding pyridine-N-oxide by oxidation using m-chloroperbenzoic acid in a solvent such as CH$_2$Cl$_2$, MeOH or mixtures thereof at room temperature. For the preparation of compounds in which R$^1$ is a pyridin-4-one, pyridine-3-one or pyrimidin-2-one, these can be prepared from the corresponding 4-methoxy-pyridine, 2-methoxy-pyridine or 2-methoxypyrimidine derivatives, by cleavage of the methoxy moiety by treatment with HCl in dioxane/water at elevated temperature or by treatment with boron tribromide in dichloromethane at −78° C. to 0° C. Further N-alkylation of the pyridin-one can be achieved by treatment with alkyl halides in a solvent such as DMA, acetone or THF in the presence of a base such as potassium carbonate.

If R$^1$ bears a methoxy group, this can be cleaved to the corresponding phenol by treatment with boron tribromide in dichloromethane at −78° C. to 0° C.

Scheme 2

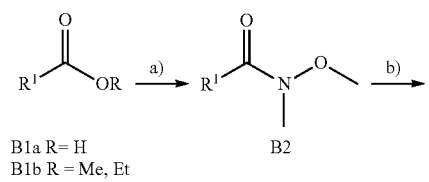

B1a R= H
B1b R = Me, Et

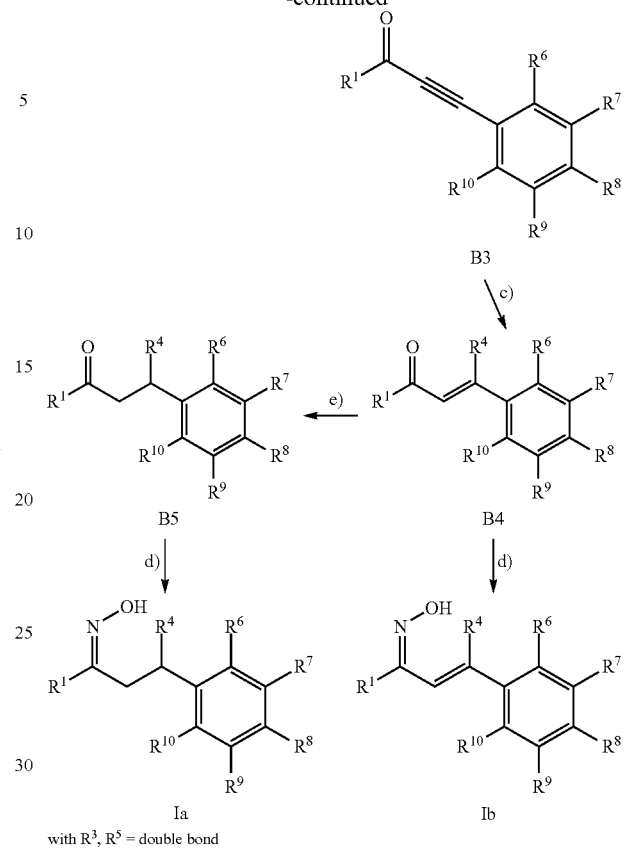

with R$^3$, R$^5$ = double bond

In Scheme 2 an alternative synthesis route to compounds of formula (I) is described starting either from the acid B1a (R=H) or the ester B1b (R=Me, Et). The acid B1a is converted to the corresponding Weinreb amide B2 by treatment with N,O-dimethylhydroxylamine hydrochloride in the presence of a coupling reagent such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetramethyluronium-tetra-fluoroborate (TPTU), O-(7-azabenzotriazol-1-yl)-1,1,3,3-tetramethyl-uronium hexafluoro-phosphate (HATU) or benzotriazol-1-yloxytris (dimethylamino)-phosphonium hexafluoro-phoshate (BOP) and a base such as ethyl-diisopropyl-amine, triethylamine or N-methylmorpholine, optionally in the presence of 4-dimethylamino-pyridine or 1-hydroxybenzo-triazole (HOBt), in a solvent such as dichloromethane, dimethylformamide, dimethylacetamide or dioxane at temperatures between 0° C. and ambient temperature. Alternatively, the Weinreb amide B2 can be prepared from the ester B1b by treatment with N,O-dimethylhydroxylamine hydrochloride in the presence of i-propylmagnesium chloride in a solvent such as diethyl ether or THF at −10° C. to 0° C. (step a). From these Weinreb amides B2 the ketone B3 is prepared by Grignard addition of R'-alkyneMgBr (with R'=R$^{6-10}$ substituted phenyl) in a solvent such as THF or diethyl ether at temperatures of 0° C. to room temperature or by addition of the lithium organic reagents prepared from the R' alkyne-H with n-BuLi in THF at temperatures of −78° C. to room temperature (step b). Copper catalyzed conjugate addition to the alkynones B3 using R$^4$ magnesium halides in the presence of copper iodide in solvents such as THF or diethyl ether provides the alkenones B4. Alternatively, the alkenones B4 can be synthesized by the addition of cuprates R⁴CuLi previously prepared from CuBr DMS, R⁴Li in a solvent such as THF at −78° C. The saturated derivative B5 can be prepared from the enone B4 by 1,4-hydroboration with 9-borabicyclo[3.3.1]nonane (9-BBN) in a solvent such as dichloromethane followed by hydrolysis with methanol (e.g. Matsumoto, Y.; Hayashi, T. *Synlett* 1991, 349-350) (step e).

The conversion of the ketone B4 or B5 to the compounds of formula Ia or Ib is achieved using hydroxylamine hydrochloride in the presence of a base such as sodium hydroxide, sodium hydrogen carbonate or sodium acetate in a solvent such as ethanol or methanol at room temperature up to reflux (step d). If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC. Compounds of the general formula Ia/Ib in addition can contain one or more stereocenters and can optionally be separated into optically pure enantiomers or diastereomers by methods well known in the art, e.g. by HPLC chromatography, chromatography on a chiral HPLC column or chromatography with a chiral eluant. Racemic compounds carrying a carboxylate or tetrazole group can also be separated into their antipodes for example via diastereomeric salts by crystallization with optically pure amines, those carrying an amine moiety can also be separated into their antipodes for example via diastereomeric salts by crystallization with optically pure acids. This chiral separation can be accomplished either on the final product of formula Ia or on the chiral intermediate B5.

If R¹ is a pyridine moiety, this can be further transformed into the corresponding pyridine-N-oxides by oxidation using m-chloroperbenzoic acid in a solvent such as CH₂Cl₂, MeOH or mixtures thereof at room temperature. For the preparation of compounds in which R¹ is a pyridin-4-one or pyridine-3-one, these can be prepared from the corresponding 2-methoxy-pyridine derivatives, by cleavage of the methoxy moiety by treatment with HCl in dioxane at elevated temperature or by treatment with boron tribromide in dichloromethane at −78° C. to 0° C. Further N-alkylation of the pyridin-one can be achieved by treatment with alkyl halides in a solvent such as DMA, acetone or THF in the presence of a base such as potassium carbonate.

If R¹ bears a methoxy group, this can be cleaved to the corresponding phenol by treatment with boron tribromide in dichloromethane at −78° C. to 0° C.

Scheme 3

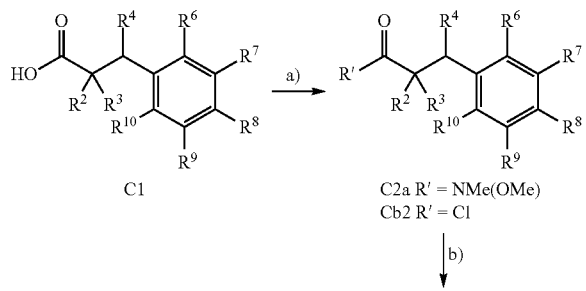

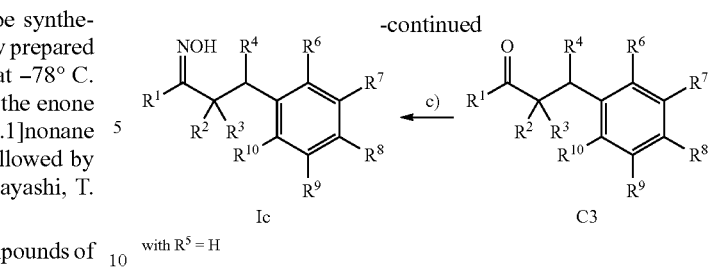

with R⁵ = H

Yet another method for the preparation of compounds of formula (I) is depicted in Scheme 3. The synthesis starts from the acid C1 which can be converted to the Weinreb amide C2a (R'=NMeOMe) or to the acid chloride C2b (R'=Cl). The acid C1 is converted to the corresponding Weinreb amide C2a by treatment with N,O-dimethylhydroxylamine hydrochloride in the presence of a coupling reagent such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetra-methyluronium-tetra-fluoroborate (TPTU), O-(7-azabenzotriazol-1-yl)-1,1,3,3-tetramethyluronium hexafluoro-phosphate (HATU) or benzotriazol-1-yloxytris(dimethylamino)phosphonium hexafluoro-phosphate (BOP) and a base such as ethyl-diisopropyl-amine, triethylamine or N-methyl-morpholine, optionally in the presence of 4-dimethylamino-pyridine or 1-hydroxybenzotriazole (HOBt), in a solvent such as dichloromethane, dimethylformamide, dimethylacetamide or dioxane at temperatures between 0° C. and ambient temperature. Alternatively, the acid C1 can be converted to the acid chloride C2 by treatment with oxalyl chloride in CH₂Cl₂ in the presence of a trace of DMF at room temperature. Treatment of the Weinreb amide C2a or acid chloride C2b with an organolithium R¹Li or organomagnesium compound R¹MgX (X=Cl, Br, I) gives the intermediate ketone C3 (step b).

If the organolithium R¹Li or organomagnesium compounds R¹MgX (with X=Cl, Br, I) are not commercially available, these can be generated in situ from the corresponding R¹—X (with X=Cl, Br, I) by treatment with n-BuLi or i-PrMgCl or i-PrMgCl LiCl at −100° C. to 0° in a solvent such as THF. The conversion of the ketone C3 to the compounds of formula (I) is achieved using hydroxylamine hydrochloride in the presence of a base such as sodium hydroxide, sodium hydrogen carbonate or sodium acetate in a solvent such as ethanol or methanol at room temperature up to reflux (step c). If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC. Compounds of the general formula I in addition can contain one or more stereocenters and can optionally be separated into optically pure enantiomers or diastereomers by methods well known in the art, e.g. by HPLC chromatography, chromatography on a chiral HPLC column or chromatography with a chiral eluant. Racemic compounds carrying a carboxylate or tetrazole group can also be separated into their antipodes for example via diastereomeric salts by crystallization with optically pure amines, those carrying an amine moiety can also be separated into their antipodes for example via diastereomeric salts by crystallization with optically pure acids. This chiral separation can be accomplished either on the final product of formula I or on the chiral intermediates C2 or C3.

If R[1] is a pyridine moiety, this can be further transformed into the corresponding pyridine-N-oxides by oxidation using m-chloroperbenzoic acid in a solvent such as $CH_2Cl_2$, MeOH or mixtures thereof at room temperature. For the preparation of compounds in which R[1] is a pyridin-4-one, pyridine-2-one or pyrimidin-2-one, these can be prepared from the corresponding 2-methoxy-pyridine derivatives, by cleavage of the methoxy moiety by treatment with HCl in dioxane at elevated temperature or by treatment with boron tribromide in dichloromethane at −78° C. to 0° C. Further N-alkylation of the pyridin-one can be achieved by treatment with alkyl halides in a solvent such as DMA, acetone or THF in the presence of a base such as potassium carbonate.

If R[1] bears a methoxy group, this can be cleaved to the corresponding phenol by treatment with boron tribromide in dichloromethane at −78° C. to 0° C.

Scheme 4

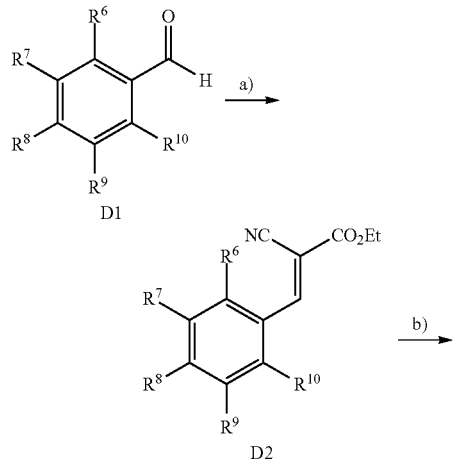

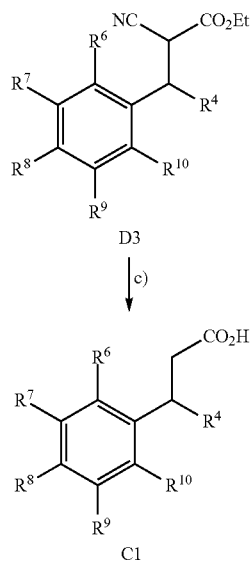

The starting material C1 ($R^2$,$R^3$=H) for the syntheses described in Scheme 3 can be prepared according to Scheme 4. The aldehyde D1 is condensed with ethyl cyanoacetate in the presence of a base such as piperidine at elevated temperature or in the presence of sodium or potassium hydroxide in a solvent such as ethanol to give the alpha,beta-unsaturated derivative D2. 1,4-addition of $R^4$-magnesium halide to compound D2 in a solvent such as toluene or THF at temperatures between 0° C. and reflux of the solvent yield ethyl 2-cyanopropanoate D3. Hydrolysis and decarboxylation under acidic conditions in acetic acid in the presence of $H_2SO_4$ at elevated temperature provides the acid C1 ($R^2$,$R^3$=H).

Scheme 5

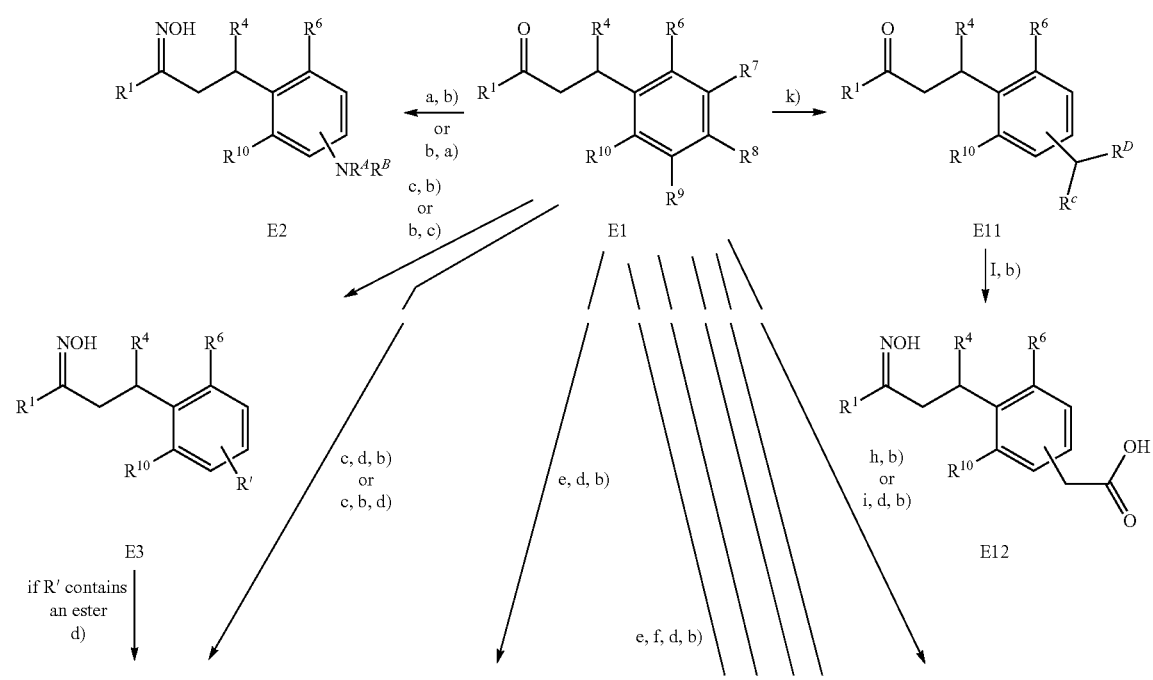

-continued

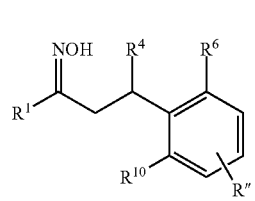
E4

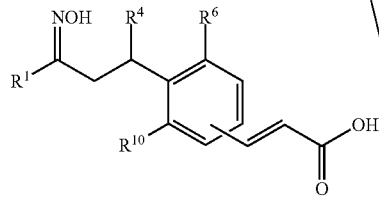
E5

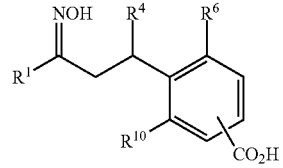
E10

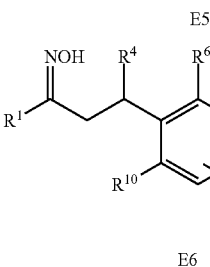
E6

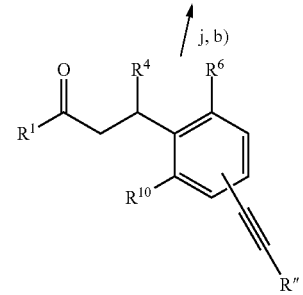
E7

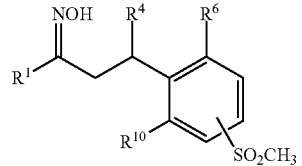
E13

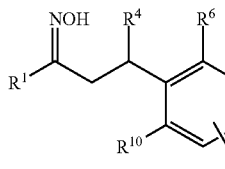
E8

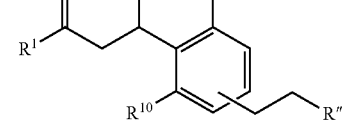
E9

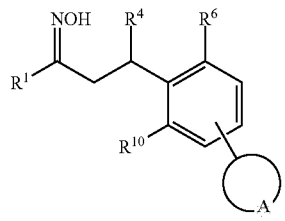
E14 for $R^7$, $R^8$, or $R^9$ = Br
$R^6$, $R^{10}$ = H

Further modifications of the substituents $R^7$, $R^8$ or $R^9$ at the aryl can be achieved by the syntheses described in Scheme 5. For the introduction of an amine moiety Buchwald-Hartwig conditions can be used. Therefore the bromo-ketone E1 ($R^7$, $R^8$ or $R^9$=Br) is reacted with a primary or secondary amine in the presence of a catalyst such as tris(dibenzylidene-acetone)dipalladium(0) and a ligand such as 2-(di-tert-butylphosphino)biphenyl or 2-dicyclohexylphosphino-2',4',6'-triisopropylbiphenyl in toluene in the presence of a base such as sodium tert-butylate (step a). This intermediate is thus converted to the compounds E2 using hydroxylamine hydrochloride in the presence of a base such as sodium hydroxide, sodium hydrogen carbonate or sodium acetate in a solvent such as ethanol or methanol at room temperature up to 200° C., optionally under microwave irradiation (step b). Alternatively, the sequence of the two synthetic steps can be inverted.

Suzuki reaction of bromo-ketone E1 ($R^7$, $R^8$ or $R^9$=Br) with a suitably substituted aryl or heteroaryl R'-boronic acid or R'-boronic acid ester such as e.g. boronic acid methyl esters, boronic acid ethylene glycol esters or boronic acid pinacol esters, in the presence of a suitable catalyst, preferably a palladium catalyst such as dichloro[1,1'-bis(diphenylphosphino)-ferrocene]palladium(II) dichloromethane adduct or tetrakis(triphenylphosphine)palladium(0) and a base, preferably sodium carbonate, sodium hydrogen carbonate, potassium fluoride, potassium carbonate, or triethylamine in solvents such as dioxane, water, toluene, N,N-dimethylformamide or mixtures thereof can be used for the introduction of suitable aryl and heteroaryl moieties. Alternatively, in the palladium catalyzed cross coupling organotrifluoroborates such as R'BF$_3$K in the presence of a palladium catalyst such as tetrakis(triphenylphosphine)palladium(0), palladium(II) acetate or dichloro[1,1'-bis(diphenylphosphino)ferrocene]palladium(II) dichloromethane adduct in the presence of cesium carbonate or potassium phosphate in solvents such as toluene, THF, dioxane, water or mixtures thereof at elevated temperatures can be used. This intermediate is thus converted to the compounds E3 using hydroxylamine hydrochloride in the presence of a base such as sodium hydroxide, sodium hydrogen carbonate or sodium acetate in a solvent such as ethanol or methanol at room temperature up to 200° C., optionally under microwave irradiation (step b).

If R' contains an ester moiety this can be hydrolyzed according to standard procedures, e.g. by treatment with an alkali hydroxide like LiOH or NaOH in a polar solvent mixture like tetrahydrofuran/ethanol/water or for tert-butyl esters, by treatment with e.g. trifluoroacetic acid, optionally in the presence of anisole in a solvent like dichloromethane or dichloroethane between 0° C. and the reflux temperature of the solvents (step d). These acids can be further transformed into amides by treating with suitable amines or amino acid esters in the presence of a coupling reagent such as N-(3-dimethylaminopropyl)-N'-ethyl-carbodiimide-hydrochloride (EDCI), 2-(benzotriazol-1-yl)-N,N,N',N'-tetramethyluronium hexafluoro phosphate (HBTU), O-(1,2-dihydro-2-oxo-1-pyridyl)-N,N,N,N-tetra-methyluronium-tetrafluoroborate (TPTU), O-(7-azabenzotriazol-1-yl)-1,1,3,3-tetramethyluronium hexafluoro-phosphate (HATU) or benzotriazol-1-yloxytris(dimethylamino)phosphonium hexafluoro-phoshate (BOP) and a base such as ethyl-diisopropyl-amine, triethylamine, N-methylmorpholine, optionally in the presence of 4-dimethylamino-pyridine or 1-hydroxybenzo-triazole (HOBt), in solvents such as dichloromethane, dimethylformamide, dimethylacetamide or dioxane at temperatures between 0° C. and ambient temperature. Alternatively, the sequence of the synthetic steps for the preparation of E4 can be inverted.

Further modification of bromo-ketone E1 ($R^7$, $R^8$ or $R^9$=Br) is also possible by Heck reaction with alkyl acrylate in the presence of a palladium catalyst such as tetrakis(triphenylphosphine)palladium(0) or palladium(II) acetate in the presence of a base such as triethylamine, potassium carbonate or sodium hydrogen carbonate in solvents such as dimethylformamide, dimethylacetamide, acetonitrile, toluene or dioxane (step e). This intermediate is thus converted in two steps to the compounds E5 by hydrolysis of the ester using standard conditions with an alkali hydroxide like LiOH or NaOH in a polar solvent mixture like tetrahydrofuran/ethanol/water followed by oxime formation using hydroxylamine hydrochloride in the presence of a base such as sodium hydroxide, sodium hydrogen carbonate or sodium acetate in a solvent such as ethanol or methanol at room temperature up to reflux (steps d, b). The corresponding saturated derivative E6 can be prepared from the product of the Heck reaction by hydrogenation using standard conditions such as Pd/C in a solvent such as ethanol, methanol or ethyl acetate prior to the hydrolysis of the ester and the oxime formation (steps f, d, b). Alternatively, the sequence of the synthetic steps can be inverted.

Sonogashira reactions of the aryl bromide E1 with suitable alkynes in THF in the presence of a base such as triethylamine or piperidine with a catalytic amount of, e.g. $Pd(PPh_3)_4$/CuI or $Pd(OAc)_2$/CuI or $PdCl_2(PPh_3)_2$/CuI at 45° C. to 80° C. give the alkynes E7. For the synthesis of compounds E7 with R"=H, it may be necessary to perform this reaction with alkynes that contain a suitable protective group, e.g., trimethylsilyl or triisopropylsilyl, followed by cleavage of this protective group using methods and reagents known in the art, e.g., potassium carbonate in methanol at room temperature in the case where R" is trimethylsilyl (step g). This intermediate E7 yields oxime E8 after treatment with hydroxylamine hydrochloride in the presence of a base such as sodium hydroxide, sodium hydrogen carbonate or sodium acetate in a solvent such as ethanol or methanol at room temperature up to reflux (step b). Hydrogenation of the alkynes E7 using standard conditions such as Pd/C in a solvent such as ethanol, methanol or ethyl acetate gives the corresponding alkanes followed by conversion to the oximes by treatment with hydroxylamine hydrochloride in the presence of a base such as sodium hydroxide, sodium hydrogen carbonate or sodium acetate in a solvent such as ethanol or methanol at room temperature up to reflux gives compounds E9 (steps f, b). The alkyne intermediates obtained after step g may be converted to the corresponding N(1)-substituted[1,2,3]-triazole derivatives. Preferably such transformations are carried out in a continuous flow reactor as described in the experimental section, in the presence of sodium azide and an alkyl bromide or iodide. This transformation is followed by oxime formation (step b) as described above.

The preparation of the acid derivative E10 can be achieved from aryl bromide E1 by palladium-catalyzed hydroxycarbonylation followed by oxime formation (steps h,b) or by palladium catalyzed methoxy carbonylation, ester hydrolysis and oxime formation (steps i,d,b). For the hydroxycarbonylation, the aryl bromide E1 can be treated with lithium formate as a carbon monoxide source in the presence of a palladium catalyst such as palladium(II) acetate and a ligand such as 1,1'-bis(diphenylphosphino) ferrocene (dppf) in the presence of acetic anhydride and a base such as N,N-diisopropylethylamine in a solvent such as DMF (e.g. Berger, P.; Bessmernykh, A.; Caille, J.-C.; Mignonac, S. *Synthesis* 2006, 3106-3110). For the methoxy carbonylation, the aryl bromide E1 is reacted with carbon monoxide and methanol in ethyl acetate in the presence of a palladium catalyst such as dichloro[1,1'-bis(diphenylphosphino)-ferrocene]palladium (II) in the presence of a base such as triethylamine. The ester hydrolysis is then achieved according to standard procedures, e.g. by treatment with an alkali hydroxide like LiOH or NaOH in a polar solvent mixture like tetrahydrofuran/ethanol/water. The intermediates derived from either route are then transferred into the oximes using hydroxylamine hydrochloride in the presence of a base such as sodium hydroxide, sodium hydrogen carbonate or sodium acetate in a solvent such as ethanol or methanol at room temperature up to reflux.

Alternatively, the acid derivative E10 can be prepared from the intermediate E7 (for R"=$CH_2OH$) by ruthenium tetroxide catalyzed oxidation using $RuCl_3$, $NaIO_4$ in a solvent mixture of $CH_3CN$, water and $CCl_4$ (step j) followed by oxime formation using hydroxylamine hydrochloride in the presence of a base such as sodium hydroxide, sodium hydrogen carbonate or sodium acetate in a solvent such as ethanol or methanol at room temperature up to 200° C., optionally under microwave irradiation (step b).

The carboxy group in the synthetic intermediates obtained after steps h, (i,d), or (g,j) can be elaborated to aromatic heterocycles using methods and reagents described in the art. For instance, [1,3,4]-oxadiazoles may be produced by reaction of the carboxylic acid intermediate with an acyl hydrazide in the presence of O-(7-azabenzotriazol-1-yl)-N, N,N',N'-tetramethyl-uronium hexafluorophosphate and diisopropylethylamine in N,N-dimethylformamide at temperatures between 20° C. and 150° C., followed by acid-catalyzed dehydrative cyclization at temperatures between 60° C. and 150° C., optionally under microwave irradiation. The heterocycle synthesis is followed by oxime formation (step b) as described above.

The preparation of acid derivative E11 is achieved from ketone E1 by palladium-catalyzed cross coupling with alkyl cyanoacetate ($R^C$=CN, $R^D$=COOMe or COOEt) or dialkyl malonate ($R^C$=$R^D$=COOMe or COOEt) in the presence of a palladium catalyst such as dichloro[1,1'-bis(diphenylphosphino)-ferrocene]palladium(II) dichloromethane adduct or tetrakis(triphenylphosphine)palladium(0) or palladium(II) acetate in the presence of a ligand such as 1,1'-bis(diphenylphosphino) ferrocene (dppf) and a base such as potassium tert-butylate in solvents such as dioxane, water, toluene, N,N-dimethylformamide or mixtures thereof (step k). Hydrolysis and decarboxylation of E11 under acidic conditions in acetic acid in the presence of $H_2SO_4$ at elevated temperature, followed by oxime formation using hydroxylamine hydrochloride in the presence of a base such as sodium hydroxide, sodium hydrogen carbonate or sodium acetate in a solvent such as ethanol or methanol at room temperature up to reflux provides the acid E12 (steps 1, b).

The preparation of methylsulfone derivative E13 is accomplished from ketone E1 by reaction with sodium methanesulfinate in the presence of copper(I) iodide, sodium hydroxide and proline, in a solvent such as dimethyl sulfoxide, at temperatures between 60° C. and 150° C., followed by oxime formation as described above (steps m, b).

Heterocyclyl derivatives of formula E14 (A is a heteroatom such as oxygen, nitrogen, or sulfur, in particular N-tert-butoxycarbonyl) can be prepared from ketone E1 by palladium/copper co-catalyzed cross coupling with heterocyclylzinc(II) halide, preferably heterocyclylzinc(II) iodide, as described in the art (e.g., Corley et al., J. Org. Chem. 2004, 69, 5120). This reaction is carried out in the presence of a suitable catalyst system, e.g., [1,1'-bis(diphenylphosphino)-ferrocene]dichloropalladium(II) dichloromethane adduct and copper(I) iodide, in a solvent such as N,N-dimethylacetamide, at temperatures between 60° C. and 100° C. (step n), followed by oxime formation as described above (step b). Heterocyclylzinc(II) halides can be prepared from the corresponding heterocyclyl halides as described in the experimental section. In the case where A is N-tert-butoxycarbonyl, the protective group can be cleaved using methods known in the art (e.g., hydrogen chloride in 1,4-dioxane or trifluoroacetic acid in dichloromethane at temperatures between 0° C. and 30° C.) and the resultant secondary amine can be elaborated to the corresponding amide, sulfonamide or sulfamide using reagents and conditions described in the experimental section.

The cross-coupling reactions starting of aryl bromide E1 described in scheme 5, especially steps b, g, and n, may also be performed on precursors of E1, e.g., Weinreb amide C2a ($R^7$, $R^8$, or $R^9$=Br or I) or aldehyde D1 ($R^7$, $R^8$, or $R^9$=Br, I or Cl).

If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC. Compounds of the general formula I in addition can contain one or more stereocenters and can optionally be separated into optically pure enantiomers or diastereomers by methods well known in the art, e.g. by HPLC chromatography, chromatography on a chiral HPLC column or chromatography with a chiral eluant. Racemic compounds carrying a carboxylate or tetrazole group can also be separated into their antipodes for example via diastereomeric salts by crystallization with optically pure amines, those carrying an amine moiety can also be separated into their antipodes for example via diastereomeric salts by crystallization with optically pure acids. This chiral separation can be accomplished either on the final product of formula I or on the chiral intermediates.

If $R^1$ is a pyridine moiety, this can be further transformed into the corresponding pyridine-N-oxides by oxidation using m-chloroperbenzoic acid in a solvent such as $CH_2Cl_2$, MeOH or mixtures thereof at room temperature. For the preparation of compounds in which $R^1$ is a pyridin-4-one or pyridine-3-one, these can be prepared from the corresponding 2-methoxy-pyridine derivatives, by cleavage of the methoxy moiety by treatment with HCl in dioxane at elevated temperature or by treatment with boron tribromide in dichloromethane at −78° C. to 0° C. Further N-alkylation of the pyridin-one can be achieved by treatment with alkyl halides in a solvent such as DMA, acetone or THF in the presence of a base such as potassium carbonate.

If $R^1$ bears a methoxy group, this can be cleaved to the corresponding phenol by treatment with boron tribromide in dichloromethane at −78° C. to 0° C.

Another synthesis of compounds of formula Id, in which $R^2$ is Ph-R" with R"=H or $C_{1-7}$-alkyl is depicted in Scheme 6. The synthesis starts from the acid F1 which can be converted to the Weinreb amide F2a (R'=NMeOMe) or to the acid chloride F2b (R'=Cl). For the conversion to the Weinreb amide F2a the acid F1 is treated with N,O-dimethylhydroxylamine hydrochloride in the presence of a coupling reagent such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetra-methyluronium-tetra-fluoroborate (TPTU), O-(7-azabenzotriazol-1-yl)-1,1,3,3-tetramethyluronium hexafluoro-phosphate (HATU) or benzotriazol-1-yloxytris(dimethylamino)phosphonium hexafluoro-phoshate (BOP) and a base such as ethyl-diisopropyl-amine, triethylamine, N-methylmorpholine, optionally in the presence of 4-dimethylamino-pyridine or 1-hydroxybenzo-triazole (HOBt), in solvents such as dichloromethane, dimethylformamide, dimethylacetamide or dioxane at temperatures between 0° C. and ambient temperature. Treatment of the Weinreb amide F2a with an organolithium $R^2CH_2Li$ or organomagnesium compound $R^2CH_2MgX$ (X=Cl, Br, I) gives the intermediate ketone F3 (step b).

Scheme 6

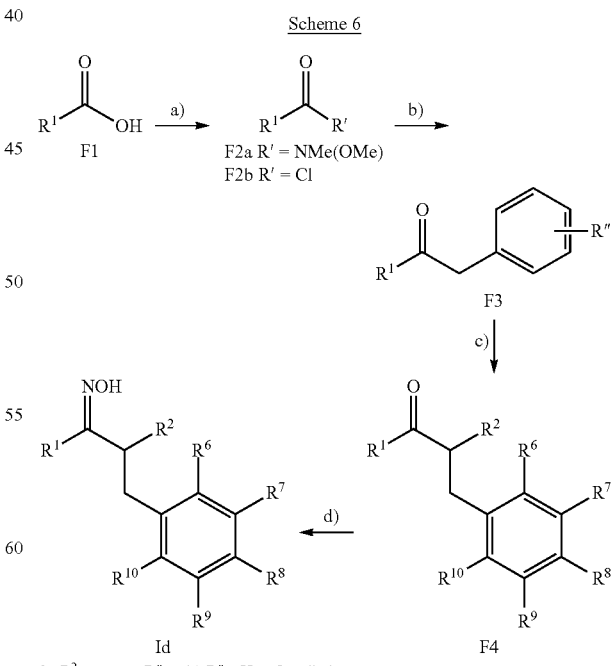

for $R^2 =$ Ph—R" with R" = H or $C_{1-7}$alkyl

Alternatively, the acid F1 can be converted to the acid chloride F2b by treatment with oxalyl chloride in $CH_2Cl_2$ in the presence of a trace of DMF at room temperature or by treatment with $SOCl_2$ (step a). Negishi coupling can be used for the preparation of the ketone F3. Therefore the acid chloride F2b is treated with zinc powder and an appropriate palladium catalyst such as tetrakis(triphenylphosphine)palladium(0), followed by the addition of an appropriate benzyl halide $R^2CH_2X$ (X=Cl, Br, I) in solvents such as toluene, THF, DMA at temperatures between −78° C. and room temperature (step b).

Alkylation of F3 with an appropriate benzyl halide $R^6R^7R^8R^9R^{10}PhCH_2Br$ (X=Cl, Br, I) in the presence of a base such as n-BuLi, LDA, tert-BuOK, NaH, LiHMDS at If $R^1$ is a pyridine moiety, this can be further transformed into the corresponding pyridine-N-oxides by oxidation using m-chloroperbenzoic acid in a solvent such as $CH_2Cl_2$, MeOH or mixtures thereof at room temperature. For the preparation of compounds in which $R^1$ is a pyridin-4-one or pyridine-3-one, these can be prepared from the corresponding 2-methoxy-pyridine derivatives, by cleavage of the methoxy moiety by treatment with HCl in dioxane at elevated temperature or by treatment with boron tribromide in dichloromethane at −78° C. to 0° C. Further N-alkylation of the pyridin-one can be achieved by treatment with alkyl halides in a solvent such as DMA, acetone or THF in the presence of a base such as potassium carbonate. If $R^1$ bears a methoxy group, this can be cleaved to the corresponding phenol by treatment with boron tribromide in dichloromethane at −78° C. to 0° C.

Scheme 7

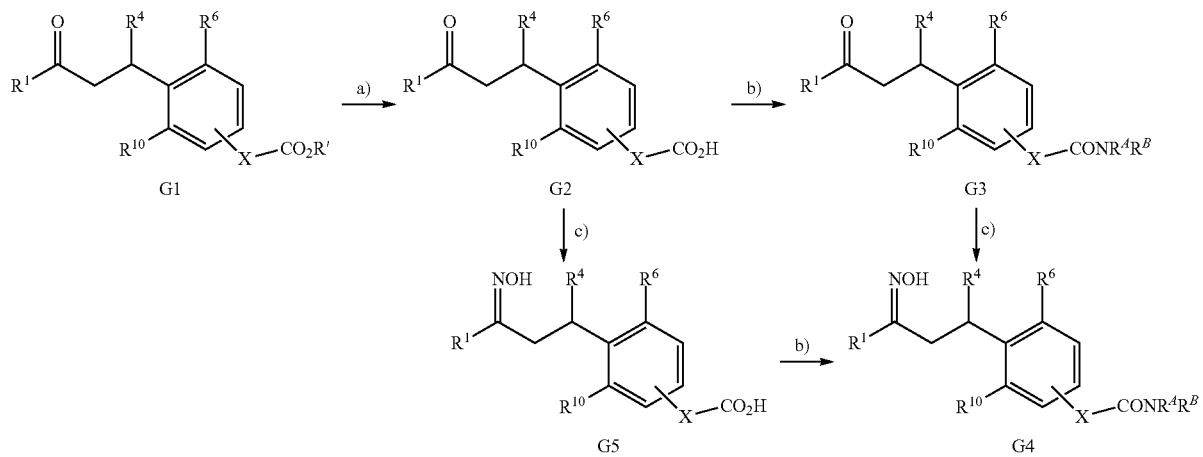

for $R^7$, $R^8$ or $R^9$ = COOR', R' = alkyl
X = single bond or $C_{1-3}$alkyl temperatures ranging from −78 to 100° C. in a solvent such as DMF, THF or $CH_2Cl_2$ provides ketone F4 (step c).

The conversion of the ketone F4 to the compounds of formula Id is achieved using hydroxylamine hydrochloride in the presence of a base such as sodium hydroxide, sodium hydrogen carbonate or sodium acetate in a solvent such as ethanol or methanol at room temperature up to reflux (step d). If necessary and desired, the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC. Compounds of the general formula Id in addition can contain one or more stereocenters and can optionally be separated into optically pure enantiomers or diastereomers by methods well known in the art, e.g. by HPLC chromatography, chromatography on a chiral HPLC column or chromatography with a chiral eluant. Racemic compounds carrying a carboxylate or tetrazole group can also be separated into their antipodes for example via diastereomeric salts by crystallization with optically pure amines, those carrying an amine moiety can also be separated into their antipodes for example via diastereomeric salts by crystallization with optically pure acids. This chiral separation can be accomplished either on the final product of formula Id or on the chiral intermediate F4.

The preparation of compounds of formula (I) containing amide substituents $R^7$, $R^8$ or $R^9$ at the aryl can be achieved by the syntheses described in Scheme 7. The ester moiety of compounds G1 ($R^7$, $R^8$ or $R^9$=COOR', R' is alkyl, preferably methyl, ethyl or tert-butyl) is hydrolyzed using standard conditions e.g. by treatment with an alkali hydroxide like LiOH or NaOH in a polar solvent mixture like tetrahydrofuran/ethanol/water or for tert-butyl esters, by treatment with e.g. trifluoroacetic acid, optionally in the presence of anisole in a solvent like dichloromethane or dichloroethane between room temperature and the reflux temperature of the solvents to give compounds G2 (step a). These acids can be further transformed into amides G3 by treating with a suitable amine or amino acid ester in the presence of a coupling reagent such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetra-methyluronium-tetra-fluoroborate (TPTU), O-(7-azabenzotriazol-1-yl)-1,1,3,3-tetramethyluronium hexafluoro-phosphate (HATU) or benzotriazol-1-yloxytris(dimethylamino)phosphonium hexafluoro-phoshate (BOP) and a base such as ethyl-diisopropyl-amine, triethylamine, N-methylmorpholine, optionally in the presence of 4-dimethylamino-pyridine or 1-hydroxybenzo-triazole (HOBt), in solvents such as dichloromethane, dimethylformamide, dimethylacetamide or dioxane at temperatures between 0° C. and ambient temperature (step b). If G3 contains an ester moiety, this can be converted to the acid as described in step a. The conversion of the ketone G3 to the compounds of formula G4 or G5 is achieved using hydroxylamine hydrochloride in the presence of a base such as sodium hydroxide, sodium hydrogen carbonate or sodium acetate in a solvent such as ethanol or methanol at room temperature up to reflux (step c). If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC. Alternatively, the sequence of the synthetic steps for the preparation of G4 can be inverted.

Scheme 8

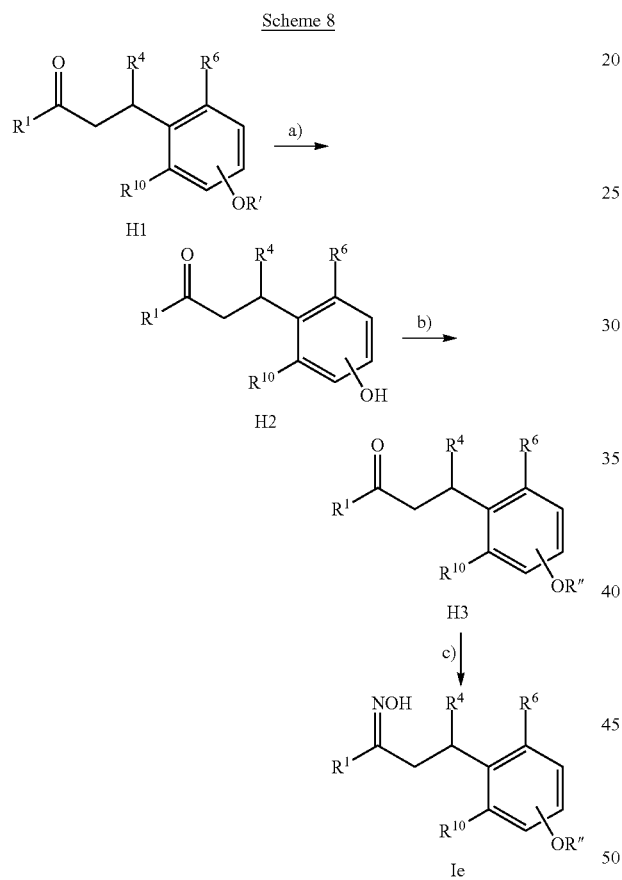

for $R^7$, $R^8$ or $R^9$ = OR'
R' = methyl, isopropyl, tert-butyl

The preparation of compounds of formula (I) containing OR" substituents $R^7$, $R^8$ or $R^9$ at the aryl can be achieved by the syntheses described in Scheme 8. If the aryl ring of intermediate H1 contains a protected phenol moiety ($R^7$, $R^8$ or $R^9$=OR', R' is preferably methyl, isopropyl or tert-butyl) it can be converted to a free phenol H2 either by treatment with strong mineral acids such as HBr, HCl or the like at elevated temperatures ranging from 20 to 150° C. or alternatively under much milder conditions using for example $BBr_3$ or $BCl_3$ in aprotic solvents such as dichloromethane, THF or the like at temperatures ranging from −50 to 50° C. (step a). Free phenol H2 itself is suitable for various coupling reactions (step b): On one hand, it can be used for example in a copper (II) mediated coupling with suitably substituted boronic acids (or the corresponding pinacol esters) in the presence of pyridine, DMAP or triethylamine or the like in aprotic solvents such as dichloromethane, acetonitrile or the like to provide diarylethers H3. On the other hand, various heteroarylphenylethers H3 can be made, e.g. by treatment of phenol H2 with a suitably functionalized chloropyridine, chloropyrazine or chloropyrimidine in the presence of a base such as DABCO, triethylamine, diisopropylamine, NaH or tert-BuOK in an appropriate solvent such as DMF, THF or similar at 0° C. up to reflux temperature of the solvent. Another possibility for the synthesis of diaryl ethers of formula H3 is to react phenols H2 with a suitable aryl halide, preferentially an aryl fluoride using a suitable base such as cesium carbonate, sodium hydride, potassium carbonate or the like in a suitable solvent such as DMF, DMSO, DMA or the like at various temperatures, preferentially ranging from room temperature to reflux temperature of the solvent. Another method to provide compounds H3 is the alkylation of phenols H2 by treatment with a base such as sodium hydride, potassium tert-butylate, potassium carbonate, silver carbonate or the like followed by treatment with an alkylation agent such as e.g a substituted alkyl or aryl-alkyl halide or triflate in suitable solvents such as THF, DMF or the like at various temperatures. Yet another method for the synthesis of compounds H3 is the Mitsunobu reaction of phenols H2 with suitably substituted alcohols in the presence of dialkylazodicarboxylates and triphenylphosphine in a solvent such as THF or dioxane. If H3 contains an ester moiety, this can be converted to the acid as described in Scheme 7 (step a). The conversion of the ketone H3 to the compounds of formula Ie is achieved using hydroxylamine hydrochloride in the presence of a base such as sodium hydroxide, sodium hydrogen carbonate or sodium acetate in a solvent such as ethanol or methanol at room temperature up to reflux (step c). If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC.

Scheme 9

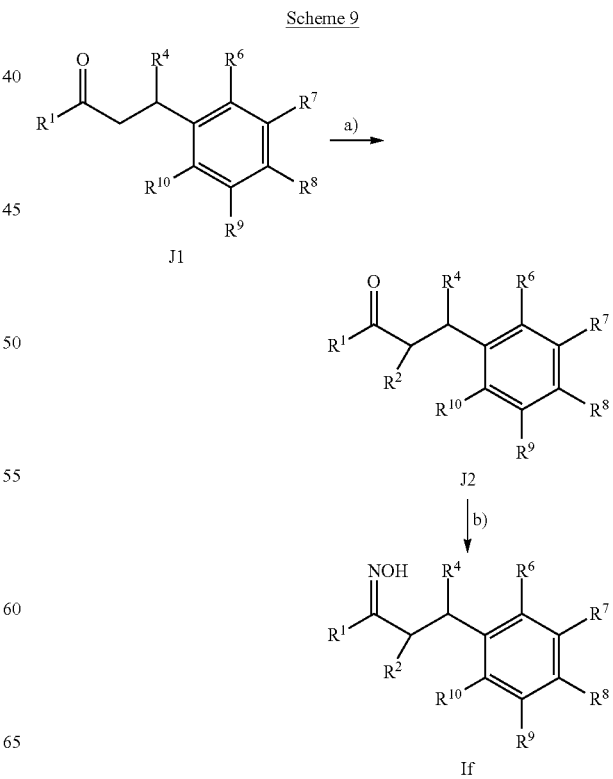

The preparation of compounds of formula If containing alkyl substituents $R^2$ can be achieved by the syntheses described in Scheme 9. Alkylation of J1 with an appropriate alkyl halide $R^2X$ (X=Cl, Br, I) or alkyl triflate in the presence of a base such as n-BuLi, LDA, tert-BuOK, NaH, LiHMDS at temperatures ranging from −78 to 100° C. in a solvent such as DMF, DMA or THF provides ketone J2 (step a). The conversion of the ketone J2 to the compounds of formula If is achieved using hydroxylamine hydrochloride in the presence of a base such as sodium hydroxide, sodium hydrogen carbonate or sodium acetate in a solvent such as ethanol or methanol at room temperature up to reflux (step b). If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC.

Scheme 10

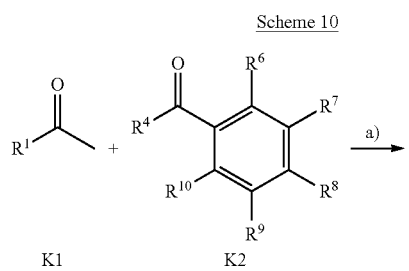

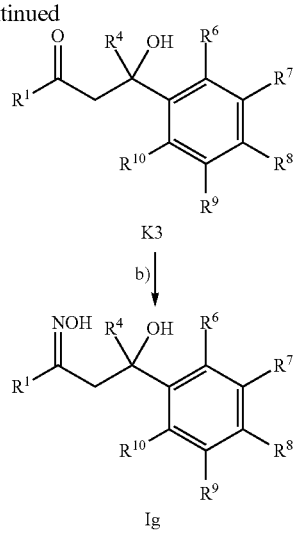

The preparation of compounds of formula Ig containing OH substituents $R^5$ can be achieved by the syntheses described in Scheme 10. Treatment of ketone K1 with a base such as NaH or LDA in a solvent such as DMF, DMA or THF at temperatures from −78° C. to room temperature followed by treatment with ketone K2 provides hydroxy-ketones K3 (step a). The conversion of the ketone K3 to the compounds of formula Ig is achieved using hydroxylamine hydrochloride in the presence of a base such as sodium hydroxide, sodium hydrogen carbonate or sodium acetate in a solvent such as ethanol or methanol at room temperature up to reflux (step b). Separation of the E and Z isomers can be achieved either by column chromatography or by HPLC.

Scheme 11

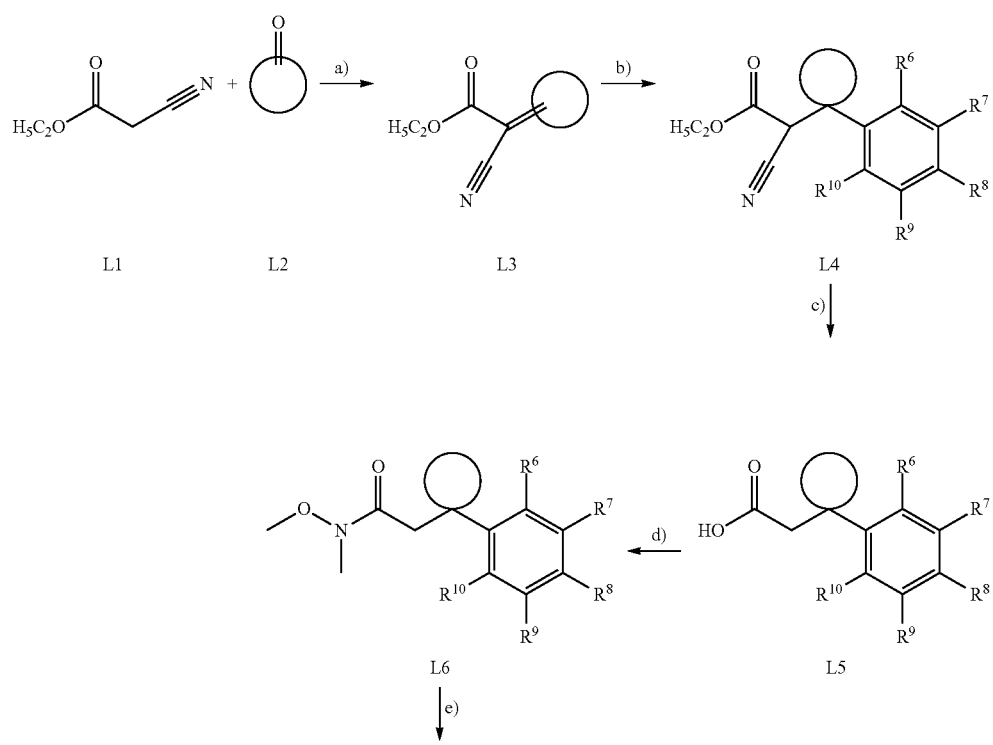

-continued

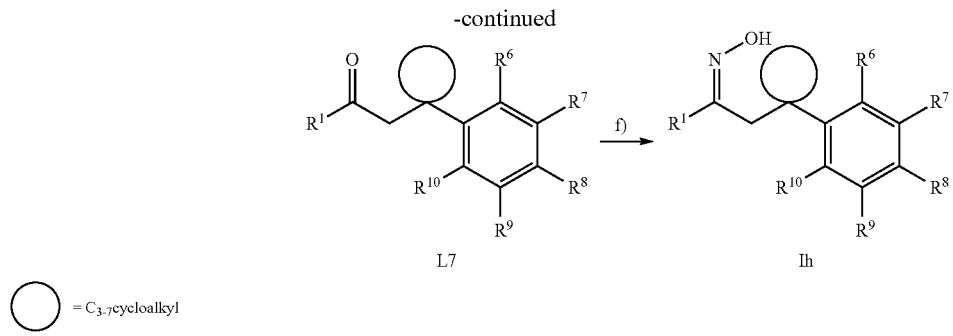

L7          Ih

◯ = $C_{3-7}$cycloalkyl

The preparation of compounds of formula Ih containing substituents $R^4$ and $R^5$ that form a $C_{3-7}$-cycloalkyl ring together with the carbon atom they are attached to can be achieved by the syntheses described in Scheme 11. A cyclic ketone L2 is condensed with ethyl cyanoacetate L1 in the presence of a base such as cesium fluoride, sodium or potassium hydroxide at elevated temperature in a solvent such as ethanol to give the alpha,beta-unsaturated derivative L3 (step a). 1,4-addition of an arylmagnesium halide to compound L3 in a solvent such as toluene or THF at temperatures between 0° C. and reflux of the solvent yields ethyl 2-cyano-propanoate L4 (step b). Hydrolysis and decarboxylation to give acid L5 can be conducted under basic conditions, e.g by treatment with KOH in a solvent mixture such as ethylene glycol/water at elevated temperature (step c). The acid L5 is converted to the corresponding Weinreb amide L6 by treatment with N,O-dimethylhydroxylamine hydrochloride in the presence of a coupling reagent such as N-(3-dimethylamino-propyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetra-methyluronium-tetra-fluoroborate (TPTU), O-(7-azabenzotriazol-1-yl)-1,1,3,3-tetramethyluronium hexafluoro-phosphate (HATU) or benzotriazol-1-yloxytris(dimethyl-amino)phosphonium hexafluoro-phosphate (BOP) and a base such as ethyl-diisopropyl-amine, triethylamine, N-methylmorpholine, optionally in the presence of 4-dimethylamino-pyridine or 1-hydroxybenzo-triazole (HOBt), in solvents such as dichloromethane, dimethylformamide, dimethylacetamide or dioxane at temperatures between 0° C. and ambient temperature (step d). Treatment of the Weinreb amide L6 with an organolithium $R^1Li$ or organomagnesium compound $R^1MgX$ (X=Cl, Br, I) gives the intermediate ketone L7 (step e). If the organolithium $R^1Li$ or organomagnesium compounds $R^1MgX$ are not commercially available, these can be generated in situ from the corresponding $R^1$—X by treatment with n-BuLi or i-PrMgCl or i-PrMgCl LiCl at −100° C. to 0° C. in a solvent such as THF. The conversion of the ketone L7 to the compounds of formula Ih is achieved using hydroxylamine hydrochloride in the presence of a base such as sodium hydroxide, sodium hydrogen carbonate or sodium acetate in a solvent such as ethanol or methanol at room temperature up to reflux (step f). If necessary and desired the ratio of E and Z isomers can be modified by treating the isolated oxime with acids such as hydrochloric acid in solvents such as ethanol, DME and dioxane or in mixtures thereof at temperatures between room temperature and reflux of the solvent. Separation of the E and Z isomers can be achieved either by column chromatography or by HPLC.

Scheme 12

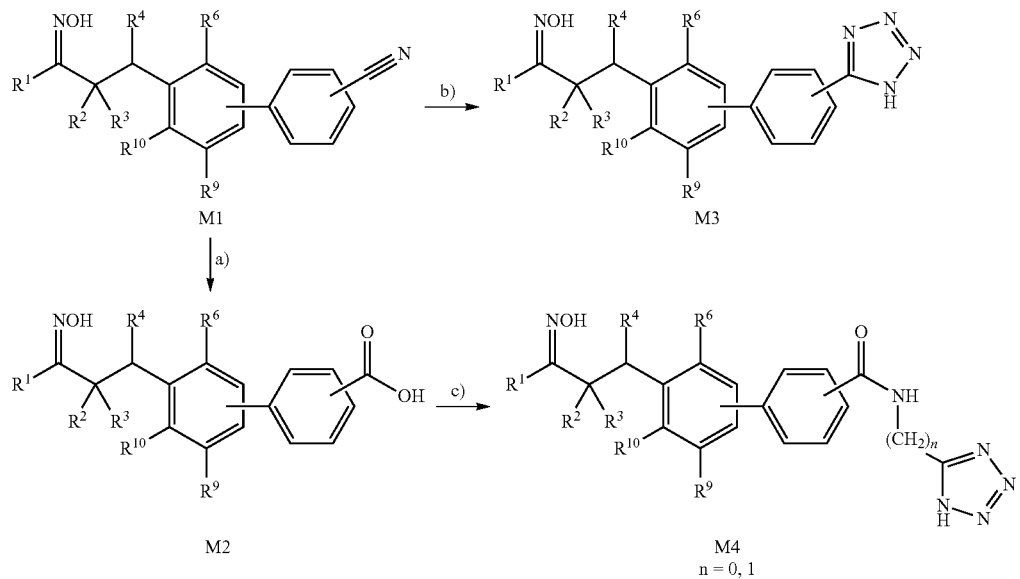

M1          M3

M2          M4
n = 0, 1

In cases in which the substituent $R^7$ or $R^8$ in compounds of general formula I is a cyano group which is either directly or via an alkyl or an additional aryl group attached to the phenyl (compounds M1, Scheme 12), the cyano group can be either hydrolyzed to the carboxylic acid under basic (e.g. with aqueous sodium or lithium hydroxide) or under acidic conditions (e.g. hydrochloric or sulfuric acid) to give the compounds M2 (step a), or can be converted to the corresponding tetrazoles M3 (step b) using standard procedures such as, e.g. by treatment with sodium azide in the presence of a Lewis acid (e.g. zinc(II) bromide) or ammonium chloride in water or organic solvents like dichloromethane or N,N-dimethylformamide at temperatures between 0° C. and the boiling point of the solvent. The carboxyl group in compounds of formula M2 can be subjected to amide couplings with amino- or amino-alkyl-substituted tetrazoles (either commercially available or that can be prepared by literature methods) applying conditions described in Scheme 7, to give compounds M4 (step c). The tetrazole group in amino- or amino-alkyl-substituted tetrazoles can be optionally protected, for example with a triphenylmethyl (trityl) protective group that can be cleaved off after the reaction step applying methods known to those skilled in the art and as described in literature.

As described herein before, the compounds of formula I of the present invention can be used as medicaments for the treatment of diseases which are associated with the modulation of GPBAR1 activity.

As compounds of formula I of the invention are agonists of the GPBAR1 receptor, the compounds will be useful for lowering glucose, lipids, and insulin resistance in diabetic patients and in non-diabetic patients who have impaired glucose tolerance or who are in a pre-diabetic condition. The compounds of formula I are further useful to ameliorate hyperinsulinemia, which often occurs in diabetic or pre-diabetic patients, by modulating the swings in the level of serum glucose that often occurs in these patients. The compounds of formula I are also useful in reducing the risks associated with metabolic syndrome, in reducing the risk of developing atherosclerosis or delaying the onset of atherosclerosis, and reducing the risk of angina, claudication, heart attack, stroke, and coronary artery disease. By keeping hyperglycemia under control, the compounds are useful to delay or for preventing vascular restenosis and diabetic retinopathy.

The compounds of formula I of the present invention are useful in improving or restoring β-cell function, so that they may be useful in treating type 1 diabetes or in delaying or preventing a patient with type 2 diabetes from needing insulin therapy. The compounds may be useful for reducing appetite and body weight in obese subjects and may therefore be useful in reducing the risk of co-morbidities associated with obesity such as hypertension, atherosclerosis, diabetes, and dyslipidemia. By elevating the levels of active GLP-1 in vivo, the compounds are useful in treating neurological disorders such as Alzheimer's disease, multiple sclerosis, and schizophrenia.

Thus, the expression "diseases which are associated with the modulation of GPBAR1 activity" means diseases such as metabolic, cardiovascular, and inflammatory diseases, for example diabetes, particularly type 2 diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, crohn's disease, disorders associated with parenteral nutrition especially during small bowel syndrome, irritable bowel syndrome (IBS), allergy diseases, fatty liver (e.g. non-alcoholic fatty liver disease, NAFLD), liver fibrosis (e.g. non-alcoholic steatohepatitis, NASH), primary sclerosing cholangitis (PSC), liver cirrhosis, primary biliary cirrhosis (PBC), liver colestasis, kidney fibrosis, anorexia nervosa, bulimia nervosa and neurological disorders such as Alzheimer's disease, multiple sclerosis, schizophrenia and impaired cognition.

In a particular aspect, the expression "diseases which are associated with the modulation of GPBAR1 activity" relates to diabetes, particularly type 2 diabetes, gestational diabetes, impaired fasting glucose, impaired glucose tolerance, hyperglycemia, metabolic syndrome, obesity, hypercholesterolemia and dyslipidemia.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the modulation of GPBAR1 activity.

Further, the invention relates to compounds of formula I as defined above for use as therapeutically active substances, particularly as therapeutically active substances for the treatment of diseases which are associated with the modulation of GPBAR1 activity. In particular, the invention relates to compounds of formula I for use in diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for use in diabetes, preferably type 2 diabetes, gestational diabetes or hyperglycemia.

In another aspect, the invention relates to a method for the treatment a of diseases which are associated with the modulation of GPBAR1 activity, which method comprises administering a therapeutically active amount of a compound of formula I to a human being or animal. In particular, the invention relates to a method for the treatment of diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for the treatment of diabetes, preferably type 2 diabetes, gestational diabetes or hyperglycemia.

The invention further relates to the use of compounds of formula I as defined above for the treatment of diseases which are associated with the modulation of GPBAR1 activity.

In addition, the invention relates to the use of compounds of formula I as defined above for the preparation of medicaments for the treatment of diseases which are associated with the modulation of GPBAR1 activity. In particular, the invention relates to the use of compounds of formula I as defined above for the preparation of medicaments for the treatment of diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for the preparation of medicaments for the treatment of diabetes, preferably type 2 diabetes, gestational diabetes or hyperglycemia.

Also contemplated herein is a combination therapy using one or more compounds of formula I or compositions of the present invention, or a pharmaceutically acceptable salts thereof, in combination with one or more other pharmaceutically active compounds independently selected from the group consisting of the following:

(a) human peroxisome proliferator activated receptor (PPAR) gamma agonists (e.g., thiazolidinediones and glitazones, e.g., rosiglitazone, troglitazone, pioglitazone, englitazone, balaglitazone, and netoglitazone), (b) biguanides such as metformin, metformin hydrochloride, buformin and phenformin, (c) dipeptidyl peptidase IV (DPP-4) inhibitors, such as sitagliptin, sitagliptin phosphate, saxagliptin, vildagliptin, alogliptin, carmegliptin, and denagliptin, (d) incretins such as glucagon-like peptide-1 (GLP-1) receptor agonists such as exenatide (Byetta™), liraglutide (Victoza™), GLP-1(7-36) amide and its analogs, GLP-1(7-37) and its analogs, AVE-0010 (ZP-10), R1583 (taspoglutide), GSK-716155 (albiglutide, GSK/Human Genome Sciences), BRX-0585 (Pfizer/Biorexis) and CJC-1134-PC (Exendin-4: PC-DAC™) or glucose-dependent insulinotropic peptide (GIP), (e) insulin or insulin analogs such as LysPro insulin or inhaled formulations comprising insulin, (f) sulfonylureas such as tolazamide, chlorpropamide, glipizide, glimepiride, glyburide, glibenclamide, tolbutamide, acetohexamide or glypizide, (g) α-glucosidase inhibitors such as miglitol, acarbose, epalrestat, or voglibose, (h) cholesterol biosynthesis inhibitors such as HMG CoA reductase inhibitors, e.g., lovastatin, simvastatin, pravastatin, fluvastatin, atorvastatin, rosuvastatin, cerivastatin, itavastin, nisvastatin and rivastatin, or squalene epoxidase inhibitors, e.g., terbinafine, (i) plasma HDL-raising agents such as CETP inhibitors e.g., anacetrapib, torcetrapib and dalcetrapib, or PPAR alpha agonists, e.g., gemfibrozil, clofibrate, fenofibrate and bezafibrate, (j) PPAR dual alpha/gamma agonists such as muraglitazar, naveglitazar, aleglitazar, tesaglitazar, peliglitazar, farglitazar and JT-501, (k) bile acid sequestrants, e.g., anion exchange resins, or quaternary amines (e.g., cholestyramine or colestipol)), or ileal bile acid transporter inhibitors (BATi);

(l) nicotinyl alcohol, nicotinic acid, niacinamide or salts thereof, (m) cholesterol absorption inhibitors such as ezetimibe or acyl-Coenzyme A:cholesterol O-acyl transferase (ACAT) inhibitors such as avasimibe, (n) selective estrogen receptor modulators such as raloxifene or tamoxifen) or LXR alpha or beta agonists, antagonists or partial agonists (e.g., 22(R)-hydroxycholesterol, 24(S)-hydroxycholesterol, T0901317 or GW3965);

(o) microsomal triglyceride transfer protein (MTP) inhibitors, alpha2-antagonists and imidazolines (e.g., midaglizole, isaglidole, deriglidole, idazoxan, efaroxan, fluparoxan), (p) insulin secretagogues such as linogliride, nateglinide, repaglinide, mitiglinide calcium hydrate or meglitinide);

(q) SGLT-2 inhibitors (e.g., dapagliflozin, sergliflozin and tofoglifozin), (s) glucokinase activators such as the compounds disclosed in e.g., WO 00/58293 A1;

(t) protein tyrosine phosphatase-1B (PTP-1B) inhibitors, (u) glucagon receptor antagonists, (v) anti-obesity agents such as fenfluramine, dexfenfluramine, phentiramine, sibutramine, orlistat, neuropeptide Y1 or Y5 antagonists, neuropeptide Y2 agonists, MC4R (melanocortin 4 receptor) agonists, cannabinoid receptor 1 (CB-1) antagonists/inverse agonists, and β3 adrenergic receptor agonists (e.g., GW-320659), nerve growth factor agonist (e.g., axokine), growth hormone agonists (e.g., AOD-9604), 5-HT (serotonin) reuptake/transporter inhibitors (e.g., Prozac), DA (dopamine) reuptake inhibitors (e.g., Buprorion), 5-HT, NA and DA reuptake blockers, steroidal plant extracts (e.g., P57), CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g., SNAP 7941), MCH2R (melanin concentrating hormone 2R) agonist/antagonists, H3 (histamine receptor 3) inverse agonists or antagonists, H1 (histamine 1 receptor) agonists, FAS (fatty acid synthase) inhibitors, ACC-2 (acetyl-CoA carboxylase-1) inhibitors, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), Topiramate, glucocorticoid antagonist, 5-HT$_{2C}$ (serotonin receptor 2C) agonists (e.g., Lorcaserin), PDE (phosphodiesterase) inhibitors, fatty acid transporter inhibitors, dicarboxylate transporter inhibitors, glucose transporter inhibitors, (w) anti-inflammatory agents such as cyclooxygenase-2 (COX-2) inhibitors (e.g., rofecoxib and celecoxib); glucocorticoids, azulfidine, thrombin inhibitors (e.g., heparin, argatroban, melagatran, dabigatran) and platelet aggregation inhibitors (e.g., glycoprotein IIb/IIIa fibrinogen receptor antagonists or aspirin), and ursodeoxycholic acid (UDCA) and norursodeoxycholic acid (norUDCA) and (y) antihypertensives such as beta blockers (e.g., angiotensin II receptor antagonists such as losartan, eprosartan, irbesartan, tasosartan, telmisartan or valsartan; angiotensin converting enzyme inhibitors such as enalapril, captopril, cilazapril, ramapril, zofenopril, lisinopril and fosinopril; calcium channel blockers such as nifedipine and diltiazam and endothelian antagonists.

Such other pharmaceutically active compounds may be administered in an amount commonly used therefore, contemporaneously or sequentially with a compound of the formula I or a pharmaceutically acceptable salt thereof. In the treatment of patients who have type 2 diabetes, insulin resistance, obesity, metabolic syndrome, neurological disorders, and co-morbidities that accompany these diseases, more than one pharmaceutically active compound is commonly administered. The compounds of formula I of this invention may generally be administered to a patient who is already taking one or more other drugs for these conditions. When a compound of formula I is used contemporaneously with one or more other pharmaceutically active compounds, a pharmaceutical composition in an unit dosage form containing such other pharmaceutically active compounds and the compound of the formula I is preferred. Thus, the invention also relates to a pharmaceutical composition containing a compound of formula I in combination with one or more other pharmaceutically active compounds as defined above. When used in combination with one or more other active ingredients, the compound of formula I of the present invention and the other pharmaceutically active compounds may be used in lower doses than when each is used singly. These kinds of pharmaceutical compositions are also included in the invention.

However, the combination therapy also includes therapies in which the compound of formula I and one or more other pharmaceutically active compounds are administered in different dosage forms, but with overlapping schedules. The invention thus also relates to a method for the treatment a of diseases which are associated with the modulation of GPBAR1 activity, which method comprises administering a therapeutically active amount of a compound of formula I in combination with one or more other pharmaceutically active compounds to a human being or animal.

The following test was carried out in order to determine the activity of the compounds of formula I:

The cDNA of the human GPBAR1 receptor (Genbank: NM_170699 with the exception of a silent C:G mutation at position 339 from the start codon) was amplified by polymerase chain reaction (PCR) from human cDNA and inserted into pCineo (Promega) by standard methods (Current Protocols in Molecular Biology, Wiley Press, ed. Ausubel et al.). The final clone was verified by DNA sequence analysis. The plasmid was transfected into CHO cells deficient in dihydrofolate reductase activity (CHO-dhfr−) using Lipofectamine plus (Invitrogen). Clones were isolated in limited dilution conditions and identified by activities in the cAMP assay using lithocholic acid as agonist. A clonal cell line displaying the greatest activity in cAMP increases was selected and identified as giving consistently good responses for up to at least 20 passages.

cAMP Assay

CHO-dhfr(minus) cells expressing human GPBAR1 receptors are seeded 17-24 hours prior to the experiment 50.000 cells per well in a black 96 well plate with flat clear bottom (Corning Costar #3904) in DMEM (Invitrogen No. 31331), 1× HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. The assay was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaked for 2 h at room temperature. The time-resolved energy transfer is measured by a TRF reader (Evotec Technologies GmbH, Hamburg Germany), equipped with a ND:YAG laser as excitation source. The plate is measured twice with the excitation at 355 nm and at the emission with a delay of 100 ns and a gate of 100 ns, total exposure time 10 s at 730 (bandwith 30 nm) or 645 nm (bandwidth 75 nm), respectively. The measured signal at 730 nm has to be corrected for the ruthenium background, the direct excitation of Alexa and the buffer control. The FRET signal is calculated as follows: FRET=T730-Alexa730-P (T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of bile acids generated from this assay were in agreement with the values published in the scientific literature. Specificity for GPBAR1 was tested in non-transfected CHO cells in the same assay as above.

The compounds according to formula I have an activity in the above assay ($EC_{50}$) preferably of 0.5 nM to 10 µM, more preferably of 0.5 nM to 1 µM and most preferably of 0.5 nM to 100 nM. For example, the following compounds showed the following human $EC_{50}$ values in the functional cAMP assay described above:

| Example | human $EC_{50}$ [µM] |
| --- | --- |
| 1 | 0.045 |
| 2 | 0.255 |
| 3 | 0.105 |
| 4 | 0.028 |
| 5 | 0.019 |
| 6 | 0.025 |
| 7 | 0.079 |
| 8 | 0.74 |
| 9 | 0.1 |
| 10 | 1.038 |
| 11 | 0.04 |
| 12 | 0.092 |
| 13 | 0.173 |
| 14 | 0.052 |
| 15 | 0.206 |
| 16 | 0.178 |
| 17 | 0.38 |
| 18 | 0.661 |
| 19 | 0.355 |
| 20 | 0.066 |
| 21 | 0.303 |
| 22 | 0.033 |
| 23 | 0.492 |
| 24 | 2.188 |
| 25 | 0.356 |
| 26 | 0.108 |
| 27 | 0.092 |
| 28 | 0.163 |
| 29 | 0.4 |
| 30 | 0.181 |
| 31 | 0.012 |
| 32 | 0.255 |
| 33 | 0.047 |
| 34 | 0.014 |
| 35 | 0.067 |
| 36 | 0.011 |
| 37 | 2.196 |
| 38 | 7.653 |
| 39 | 0.075 |
| 40 | 0.034 |
| 41 | 0.036 |
| 42 | 0.156 |
| 43 | 0.847 |
| 44 | 0.421 |
| 45 | 1.156 |
| 46 | 1.359 |
| 47 | 0.548 |
| 48 | 4.359 |
| 49 | 2.915 |
| 50 | 0.769 |
| 51 | 0.933 |
| 52 | 0.763 |
| 53 | 6.759 |
| 54 | 2.584 |
| 55 | 0.117 |
| 56 | 0.203 |
| 57 | 0.073 |
| 58 | 0.076 |
| 59 | 0.017 |
| 60 | 0.81 |
| 61 | 4.592 |
| 62 | 2.705 |
| 63 | 2.725 |
| 64 | 0.38 |
| 65 | 0.039 |
| 66 | 0.3 |
| 67 | 0.132 |
| 68 | 0.341 |
| 69 | 1.891 |
| 70 | 2.73 |
| 71 | 1.621 |
| 72 | 0.221 |
| 73 | 4.431 |
| 74 | 0.218 |
| 75 | 0.02 |
| 76 | 0.49 |
| 77 | 0.269 |

| Example | human EC$_{50}$ [μM] |
|---|---|
| 78 | 0.381 |
| 79 | 0.285 |
| 80 | 0.709 |
| 81 | 0.295 |
| 82 | 0.043 |
| 83 | 0.455 |
| 84 | 0.027 |
| 85 | 0.001 |
| 86 | 0.256 |
| 87 | 0.241 |
| 88 | 0.012 |
| 89 | 0.007 |
| 90 | 0.01 |
| 91 | 0.057 |
| 92 | 1.052 |
| 93 | 0.011 |
| 94 | 0.43 |
| 95 | 0.039 |
| 96 | 0.003 |
| 97 | 0.177 |
| 98 | 0.146 |
| 99 | 5.045 |
| 100 | 0.514 |
| 101 | 1.7 |
| 102 | 0.323 |
| 103 | 0.589 |
| 104 | 0.578 |
| 105 | 1.023 |
| 106 | 0.255 |
| 107 | 0.153 |
| 108 | 0.076 |
| 109 | 0.702 |
| 110 | 0.116 |
| 111 | 0.027 |
| 112 | 0.016 |
| 113 | 0.215 |
| 114 | 1.085 |
| 115 | 0.041 |
| 116 | 0.005 |
| 117 | 0.102 |
| 118 | 0.028 |
| 119 | 0.227 |
| 120 | 0.184 |
| 121 | 0.024 |
| 122 | 0.201 |
| 123 | 4.536 |
| 124 | 0.017 |
| 125 | 2.212 |
| 126 | 0.061 |
| 127 | 0.046 |
| 128 | 0.65 |
| 129 | 0.591 |
| 130 | 0.087 |
| 131 | 0.014 |
| 132 | 0.046 |
| 133 | 0.114 |
| 134 | 0.02 |
| 135 | 0.029 |
| 136 | 0.024 |
| 137 | 0.038 |
| 138 | 0.155 |
| 139 | 0.017 |
| 140 | 0.012 |
| 141 | 0.008 |
| 142 | 0.002 |
| 143 | 0.001 |
| 144 | 0.017 |
| 145 | 0.001 |
| 146 | 0.164 |
| 147 | 0.467 |
| 148 | 0.026 |
| 149 | 0.14 |
| 150 | 0.008 |
| 151 | 3.285 |
| 152 | 5.119 |
| 153 | 0.151 |
| 154 | 0.549 |
| 155 | 8.619 |
| 156 | 6.136 |
| 157 | 3.638 |
| 158 | 1.032 |
| 159 | 5.562 |
| 160 | 1.309 |
| 161 | 0.119 |
| 162 | 0.008 |
| 163 | 0.173 |
| 164 | 0.004 |
| 165 | 0.55 |
| 166 | 0.14 |
| 167 | 0.318 |
| 168 | 0.058 |
| 169 | 0.11 |
| 170 | 0.453 |
| 171 | 4.003 |
| 172 | 0.056 |
| 173 | 1.933 |
| 174 | 0.268 |
| 175 | 1.314 |
| 176 | 0.369 |
| 177 | 0.256 |
| 178 | 0.042 |
| 179 | 0.165 |
| 180 | 3.447 |
| 181 | 0.022 |
| 182 | 0.602 |
| 183 | 0.021 |
| 184 | 0.439 |
| 185 | 0.012 |
| 186 | 0.179 |
| 187 | 0.021 |
| 188 | 0.656 |
| 189 | 0.871 |
| 190 | 4.391 |
| 191 | 0.375 |
| 192 | 0.107 |
| 193 | 0.019 |
| 194 | 0.218 |
| 195 | 0.028 |
| 196 | 0.184 |
| 197 | 0.012 |
| 198 | 9.641 |
| 199 | 0.023 |
| 200 | 0.558 |
| 201 | 1.262 |
| 202 | 0.172 |
| 203 | 0.012 |
| 204 | 0.165 |
| 205 | 0.555 |
| 206 | 0.109 |
| 207 | 0.711 |
| 208 | 0.093 |
| 209 | 0.443 |
| 210 | 6.89 |
| 211 | 5.98 |
| 212 | 0.153 |
| 213 | 1.31 |
| 214 | 1.22 |
| 215 | 0.81 |
| 216 | 0.255 |
| 217 | 0.7 |
| 218 | 1.64 |
| 219 | 1.16 |
| 220 | 0.68 |
| 221 | 4.08 |
| 222 | 3.59 |
| 223 | 0.009 |
| 224 | 0.006 |
| 225 | 0.049 |
| 226 | 0.038 |
| 227 | 0.055 |
| 228 | 0.018 |
| 229 | 0.022 |
| 230 | 0.018 |
| 231 | 0.283 |

| Example | human EC$_{50}$ [μM] |
|---|---|
| 232 | 0.137 |
| 233 | 0.186 |
| 234 | 0.38 |
| 235 | 0.043 |
| 236 | 1.2 |
| 237 | 0.025 |
| 238 | 0.023 |
| 239 | 0.024 |
| 240 | 0.031 |
| 241 | 0.17 |
| 242 | 0.37 |
| 243 | 0.02 |
| 244 | 0.26 |
| 245 | 0.25 |
| 246 | 2.18 |
| 247 | 0.22 |
| 248 | 0.07 |
| 249 | 0.03 |
| 250 | 1.35 |
| 251 | 0.48 |
| 252 | 0.01 |
| 253 | 0.14 |
| 254 | 0.06 |
| 255 | 0.03 |
| 256 | 0.01 |
| 257 | 0.02 |
| 258 | 0.01 |
| 259 | 0.05 |
| 260 | 0.04 |
| 261 | 0.028 |
| 262 | 0.278 |
| 263 | 3.214 |
| 264 | 0.002 |
| 265 | 0.012 |
| 266 | 0.005 |
| 267 | 0.018 |
| 268 | 0.013 |
| 269 | 0.002 |
| 270 | 0.005 |
| 271 | 0.011 |
| 272 | 0.116 |
| 273 | 0.031 |
| 274 | 0.08 |
| 275 | 0.026 |
| 276 | 0.059 |
| 277 | 0.021 |
| 278 | 0.015 |
| 279 | 0.011 |
| 280 | 0.019 |
| 281 | 0.023 |
| 282 | 0.648 |
| 283 | 0.051 |
| 284 | 0.002 |
| 285 | 0.004 |
| 286 | 2.41 |
| 287 | 0.002 |
| 288 | 0.034 |
| 289 | 0.023 |
| 290 | 0.037 |
| 291 | 0.365 |
| 292 | 0.006 |
| 293 | 0.012 |
| 294 | 0.021 |
| 295 | 0.024 |
| 296 | 0.032 |
| 297 | 0.013 |
| 298 | 0.411 |
| 299 | 0.028 |
| 300 | 0.055 |
| 301 | 4.101 |
| 302 | 0.32 |
| 303 | 0.816 |
| 304 | 0.506 |
| 305 | 1.633 |
| 306 | 0.511 |
| 307 | 0.116 |
| 308 | 0.592 |
| 309 | 0.13 |
| 310 | 0.153 |
| 311 | 0.253 |
| 312 | 0.326 |
| 313 | 0.266 |
| 314 | 0.084 |
| 315 | 0.647 |
| 316 | 0.319 |
| 317 | 0.01 |
| 318 | 0.193 |
| 319 | 2.523 |
| 320 | 3.371 |
| 321 | 5.2 |
| 322 | 3.957 |
| 323 | 0.179 |
| 324 | 0.566 |
| 325 | 0.104 |
| 326 | 0.137 |
| 327 | 0.197 |
| 328 | 0.011 |
| 329 | 0.062 |
| 330 | 0.092 |
| 331 | 0.038 |
| 332 | 0.129 |
| 333 | 0.073 |
| 334 | 0.068 |
| 335 | 0.113 |
| 336 | 0.33 |
| 337 | 0.014 |
| 338 | 0.06 |
| 339 | 0.09 |
| 340 | 0.221 |
| 341 | 0.164 |
| 342 | 0.993 |
| 343 | 3.754 |
| 344 | 0.186 |
| 345 | >10 |
| 346 | 0.042 |
| 347 | 0.119 |
| 348 | 0.071 |
| 349 | 0.267 |
| 350 | 0.129 |
| 351 | 0.452 |
| 352 | 0.081 |
| 353 | 0.274 |
| 354 | 0.489 |
| 355 | 0.11 |
| 356 | 0.09 |
| 357 | 0.091 |
| 358 | 0.014 |
| 359 | 0.026 |
| 360 | 4.764 |
| 361 | 2.303 |
| 362 | 1.998 |
| 363 | 0.028 |
| 364 | 0.004 |
| 365 | 0.233 |
| 366 | 0.171 |
| 367 | 0.001 |
| 368 | 0.018 |
| 369 | 0.002 |
| 370 | 0.001 |
| 371 | 0.024 |
| 372 | 0.134 |
| 373 | 0.007 |
| 374 | 0.031 |
| 375 | 0.075 |
| 376 | 0.014 |
| 377 | 0.012 |
| 378 | 0.145 |
| 379 | 0.014 |
| 380 | 0.418 |
| 381 | 0.05 |
| 382 | 0.041 |
| 383 | 0.327 |
| 384 | 0.168 |
| 385 | 0.698 |

| Example | human EC$_{50}$ [µM] |
|---|---|
| 386 | 0.169 |
| 387 | 0.371 |
| 388 | 0.172 |
| 389 | 0.033 |
| 390 | 0.053 |
| 391 | 0.122 |
| 392 | 0.054 |
| 393 | 0.095 |
| 394 | 0.302 |
| 395 | 0.032 |
| 396 | 0.029 |
| 397 | 0.017 |
| 398 | 0.003 |
| 399 | 0.165 |
| 400 | 0.049 |
| 401 | 0.005 |
| 402 | 0.006 |
| 403 | 0.138 |
| 404 | 0.005 |
| 405 | 0.008 |
| 406 | 0.009 |
| 407 | 0.012 |
| 408 | 0.118 |
| 409 | 0.21 |
| 410 | 0.011 |
| 411 | 0.995 |
| 412 | 0.03 |
| 413 | 0.018 |
| 414 | 0.018 |
| 415 | n.a. |
| 416 | 0.018 |
| 417 | 0.008 |
| 418 | 0.004 |
| 419 | 0.008 |
| 420 | 0.015 |
| 421 | 0.03 |
| 422 | 0.011 |
| 423 | 0.002 |
| 424 | 0.001 |
| 425 | 0.014 |
| 426 | 0.041 |
| 427 | 0.004 |
| 428 | 0.018 |
| 429 | 0.002 |
| 430 | 0.021 |
| 431 | 0.465 |
| 432 | 0.057 |
| 433 | 0.055 |
| 434 | 0.049 |
| 435 | 0.066 |
| 436 | 0.062 |
| 437 | 0.075 |
| 438 | 0.132 |
| 439 | 0.081 |
| 440 | 0.148 |
| 441 | 0.039 |
| 442 | 0.109 |
| 443 | 0.098 |
| 444 | 0.103 |
| 445 | 0.027 |
| 446 | 0.059 |
| 447 | 0.012 |
| 448 | 0.018 |
| 449 | 0.009 |
| 450 | 0.416 |
| 451 | 0.024 |
| 452 | 0.015 |
| 453 | 0.005 |
| 454 | 0.27 |
| 455 | 0.012 |
| 456 | 0.016 |
| 457 | 0.017 |
| 458 | 0.022 |
| 459 | 0.364 |
| 460 | 0.421 |
| 461 | 0.156 |
| 462 | 0.153 |
| 463 | 0.154 |
| 464 | 0.152 |
| 465 | 0.35 |
| 466 | 0.347 |
| 467 | 0.348 |
| 468 | 0.349 |
| 469 | 0.42 |
| 470 | 0.061 |
| 471 | 0.17 |
| 472 | n.a. |
| 473 | 0.029 |
| 474 | 0.043 |
| 475 | 0.166 |
| 476 | 0.049 |
| 477 | 0.111 |
| 478 | 0.375 |
| 479 | 0.013 |
| 480 | 0.02 |
| 481 | 0.153 |
| 482 | 0.127 |
| 483 | 0.031 |
| 484 | 0.01 |
| 485 | 0.021 |
| 486 | 0.024 |
| 487 | 0.656 |
| 488 | 0.612 |
| 489 | 0.582 |
| 490 | 0.024 |
| 491 | 0.017 |
| 492 | 0.018 |
| 493 | 0.666 |
| 494 | 0.021 |
| 495 | 1.817 |
| 496 | 0.197 |
| 497 | 0.041 |
| 498 | 0.007 |
| 499 | 4.502 |
| 500 | 0.268 |
| 501 | 0.225 |
| 502 | 0.477 |
| 503 | 0.025 |
| 504 | 0.028 |
| 505 | 0.013 |
| 506 | 0.634 |
| 507 | 2.371 |
| 508 | 0.405 |
| 509 | 0.099 |
| 510 | 0.048 |
| 511 | 0.036 |

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations

CAS RN=Chemical Abstracts registry number, 9-BBN=9-borabicyclo[3.3.1]nonane, $BBr_3$=boron tribromide, BOP=benzotriazol-1-yloxytris(dimethylamino)phosphonium hexafluorophosphate, CuBr DMS=copper bromide dimethylsulfide complex, CuI=copper iodide, DMA=dimethylacetamide, DME=1,2-dimethoxyethane, DMF=N,N-dimethylformamide, EI=electron impact, $ESI^-$=negative electrospray ionization, $ESI^+$=positive electrospray ionization, $Et_3N$=triethylamine, EtOAc=ethyl acetate, h=hour, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, min=minutes, $KHSO_4$=potassium hydrogen sulfate, LiOH=lithium hydroxide, $MgSO_4$=magnesium sulfate, MPLC=medium performance liquid chromatography, MS=mass spectrum, NaH=sodium hydride, $NaHCO_3$=sodium hydrogen carbonate, NaOH=sodium hydroxide, $Na_2SO_4$=sodium sulfate, $NH_4Cl$=ammonium chloride, P=protecting group, R=any group, rt=room temperature, $SiO_2$=silica gel, TBME=tert-butylmethylether, TBTU=O-benzotriazolyl tetramethylisouronium tetrafluoroborate, $TiCl_4$=titanium tetrachloride, THF=tetrahydrofuran, X=halogen.

Examples 1 and 2

(E)-3-(4-Dimethylamino-phenyl)-3-phenyl-1-pyridin-4-yl-propan-1-one oxime and (Z)-3-(4-dimethylamino-phenyl)-3-phenyl-1-pyridin-4-yl-propan-1-one oxime (E and Z oximes)

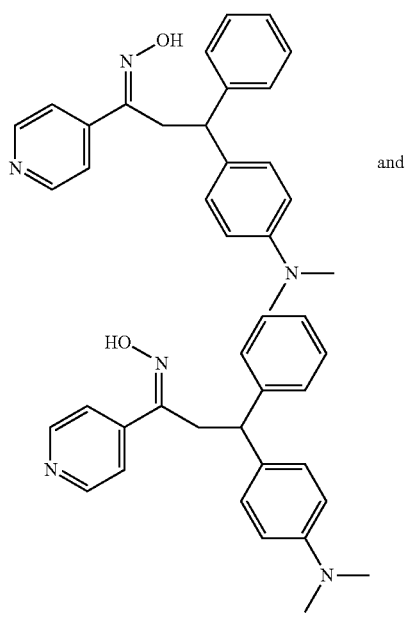

Step 1: 3-(4-Dimethylamino-phenyl)-3-phenyl-1-pyridin-4-yl-propan-1-one

Under an argon atmosphere, a solution of diethylzinc in hexane (1.0 M, 31 mL) was added to a solution of phenyl boronic acid (1.26 g) in anhydrous toluene (80 mL). The mixture was stirred at 60° C. overnight, was cooled to 0° C. and a solution of (E)-3-(4-dimethylamino-phenyl)-1-pyridin-4-yl-propenone (CAS RN: [18461-18-2], 1.05 g) in anhydrous toluene (20 mL) was added. After stirring at room temperature for 3 h, a saturated aqueous solution of $NH_4Cl$ was added, the phases were separated and the inorganic layer was extracted with EtOAc. The combined organic layers were washed with brine, dried over $Na_2SO_4$, filtered and concentrated in vacuo. Column chromatography on silica gel (EtOAc/n-heptane 2:1) followed by trituration from n-heptane gave the title compound (840 mg, 62%) as a yellow solid, MS ($ESI^+$): m/z=331.2 ([M+H]$^+$).

Step 2: (E)-3-(4-Dimethylamino-phenyl)-3-phenyl-1-pyridin-4-yl-propan-1-one oxime and (Z)-3-(4-dimethylamino-phenyl)-3-phenyl-1-pyridin-4-yl-propan-1-one oxime A solution of 3-(4-dimethylamino-phenyl)-3-phenyl-1-pyridin-4-yl-propan-1-one (838 mg), hydroxylamine hydrochloride (353 mg) and sodium hydrogencarbonate (426 mg) in ethanol/water (21 mL, 20:1) was heated under reflux for 2 hours. A saturated aqueous solution of $NH_4Cl$ was added to the reaction mixture and extraction was made with EtOAc (2×). The organic layers were combined, washed with brine, dried over $Na_2SO_4$, filtered and concentrated in vacuo. Column chromatography on silica gel (EtOAc/n-heptane 2:1) gave (E)-3-(4-dimethylamino-phenyl)-3-phenyl-1-pyridin-4-yl-propan-1-one oxime (420 mg, 48%) as a white foam, MS (ESI⁺): m/z=346.1 ([M+H]⁺), (Z)-3-(4-dimethylamino-phenyl)-3-phenyl-1-pyridin-4-yl-propan-1-one oxime (20 mg, 2%) as a colorless oil, MS (ESI⁺): m/z=346.1 ([M+H]⁺) and 3-(4-dimethylamino-phenyl)-3-phenyl-1-pyridin-4-yl-propan-1-one oxime as a mixture of isomers (313 mg, 36%), MS (ESI⁺): m/z=346.1 ([M+H]⁺).

Examples 3 and 4

(+)-(E)-3-(4-Dimethylamino-phenyl)-3-phenyl-1-pyridin-4-yl-propan-1-one oxime and (−)-(E)-3-(4-dimethylamino-phenyl)-3-phenyl-1-pyridin-4-yl-propan-1-one oxime

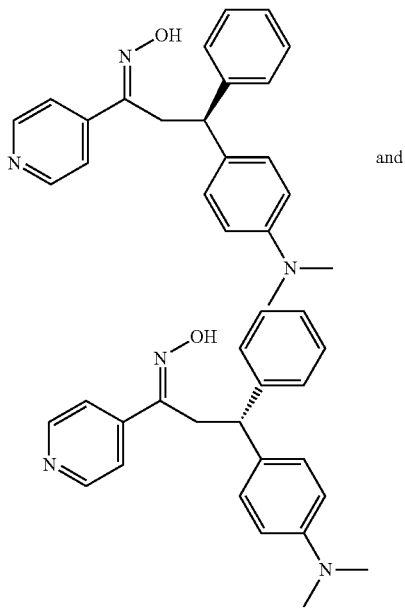

and

Chiral HPLC separation of 3-(4-dimethylamino-phenyl)-3-phenyl-1-pyridin-4-yl-propan-1-one oxime (Chiralpak AD, 10% EtOH/n-heptane) yielded (+)-(E)-3-(4-dimethylamino-phenyl)-3-phenyl-1-pyridin-4-yl-propan-1-one oxime as a white foam, MS (ESI⁺): m/z=346.1 ([M+H]⁺) and (−)-(E)-3-(4-dimethylamino-phenyl)-3-phenyl-1-pyridin-4-yl-propan-1-one oxime as a white foam, MS (ESI⁺): m/z=346.1 ([M+H]⁺).

Example 5

(E)-3-(4-Bromo-phenyl)-3-phenyl-1-pyridin-4-yl-propan-1-one oxime

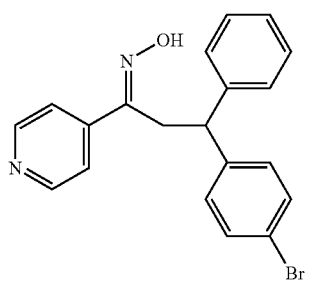

Step 1: 3-(4-Bromo-phenyl)-3-phenyl-1-pyridin-4-yl-propan-1-one

In analogy to example 1, step 1, from (E)-3-(4-bromo-phenyl)-1-pyridin-4-yl-propenone (CAS RN: [16232-03-4]) and phenylboronic acid was prepared the title compound as a yellow oil, MS (ESI⁺): m/z=366.1 ([M+H]⁺, 1Br).

Step 2: (E)-3-(4-Bromo-phenyl)-3-phenyl-1-pyridin-4-yl-propan-1-one oxime

In analogy to example 1, step 2, from 3-(4-bromo-phenyl)-3-phenyl-1-pyridin-4-yl-propan-1-one and hydroxylamine hydrochloride in the presence of NaHCO₃ was prepared (E)-3-(4-bromo-phenyl)-3-phenyl-1-pyridin-4-yl-propan-1-one oxime as a white solid, MS (ESI⁺): m/z=381.1 ([M+H]⁺, 1Br).

Example 6

(E)-3-(4-Dimethylamino-phenyl)-1-pyridin-4-yl-3-o-tolyl-propan-1-one oxime

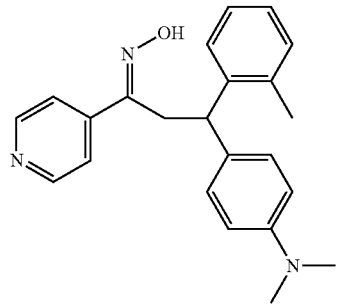 [SMILES: Cc1ccccc1C(C/C(=N\O)c1ccncc1)c1ccc(N(C)C)cc1]

Step 1: 3-(4-Dimethylamino-phenyl)-1-pyridin-4-yl-3-o-tolyl-propan-1-one

In analogy to example 1, step 1, from (E)-3-(4-dimethylamino-phenyl)-1-pyridin-4-yl-propenone (CAS RN: [18461-18-2]) and o-tolyl boronic acid was prepared the title compound as a yellow solid, MS (ESI⁺): m/z=345.2 ([M+H]⁺).

Step 2: (E)-3-(4-Dimethylamino-phenyl)-1-pyridin-4-yl-3-o-tolyl-propan-1-one oxime In analogy to example 1, step 2, from 3-(4-dimethylamino-phenyl)-1-pyridin-4-yl-3-o-tolyl-propan-1-one and hydroxylamine hydrochloride in the presence of NaHCO₃ was prepared the title compound as a white foam, MS (ESI⁺): m/z=360.2 ([M+H]⁺).

Example 7

3-(4-Dimethylamino-phenyl)-1-pyridin-4-yl-3-m-tolyl-propan-1-one oxime

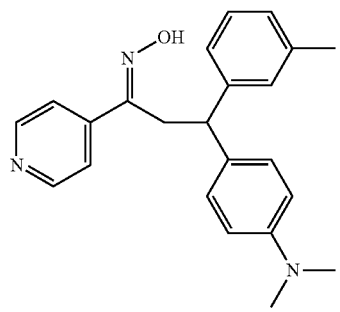 [SMILES: Cc1cccc(C(C/C(=N\O)c2ccncc2)c2ccc(N(C)C)cc2)c1]

Step 1: 3-(4-Dimethylamino-phenyl)-1-pyridin-4-yl-3-m-tolyl-propan-1-one

In analogy to example 1, step 1, from (E)-3-(4-dimethylamino-phenyl)-1-pyridin-4-yl-propenone (CAS RN: [18461-18-2]) and m-tolyl boronic acid was prepared the title compound as an orange liquid, MS (ESI⁺): m/z=345.1 ([M+H]⁺).

Step 2: 3-(4-Dimethylamino-phenyl)-1-pyridin-4-yl-3-m-tolyl-propan-1-one oxime In analogy to example 1, step 2, from 3-(4-dimethylamino-phenyl)-1-pyridin-4-yl-3-m-tolyl-propan-1-one and hydroxylamine hydrochloride in the presence of NaHCO₃ was prepared the title compound as a mixture of E and Z isomers (3:1) as a yellow foam, MS (ESI⁺): m/z=360.1 ([M+H]⁺).

Examples 8 to 10

(+)-(E)-3-(4-Dimethylamino-phenyl)-1-pyridin-4-yl-3-p-tolyl-propan-1-one oxime, (−)-(E)-3-(4-dimethylamino-phenyl)-1-pyridin-4-yl-3-p-tolyl-propan-1-one oxime and (Z)-3-(4-dimethylamino-phenyl)-1-pyridin-4-yl-3-p-tolyl-propan-1-one oxime

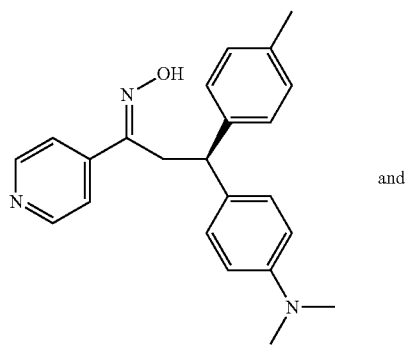

and

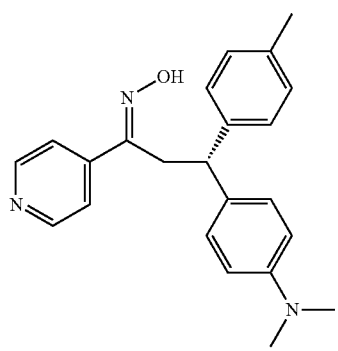

and

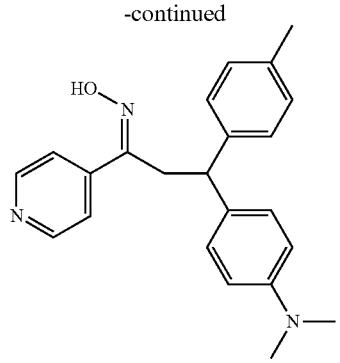

Step 1: 3-(4-Dimethylamino-phenyl)-1-pyridin-4-yl-3-p-tolyl-propan-1-one

In analogy to example 1, step 1, from (E)-3-(4-dimethylamino-phenyl)-1-pyridin-4-yl-propenone (CAS RN: [18461-18-2]) and p-tolyl boronic acid was prepared the title compound as a yellow oil, MS (ESI⁺): m/z=345.2 ([M+H]⁺).

Step 2: 3-(4-Dimethylamino-phenyl)-1-pyridin-4-yl-3-p-tolyl-propan-1-one oxime In analogy to example 1, step 2, from 3-(4-dimethylamino-phenyl)-1-pyridin-4-yl-3-p-tolyl-propan-1-one and hydroxylamine hydrochloride in the presence of NaHCO₃ was prepared the title compound as a mixture of E and Z isomers as a yellow oil, MS (ESI⁺): m/z=360.2 ([M+H]⁺).

Step 3: (+)-(E)-3-(4-Dimethylamino-phenyl)-1-pyridin-4-yl-3-p-tolyl-propan-1-one oxime, (−)-(E)-3-(4-dimethylamino-phenyl)-1-pyridin-4-yl-3-p-tolyl-propan-1-one oxime and (Z)-3-(4-dimethylamino-phenyl)-1-pyridin-4-yl-3-p-tolyl-propan-1-one oxime Chiral HPLC separation of 3-(4-dimethylamino-phenyl)-1-pyridin-4-yl-3-p-tolyl-propan-1-one oxime (Chiralpak AD, 15% ethanol in n-heptane) yielded (+)-(E)-3-(4-dimethylamino-phenyl)-1-pyridin-4-yl-3-p-tolyl-propan-1-one oxime as a colorless oil, MS (ESI⁺): m/z=360.2 ([M+H]⁺), (−)-(E)-3-(4-dimethylamino-phenyl)-1-pyridin-4-yl-3-p-tolyl-propan-1-one oxime as a white solid, MS (ESI⁺): m/z=360.1 ([M+H]⁺) and (Z)-3-(4-dimethylamino-phenyl)-1-pyridin-4-yl-3-p-tolyl-propan-1-one oxime as a colorless oil, MS (ESI⁺): m/z=360.2 ([M+H]⁺).

Example 11

3-(3-Bromo-phenyl)-1-pyridin-4-yl-3-o-tolyl-propan-1-one oxime

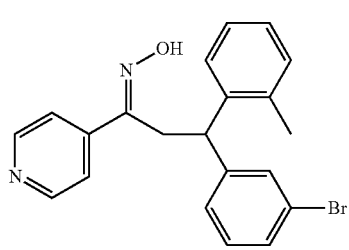 [SMILES: Cc1ccccc1C(C/C(=N\O)c1ccncc1)c1cccc(Br)c1]

Step 1: 3-(3-Bromo-phenyl)-1-pyridin-4-yl-propenone

3-Bromobenzaldehyde (6.3 mL), 4-acetylpyridine (6.0 mL) and sodium hydroxide pellets (2.16 g) were combined using a mortar and pestle, and the mixture was aggregated until a pale yellow powder formed (10-15 min). The powder was washed with water/ethanol (10:3) and the crude product was purified by column chromatography on silica gel (EtOAc/n-heptane 1:1) to give the title compound (1.54 g, 10%) as a yellow solid, MS (ESI+): m/z=287.9 ([M+H]+, 1Br).

Step 2: 3-(3-Bromo-phenyl)-3-o-tolyl-1-pyridin-4-yl-propan-1-one

In analogy to example 1, step 1, from (E)-3-(3-bromo-phenyl)-1-pyridin-4-yl-propenone and o-tolylboronic acid was prepared the title compound as a colorless oil, MS (ESI+): m/z=380.1 ([M+H]+, 1Br).

Step 3: 3-(3-Bromo-phenyl)-1-pyridin-4-yl-3-o-tolyl-propan-1-one oxime

In analogy to example 1, step 2, from 3-(3-bromo-phenyl)-3-o-tolyl-1-pyridin-4-yl-propan-1-one and hydroxylamine hydrochloride in the presence of NaHCO₃ was prepared the title compound as a mixture of E and Z isomers (3:1) as a white foam, MS (ESI+): m/z=395.0 ([M+H]+, 1Br).

Example 12

(E)-3-(3-Bromo-phenyl)-3-phenyl-1-pyridin-4-yl-propan-1-one oxime

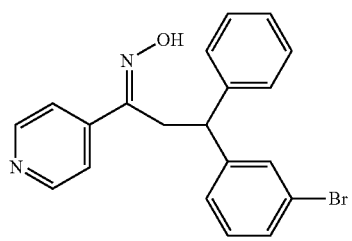 [SMILES: O/N=C(\CC(c1ccccc1)c1cccc(Br)c1)c1ccncc1]

Step 1: 3-(3-Bromo-phenyl)-3-phenyl-1-pyridin-4-yl-propan-1-one

In analogy to example 1, step 1, from (E)-3-(3-bromo-phenyl)-1-pyridin-4-yl-propenone (example 11) and phenylboronic acid was prepared the title compound as a colorless oil, MS (ESI+): m/z=380.1 ([M+H]+, 1Br).

Step 2: (E)-3-(3-Bromo-phenyl)-3-phenyl-1-pyridin-4-yl-propan-1-one oxime

In analogy to example 1, step 2, from 3-(3-bromo-phenyl)-3-phenyl-1-pyridin-4-yl-propan-1-one and hydroxylamine hydrochloride in the presence of NaHCO₃ was prepared the title compound as a colorless oil, MS (ESI+): m/z=381.0 ([M+H]+, 1Br).

Example 13

3-(3-Bromo-phenyl)-1-pyridin-4-yl-pentan-1-one oxime

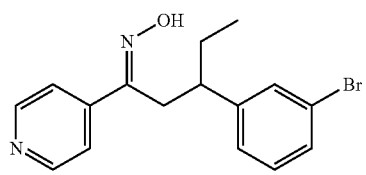 [SMILES: CCC(C/C(=N\O)c1ccncc1)c1cccc(Br)c1]

As a byproduct from the crude reaction mixture of example 12, step 2, HPLC separation (Chiralpak AD column, 10% isopropanol in n-heptane) provided 3-(3-bromo-phenyl)-1-pyridin-4-yl-pentan-1-one oxime as a mixture of E and Z isomers (4:1) as a colorless oil, MS (ESI+): m/z=333.0 ([M+H]+, 1Br).

Example 14

(E)-3,3-Diphenyl-1-pyridin-4-yl-propan-1-one oxime

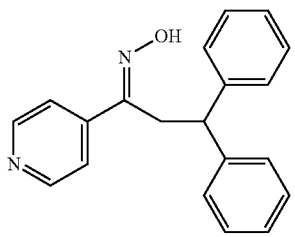 [SMILES: O/N=C(\CC(c1ccccc1)c1ccccc1)c1ccncc1]

Step 1: 3,3-Diphenyl-1-pyridin-4-yl-propan-1-one

In analogy to example 1, step 1, from (E)-3-phenyl-1-pyridin-4-yl-propenone (CAS RN: [53940-08-2]) and phenylboronic acid was prepared the title compound as a yellow oil, MS (ESI+): m/z=288.0 ([M+H]+).

Step 2: (E)-3,3-Diphenyl-1-pyridin-4-yl-propan-1-one oxime

In analogy to example 1, step 2, from 3,3-diphenyl-1-pyridin-4-yl-propan-1-one and hydroxylamine hydrochloride in the presence of NaHCO₃ was prepared the title compound as a white solid, MS (ESI⁺): m/z=303.1 ([M+H]⁺).

Example 15

(E)-3-(4-Bromo-phenyl)-1-(1-oxy-pyridin-4-yl)-3-phenyl-propan-1-one oxime

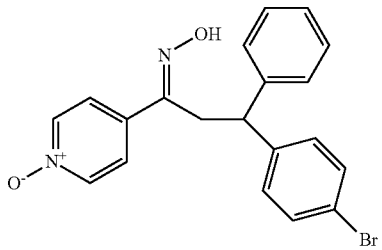 [SMILES: [O-][n+]1ccc(/C(CC(c2ccccc2)c2ccc(Br)cc2)=N/O)cc1]

To a solution of (E)-3-(4-bromo-phenyl)-3-phenyl-1-pyridin-4-yl-propan-1-one oxime (example 5, 75 mg) in dichloromethane (2 mL) and methanol (0.5 mL) was added 3-chloroperoxybenzoic acid (57 mg). The reaction mixture was stirred at rt for 3 hours, a saturated aqueous solution of NaHCO₃ was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc to CH₂Cl₂/MeOH 9:1) to yield (E)-3-(4-bromo-phenyl)-1-(1-oxy-pyridin-4-yl)-3-phenyl-propan-1-one oxime (78 mg, 98%) as a colorless oil, MS (ESI⁺): m/z=397.0 ([M+H]⁺, 1Br).

Example 16

(E)-3-(4-Cyclopropyl-phenyl)-3-phenyl-1-pyridin-4-yl-propan-1-one oxime

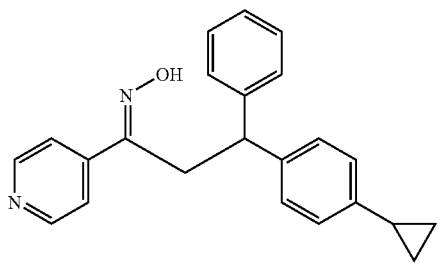 [SMILES: O/N=C(\CC(c1ccccc1)c1ccc(C2CC2)cc1)c1ccncc1]

To a solution of (E)-3-(4-bromo-phenyl)-3-phenyl-1-pyridin-4-yl-propan-1-one oxime (example 5, 100 mg) in toluene (0.9 mL) and water (0.1 mL) was added potassium cyclopropyltrifluoroborate (47 mg), tri-potassium phosphate monohydrate (199 mg) and tetrakis(triphenylphosphine) palladium (0) (6 mg). The mixture was heated to 100° C. overnight. After cooling to rt a saturated aqueous solution of NaHCO₃ was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 1:1) to yield (E)-3-(4-cyclopropyl-phenyl)-3-phenyl-1-pyridin-4-yl-propan-1-one oxime (43 mg, 49%) as a white foam, MS (ESI⁺): m/z=343.3 ([M+H]⁺).

Example 17

3-(4-Dimethylamino-phenyl)-3-(3,4-dimethyl-phenyl)-1-pyridin-4-yl-propan-1-one oxime

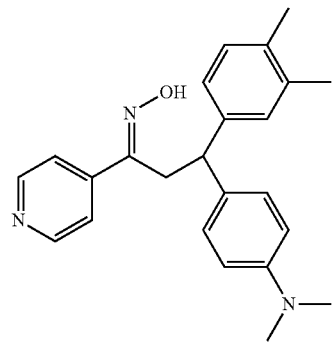 [SMILES: Cc1ccc(C(C/C(=N\O)c2ccncc2)c2ccc(N(C)C)cc2)cc1C]

Step 1: 3-(4-Dimethylamino-phenyl)-3-(3,4-dimethyl-phenyl)-1-pyridin-4-yl-propan-1-one In analogy to example 1, step 1, from (E)-3-(4-dimethylamino-phenyl)-1-pyridin-4-yl-propenone (CAS RN: [18461-18-2]) and 3,4-dimethylbenzeneboronic acid was prepared the title compound as an orange oil, MS (ESI⁺): m/z=359.3 ([M+H]⁺).

Step 2: 3-(4-Dimethylamino-phenyl)-3-(3,4-dimethyl-phenyl)-1-pyridin-4-yl-propan-1-one oxime In analogy to example 1, step 2, from 3-(4-dimethylamino-phenyl)-3-(3,4-dimethyl-phenyl)-1-pyridin-4-yl-propan-1-one and hydroxylamine hydrochloride in the presence of NaHCO₃ was prepared the title compound as a mixture of E and Z isomers (2.3:1) as a yellow foam, MS (ESI⁺): m/z=374.3 ([M+H]⁺).

Example 18

3-(4-Dimethylamino-phenyl)-3-(3,5-dimethyl-phenyl)-1-pyridin-4-yl-propan-1-one oxime

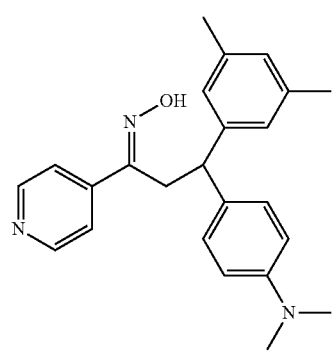 [SMILES: Cc1cc(C)cc(C(C/C(=N\O)c2ccncc2)c2ccc(N(C)C)cc2)c1]

Step 1: 3-(4-Dimethylamino-phenyl)-3-(3,5-dimethyl-phenyl)-1-pyridin-4-yl-propan-1-one In analogy to example 1, step 1, from (E)-3-(4-dimethylamino-phenyl)-1-pyridin-4-yl-propenone (CAS RN: [18461-18-2]) and 3,5-dimethyl-phenyl boronic acid was prepared the title compound as an orange oil, MS (ESI⁺): m/z=359.3 ([M+H]⁺).

Step 2: 3-(4-Dimethylamino-phenyl)-3-(3,5-dimethyl-phenyl)-1-pyridin-4-yl-propan-1-one oxime In analogy to example 1, step 2, from 3-(4-dimethylamino-phenyl)-3-(3,5-dimethyl-phenyl)-1-pyridin-4-yl-propan-1-one and hydroxylamine hydrochloride in the presence of NaHCO$_3$ was prepared the title compound as a mixture of E and Z isomers (2.9:1) as a light yellow foam, MS (ESI$^+$): m/z=374.3 ([M+H]$^+$).

Example 19

(E)-3-(3'-Methanesulfonyl-biphenyl-4-yl)-3-phenyl-1-pyridin-4-yl-propan-1-one oxime

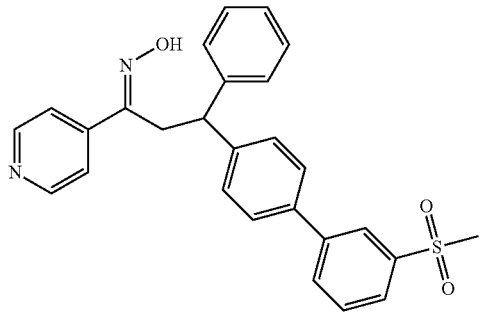 [SMILES: CS(=O)(=O)c1cccc(-c2ccc(C(C/C(=N\O)c3ccncc3)c3ccccc3)cc2)c1]

To a stirred solution of (E)-3-(4-bromo-phenyl)-3-phenyl-1-pyridin-4-yl-propan-1-one oxime (example 5, 10 mg), (3-methylsulfonylphenyl)boronic acid (58 mg), tetrakis-(triphenylphosphine)palladium (0) (30 mg) in 1,2-dimethoxyethane (2 mL) was added potassium carbonate (90 mg). The mixture was stirred at 80° C. overnight. Water was added, the phases were separated and the inorganic one was extracted with diethyl ether (2×). The combined organic layers were washed with brine, dried over Na$_2$SO$_4$, filtered and concentrated in vacuo. The crude product was purified by flash chromatography on silica gel (EtOAc/n-heptane 2:1 to EtOAc) to yield (E)-3-(3'-methanesulfonyl-biphenyl-4-yl)-3-phenyl-1-pyridin-4-yl-propan-1-one oxime (21 mg, 18%) as a light yellow foam, MS (ESI$^+$): m/z=457.2 ([M+H]$^+$).

Example 20

(E)-3-(4'-Methanesulfonyl-biphenyl-4-yl)-3-phenyl-1-pyridin-4-yl-propan-1-one oxime

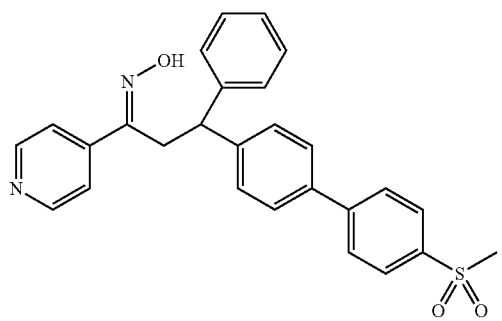 [SMILES: CS(=O)(=O)c1ccc(-c2ccc(C(C/C(=N\O)c3ccncc3)c3ccccc3)cc2)cc1]

In analogy to example 19, from (E)-3-(4-bromo-phenyl)-3-phenyl-1-pyridin-4-yl-propan-1-one oxime (example 5) and (4-methylsulfonylphenyl)boronic acid was prepared the title compound as a light yellow foam, MS (ESI$^+$): m/z=457.2 ([M+H]$^+$).

Example 21

4'-{3-[(E)-Hydroxyimino]-1-phenyl-3-pyridin-4-yl-propyl}-biphenyl-4-sulfonic acid methylamide

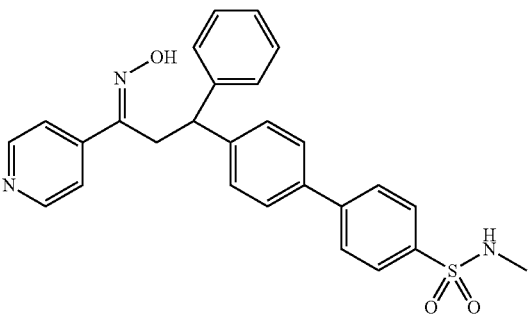 [SMILES: CNS(=O)(=O)c1ccc(-c2ccc(C(C/C(=N\O)c3ccncc3)c3ccccc3)cc2)cc1]

In analogy to example 19, from (E)-3-(4-bromo-phenyl)-3-phenyl-1-pyridin-4-yl-propan-1-one oxime (example 5) and (4-methylaminosulfonyl)benzene boronic acid was prepared the title compound as a colorless oil, MS (ESI$^+$): m/z=472.3 ([M+H]$^+$).

Example 22

(E)-3-Phenyl-1-pyridin-4-yl-3-(4-pyrimidin-5-yl-phenyl)-propan-1-one oxime

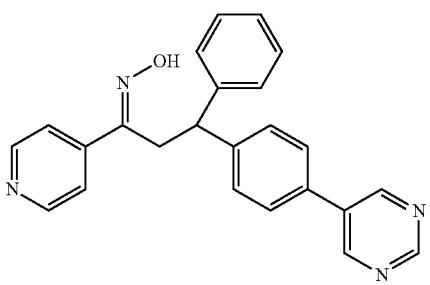 [SMILES: O/N=C(\CC(c1ccccc1)c1ccc(-c2cncnc2)cc1)c1ccncc1]

To a stirred solution of (E)-3-(4-bromo-phenyl)-3-phenyl-1-pyridin-4-yl-propan-1-one oxime (example 5, 10 mg) and pyrimidine-5-boronic acid (49 mg) in a mixture of DMA/H$_2$O (2.1 mL, 20:1) tetrakis(triphenylphosphine)palladium (0) (36 mg), triphenylphosphine (17 mg) and potassium fluoride (31 mg) were added. The mixture was irradiated in the microwave at 140° C. for 15 min. A saturated aqueous solution of NH$_4$Cl was added, the phases were separated and the inorganic one was extracted with EtOAc (2×). The combined organic layers were washed with brine, dried over Na$_2$SO$_4$, filtered and concentrated in vacuo. The crude product was purified by flash chromatography on an ISOLUTE Flash NH$_2$ cartridge (EtOAc) to yield the title compound (45 mg, 45%) as a white foam, MS (ESI+): m/z=381.1 ([M+H]+).

Example 23

(E)-3-(3'-Methanesulfonyl-biphenyl-3-yl)-3-phenyl-1-pyridin-4-yl-propan-1-one oxime

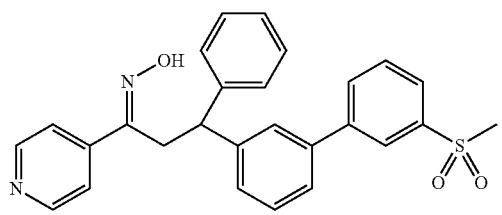 [SMILES: CS(=O)(=O)c1cccc(-c2cccc(C(C/C(=N\O)c3ccncc3)c3ccccc3)c2)c1]

In analogy to example 22, from (E)-3-(3-bromo-phenyl)-3-phenyl-1-pyridin-4-yl-propan-1-one oxime (example 12) and (3-methylsulfonylphenyl)boronic acid was prepared the title compound as a white foam, MS (ESI+): m/z=457.2 ([M+H]+).

Example 24

(E)-3-(4'-Methanesulfonyl-biphenyl-3-yl)-3-phenyl-1-pyridin-4-yl-propan-1-one oxime

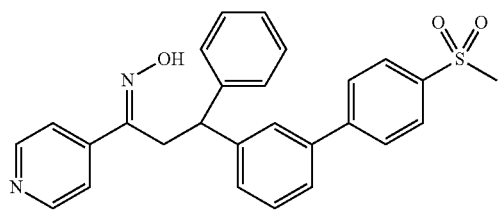 [SMILES: CS(=O)(=O)c1ccc(-c2cccc(C(C/C(=N\O)c3ccncc3)c3ccccc3)c2)cc1]

In analogy to example 22, from (E)-3-(3-bromo-phenyl)-3-phenyl-1-pyridin-4-yl-propan-1-one oxime (example 12) and (4-methylsulfonylphenyl)boronic acid was prepared the title compound as a colorless oil, MS (ESI+): m/z=457.3 ([M+H]+).

Example 25

(E)-3-[4-(6-Methyl-pyridin-3-yl)-phenyl]-3-phenyl-1-pyridin-4-yl-propan-1-one oxime

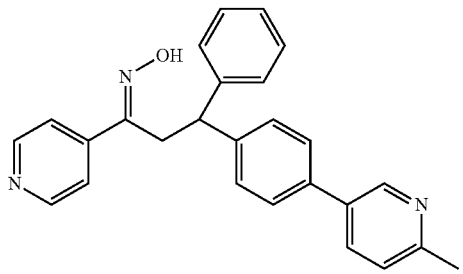 [SMILES: Cc1ccc(-c2ccc(C(C/C(=N\O)c3ccncc3)c3ccccc3)cc2)cn1]

In analogy to example 22, from (E)-3-(4-bromo-phenyl)-3-phenyl-1-pyridin-4-yl-propan-1-one oxime (example 5) and 6-methylpyridine-3-boronic acid was prepared the title compound as a colorless oil, MS (ESI+): m/z=394.1 ([M+H]+).

Example 26

(E)-3-(4'-Ethanesulfonyl-biphenyl-4-yl)-3-phenyl-1-pyridin-4-yl-propan-1-one oxime

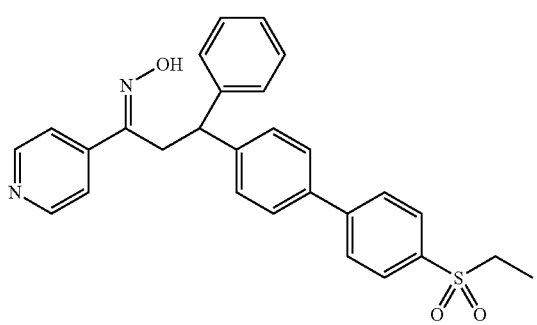 [SMILES: CCS(=O)(=O)c1ccc(-c2ccc(C(C/C(=N\O)c3ccncc3)c3ccccc3)cc2)cc1]

In analogy to example 22, from (E)-3-(4-bromo-phenyl)-3-phenyl-1-pyridin-4-yl-propan-1-one oxime (example 5) and 4-(ethanesulfonyl)benzeneboronic acid was prepared the title compound as a white foam, MS (ESI+): m/z=471.1 ([M+H]+).

Example 27

(E)-3-(4'-Hydroxymethyl-biphenyl-4-yl)-3-phenyl-1-pyridin-4-yl-propan-1-one oxime

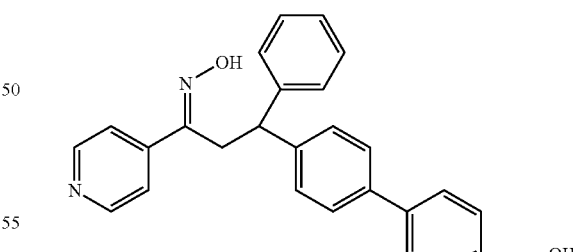

In analogy to example 22, from (E)-3-(4-bromo-phenyl)-3-phenyl-1-pyridin-4-yl-propan-1-one oxime (example 5) and 4-(hydroxymethyl)phenylboronic acid was prepared the title compound as a yellow foam, MS (ESI+): m/z=409.2 ([M+H]+).

Example 28

(4'-{3-[(E)-Hydroxyimino]-1-phenyl-3-pyridin-4-yl-propyl}-biphenyl-3-yloxy)-acetic acid ethyl ester

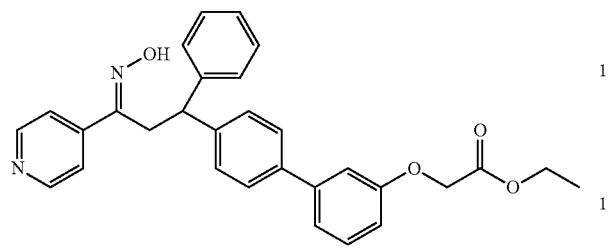

In analogy to example 22, from (E)-3-(4-bromo-phenyl)-3-phenyl-1-pyridin-4-yl-propan-1-one oxime (example 5) and 3-(ethoxycarbonyl)methoxyphenylboronic acid pinacol ester was prepared the title compound as a colorless oil, MS (ESI$^+$): m/z=481.3 ([M+H]$^+$).

Example 29

3-(4'-Methanesulfonyl-biphenyl-3-yl)-1-pyridin-4-yl-3-o-tolyl-propan-1-one oxime

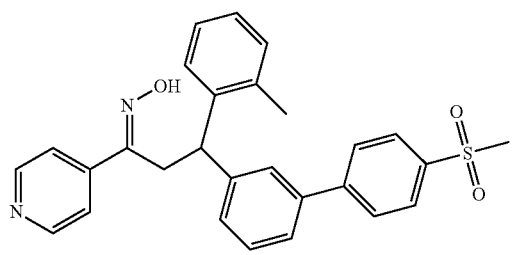 [SMILES: Cc1ccccc1C(C/C(=N\O)c1ccncc1)c1cccc(-c2ccc(S(C)(=O)=O)cc2)c1]

In analogy to example 22, from 3-(3-bromo-phenyl)-1-pyridin-4-yl-3-o-tolyl-propan-1-one oxime (example 11) and (4-methylsulfonylphenyl)boronic acid was prepared the title compound as a mixture of E and Z isomers (3:1) as a yellow oil, MS (ESI$^+$): m/z=471.1 ([M+H]$^+$).

Example 30

3-(3'-Methanesulfonyl-biphenyl-3-yl)-1-pyridin-4-yl-3-o-tolyl-propan-1-one oxime

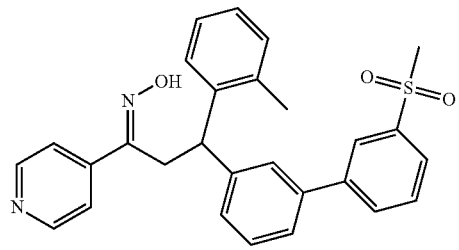 [SMILES: Cc1ccccc1C(C/C(=N\O)c1ccncc1)c1cccc(-c2cccc(S(C)(=O)=O)c2)c1]

In analogy to example 22, from 3-(3-bromo-phenyl)-1-pyridin-4-yl-3-o-tolyl-propan-1-one oxime (example 11) and (3-methylsulfonylphenyl)boronic acid was prepared the title compound as a mixture of E and Z isomers (3:1) as a white foam, MS (ESI$^+$): m/z=471.2 ([M+H]$^+$).

Example 31

3-(4-Bromo-phenyl)-1-pyridin-4-yl-3-o-tolyl-propan-1-one oxime

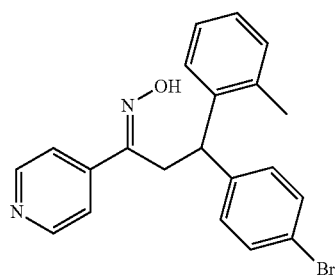 [SMILES: Cc1ccccc1C(C/C(=N\O)c1ccncc1)c1ccc(Br)cc1]

Step 1: 3-(4-Bromo-phenyl)-1-pyridin-4-yl-3-o-tolyl-propan-1-one

In analogy to example 1, step 1, from 3-(4-bromo-phenyl)-1-pyridin-4-yl-propenone (CAS RN: [16232-03-4]) and o-tolylboronic acid was prepared the title compound as yellow foam, MS (ESI$^+$): m/z=380.1 ([M+H]$^+$, 1Br).

Step 2: 3-(4-Bromo-phenyl)-1-pyridin-4-yl-3-o-tolyl-propan-1-one oxime

In analogy to example 1, step 2, from 3-(4-bromo-phenyl)-1-pyridin-4-yl-3-o-tolyl-propan-1-one and hydroxylamine hydrochloride in the presence of NaHCO$_3$ was prepared the title compound as a mixture of E and Z isomers (2.5:1) as a white foam, MS (ESI$^+$): m/z=395.1 ([M+H]$^+$, 1Br).

Example 32

3-(3'-Methanesulfonyl-biphenyl-4-yl)-1-pyridin-4-yl-3-o-tolyl-propan-1-one oxime

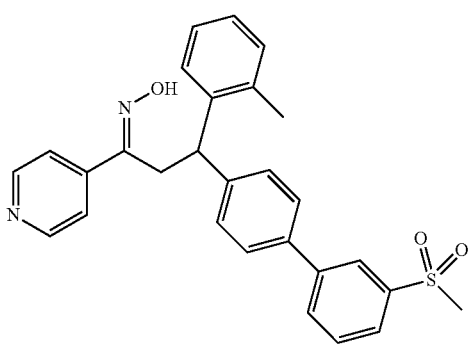 [SMILES: Cc1ccccc1C(C/C(=N\O)c1ccncc1)c1ccc(-c2cccc(S(C)(=O)=O)c2)cc1]

In analogy to example 22, from 3-(4-bromo-phenyl)-1-pyridin-4-yl-3-o-tolyl-propan-1-one oxime (example 31) and (3-methylsulfonylphenyl)boronic acid was prepared the title compound as a mixture of E and Z isomers (2:1) as a white foam, MS (ESI$^+$): m/z=471.1 ([M+H]$^+$).

Example 33

3-(4'-Methanesulfonyl-biphenyl-4-yl)-1-pyridin-4-yl-3-o-tolyl-propan-1-one oxime

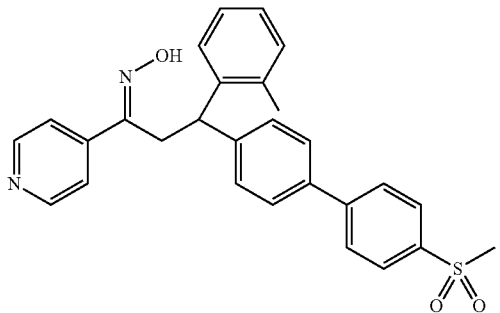 [SMILES: Cc1ccccc1C(C/C(=N\O)c1ccncc1)c1ccc(-c2ccc(S(C)(=O)=O)cc2)cc1]

In analogy to example 22, from 3-(4-bromo-phenyl)-1-pyridin-4-yl-3-o-tolyl-propan-1-one oxime (example 31) and 4-(methylsulfonyl)phenylboronic acid was prepared the title compound as a mixture of E and Z isomers (2:1) as a white solid, MS (ESI$^+$): m/z=471.1 ([M+H]$^+$).

Example 34

1-Pyridin-4-yl-3-(4-pyrimidin-5-yl-phenyl)-3-o-tolyl-propan-1-one oxime

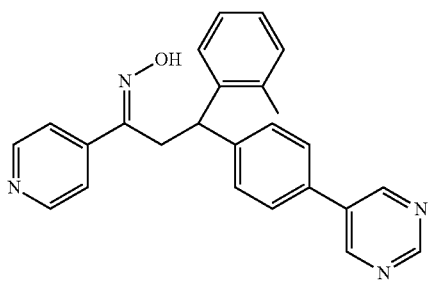

In analogy to example 22, from 3-(4-bromo-phenyl)-1-pyridin-4-yl-3-o-tolyl-propan-1-one oxime (example 31) and pyrimidine-5-boronic acid was prepared the title compound as a mixture of E and Z isomers (2.3:1) as a white foam, MS (ESI$^+$): m/z=395.2 ([M+H]$^+$).

Examples 35 to 38

(+)-(E)-1-Pyridin-4-yl-3-(4-pyrimidin-5-yl-phenyl)-3-o-tolyl-propan-1-one oxime, (−)-(E)-1-pyridin-4-yl-3-(4-pyrimidin-5-yl-phenyl)-3-o-tolyl-propan-1-one oxime, (−)-(Z)-1-pyridin-4-yl-3-(4-pyrimidin-5-yl-phenyl)-3-o-tolyl-propan-1-one oxime and (+)-(Z)-1-pyridin-4-yl-3-(4-pyrimidin-5-yl-phenyl)-3-o-tolyl-propan-1-one oxime

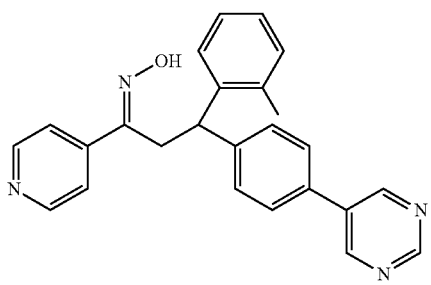 [SMILES: Cc1ccccc1C(C/C(=N\O)c1ccncc1)c1ccc(-c2cncnc2)cc1]

(+)-(E)-Isomer
(−)-(E)-Isomer

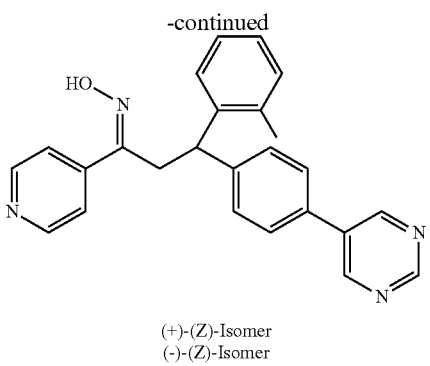

(+)-(Z)-Isomer
(−)-(Z)-Isomer

Separation of 1-pyridin-4-yl-3-(4-pyrimidin-5-yl-phenyl)-3-o-tolyl-propan-1-one oxime (example 34) by chiral HPLC on a Chiralpak AD column with 30% ethanol in n-heptane yielded (+)-(E)-1-pyridin-4-yl-3-(4-pyrimidin-5-yl-phenyl)-3-o-tolyl-propan-1-one oxime as a white solid, MS (ESI$^+$): m/z=395.2 ([M+H]$^+$), (−)-(E)-1-pyridin-4-yl-3-(4-pyrimidin-5-yl-phenyl)-3-o-tolyl-propan-1-one oxime as a white solid, MS (ESI$^+$): m/z=395.2 ([M+H]$^+$), (−)-(Z)-1-pyridin-4-yl-3-(4-pyrimidin-5-yl-phenyl)-3-o-tolyl-propan-1-one oxime as a white solid, MS (ESI$^+$): m/z=395.2 ([M+H]$^+$) and (+)-(Z)-1-pyridin-4-yl-3-(4-pyrimidin-5-yl-phenyl)-3-o-tolyl-propan-1-one oxime as a white solid, MS (ESI$^+$): m/z=395.2 ([M+H]$^+$).

Example 39

(E)-3-{4-[(2-Methoxy-ethyl)-methyl-amino]-phenyl}-1-pyridin-4-yl-3-o-tolyl-propan-1-one oxime

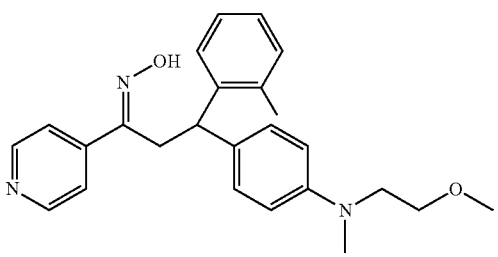 [SMILES: COCCN(C)c1ccc(C(C/C(=N\O)c2ccncc2)c2ccccc2C)cc1]

To a suspension of tris(dibenzylideneacetone)dipalladium (23 mg), sodium tert-butylate (83 mg), 2(di-tertbutylphosphino)biphenyl (15 mg) and 3-(4-bromo-phenyl)-1-pyridin-4-yl-3-o-tolyl-propan-1-one oxime (example 31, 200 mg) in toluene (10 mL) was added a solution of N (2-methoxyethyl)methylamine (158 mg) in toluene (10 mL). The reaction mixture was stirred at 80° C. overnight, cooled to room temperature and a saturated aqueous solution of NH$_4$Cl was added. The phases were separated and the inorganic layer was extracted with EtOAc (2×). The combined organic layers were washed with brine, dried over Na$_2$SO$_4$, filtered and concentrated in vacuo. Column chromatography on silica gel (EtOAc/n-heptane 2:1 to EtOAc) yielded (E)-3-{4-[(2-methoxy-ethyl)-methyl-amino]-phenyl}-1-pyridin-4-yl-3-o-tolyl-propan-1-one oxime containing less than 10% of the Z isomer (88 mg, 43%) as a yellow foam, MS (ESI$^+$): m/z=404.3 ([M+H]$^+$).

Example 40

3-(4-Piperidin-1-yl-phenyl)-1-pyridin-4-yl-3-o-tolyl-propan-1-one oxime

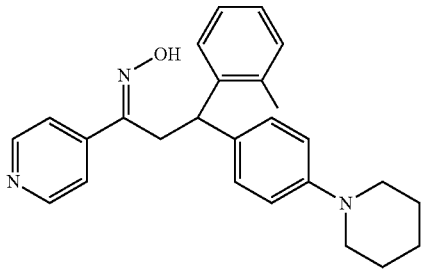 [SMILES: Cc1ccccc1C(C/C(=N\O)c1ccncc1)c1ccc(N2CCCCC2)cc1]

In analogy to example 39, from 3-(4-bromo-phenyl)-1-pyridin-4-yl-3-o-tolyl-propan-1-one oxime (example 31) and piperidine was prepared 3-(4-piperidin-1-yl-phenyl)-1-pyridin-4-yl-3-o-tolyl-propan-1-one oxime as a mixture of E and Z isomers (2:1) as a light yellow oil, MS (ESI$^+$): m/z=400.3 ([M+H]$^+$).

Example 41

3-(4-Morpholin-4-yl-phenyl)-1-pyridin-4-yl-3-o-tolyl-propan-1-one oxime

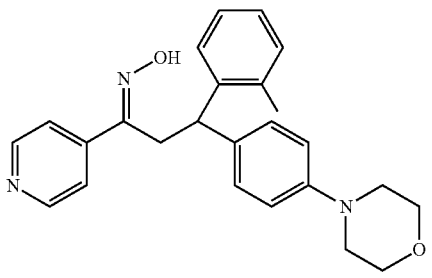 [SMILES: Cc1ccccc1C(C/C(=N\O)c1ccncc1)c1ccc(N2CCOCC2)cc1]

In analogy to example 39, from 3-(4-bromo-phenyl)-1-pyridin-4-yl-3-o-tolyl-propan-1-one oxime (example 31) and morpholine was prepared 3-(4-morpholin-4-yl-phenyl)-1-pyridin-4-yl-3-o-tolyl-propan-1-one oxime as a mixture of E and Z isomers (2:1) as a yellow oil, MS (ESI$^+$): m/z=402.3 ([M+H]$^+$).

Example 42

3-(4-Diethylamino-phenyl)-1-pyridin-4-yl-3-o-tolyl-propan-1-one oxime

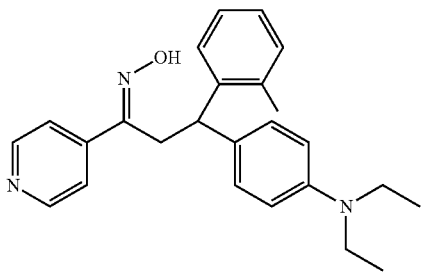 [SMILES: CCN(CC)c1ccc(C(C/C(=N\O)c2ccncc2)c2ccccc2C)cc1]

In analogy to example 39, from 3-(4-bromo-phenyl)-1-pyridin-4-yl-3-o-tolyl-propan-1-one oxime (example 31) and diethylamine was prepared 3-(4-diethylamino-phenyl)-1-pyridin-4-yl-3-o-tolyl-propan-1-one oxime as a mixture of E and Z isomers (6:1) as a yellow oil, MS (ESI$^+$): m/z=388.2 ([M+H]$^+$).

Examples 43 and 44

(Z)-3-(4-Bromo-phenyl)-1-pyridin-4-yl-2-o-tolyl-propan-1-one oxime and (E)-3-(4-bromo-phenyl)-1-pyridin-4-yl-2-o-tolyl-propan-1-one oxime

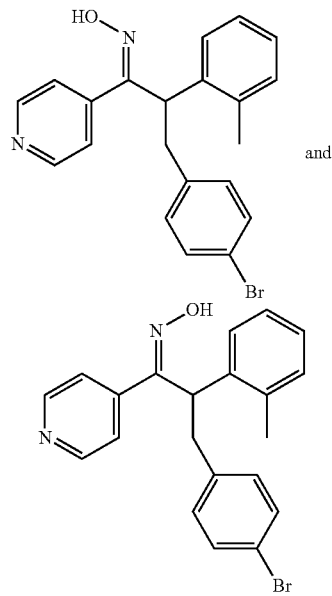

and

Step 1: 3-(4-Bromo-phenyl)-1-pyridin-4-yl-2-o-tolyl-propan-1-one

To a solution of 1-pyridin-4-yl-2-otolyl-ethanone (CAS RN: [1184032-72-1]) (300 mg) in THF (10 mL) was added sodium hydride (55% in mineral oil, 65 mg) at rt and the mixture was heated to 45° C. for 3 hours. The reaction mixture was then cooled down to 0° C., and a solution of 4-bromobenzylbromide (390 mg) in THF (2 mL) was added dropwise. The mixture was then stirred at 50° C. for 3 hours. Ice and water were added to the reaction mixture, the phases were separated and the inorganic layer was extracted with EtOAc (2×). The combined organic layers were washed with brine, dried over Na$_2$SO$_4$, filtered and concentrated in vacuo. Column chromatography on silica gel (EtOAc/n-heptane 1:2) yielded the title compound (105 mg, 19%) as a yellow oil, MS (EI$^+$): m/z=379 ([M]$^+$, 1Br).

Step 2: (Z)-3-(4-Bromo-phenyl)-1-pyridin-4-yl-2-o-tolyl-propan-1-one oxime and (E)-3-(4-bromo-phenyl)-1-pyridin-4-yl-2-o-tolyl-propan-1-one oxime In analogy to example 1, step 2, from 3-(4-bromo-phenyl)-1-pyridin-4-yl-2-o-tolyl-propan-1-one and hydroxylamine hydrochloride in the presence of NaHCO$_3$ was prepared (Z)-3-(4-bromo-phenyl)-1-pyridin-4-yl-2-o-tolyl-propan-1-one oxime as a white foam, MS (ESI$^+$): m/z=395.0 ([M+H]$^+$, 1Br)

and (E)-3-(4-bromo-phenyl)-1-pyridin-4-yl-2-o-tolyl-propan-1-one oxime as a white foam, MS (ESI+): m/z=395.0 ([M+H]+, 1Br).

Example 45

3-(4-Bromo-phenyl)-1-(2,6-dimethyl-pyridin-4-yl)-2-phenyl-propan-1-one oxime

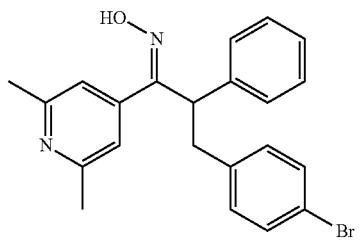 [SMILES: Cc1cc(/C(=N\O)C(Cc2ccc(Br)cc2)c2ccccc2)cc(C)n1]

Steps 1 and 2: 2,6-Dimethyl-isonicotinic acid butyl ester

To a suspension of 2,6-dichloropyridine-4-carboxylic acid (16 g) (CAS RN: [5398-44-7]) in n-butanol (150 mL) was added thionylchloride (9.1 mL) dropwise. The reaction mixture was heated to reflux for 1.5 hours, cooled to room temperature and then a saturated aqueous solution of NaHCO$_3$ (160 mL) was added (pH~7). The mixture was extracted with EtOAc (2×150 mL). The combined organic layers were washed with brine, dried over Na$_2$SO$_4$, filtered and concentrated in vacuo to give 2,6-dichloro-isonicotinic acid butyl ester (21.51 g) as crude product, which was directly subjected to the next step.

To a solution of crude 2,6-dichloro-isonicotinic acid butyl ester (21.51 g) and tetrakis(triphenylphosphine)palladium (0) (3.0 g) in toluene (250.0 mL) was added dimethylzinc (2M in toluene, 65.0 mL) dropwise. The reaction mixture was stirred at reflux for 2.5 hours, cooled to room temperature and then a saturated aqueous solution of NaHCO$_3$ (250 mL) was added dropwise. The phases were separated and the inorganic one was extracted with diethylether (2×200 mL). The combined organic layers were washed with brine, dried over Na$_2$SO$_4$, filtered and concentrated in vacuo. The crude product was purified by flash chromatography on silica gel (EtOAc/n-heptane 1:4) to yield 2,6-dimethyl-isonicotinic acid butyl ester (16.67 g, 96%, 2 steps) as yellow liquid, MS (ESI+): m/z=208.0 [M+H]+.

Step 3: N-Methoxy-2,6,N-trimethyl-isonicotinamide

Under argon a suspension of 2,6-dimethyl-isonicotinic acid butyl ester (16.67 g) and N,O-dimethylhydroxylamine hydrochloride (12.2 g) in THF (150 mL) was cooled down to −20° C. A solution of isopropylmagnesium chloride (2M in THF, 120.6 mL) was added over 20 min maintaining the temperature below −5° C. The mixture was stirred for 2.5 hours at −10° C. and quenched with a saturated aqueous solution of NH$_4$Cl (200 mL). The phases were separated and the inorganic one was extracted with EtOAc (2×). The combined organic layers were washed with brine, dried over Na$_2$SO$_4$, filtered and concentrated in vacuo. Column chromatography on silica gel (EtOAc/n-heptane 2:1 to EtOAc) yielded the title compound (14.1 g, 90%) as a yellow liquid, MS (ESI+): m/z=195.0 [M+H]+.

Step 4: 1-(2,6-Dimethyl-pyridin-4-yl)-2-phenyl-ethanone

At −78° C., to a solution of N-methoxy-2,6,N-trimethyl-isonicotinamide (1 g) and benzyl bromide (0.73 mL) in THF (30 mL) was added n-BuLi (1.6M in hexane, 6.6 mL) dropwise. The reaction was stirred at −78° C. for 3 hours. A saturated aqueous solution of NH$_4$Cl (200 mL) was added, the phases were separated and the inorganic one was extracted with EtOAc (2×). The combined organic layers were washed with brine, dried over Na$_2$SO$_4$, filtered and concentrated in vacuo. Column chromatography on silica gel (EtOAc/n-heptane 1:2) yielded the title compound (1.8 g, 99%) as a colorless liquid, MS (ESI+): m/z=226.1 [M+H]+.

Step 5: 3-(4-Bromo-phenyl)-1-(2,6-dimethyl-pyridin-4-yl)-2-phenyl-propan-1-one

In analogy to example 43, step 1, from 1-(2,6-dimethyl-pyridin-4-yl)-2-phenyl-ethanone and 4-bromobenzylbromide was prepared the title compound as a yellow oil, MS (ESI+): m/z=394.0 ([M+H]+, 1Br).

Step 6: 3-(4-Bromo-phenyl)-1-(2,6-dimethyl-pyridin-4-yl)-2-phenyl-propan-1-one oxime In analogy to example 1, step 2, from 3-(4-bromo-phenyl)-1-(2,6-dimethyl-pyridin-4-yl)-2-phenyl-propan-1-one and hydroxylamine hydrochloride in the presence of NaHCO$_3$ was prepared 3-(4-bromo-phenyl)-1-(2,6-dimethyl-pyridin-4-yl)-2-phenyl-propan-1-one oxime as a mixture of E and Z isomers (1:2) as a white foam, MS (ESI+): m/z=409.2 ([M+H]+, 1Br).

Example 46

3-(4-Bromo-phenyl)-1-(2-chloro-pyridin-4-yl)-3-phenyl-propan-1-one oxime

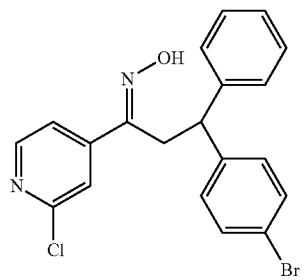 [SMILES: O/N=C(\CC(c1ccccc1)c1ccc(Br)cc1)c1ccnc(Cl)c1]

Step 1: 3-(4-Bromo-phenyl)-1-(2-chloro-pyridin-4-yl)-propenone

In analogy to example 11, step 1, from 4-bromobenzaldehyde and 1-(2-chloropyridin-4-yl)ethanone (CAS RN: [23794-15-2]) was prepared the title compound as a yellow solid, MS (EI+): m/z=321 ([M]+, 1Br,1Cl).

Steps 2 and 3: 3-(4-bromo-phenyl)-1-(2-chloro-pyridin-4-yl)-3-phenyl-propan-1-one oxime In analogy to example 1, step 1, from 3-(4-bromo-phenyl)-1-(2-chloro-pyridin-4-yl)-propenone and phenylboronic acid was prepared 3-(4-bromo-phenyl)-1-(2-chloro-pyridin-4-yl)-3-phenyl-propan-1-one as a yellow solid, which was directly subjected to the next step.
In analogy to example 1, step 2, from 3-(4-bromo-phenyl)-1-(2-chloro-pyridin-4-yl)-3-phenyl-propan-1-one and hydroxylamine hydrochloride in the presence of NaHCO$_3$ was prepared the title compound as a mixture of E and Z isomers (2.6:1) as a colorless oil, MS (ESI$^-$): m/z=413.0 ([M–H]$^-$, 1Br,1Cl).

Example 47

(E)-3-(4-Bromo-phenyl)-1-(2,6-dichloro-pyridin-4-yl)-3-phenyl-propan-1-one oxime

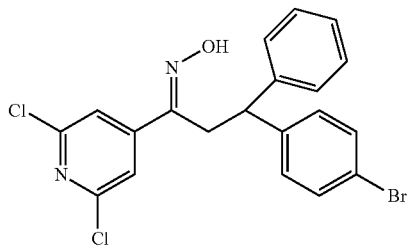 [SMILES: O/N=C(\CC(c1ccccc1)c1ccc(Br)cc1)c1cc(Cl)nc(Cl)c1]

Steps 1 and 2: 3-(4-Bromo-phenyl)-1-(2,6-dichloro-pyridin-4-yl)-3-phenyl-propan-1-one In analogy to example 11, step 1, from 4-bromobenzaldehyde and 1-[2,6-dichloropyridin-4-yl]ethanone (CAS RN: [185319-20-4]) was prepared 3-(4-bromo-phenyl)-1-(2,6-dichloro-pyridin-4-yl)-propenone as a yellow solid, which was directly subjected to the next step. In analogy to example 1, step 1, from 3-(4-bromo-phenyl)-1-(2,6-dichloro-pyridin-4-yl)-propenone and phenylboronic acid was prepared the title compound as a colorless oil, MS (EI$^+$): m/z=433 ([M]$^+$, 1Br, 1Cl).

Step 3: 3-(4-Bromo-phenyl)-1-(2,6-dichloro-pyridin-4-yl)-3-phenyl-propan-1-one oxime In analogy to example 1, step 2, from (E)-3-(4-bromo-phenyl)-1-(2,6-dichloro-pyridin-4-yl)-3-phenyl-propan-1-one and hydroxylamine hydrochloride in the presence of NaHCO$_3$ was prepared the title compound as a white foam, MS (ESI$^+$): m/z=449.0 ([M+H]$^+$, 1Br,1Cl).

Example 48

(E)-3-(4-Bromo-phenyl)-3-o-tolyl-1-(2,3,5-trifluoro-phenyl)-propan-1-one oxime

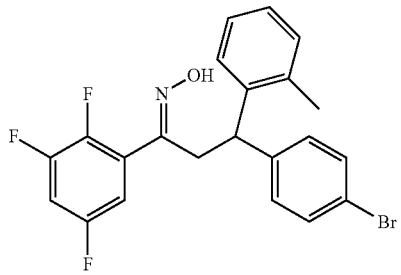 [SMILES: Cc1ccccc1C(C/C(=N\O)c1cc(F)cc(F)c1F)c1ccc(Br)cc1]

Steps 1 and 2: 3-(4-Bromo-phenyl)-3-o-tolyl-1-(2,3,5-trifluoro-phenyl)-propan-1-one In analogy to example 11, step 1, from 4-bromobenzaldehyde and 2,3,5-trifluoroacetophenone (CAS RN: [243459-93-0]) was prepared (E)-3-(4-bromo-phenyl)-1-(2,3,5-trifluoro-phenyl)-propenone as a yellow solid, which was directly subjected to the next step. In analogy to example example 1, step 1, from (E)-3-(4-bromo-phenyl)-1-(2,3,5-trifluoro-phenyl)-propenone and phenylboronic acid was prepared the title compound as a colorless oil, MS (EI): m/z=432 ([M]$^+$, 1Br).

Step 3: (E)-3-(4-bromo-phenyl)-3-o-tolyl-1-(2,3,5-trifluoro-phenyl)-propan-1-one oxime In analogy to example 1, step 2, from 3-(4-bromo-phenyl)-3-o-tolyl-1-(2,3,5-trifluoro-phenyl)-propan-1-one and hydroxylamine hydrochloride in the presence of NaHCO$_3$ was prepared the title compound as a white foam, MS (ESI$^-$): m/z=446.0 ([M–H]$^-$, 1Br).

Example 49

3-(4-Bromo-phenyl)-1-(2,5-dichloro-phenyl)-3-o-tolyl-propan-1-one oxime

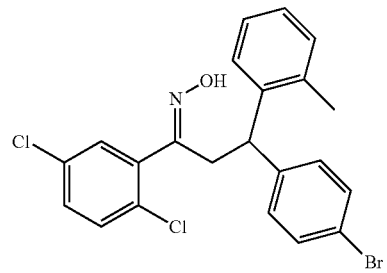 [SMILES: Cc1ccccc1C(C/C(=N\O)c1cc(Cl)ccc1Cl)c1ccc(Br)cc1]

Steps 1-3: 3-(4-Bromo-phenyl)-1-(2,5-dichloro-phenyl)-3-o-tolyl-propan-1-one oxime To a solution of 4-bromobenzaldehyde (1.5 g) and 2,5-dichloroacetophenone (2.30 g) in MeOH (12 mL) was added 2M NaOH (12.16 mL) at 0° C. The solution was stirred at 50° C. for 2 hours and at rt overnight. The precipitate was removed by filtration and was washed with a mixture of MeOH:water (1:1). The crude product was purified by column chromatography on silica gel (EtOAc) to yield 3-(4-bromo-phenyl)-1-(2,5-dichloro-phenyl)-propenone as a yellow oil (2.98 g), which was directly subjected to the next reaction.

In analogy to example 1, step 1, from 3-(4-bromo-phenyl)-1-(2,5-dichloro-phenyl)-propenone and o-tolylboronic acid was prepared 3-(4-bromo-phenyl)-1-(2,5-dichloro-phenyl)-3-o-tolyl-propan-1-one as light yellow oil, which was directly subjected to the next step.

In analogy to example 1, step 2, from 3-(4-bromo-phenyl)-1-(2,5-dichloro-phenyl)-3-o-tolyl-propan-1-one and hydroxylamine hydrochloride in the presence of NaHCO$_3$ was prepared the title compound as a mixture of E and Z isomers (2.4:1) as a white foam, MS (EI): m/z=463 ([M]+, 1Br).

Examples 50 and 51

(+)-(E)-3-(4-Bromo-phenyl)-1-(2,5-dichloro-phenyl)-3-o-tolyl-propan-1-one oxime and (−)-(E)-3-(4-bromo-phenyl)-1-(2,5-dichloro-phenyl)-3-o-tolyl-propan-1-one oxime

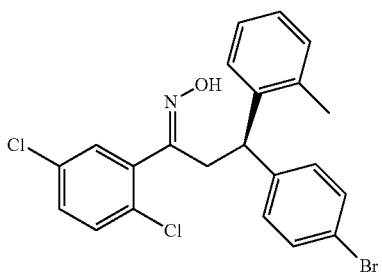

and

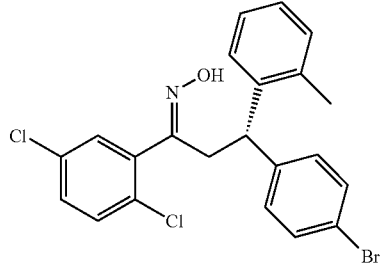

Separation of 3-(4-bromo-phenyl)-1-(2,5-dichloro-phenyl)-3-o-tolyl-propan-1-one oxime (example 49) by chiral HPLC on a Chiralpak AD column with 5% isopropanol inn-heptane gave (+)-(E)-3-(4-bromo-phenyl)-1-(2,5-dichloro-phenyl)-3-o-tolyl-propan-1-one oxime as a white foam, MS (ESI−): m/z=459.9 ([M−H]−, 1Br,1Cl) and (−)-(E)-3-(4-bromo-phenyl)-1-(2,5-dichloro-phenyl)-3-o-tolyl-propan-1-one oxime as a white foam, MS (ESI−): m/z=460.0 ([M−H]−, 1Br,1Cl).

Example 52

(E)-3-(4-Bromo-phenyl)-1-(2,5-difluoro-phenyl)-3-o-tolyl-propan-1-one oxime

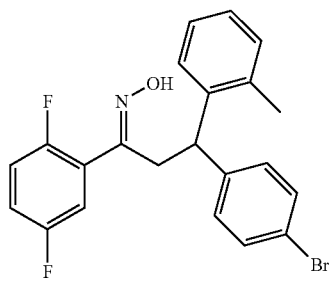 [SMILES: Cc1ccccc1C(C/C(=N\O)c1cc(F)ccc1F)c1ccc(Br)cc1]

Step 1: 3-(4-Bromo-phenyl)-1-(2,5-difluoro-phenyl)-propenone

In analogy to example 49, step 1, from 4-bromobenzaldehyde and 2,5-difluoro-acetophenone was prepared the title compound as yellow solid, MS (ESI+): m/z=323.1 ([M+H]+, 1Br).

Step 2: 3-(4-Bromo-phenyl)-1-(2,5-difluoro-phenyl)-3-o-tolyl-propan-1-one

In analogy to example 1, step 1, from 3-(4-bromo-phenyl)-1-(2,5-difluoro-phenyl)-propenone and o-tolylboronic acid was prepared the title compound as colorless oil, MS (EI): m/z=414 ([M]+, 1Br).

Step 3: (E)-3-(4-Bromo-phenyl)-1-(2,5-difluoro-phenyl)-3-o-tolyl-propan-1-one oxime In analogy to example 1, step 2, from 3-(4-bromo-phenyl)-1-(2,5-difluoro-phenyl)-3-o-tolyl-propan-1-one and hydroxylamine hydrochloride in the presence of NaHCO3 was prepared the title compound as a white foam, MS (ESI−): m/z=428.0 ([M−H]−, 1Br).

Example 53

(E)-3-(4-bromo-phenyl)-1-(3,5-difluoro-phenyl)-3-o-tolyl-propan-1-one oxime

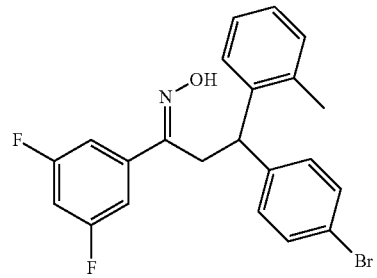 [SMILES: Cc1ccccc1C(C/C(=N\O)c1cc(F)cc(F)c1)c1ccc(Br)cc1]

Step 1: 3-(4-Bromo-phenyl)-1-(3,5-difluoro-phenyl)-propenone

In analogy to example 49, step 1, from 4-bromobenzaldehyde and 3,5-difluoroaceto-phenone was prepared the title compound as yellow solid, MS (EI): m/z=322 ([M]+, 1Br).

Step 2: 3-(4-Bromo-phenyl)-1-(3,5-difluoro-phenyl)-3-o-tolyl-propan-1-one

In analogy to example 1, step 1, from 3-(4-bromo-phenyl)-1-(3,5-difluoro-phenyl)-propenone and o-tolylboronic acid was prepared the title compound as colorless solid, MS (EI): m/z=414 ([M]+, 1Br).

Step 3: (E)-3-(4-bromo-phenyl)-1-(3,5-difluoro-phenyl)-3-o-tolyl-propan-1-one oxime In analogy to example 1, step 2, from 3-(4-bromo-phenyl)-1-(3,5-difluoro-phenyl)-3-o-tolyl-propan-1-one and hydroxylamine hydrochloride in the presence of NaHCO₃ was prepared the title compound as a white foam, MS (EI): m/z=429 ([M]⁺, 1Br).

Example 54

(E)-1-(3,5-Difluoro-phenyl)-3-(4-pyrimidin-5-yl-phenyl)-3-o-tolyl-propan-1-one oxime

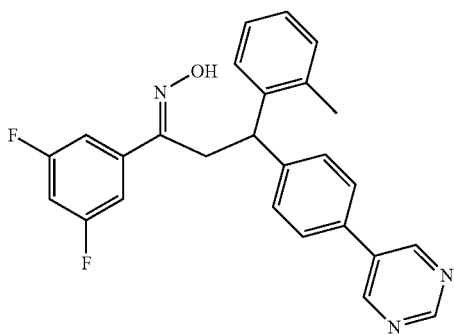 [SMILES: Cc1ccccc1C(C/C(=N\O)c1cc(F)cc(F)c1)c1ccc(-c2cncnc2)cc1]

In analogy to example 22, from (E)-3-(4-bromo-phenyl)-1-(3,5-difluoro-phenyl)-3-o-tolyl-propan-1-one oxime (example 53) and pyrimidine-5-boronic acid was prepared the title compound as a white foam, MS (ESI⁺): m/z=430.3 ([M+H]⁺).

Example 55

1-(2-Chloro-5-fluoro-pyridin-4-yl)-3,3-diphenyl-propan-1-one oxime

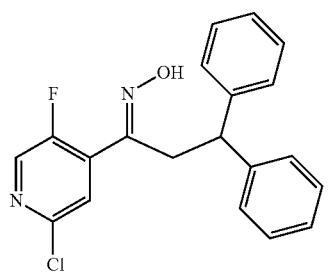 [SMILES: O/N=C(\CC(c1ccccc1)c1ccccc1)c1cc(Cl)ncc1F]

Step 1: N-Methoxy-N-methyl-3,3-diphenyl-propionamide

To a solution of 3,3-diphenylpropionic acid ((CAS RN: [606-83-7]), 1.5 g) in DMF (17 mL) was added TBTU (3.0 g) and Et₃N (2.8 mL) at 0° C. The reaction mixture was stirred at rt for 10 min and again was cooled down to 0° C. N,O-dimethylhydroxylamine hydrochloride (0.78 g) was added and the mixture was stirred at rt for 2 days. A saturated solution of NaHCO₃ and TBME were added, the phases were separated and the inorganic one was extracted with TBME. The combined organic layers were washed with 1M KHSO₄ followed by brine, dried over Na₂SO₄, filtered and concentrated in vacuo. The crude product was purified by flash chromatography on silica gel (EtOAc/n-heptane 1:1) to yield the title compound as a light brown oil (1.5 g, 84%), MS (ESI⁺): m/z=270.2 ([M+H]⁺).

Step 2: 1-(2-Chloro-5-fluoro-pyridin-4-yl)-3,3-diphenyl-propan-1-one

At −70° C. to a solution of 2-chloro-5-fluoro-4-iodopyridine (873 mg) in THF (20 mL) was added n-butyllithium (2.2 mL, 1.6M in hexane) over a period of 15 min slowly. To that solution N-methoxy-N-methyl-3,3-diphenyl-propionamide (200 mg) in THF (8 mL) was added and stirring was continued at that temperature for 1 h. A saturated solution of NH₄Cl was added, the mixture was diluted with EtOAc, the phases were separated and the inorganic one was extracted with EtOAc (2×). The combined organic layers were washed with brine, dried over Na₂SO₄, filtered and concentrated in vacuo. The crude product was purified by flash chromatography on silica gel (CH₂Cl₂/n-heptane 1:2) to yield the title compound as a white solid, MS (ESI⁺): m/z=340.09 ([M+H]⁺, 1Cl).

Step 3: 1-(2-Chloro-5-fluoro-pyridin-4-yl)-3,3-diphenyl-propan-1-one oxime

In analogy to example 1, step 2, from 1-(2-chloro-5-fluoro-pyridin-4-yl)-3,3-diphenyl-propan-1-one and hydroxylamine hydrochloride in the presence of NaHCO₃ was prepared 1-(2-chloro-5-fluoro-pyridin-4-yl)-3,3-diphenyl-propan-1-one oxime as a mixture of E and Z isomers (1.8:1) as a white foam, MS (EI): m/z=354 ([M]⁺, 1Cl).

Example 56

(E)-1-(2-Fluoro-6-methyl-pyridin-4-yl)-3,3-diphenyl-propan-1-one oxime

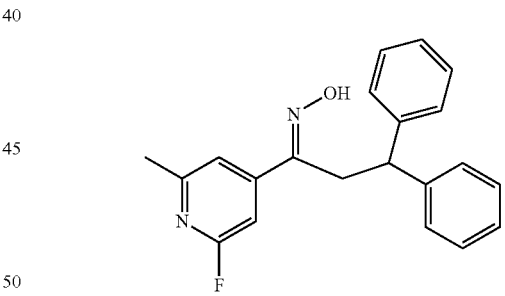

Step 1: 1-(2-Fluoro-6-methyl-pyridin-4-yl)-3,3-diphenyl-propan-1-one

In analogy to example 55, step 2, from N-methoxy-N-methyl-3,3-diphenyl-propionamide and 2-fluoro-4-iodo-6-picoline was prepared the title compound as an off-white solid, MS (ESI⁺): m/z=320.1449 ([M+H]⁺).

Step 2: (E)-1-(2-Fluoro-6-methyl-pyridin-4-yl)-3,3-diphenyl-propan-1-one oxime

In analogy to example 1, step 2, from 1-(2-fluoro-6-methyl-pyridin-4-yl)-3,3-diphenyl-propan-1-one and hydroxylamine hydrochloride in the presence of NaHCO₃ was prepared the title compound as a white oil, MS (ESI⁺): m/z=335.1553 ([M+H]⁺).

Example 57

1-(2-Methyl-pyridin-4-yl)-3,3-diphenyl-propan-1-one oxime

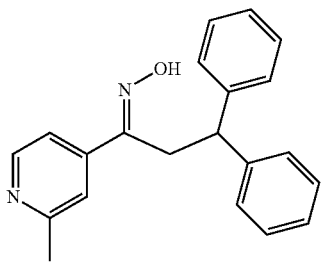 [SMILES: Cc1cc(/C(CC(c2ccccc2)c2ccccc2)=N/O)ccn1]

Step 1: 1-(2-Methyl-pyridin-4-yl)-3,3-diphenyl-propan-1-one

In analogy to example 55, step 2, the title compounds was prepared from N-methoxy-N-methyl-3,3-diphenyl-propionamide and 4-bromo-2-methylpyridine as a colorless oil, MS (ESI⁺): m/z=302.15 ([M+H]⁺).

Step 2: 1-(2-Methyl-pyridin-4-yl)-3,3-diphenyl-propan-1-one oxime

In analogy to example 1, step 2, from 1-(2-methyl-pyridin-4-yl)-3,3-diphenyl-propan-1-one and hydroxylamine hydrochloride in the presence of NaHCO₃ was prepared 1-(2-methyl-pyridin-4-yl)-3,3-diphenyl-propan-1-one oxime as a mixture of E and Z isomers (3:1) as a white foam, MS (ESI⁺): m/z=317.16 ([M+H]⁺).

Example 58

1-(5-Chloro-2-fluoro-pyridin-4-yl)-3,3-diphenyl-propan-1-one oxime

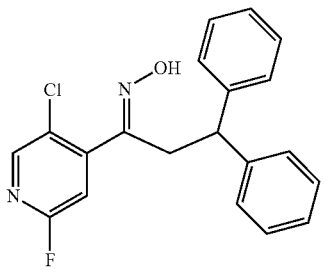 [SMILES: O/N=C(\CC(c1ccccc1)c1ccccc1)c1cc(F)ncc1Cl]

Step 1: 1-(5-Chloro-2-fluoro-pyridin-4-yl)-3,3-diphenyl-propan-1-one

In analogy to example 55, step 2, the title compound was prepared from N-methoxy-N-methyl-3,3-diphenyl-propionamide and 5-chloro-2-fluoro-4-iodopyridine as a light yellow liquid, MS (EI): m/z=339 ([M]⁺, 1Cl).

Step 2: 1-(5-Chloro-2-fluoro-pyridin-4-yl)-3,3-diphenyl-propan-1-one oxime

In analogy to example 1, step 2, from 1-(5-chloro-2-fluoro-pyridin-4-yl)-3,3-diphenyl-propan-1-one and hydroxylamine hydrochloride in the presence of NaHCO₃ was prepared 1-(5-chloro-2-fluoro-pyridin-4-yl)-3,3-diphenyl-propan-1-one oxime as a mixture of E and Z isomers (1.5:1) as a white foam, MS (EI): m/z=354 ([M]⁺, 1Cl).

Example 59

1-(2-Fluoro-5-methyl-pyridin-4-yl)-3,3-diphenyl-propan-1-one oxime

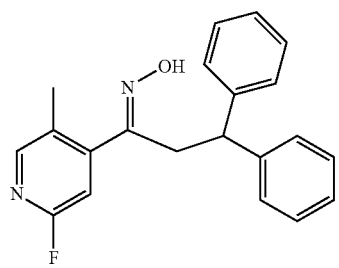 [SMILES: Cc1cnc(F)cc1/C(CC(c1ccccc1)c1ccccc1)=N/O]

Step 1: 1-(2-Fluoro-5-methyl-pyridin-4-yl)-3,3-diphenyl-propan-1-one

In analogy to example 55, step 2, the title compound was prepared from N-methoxy-N-methyl-3,3-diphenyl-propionamide and 2-fluoro-4-iodo-5-picoline (CAS RN: [153034-94-7]) as a yellow liquid, MS (ESI⁺): m/z=320.1 ([M+H]⁺).

Step 2: 1-(2-Fluoro-5-methyl-pyridin-4-yl)-3,3-diphenyl-propan-1-one oxime

In analogy to example 1, step 2, from 1-(2-fluoro-5-methyl-pyridin-4-yl)-3,3-diphenyl-propan-1-one and hydroxylamine hydrochloride in the presence of NaHCO₃ was prepared the title compound as a mixture of E and Z isomers (1.5:1) as a white oil, MS (ESI⁺): m/z=335.1 ([M+H]⁺).

Example 60

(E)-2-(10,11-Dihydro-5H-dibenzo[a,d]cyclohepten-5-yl)-1-pyridin-4-yl-ethanone oxime

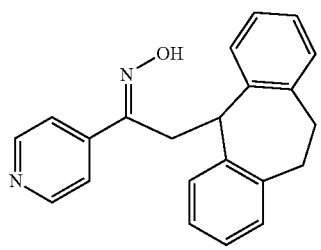 [SMILES: O/N=C(\CC1c2ccccc2CCc2ccccc21)c1ccncc1]

Step 1: 2-(10,11-Dihydro-5H-dibenzo[a,d]cyclohepten-5-yl)-N-methoxy-N-methyl-acetamide In analogy to example 55, step 1, from 10,11-dihydro-5H-dibenzo[a,d]cycloheptene-5-acetic acid (CAS RN: [4037-50-7]) and N,O-dimethylhydroxylamine hydrochloride was prepared the title compound as a colorless oil, MS (ESI⁺): m/z=296.3 ([M+H]⁺).

Step 2: 2-(10,11-Dihydro-5H-dibenzo[a,d]cyclohepten-5-yl)-1-pyridin-4-yl-ethanone In analogy to example 55, step 2, from 2-(10,11-dihydro-5H-dibenzo[a,d]cyclohepten-5-yl)-N-methoxy-N-methyl-acetamide and 4-iodopyridine was prepared the title compound as a white solid, MS (ESI⁺): m/z=314.1 ([M+H]⁺).

Step 3: 2-(10,11-Dihydro-5H-dibenzo[a,d]cyclohepten-5-yl)-1-pyridin-4-yl-ethanone oxime In analogy to example 1, step 2, from 2-(10,11-dihydro-5H-dibenzo[a,d]cyclohepten-5-yl)-1-pyridin-4-yl-ethanone and hydroxylamine hydrochloride in the presence of NaHCO₃ was prepared the title compound containing less than 5% of the Z-isomer as a white solid, MS (ESI⁺): m/z= ([M+H]⁺).

Example 61

2-(9H-Fluoren-9-yl)-1-pyridin-4-yl-ethanone oxime

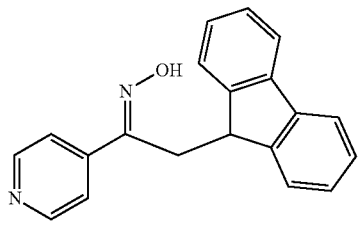 [SMILES: O/N=C(\CC1c2ccccc2-c2ccccc21)c1ccncc1]

Step 1: 2-(9H-Fluoren-9-yl)-N-methoxy-N-methyl-acetamide

In analogy to example 55, step 1, from fluorene-9-acetic acid (CAS RN: [6284-80-6]) and N,O-dimethylhydroxylamine hydrochloride was prepared the title compound as an off-white oil, MS (ESI⁺): m/z=268.1 ([M+H]⁺).

Step 2: 2-(9H-Fluoren-9-yl)-1-pyridin-4-yl-ethanone

In analogy to example 55, step 2, from 2-(9H-fluoren-9-yl)-N-methoxy-N-methyl-acetamide and 4-iodopyridine using isopropylmagnesium chloride lithium chloride complex in THF at rt (instead of n-BuLi at −70° C.) was prepared the title compound as yellow oil, MS (ESI⁺): m/z=286.1 ([M+H]⁺).

Step 3: 2-(9H-Fluoren-9-yl)-1-pyridin-4-yl-ethanone oxime

In analogy to example 1, step 2, from 2-(9H-fluoren-9-yl)-1-pyridin-4-yl-ethanone and hydroxylamine hydrochloride in the presence of NaHCO₃ was prepared the title compound as a mixture of E and Z isomers (1:1) as a white foam, MS (ESI⁺): m/z=301.3 ([M+H]⁺).

Example 62

3-(4-Dimethylamino-phenyl)-3-(1H-indol-3-yl)-1-pyridin-4-yl-propan-1-one oxime

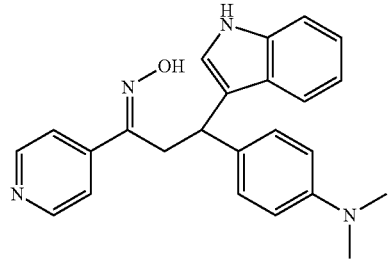 [SMILES: CN(C)c1ccc(C(C/C(=N\O)c2ccncc2)c2c[nH]c3ccccc23)cc1]

Step 1: 3-(4-Dimethylamino-phenyl)-3-(1H-indol-3-yl)-1-pyridin-4-yl-propan-1-one To a stirred solution of (E)-3-(4-dimethylamino-phenyl)-1-pyridin-4-yl-propenone (CAS RN: [18461-18-2], 200 mg) and indole (93 mg) in acetonitrile (2 mL) was added antimony (III) chloride (181 mg), and the reaction mixture was refluxed for 4 hours. Water was added to the reaction mixture, and the mixture was extracted with EtOAc (2×). The combined organic layers were washed with brine, dried over Na₂SO₄, filtered and concentrated in vacuo. Column chromatography on silica gel (EtOAc/n-heptane 1:1 to EtOAc) yielded the title compound as a yellow solid (150 mg, 51%), MS (ESI⁺): m/z=370.2 ([M+H]⁺).

Step 2: 3-(4-Dimethylamino-phenyl)-3-(1H-indol-3-yl)-1-pyridin-4-yl-propan-1-one oxime In analogy to example 1, step 2, from 3-(4-dimethylamino-phenyl)-3-(1H-indol-3-yl)-1-pyridin-4-yl-propan-1-one and hydroxylamine hydrochloride in the presence of NaHCO₃ was prepared the title compound as a mixture of E and Z isomers (2.8:1) as a yellow foam, MS (ESI⁺): m/z=385.4 ([M+H]⁺).

Example 63

3-(4-Dimethylamino-phenyl)-3-(2-methyl-1H-indol-3-yl)-1-pyridin-4-yl-propan-1-one oxime

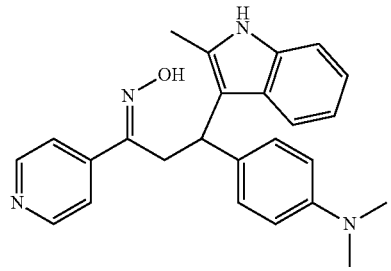 [SMILES: Cc1[nH]c2ccccc2c1C(C/C(=N\O)c1ccncc1)c1ccc(N(C)C)cc1]

Step 1: 3-(4-Dimethylamino-phenyl)-3-(2-methyl-1H-indol-3-yl)-1-pyridin-4-yl-propan-1-one In analogy to example 62, step 1, from (E)-3-(4-dimethylamino-phenyl)-1-pyridin-4-yl-propenone (CAS RN: [18461-18-2]) and 2-methylindole (CAS RN: [90-25-5]) was prepared the title compound as a yellow foam, MS (ESI$^+$): m/z=384.3 ([M+H]$^+$).

Step 2: 3-(4-Dimethylamino-phenyl)-3-(2-methyl-1H-indol-3-yl)-1-pyridin-4-yl-propan-1-one oxime In analogy to example 1, step 2, from 3-(4-dimethylamino-phenyl)-3-(2-methyl-1H-indol-3-yl)-1-pyridin-4-yl-propan-1-one and hydroxylamine hydrochloride in the presence of NaHCO$_3$ was prepared the title compound as a mixture of E and Z isomers (8.8:1) as a yellow foam, MS (ESI$^+$): m/z=399.3 ([M+H]$^+$).

Example 64

(E)-3-(4-Dimethylamino-phenyl)-3-pyridin-2-yl-1-pyridin-4-yl-propan-1-one oxime

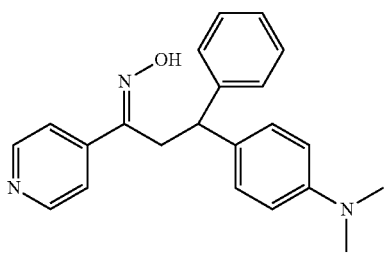 [SMILES: CN(C)c1ccc(C(C/C(=N\O)c2ccncc2)c2ccccc2)cc1]

Step 1: 3-(4-Dimethylamino-phenyl)-3-pyridin-2-yl-1-pyridin-4-yl-propan-1-one To copper(I) iodide (151 mg) dissolved in dipropylsulfide (0.226 mL) was added diethylether (7 mL) and the resulting solution was cooled to 0° C. To this solution a freshly prepared solution of 2-pyridyllithium (prepared from 2-bromopyridine (0.15 mL) in ether (1 mL) with n-BuLi (1.6M in hexane, 0.99 mL) at −70° C., and stirred for 5 min prior to use) was added via a syringe. The dark solution was stirred for additional 15 min and then was added to a solution of (E)-3-(4-dimethylamino-phenyl)-1-pyridin-4-yl-propenone (CAS RN: [18461-18-2], 200 mg) in diethylether (1.5 mL) at 0° C. The reaction was stirred at 0° C. for 3 hours and rt overnight. Additional 2-pyridyl copper reagent was prepared and added at 0° C. Stirring was continued at 0° C. for 2 hours and at rt overnight. The reaction mixture was quenched with a saturated aqueous solution of NaHCO$_3$, the phases were separated and the inorganic one was extracted with EtOAc (2×). The combined organic layers were washed with brine, dried over Na$_2$SO$_4$, filtered and concentrated in vacuo. Column chromatography on silica gel (EtOAc/n-heptane 2:1) yielded the title compound (41 mg, 16%) as an orange oil, MS (ESI$^+$): m/z=332.3 ([M+H]$^+$).

Step 2: (E)-3-(4-Dimethylamino-phenyl)-3-pyridin-2-yl-1-pyridin-4-yl-propan-1-one oxime In analogy to example 1, step 2, from 3-(4-dimethylamino-phenyl)-3-pyridin-2-yl-1-pyridin-4-yl-propan-1-one and hydroxylamine hydrochloride in the presence of NaHCO$_3$ was prepared the title compound as a yellow foam, MS (ESI$^+$): m/z=347.2 ([M+H]$^+$).

Example 65

(E)-3-(4-Dimethylamino-phenyl)-3-(3-methyl-pyridin-2-yl)-1-pyridin-4-yl-propan-1-one oxime

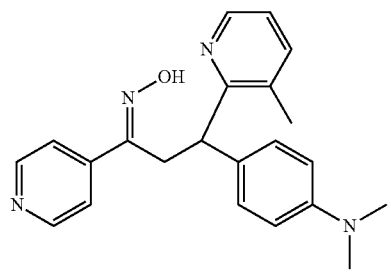 [SMILES: Cc1cccnc1C(C/C(=N\O)c1ccncc1)c1ccc(N(C)C)cc1]

Step 1: 3-(4-Dimethylamino-phenyl)-3-(3-methyl-pyridin-2-yl)-1-pyridin-4-yl-propan-1-one In analogy to example 64, step 1, from (E)-3-(4-dimethylamino-phenyl)-1-pyridin-4-yl-propenone (CAS RN: [18461-18-2]) and 2-bromo-3-methylpyridine (CAS RN: [3430-17-9]) was prepared the title compound as a yellow oil, MS (ESI$^+$): m/z=346.1 ([M+H]$^+$).

Step 2: (E)-3-(4-Dimethylamino-phenyl)-3-(3-methyl-pyridin-2-yl)-1-pyridin-4-yl-propan-1-one oxime In analogy to example 1, step 2, from 3-(4-dimethylamino-phenyl)-3-(3-methyl-pyridin-2-yl)-1-pyridin-4-yl-propan-1-one and hydroxylamine hydrochloride in the presence of NaHCO$_3$ was prepared the title compound as a yellow foam, MS (ESI$^+$): m/z=361.3 ([M+H]$^+$).

Example 66

1-(2,6-Dimethyl-pyridin-4-yl)-3,3-diphenyl-propenone oxime

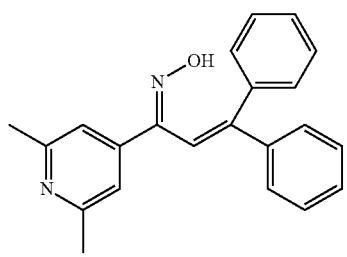 [SMILES: Cc1cc(/C(C=C(c2ccccc2)c2ccccc2)=N/O)cc(C)n1]

Step 1: 1-(2,6-Dimethyl-pyridin-4-yl)-3-phenyl-propynone

To a solution of N-methoxy-2,6,N-trimethyl-isonicotinamide (example 45, step 3, 3.0 g) in THF (75 mL) was added phenylethynylmagnesium bromide (1M in THF, 30.9 mL) at 0° C. The reaction mixture was stirred at 0° C. for 1 hour, at room temperature for 1.5 hours and was then quenched by the addition of a saturated aqueous solution of NH₄Cl (20 mL). The mixture was stirred for additional 30 min. The phases were separated and the inorganic one was extracted with EtOAc (2×). The combined organic layers were washed with brine, dried over Na₂SO₄, filtered and concentrated in vacuo. Column chromatography on silica gel (EtOAc/n-heptane 1:1) yielded the title compound (2.77 g, 76%) as an off-white solid, MS (ESI⁺): m/z=236.1 ([M+H]⁺).

Step 2: 1-(2,6-Dimethyl-pyridin-4-yl)-3,3-diphenyl-propenone

At −78° C., to a suspension of CuBr.DMS (2.9 g) in THF (60 mL) was added phenyllithium (2M in dibutylether, 7.1 mL) dropwise. After stirring the mixture for 1.5 hours at −78° C., 1-(2,6-dimethyl-pyridin-4-yl)-3-phenyl-propynone (2.77 g) in THF (15 mL) was added and stirring was continued at −78° C. for 1.5 hours. The reaction was quenched by the addition of a saturated aqueous solution of NH₄Cl. The phases were separated and the inorganic one was extracted with EtOAc (2×). The combined organic layers were washed with brine, dried over Na₂SO₄, filtered and concentrated in vacuo. Column chromatography on silica gel (EtOAc/n-heptane 1:2) yielded the title compound (2.22 g, 60%) as a yellow solid, MS (ESI⁺): m/z=314.1 ([M+H]⁺).

Step 3: 1-(2,6-Dimethyl-pyridin-4-yl)-3,3-diphenyl-propenone oxime

In analogy to example 1, step 2, from 1-(2,6-dimethyl-pyridin-4-yl)-3,3-diphenyl-propenone and hydroxylamine hydrochloride in the presence of NaHCO₃ was prepared the title compound as a mixture of E and Z isomers (1:1) as a white foam, MS (ESI⁺): m/z=329.2 ([M+H]⁺).

Example 67

1-(2,6-Dimethyl-pyridin-4-yl)-3,3-diphenyl-propan-1-one oxime

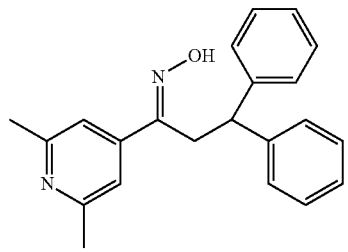 [SMILES: Cc1cc(/C(CC(c2ccccc2)c2ccccc2)=N/O)cc(C)n1]

Step 1: 1-(2,6-Dimethyl-pyridin-4-yl)-3,3-diphenyl-propan-1-one

Under argon, to a solution of 9-borabicyclo[3.3.1]nonane (9-BBN, 0.5M in THF, 0.7 mL) (CAS RN: [280-64-8]) in dry dichloromethane (0.5 mL) was added a solution of 1-(2,6-dimethyl-pyridin-4-yl)-3,3-diphenyl-propenone (100 mg, example 66, step 2) in dry dichloromethane (0.5 mL) dropwise. The mixture was stirred at room temperature overnight. Methanol (1 mL) was added and the reaction mixture was stirred vigorously for 10 min. The solution was concentrated and the crude product was purified by column chromatography on silica gel (EtOAc/n-heptane 1:1) to yield the title compound (60 mg, 60%) as a light yellow solid, MS (ESI⁺): m/z=316.1 ([M+H]⁺).

Step 2: 1-(2,6-Dimethyl-pyridin-4-yl)-3,3-diphenyl-propan-1-one oxime

In analogy to example 1, step 2, from 1-(2,6-dimethyl-pyridin-4-yl)-3,3-diphenyl-propan-1-one and hydroxylamine hydrochloride in the presence of NaHCO₃ was prepared the title compound as a mixture of E and Z isomers (3:1) as a white foam, MS (ESI⁺): m/z=331.2 ([M+H]⁺).

Example 68

(E)-1-(2,6-Dimethyl-pyridin-4-yl)-3-phenyl-3-pyridin-2-yl-propan-1-one oxime

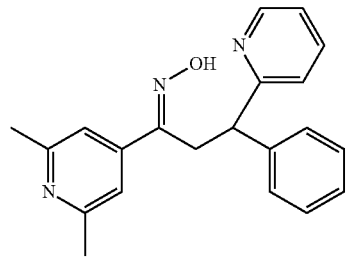 [SMILES: Cc1cc(/C(CC(c2ccccc2)c2ccccn2)=N/O)cc(C)n1]

Step 1: 1-(2,6-Dimethyl-pyridin-4-yl)-3-pyridin-2-yl-propynone

To a solution of 2-ethynylpyridine (80 mg) in THF (4 mL) was added n-BuLi (1.6M in hexane, 0.39 mL) at −78° C. The reaction was stirred at that temperature for 15 min and then a solution of N-methoxy-2,6,N-trimethyl-isonicotinamide (100 mg, example 45, step 3) in THF (1 mL) was added. The reaction mixture was stirred at −78° C. for 5 min, at 0° C. for 1.5 hours and then was quenched by adding water. The phases were separated and the inorganic one was extracted with EtOAc (3×). The combined organic layers were washed with brine, dried over Na₂SO₄, filtered and concentrated in vacuo. Column chromatography on silica gel (EtOAc/n-heptane 1:2 to EtOAc) yielded the title compound (77 mg, 66%) as brown oil, MS (ESI⁺): m/z=237.2 ([M+H]⁺).

Step 2: 1-(2,6-Dimethyl-pyridin-4-yl)-3-phenyl-3-pyridin-2-yl-propenone

In analogy to example 66, step 2, from 1-(2,6-dimethyl-pyridin-4-yl)-3-pyridin-2-yl-propynone and phenyllithium was prepared the title compound as an orange oil, MS (ESI⁺): m/z=315.0 ([M+H]⁺).

Step 3: 1-(2,6-Dimethyl-pyridin-4-yl)-3-phenyl-3-pyridin-2-yl-propan-1-one

In analogy to example 67, step 1, from 1-(2,6-dimethyl-pyridin-4-yl)-3-phenyl-3-pyridin-2-yl-propenone with 9-BBN was prepared the title compound as a yellow oil, MS (ESI⁺): m/z=317.2 ([M+H]⁺).

Step 4: (E)-1-(2,6-Dimethyl-pyridin-4-yl)-3-phenyl-3-pyridin-2-yl-propan-1-one oxime In analogy to example 1, step 2, from 1-(2,6-dimethyl-pyridin-4-yl)-3-phenyl-3-pyridin-2-yl-propan-1-one and hydroxylamine hydrochloride in the presence of NaHCO₃ was prepared the title compound as a light yellow foam, MS (ESI⁺): m/z=332.3 ([M+H]⁺).

Example 69

3-{3-[(E)-Hydroxyimino]-1-phenyl-3-pyridin-4-yl-propyl}-benzoic acid

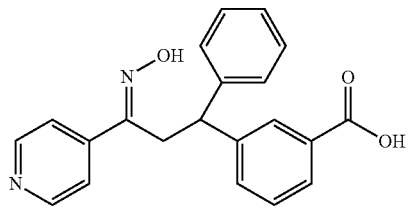 [SMILES: O=C(O)c1cccc(C(C/C(=N\O)c2ccncc2)c2ccccc2)c1]

At −78° C., to a solution of (E)-3-(3-bromo-phenyl)-3-phenyl-1-pyridin-4-yl-propan-1-one oxime (60 mg, example 12) in THF (1.5 mL) n-BuLi (1.6 M in hexane, 0.11 mL) was added dropwise. After stirring for 30 mins at that temperature carbon dioxide gas was bubbled into the solution for 5 min at −78° C. The reaction mixture was then warmed up to 0° C. and stirred for 15 min. The reaction was quenched by adding 1N aqueous KHSO₄ solution, the phases were separated and the inorganic one was extracted with EtOAc (2×). The combined organic layers were washed with brine, dried over Na₂SO₄, filtered and concentrated in vacuo. Column chromatography on silica gel (CH₂Cl₂/MeOH 97:3) yielded 3-{3-[(E)-hydroxyimino]-1-phenyl-3-pyridin-4-yl-propyl}-benzoic acid (16 mg, 29%) as a yellow foam, MS (ESI⁺): m/z=347.1391 ([M+H]⁺).

Example 70

4-{3-[Hydroxyimino]-3-pyridin-4-yl-1-o-tolyl-propyl}-benzoic acid

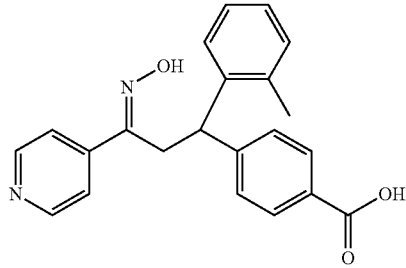 [SMILES: Cc1ccccc1C(C/C(=N\O)c1ccncc1)c1ccc(C(=O)O)cc1]

In analogy to example 69, from 3-(4-bromo-phenyl)-3-phenyl-1-pyridin-4-yl-propan-1-one oxime was prepared 4-{3-[hydroxyimino]-3-pyridin-4-yl-1-o-tolyl-propyl}-benzoic acid as a mixture of E and Z isomers (1.5:1) as a white solid, MS (ESI⁺): m/z=361.1532 ([M+H]⁺).

Example 71

3-{3-[Hydroxyimino]-3-pyridin-4-yl-1-o-tolyl-propyl}-benzoic acid

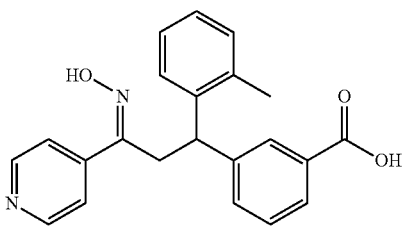 [SMILES: Cc1ccccc1C(C/C(=N/O)c1ccncc1)c1cccc(C(=O)O)c1]

In analogy to example 69, from 3-(3-bromo-phenyl)-1-pyridin-4-yl-3-o-tolyl-propan-1-one oxime (example 12) was prepared 3-{3-[hydroxyimino]-3-pyridin-4-yl-1-o-tolyl-propyl}-benzoic acid as a mixture of E and Z isomers (1:2.5) as a light yellow foam, MS (ESI⁺): m/z=361.1538 ([M+H]⁺).

Examples 72 and 73

(E)-1-(2,6-Dichloro-pyridin-4-yl)-3,3-diphenyl-propan-1-one oxime and (Z)-1-(2,6-dichloro-pyridin-4-yl)-3,3-diphenyl-propan-1-one oxime

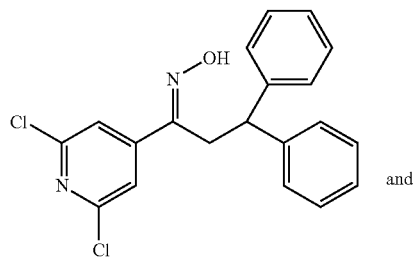

and

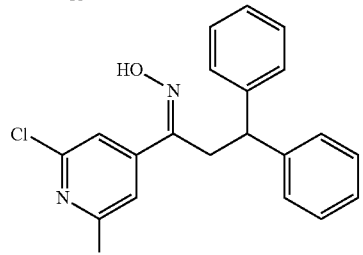

Step 1: N-Methoxy-N-methyl-3,3-diphenyl-propionamide

To a solution of 3,3-diphenylpropionic acid (CAS RN: [606-83-7], 1.5 g) in DMF (17 mL) was added TBTU (2.98 g) and Et₃N (2.1 mL) at 0° C. The reaction mixture was stirred at rt for 10 min and again cooled down to 0° C. N,O-dimethylhydroxylamine hydrochloride (0.78 g) was added and the mixture was stirred at rt for 1 hour. A saturated aqueous solution of NaHCO₃ was added, the phases were separated and the inorganic one was extracted with TBME (2×). The combined organic layers were washed with 1N aqueous KHSO₄ and brine, dried over Na₂SO₄, filtered and concentrated in vacuo. The crude product was purified by flash chromatography on silica gel (EtOAc/n-heptane 1:1) to yield the title compound (1.52 g, 85%) as a colorless oil, MS (ESI⁺): m/z=270.2 ([M+H]⁺).

Steps 2 and 3: (E)-1-(2,6-Dichloro-pyridin-4-yl)-3,3-diphenyl-propan-1-one oxime and (Z)-1-(2,6-dichloro-pyridin-4-yl)-3,3-diphenyl-propan-1-one oxime At −70° C. to a solution of 2,6-dichloro-4-iodopyridine (1.02 g) in THF (20 mL) was added n-BuLi (1.6 M in hexane, 2.3 mL) dropwise. The mixture was stirred for additional 15 min at which timepoint a solution of N-methoxy-N-methyl-3,3-diphenyl-propionamide (200 mg) in THF (10 mL) was added. The reaction mixture was stirred for 1 hour at −70° C. A saturated aqueous solution of NH₄Cl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 1:10) to yield 1-(2,6-dichloro-pyridin-4-yl)-3,3-diphenyl-propan-1-one (465 mg, 88%) as a yellow oil, which was directly subjected to the next step.

In analogy to example 1, step 2, from 1-(2,6-dichloro-pyridin-4-yl)-3,3-diphenyl-propan-1-one and hydroxylamine hydrochloride in the presence of NaHCO₃ was prepared (E)-1-(2,6-dichloro-pyridin-4-yl)-3,3-diphenyl-propan-1-one oxime as a white solid, MS (ESI⁻): m/z=368.9 ([M−H]⁻, 1Cl) and (Z)-1-(2,6-dichloro-pyridin-4-yl)-3,3-diphenyl-propan-1-one oxime as a colorless oil, MS (ESI⁻): m/z=368.9 ([M−H]⁻, 1Cl).

Example 74

4'-[3-[Hydroxyimino]-3-(2-methyl-pyridin-4-yl)-1-o-tolyl-propyl]-biphenyl-4-carboxylic acid methyl ester

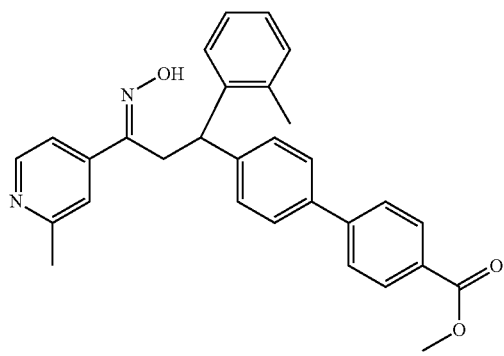 [SMILES: COC(=O)c1ccc(-c2ccc(C(C/C(=N\O)c3ccnc(C)c3)c3ccccc3C)cc2)cc1]

Step 1: 3-(4-Bromo-phenyl)-2-cyano-acrylic acid ethyl ester

To a solution of 4-bromo-benzaldehyde (5 g) and ethyl cyanoacetate (2.9 mL) in toluene (50 mL) was added piperidine (0.046 mL), and the mixture was stirred at reflux for 2 h with a Dean-Stark separator. The mixture was cooled to rt, stirred overnight and toluene was evaporated in vacuo. The crude residue was crystallized from EtOAc to yield the title compound (6.77 g, 90%) as a light yellow solid, MS (EI): m/z=279 ([M]⁺, 1Br).

Step 2: 3-(4-Bromo-phenyl)-2-cyano-3-o-tolyl-propionic acid ethyl ester

A solution of 3-(4-bromo-phenyl)-2-cyano-acrylic acid ethyl ester (6.65 g) in toluene (50 mL) was added to a solution of o-tolylmagnesium chloride in THF (1M, 30.9) at 0° C. After the addition was complete, the solution was heated to 85° C. for 1.5 hours, and stirring was continued at rt overnight. The mixture was heated for additional 2 hours to 85° C., cooled and poured onto ice. 1M HCl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (Et₂O/n-heptane 1:3) to yield the title compound (6.45 g, 73%) as a light yellow oil, MS (ESI⁻): m/z=370.0444 ([M−H]⁻, 1Br).

Step 3: 3-(4-Bromo-phenyl)-3-otolyl-propionic acid

To a solution of 3-(4-bromo-phenyl)-2-cyano-3-o-tolyl-propionic acid ethyl ester (6.65 g) in acetic acid (48 mL) was added water (18 mL) and concentrated H₂SO₄ (17.6 mL) at 0° C. The mixture was refluxed for 2 days, cooled and poured on ice, extracted with EtOAc (3×) and methylene chloride. The organic layers were washed with brine, dried over Na₂SO₄, filtered and concentrated in vacuo. The crude product was precipitated from EtOAc:n-heptane to yield the title compound (3.8 g, 67%) as a white solid, MS (ESI⁻): m/z=317.0181 ([M−H]⁻).

Step 4: 3-(4-Bromo-phenyl)-N-methoxy-N-methyl-3-o-tolyl-propionamide

To a solution of 3-(4-bromo-phenyl)-3-o-tolyl-propionic acid (3.7 g) in DMF (45 mL) was added TBTU (5.2 g) and Et₃N (4.8 mL) at 0° C. The reaction mixture was stirred at rt for 10 min and again cooled down to 0° C. N,O-dimethylhydroxylamine hydrochloride (1.36 g) was added and the mixture was stirred at rt for 1.5 hour. A saturated solution of NH₄Cl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 1:2) to yield the title compound as a colorless oil (4.1 g, 97%), MS (ESI⁺): m/z=362.0750 ([M+H]⁺, 1Br).

Step 5: 3-(4-Bromo-phenyl)-1-(2-methyl-pyridin-4-yl)-3-o-tolyl-propan-1-one

To a solution of n-BuLi (12.9 mL 1.6 M in hexane) was added dropwise a solution of 4-bromo-2-methylpyridine (3.56 g) in THF (170 mL) at −70° C. over a period of 20 min. The reaction mixture was stirred at −70° C. for 5 min, before a solution of 3-(4-bromo-phenyl)-N-methoxy-N-methyl-3-o-tolyl-propionamide (2.5 g) in THF (100 mL) was added dropwise. After the addition was complete, the mixture was stirred at −70° C. for 3 hours. A saturated solution of NH₄Cl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 1:1) to give the title compound as an yellow oil (1.49 g, 55%), MS (ESI⁺): m/z=394.0797 ([M+H]⁺, 1Br).

Step 6: 4'-[3-(2-Methyl-pyridin-4-yl)-3-oxo-1-o-tolyl-propyl]-biphenyl-4-carboxylic acid methyl ester To a stirred solution of 3-(4-bromo-phenyl)-1-(2-methyl-pyridin-4-yl)-3-o-tolyl-propan-1-one (400 mg), (4-methoxy-carbonylphenyl)boronic acid (275 mg), dichlor(1,1'-bis(diphenyl-phosphino)-ferrocene)palladium (II) dichloromethane adduct (41 mg) in dioxane (3 mL) and water (2.6 mL) was added a 2 M aqueous sodium carbonate solution (1.52 mL). The mixture was stirred at 80° C. for 1.5 h. A saturated solution of NH₄Cl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 1:1) to yield the title compound as a yellow foam (400 mg, 88%), MS (ESI⁺): m/z=450.2063 ([M+H]⁺).

Step 7: 4'-[3-[Hydroxyimino]-3-(2-methyl-pyridin-4-yl)-1-o-tolyl-propyl]-biphenyl-4-carboxylic acid methyl ester A solution of 4'-[3-(2-methyl-pyridin-4-yl)-3-oxo-1-o-tolyl-propyl]-biphenyl-4-carboxylic acid methyl ester (36 mg), hydroxylamine hydrochloride (11 mg) and sodium hydrogencarbonate (14 mg) in a mixture of ethanol (0.5 mL) and water (0.1 mL) was heated under reflux for 1.5 hours. A saturated solution of NH₄Cl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 2:1) to yield the title compound as a mixture of E and Z isomers (3.3:1) as a white foam (28 mg, 75%), MS (ESI⁺): m/z=465.2 ([M+H]⁺).

Example 75

4'-[3-[Hydroxyimino]-3-(2-methyl-pyridin-4-yl)-1-o-tolyl-propyl]-biphenyl-4-carboxylic acid

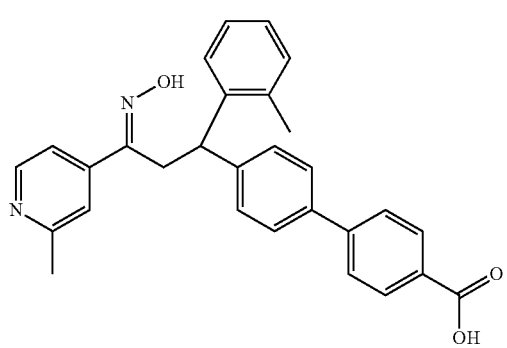 [SMILES: Cc1cc(/C(CC(c2ccc(-c3ccc(C(=O)O)cc3)cc2)c2ccccc2C)=N/O)ccn1]

To a solution of 4'-[3-[hydroxyimino]-3-(2-methyl-pyridin-4-yl)-1-o-tolyl-propyl]-biphenyl-4-carboxylic acid methyl ester (352 mg) in THF (7.5 mL) was added a drop of methanol and a 1 M aqueous lithium hydroxide solution (7.6 mL) at 0° C. The reaction mixture was stirred at rt for 2 hours. A 1M aqueous solution of KHSO₄ (7.5 mL) was added, the phases were separated and an extraction was made with EtOAc and a saturated solution of NH₄Cl. The combined organic layers were washed with brine, dried over Na₂SO₄, filtered and concentrated in vacuo. The crude product was purified by flash chromatography on silica gel (CH₂Cl₂/MeOH 9:1) to yield 4'-[3-[hydroxyimino]-3-(2-methyl-pyridin-4-yl)-1-o-tolyl-propyl]-biphenyl-4-carboxylic acid as a mixture of E and Z isomers (3:1) as a white foam (288 mg, 84%), MS (ESI⁻): m/z=449.2 ([M−H]⁻).

Example 76

4'-{3-[(E)-Hydroxyimino]-1-phenyl-3-pyridin-4-yl-propyl}-biphenyl-3-carboxylic acid

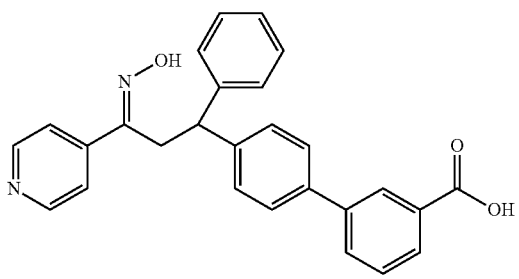 [SMILES: O=C(O)c1cccc(-c2ccc(C(C/C(=N\O)c3ccncc3)c3ccccc3)cc2)c1]

In analogy to example 19, from (E)-3-(4-bromo-phenyl)-3-phenyl-1-pyridin-4-yl-propan-1-one oxime (example 5) and 3-methoxycarbonylphenylboronic acid was prepared 4'-{3-[(E)-hydroxyimino]-1-phenyl-3-pyridin-4-yl-propyl}-biphenyl-3-carboxylic acid methyl ester, which was directly subjected to the next step.

In analogy to example 75, from 4'-{3-[(E)-hydroxyimino]-1-phenyl-3-pyridin-4-yl-propyl}-biphenyl-3-carboxylic acid methyl ester was prepared 4'-{3-[(E)-hydroxyimino]-1-phenyl-3-pyridin-4-yl-propyl}-biphenyl-3-carboxylic acid as a colorless oil, MS (ESI⁻): m/z=421.0 ([M−H]⁻).

Example 77

4'-{3-[(E)-Hydroxyimino]-1-phenyl-3-pyridin-4-yl-propyl}-biphenyl-4-carboxylic acid

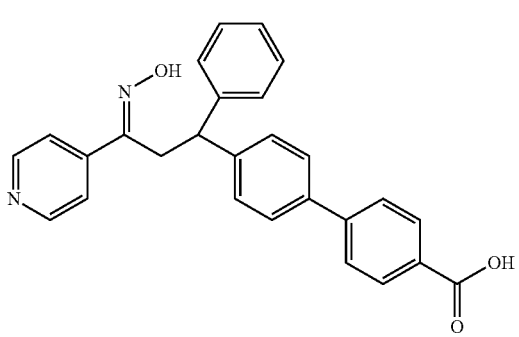 [SMILES: O=C(O)c1ccc(-c2ccc(C(C/C(=N\O)c3ccncc3)c3ccccc3)cc2)cc1]

Step 1: 4'-{3-[(E)-Hydroxyimino]-1-phenyl-3-pyridin-4-yl-propyl}-biphenyl-4-carboxylic acid methyl ester In analogy to example 19, from (E)-3-(4-bromo-phenyl)-3-phenyl-1-pyridin-4-yl-propan-1-one oxime (example 5) and 4-methoxycarbonylphenylboronic acid was prepared the title compound as yellow oil, MS (ESI⁺): m/z=437.2 ([M+H]⁺).

Step 2: 4'-{3-[(E)-Hydroxyimino]-1-phenyl-3-pyridin-4-yl-propyl}-biphenyl-4-carboxylic acid In analogy to example 75, from 4'-{3-[(E)-hydroxyimino]-1-phenyl-3-pyridin-4-yl-propyl}-biphenyl-3-carboxylic acid methyl ester was prepared the title compound as a colorless oil, MS (ESI⁺): m/z=423.3 ([M+H]⁺).

Example 78

4'-[3-[Hydroxyimino]-3-(2-methyl-pyridin-4-yl)-1-o-tolyl-propyl]-biphenyl-3-carboxylic acid ethyl ester

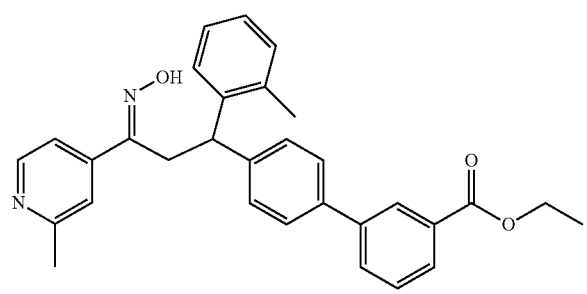 [SMILES: CCOC(=O)c1cccc(-c2ccc(C(C/C(=N\O)c3ccnc(C)c3)c3ccccc3C)cc2)c1]

Step 1: 4'-[3-(2-Methyl-pyridin-4-yl)-3-oxo-1-o-tolyl-propyl]-biphenyl-3-carboxylic acid ethyl ester In analogy to example 74, step 6, from 3-(4-bromo-phenyl)-1-(2-methyl-pyridin-4-yl)-3-o-tolyl-propan-1-one (example 74, step 5) and 3-ethoxycarbonylphenylboronic acid was prepared the title compound as a yellow oil, MS (ESI⁺): m/z=464.22 ([M+H]⁺).

Step 2: 4'-[3-[Hydroxyimino]-3-(2-methyl-pyridin-4-yl)-1-o-tolyl-propyl]-biphenyl-3-carboxylic acid ethyl ester In analogy to example 74, step 7, from 4'-[3-(2-methyl-pyridin-4-yl)-3-oxo-1-o-tolyl-propyl]-biphenyl-3-carboxylic acid ethyl ester and hydroxylamine hydrochloride in the presence of NaHCO₃ was prepared the title compound as a mixture of E and Z isomers (3.4:1) as a white foam, MS (ESI⁺): m/z=479.2319 ([M+H]⁺).

Example 79

4'-[3-[Hydroxyimino]-3-(2-methyl-pyridin-4-yl)-1-o-tolyl-propyl]-biphenyl-3-carboxylic acid

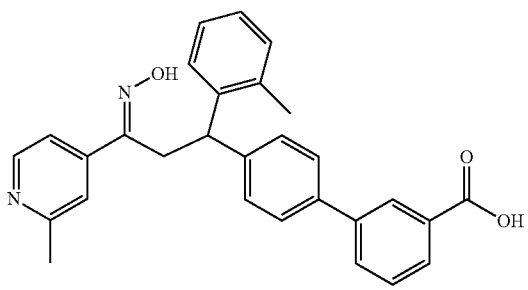 [SMILES: Cc1cc(/C(CC(c2ccc(-c3cccc(C(=O)O)c3)cc2)c2ccccc2C)=N/O)ccn1]

In analogy to example 75, from 4'-[3-[hydroxyimino]-3-(2-methyl-pyridin-4-yl)-1-o-tolyl-propyl]-biphenyl-3-carboxylic acid ethyl ester was prepared 4'-[3-[hydroxyimino]-3-(2-methyl-pyridin-4-yl)-1-o-tolyl-propyl]-biphenyl-3-carboxylic acid as a mixture of E and Z isomers (3.5:1) as a colorless oil, MS (ESI⁺): m/z=451.20 ([M+H]⁺).

Example 80

{4-[3-[Hydroxyimino]-3-(2-methyl-pyridin-4-yl)-1-o-tolyl-propyl]-phenyl}-acetic acid

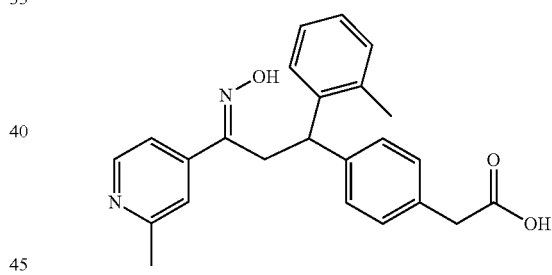

Steps 1 and 2: {4-[3-(2-Methyl-pyridin-4-yl)-3-oxo-1-o-tolyl-propyl]-phenyl}-acetic acid To a solution of 3-(4-bromo-phenyl)-1-(2-methyl-pyridin-4-yl)-3-o-tolyl-propan-1-one (example 74, step 5) (70 mg) in dioxane (2 mL) ethyl cyanoacetate (30.1 mg) was added. To this mixture dichlor(1,1'-bis(diphenylphosphino)ferrocene) palladium (II) dichloromethane adduct (7.2 mg) and potassium tert-butoxide (60 mg) were added. The reaction mixture was stirred at 80° C. for 2 hours. A saturated solution of NH₄Cl was added, the phases were separated and the inorganic one was extracted with EtOAc (2×). The combined organic layers were washed with brine, dried over Na₂SO₄, filtered and concentrated in vacuo. The crude product was purified by flash chromatography on silica gel (EtOAc/n-heptane 1:1 to EtOAc) to yield cyano-{4-[3-(2-methyl-pyridin-4-yl)-3-oxo-1-o-tolyl-propyl]-phenyl}-acetic acid ethyl ester (28 mg, 37%) as a light yellow oil, which was directly subjected to the next step.

In analogy to example 74, step 3, from cyano-{4-[3-(2-methyl-pyridin-4-yl)-3-oxo-1-o-tolyl-propyl]-phenyl}-acetic acid ethyl ester was prepared the title compound as a colorless oil, MS (ESI⁻): m/z=372.1 ([M–H]⁻).

Step 3: {4-[3-[Hydroxyimino]-3-(2-methyl-pyridin-4-yl)-1-o-tolyl-propyl]-phenyl}-acetic acid In analogy to example 74, step 7, from {4-[3-(2-methyl-pyridin-4-yl)-3-oxo-1-o-tolyl-propyl]-phenyl}-acetic acid and hydroxylamine hydrochloride in the presence of NaHCO₃ was prepared the title compound as a mixture of E and Z isomers (3.6:1) as a colorless oil, MS (ESI⁺): m/z=389.19 ([M+H]⁺).

Example 81

2-Fluoro-4'-[3-[hydroxyimino]-3-(2-methyl-pyridin-4-yl)-1-o-tolyl-propyl]-biphenyl-4-carboxylic acid methyl ester

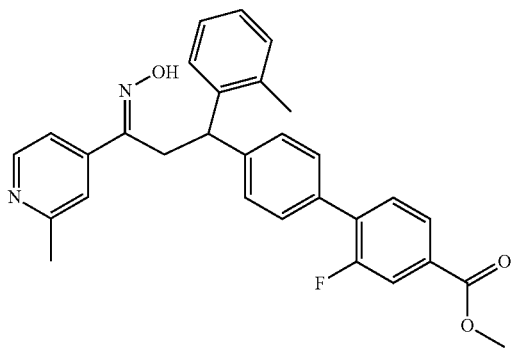 [SMILES: COC(=O)c1ccc(-c2ccc(C(C/C(=N\O)c3ccnc(C)c3)c3ccccc3C)cc2)c(F)c1]

Step 1: 2-Fluoro-4'-[3-(2-methyl-pyridin-4-yl)-3-oxo-1-o-tolyl-propyl]-biphenyl-4-carboxylic acid methyl ester In analogy to example 74, step 6, from 3-(4-bromo-phenyl)-1-(2-methyl-pyridin-4-yl)-3-o-tolyl-propan-1-one (example 74, step 5) and 2-fluoro-4-(methoxycarbonyl)phenylboronic acid was prepared the title compound as a light brown oil, MS (ESI⁺): m/z=468.1961 ([M+H]⁺).

Step 2: 2-Fluoro-4'-[3-[hydroxyimino]-3-(2-methyl-pyridin-4-yl)-1-o-tolyl-propyl]-biphenyl-4-carboxylic acid methyl ester In analogy to example 74, step 7, from 2-fluoro-4'-[3-(2-methyl-pyridin-4-yl)-3-oxo-1-o-tolyl-propyl]-biphenyl-4-carboxylic acid methyl ester and hydroxylamine hydrochloride in the presence of NaHCO₃ was prepared the title compound as a mixture of E and Z isomers (2.8:1) as a white foam, MS (ESI⁺): m/z=483.2073 ([M+H]⁺).

Example 82

2-Fluoro-4'-[3-[hydroxyimino]-3-(2-methyl-pyridin-4-yl)-1-o-tolyl-propyl]-biphenyl-4-carboxylic acid

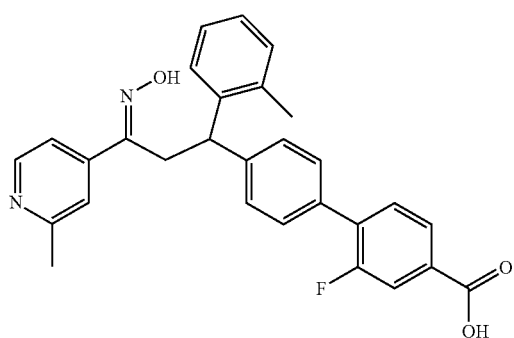 [SMILES: Cc1cc(/C(CC(c2ccc(-c3ccc(C(=O)O)cc3F)cc2)c2ccccc2C)=N/O)ccn1]

In analogy to example 75, from 2-fluoro-4'-[3-[hydroxyimino]-3-(2-methyl-pyridin-4-yl)-1-otolyl-propyl]-biphenyl-4-carboxylic acid methyl ester was prepared 2-fluoro-4'-[3-[hydroxyimino]-3-(2-methyl-pyridin-4-yl)-1-o-tolyl-propyl]-biphenyl-4-carboxylic acid as a mixture of E and Z isomers (2.4:1) as a white foam, MS (ESI⁺): m/z=469.1922 ([M+H]⁺).

Example 83

3-Chloro-4'-[3-[hydroxyimino]-3-(2-methyl-pyridin-4-yl)-1-o-tolyl-propyl]-biphenyl-4-carboxylic acid methyl ester

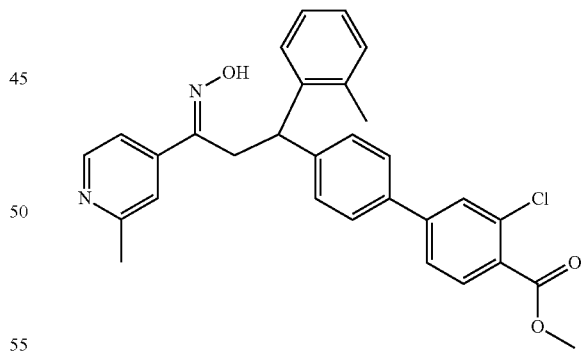

Step 1: 3-Chloro-4'-[3-(2-methyl-pyridin-4-yl)-3-oxo-1-o-tolyl-propyl]-biphenyl-4-carboxylic acid methyl ester In analogy to example 74, step 6, from 3-(4-bromo-phenyl)-1-(2-methyl-pyridin-4-yl)-3-o-tolyl-propan-1-one (example 74, step 5) and (3-chloro-4-methoxycarbonyl)benzeneboronic acid was prepared the title compound as a colorless oil, MS (ESI⁺): m/z=484.1680 ([M+H]⁺, 1Cl).

Step 2: 3-Chloro-4'-[3-[hydroxyimino]-3-(2-methyl-pyridin-4-yl)-1-o-tolyl-propyl]-biphenyl-4-carboxylic acid methyl ester In analogy to example 74, step 7, from 3-chloro-4'-[3-(2-methyl-pyridin-4-yl)-3-oxo-1-o-tolyl-propyl]-biphenyl-4-carboxylic acid methyl ester and hydroxylamine hydrochloride in the presence of NaHCO$_3$ was prepared the title compound as a mixture of E and Z isomers (4.2:1) as a colorless oil, MS (ESI$^+$): m/z=499.3 ([M+H]$^+$, 1Cl).

Example 84

3-Chloro-4'-[3-[hydroxyimino]-3-(2-methyl-pyridin-4-yl)-1-o-tolyl-propyl]-biphenyl-4-carboxylic acid

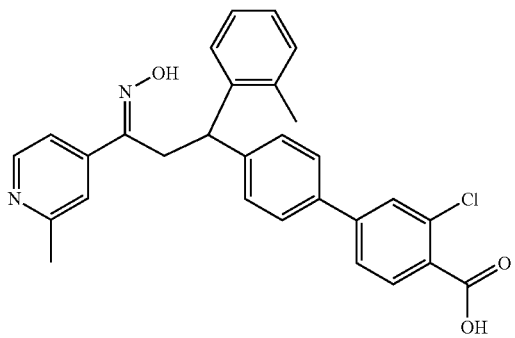 [SMILES: Cc1cc(/C(CC(c2ccc(-c3ccc(C(=O)O)c(Cl)c3)cc2)c2ccccc2C)=N/O)ccn1]

In analogy to example 75, from 3-chloro-4'-[3-[hydroxyimino]-3-(2-methyl-pyridin-4-yl)-1-o-tolyl-propyl]-biphenyl-4-carboxylic acid methyl ester (example 83) was prepared 3-chloro-4'-[3-[hydroxyimino]-3-(2-methyl-pyridin-4-yl)-1-o-tolyl-propyl]-biphenyl-4-carboxylic acid as a mixture of E and Z isomers (4.2:1) as a colorless oil, MS (ESI$^+$): m/z=485.1626 ([M+H]$^+$).

Example 85

3-[4-(3-Hydroxy-prop-1-ynyl)-phenyl]-1-(2-methyl-pyridin-4-yl)-3-o-tolyl-propan-1-one oxime

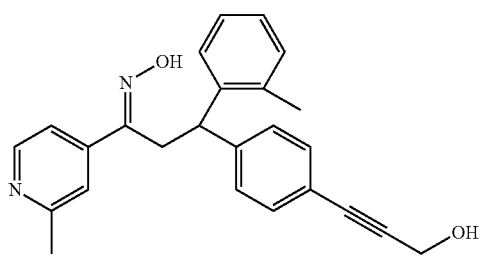 [SMILES: Cc1cc(/C(CC(c2ccc(C#CCO)cc2)c2ccccc2C)=N/O)ccn1]

Step 1: 3-[4-(3-Hydroxy-prop-1-ynyl)-phenyl]-1-(2-methyl-pyridin-4-yl)-3-o-tolyl-propan-1-one To 3-(4-bromo-phenyl)-1-(2-methyl-pyridin-4-yl)-3-o-tolyl-propan-1-one ((example 74, step 5), 400 mg) in triethylamine (4.1 mL) tetrakis(triphenylphosphine)palladium (59 mg) and CuI (10 mg) were added. At 80° C. 2-propyn-1-ol (0.12 mL) was added slowly, and the solution was stirred at that temperature for 3 hours. The solution was concentrated in vacuo and redissolved in EtOAc and a saturated solution of NH$_4$Cl. The phases were separated and the inorganic one extracted with EtOAc. The combined organic layers were washed with brine, dried over Na$_2$SO$_4$, filtered and concentrated in vacuo. The crude product was purified by flash chromatography on silica gel (EtOAc/n-heptane 2:1) to yield the title compound (264 mg, 70%) as a yellow oil, MS (ESI$^+$): m/z=370.1 ([M+H]$^+$).

Step 2: 3-[4-(3-Hydroxy-prop-1-ynyl)-phenyl]-1-(2-methyl-pyridin-4-yl)-3-o-tolyl-propan-1-one oxime In analogy to example 74, step 7, from 3-[4-(3-hydroxy-prop-1-ynyl)-phenyl]-1-(2-methyl-pyridin-4-yl)-3-o-tolyl-propan-1-one and hydroxylamine hydrochloride in the presence of NaHCO$_3$ was prepared the title compound as a mixture of E and Z isomers (6.4:1) as a colorless oil, MS (ESI$^+$): m/z=385.1908 ([M+H]$^+$).

Example 86

4-[3-[Hydroxyimino]-3-(2-methyl-pyridin-4-yl)-1-o-tolyl-propyl]-benzoic acid

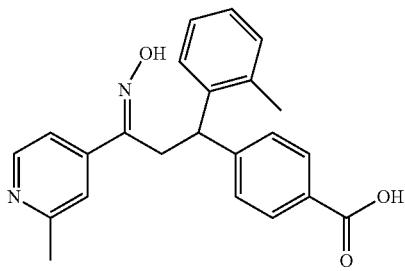 [SMILES: Cc1cc(/C(CC(c2ccc(C(=O)O)cc2)c2ccccc2C)=N/O)ccn1]

Step 1: 4-[3-(2-Methyl-pyridin-4-yl)-3-oxo-1-o-tolyl-propyl]-benzoic acid

3-[4-(3-hydroxy-prop-1-ynyl)-phenyl]-1-(2-methyl-pyridin-4-yl)-3-o-tolyl-propan-1-one (60 mg) was dissolved in carbon tetrachloride (0.6 mL), acetonitrile (0.6 ml) and water (0.9 mL). To this biphasic solution sodium metaperiodate (143 mg) and ruthenium (III) chloride hydrate (24 mg) were added at rt and the mixture was stirred at rt for 1 hour. Water was added to the crude mixture and the inorganic phase was extracted with dichloromethane (2×). The combined organic layers were washed with brine, dried over Na$_2$SO$_4$, filtered and concentrated in vacuo. The crude product was purified by flash chromatography on silica gel (CH$_2$Cl$_2$/MeOH 9:1) to yield the title compound (20 mg, 34%) as a white solid, MS (ESI$^-$): m/z=358.0 ([M−H]$^-$).

Step 2: 4-[3-[Hydroxyimino]-3-(2-methyl-pyridin-4-yl)-1-o-tolyl-propyl]-benzoic acid In analogy to example 74, step 7, from 4-[3-(2-methyl-pyridin-4-yl)-3-oxo-1-o-tolyl-propyl]-benzoic acid and hydroxylamine hydrochloride in the presence of NaHCO$_3$ was prepared the title compound as a mixture of E and Z isomers (3.3:1) as a colorless oil, MS (ESI+): m/z=375.1702 ([M+H]+).

Example 87

3-{4-[3-[Hydroxyimino]-3-(2-methyl-pyridin-4-yl)-1-o-tolyl-propyl]-phenyl}-acrylic acid

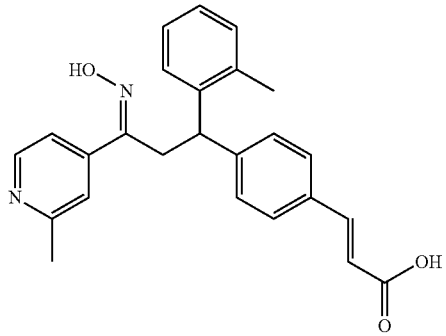 [SMILES: Cc1cc(/C(CC(c2ccc(/C=C/C(=O)O)cc2)c2ccccc2C)=N\O)ccn1]

Step 1: 3-{4-[3-(2-Methyl-pyridin-4-yl)-3-oxo-1-o-tolyl-propyl]-phenyl}-acrylic acid methyl ester To 3-(4-bromo-phenyl)-1-(2-methyl-pyridin-4-yl)-3-o-tolyl-propan-1-one ((example 74, step 5), 300 mg) in DMF (3 mL) tetrakis(triphenylphosphine)palladium (130 mg), methyl acrylate (0.103 mL) and triethylamine (0.16 mL) were added. The reaction mixture was stirred at 100° C. overnight, was cooled to room temperature and diluted with EtOAc and a saturated solution of ammonium chloride. The phases were separated and the inorganic one extracted with EtOAc. The combined organic layers were washed with brine, dried over Na₂SO₄, filtered and concentrated in vacuo. The crude product was purified by flash chromatography on silica gel (EtOAc/n-heptane 1:1) to yield the title compound (62 mg, 20%) as a yellow oil, MS (ESI+): m/z=400.1912 ([M+H]+).

Step 2: 3-{4-[3-(2-Methyl-pyridin-4-yl)-3-oxo-1-o-tolyl-propyl]-phenyl}-acrylic acid In analogy to example 75, from 3-{4-[3-(2-methyl-pyridin-4-yl)-3-oxo-1-o-tolyl-propyl]-phenyl}-acrylic acid methyl ester was prepared the title compound, MS (ESI+): m/z=386.2 ([M+H]+).

Step 3: 3-{4-[3-[Hydroxyimino]-3-(2-methyl-pyridin-4-yl)-1-o-tolyl-propyl]-phenyl}-acrylic acid In analogy to example 74, step 7, from 3-{4-[3-(2-methyl-pyridin-4-yl)-3-oxo-1-o-tolyl-propyl]-phenyl}-acrylic acid and hydroxylamine hydrochloride in the presence of NaHCO₃ was prepared the title compound as a mixture of Z to E isomers (1.7:1) as a colorless oil, MS (ESI+): m/z=401.1859 ([M+H]+).

Example 88

3-[4-(3-Hydroxy-propyl)-phenyl]-1-(2-methyl-pyridin-4-yl)-3-o-tolyl-propan-1-one oxime

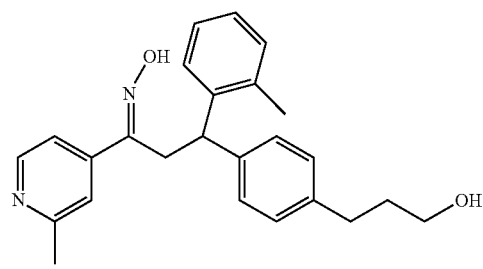 [SMILES: Cc1cc(/C(CC(c2ccc(CCCO)cc2)c2ccccc2C)=N/O)ccn1]

Steps 1 and 2: 3-[4-(3-Hydroxy-propyl)-phenyl]-1-(2-methyl-pyridin-4-yl)-3-o-tolyl-propan-1-one oxime 3-[4-(3-Hydroxy-prop-1-ynyl)-phenyl]-1-(2-methyl-pyridin-4-yl)-3-o-tolyl-propan-1-one (example 85, step 1; 40 mg) in ethyl acetate (6 mL) was hydrogenated in the presence of Pd (5% on carbon, 7 mg) at room temperature for 1.5 hours. The solution was filtered over decalite, the filter residue was washed with ethyl acetate, and the solution was evaporated to yield 3-[4-(3-hydroxy-propyl)-phenyl]-1-(2-methyl-pyridin-4-yl)-3-o-tolyl-propan-1-one (41 mg, 64%) as a colorless oil, which was directly subjected to the next step.

In analogy to example 74, step 7, from 3-[4-(3-hydroxy-propyl)-phenyl]-1-(2-methyl-pyridin-4-yl)-3-o-tolyl-propan-1-one and hydroxylamine hydrochloride in the presence of NaHCO₃ was prepared 3-[4-(3-hydroxy-propyl)-phenyl]-1-(2-methyl-pyridin-4-yl)-3-o-tolyl-propan-1-one oxime as a mixture of E and Z isomers (2.7:1) as a colorless oil, MS (ESI+): m/z=389.2 ([M+H]+).

Example 89

3-({4'-[3-[Hydroxyimino]-3-(2-methyl-pyridin-4-yl)-1-o-tolyl-propyl]-biphenyl-4-carbonyl}-amino)-propionic acid

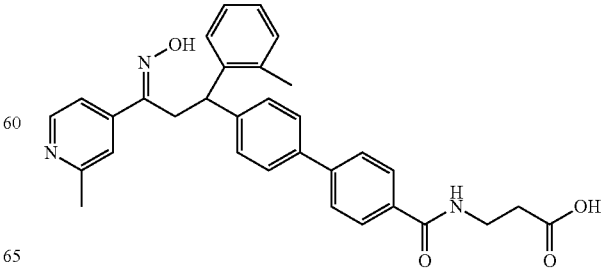

Step 1: 4'-[3-(2-Methyl-pyridin-4-yl)-3-oxo-1-o-tolyl-propyl]-biphenyl-4-carboxylic acid In analogy to example 75, from 4'-[3-(2-methyl-pyridin-4-yl)-3-oxo-1-o-tolyl-propyl]-biphenyl-4-carboxylic acid methyl ester (example 74, step 6) was prepared the title compound as a colorless oil, MS (ESI⁺): m/z=436.1906 ([M+H]⁺).

Step 2: 3-({4'-[3-(2-Methyl-pyridin-4-yl)-3-oxo-1-o-tolyl-propyl]-biphenyl-4-carbonyl}-amino)-propionic acid ethyl ester To a solution of 4'-[3-(2-methyl-pyridin-4-yl)-3-oxo-1-o-tolyl-propyl]-biphenyl-4-carboxylic acid (50 mg) in THF (1 mL) was added TBTU (41 mg) and triethylamine (0.048 mL) and the resulting mixture was stirred at room temperature for 10 min. Beta-alanine ethyl ester hydrochloride (21.2 mg) was added and the reaction mixture was stirred at rt overnight. A saturated solution of NH₄Cl and EtOAc were added, the phases were separated and the inorganic one was extracted with EtOAc (2×). The combined organic layers were washed with brine, dried over Na₂SO₄, filtered and concentrated in vacuo to yield the title compound (72 mg) as a light yellow oil, MS (ESI⁺): m/z=535.3 ([M+H]⁺).

Step 3: 3-({4'-[3-(2-Methyl-pyridin-4-yl)-3-oxo-1-o-tolyl-propyl]-biphenyl-4-carbonyl}-amino)-propionic acid In analogy to example 75, from 3-({4'-[3-(2-methyl-pyridin-4-yl)-3-oxo-1-o-tolyl-propyl]-biphenyl-4-carbonyl}-amino)-propionic acid ethyl ester was prepared the title compound, MS (ESI⁺): m/z=507.2 ([M+H]⁺).

Step 4: 3-({4'-[3-[Hydroxyimino]-3-(2-methyl-pyridin-4-yl)-1-o-tolyl-propyl]-biphenyl-4-carbonyl}-amino)-propionic acid In analogy to example 74, step 7, from 3-({4'-[3-(2-methyl-pyridin-4-yl)-3-oxo-1-o-tolyl-propyl]-biphenyl-4-carbonyl}-amino)-propionic acid and hydroxylamine hydrochloride in the presence of NaHCO₃ was prepared the title compound as a mixture of E and Z isomers (4:1) as a colorless oil, MS (ESI⁺): m/z=522.2376 ([M+H]⁺).

Example 90

({4'-[3-[Hydroxyimino]-3-(2-methyl-pyridin-4-yl)-1-o-tolyl-propyl]-biphenyl-4-carbonyl}-amino)-acetic acid

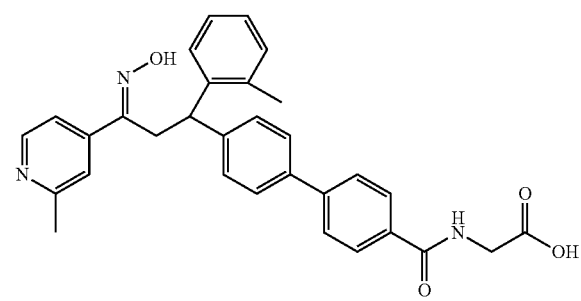 [SMILES: Cc1cc(/C(CC(c2ccc(-c3ccc(C(=O)NCC(=O)O)cc3)cc2)c2ccccc2C)=N/O)ccn1]

Step 1: ({4'-[3-(3-Methyl-pyyridin-4-yl)-3-oxo-1-o-tolyl-propyl]-biphenyl-4-carbonyl}-amino)-acetic acid methyl ester In analogy to example 89, step 2, from 4'-[3-(2-methyl-pyridin-4-yl)-3-oxo-1-o-tolyl-propyl]-biphenyl-4-carboxylic acid and glycine methyl ester hydrochloride was prepared the title compound as a colorless oil, MS (ESI⁺): m/z=507.2 ([M+H]⁺).

Steps 2 and 3: ({4'-[3-[Hydroxyimino]-3-(2-methyl-pyridin-4-yl)-1-o-tolyl-propyl]-biphenyl-4-carbonyl}-amino)-acetic acid In analogy to example 89, step 3, from ({4'-[3-(2-methyl-pyridin-4-yl)-3-oxo-1-o-tolyl-propyl]-biphenyl-4-carbonyl}-amino)-acetic acid methyl ester was prepared ({4'-[3-(2-methyl-pyridin-4-yl)-3-oxo-1-o-tolyl-propyl]-biphenyl-4-carbonyl}-amino)-acetic acid, which was directly subjected to the next step.

In analogy to example 74, step 7, from ({4'-[3-(2-methyl-pyridin-4-yl)-3-oxo-1-o-tolyl-propyl]-biphenyl-4-carbonyl}-amino)-acetic acid and hydroxylamine hydrochloride in the presence of NaHCO₃ was prepared the title compound as a mixture of E and Z isomers (3.8:1) as a white solid, MS (ESI⁺): m/z=508.2 ([M+H]⁺).

Examples 91 to 94

4'-[(S)-3-[(E)-Hydroxyimino]-3-(2-methyl-pyridin-4-yl)-1-o-tolyl-propyl]-biphenyl-4-carboxylic acid 4'-[(S)-3-[(Z)-hydroxyimino]-3-(2-methyl-pyridin-4-yl)-1-o-tolyl-propyl]-biphenyl-4-carboxylic acid 4'-[(R)-3-[(E)-hydroxyimino]-3-(2-methyl-pyridin-4-yl)-1-o-tolyl-propyl]-biphenyl-4-carboxylic acid and 4'-[(R)-3-[(Z)-hydroxyimino]-3-(2-methyl-pyridin-4-yl)-1-o-tolyl-propyl]-biphenyl-4-carboxylic acid

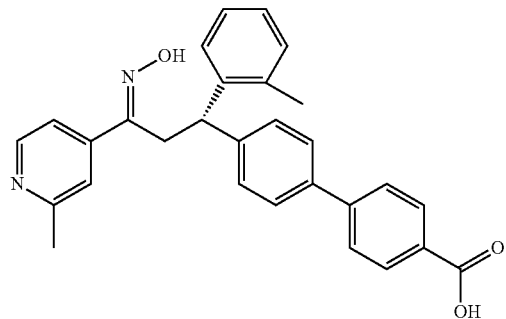

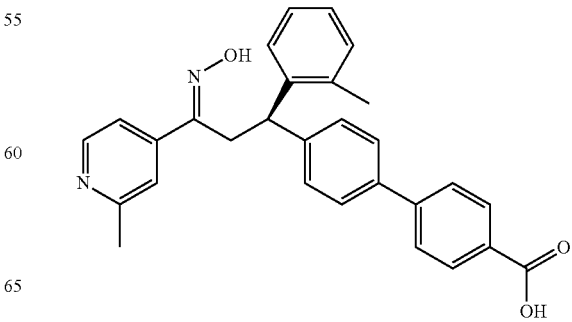

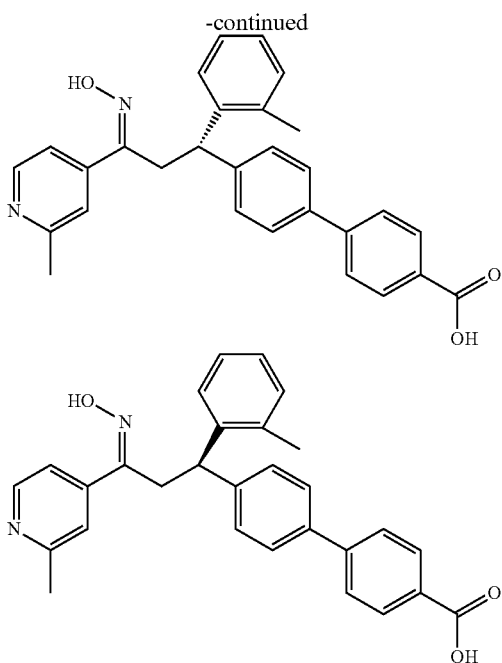

Separation of 4'-[3-[hydroxyimino]-3-(2-methyl-pyridin-4-yl)-1-o-tolyl-propyl]-biphenyl-4-carboxylic acid (example 75) by chiral HPLC (Chiralpak AD, 15% (ethanol+0.5% formic acid) in heptane) yielded 4'-[(S)-3-[(E)-hydroxyimino]-3-(2-methyl-pyridin-4-yl)-1-o-tolyl-propyl]-biphenyl-4-carboxylic acid as a colorless oil, MS (ESI+): m/z=451.2010 ([M+H]+) and 4'-[(S)-3-[(Z)-hydroxyimino]-3-(2-methyl-pyridin-4-yl)-1-o-tolyl-propyl]-biphenyl-4-carboxylic acid as a colorless oil, MS (ESI+): m/z=451.2013 ([M+H]+), and an additional fraction which was further separated by chiral HPLC (Reprosil-Chiral-NR, 15% (ethanol+0.5% formic acid)/heptane) to give 4'-[(R)-3-[(E)-hydroxyimino]-3-(2-methyl-pyridin-4-yl)-1-o-tolyl-propyl]-biphenyl-4-carboxylic acid a colorless oil, MS (ESI+): m/z=451.2010 ([M+H]+) and 4'-[(R)-3-[(Z)-hydroxyimino]-3-(2-methyl-pyridin-4-yl)-1-o-tolyl-propyl]-biphenyl-4-carboxylic acid as a colorless oil, MS (ESI+): m/z=451.2017 ([M+H]+).

Example 95

(S)-2-({4'-[(S)-3-[Hydroxyimino]-3-(2-methyl-pyridin-4-yl)-1-o-tolyl-propyl]-biphenyl-4-carbonyl}-amino)-propionic acid

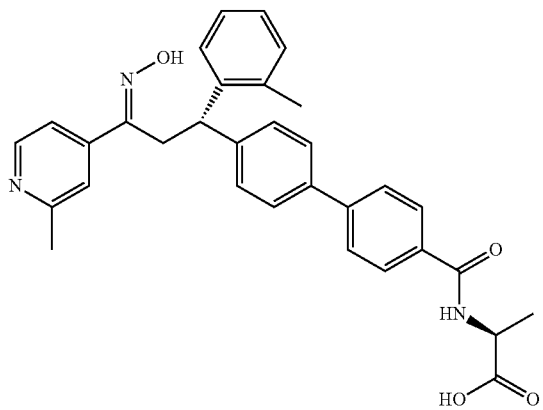 [SMILES: Cc1cc(/C(C[C@@H](c2ccc(-c3ccc(C(=O)N[C@@H](C)C(=O)O)cc3)cc2)c2ccccc2C)=N/O)ccn1]

Step 1: 4'-[(S)-3-(2-methyl-pyridin-4-yl)-3-oxo-1-o-tolyl-propyl]-biphenyl-4-carboxylic acid and 4'-[(R)-3-(2-methyl-pyridin-4-yl)-3-oxo-1-o-tolyl-propyl]-biphenyl-4-carboxylic acid Separation of 4'-[3-(2-methyl-pyridin-4-yl)-3-oxo-1-o-tolyl-propyl]-biphenyl-4-carboxylic acid (example 89, step 1) by chiral HPLC (Chiralpak AD-H, 20% (ethanol+0.5% formic acid)/heptane) yielded 4'-[(S)-3-(2-methyl-pyridin-4-yl)-3-oxo-1-o-tolyl-propyl]-biphenyl-4-carboxylic acid, MS (ESI+): m/z=436.1913 ([M+H]+) and 4'-[(R)-3-(2-methyl-pyridin-4-yl)-3-oxo-1-o-tolyl-propyl]-biphenyl-4-carboxylic acid as a white solid, MS (ESI+): m/z=436.1918 ([M+H]+).

Step 2: (S)-2-({4'-[(S)-3-(2-Methyl-pyridin-4-yl)-3-oxo-1-o-tolyl-propyl]-biphenyl-4-carbonyl}-amino)-propionic acid ethyl ester In analogy to example 89, step 2, from 4'-[(S)-3-(2-methyl-pyridin-4-yl)-3-oxo-1-o-tolyl-propyl]-biphenyl-4-carboxylic acid and L-alanine ethyl ester hydrochloride was prepared the title compound as a light yellow oil, MS (ESI+): m/z=535.3 ([M+H]+).

Step 3: (S)-2-({4'-[(S)-3-(2-methyl-pyridin-4-yl)-3-oxo-1-o-tolyl-propyl]-biphenyl-4-carbonyl}-amino)-propionic acid In analogy to example 75, from (S)-2-({4'-[(S)-3-(2-methyl-pyridin-4-yl)-3-oxo-1-o-tolyl-propyl]-biphenyl-4-carbonyl}-amino)-propionic acid ethyl ester was prepared the title compound as a white solid, MS (ESI+): m/z=507.2281 ([M+H]+).

Step 4: (S)-2-({4'-[(S)-3-hydroxyimino]-3-(2-methyl-pyridin-4-yl)-1-o-tolyl-propyl]-biphenyl-4-carbonyl}-amino)-propionic acid In analogy to example 74, step 7, from (S)-2-({4'-[(S)-3-(2-methyl-pyridin-4-yl)-3-oxo-1-o-tolyl-propyl]-biphenyl-4-carbonyl}-amino)-propionic acid and hydroxylamine hydrochloride in the presence of NaHCO3 was prepared the title compound as a mixture of E and Z isomers (3:1) as a white solid, MS (ESI+): m/z=522.3 ([M+H]+).

Example 96

({4'-[(R)-3-[(E)-Hydroxyimino]-3-(2-methyl-pyridin-4-yl)-1-o-tolyl-propyl]-biphenyl-4-carbonyl}-amino)-acetic acid

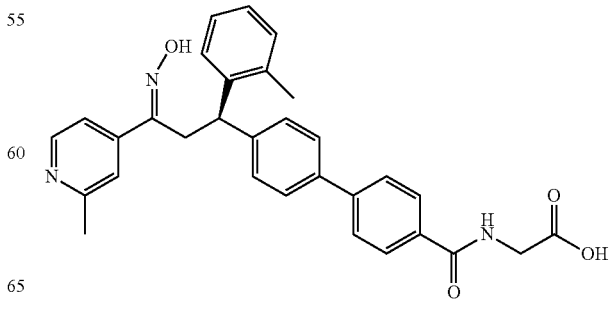

Step 1: ({4'-[(R)-3-(2-Methyl-pyridin-4-yl)-3-oxo-1-o-tolyl-propyl]-biphenyl-4-carbonyl}-amino)-acetic acid methyl ester In analogy to example 89, step 2, from 4'-[(R)-3-(2-methyl-pyridin-4-yl)-3-oxo-1-o-tolyl-propyl]-biphenyl-4-carboxylic acid (example 95, step 1) and glycine methyl ester hydrochloride was prepared the title compound as light yellow foam, MS (ESI$^+$): m/z=507.2282 ([M+H]$^+$).

Steps 2 and 3: ({4'-[(R)-3-[(E)-Hydroxyimino]-3-(2-methyl-pyridin-4-yl)-1-o-tolyl-propyl]-biphenyl-4-carbonyl}-amino)-acetic acid In analogy to example 75, from ({4'-[(R)-3-(2-methyl-pyridin-4-yl)-3-oxo-1-o-tolyl-propyl]-biphenyl-4-carbonyl}-amino)-acetic acid methyl ester was prepared ({4'-[(R)-3-(2-methyl-pyridin-4-yl)-3-oxo-1-o-tolyl-propyl]-biphenyl-4-carbonyl}-amino)-acetic acid which was directly subjected to the next step.

In analogy to example 74, step 7, from ({4'-[(R)-3-(2-methyl-pyridin-4-yl)-3-oxo-1-o-tolyl-propyl]-biphenyl-4-carbonyl}-amino)-acetic acid and hydroxylamine hydrochloride in the presence of NaHCO$_3$ was prepared ({4'-[(R)-3-[hydroxyimino]-3-(2-methyl-pyridin-4-yl)-1-o-tolyl-propyl]-biphenyl-4-carbonyl}-amino)-acetic acid as a mixture of isomers which was separated by chiral HPLC (Reprosil-Chiral-NR, 70% n-heptane, 30% ethanol+0.5% formic acid) to give the title compound as a white solid, MS (ESI$^+$): m/z=508.3 ([M+H]$^+$).

Example 97

4'-[(S)-3-[Hydroxyimino]-3-(2-methyl-pyridin-4-yl)-1-o-tolyl-propyl]-biphenyl-4-carboxylic acid ((R)-1-phenyl-ethyl)-amide

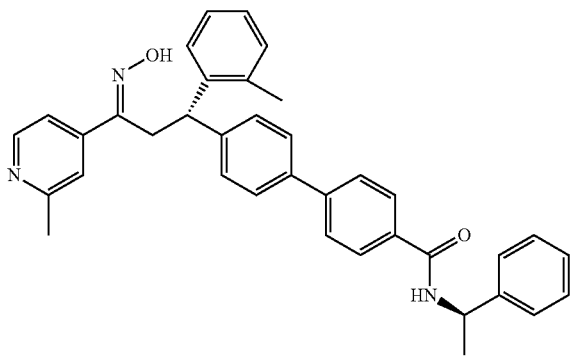 [SMILES: Cc1cc(/C(C[C@@H](c2ccc(-c3ccc(C(=O)N[C@H](C)c4ccccc4)cc3)cc2)c2ccccc2C)=N/O)ccn1]

Step 1: 4'-[(S)-3-(2-Methyl-pyridin-4-yl)-3-oxo-1-o-tolyl-propyl]-biphenyl-4-carboxylic acid ((R)-1-phenyl-ethyl)-amide In analogy to example 89, step 2, from 4'-[(S)-3-(2-methyl-pyridin-4-yl)-3-oxo-1-o-tolyl-propyl]-biphenyl-4-carboxylic acid (example 95, step 1) and (R)-(+)-1-phenylethylamine was prepared the title compound as a white foam, MS (ESI$^+$): m/z=539.4 ([M+H]$^+$).

Step 2: 4'-[(S)-3-[Hydroxyimino]-3-(2-methyl-pyridin-4-yl)-1-o-tolyl-propyl]-biphenyl-4-carboxylic acid ((R)-1-phenyl-ethyl)-amide In analogy to example example 74, step 7, from 4'-[(S)-3-(2-methyl-pyridin-4-yl)- 3-oxo-1-o-tolyl-propyl]-biphenyl-4-carboxylic acid ((R)-1-phenyl-ethyl)-amide and hydroxylamine hydrochloride in the presence of NaHCO$_3$ was prepared the title compound as a mixture of E and Z isomers (3.4:1) as a colorless oil, MS (ESI$^+$): m/z=553.702 ([M+H]$^+$).

Example 98

3-(3-Bromo-phenyl)-1-(2-methyl-pyridin-4-yl)-3-o-tolyl-propan-1-one oxime

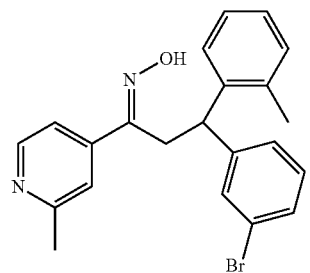 [SMILES: Cc1cc(/C(CC(c2cccc(Br)c2)c2ccccc2C)=N/O)ccn1]

Step 1: 3-(3-Bromo-phenyl)-2-cyano-acrylic acid ethyl ester

In analogy to example 74, step 1, from 3-bromobenzaldehyde and ethyl cyanoacetate was prepared the title compound as a white solid, MS (EI$^+$): m/z=279 ([M]$^+$, 1Br).

Step 2: 3-(3-Bromo-phenyl)-2-cyano-3-o-tolyl-propionic acid ethyl ester

In analogy to example 74, step 2, from 3-(3-bromo-phenyl)-2-cyano-acrylic acid ethyl ester and o-tolylmagnesium chloride was prepared the title compound as a colorless oil, MS (ESI$^-$): m/z=370.04 (([M−H]$^-$), 1Br).

Step 3: 3-(3-Bromo-phenyl)-3-o-tolyl-propionic acid

In analogy to example 74, step 3, from 3-(3-bromo-phenyl)-2-cyano-3-otolyl-propionic acid ethyl ester was prepared the title compound as a white solid, MS (ESI$^-$): m/z=317.02 ([M−H]$^-$), 1Br).

Step 4: 3-(3-Bromo-phenyl)-N-methoxy-N-methyl-3-o-tolyl-propionamide

In analogy to example 74, step 4, from 3-(3-bromo-phenyl)-3-o-tolyl-propionic acid and N,O-dimethylhydroxylamine hydrochloride was prepared the title compound as a white solid, mp 89° C., MS (ESI$^+$): m/z=362.07 ([M+H]$^+$, 1 Br).

Step 5: 3-(3-Bromo-phenyl)-1-(2-methyl-pyridin-4-yl)-3-o-tolyl-propan-1-one

In analogy to example 74, step 5, from 3-(3-bromo-phenyl)-N-methoxy-N-methyl-3-o tolyl-propionamide and 4-bromo-2-methylpyridine was prepared the title compound as a colorless oil, MS (ESI$^+$): m/z=394.08 ([M+H]$^+$, 1 Br).

Step 6: 3-(3-Bromo-phenyl)-1-(2-methyl-pyridin-4-yl)-3-o-tolyl-propan-1-one oxime In analogy to example 74, step 7, from 3-(3-bromo-phenyl)-1-(2-methyl-pyridin-4-yl)-3-o-tolyl-propan-1-one and hydroxylamine hydrochloride in the presence of NaHCO$_3$ was prepared the title compound as a mixture of E and Z isomers (5.7:1) as a white foam, MS (ESI$^+$): m/z=409.0895 ([M+H]$^+$, 1Br).

141

Example 99

5-{3-[3-[Hydroxyimino]-3-(2-methyl-pyridin-4-yl)-1-o-tolyl-propyl]-phenyl}-pyridine-2-carboxylic acid

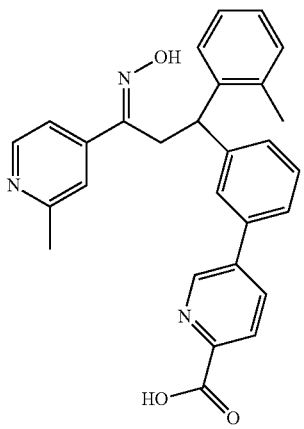 [SMILES: Cc1cc(/C(CC(c2cccc(-c3ccc(C(=O)O)nc3)c2)c2ccccc2C)=N/O)ccn1]

Step 1: 5-{3-[3-(2-Methyl-pyridin-4-yl)-3-oxo-1-o-tolyl-propyl]-phenyl}-pyridine-2-carboxylic acid In analogy to example 74, step 6, from 3-(3-bromo-phenyl)-1-(2-methyl-pyridin-4-yl)-3-o-tolyl-propan-1-one (example 98, step 5) and 2-(methylcarboxy)pyridine-5-boronic acid (4 h at 80° C., 40 h at rt) was prepared the title compound as an off-white semisolid, MS (ESI⁻): m/z=435.2 ([M−H]⁻, 1Br).

Step 2: 5-{3-[3-[Hydroxyimino]-3-(2-methyl-pyridin-4-yl)-1-o-tolyl-propyl]-phenyl}-pyridine-2-carboxylic acid In analogy to example 74, step 7, from 5-{3-[3-(2-methyl-pyridin-4-yl)-3-oxo-1-o-tolyl-propyl]-phenyl}-pyridine-2-carboxylic acid and hydroxylamine hydrochloride in the presence of NaHCO₃ was prepared the title compound as a mixture of E and Z isomers (3:1) as a white solid, MS (ESI⁺): m/z=452.4 [M+H]⁺.

Example 100

3-Fluoro-3'-[3-[hydroxyimino]-3-(2-methyl-pyridin-4-yl)-1-o-tolyl-propyl]-biphenyl-4-carboxylic acid methyl ester

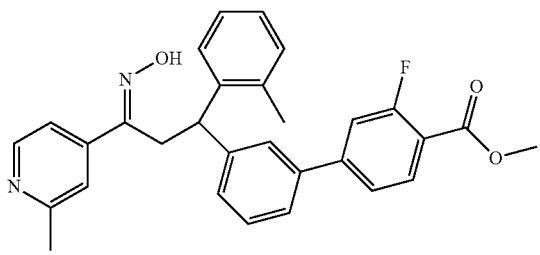 [SMILES: COC(=O)c1ccc(-c2cccc(C(C/C(=N\O)c3ccnc(C)c3)c3ccccc3C)c2)cc1F]

142

Step 1: 3-Fluoro-3'-[3-(2-methyl-pyridin-4-yl)-3-oxo-1-o-tolyl-propyl]-biphenyl-4-carboxylic acid methyl ester In analogy to example 74, step 6, from 3-(3-bromo-phenyl)-1-(2-methyl-pyridin-4-yl)-3-o-tolyl-propan-1-one (example 98, step 5) and (3-fluoro-4-methoxycarbonyl)phenylboronic acid was prepared the title compound as a colorless oil, MS (ESI⁺): m/z=468.2 ([M+H]⁺).

Step 2: 3-Fluoro-3'-[3-[hydroxyimino]-3-(2-methyl-pyridin-4-yl)-1-o-tolyl-propyl]-biphenyl-4-carboxylic acid methyl ester In analogy to example 74, step 7, from 3-fluoro-3'-[3-(2-methyl-pyridin-4-yl)-3-oxo-1-o-tolyl-propyl]-biphenyl-4-carboxylic acid methyl ester and hydroxylamine hydrochloride in the presence of NaHCO₃ was prepared the title compound as a mixture of E and Z isomers (4.4:1) as a white foam, MS (ESI⁺): m/z=483.2 ([M+H]⁺).

Example 101

3-Fluoro-3'-[3-[(E)-hydroxyimino]-3-(2-methyl-pyridin-4-yl)-1-o-tolyl-propyl]-biphenyl-4-carboxylic acid

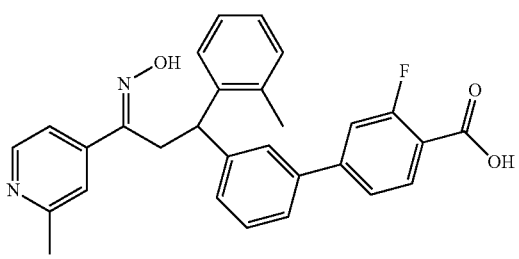

In analogy to example 75, from 3-fluoro-3'-[3-[hydroxyimino]-3-(2-methyl-pyridin-4-yl)-1-o-tolyl-propyl]-biphenyl-4-carboxylic acid methyl ester was prepared 3-fluoro-3'-[3-[(E)-hydroxyimino]-3-(2-methyl-pyridin-4-yl)-1-o-tolyl-propyl]-biphenyl-4-carboxylic acid which contains less than 8% of the Z isomer as a white solid, MS (ESI⁺): m/z=469.19 ([M+H]⁺).

Example 102

3'-[3-[Hydroxyimino]-3-(2-methyl-pyridin-4-yl)-1-o-tolyl-propyl]-biphenyl-3-carboxylic acid

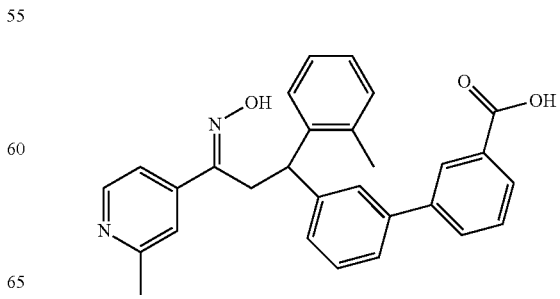

Step 1: 3'-[3-(2-Methyl-pyridin-4-yl)-3-oxo-1-o-tolyl-propyl]-biphenyl-3-carboxylic acid In analogy to example 74, step 6, from 3-(3-bromo-phenyl)-1-(2-methyl-pyridin-4-yl)-3-o-tolyl-propan-1-one (example 98, step 5) and 3-carboxyphenylboronic acid was prepared the title compound as an off-white solid, MS (ESI⁻): m/z=434.3 ([M–H]⁻).

Step 2: 3'-[3-[Hydroxyimino]-3-(2-methyl-pyridin-4-yl)-1-o-tolyl-propyl]-biphenyl-3-carboxylic acid In analogy to example 74, step 7, from 3'-[3-(2-methyl-pyridin-4-yl)-3-oxo-1-o-tolyl-propyl]-biphenyl-3-carboxylic acid and hydroxylamine hydrochloride in the presence of NaHCO₃ was prepared the title compound as a mixture of E and Z isomers (8.5:1) as an off-white solid, MS (ESI⁺): m/z=451.20 ([M+H]⁺).

Example 103

(E)-3'-[3-[Hydroxyimino]-3-(2-methyl-pyridin-4-yl)-1-o-tolyl-propyl]-biphenyl-4-carboxylic acid

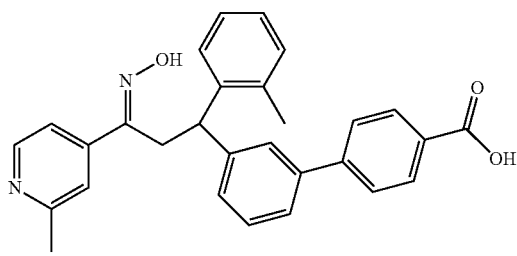 [SMILES: Cc1cc(/C(CC(c2cccc(-c3ccc(C(=O)O)cc3)c2)c2ccccc2C)=N/O)ccn1]

Step 1: 3'-[3-(2-Methyl-pyridin-4-yl)-3-oxo-1-o-tolyl-propyl]-biphenyl-4-carboxylic acid methyl ester In analogy to example 19, from 3-(3-bromo-phenyl)-1-(2-methyl-pyridin-4-yl)-3-o-tolyl-propan-1-one (example 98, step 5) and 4-methoxycarbonyl-phenylboronic acid was prepared the title compound as a yellow foam, MS (ESI⁺): m/z=450.3 ([M+H]⁺).

Steps 2 and 3: (E)-3'-[3-[Hydroxyimino]-3-(2-methyl-pyridin-4-yl)-1-o-tolyl-propyl]-biphenyl-4-carboxylic acid In analogy to example 74, step 7, from 3'-[3-(2-methyl-pyridin-4-yl)-3-oxo-1-o-tolyl-propyl]-biphenyl-4-carboxylic acid methyl ester and hydroxylamine hydrochloride in the presence of NaHCO₃ was prepared 3'-[3-[hydroxyimino]-3-(2-methyl-pyridin-4-yl)-1-o-tolyl-propyl]-biphenyl-4-carboxylic acid methyl ester, which was directly subjected to the next step. In analogy to example 75, from 3'-[3-[hydroxyimino]-3-(2-methyl-pyridin-4-yl)-1-o-tolyl-propyl]-biphenyl-4-carboxylic acid methyl ester was prepared (E)-3'-[3-[hydroxyimino]-3-(2-methyl-pyridin-4-yl)-1-o-tolyl-propyl]-biphenyl-4-carboxylic acid which contains less than 10% of the Z isomer as an off-white solid, MS (ESI⁺): m/z=451.20 ([M+H]⁺).

Example 104

3-(4'-Methanesulfonyl-biphenyl-3-yl)-1-(2-methyl-pyridin-4-yl)-3-o-tolyl-propan-1-one oxime

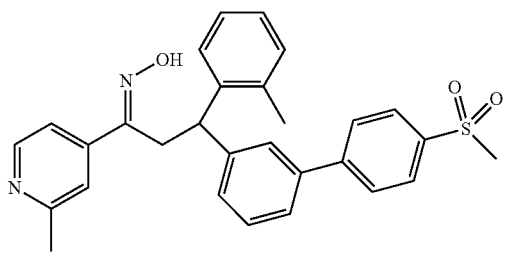 [SMILES: Cc1cc(/C(CC(c2cccc(-c3ccc(S(C)(=O)=O)cc3)c2)c2ccccc2C)=N/O)ccn1]

Step 1: 3-(4'-Methanesulfonyl-biphenyl-3-yl)-1-(2-methyl-pyridin-4-yl)-3-o-tolyl-propan-1-one In analogy to example 22, from 3-(3-bromo-phenyl)-1-(2-methyl-pyridin-4-yl)-3-o-tolyl-propan-1-one (example 98, step 5) and 4-(methylsulfonyl)phenylboronic acid was prepared the title compound as light yellow foam, MS (ESI⁺): m/z=470.2 ([M+H]⁺).

Step 2: 3-(4'-Methane sulfonyl-biphenyl-3-yl)-1-(2-methyl-pyridin-4-yl)-3-o-tolyl-propan-1-one oxime In analogy to example 74, step 7, 3-(4'-methanesulfonyl-biphenyl-3-yl)-1-(2-methyl-pyridin-4-yl)-3-o-tolyl-propan-1-one and hydroxylamine hydrochloride in the presence of NaHCO₃ was prepared the title compound as a mixture of E and Z isomers (4.8:1) as a white foam, MS (ESI⁺): m/z=485.19 ([M+H]⁺).

Example 105

{3-[3-[(E)-Hydroxyimino]-3-(2-methyl-pyridin-4-yl)-1-o-tolyl-propyl]-phenyl}-acetic acid

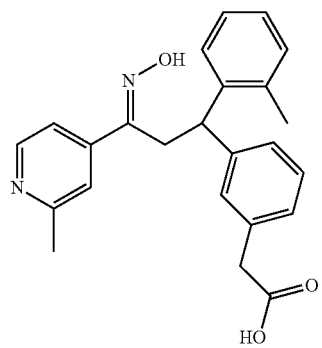 [SMILES: Cc1cc(/C(CC(c2cccc(CC(=O)O)c2)c2ccccc2C)=N/O)ccn1]

Step 1: Cyano-{3-[3-(2-methyl-pyridin-4-yl)-3-oxo-1-o-tolyl-propyl]-phenyl}-acetic acid ethyl ester In analogy to example 80, step 1, from 3-(3-bromo-phenyl)-1-(2-methyl-pyridin-4-yl)-3-o-tolyl-propan-1-one (example 98, step 5) and ethyl cyanoacetate was prepared the title compound as a light yellow oil, MS (ESI⁺): m/z=427.2 ([M+H]⁺).

Step 2: {3-[3-(2-Methyl-pyridin-4-yl)-3-oxo-1-o-tolyl-propyl]-phenyl}-acetic acid In analogy to example 74, step 3, from cyano-{3-[3-(2-methyl-pyridin-4-yl)-3-oxo-1-o-tolyl-propyl]-phenyl}-acetic acid ethyl ester was prepared the title compound as a colorless oil, MS (ESI⁺): m/z=374.17 ([M+H]⁺).

Step 3: {3-[3-[(E)-Hydroxyimino]-3-(2-methyl-pyridin-4-yl)-1-o-tolyl-propyl]-phenyl}-acetic acid In analogy to example 74, step 7, from {3-[3-(2-methyl-pyridin-4-yl)-3-oxo-1-o-tolyl-propyl]-phenyl}-acetic acid was prepared the title compound which contains less than 6% of the Z isomer as a white solid, MS (ESI⁺): m/z=389.19 ([M+H]⁺).

Example 106

3-[3-(3-Hydroxy-prop-1-ynyl)-phenyl]-1-(2-methyl-pyridin-4-yl)-3-o-tolyl-propan-1-one oxime

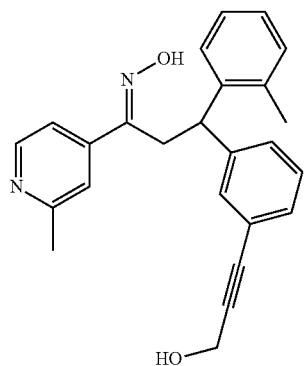 [SMILES: Cc1cc(/C(CC(c2cccc(C#CCO)c2)c2ccccc2C)=N/O)ccn1]

Step 1: 3-[3-(3-Hydroxy-prop-1-ynyl)-phenyl]-1-(2-methyl-pyridin-4-yl)-3-o-tolyl-propan-1-one In analogy to example 85, step 1, from 3-(3-bromo-phenyl)-1-(2-methyl-pyridin-4-yl)-3-o-tolyl-propan-1-one (example 98, step 5) and 2-propyn-1-ol was prepared the title compound as a white foam, MS (ESI⁺): m/z=370.18 ([M+H]⁺).

Step 2: 3-[3-(3-Hydroxy-prop-1-ynyl)-phenyl]-1-(2-methyl-pyridin-4-yl)-3-o-tolyl-propan-1-one oxime In analogy to example 74, step 7, from 3-[3-(3-hydroxy-prop-1-ynyl)-phenyl]-1-(2-methyl-pyridin-4-yl)-3-o-tolyl-propan-1-one and hydroxylamine hydrochloride in the presence of NaHCO₃ was prepared the title compound as a mixture of E and Z isomers (3:1) as a white foam, MS (ESI⁺): m/z=385.1 ([M+H]⁺).

Example 107

3-[3-(3-Hydroxy-propyl)-phenyl]-1-(2-methyl-pyridin-4-yl)-3-o-tolyl-propan-1-one oxime

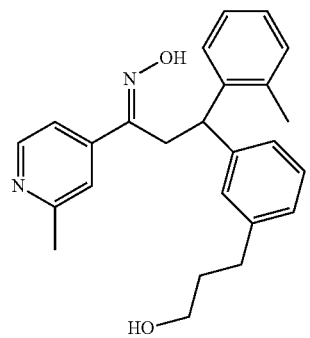 [SMILES: Cc1cc(/C(CC(c2cccc(CCCO)c2)c2ccccc2C)=N/O)ccn1]

Step 1: 3-[3-(3-Hydroxy-propyl)-phenyl]-1-(2-methyl-pyridin-4-yl)-3-o-tolyl-propan-1-one In analogy to example 88, step 1, from 3-[3-(3-hydroxy-prop-1-ynyl)-phenyl]-1-(2-methyl-pyridin-4-yl)-3-o-tolyl-propan-1-one was prepared the title compound as a colorless oil, MS (ESI⁺): m/z=374.2 ([M+H]⁺).

Step 2: 3-[3-(3-Hydroxy-propyl)-phenyl]-1-(2-methyl-pyridin-4-yl)-3-o-tolyl-propan-1-one oxime In analogy to example 74, step 7, from 3-[3-(3-hydroxy-propyl)-phenyl]-1-(2-methyl-pyridin-4-yl)-3-o-tolyl-propan-1-one and hydroxylamine hydrochloride in the presence of NaHCO₃ was prepared the title compound as a mixture of E and Z isomers (3:1) as a colorless oil, MS (ESI⁺): m/z=389.2 ([M+H]⁺).

Example 108

({3'-[3-[(E)-Hydroxyimino]-3-(2-methyl-pyridin-4-yl)-1-o-tolyl-propyl]-biphenyl-3-carbonyl}-amino)-acetic acid

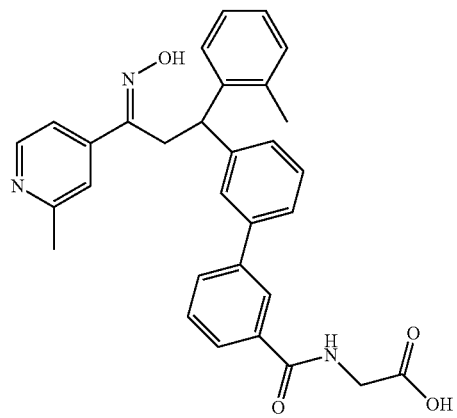 [SMILES: Cc1cc(/C(CC(c2cccc(-c3cccc(C(=O)NCC(=O)O)c3)c2)c2ccccc2C)=N/O)ccn1]

Step 1 and 2: ({3'-[3-(2-Methyl-pyridin-4-yl)-3-oxo-1-o-tolyl-propyl]-biphenyl-3-carbonyl}-amino)-acetic acid In analogy to example 89, step 2, from 3'-[3-(2-methyl-pyridin-4-yl)-3-oxo-1-o-tolyl-propyl]-biphenyl-3-carboxylic acid (example 102, step 1) and glycine methyl ester hydrochloride was prepared ({3'-[3-(2-methyl-pyridin-4-yl)-3-oxo-1-o-tolyl-propyl]-biphenyl-3-carbonyl}-amino)-acetic acid methyl ester as a white foam, which was directly subjected to the next step. In analogy to example 75, from ({3'-[3-(2-methyl-pyridin-4-yl)-3-oxo-1-o-tolyl-propyl]-biphenyl-3-carbonyl}-amino)-acetic acid methyl ester was prepared the title compound as a white foam, MS (ESI−): m/z=491.3 ([M−H]−).

Step 3: ({3'-[3-[(E)-Hydroxyimino]-3-(2-methyl-pyridin-4-yl)-1-o-tolyl-propyl]-biphenyl-3-carbonyl}-amino)-acetic acid In analogy to example 74, step 4, from ({3'-[3-(2-methyl-pyridin-4-yl)-3-oxo-1-o-tolyl-propyl]-biphenyl-3-carbonyl}-amino)-acetic acid and hydroxylamine hydrochloride in the presence of NaHCO$_3$ was prepared the title compound which precipitated as a white solid on work up, MS (ESI−): m/z=506.2 ([M−H]−).

Example 109

3-(4-Bromo-phenyl)-1-(2-methoxy-pyridin-4-yl)-3-o-tolyl-propan-1-one oxime

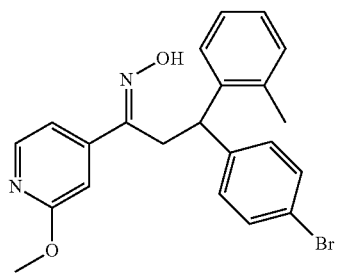 [SMILES: COc1cc(/C(CC(c2ccc(Br)cc2)c2ccccc2C)=N/O)ccn1]

Step 1: 3-(4-Bromo-phenyl)-1-(2-methoxy-pyridin-4-yl)-3-o-tolyl-propan-1-one

In analogy to example 74, step 5, from 3-(3-bromo-phenyl)-N-methoxy-N-methyl-3-o-tolyl-propionamide (example 98, step 4) and 4-bromo-2-methoxypyridine was prepared the title compound as a colorless oil, MS (ESI+): m/z=410.2 ([M+H]+, 1Br).

Step 2: 3-(4-Bromo-phenyl)-1-(2-methoxy-pyridin-4-yl)-3-o-tolyl-propan-1-one oxime In analogy to example 74, step 7, from 3-(4-bromo-phenyl)-1-(2-methoxy-pyridin-4-yl)-3-o-tolyl-propan-1-one and hydroxylamine hydrochloride in the presence of NaHCO$_3$ was prepared the title compound as a mixture of E and Z isomers (2.7:1) as a white foam, MS (ESI+): m/z=425.1 ([M+H]+, 1Br).

Example 110

4-{3-(4-Bromo-phenyl)-1-[(E)-hydroxyimino]-3-o-tolyl-propyl}-1-methyl-1H-pyridin-2-one

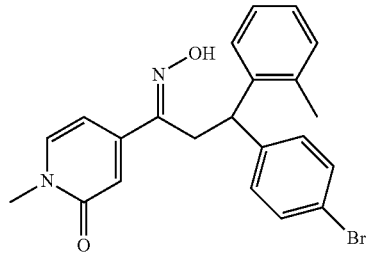 [SMILES: Cc1ccccc1C(C/C(=N\O)c1ccn(C)c(=O)c1)c1ccc(Br)cc1]

Step 1: 4-[3-(4-Bromo-phenyl)-3-o-tolyl-propionyl]-1H-pyridin-2-one

To a solution of 3-(4-bromo-phenyl)-1-(2-methoxy-pyridin-4-yl)-3-o-tolyl-propan-1-one (example 109, step 1; 190 mg) in dioxane (9 mL) was added concentrated hydrochloric acid (1 mL) and the mixture was heated to 100° C. for 2 h. The solution was cooled to rt and added to a mixture of water and EtOAc. The inorganic phase was extracted with EtOAc and the combined organic phases were washed with brine, dried over Na$_2$SO$_4$, filtered and concentrated in vacuo to yield the crude title compound as a white foam, MS (ESI+): m/z=396.1 ([M+H]+, 1Br).

Step 2: 4-[3-(4-Bromo-phenyl)-3-o-tolyl-propionyl]-1-methyl-1H-pyridin-2-one

To a solution of 4-[3-(4-bromo-phenyl)-3-o-tolyl-propionyl]-1H-pyridin-2-one (150 mg) in DMA (1 mL) was added potassium carbonate (58 mg) and methyl iodide (0.06 mL). The mixture was stirred at rt for 6 h, water and TBME were added. The phases were separated and the inorganic phase was extracted with TBME and EtOAc. The combined organic phases were washed with brine, dried over Na$_2$SO$_4$, filtered and concentrated in vacuo. The crude product was purified by flash chromatography on silica gel (EtOAc/n-heptane 1:10 to EtOAc) to yield the title compound as a light yellow foam, MS (ESI+): m/z=410.2 ([M+H]+, 1Br).

Step 3: 4-{3-(4-Bromo-phenyl)-1-[(E)-hydroxyimino]-3-o-tolyl-propyl}-1-methyl-1H-pyridin-2-one In analogy to example 74, step 7, from 4-[3-(4-bromo-phenyl)-3-o-tolyl-propionyl]-1-methyl-1H-pyridin-2-one and hydroxylamine hydrochloride in the presence of NaHCO$_3$ was prepared the title compound as a white solid, MS (ESI+): m/z=425.1 ([M+H]+, 1Br).

Example 111

5-{4-[3-[Hydroxyimino]-3-(2-methyl-pyridin-4-yl)-1-o-tolyl-propyl]-phenyl}-pent-4-ynoic acid

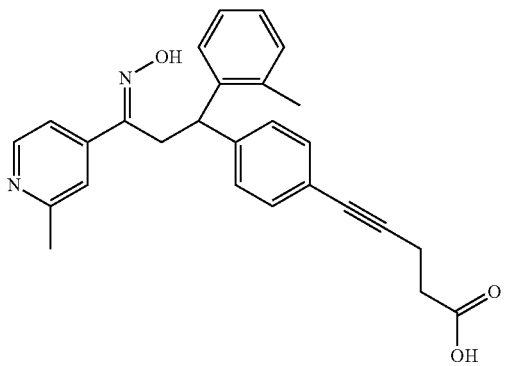 [SMILES: Cc1cc(/C(CC(c2ccc(C#CCCC(=O)O)cc2)c2ccccc2C)=N/O)ccn1]

Step 1: 5-{4-[3-(2-Methyl-pyridin-4-yl)-3-oxo-1-o-tolyl-propyl]-phenyl}-pent-4-ynoic acid methyl ester In analogy to example 85, step 1, from 3-(4-bromo-phenyl)-1-(2-methyl-pyridin-4-yl)-3-o-tolyl-propan-1-one (example 74, step 5) and pent-4-ynoic acid methyl ester was prepared the title compound as a brown oil, MS (ESI+): m/z=426.2067 ([M+H]+).

Steps 2 and 3: 5-{4-[3-[Hydroxyimino]-3-(2-methyl-pyridin-4-yl)-1-o-tolyl-propyl]-phenyl}-pent-4-ynoic acid In analogy to example 75, from 5-{4-[3-(2-methyl-pyridin-4-yl)-3-oxo-1-o-tolyl-propyl]-phenyl}-pent-4-ynoic acid methyl ester was prepared 5-{4-[3-(2-methyl-pyridin-4-yl)-3-oxo-1-o-tolyl-propyl]-phenyl}-pent-4-ynoic acid, which was directly subjected to the next step.

In analogy to example 74, step 7, from 5-{4-[3-(2-methyl-pyridin-4-yl)-3-oxo-1-o-tolyl-propyl]-phenyl}-pent-4-ynoic acid and hydroxylamine hydrochloride in the presence of NaHCO$_3$ was prepared the title compound as a mixture of E and Z isomers (4.2:1) as a colorless oil, MS (ESI−): m/z=425.1862 ([M−H]−).

Example 112

3-Fluoro-4'-[3-[hydroxyimino]-3-(2-methyl-pyridin-4-yl)-1-o-tolyl-propyl]-biphenyl-4-carboxylic acid

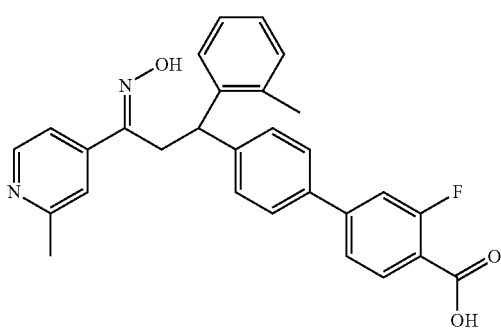 [SMILES: Cc1cc(/C(CC(c2ccc(-c3ccc(C(=O)O)c(F)c3)cc2)c2ccccc2C)=N/O)ccn1]

Step 1: 3-Fluoro-4'-[3-(2-methyl-pyridin-4-yl)-3-oxo-1-o-tolyl-propyl]-biphenyl-4-carboxylic acid methyl ester In analogy to example 74, step 6, from 3-(4-bromo-phenyl)-1-(2-methyl-pyridin-4-yl)-3-o-tolyl-propan-1-one and 3-fluoro-4-methoxycarbonylphenyl boronic acid was prepared the title compound as a yellow oil, MS (ESI+): m/z=468.1977 ([M+H]+).

Steps 2 and 3: 3-Fluoro-4'-[3-[hydroxyimino]-3-(2-methyl-pyridin-4-yl)-1-o-tolyl-propyl]-biphenyl-4-carboxylic acid In analogy to example 75, from 3-fluoro-4'-[3-(2-methyl-pyridin-4-yl)-3-oxo-1-o-tolyl-propyl]-biphenyl-4-carboxylic acid methyl ester was prepared 3-fluoro-4'-[3-(2-methyl-pyridin-4-yl)-3-oxo-1-o-tolyl-propyl]-biphenyl-4-carboxylic acid, which was directly subjected to the next reaction.

In analogy to example 74, step 7, from 3-fluoro-4'-[3-(2-methyl-pyridin-4-yl)-3-oxo-1-o-tolyl-propyl]-biphenyl-4-carboxylic acid and hydroxylamine hydrochloride in the presence of NaHCO$_3$ was prepared the title compound as a mixture of E and Z isomers (5.8:1) as a colorless oil, MS (ESI+): m/z=469.1917 ([M+H]+).

Example 113

4-Fluoro-4'-[3-[hydroxyimino]-3-(2-methyl-pyridin-4-yl)-1-o-tolyl-propyl]-biphenyl-3-carboxylic acid

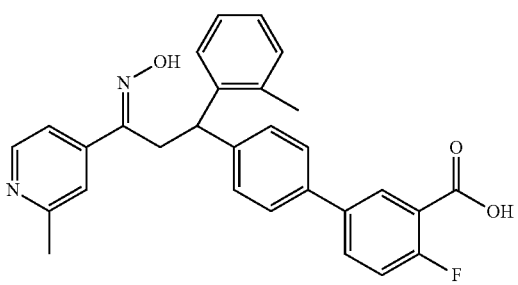 [SMILES: Cc1cc(/C(CC(c2ccc(-c3ccc(F)c(C(=O)O)c3)cc2)c2ccccc2C)=N/O)ccn1]

Step 1: 4-Fluoro-4'-[3-(2-methyl-pyridin-4-yl)-3-oxo-1-o-tolyl-propyl]-biphenyl-3-carboxylic acid methyl ester In analogy to example 74, step 6, from 3-(4-bromo-phenyl)-1-(2-methyl-pyridin-4-yl)-3-o-tolyl-propan-1-one and (4-fluoro-3-methoxycarbonylphenyl)boronic acid was prepared the title compound as a yellow oil, MS (ESI+): m/z=468.1977 ([M+H]+).

Steps 2 and 3: 4-Fluoro-4'-[3-[hydroxyimino]-3-(2-methyl-pyridin-4-yl)-1-o-tolyl-propyl]-biphenyl-3-carboxylic acid In analogy to example 75, from 4-fluoro-4'-[3-(2-methyl-pyridin-4-yl)-3-oxo-1-o-tolyl-propyl]-biphenyl-3-carboxylic acid methyl ester was prepared 4-fluoro-4'-[3-(2-methyl-pyridin-4-yl)-3-oxo-1-o-tolyl-propyl]-biphenyl-3-carboxylic acid, which was directly subjected to the next step.

In analogy to example 74, step 7, from 4-fluoro-4'-[3-(2-methyl-pyridin-4-yl)-3-oxo-1-o-tolyl-propyl]-biphenyl-3-carboxylic acid and hydroxylamine hydrochloride in the presence of NaHCO$_3$ was prepared the title compound as a mixture of E and Z isomers (3:1) as a colorless oil, MS (ESI+): m/z=469.1910 ([M+H]+).

Example 114

3-(4-Bromo-phenyl)-5-methyl-1-pyridin-4-yl-hexan-1-one oxime

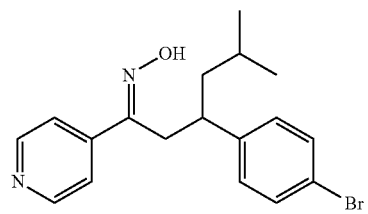 [SMILES: CC(C)CC(C/C(=N\O)c1ccncc1)c1ccc(Br)cc1]

Step 1: 3-(4-Bromo-phenyl)-5-methyl-1-pyridin-4-yl-hexan-1-one

At 0° C., to a suspension of CuI (73 mg) in THF (1 mL) was added isobutylmagnesium chloride (0.38 mL, 2M in diethyl-ether) dropwise. The reaction was stirred at 0° C. for 1 hour at which timepoint the suspension had turned brown. To this reaction mixture a suspension of CuI (66 mg) and 3-(4-bromo-phenyl)-1-pyridin-4-yl-propenone (100 mg) in THF (1 mL) was added at 0° C., and the mixture was stirred at 0° C. for 2 hours. A saturated solution of NH$_4$Cl was added, the phases were separated and the inorganic one was extracted with EtOAc (2×). The combined organic layers were washed with brine, dried over Na$_2$SO$_4$, filtered and concentrated in vacuo. The crude product was purified by flash chromatography on silica gel (EtOAc/n-heptane 1:2 to EtOAc) to yield the title compound (30 mg, 25%) as yellow oil, MS (ESI$^+$): m/z=346.0 ([M+H]$^+$, 1Br).

Step 2: 3-(4-Bromo-phenyl)-5-methyl-1-pyridin-4-yl-hexan-1-one oxime

In analogy to example 74, step 7, from 3-(4-bromo-phenyl)-5-methyl-1-pyridin-4-yl-hexan-1-one and hydroxylamine hydrochloride in the presence of NaHCO$_3$ was prepared the title compound as a mixture of E and Z isomers (2.7:1) as a colorless oil, MS (ESI$^+$): m/z=361.2 ([M+H]$^+$, 1Br).

Example 115

5-{4-[3-[Hydroxyimino]-3-(2-methyl-pyridin-4-yl)-1-o-tolyl-propyl]-phenyl}-pentanoic acid

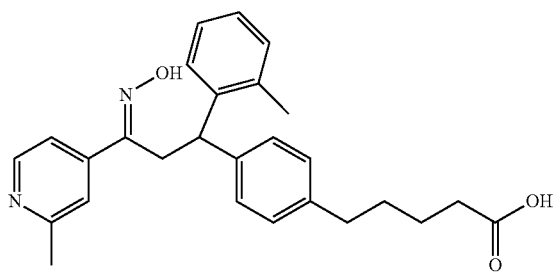 [SMILES: Cc1cc(/C(CC(c2ccc(CCCCC(=O)O)cc2)c2ccccc2C)=N/O)ccn1]

5-{4-[3-[Hydroxyimino]-3-(2-methyl-pyridin-4-yl)-1-o-tolyl-propyl]-phenyl}-pent-4-ynoic acid as a mixture of E and Z isomers (4.2:1) (example 84; 50 mg) in methanol (2 mL) was hydrogenated in the presence of Pd (5% on carbon, 6 mg) at room temperature for 5 hours. The solution was filtered over decalite, the filter residue was washed with methanol, and the solution was evaporated. The crude product was purified by flash chromatography on silica gel (gradient CH$_2$Cl$_2$ to CH$_2$Cl$_2$/MeOH 1:1) to yield 5-{4-[3-[hydroxyimino]-3-(2-methyl-pyridin-4-yl)-1-o-tolyl-propyl]-phenyl}-pentanoic acid as a mixture of E and Z isomers (4.4:1) as a colorless oil, MS (ESI$^+$): m/z=431.4 ([M+H]$^+$).

Example 116

(E)-3-(4-Bromo-phenyl)-3-(3-methyl-pyridin-2-yl)-1-(2-methyl-pyridin-4-yl)-propan-1-one oxime

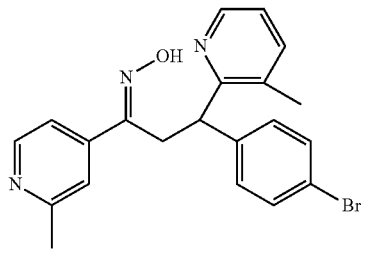 [SMILES: Cc1cc(/C(CC(c2ccc(Br)cc2)c2ncccc2C)=N/O)ccn1]

Step 1: 3-(4-Bromo-phenyl)-3-(3-methyl-pyridin-2-yl)-1-(2-methyl-pyridin-4-yl)-propan-1-one To a solution of 2-bromo-3-methylpyridine (0.35 mL) in diethyl ether (4 mL) n-BuLi (2.4 mL, 1.6 M in hexane) was added at –70° C. and the solution was stirred for 10 min at that temperature. This solution was then added to a solution previously prepared from copper (I) iodide (296 mg) and diisopropyl sulfide (0.44 mL) in diethyl ether (28 mL) at 0° C. The combined solution was stirred for 15 min at 0° C., and a solution of 3-(4-bromo-phenyl)-1-(2-methyl-pyridin-4-yl)-propenone (470 mg) in diethyl ether (8 mL) was added. The mixture was stirred at 0° C. for 3 hours, then additional cuprate solution was added (prepared as described above). Stirring was continued for 2 h at 0° C. and rt overnight. A saturated solution of NaHCO$_3$ was added, the phases were separated and the inorganic one was extracted with EtOAc (2×). The combined organic layers were washed with brine, dried over Na$_2$SO$_4$, filtered and concentrated in vacuo. The crude product was purified by flash chromatography on silica gel (EtOAc/n-heptane 1:9 to EtOAc) to yield the title compound as a yellow oil, MS (ESI$^+$): m/z=395.0 ([M+H]$^+$, 1Br).

Step 2: (E)-3-(4-Bromo-phenyl)-3-(3-methyl-pyridin-2-yl)-1-(2-methyl-pyridin-4-yl)-propan-1-one oxime In analogy to example 74, step 7, from 3-(4-bromo-phenyl)-3-(3-methyl-pyridin-2-yl)-1-(2-methyl-pyridin-4-yl)-propan-1-one and hydroxylamine hydrochloride in the presence of NaHCO$_3$ was prepared the title compound which contains less than 6% of the Z isomer as a colorless oil, MS (ESI⁺): m/z=410.0872 ([M+H]⁺, 1Br).

Example 117

(E)-4'-[3-[Hydroxyimino]-3-(2-methyl-pyridin-4-yl)-1-(3-methyl-pyridin-2-yl)-propyl]-biphenyl-4-carboxylic acid

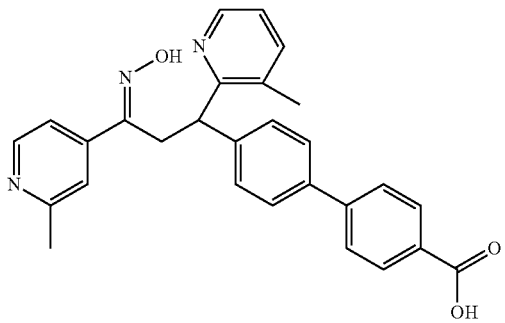 [SMILES: Cc1cc(/C(CC(c2ccc(-c3ccc(C(=O)O)cc3)cc2)c2ncccc2C)=N/O)ccn1]

In analogy to example 74, step 6, from 3-(4-bromo-phenyl)-3-(3-methyl-pyridin-2-yl)-1-(2-methyl-pyridin-4-yl)-propan-1-one oxime (example 116) and 4-carboxyphenylboronic acid was prepared (E)-4'-[3-[hydroxyimino]-3-(2-methyl-pyridin-4-yl)-1-(3-methyl-pyridin-2-yl)-propyl]-biphenyl-4-carboxylic acid which contains less than 6% of the Z isomer as a white powder, MS (ESI⁺): m/z=452.1971 ([M+H]⁺).

Example 118

3-(4-Bromo-phenyl)-1-(2-methyl-pyridin-4-yl)-3-o-tolyl-propan-1-one oxime

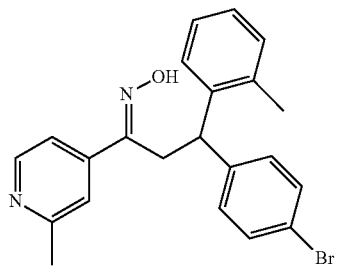 [SMILES: Cc1cc(/C(CC(c2ccc(Br)cc2)c2ccccc2C)=N/O)ccn1]

In analogy to example 74, step 7, from 3-(4-bromo-phenyl)-1-(2-methyl-pyridin-4-yl)-3-o-tolyl-propan-1-one (example 74, step 6) and hydroxylamine hydrochloride in the presence of NaHCO₃ was prepared 3-(4-bromo-phenyl)-1-(2-methyl-pyridin-4-yl)-3-o-tolyl-propan-1-one oxime as a mixture of E and Z isomers (3.3:1) as a white foam, MS (ESI⁺): m/z=409.0895 ([M+H]⁺, 1Br).

Example 119

3-(4-Bromo-phenyl)-1-(2-chloro-pyridin-4-yl)-3-o-tolyl-propan-1-one oxime

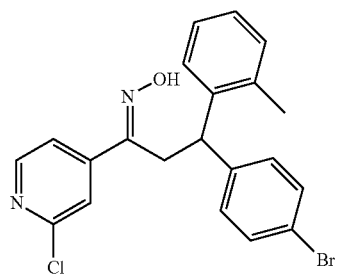 [SMILES: Cc1ccccc1C(C/C(=N\O)c1ccnc(Cl)c1)c1ccc(Br)cc1]

In analogy to example 74, step 5, from 3-(4-bromo-phenyl)-N-methoxy-N-methyl-3-o-tolyl-propionamide (example 74, step 4) and 2-chloro-4-iodopyridine (CAS RN: [153034-86-7]) was prepared 3-(4-bromo-phenyl)-1-(2-chloro-pyridin-4-yl)-3-o-tolyl-propan-1-one as a colorless oil, which was directly subjected to the next step.

In analogy to example 74, step 7, from 3-(4-bromo-phenyl)-1-(2-chloro-pyridin-4-yl)-3-o-tolyl-propan-1-one and hydroxylamine hydrochloride in the presence of NaHCO₃ was prepared 3-(4-bromo-phenyl)-1-(2-chloro-pyridin-4-yl)-3-o-tolyl-propan-1-one oxime as a mixture of E and Z isomers (2.1:1) as a white solid, MS (EI): m/z=428 ([M]⁺, 1Br, 1Cl).

Example 120

(E)-3-(4-Bromo-phenyl)-1-(2,6-dichloro-pyridin-4-yl)-3-o-tolyl-propan-1-one oxime

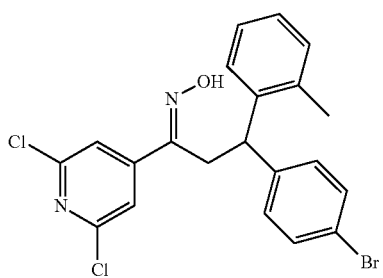 [SMILES: Cc1ccccc1C(C/C(=N\O)c1cc(Cl)nc(Cl)c1)c1ccc(Br)cc1]

In analogy to example 74, step 5, from 3-(4-bromo-phenyl)-N-methoxy-N-methyl-3-o-tolyl-propionamide (example 74, step 4) and 2,6-dichloro-4-iodopyridine (CAS RN: [98027-84-0]) was prepared 3-(4-bromo-phenyl)-1-(2,6-dichloro-pyridin-4-yl)-3-o-tolyl-propan-1-one as a white solid, which was directly subjected to the next reaction.

In analogy to example 74, step 7, from 3-(4-bromo-phenyl)-1-(2,6-dichloro-pyridin-4-yl)-3-o-tolyl-propan-1-one and hydroxylamine hydrochloride in the presence of NaHCO₃ was prepared (E)-3-(4-bromo-phenyl)-1-(2,6- dichloro-pyridin-4-yl)-3-o-tolyl-propan-1-one oxime as a white solid, MS (ESI⁻): m/z=460.9832 ([M–H]⁻, 1Br).

Example 121

3-(4-Bromo-phenyl)-1-(5-chloro-2-fluoro-pyridin-4-yl)-3-o-tolyl-propan-1-one oxime

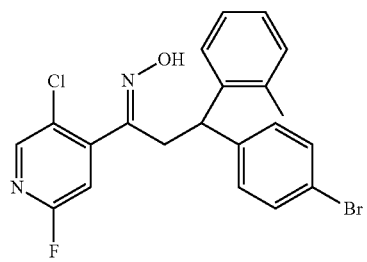 [SMILES: Cc1ccccc1C(C/C(=N\O)c1cc(F)ncc1Cl)c1ccc(Br)cc1]

Step 1: 3-(4-Bromo-phenyl)-1-(5-chloro-2-fluoro-pyridin-4-yl)-3-o-tolyl-propan-1-one In analogy to example 74, step 5, from 3-(4-bromo-phenyl)-N-methoxy-N-methyl-3-o-tolyl-propionamide (example 74, step 4) and 5-chloro-2-fluoro-4-iodopyridine (CAS RN: [659731-48-3]) was prepared the title compound as a light yellow oil, MS (ESI⁻): m/z=430.0014 ([M–H]⁻, 1Br).

Step 2: 3-(4-Bromo-phenyl)-1-(5-chloro-2-fluoro-pyridin-4-yl)-3-o-tolyl-propan-1-one oxime In analogy to example 74, step 7, from 3-(4-bromo-phenyl)-1-(5-chloro-2-fluoro-pyridin-4-yl)-3-o-tolyl-propan-1-one and hydroxylamine hydrochloride in the presence of NaHCO₃ was prepared the title compound as a mixture of E and Z isomers (1.6:1) as a white foam, MS (ESI⁻): m/z=445.0124 ([M–H]⁻, 1Br).

Example 122

(E)-3-(3-Bromo-phenyl)-1-(2-fluoro-6-methyl-pyridin-4-yl)-3-o-tolyl-propan-1-one oxime

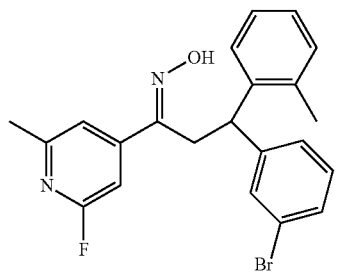 [SMILES: Cc1cc(/C(CC(c2cccc(Br)c2)c2ccccc2C)=N/O)cc(F)n1]

Step 1: 3-(3-Bromo-phenyl)-1-(2-fluoro-6-methyl-pyridin-4-yl)-3-o-tolyl-propan-1-one In analogy to example 74, step 5, from 3-(3-bromo-phenyl)-N-methoxy-N-methyl-3-o-tolyl-propionamide (example 98, step 4) and 2-fluoro-4-iodo-6-picoline (CAS RN: [884494-45-5]) was prepared the title compound as colorless oil, MS (ESI⁺): m/z=412.1 ([M+H]⁺, 1Br).

Step 2: (E)-3-(3-Bromo-phenyl)-1-(2-fluoro-6-methyl-pyridin-4-yl)-3-o-tolyl-propan-1-one oxime In analogy to example 74, step 7, from 3-(3-bromo-phenyl)-1-(2-fluoro-6-methyl-pyridin-4-yl)-3-o-tolyl-propan-1-one and hydroxylamine hydrochloride in the presence of NaHCO₃ was prepared the title compound as a white foam, MS (ESI⁺): m/z=427.0801 ([M+H]⁺, 1Br).

Example 123

(E)-3-(3-Bromo-phenyl)-1-(5-bromo-pyridin-3-yl)-3-o-tolyl-propan-1-one oxime

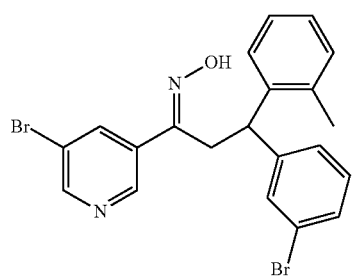 [SMILES: Cc1ccccc1C(C/C(=N\O)c1cncc(Br)c1)c1cccc(Br)c1]

Step 1: 3-(3-Bromo-phenyl)-1-(5-bromo-pyridin-3-yl)-3-o-tolyl-propan-1-one

In analogy to example 74, step 5, from 3-(3-bromo-phenyl)-N-methoxy-N-methyl-3-o-tolyl-propionamide (example 98, step 4) and 3,5-dibromopyridine (CAS RN: [625-92-3]) using i-propylmagnesium bromide instead of n-butyllithium was prepared the title compound as a white solid, MS (ESI⁺): m/z=457.9738 ([M+H]⁺, 1Br).

Step 2: (E)-3-(3-Bromo-phenyl)-1-(5-bromo-pyridin-3-yl)-3-o-tolyl-propan-1-one oxime In analogy to example 74, step 7, from 3-(3-bromo-phenyl)-1-(5-bromo-pyridin-3-yl)-3-o-tolyl-propan-1-one and hydroxylamine hydrochloride in the presence of NaHCO₃ was prepared the title compound as a white solid, MS (ESI⁺): m/z=472.9850 ([M+H]⁺, 1Br).

Example 124

3-(4-Bromo-phenyl)-1-(2-fluoro-5-methyl-pyridin-4-yl)-3-o-tolyl-propan-1-one oxime

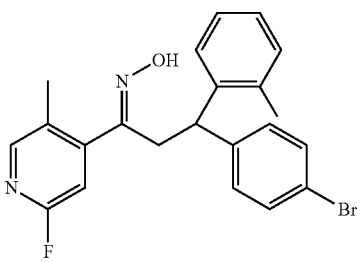 [SMILES: Cc1cnc(F)cc1/C(CC(c1ccc(Br)cc1)c1ccccc1C)=N/O]

Step 1: 3-(4-Bromo-phenyl)-1-(2-fluoro-5-methyl-pyridin-4-yl)-3-o-tolyl-propan-1-one In analogy to example 74, step 5, from 3-(4-bromo-phenyl)-N-methoxy-N-methyl-3-o-tolyl-propionamide (example 74, step 4) and 2-fluoro-4-iodo-5-picoline (CAS RN: [153034-94-7]) was prepared the title compound as a light yellow oil, MS (ESI⁻): m/z=410.0558 ([M–H]⁻, 1Br).

Step 2: 3-(4-Bromo-phenyl)-1-(2-fluoro-5-methyl-pyridin-4-yl)-3-o-tolyl-propan-1-one oxime In analogy to example 74, step 7, from 3-(4-bromo-phenyl)-1-(2-fluoro-5-methyl-pyridin-4-yl)-3-otolyl-propan-1-one and hydroxylamine hydrochloride in the presence of NaHCO$_3$ was prepared the title compound as a mixture of E and Z isomers (1.6:1) as a colorless oil, MS (ESI$^+$): m/z=427.0813 ([M+H]$^+$, 1Br).

Example 125

3-(4-Bromo-phenyl)-1-quinolin-6-yl-3-o-tolyl-propan-1-one oxime

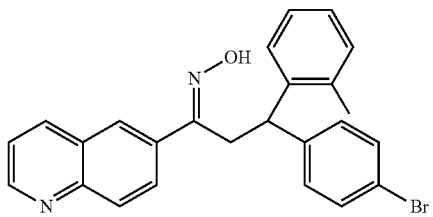 [SMILES: Cc1ccccc1C(C/C(=N\O)c1ccc2ncccc2c1)c1ccc(Br)cc1]

Step 1: 3-(4-Bromo-phenyl)-1-quinolin-6-yl-3-o-tolyl-propan-1-one

In analogy to example 74, step 5, from 3-(4-bromo-phenyl)-N-methoxy-N-methyl-3-o-tolyl-propionamide (example 74, step 4) and 6-bromoquinoline (CAS RN: [5332-25-2]) was prepared the title compound as a yellow oil, MS (ESI$^+$): m/z=430.0791 ([M+H]$^+$, 1Br).

Step 2: 3-(4-Bromo-phenyl)-1-quinolin-6-yl-3-o-tolyl-propan-1-one oxime

In analogy to example 74, step 7, from 3-(4-bromo-phenyl)-1-quinolin-6-yl-3-o-tolyl-propan-1-one and hydroxylamine hydrochloride in the presence of NaHCO$_3$ was prepared the title compound as a mixture of E and Z isomers (5.6:1) as a white foam, MS (ESI$^+$): m/z=445.0907 ([M+H]$^+$, 1Br).

Example 126

3-(4-Bromo-phenyl)-1-(2-fluoro-6-methyl-pyridin-4-yl)-3-o-tolyl-propan-1-one oxime

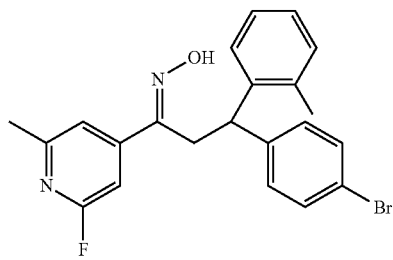 [SMILES: Cc1cc(/C(CC(c2ccc(Br)cc2)c2ccccc2C)=N/O)cc(F)n1]

Step 1: 3-(4-Bromo-phenyl)-1-(2-fluoro-6-methyl-pyridin-4-yl)-3-o-tolyl-propan-1-one In analogy to example 74, step 5, from 3-(4-bromo-phenyl)-N-methoxy-N-methyl-3-o-tolyl-propionamide (example 74, step 4) and 2-fluoro-4-iodo-6-picoline (CAS RN: [884494-45-5]) was prepared the title compound as a colorless oil, MS (EI): m/z=411 ([M]$^+$, 1Br).

Step 2: 3-(4-Bromo-phenyl)-1-(2-fluoro-6-methyl-pyridin-4-yl)-3-o-tolyl-propan-1-one oxime In analogy to example 74, step 7, from 3-(4-bromo-phenyl)-1-(2-fluoro-6-methyl-pyridin-4-yl)-3-o-tolyl-propan-1-one and hydroxylamine hydrochloride in the presence of NaHCO$_3$ was prepared the title compound as a mixture of E and Z isomers (2.4:1) as a colorless oil, MS (ESI$^+$): m/z=427.0804 ([M+H]$^+$, 1Br).

Example 127

3-(4-Bromo-phenyl)-1-(2-chloro-5-fluoro-pyridin-4-yl)-3-o-tolyl-propan-1-one oxime

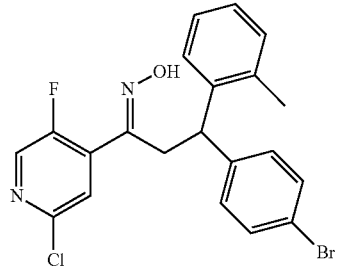 [SMILES: Cc1ccccc1C(C/C(=N\O)c1cc(Cl)ncc1F)c1ccc(Br)cc1]

Step 1: 3-(4-Bromo-phenyl)-1-(2-chloro-5-fluoro-pyridin-4-yl)-3-o-tolyl-propan-1-one In analogy to example 74, step 5, from 3-(4-bromo-phenyl)-N-methoxy-N-methyl-3-o-tolyl-propionamide (example 74, step 4) and 2-chloro-5-fluoro-4-iodopyridine (CAS RN: [659731-48-3]) was prepared the title compound as a white solid, MS (ESI$^-$): m/z=430.0013 ([M−H]$^-$, 1Br).

Step 2: 3-(4-Bromo-phenyl)-1-(2-chloro-5-fluoro-pyridin-4-yl)-3-o-tolyl-propan-1-one oxime In analogy to example 74, step 7, from 3-(4-bromo-phenyl)-1-(2-chloro-5-fluoro-pyridin-4-yl)-3-o-tolyl-propan-1-one and hydroxylamine hydrochloride in the presence of NaHCO$_3$ was prepared the title compound as a mixture of E and Z isomers (1.6:1) as a colorless oil, MS (ESI$^+$): m/z=447.733 ([M+H]$^+$).

Example 128

(E)-3-(4-Bromo-phenyl)-1-(2-fluoro-5-methyl-pyridin-3-yl)-3-o-tolyl-propan-1-one oxime

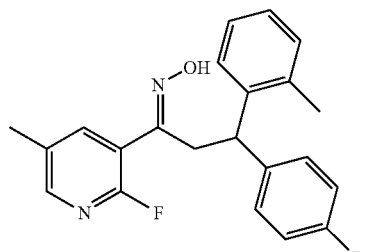

Step 1: 3-(4-Bromo-phenyl)-1-(2-fluoro-5-methyl-pyridin-3-yl)-3-o-tolyl-propan-1-one In analogy to example 74, step 5, from 3-(4-bromo-phenyl)-N-methoxy-N-methyl-3-o-tolyl-propionamide (example 74, step 4) and 2-fluoro-5-methylpyridine (CAS RN: [2369-19-9]) was prepared the title compound as a colorless oil, MS (ESI$^+$): m/z=411 ([M]$^+$, 1Br).

Step 2: (E)-3-(4-Bromo-phenyl)-1-(2-fluoro-5-methyl-pyridin-3-yl)-3-o-tolyl-propan-1-one oxime In analogy to example 74, step 7, from 3-(4-bromo-phenyl)-1-(2-fluoro-5-methyl-pyridin-3-yl)-3-o-tolyl-propan-1-one and hydroxylamine hydrochloride in the presence of NaHCO$_3$ was prepared the title compound as a colorless oil, MS (ESI$^+$): m/z=427.0814 ([M+H]$^+$, 1Br).

Example 129

3-(4-Bromo-phenyl)-4,4-dimethyl-1-(2-methyl-pyridin-4-yl)-pentan-1-one oxime

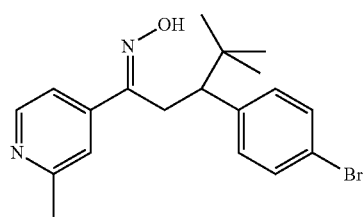 [SMILES: Cc1cc(/C(CC(c2ccc(Br)cc2)C(C)(C)C)=N/O)ccn1]

Step 1: 3-(4-Bromo-phenyl)-4,4-dimethyl-pentanoic acid methoxy-methyl-amide

In analogy to example 74, step 4, from 3-(4-bromo-phenyl)-4,4-dimethyl-pentanoic acid (CAS RN: [1017356-66-9]) and N,O-dimethylhydroxylamine hydrochloride was prepared the title compound as a white solid, MS (ESI$^+$): m/z=328.0895 ([M+H]$^+$, 1Br).

Steps 2 and 3: 3-(4-Bromo-phenyl)-4,4-dimethyl-1-(2-methyl-pyridin-4-yl)-pentan-1-one oxime In analogy to example 74, step 5, from 3-(4-bromo-phenyl)-4,4-dimethyl-pentanoic acid methoxy-methyl-amide and 2-fluoro-4-iodo-5-picoline (CAS RN: [153034-94-7]) was prepared 3-(4-bromo-phenyl)-1-(2-fluoro-5-methyl-pyridin-4-yl)-4,4-dimethyl-pentan-1-one as a colorless oil, which was directly subjected to the next step.

In analogy to example 74, step 7, from 3-(4-bromo-phenyl)-1-(2-fluoro-5-methyl-pyridin-4-yl)-4,4-dimethyl-pentan-1-one and hydroxylamine hydrochloride in the presence of NaHCO$_3$ was prepared the title compound as a mixture of E and Z isomers (3.7:1) as a white foam, MS (ESI$^+$): m/z=375.1062 ([M+H]$^+$, 1Br).

Example 130

4'-{3-(2-Fluoro-5-methyl-pyridin-4-yl)-3-[hydroxyimino]-1-o-tolyl-propyl}-biphenyl-4-carboxylic acid

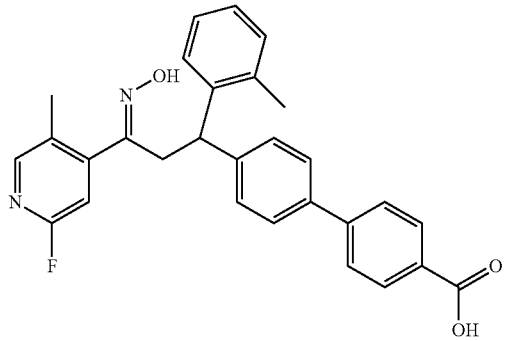 [SMILES: Cc1cnc(F)cc1/C(CC(c1ccc(-c2ccc(C(=O)O)cc2)cc1)c1ccccc1C)=N/O]

Step 1: 4'-[3-(2-Fluoro-5-methyl-pyridin-4-yl)-3-oxo-1-o-tolyl-propyl]-biphenyl-4-carboxylic acid methyl ester In analogy to example 74, step 6, from 3-(4-bromo-phenyl)-1-(2-fluoro-5-methyl-pyridin-4-yl)-3-o-tolyl-propan-1-one (example 124, step 1) and 4-methoxycarbonylphenyl) boronic acid was prepared the title compound as a colorless oil, MS (ESI$^+$): m/z=468.1961 ([M+H]$^+$).

Step 2: 4'-[3-(2-Fluoro-5-methyl-pyridin-4-yl)-3-oxo-1-o-tolyl-propyl]-biphenyl-4-carboxylic acid In analogy to example 75, from 4'-[3-(2-fluoro-5-methyl-pyridin-4-yl)-3-oxo-1-o-tolyl-propyl]-biphenyl-4-carboxylic acid methyl ester was prepared the title compound as a light yellow foam, MS (ESI$^-$): m/z=452.1661 ([M−H]$^-$).

Step 3: 4'-{3-(2-Fluoro-5-methyl-pyridin-4-yl)-3-[hydroxyimino]-1-o-tolyl-propyl}-biphenyl-4-carboxylic acid In analogy to example 74, step 7, from 4'-[3-(2-fluoro-5-methyl-pyridin-4-yl)-3-oxo-1-o-tolyl-propyl]-biphenyl-4-carboxylic acid and hydroxylamine hydrochloride in the presence of NaHCO$_3$ was prepared the title compound as a mixture of E and Z isomers (1.7:1) as a colorless oil, MS (ESI$^+$): m/z=469.1924 ([M+H]$^+$).

Example 131

3-Fluoro-4'-[3-[(E)-hydroxyimino]-3-(2-methyl-pyridin-4-yl)-1-o-tolyl-propyl]-biphenyl-4-carboxylic acid

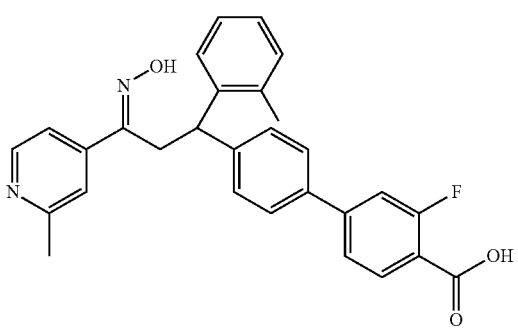 [SMILES: Cc1cc(/C(CC(c2ccc(-c3ccc(C(=O)O)c(F)c3)cc2)c2ccccc2C)=N/O)ccn1]

To a suspension of 3-fluoro-4'-[3-[hydroxyimino]-3-(2-methyl-pyridin-4-yl)-1-o-tolyl-propyl]-biphenyl-4-carboxylic acid (example 112; 151 mg) in DME (2.5 mL) was added HCl in dioxane (4M, 0.8 mL) at rt. The reaction mixture was stirred at 50° C. for 4 hours, was concentrated and dissolved in ethyl acetate (5 mL) and a saturated aqueous solution of NaHCO$_3$ (0.1 mL). A saturated aqueous solution of NH$_4$Cl was added, the phases were separated and the inorganic one was extracted with EtOAc (2x). The combined organic phases were washed with brine, dried over Na$_2$SO$_4$, filtered and concentrated in vacuo to give 3-fluoro-4'-[3-[(E)-hydroxyimino]-3-(2-methyl-pyridin-4-yl)-1-o-tolyl-propyl]-biphenyl-4-carboxylic acid as a yellow solid, MS (ESI$^+$): m/z=469.3 ([M+H]$^+$).

Example 132

(E)-3-(4-Bromo-phenyl)-1-(2-methyl-pyridin-4-yl)-3-(2-trifluoromethyl-phenyl)-propan-1-one oxime

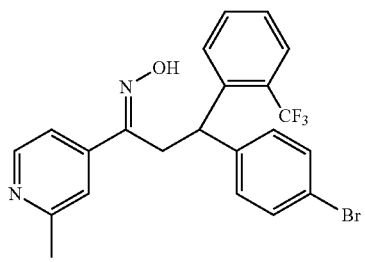 [SMILES: Cc1cc(/C(CC(c2ccc(Br)cc2)c2ccccc2C(F)(F)F)=N/O)ccn1]

Steps 1 and 2: 3-(4-Bromo-phenyl)-2-cyano-3-(2-trifluoromethyl-phenyl)-propionic acid ethyl ester In analogy to example 74, step 1, from 4-bromobenzaldehyde and ethyl cyanoacetate was prepared (E)-3-(4-bromo-phenyl)-2-cyano-acrylic acid ethyl ester as a yellow solid, which was directly subjected to the following step.

In analogy to example 74, step 2, from (E)-3-(4-bromo-phenyl)-2-cyano-acrylic acid ethyl ester and 2-bromobenzotrifluoride (CAS RN: [392-83-6]) was prepared the title compound as a brown oil, MS (ESI$^-$): m/z=424.0 ([M-H]$^-$, 1Br).

Steps 3 and 4: 3-(4-Bromo-phenyl)-N-methoxy-N-methyl-3-(2-trifluoromethyl-phenyl)-propionamide In analogy to example 74, step 3, from 3-(4-bromo-phenyl)-2-cyano-3-(2-trifluoromethyl-phenyl)-propionic acid ethyl ester was prepared 3-(4-bromo-phenyl)-3-(2-trifluoromethyl-phenyl)-propionic acid as a brown powder, which was directly subjected to the next step.

In analogy to example 74, step 4, from 3-(4-bromo-phenyl)-3-(2-trifluoromethyl-phenyl)-propionic acid and N,O-dimethylhydroxylamine hydrochloride was prepared the title compound as a brown viscous oil, MS (ESI$^+$): m/z=416.2 ([M+H]$^+$, 1Br).

Step 5: 3-(4-Bromo-phenyl)-1-(2-methyl-pyridin-4-yl)-3-(2-trifluoromethyl-phenyl)-propan-1-one In analogy to example 74, step 5, from 3-(4-bromo-phenyl)-N-methoxy-N-methyl-3-(2-trifluoromethyl-phenyl)-propionamide and 4-bromo-2-methylpyridine was prepared the title compound as a white solid, MS (ESI$^+$): m/z=448.0 ([M+H]$^+$, 1Br).

Step 6: (E)-3-(4-Bromo-phenyl)-1-(2-methyl-pyridin-4-yl)-3-(2-trifluoromethyl-phenyl)-propan-1-one oxime A solution of 3-(4-bromo-phenyl)-1-(2-methyl-pyridin-4-yl)-3-(2-trifluoromethyl-phenyl)-propan-1-one (80 mg), hydroxylamine hydrochloride (37 mg) and sodium hydrogencarbonate (45 mg) in a mixture of ethanol (4 mL) and water (0.7 mL) was heated under reflux for 2 hours. A saturated solution of NH$_4$Cl was added, the phases were separated and the inorganic one was extracted with EtOAc (2x). The combined organic layers were washed with brine, dried over Na$_2$SO$_4$, filtered and concentrated in vacuo. The crude product was dissolved in DME (5 mL) and HCl in dioxane (4M, 0.45 mL) were added at rt. The reaction mixture was stirred at 50° C. overnight, was concentrated and dissolved in ethyl acetate (5 mL) and a saturated aqueous solution of NaHCO$_3$ (0.1 mL). A saturated aqueous solution of NH$_4$Cl was added, the phases were separated and the inorganic one was extracted with EtOAc (2x). The combined organic phases were washed with brine, dried over Na$_2$SO$_4$, filtered and concentrated in vacuo. The crude product was purified by flash chromatography on silica gel (CH$_2$Cl$_2$/MeOH 95:5) to yield the title compound (65 mg, 79%) as a white foam, MS (ESI$^+$): m/z=463.1 ([M+H]$^+$, 1Br).

Example 133

(E)-3-(4'-Methanesulfonyl-biphenyl-4-yl)-1-(2-methyl-pyridin-4-yl)-3-(2-trifluoromethyl-phenyl)-propan-1-one oxime

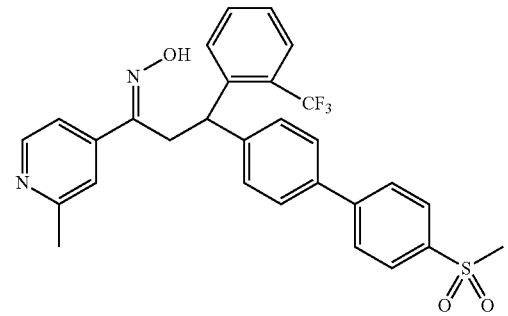 [SMILES: Cc1cc(/C(CC(c2ccc(-c3ccc(S(C)(=O)=O)cc3)cc2)c2ccccc2C(F)(F)F)=N/O)ccn1]

Step 1: 3-(4'-Methane sulfonyl-biphenyl-4-yl)-1-(2-methyl-pyridin-4-yl)-3-(2-trifluoromethyl-phenyl)-propan-1-one In analogy to example 74, step 6, from 3-(4-bromo-phenyl)-1-(2-methyl-pyridin-4-yl)-3-(2-trifluoro-methyl-phenyl)-propan-1-one (example 132, step 5) and 4-(methylsulfonyl)-phenylboronic acid (CAS RN: [149104-88-1]) was prepared the title compound as a white foam, MS (ESI$^+$): m/z=524.2 ([M+H]$^+$).

Step 2: (E)-3-(4'-methanesulfonyl-biphenyl-4-yl)-1-(2-methyl-pyridin-4-yl)-3-(2-trifluoromethyl-phenyl)-propan-1-one oxime In analogy to example 132, step 6, from 3-(4'-methanesulfonyl-biphenyl-4-yl)-1-(2-methyl-pyridin-4-yl)-3-(2-trifluoromethyl-phenyl)-propan-1-one and hydroxylamine hydrochloride in the presence of NaHCO$_3$ was prepared the title compound as a white foam, MS (ESI$^+$): m/z=539.2 ([M+H]$^+$).

Example 134

4'-[3-[(E)-Hydroxyimino]-3-(2-methyl-pyridin-4-yl)-1-(2-trifluoromethyl-phenyl)-propyl]-biphenyl-4-carboxylic acid

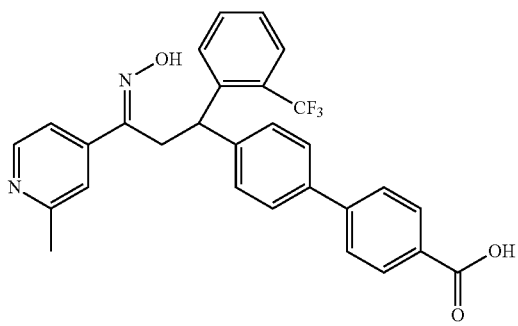 [SMILES: Cc1cc(/C(CC(c2ccc(-c3ccc(C(=O)O)cc3)cc2)c2ccccc2C(F)(F)F)=N/O)ccn1]

Step 1: 4'-[3-(2-Methyl-pyridin-4-yl)-3-oxo-1-(2-trifluoromethyl-phenyl)-propyl]-biphenyl-4-carboxylic acid In analogy to example 74, step 6, from 3-(4-bromo-phenyl)-1-(2-methyl-pyridin-4-yl)-3-(2-trifluoro-methyl-phenyl)-propan-1-one (example 132, step 5) and 4-carboxyphenylboronic acid (CAS RN: [14047-29-1]) was prepared the title compound as a yellow solid, MS (ESI$^-$): m/z=488.148 ([M−H]$^-$).

Step 2: 4'-[3-[(E)-Hydroxyimino]-3-(2-methyl-pyridin-4-yl)-1-(2-trifluoromethyl-phenyl)-propyl]-biphenyl-4-carboxylic acid In analogy to example 132, step 6, from 4'-[3-(2-methyl-pyridin-4-yl)-3-oxo-1-(2-trifluoromethyl-phenyl)-propyl]-biphenyl-4-carboxylic acid and hydroxylamine hydrochloride in the presence of NaHCO$_3$ was prepared the title compound as a light yellow solid, MS (ESI$^+$): m/z=505.173 ([M+H]$^+$).

Example 135

3-Fluoro-4'-[3-[(E)-hydroxyimino]-3-(2-methyl-pyridin-4-yl)-1-(2-trifluoromethyl-phenyl)-propyl]-biphenyl-4-carboxylic acid

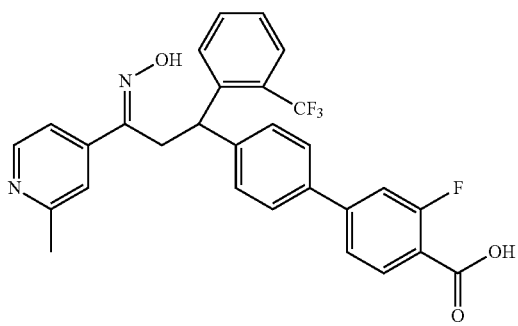 [SMILES: Cc1cc(/C(CC(c2ccc(-c3ccc(C(=O)O)c(F)c3)cc2)c2ccccc2C(F)(F)F)=N/O)ccn1]

Step 1: 3-Fluoro-4'-[3-(2-methyl-pyridin-4-yl)-3-oxo-1-(2-trifluoromethyl-phenyl)-propyl]-biphenyl-4-carboxylic acid In analogy to example 74, step 6, from 3-(4-bromo-phenyl)-1-(2-methyl-pyridin-4-yl)-3-(2-trifluoro-methyl-phenyl)-propan-1-one (example 132, step 5) and 4-carboxy-3-fluoro-phenylboronic acid (CAS RN: [120153-08-4]) was prepared the title compound as a brown foam, MS (ESI$^+$): m/z=508.1 ([M+H]$^+$).

Step 2: 3-Fluoro-4'-[3-[(E)-hydroxyimino]-3-(2-methyl-pyridin-4-yl)-1-(2-trifluoromethyl-phenyl)-propyl]-biphenyl-4-carboxylic acid In analogy to example 132, step 6, from 3-fluoro-4'-[3-(2-methyl-pyridin-4-yl)-3-oxo-1-(2-trifluoromethyl-phenyl)-propyl]-biphenyl-4-carboxylic acid and hydroxylamine hydrochloride in the presence of NaHCO$_3$ was prepared the title compound as a white solid, MS (ESI$^-$): m/z=521.2 ([M−H]$^-$).

Example 136

(E)-3-[4-(4-Methanesulfonyl-piperazin-1-yl)-phenyl]-1-pyridin-4-yl-3-o-tolyl-propan-1-one oxime

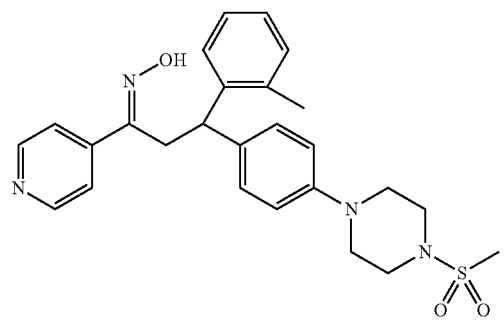 [SMILES: Cc1ccccc1C(C/C(=N\O)c1ccncc1)c1ccc(N2CCN(S(C)(=O)=O)CC2)cc1]

In analogy to example 39, from (E)-3-(4-bromo-phenyl)-1-pyridin-4-yl-3-o-tolyl-propan-1-one oxime (example 31) and 1-methanesulfonyl-piperazine (CAS RN: [55276-43-2]) was prepared the title compound as an off-white foam, MS (ESI$^+$): m/z=479.2 ([M+H]$^+$).

Example 137

(E)-3-[4-(4-Methanesulfonyl-piperazin-1-yl)-phenyl]-1-(2-methyl-pyridin-4-yl)-3-(2-trifluoromethyl-phenyl)-propan-1-one oxime

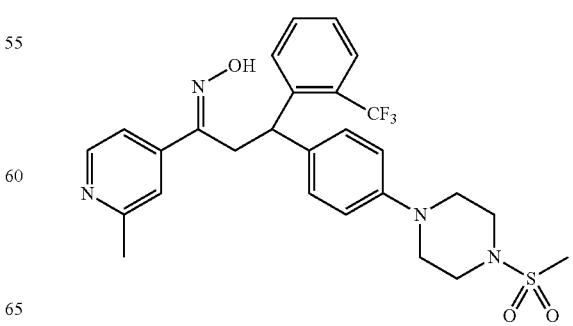

In analogy to example 39, from (E)-3-(4-bromo-phenyl)-1-(2-methyl-pyridin-4-yl)-3-(2-trifluoromethyl-phenyl)-propan-1-one oxime (example 132) and 1-methanesulfonyl-piperazine (CAS RN: [55276-43-2]) was prepared the title compound as a yellow foam, MS (ESI⁺): m/z=547.3 ([M+H]⁺).

Example 138

(E)-3-(4-Bromophenyl)-3-(4-chloro-2-methylphenyl)-1-(2-methylpyridin-4-yl)propan-1-one oxime

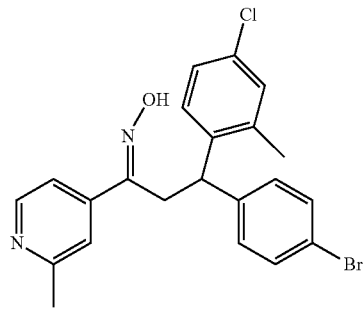 [SMILES: Cc1cc(/C(CC(c2ccc(Br)cc2)c2ccc(Cl)cc2C)=N/O)ccn1]

Step 1: Ethyl 3-(4-bromophenyl)-3-(4-chloro-2-methylphenyl)-2-cyanopropanoate

In analogy to example 74, step 2, from 3-(4-bromo-phenyl)-2-cyano-acrylic acid ethyl ester (example 74, step 1) and 4-chloro-2-tolylmagnesium bromide was prepared the title compound as a yellow oil, MS (ESI⁺): m/z=406.00 [M+H]⁺.

Step 2: 3-(4-Bromophenyl)-3-(4-chloro-2-methylphenyl)propanoic acid

In analogy to example 74, step 3, from ethyl 3-(4-bromophenyl)-3-(4-chloro-2-methylphenyl)-2-cyanopropanoate was prepared the title compound as a white solid, MS (ESI⁺): m/z=352.98 [M+H]⁺.

Step 3: 3-(4-Bromophenyl)-3-(4-chloro-2-methylphenyl)-N-methoxy-N-methylpropanamide In analogy to example 74, step 4, from 3-(4-bromophenyl)-3-(4-chloro-2-methylphenyl)-propanoic acid and N,O-dimethylhydroxylamine hydrochloride was prepared the title compound as a colorless oil, MS (ESI⁺): m/z=398.03 [M+H]⁺.

Step 4: 3-(4-Bromophenyl)-3-(4-chloro-2-methylphenyl)-1-(2-methylpyridin-4-yl)propan-1-one In analogy to example 74, step 5, from 3-(4-bromophenyl)-3-(4-chloro-2-methylphenyl)-N-methoxy-N-methylpropanamide and 4-bromo-2-methylpyridine was prepared the title compound as a light brown solid, MS (ESI⁺): m/z=430.04 [M+H]⁺.

Step 5: (E)-3-(4-Bromophenyl)-3-(4-chloro-2-methylphenyl)-1-(2-methylpyridin-4-yl)propan-1-one oxime In analogy to example 74, step 7, from 3-(4-bromophenyl)-3-(4-chloro-2-methylphenyl)-1-(2-methylpyridin-4-yl)propan-1-one and hydroxylamine hydrochloride in the presence of NaHCO₃ was prepared the title compound which contains less than 10% of the Z isomer as a white foam, MS (ESI⁺): m/z=445.05 [M+H]⁺.

Example 139

(E)-4'-(1-(4-chloro-2-methylphenyl)-3-(hydroxyimino)-3-(2-methylpyridin-4-yl)propyl)biphenyl-4-carboxylic acid

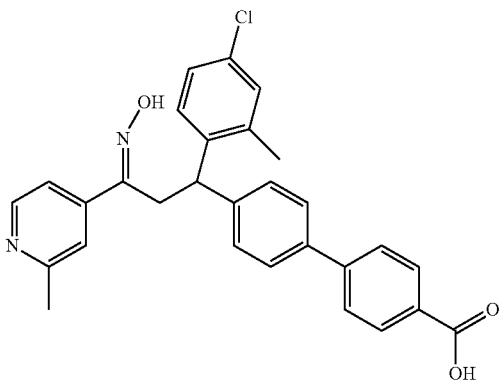 [SMILES: Cc1cc(/C(CC(c2ccc(-c3ccc(C(=O)O)cc3)cc2)c2ccc(Cl)cc2C)=N/O)ccn1]

In analogy to example 74, step 6, from 3-(4-bromophenyl)-3-(4-chloro-2-methylphenyl)-1-(2-methylpyridin-4-yl)propan-1-one oxime (example 138) and 4-carboxyphenylboronic acid was prepared the title compound as a light brown foam, MS (ESI⁺): m/z=485.162 [M+H]⁺.

Example 140

(E)-3-(4-Bromophenyl)-3-(4-fluoro-2-methylphenyl)-1-(2-methylpyridin-4-yl)propan-1-one oxime

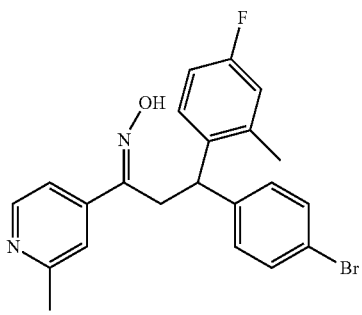 [SMILES: Cc1cc(/C(CC(c2ccc(Br)cc2)c2ccc(F)cc2C)=N/O)ccn1]

Step 1: Ethyl 3-(4-bromophenyl)-2-cyano-3-(4-fluoro-2-methylphenyl)propanoate

In analogy to example 74, step 2, from 3-(4-bromo-phenyl)-2-cyano-acrylic acid ethyl ester (example 74, step 1) and 4-fluoro-2-tolylmagnesium bromide was prepared the title compound as a yellow oil, MS (ESI⁻): m/z=390.03 [M−H]⁻.

Step 2: 3-(4-Bromophenyl)-3-(4-fluoro-2-methylphenyl)-propanoic acid

In analogy to example 74, step 3, from ethyl 3-(4-bromophenyl)-2-cyano-3-(4-fluoro-2-methylphenyl)propanoate was prepared the title compound as a white solid, MS (ESI⁺): m/z=335.01 [M+H]⁺.

Step 3: 3-(4-Bromophenyl)-3-(4-fluoro-2-methylphenyl)-N-methoxy-N-methylpropanamide In analogy to example 74, step 4, from 3-(4-bromophenyl)-3-(4-fluoro-2-methylphenyl)-propanoic acid and N,O-dimethylhydroxylamine hydrochloride was prepared the title compound as a colorless oil, MS (ESI⁺): m/z=382.06 [M+H]⁺.

Step 4: 3-(4-Bromophenyl)-3-(4-fluoro-2-methylphenyl)-1-(2-methylpyridin-4-yl)propan-1-one In analogy to example 74, step 5, from 3-(4-bromophenyl)-3-(4-fluoro-2-methylphenyl)-N-methoxy-N-methylpropanamide and 4-bromo-2-methylpyridine was prepared the title compound as a white solid, MS (ESI⁺): m/z=414.07 [M+H]⁺.

Step 5: (E)-3-(4-Bromophenyl)-3-(4-fluoro-2-methylphenyl)-1-(2-methylpyridin-4-yl)propan-1-one oxime In analogy to example 74, step 7, from 3-(4-bromophenyl)-3-(4-fluoro-2-methylphenyl)-1-(2-methylpyridin-4-yl)propan-1-one and hydroxylamine hydrochloride in the presence of NaHCO₃ was prepared the title compound which contains less than 10% of the Z isomer as a white foam, MS (ESI⁺): m/z=427.08 [M+H]⁺.

Example 141

(E)-4'-(1-(4-Fluoro-2-methylphenyl)-3-(hydroxyimino)-3-(2-methylpyridin-4-yl)propyl)biphenyl-4-carboxylic acid

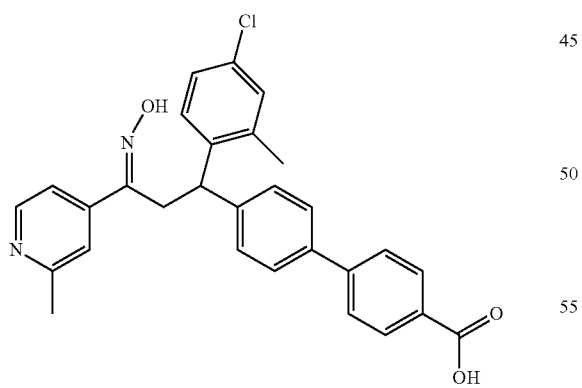

In analogy to example 74, step 6, from 3-(4-bromophenyl)-3-(4-fluoro-2-methylphenyl)-1-(2-methylpyridin-4-yl)propan-1-one oxime (example 140) and 4-carboxyphenylboronic acid was prepared (E)-4'-(1-(4-fluoro-2-methylphenyl)-3-(hydroxyimino)-3-(2-methylpyridin-4-yl)propyl)biphenyl-4-carboxylic acid which contains less than 10% of the Z isomer as an off-white foam, MS (ESI⁺): m/z=469.1 [M+H]⁺.

Example 142

(E,R)-3-(4-Bromophenyl)-1-(2-methylpyridin-4-yl)-3-o-tolylpropan-1-one oxime

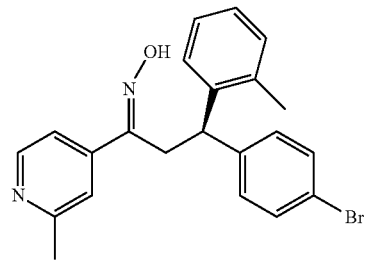 [SMILES: Cc1cc(/C(C[C@H](c2ccc(Br)cc2)c2ccccc2C)=N/O)ccn1]

Step 1: (S)-3-(4-Bromo-phenyl)-N-methoxy-N-methyl-3-otolyl-propionamide and (R)-3-(4-bromo-phenyl)-N-methoxy-N-methyl-3-o-tolyl-propionamide Separation of 3-(4-bromo-phenyl)-N-methoxy-N-methyl-3-o-tolyl-propionamide (example 74, step 4) by chiral HPLC (Chiralpak, 3% ethanol/heptane) yielded (S)-3-(4-bromo-phenyl)-N-methoxy-N-methyl-3-o-tolyl-propionamide as a light yellow oil, MS (ESI⁺): m/z=362.0752 ([M+H]⁺, 1Br) and (R)-3-(4-bromo-phenyl)-N-methoxy-N-methyl-3-o-tolyl-propionamide as a light yellow oil, MS (ESI⁺): m/z=362.0751 ([M+H]⁺, 1Br).

Step 2: (R)-3-(4-Bromo-phenyl)-1-(2-methyl-pyridin-4-yl)-3-o-tolyl-propan-1-one

In analogy to example 74, step 5, from (R)-3-(4-bromophenyl)-N-methoxy-N-methyl-3-o-tolyl-propionamide and 4-bromo-2-methylpyridine was prepared the title compound as yellow solid, MS (ESI⁺): m/z=394.0797 ([M+H]⁺, 1Br).

Step 3: (E,R)-3-(4-Bromophenyl)-1-(2-methylpyridin-4-yl)-3-o-tolylpropan-1-one oxime In analogy to example 132, step 6, from (R)-3-(4-bromophenyl)-1-(2-methyl-pyridin-4-yl)-3-o-tolyl-propan-1-one and hydroxylamine hydrochloride in the presence of NaHCO₃ was prepared the title compound as a white foam, MS (ESI⁺): m/z=409.2 ([M+H]⁺, 1Br).

Example 143

(E,R)-1-(2-Methyl-pyridin-4-yl)-3-(4-pyrimidin-5-yl-phenyl)-3-o-tolyl-propan-1-one oxime

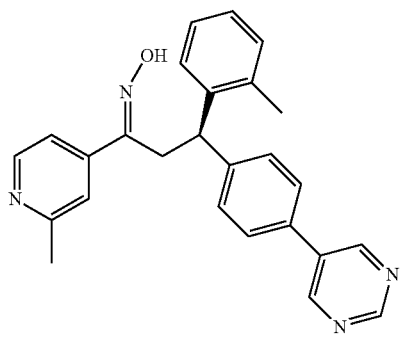 [SMILES: Cc1cc(/C(C[C@H](c2ccc(-c3cncnc3)cc2)c2ccccc2C)=N/O)ccn1]

In analogy to example 22, from (E,R)-3-(4-bromophenyl)-1-(2-methylpyridin-4-yl)-3-o-tolylpropan-1-one oxime (example 142, step 1) and pyrimidine-5-boronic acid was prepared the title compound as a white foam, MS (ESI⁺): m/z=409.3 ([M+H]⁺).

Example 144

(E,R)-1-(2-Methylpyridin-4-yl)-3-(4-(4-(methylsulfonyl)piperazin-1-yl)phenyl)-3-o-tolylpropan-1-one oxime

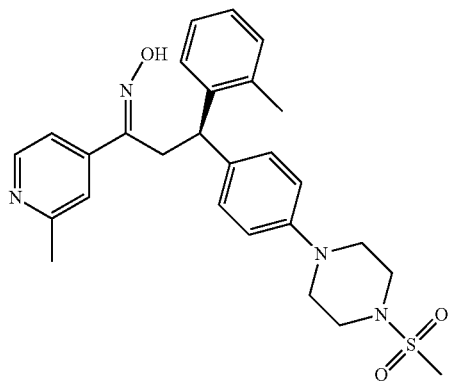 [SMILES: Cc1cc(/C(C[C@H](c2ccc(N3CCN(S(C)(=O)=O)CC3)cc2)c2ccccc2C)=N/O)ccn1]

In analogy to example 39, from (E,R)-3-(4-bromophenyl)-1-(2-methylpyridin-4-yl)-3-o-tolylpropan-1-one oxime (example 142, step 1) and 1-methanesulfonyl-piperazine (CAS RN: [55276-43-2]) was prepared the title compound as a yellow solid, MS (ESI⁺): m/z=493.3 ([M+H]⁺).

Example 145

(E,R)-3-(4-(4-Hydroxypiperidin-1-yl)phenyl)-1-(2-methylpyridin-4-yl)-3-o-tolylpropan-1-one oxime

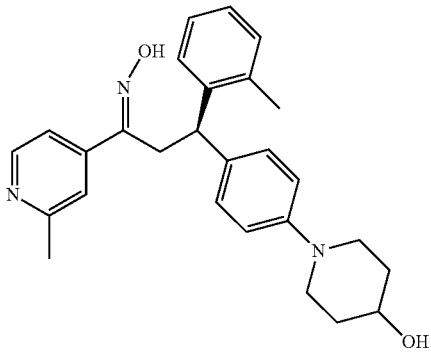 [SMILES: Cc1cc(/C(C[C@H](c2ccc(N3CCC(O)CC3)cc2)c2ccccc2C)=N/O)ccn1]

In analogy to example 39, from (E,R)-3-(4-bromophenyl)-1-(2-methylpyridin-4-yl)-3-o-tolylpropan-1-one oxime (example 142, step 1) and 4-hydroxypiperidine was prepared the title compound as a yellow foam, MS (ESI⁺): m/z=430.2 ([M+H]⁺).

Example 146

(E,R)-4'-(3-(2,6-Dichloropyridin-4-yl)-3-(hydroxyimino)-1-o-tolylpropyl)biphenyl-4-carboxylic acid

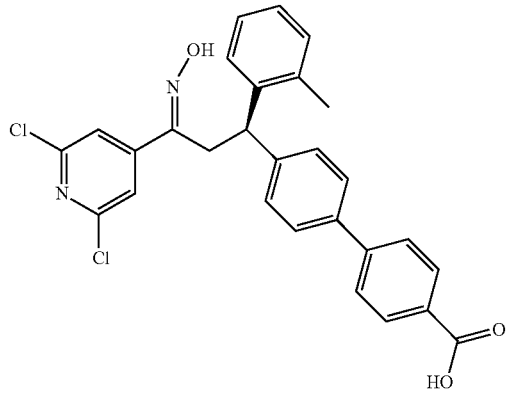 [SMILES: Cc1ccccc1[C@H](C/C(=N\O)c1cc(Cl)nc(Cl)c1)c1ccc(-c2ccc(C(=O)O)cc2)cc1]

Step 1: (R)-4'-(3-(Methoxy(methyl)amino)-3-oxo-1-o-tolylpropyl)biphenyl-4-carboxylic acid In analogy to example 74, step 6, from (R)-3-(4-bromophenyl)-N-methoxy-N-methyl-3-o-tolylpropanamide (example 142, step 1) and 4-boronobenzoic acid (CAS RN: [14047-29-1]) was prepared (R)-4'-(3-(methoxy(methyl)amino)-3-oxo-1-o-tolylpropyl)biphenyl-4-carboxylic acid as a light brown foam, MS (ESI⁻): m/z=402.1 ([M–H]⁻).

Steps 2 and 3: (R)-4'-(3-(2,6-Dichloropyridin-4-yl)-3-oxo-1-o-tolylpropyl)biphenyl-4-carboxylic acid To a solution of (R)-4'-(3-(methoxy(methyl)amino)-3-oxo-1-o-tolylpropyl)biphenyl-4-carboxylic acid (1.59 g) in dioxane (10 ml) LiOH in dioxane/water (0.067M, 52.9 ml) was added. The mixture was stirred at rt and was concentrated in vacuo to give crude (R)-4'-(3-(methoxy(methyl)amino)-3-oxo-1-o-tolylpropyl)biphenyl-4-carboxylic acid, lithium salt, which was directly subjected to the next reaction.

In analogy to example 74, step 5, from (R)-4'-(3-(methoxy(methyl)amino)-3-oxo-1-tolylpropyl)biphenyl-4-carboxylic acid, lithium salt and 2,6-dichloro-4-iodopyridine was prepared the title compound as light brown foam, MS (ESI⁻): m/z=488.2 ([M–H]⁻, 1Cl).

Step 3: (E,R)-4'-(3-(2,6-Dichloropyridin-4-yl)-3-(hydroxyimino)-1-o-tolylpropyl)biphenyl-4-carboxylic acid In analogy to example 132, step 6, from (R)-4'-(3-(2,6-dichloropyridin-4-yl)-3-oxo-1-o-tolylpropyl)biphenyl-4-carboxylic acid and hydroxylamine hydrochloride in the presence of NaHCO₃ was prepared the title compound as an off-white foam, MS (ESI⁻): m/z=503.09 ([M−H]⁻, 1Cl).

Example 147

(E)-3-(4-Bromo-phenyl)-3-(4-chloro-2-fluoro-phenyl)-1-(2-methyl-pyridin-4-yl)-propan-1-one oxime

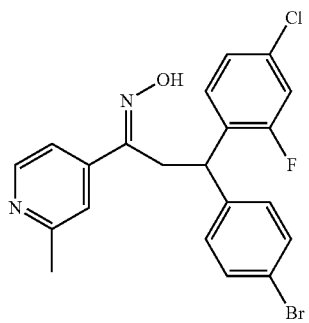 [SMILES: Cc1cc(/C(CC(c2ccc(Br)cc2)c2ccc(Cl)cc2F)=N/O)ccn1]

Step 1: 2-Methyl-isonicotinic acid ethyl ester

A solution of 2-methyl-isonicotinic acid (2.50 g) in thionyl chloride (43.4 g, 26.5 mL) was heated to reflux for 2 h. The reaction mixture was concentrated under reduced pressure, remaining thionyl chloride removed by azeotropic distillation with toluene and the residue dissolved in ethanol (70 mL). After heating to reflux for 12 h, ethanol was removed by distillation and to the residue was added a sat. solution of NaHCO₃ (100 mL). Extraction with ethyl acetate (3×50 mL) and drying of the combined organic phases over MgSO₄ provided after evaporation of the organic solvent the title compound as a light brown liquid (3.20 g, 96%), which was used for the consecutive step without any further purification, MS (ESI⁺): m/z=166.1 [M+H]⁺.

Step 2: 1-(2-Methyl-pyridin-4-yl)-ethanone

To a solution of 2-methyl-isonicotinic acid ethyl ester (3.20 g) and tert-butyl acetate in n-heptane at −5° C. was slowly added lithium hexamethyldisilazide (46.5 mL; 1 M solution in THF). After stirring for 2 h, a solution of sulfuric acid (4.13 mL) in water (20 mL) was added within 20 min keeping the reaction temperature below 10° C. After the addition was completed, the reaction mixture was heated to reflux overnight. Extraction over a sat. solution of NaHCO₃ (100 mL) with ethyl acetate (3×50 mL) and drying of the combined organic phases over Na₂SO₄ provided after evaporation of the organic solvent the title compound as a light brown liquid (2.40 g, 92%), which was used for the consecutive step without any further purification, MS (ESI⁺): m/z=136.0 [M+H]⁺.

Step 3: (E)-3-(4-Chloro-2-fluoro-phenyl)-1-(2-methyl-pyridin-4-yl)-propenone

To a solution of 1-(2-methyl-pyridin-4-yl)-ethanone (1.10 g) and 4-chloro-2-fluorobenzaldehyde (1.55 g) in ethanol (12.5 mL) was added piperidine (0.21 g, 0.24 mL) and the reaction mixture heated by microwave irradiation to 110° C. for 1 h. Evaporation of the solvent under reduced pressure and purification of the crude reaction product by silica column chromatography eluting with a mixture of n-heptane/ethyl acetate (2:1) afforded 0.70 g (31%) of the title compound as a light brown solid, MS (ESI⁺): m/z=276.0 [M+H]⁺.

Step 4: 3-(4-Bromo-phenyl)-3-(4-chloro-2-fluoro-phenyl)-1-(2-methyl-pyridin-4-yl)-propan-1-one In analogy to example 1, step 1, 4-bromobenzeneboronic acid was first reacted with diethylzinc. The product of this reaction was treated with (E)-3-(4-chloro-2-fluoro-phenyl)-1-(2-methyl-pyridin-4-yl)-propenone to give the title compound as a light yellow oil, MS (ESI⁺): m/z=434.0 [M+H]⁺.

Step 5: (E)-3-(4-Bromo-phenyl)-3-(4-chloro-2-fluoro-phenyl)-1-(2-methyl-pyridin-4-yl)-propan-1-one oxime In analogy to example 1, step 2, 3-(4-bromo-phenyl)-3-(4-chloro-2-fluoro-phenyl)-1-(2-methyl-pyridin-4-yl)-propan-1-one was reacted with hydroxylamine hydrochloride in the presence of NaHCO₃ to give the title compound containing 10% of the corresponding Z isomer as an off-white powder, MS (ESI⁺): m/z=448.9 [M+H]⁺.

Example 148

4'-[1-(4-Chloro-2-fluoro-phenyl)-3-[(E)-hydroxyimino]-3-(2-methyl-pyridin-4-yl)-propyl]-biphenyl-4-carboxylic acid

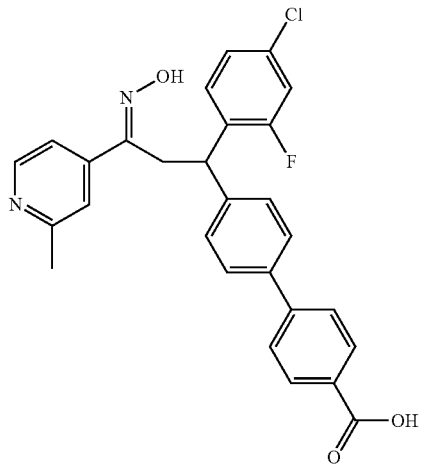

In analogy to example 74, step 6, (E)-3-(4-bromo-phenyl)-3-(4-chloro-2-fluoro-phenyl)-1-(2-methyl-pyridin-4-yl)-propan-1-one oxime (example 147, step 5) was reacted with 4-carboxyphenylboronic acid in the presence of dichloro(1,1'-bis(diphenylphosphino) ferrocene)palladium(II) dichloromethane adduct in a mixture of 1,4-dioxane, water and 2 M aqueous sodium carbonate solution to give the title compound as an off-white solid, MS (ESI+): m/z=489.3 [M+H]+.

Example 149

4-{4-[1-(4-Chloro-2-fluoro-phenyl)-3-[(E)-hydroxy-imino]-3-(2-methyl-pyridin-4-yl)-propyl]-phenyl}-thiophene-2-carboxylic acid ethyl ester

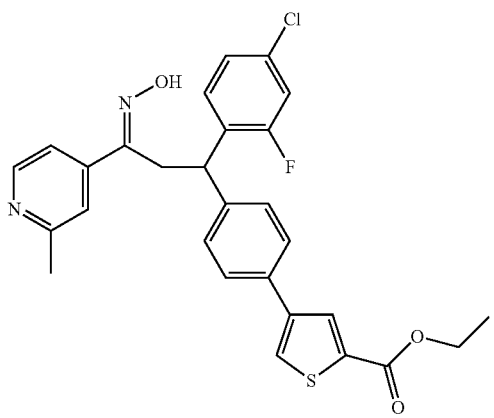

In analogy to example 74, step 6, (E)-3-(4-bromo-phenyl)-3-(4-chloro-2-fluoro-phenyl)-1-(2-methyl-pyridin-4-yl)-propan-1-one oxime (example 147, step 5) was reacted with 5-(ethoxycarbonyl)thiophen-3-ylboronic acid in the presence of dichloro(1,1'-bis(diphenylphosphino)ferrocene)palladium (II) dichloromethane adduct in a mixture of 1,4-dioxane, water and 2 M aqueous sodium carbonate solution under heating by microwave irradiation to 100° C. for 30 min providing the title compound as an off-white solid, MS (ESI+): m/z=523.2 [M+H]+.

Example 150

4-{4-[1-(4-Chloro-2-fluoro-phenyl)-3-[(E)-hydroxy-imino]-3-(2-methyl-pyridin-4-yl)-propyl]-phenyl}-thiophene-2-carboxylic acid

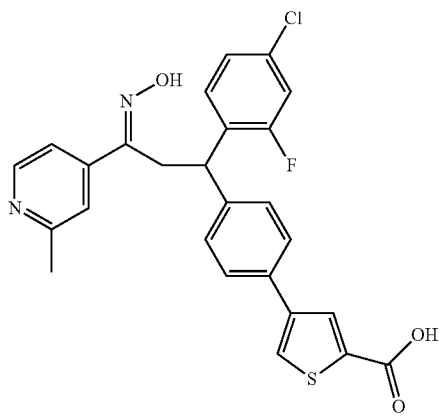

To a solution of 4-{4-[1-(4-chloro-2-fluoro-phenyl)-3-[(E)-hydroxyimino]-3-(2-methyl-pyridin-4-yl)-propyl]-phenyl}-thiophene-2-carboxylic acid ethyl ester (15 mg) in dioxane/water (1.5 mL, 1:1) was added LiOH (7.2 mg) and the reaction mixture heated by microwave irradiation to 100° C. for 30 min. Formic acid was added to neutralize LiOH and the solvent mixture removed by evaporation under reduced pressure. Purification of the crude reaction product by silica column chromatography eluting with a mixture of dichloromethane/methanol (95:5, containing 4% formic acid) provided 14 mg (98%) of the title compound as an off-white powder, MS (ESI+): m/z=495.1 [M+H]+.

Example 151

(E)-3-(4-Bromo-phenyl)-1-(4-hydroxy-phenyl)-3-o-tolyl-propan-1-one oxime

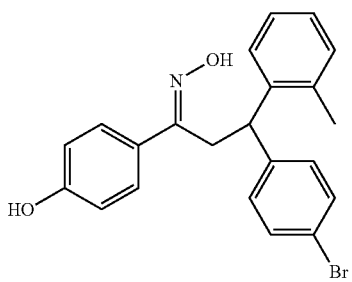

Step 1: 3-(4-Bromo-phenyl)-1-(4-methoxy-phenyl)-3-o-tolyl-propan-1-one

A stirred solution of 4-bromoanisole (639 mg) in THF (15 ml) under argon was cooled to −78° C. A solution of n-butyl-lithium (2.07 ml, 1.6 M in hexane) was added slowly while keeping the temperature below −70° C. After stirring for 40 min, a solution of 3-(4-bromo-phenyl)-N-methoxy-N-methyl-3-o-tolyl-propionamide (400 mg, example 74, step 4) in THF (15 ml) was added while keeping the temperature below −70° C. The mixture was stirred at this temperature for 1 hour. The reaction was stopped by addition of saturated aqueous ammonium chloride solution (15 ml). Water was added and the mixture was extracted with ethyl acetate (3×). The combined organic phase was washed with water and brine, dried using MgSO4, filtered and concentrated to dryness. The product was purified by chromatography (SiO2, cyclohexane/ethyl acetate 1:0 to 3:2) to give the title compound (390 mg) as a light yellow oil, MS (ESI+): m/z=409.2 [M+H]+.

Step 2: 3-(4-Bromo-phenyl)-1-(4-hydroxy-phenyl)-3-o-tolyl-propan-1-one

A stirred solution of 3-(4-bromo-phenyl)-1-(4-methoxy-phenyl)-3-o-tolyl-propan-1-one (214 mg) in dichloromethane (5.1 ml) under argon was cooled to −78° C. A solution of BBr3 (2.09 ml, 1 M in dichloromethane) was added dropwise. The mixture was stirred at −78° C. for 45 min, at 0° C. for 4 h and at room temperature for 30 min. Since the reaction was not complete, the mixture was again cooled to −78° C. and a solution of BBr3 (1 ml, 1 M in dichloromethane) was added. The mixture was stirred at −78° C. for 30 min and at 0° C. for 4.5 h. Water and a saturated aqueous NaHCO3 solution were added and the mixture was extracted with dichloromethane. The organic phase was washed with water, dried using MgSO4, filtered and concentrated to dryness. The product was purified by chromatography (SiO2, cyclohexane/ethyl acetate 1:0 to 7:3) to give the title compound (21 mg) as a light brown solid, MS (ESI⁺): m/z=394.8 [M−H]⁻.

Step 3: (E)-3-(4-Bromo-phenyl)-1-(4-hydroxy-phenyl)-3-o-tolyl-propan-1-one oxime A suspension of 3-(4-bromo-phenyl)-1-(4-hydroxy-phenyl)-3-o-tolyl-propan-1-one (16 mg), hydroxylamine hydrochloride (7 mg) and NaHCO₃ (6.8 mg) in ethanol (0.455 ml) and water (0.016 ml) was heated to reflux for 2.5 h. After cooling to room temperature, a saturated aqueous solution of ammonium chloride was added and the mixture was extracted with dichloromethane. The organic phase was washed with brine, dried using MgSO₄, filtered and concentrated to dryness. The product was purified by preparative TLC (SiO₂, dichloromethane/methanol 9:1) to give the title compound containing less than 10% of the corresponding Z isomer (13 mg) as an off-white foam, MS (ESI⁺): m/z=408.1 [M−H]⁻.

Example 152

(E)-3-(4-Bromo-phenyl)-1-(4-hydroxy-3,5-dimethyl-phenyl)-3-o-tolyl-propan-1-one oxime

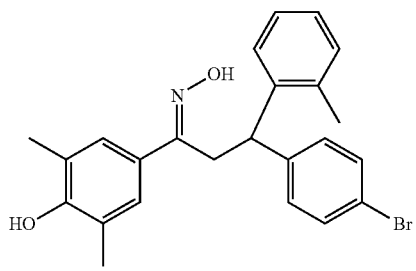 [SMILES: Cc1ccccc1C(C/C(=N\O)c1cc(C)c(O)c(C)c1)c1ccc(Br)cc1]

Step 1: 3-(4-Bromo-phenyl)-1-(4-methoxy-3,5-dimethyl-phenyl)-3-o-tolyl-propan-1-one In analogy to example 151, step 1, 4-bromo-2,6-dimethylanisole was reacted first with n-butyllithium and later with 3-(4-bromo-phenyl)-N-methoxy-N-methyl-3-o-tolyl-propionamide (example 74, step 4) to give the title compound as a light yellow solid, MS (ESI⁺): m/z=437.4 [M+H]⁺.

Step 2: 3-(4-Bromo-phenyl)-1-(4-hydroxy-3,5-dimethyl-phenyl)-3-o-tolyl-propan-1-one In analogy to example 151, step 2, 3-(4-bromo-phenyl)-1-(4-methoxy-3,5-dimethyl-phenyl)-3-o-tolyl-propan-1-one was treated with BBr₃ in dichloromethane to give the title compound as a light yellow solid, MS (ESI⁺): m/z=420.9 [M−H]⁻.

Step 3: (E)-3-(4-Bromo-phenyl)-1-(4-hydroxy-3,5-dimethyl-phenyl)-3-o-tolyl-propan-1-one oxime In analogy to example 151, step 3, 3-(4-bromo-phenyl)-1-(4-hydroxy-3,5-dimethyl-phenyl)-3-o-tolyl-propan-1-one was reacted with hydroxylamine hydrochloride in the presence of NaHCO₃ to give the title compound containing less than 10% of the corresponding Z isomer as an off-white solid, MS (ESI⁺): m/z=436.2 [M−H]⁻.

Example 153

(E)-2-Methyl-3,3-diphenyl-1-pyridin-4-yl-propan-1-one oxime

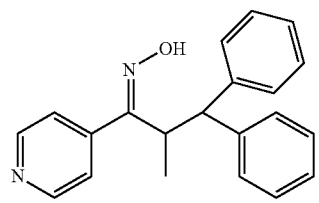 [SMILES: CC(/C(=N\O)c1ccncc1)C(c1ccccc1)c1ccccc1]

Step 1: 2-Methyl-3,3-diphenyl-1-pyridin-4-yl-propan-1-one

To a solution of 3,3-diphenyl-1-pyridin-4-yl-propan-1-one (200 mg, example 14, step 1) in THF (11 ml) was added NaH (33 mg as a 55% suspension in mineral oil) at room temperature. The mixture was stirred for 1.5 h and placed in an ice bath. Iodomethane (109 mg) was added. The mixture was stirred for 1 h at 0° C. and for 2 h at room temperature. N,N-dimethylacetamide (0.5 ml) was added and the mixture was stirred overnight at room temperature. Ice water was added and the mixture was extracted with ethyl acetate. The organic phase was dried using MgSO₄, filtered and concentrated to dryness. The product was purified by chromatography (SiO₂, cyclohexane/ethyl acetate 1:0 to 0:1) to give the title compound (148 mg) as an off-white solid, MS (ESI⁺): m/z=302.3 [M+H]⁺.

Step 2: (E)-2-Methyl-3,3-diphenyl-1-pyridin-4-yl-propan-1-one oxime

In analogy to example 151, step 3, 2-methyl-3,3-diphenyl-1-pyridin-4-yl-propan-1-one was reacted with hydroxylamine hydrochloride in the presence of NaHCO₃ to give the title compound as an off-white solid, MS (ESI⁺): m/z=317.16 [M+H]⁺.

Example 154

(E)-3-Hydroxy-3,3-diphenyl-1-pyridin-4-yl-propan-1-one oxime

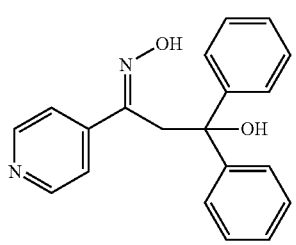

Step 1: 3-Hydroxy-3,3-diphenyl-1-pyridin-4-yl-propan-1-one

To a stirred solution of 4-acetylpyridine (1.25 g) in N,N-dimethylacetamide (10 ml) was added NaH (0.413 g, as a 55% suspension in mineral oil) at 0° C. After stirring for 30 min, benzophenone (1.882 g) was added. After 30 min, the cooling bath was removed. The mixture was stirred overnight at room temperature. The mixture was cooled to 0° C. NaH (0.413 g, as a 55% suspension in mineral oil) was added and the mixture was stirred for 3 h. Water and ethyl acetate were added. The pH was adjusted to 8 using 1 M aqueous HCl. The mixture was extracted with ethyl acetate. The organic phase was dried using MgSO$_4$, filtered and concentrated to dryness. The product was purified by chromatography (SiO$_2$, cyclohexane/ethyl acetate 1:0 to 0:1) to give the title compound (119 mg) as a colorless solid, MS (ESI$^+$): m/z=304.2 [M+H]$^+$.

Step 2: (E)-3-Hydroxy-3,3-diphenyl-1-pyridin-4-yl-propan-1-one oxime

To a solution of 3-hydroxy-3,3-diphenyl-1-pyridin-4-yl-propan-1-one (115 mg) in methanol (4 ml) were added hydroxylamine hydrochloride (63 mg) and sodium acetate (75 mg). The mixture was stirred at room temperature for 6 h. Water was added and the mixture was extracted with ethyl acetate. The organic phase was dried using MgSO$_4$, filtered and concentrated to dryness. The product was purified by chromatography (SiO$_2$, cyclohexane/ethyl acetate 4:1 to 1:3) to give the title compound (60 mg) as a colorless solid, MS (ESI$^+$): m/z=319.1 [M+H]$^+$.

Example 155

(Z)-3-Hydroxy-3,3-diphenyl-1-pyridin-4-yl-propan-1-one oxime

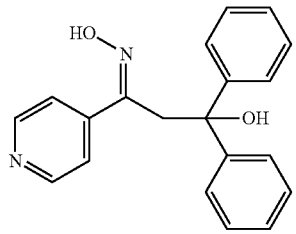

The title compound (38 mg) was obtained as a side product of example 154, step 2 as a colorless solid, MS (ESI$^+$): m/z=319.1 [M+H]$^+$.

Example 156

(E)-3-(4-Bromo-phenyl)-1-pyrazin-2-yl-3-o-tolyl-propan-1-one oxime

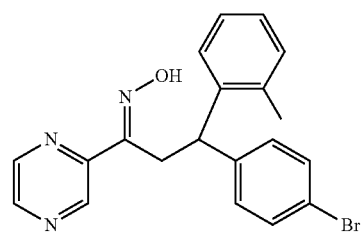 [SMILES: Cc1ccccc1C(C/C(=N\O)c1cnccn1)c1ccc(Br)cc1]

Step 1: 3-(4-Bromo-phenyl)-1-pyrazin-2-yl-3-o-tolyl-propan-1-one

In analogy to example 151, step 1, 2-bromopyrazine was reacted first with n-butyllithium and later with 3-(4-bromo-phenyl)-N-methoxy-N-methyl-3-o-tolyl-propionamide (example 74, step 4) to give the title compound as a colorless solid, MS (ESI$^+$): m/z=381.2 [M+H]$^+$.

Step 2: (E)-3-(4-Bromo-phenyl)-1-pyrazin-2-yl-3-o-tolyl-propan-1-one oxime

In analogy to example 151, step 3, 3-(4-bromo-phenyl)-1-pyrazin-2-yl-3-o-tolyl-propan-1-one was reacted with hydroxylamine hydrochloride in the presence of NaHCO$_3$ to give the title compound containing about 10% of the corresponding Z isomer as a colorless foam, MS (ESI$^-$): m/z=393.8 [M–H]$^-$.

Example 157

(E)-3-(4-Bromo-phenyl)-1-(7-chloro-quinolin-4-yl)-3-o-tolyl-propan-1-one oxime

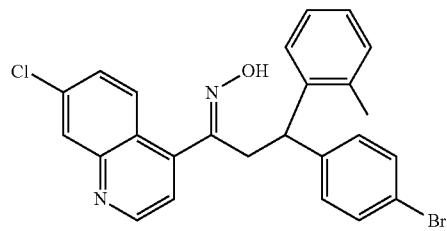 [SMILES: Cc1ccccc1C(C/C(=N\O)c1ccnc2cc(Cl)ccc12)c1ccc(Br)cc1]

In analogy to example 151, step 1, 7-chloro-4-iodoquinoline was reacted first with n-butyllithium and later with 3-(4-bromo-phenyl)-N-methoxy-N-methyl-3-o-tolyl-propionamide (example 74, step 4). The product of this reaction could not be obtained pure and was reacted in analogy to example 151, step 3, with hydroxylamine hydrochloride in the presence of NaHCO$_3$ to give the title compound containing less than 10% of the corresponding Z isomer as a colorless solid, MS (ESI$^-$): m/z=478.9 [M–H]$^-$.

Example 158

(E)-2-[1-(4-Methoxy-phenyl)-cyclohexyl]-1-(2-methyl-pyridin-4-yl)-ethanone oxime

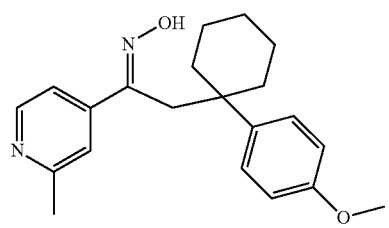 [SMILES: COc1ccc(C2(C/C(=N\O)c3ccnc(C)c3)CCCCC2)cc1]

Step 1: Cyano-[1-(4-methoxy-phenyl)-cyclohexyl]-acetic acid ethyl ester

To a stirred solution of 4-anisylmagnesium bromide (33.64 ml, 1 M in THF) cooled in an ice bath was added a solution of cyano-cyclohexylidene-acetic acid ethyl ester (5 g, CAS RN: [6802-76-2]) in toluene (55 ml) at a maximum temperature of 5° C. The mixture was stirred for 5 min and the warmed to 85° C. for 3.5 h. The mixture was stirred overnight at room temperature. The mixture was poured onto ice. 1 M HCl was added and the mixture was extracted with ethyl acetate. The organic phase was washed with brine, dried (MgSO₄), filtered and concentrated to dryness. The product was purified by filtration over a glass frit filled with silica gel using n-heptane/diethyl ether 1:0 to 88:12 as a solvent. Pure product (4.7 g) and slightly impure product (1.8 g) were obtained as light yellow oils, MS (ESI⁺): m/z=319.2 [M+NH₄]⁺.

Step 2: [1-(4-Methoxy-phenyl)-cyclohexyl]-acetic acid

A mixture of cyano-[1-(4-methoxy-phenyl)-cyclohexyl]-acetic acid ethyl ester (1.84 g), potassium hydroxide (1.27 g), ethylene glycol (5 ml) and water (0.025 ml) was heated to 180° C. for 21 h. After cooling to room temperature, water was added and washed with diethyl ether. The aqueous phase was acidified using concentrated HCl and extracted with dichloromethane. The organic phase was washed with brine, dried (MgSO₄), filtered and concentrated to dryness to give the title compound as an off-white solid (1.21 g), MS (ESI⁻): m/z=247.1 [M−H]⁻.

Step 3: N-Methoxy-2-[1-(4-methoxy-phenyl)-cyclohexyl]-N-methyl-acetamide

To a solution of [1-(4-methoxy-phenyl)-cyclohexyl]-acetic acid (1.2 g) in dichloromethane (9.7 ml) was added N,O-dimethylhydroxylamine hydrochloride (577 mg). The mixture was cooled in an ice bath. 1,1'-Carbonyldiimidazole (1.01 g) was added. The mixture was stirred for 5 min at 0° C. and for 2 days at room temperature. A mixture of water and 1 M HCl was added and the mixture was extracted with ethyl acetate. The organic phase was washed with brine, dried (MgSO₄), filtered and concentrated to dryness. The product was purified by chromatography (20 g NH₃-modified SiO₂, cyclohexane/ethyl acetate 1:0 to 3:2) to give the title compound (1.13 g) as a colorless oil, MS (ESI⁺): m/z=292.2 [M+H]⁺.

Step 4: 2-[1-(4-Methoxy-phenyl)-cyclohexyl]-1-(2-methyl-pyridin-4-yl)-ethanone In analogy to example 151, step 1, 4-bromo-2-methylpyridine was reacted first with n-butyllithium and later with N-methoxy-2-[1-(4-methoxy-phenyl)-cyclohexyl]-N-methyl-acetamide to give the title compound as a light yellow oil, MS (ESI⁺): m/z=324.3 [M+H]⁺.

Step 5: (E)-2-[1-(4-Methoxy-phenyl)-cyclohexyl]-1-(2-methyl-pyridin-4-yl)-ethanone oxime In analogy to example 151, step 3, 2-[1-(4-methoxy-phenyl)-cyclohexyl]-1-(2-methyl-pyridin-4-yl)-ethanone was reacted with hydroxylamine hydrochloride in the presence of NaHCO₃ to give the title compound as a colorless solid, MS (ESI⁺): m/z=339.3 [M+H]⁺.

Example 159

(Z)-2-[1-(4-Methoxy-phenyl)-cyclohexyl]-1-(2-methyl-pyridin-4-yl)-ethanone oxime

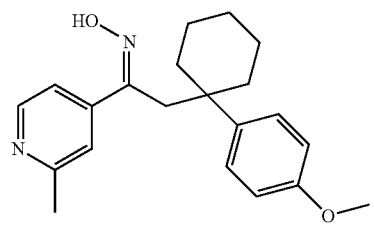 [SMILES: COc1ccc(C2(C/C(=N/O)c3ccnc(C)c3)CCCCC2)cc1]

The title compound was obtained as a side product of example 158, step 5 as a colorless foam, MS (ESI⁺): m/z=339.3 [M+H]⁺.

Example 160

5-{1-[(E)-Hydroxyimino]-3,3-diphenyl-propyl}-1H-pyridin-2-one

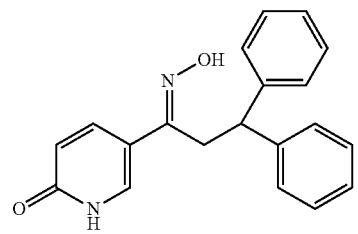 [SMILES: O=c1ccc(/C(CC(c2ccccc2)c2ccccc2)=N/O)c[nH]1]

Step 1: 6,N-Dimethoxy-N-methyl-nicotinamide

In analogy to example 158, step 3, 6-methoxynicotinic acid was reacted with N,O-dimethylhydroxylamine hydrochloride and 1,1'-carbonyldiimidazole to give the title compound as a colorless oil, MS (ESI⁺): m/z=197.3 [M+H]⁺.

Step 2: 1-(6-Methoxy-pyridin-3-yl)-3-phenyl-propynone

To a solution of 6,N-dimethoxy-N-methyl-nicotinamide (1.14 g) in THF (20 ml) was added a solution of phenylethynylmagnesium bromide (11.62 ml, 1 M in THF) at 0° C. The mixture was stirred at 0° C. for 1.5 h and at room temperature for 3 h. A solution of phenylethynylmagnesium bromide (2.91 ml, 1 M in THF) was added and the mixture was stirred overnight at room temperature. A solution of phenylethynylmagnesium bromide (5.81 ml, 1 M in THF) was added and the mixture was stirred for 24 h at room temperature. An aqueous solution of ammonium chloride was added and the mixture was stirred for 30 min. Ice water was added and the mixture was extracted with ethyl acetate. The organic phase was washed with water, dried (MgSO₄), filtered and concentrated to dryness. The product was purified by chromatography (SiO₂, cyclohexane/ethyl acetate 1:0 to 0:1) to give the title compound (0.934 g) as an off-white solid, MS (ESI⁺): m/z=238.1 [M+H]⁺.

Step 3: 1-(6-Methoxy-pyridin-3-yl)-3,3-diphenyl-propenone

To a solution of 1-(6-methoxy-pyridin-3-yl)-3-phenyl-propynone (275 mg) in 1,4-dioxane (2.5 ml) were added phenylboronic acid (170 mg), tetrakis(triphenylphosphine) palladium(0) (41 mg) and acetic acid (7 mg). The mixture was stirred at room temperature for 10 min, at 80° C. for 10 h and at 60° C. overnight. The mixture was concentrated to dryness. The product was purified by chromatography (SiO$_2$, cyclohexane/ethyl acetate 1:0 to 85:15) to give the title compound (144 mg) as a yellow oil, MS (ESI$^+$): m/z=316.2 [M+H]$^+$.

Step 4: 1-(6-Methoxy-pyridin-3-yl)-3,3-diphenyl-propan-1-one

To a solution of 1-(6-methoxy-pyridin-3-yl)-3,3-diphenyl-propenone (135 mg) in dichloromethane (1.7 ml) was added catecholborane (81 mg, 95% pure). The mixture was stirred for 2.5 h at room temperature. Water (5 ml) was added and the mixture was stirred for 1 h. The mixture was extracted with dichloromethane. The organic phase was dried (MgSO$_4$), filtered and concentrated to dryness. The product was purified by chromatography (SiO$_2$, cyclohexane/ethyl acetate 1:0 to 85:15) to give the title compound (56 mg) as an off-white solid, MS (ESI$^+$): m/z=318.2 [M+H]$^+$.

Step 5: 5-(3,3-Diphenyl-propionyl)-1H-pyridin-2-one

To a solution of 1-(6-methoxy-pyridin-3-yl)-3,3-diphenyl-propan-1-one (468 mg) in 1,4-dioxane (25 ml) was added concentrated aqueous HCl (2.69 ml). The mixture was stirred for 2 h at 100° C. After cooling to room temperature, the mixture was poured into ice and extracted with ethyl acetate. The organic phase was dried (MgSO$_4$), filtered and concentrated to dryness. The product was purified by chromatography (SiO$_2$, dichloromethane/methanol 1:0 to 4:1) to give the title compound (127 mg) as a colorless solid, MS (ESI$^-$): m/z=302.0 [M−H]$^-$.

Step 6: 5-{1-[(E)-Hydroxyimino]-3,3-diphenyl-propyl}-1H-pyridin-2-one

In analogy to example 151, step 3, 5-(3,3-diphenyl-propionyl)-1H-pyridin-2-one was reacted with hydroxylamine hydrochloride in the presence of NaHCO$_3$ to give the title compound containing less than 10% of the corresponding Z isomer as a colorless solid, MS (ESI$^-$): m/z=317.1 [M−H]$^-$.

Example 161

5-{1-[(E)-Hydroxyimino]-3,3-diphenyl-propyl}-1-methyl-1H-pyridin-2-one

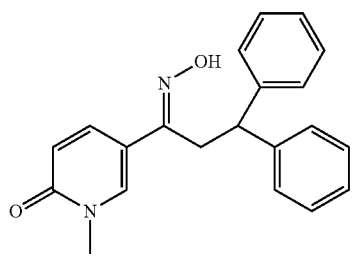 [SMILES: Cn1cc(/C(CC(c2ccccc2)c2ccccc2)=N/O)ccc1=O]

Step 1: 5-(3,3-Diphenyl-propionyl)-1-methyl-1H-pyridin-2-one

To a solution of 5-(3,3-diphenyl-propionyl)-1H-pyridin-2-one (60 mg, example 160, step 5) in N,N-dimethylacetamide (1 ml) were added powdered potassium carbonate (30 mg) and iodomethane (30 mg). The mixture was stirred at room temperature for 5.5 h. Water was added and the mixture was extracted with ethyl acetate. The organic phase was dried (MgSO$_4$), filtered and concentrated to dryness. The product was purified by chromatography (SiO$_2$, dichloromethane/methanol 1:0 to 85:15) to give the title compound (54 mg) as a colorless solid, MS (ESI$^+$): m/z=318.2 [M+H]$^+$.

Step 2: 5-{1-[(E)-Hydroxyimino]-3,3-diphenyl-propyl}-1-methyl-1H-pyridin-2-one In analogy to example 151, step 3, 5-(3,3-diphenyl-propionyl)-1-methyl-1H-pyridin-2-one was reacted with hydroxylamine hydrochloride in the presence of NaHCO$_3$ to give the title compound containing less than 10% of the corresponding Z isomer as a colorless solid, MS (ESI$^+$): m/z=333.3 [M+H]$^+$.

Example 162

5-{3-(4-Bromo-phenyl)-1-[(E)-hydroxyimino]-3-o-tolyl-propyl}-1-methyl-1H-pyridin-2-one

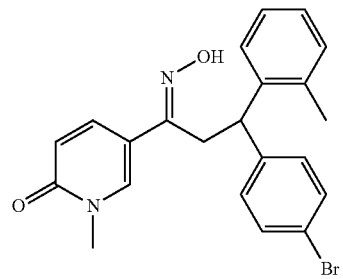 [SMILES: Cc1ccccc1C(C/C(=N\O)c1ccc(=O)n(C)c1)c1ccc(Br)cc1]

Step 1: 3-(4-Bromo-phenyl)-1-(6-methoxy-pyridin-3-yl)-3-o-tolyl-propan-1-one In analogy to example 151, step 1, 5-bromo-2-methoxypyridine was reacted first with n-butyllithium and later with 3-(4-bromo-phenyl)-N-methoxy-N-methyl-3-o-tolyl-propionamide (example 74, step 4) to give the title compound as a colorless oil, MS (ESI$^+$): m/z=410.2 [M+H]$^+$.

Step 2: 5-[3-(4-Bromo-phenyl)-3-o-tolyl-propionyl]-1H-pyridin-2-one

To a solution of 3-(4-bromo-phenyl)-1-(6-methoxy-pyridin-3-yl)-3-o-tolyl-propan-1-one (384 mg) in 1,4-dioxane (16 ml) was added concentrated aqueous HCl (17 ml). The mixture was stirred for 1.5 h at 100° C. After cooling to room temperature, the mixture was poured into ice and extracted with ethyl acetate. The organic phase was dried (MgSO$_4$), filtered and concentrated to dryness. The product was purified by chromatography (SiO$_2$, dichloromethane/methanol 1:0 to 9:1) to give the title compound (338 mg) as a colorless foam, MS (ESI$^-$): m/z=393.8 [M−H]$^-$.

Step 3: 5-[3-(4-Bromo-phenyl)-3-o-tolyl-propionyl]-1-methyl-1H-pyridin-2-one In analogy to example 161, step 1, 5-[3-(4-bromo-phenyl)-3-o-tolyl-propionyl]-1H-pyridin-2-one was reacted with iodomethane in the presence of potassium carbonate to give the title compound as a colorless solid, MS (ESI$^+$): m/z=410.2 [M+H]$^+$.

Step 4: 5-{3-(4-Bromo-phenyl)-1-[(E)-hydroxy-imino]-3-o-tolyl-propyl}-1-methyl-1H-pyridin-2-one In analogy to example 151, step 3, 5-[3-(4-bromo-phenyl)-3-o-tolyl-propionyl]-1-methyl-1H-pyridin-2-one was reacted with hydroxylamine hydrochloride in the presence of NaHCO$_3$ to give the title compound as a colorless solid, MS (ESI$^+$): m/z=425.1 [M+H]$^+$.

Example 163

5-{3-(4-Bromo-phenyl)-1-[(Z)-hydroxyimino]-3-o-tolyl-propyl}-1-methyl-1H-pyridin-2-one

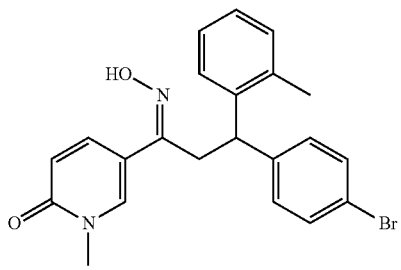 [SMILES: Cc1ccccc1C(C/C(=N/O)c1ccc(=O)n(C)c1)c1ccc(Br)cc1]

The title compound was obtained as a side product of example 162, step 4 as a colorless solid, MS (ESI$^+$): m/z=425.1 [M+H]$^+$.

Example 164

5-{3-(4-Bromo-phenyl)-1-[(E)-hydroxyimino]-3-o-tolyl-propyl}-1-ethyl-1H-pyridin-2-one

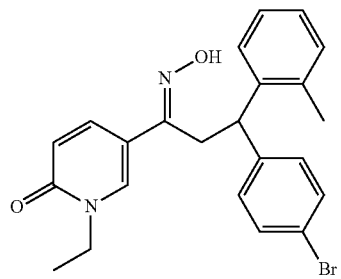 [SMILES: CCn1cc(/C(CC(c2ccc(Br)cc2)c2ccccc2C)=N/O)ccc1=O]

Step 1: 5-[3-(4-Bromo-phenyl)-3-otolyl-propionyl]-1-ethyl-1H-pyridin-2-one

In analogy to example 161, step 1, 5-[3-(4-bromo-phenyl)-3-o-tolyl-propionyl]-1H-pyridin-2-one (example 162, step 3) was reacted with iodoethane in the presence of potassium carbonate to give the title compound as a colorless foam, MS (ESI$^+$): m/z=424.1 [M+H]$^+$.

Step 2: 5-{3-(4-Bromo-phenyl)-1-[(E)-hydroxy-imino]-3-o-tolyl-propyl}-1-ethyl-1H-pyridin-2-one In analogy to example 151, step 3, 5-[3-(4-bromo-phenyl)-3-o-tolyl-propionyl]-1-ethyl-1H-pyridin-2-one was reacted with hydroxylamine hydrochloride in the presence of NaHCO$_3$ to give the title compound as a colorless solid, MS (ESI$^+$): m/z=439.3 [M+H]$^+$.

Example 165

5-{3-(4-Bromo-phenyl)-1-[(Z)-hydroxyimino]-3-o-tolyl-propyl}-1-ethyl-1H-pyridin-2-one

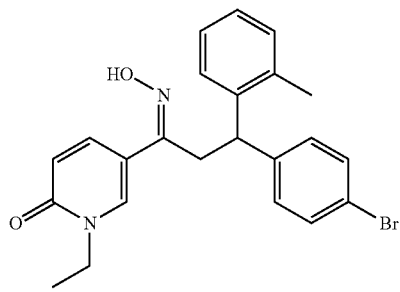 [SMILES: CCn1cc(/C(CC(c2ccc(Br)cc2)c2ccccc2C)=N\O)ccc1=O]

The title compound was obtained as a side product of example 164, step 2 as a colorless solid, MS (ESI$^+$): m/z=439.1 [M+H]$^+$.

Example 166

4'-[3-[(E)-Hydroxyimino]-3-(1-methyl-6-oxo-1,6-dihydro-pyridin-3-yl)-1-o-tolyl-propyl]-biphenyl-4-carboxylic acid

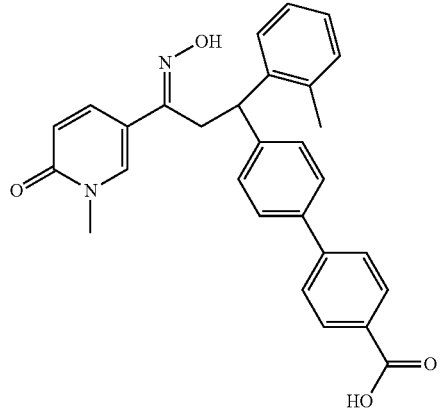

Step 1: 4'-[3-(1-Methyl-6-oxo-1,6-dihydro-pyridin-3-yl)-3-oxo-1-o-tolyl-propyl]-biphenyl-4-carboxylic acid To a stirred suspension of 5-[3-(4-bromo-phenyl)-3-o-tolyl-propionyl]-1-methyl-1H-pyridin-2-one (50 mg, example 162, step 3) and 4-carboxyphenylboronic acid (32 mg) in 1,4-dioxane (0.4 ml) under argon were added dichloro(1,1'-bis(diphenylphosphino)ferrocene)-palladium(II) dichloromethane adduct (4.5 mg), water (0.3 ml) and 2 M aqueous sodium carbonate solution (0.18 ml). The mixture was stirred at 80° C. for 2 h. After cooling to room temperature, the mixture was filtered. The filter cake was washed with ethyl acetate and with a saturated KHSO₄ solution. The combined filtrate was extracted with ethyl acetate. The organic phase was dried (MgSO₄), filtered and concentrated to dryness. The product was purified by chromatography (SiO₂, dichloromethane/methanol 1:0 to 9:1) to give the title compound (75 mg, not totally pure) as a colorless solid, MS (ESI⁻): m/z=450.2 [M−H]⁻.

Step 2: 4'-[3-[(E)-Hydroxyimino]-3-(1-methyl-6-oxo-1,6-dihydro-pyridin-3-yl)-1-o-tolyl-propyl]-biphenyl-4-carboxylic acid In analogy to example 151, step 3, 4'-[3-(1-methyl-6-oxo-1,6-dihydro-pyridin-3-yl)-3-oxo-1-o-tolyl-propyl]-biphenyl-4-carboxylic acid was reacted with hydroxylamine hydrochloride in the presence of NaHCO₃ to give the title compound as a colorless solid, MS (ESI⁺): m/z=467.3 [M+H]⁺.

Example 167

4'-[(S)-3-[(E)-Hydroxyimino]-3-(1-methyl-6-oxo-1,6-dihydro-pyridin-3-yl)-1-o-tolyl-propyl]-biphenyl-4-carboxylic acid

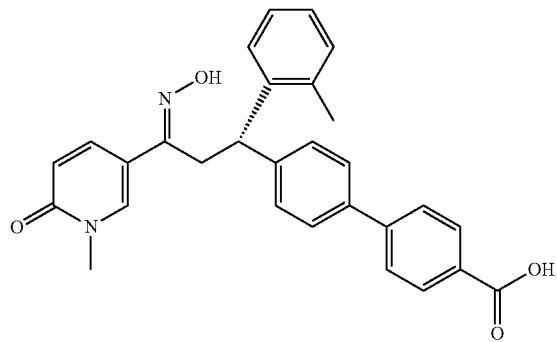 [SMILES: Cc1ccccc1[C@@H](C/C(=N\O)c1ccc(=O)n(C)c1)c1ccc(-c2ccc(C(=O)O)cc2)cc1]

and

Example 168

4'-[(R)-3-[(E)-Hydroxyimino]-3-(1-methyl-6-oxo-1,6-dihydro-pyridin-3-yl)-1-o-tolyl-propyl]-biphenyl-4-carboxylic acid

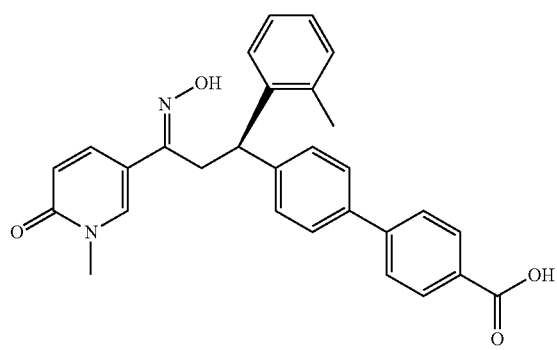 [SMILES: Cc1ccccc1[C@H](C/C(=N\O)c1ccc(=O)n(C)c1)c1ccc(-c2ccc(C(=O)O)cc2)cc1]

4'-[3-[(E)-Hydroxyimino]-3-(1-methyl-6-oxo-1,6-dihydro-pyridin-3-yl)-1-o-tolyl-propyl]-biphenyl-4-carboxylic acid (example 166) was separated into the enantiomers using Chiralpak AD as the stationary phase and 30% (ethanol+0.5% HCOOH)/70% n-heptane as the mobile phase to give the title compounds as off-white solids.

Example 169

3-Fluoro-4'-[3-[(E)-hydroxyimino]-3-(1-methyl-6-oxo-1,6-dihydro-pyridin-3-yl)-1-o-tolyl-propyl]-biphenyl-4-carboxylic acid

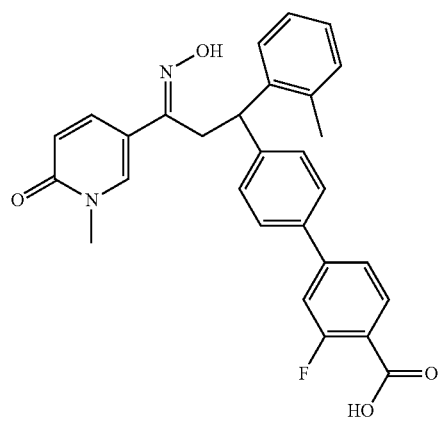

Step 1: 3-Fluoro-4'-[3-(1-methyl-6-oxo-1,6-dihydro-pyridin-3-yl)-3-oxo-1-o-tolyl-propyl]-biphenyl-4-carboxylic acid methyl ester In analogy to example 166, step 1, 5-[3-(4-bromo-phenyl)-3-o-tolyl-propionyl]-1-methyl-1H-pyridin-2-one (example 162, step 3) was reacted with 3-fluoro-4-methoxycarbonylphenylboronic acid in the presence of dichloro(1,1'-bis(diphenylphosphino)ferrocene)palladium(II) dichloromethane adduct in a mixture of 1,4-dioxane, water and 2 M aqueous sodium carbonate solution to give the title compound as an off-white solid, MS (ESI⁺): m/z=484.3 [M+H]⁺.

Step 2: 3-Fluoro-4'-[3-(1-methyl-6-oxo-1,6-dihydro-pyridin-3-yl)-3-oxo-1-o-tolyl-propyl]-biphenyl-4-carboxylic acid To a suspension of 3-fluoro-4'-[3-(1-methyl-6-oxo-1,6-dihydro-pyridin-3-yl)-3-oxo-1-o-tolyl-propyl]-biphenyl-4-carboxylic acid methyl ester (35 mg) in THF (0.2 ml) and MeOH (0.2 ml) was added a 1M aqueous LiOH solution (0.145 ml) at 0° C. The mixture was stirred at 0° C. for 30 min and at room temperature for 1 h. Since the reaction was not finished, 1 M aqueous LiOH solution (0.435 ml) was added portionwise while stirring for another 24 h at room temperature. The reaction mixture was acidified using 1 M HCl. The organic solvents were removed under vacuum. The precipitated solid was collected by filtration, washed with water and dried to give the title compound (29 mg) as a colorless solid, MS (ESI⁻): m/z=468.2 [M−H]⁻.

Step 3: 3-Fluoro-4'-[3-[(E)-hydroxyimino]-3-(1-methyl-6-oxo-1,6-dihydro-pyridin-3-yl)-1-o-tolyl-propyl]-biphenyl-4-carboxylic acid In analogy to example 151, step 3, 3-fluoro-4'-[3-(1-methyl-6-oxo-1,6-dihydro-pyridin-3-yl)-3-oxo-1-o-tolyl-propyl]-biphenyl-4-carboxylic acid was reacted with hydroxy-

Example 170

5-{3-(4-Bromo-phenyl)-1-[(E)-hydroxyimino]-5-methyl-hexyl}-1-methyl-1H-pyridin-2-one

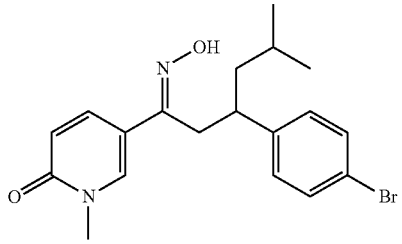 [SMILES: CC(C)CC(C/C(=N\O)c1ccc(=O)n(C)c1)c1ccc(Br)cc1]

Step 1: (E)-3-(4-Bromo-phenyl)-1-(6-methoxy-pyridin-3-yl)-propenone

To a solution of 5-acetyl-2-methoxypyridine (2.317 g) in methanol (50 ml) were added 4-bromobenzaldehyde (3.120 g) and potassium hydroxide (0.946 g). The mixture was stirred at room temperature for 2.5 h. The mixture was placed in an ice bath. The precipitated solid was collected by filtration, washed with methanol and dried to give the title compound as a colorless solid (4.281 g), MS (ESI$^+$): m/z=318.1 [M+H]$^+$.

Step 2: 3-(4-Bromo-phenyl)-1-(6-methoxy-pyridin-3-yl)-5-methyl-hexan-1-one

To a stirred suspension of CuI (18 mg) in THF (3 ml) under argon at 0° C. was added isobutylmagnesium chloride (1.04 ml, 2 M solution in diethyl ether). The mixture was stirred at 0° C. for 50 min to give a dark suspension. (E)-3-(4-Bromo-phenyl)-1-(6-methoxy-pyridin-3-yl)-propenone (300 mg) was added. The mixture was stirred at 0° C. for 140 min. Saturated aqueous ammonium chloride solution was added and the mixture was extracted with ethyl acetate. The organic phase was dried (MgSO$_4$), filtered and concentrated to dryness. The product was purified by chromatography (SiO$_2$, cyclohexane/ethyl acetate 1:0 to 7:3) to give the title compound (279 mg) as a light yellow oil, MS (ESI$^+$): m/z=376.2 [M+H]$^+$.

Step 3: 5-[3-(4-Bromo-phenyl)-5-methyl-hexanoyl]-1H-pyridin-2-one

In analogy to example 162, step 2, 3-(4-bromo-phenyl)-1-(6-methoxy-pyridin-3-yl)-5-methyl-hexan-1-one was reacted with concentrated aqueous HCl in 1,4-dioxane to give the title compound as a colorless oil, MS (ESI$^+$): m/z=362.1 [M+H]$^+$.

Step 4: 5-[3-(4-Bromo-phenyl)-5-methyl-hexanoyl]-1-methyl-1H-pyridin-2-one

In analogy to example 161, step 1, 5-[3-(4-bromo-phenyl)-5-methyl-hexanoyl]-1H-pyridin-2-one was reacted with iodomethane in the presence of potassium carbonate to give the title compound as a colorless oil, MS (ESI$^+$): m/z=376.2 [M+H]$^+$.

Step 5: 5-{3-(4-Bromo-phenyl)-1-[(E)-hydroxyimino]-5-methyl-hexyl}-1-methyl-1H-pyridin-2-one In analogy to example 151, step 3, 5-[3-(4-bromo-phenyl)-5-methyl-hexanoyl]-1-methyl-1H-pyridin-2-one was reacted with hydroxylamine hydrochloride in the presence of NaHCO$_3$ to give the title compound as a colorless solid, MS (ESI$^+$): m/z=391.1 [M+H]$^+$.

Example 171

5-{3-(4-Bromo-phenyl)-1-[(Z)-hydroxyimino]-5-methyl-hexyl}-1-methyl-1H-pyridin-2-one

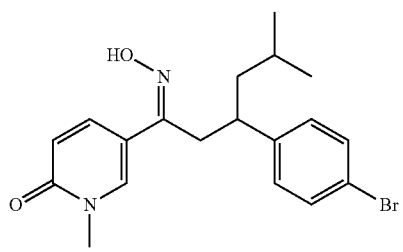 [SMILES: CC(C)CC(C/C(=N/O)c1ccc(=O)n(C)c1)c1ccc(Br)cc1]

The title compound was obtained as a side product of example 170, step 5 as a colorless solid, MS (ESI$^+$): m/z=391.1 [M+H]$^+$.

Example 172

5-{3-(4-Bromo-phenyl)-3-cyclopentyl-1-[(E)-hydroxyimino]-propyl}-1-methyl-1H-pyridin-2-one

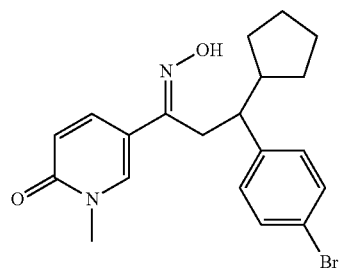 [SMILES: Cn1cc(/C(CC(c2ccc(Br)cc2)C2CCCC2)=N/O)ccc1=O]

Step 1: 3-(4-Bromo-phenyl)-3-cyclopentyl-1-(6-methoxy-pyridin-3-yl)-propan-1-one In analogy to example 170, step 2, (E)-3-(4-bromo-phenyl)-1-(6-methoxy-pyridin-3-yl)-propenone (example 170, step 1) was reacted with cyclopentylmagnesium bromide in the presence of CuI to give the title compound as a light yellow oil, MS (ESI$^+$): m/z=388.2 [M+H]$^+$.

Step 2: 5-[3-(4-Bromo-phenyl)-3-cyclopentyl-propionyl]-1H-pyridin-2-one

In analogy to example 162, step 2, 3-(4-bromo-phenyl)-3-cyclopentyl-1-(6-methoxy-pyridin-3-yl)-propan-1-one was reacted with concentrated aqueous HCl in 1,4-dioxane to give the title compound as a colorless foam, MS (ESI⁺): m/z=374.0 [M+H]⁺.

Step 3: 5-[3-(4-Bromo-phenyl)-3-cyclopentyl-propionyl]-1-methyl-1H-pyridin-2-one In analogy to example 161, step 1, 5-[3-(4-bromo-phenyl)-3-cyclopentyl-propionyl]-1H-pyridin-2-one was reacted with iodomethane in the presence of potassium carbonate to give the title compound as a colorless foam, MS (ESI⁺): m/z=388.2 [M+H]⁺.

Step 4: 5-{3-(4-Bromo-phenyl)-3-cyclopentyl-1-[(E)-hydroxyimino]-propyl}-1-methyl-1H-pyridin-2-one In analogy to example 151, step 3, 5-[3-(4-bromo-phenyl)-3-cyclopentyl-propionyl]-1-methyl-1H-pyridin-2-one was reacted with hydroxylamine hydrochloride in the presence of NaHCO₃ to give the title compound as a colorless solid, MS (ESI⁺): m/z=403.2 [M+H]⁺.

Example 173

5-{3-(4-Bromo-phenyl)-3-cyclopentyl-1-[(Z)-hydroxyimino]-propyl}-1-methyl-1H-pyridin-2-one

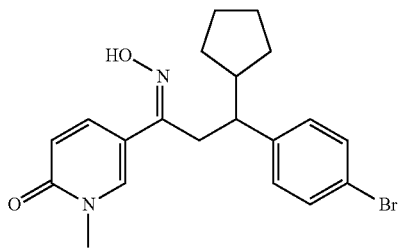 [SMILES: Cn1cc(/C(CC(c2ccc(Br)cc2)C2CCCC2)=N\O)ccc1=O]

The title compound was obtained as a side product of example 172, step 4 as a colorless solid, MS (ESI⁺): m/z=403.2 [M+H]⁺.

Example 174

5-{3-(4-Bromo-phenyl)-1-[(E)-hydroxyimino]-hexyl}-1-methyl-1H-pyridin-2-one

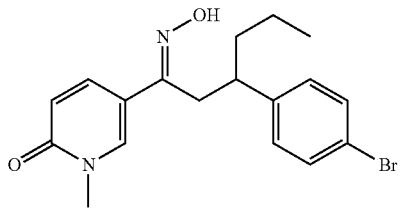 [SMILES: CCCC(C/C(=N\O)c1ccc(=O)n(C)c1)c1ccc(Br)cc1]

Step 1: 3-(4-Bromo-phenyl)-1-(6-methoxy-pyridin-3-yl)-hexan-1-one

In analogy to example 170, step 2, (E)-3-(4-bromo-phenyl)-1-(6-methoxy-pyridin-3-yl)-propenone (example 170, step 1) was reacted with n-propylmagnesium bromide in the presence of CuI to give the title compound as a light yellow oil, MS (ESI⁺): m/z=362.1 [M+H]⁺.

Step 2: 5-[3-(4-Bromo-phenyl)-hexanoyl]-1H-pyridin-2-one

In analogy to example 162, step 2, 3-(4-bromo-phenyl)-1-(6-methoxy-pyridin-3-yl)-hexan-1-one was reacted with concentrated aqueous HCl in 1,4-dioxane to give the title compound as a colorless solid, MS (ESI⁺): m/z=350.2 [M+H]⁺.

Step 3: 5-[3-(4-Bromo-phenyl)-hexanoyl]-1-methyl-1H-pyridin-2-one

In analogy to example 161, step 1, 5-[3-(4-bromo-phenyl)-hexanoyl]-1H-pyridin-2-one was reacted with iodomethane in the presence of potassium carbonate to give the title compound as a light yellow oil, MS (ESI⁺): m/z=362 [M+H]⁺.

Step 4: 5-{3-(4-Bromo-phenyl)-1-[(E)-hydroxyimino]-hexyl}-1-methyl-1H-pyridin-2-one In analogy to example 151, step 3, 5-[3-(4-bromo-phenyl)-hexanoyl]-1-methyl-1H-pyridin-2-one was reacted with hydroxylamine hydrochloride in the presence of NaHCO₃ to give the title compound as a colorless solid, MS (ESI⁺): m/z=377.1 [M+H]⁺.

Example 175

5-{3-(4-Bromo-phenyl)-7,7,7-trifluoro-1-[(E)-hydroxyimino]-heptyl}-1-methyl-1H-pyridin-2-one

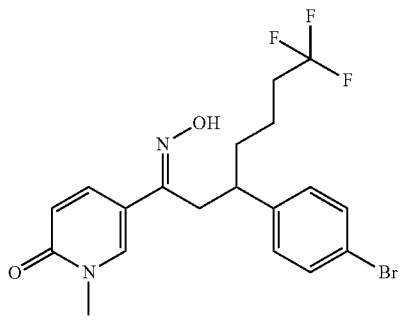 [SMILES: Cn1cc(/C(CC(CCCC(F)(F)F)c2ccc(Br)cc2)=N/O)ccc1=O]

Step 1: 3-(4-Bromo-phenyl)-7,7,7-trifluoro-1-(6-methoxy-pyridin-3-yl)-heptan-1-one In analogy to example 170, step 2, (E)-3-(4-bromo-phenyl)-1-(6-methoxy-pyridin-3-yl)-propenone (example 170, step 1) was reacted in the presence of CuI with the Grignard reagent prepared from 1-bromo-4,4,4-trifluorobutane to give the title compound as a light yellow oil, MS (ESI⁺): m/z=430.2 [M+H]⁺.

Step 2: 5-[3-(4-Bromo-phenyl)-7,7,7-trifluoro-heptanoyl]-1H-pyridin-2-one

In analogy to example 162, step 2, 3-(4-bromo-phenyl)-7,7,7-trifluoro-1-(6-methoxy-pyridin-3-yl)-heptan-1-one was reacted with concentrated aqueous HCl in 1,4-dioxane to give the title compound as a light yellow oil, MS (ESI⁺): m/z=416.1 [M+H]⁺.

Step 3: 5-[3-(4-Bromo-phenyl)-7,7,7-trifluoro-heptanoyl]-1-methyl-1H-pyridin-2-one In analogy to example 161, step 1, 5-[3-(4-bromo-phenyl)-7,7,7-trifluoro-heptanoyl]-1H-pyridin-2-one was reacted with iodomethane in the presence of potassium carbonate to give the title compound as a light yellow oil, MS (ESI⁺): m/z=430.2 [M+H]⁺.

Step 4: 5-{3-(4-Bromo-phenyl)-7,7,7-trifluoro-1-[(E)-hydroxyimino]-heptyl}-1-methyl-1H-pyridin-2-one In analogy to example 151, step 3, 5-[3-(4-bromo-phenyl)-7,7,7-trifluoro-heptanoyl]-1-methyl-1H-pyridin-2-one was reacted with hydroxylamine hydrochloride in the presence of NaHCO₃ to give the title compound containing 14% of the corresponding Z isomer as a colorless solid, MS (ESI⁺): m/z=445.3 [M+H]⁺.

Example 176

5-{3-(4-Bromo-phenyl)-1-[(E)-hydroxyimino]-hex-5-enyl}-1-methyl-1H-pyridin-2-one

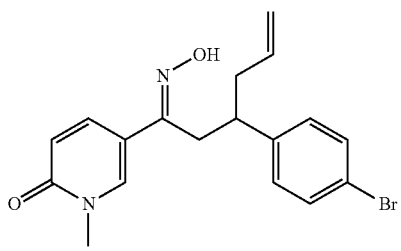 [SMILES: C=CCC(C/C(=N\O)c1ccc(=O)n(C)c1)c1ccc(Br)cc1]

Step 1: 3-(4-Bromo-phenyl)-1-(6-methoxy-pyridin-3-yl)-hex-5-en-1-one

To a suspension of (E)-3-(4-bromo-phenyl)-1-(6-methoxy-pyridin-3-yl)-propenone (example 170, step 1, 200 mg) in dichloromethane (3 ml) was slowly added TiCl₄ (1 M in dichloromethane, 0.63 ml). The mixture was stirred at room temperature for 5 min. Allyltrimethylsilane (79 mg) was added slowly. The mixture was stirred at room temperature for 30 min. Ice water was added and the mixture was extracted with ethyl acetate. The organic phase was dried using MgSO₄, filtered and concentrated to dryness. The product was purified by chromatography (SiO₂, cyclohexane/ethyl acetate 1:0 to 7:3) to give the title compound (135 mg) as a light yellow oil, MS (ESI⁺): m/z=360.1 [M+H]⁺.

Step 2: 5-[3-(4-Bromo-phenyl)-hex-5-enoyl]-1H-pyridin-2-one

In analogy to example 162, step 2, 3-(4-bromo-phenyl)-1-(6-methoxy-pyridin-3-yl)-hex-5-en-1-one was reacted with concentrated aqueous HCl in 1,4-dioxane to give the title compound as an off-white foam, MS (ESI⁻): m/z=344.0 [M−H]⁻.

Step 3: 5-[3-(4-Bromo-phenyl)-hex-5-enoyl]-1-methyl-1H-pyridin-2-one

In analogy to example 161, step 1, 5-[3-(4-bromo-phenyl)-hex-5-enoyl]-1H-pyridin-2-one was reacted with iodomethane in the presence of potassium carbonate to give the title compound as a colorless oil, MS (ESI⁺): m/z=360.1 [M+H]⁺.

Step 4: 5-{3-(4-Bromo-phenyl)-1-[(E)-hydroxyimino]-hex-5-enyl}-1-methyl-1H-pyridin-2-one In analogy to example 151, step 3, 5-[3-(4-bromo-phenyl)-hex-5-enoyl]-1-methyl-1H-pyridin-2-one was reacted with hydroxylamine hydrochloride in the presence of NaHCO₃ to give the title compound as a colorless solid, MS (ESI⁻): m/z=373.1 [M−H]⁻.

Example 177

5-{3-(4-Bromo-phenyl)-1-[(E)-hydroxyimino]-heptyl}-1-methyl-1H-pyridin-2-one

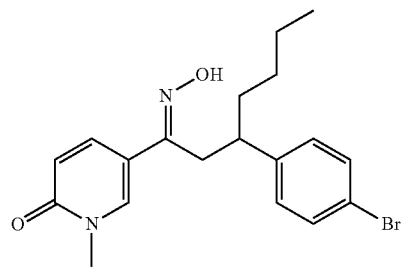 [SMILES: CCCCC(C/C(=N\O)c1ccc(=O)n(C)c1)c1ccc(Br)cc1]

Step 1: 3-(4-Bromo-phenyl)-1-(6-methoxy-pyridin-3-yl)-heptan-1-one

In analogy to example 170, step 2, (E)-3-(4-bromo-phenyl)-1-(6-methoxy-pyridin-3-yl)-propenone (example 170, step 1) was reacted with n-butylmagnesium chloride in the presence of CuI to give the title compound as a light yellow oil, MS (ESI⁺): m/z=376.2 [M+H]⁺.

Step 2: 5-[3-(4-Bromo-phenyl)-heptanoyl]-1H-pyridin-2-one

In analogy to example 162, step 2, 3-(4-bromo-phenyl)-1-(6-methoxy-pyridin-3-yl)-heptan-1-one was reacted with concentrated aqueous HCl in 1,4-dioxane to give the title compound as a colorless foam, MS (ESI⁺): m/z=362.1 [M+H]⁺.

Step 3: 5-[3-(4-Bromo-phenyl)-heptanoyl]-1-methyl-1H-pyridin-2-one

In analogy to example 161, step 1, 5-[3-(4-bromo-phenyl)-heptanoyl]-1H-pyridin-2-one was reacted with iodomethane in the presence of potassium carbonate to give the title compound as a colorless solid, MS (ESI⁺): m/z=376.2 [M+H]⁺.

Step 4: 5-{3-(4-Bromo-phenyl)-1-[(E)-hydroxyimino]-heptyl}-1-methyl-1H-pyridin-2-one In analogy to example 151, step 3, 5-[3-(4-bromo-phenyl)-heptanoyl]-1-methyl-1H-pyridin-2-one was reacted with hydroxylamine hydrochloride in the presence of NaHCO₃ to give the title compound containing 4% of the corresponding Z isomer as a colorless foam, MS (ESI⁺): m/z=391.3 [M+H]⁺.

Example 178

5-{3-(4-Bromo-phenyl)-3-cyclohexyl-1-[(E)-hydroxyimino]-propyl}-1-methyl-1H-pyridin-2-one

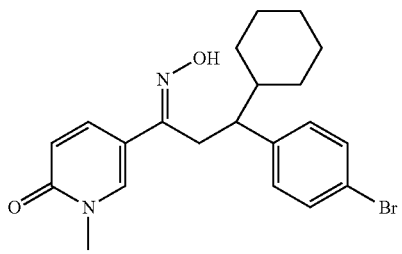 [SMILES: Cn1cc(/C(CC(c2ccc(Br)cc2)C2CCCCC2)=N/O)ccc1=O]

Step 1: 3-(4-Bromo-phenyl)-3-cyclohexyl-1-(6-methoxy-pyridin-3-yl)-propan-1-one In analogy to example 170, step 2, (E)-3-(4-bromo-phenyl)-1-(6-methoxy-pyridin-3-yl)-propenone (example 170, step 1) was reacted with cyclohexylmagnesium chloride in the presence of CuI to give the title compound as a light yellow oil, MS (ESI⁺): m/z=402.3 [M+H]⁺.

Step 2: 5-[3-(4-Bromo-phenyl)-3-cyclohexyl-propionyl]-1H-pyridin-2-one

In analogy to example 162, step 2, 3-(4-bromo-phenyl)-3-cyclohexyl-1-(6-methoxy-pyridin-3-yl)-propan-1-one was reacted with concentrated aqueous HCl in 1,4-dioxane to give the title compound as a colorless solid, MS (ESI⁺): m/z=388.2 [M+H]⁺.

Step 3: 5-[3-(4-Bromo-phenyl)-3-cyclohexyl-propionyl]-1-methyl-1H-pyridin-2-one In analogy to example 161, step 1, 5-[3-(4-bromo-phenyl)-3-cyclohexyl-propionyl]-1H-pyridin-2-one was reacted with iodomethane in the presence of potassium carbonate to give the title compound as a light pink solid, MS (ESI⁺): m/z=402.2 [M+H]⁺.

Step 4: 5-{3-(4-Bromo-phenyl)-3-cyclohexyl-1-[(E)-hydroxyimino]-propyl}-1-methyl-1H-pyridin-2-one In analogy to example 151, step 3, 5-[3-(4-bromo-phenyl)-3-cyclohexyl-propionyl]-1-methyl-1H-pyridin-2-one was reacted with hydroxylamine hydrochloride in the presence of NaHCO₃ to give the title compound as a colorless foam, MS (ESI⁺): m/z=417.2 [M+H]⁺.

Example 179

5-{3-(4-Bromo-phenyl)-3-cyclobutyl-1-[(E)-hydroxyimino]-propyl}-1-methyl-1H-pyridin-2-one

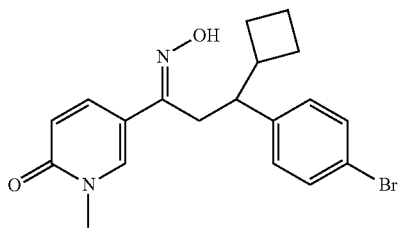 [SMILES: Cn1cc(/C(CC(c2ccc(Br)cc2)C2CCC2)=N/O)ccc1=O]

Step 1: 3-(4-Bromo-phenyl)-3-cyclobutyl-1-(6-methoxy-pyridin-3-yl)-propan-1-one In analogy to example 170, step 2, (E)-3-(4-bromo-phenyl)-1-(6-methoxy-pyridin-3-yl)-propenone (example 170, step 1) was reacted in the presence of CuI with the Grignard reagent prepared from cyclobutyl bromide to give the title compound as a light yellow oil, MS (ESI⁺): m/z=374.2 [M+H]⁺.

Steps 2-3: 5-[3-(4-Bromo-phenyl)-3-cyclobutyl-propionyl]-1-methyl-1H-pyridin-2-one In analogy to example 162, step 2, 3-(4-bromo-phenyl)-3-cyclobutyl-1-(6-methoxy-pyridin-3-yl)-propan-1-one was reacted with concentrated aqueous HCl in 1,4-dioxane to give 5-[3-(4-bromo-phenyl)-3-cyclobutyl-propionyl]-1H-pyridin-2-one as a light yellow oil, which was directly subjected to the next step.

In analogy to example 161, step 1, 5-[3-(4-bromo-phenyl)-3-cyclobutyl-propionyl]-1H-pyridin-2-one was reacted with iodomethane in the presence of potassium carbonate to give the title compound as a light yellow oil, MS (ESI⁺): m/z=374.1 [M+H]⁺.

Step 4: 5-{3-(4-Bromo-phenyl)-3-cyclobutyl-1-[(E)-hydroxyimino]-propyl}-1-methyl-1H-pyridin-2-one In analogy to example 151, step 3, 5-[3-(4-bromo-phenyl)-3-cyclobutyl-propionyl]-1-methyl-1H-pyridin-2-one was reacted with hydroxylamine hydrochloride in the presence of NaHCO₃ to give the title compound as a colorless solid, MS (ESI⁺): m/z=389.1 [M+H]⁺.

Example 180

5-[3-(4-Bromo-phenyl)-1-[(E)-hydroxyimino]-4-(4-trifluoromethoxy-phenyl)-butyl]-1-methyl-1H-pyridin-2-one

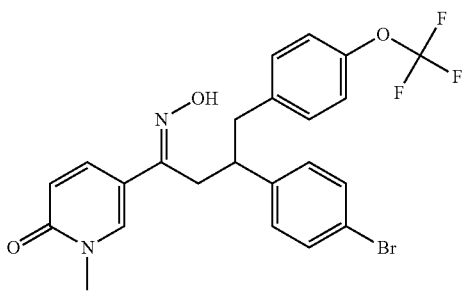 [SMILES: Cn1cc(/C(CC(Cc2ccc(OC(F)(F)F)cc2)c2ccc(Br)cc2)=N/O)ccc1=O]

In analogy to example 170, step 2, (E)-3-(4-bromo-phenyl)-1-(6-methoxy-pyridin-3-yl)-propenone (example 170, step 1) was reacted with 4-(trifluoromethoxy)benzylmagnesium bromide in the presence of CuI. The product of this reaction could not be obtained pure and was reacted in analogy to example 162, step 2, with concentrated aqueous HCl in 1,4-dioxane. The product of this reaction was reacted in analogy to example 161, step 1, with iodomethane in the presence of potassium carbonate. Finally, the product of this reaction was reacted in analogy to example 151, step 3 with hydroxylamine hydrochloride in the presence of NaHCO$_3$ to give the title compound as a colorless solid, MS (ESI$^+$): m/z=509.3 [M+H]$^+$.

Example 181

5-{3-(4-Bromo-phenyl)-1-[(E)-hydroxyimino]-3-o-tolyl-propyl}-1-isopropyl-1H-pyridin-2-one

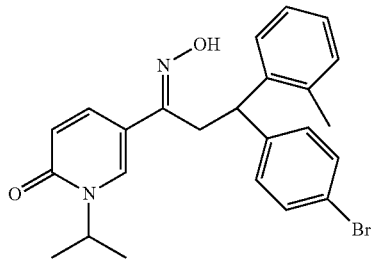 [SMILES: Cc1ccccc1C(C/C(=N\O)c1ccc(=O)n(C(C)C)c1)c1ccc(Br)cc1]

Step 1: 5-[3-(4-Bromo-phenyl)-3-o-tolyl-propionyl]-1-isopropyl-1H-pyridin-2-one

In analogy to example 161, step 1, 5-[3-(4-bromo-phenyl)-3-o-tolyl-propionyl]-1-methyl-1H-pyridin-2-one (example 162, step 3) was reacted with isopropyl iodide in the presence of potassium carbonate to give the title compound as a colorless foam, MS (ESI$^+$): m/z=438.2 [M+H]$^+$.

Step 2: 5-{3-(4-Bromo-phenyl)-1-[(E)-hydroxyimino]-3-o-tolyl-propyl}-1-isopropyl-1H-pyridin-2-one In analogy to example 151, step 3, 5-[3-(4-bromo-phenyl)-3-o-tolyl-propionyl]-1-isopropyl-1H-pyridin-2-one was reacted with hydroxylamine hydrochloride in the presence of NaHCO$_3$ to give the title compound as a colorless foam, MS (ESI$^+$): m/z=453.2 [M+H]$^+$.

Example 182

5-{3-(4-Bromo-phenyl)-1-[(Z)-hydroxyimino]-3-o-tolyl-propyl}-1-isopropyl-1H-pyridin-2-one

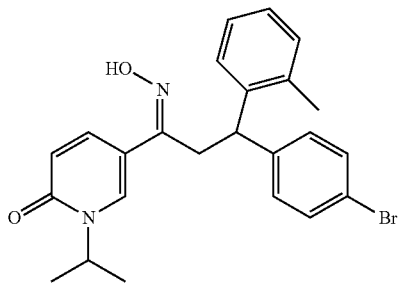

The title compound was obtained as a side product of example 181, step 2 as a colorless foam, MS (ESI$^+$): m/z=453.2 [M+H]$^+$.

Example 183

5-{3-(4-Bromo-phenyl)-1-[(E)-hydroxyimino]-3-o-tolyl-propyl}-1-cyclopropylmethyl-1H-pyridin-2-one

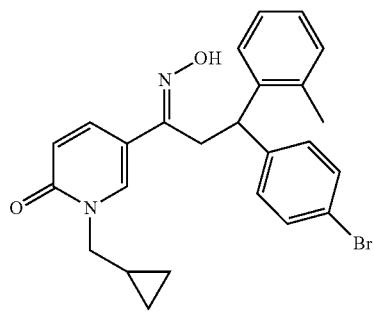

Step 1: 5-[3-(4-Bromo-phenyl)-3-o-tolyl-propionyl]-1-cyclopropylmethyl-1H-pyridin-2-one In analogy to example 161, step 1, 5-[3-(4-bromo-phenyl)-3-o-tolyl-propionyl]-1-methyl-1H-pyridin-2-one (example 162, step 3) was reacted with (bromomethyl)cyclopropane in the presence of potassium carbonate to give the title compound as a colorless foam, MS (ESI$^+$): m/z=450.2 [M+H]$^+$.

Step 2: 5-{3-(4-Bromo-phenyl)-1-[(E)-hydroxyimino]-3-o-tolyl-propyl}-1-cyclopropylmethyl-1H-pyridin-2-one In analogy to example 151, step 3, 5-[3-(4-bromo-phenyl)-3-o-tolyl-propionyl]-1-cyclopropylmethyl-1H-pyridin-2-one was reacted with hydroxylamine hydrochloride in the presence of NaHCO$_3$ to give the title compound as a colorless foam, MS (ESI$^+$): m/z=465.1 [M+H]$^+$.

Example 184

5-{3-(4-Bromo-phenyl)-1-[(Z)-hydroxyimino]-3-o-tolyl-propyl}-1-cyclopropylmethyl-1H-pyridin-2-one

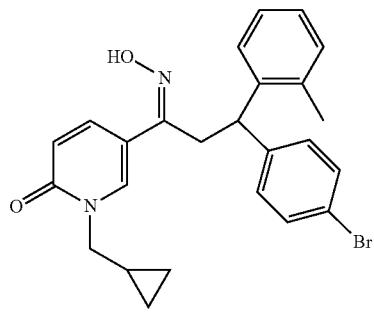

The title compound was obtained as a side product of example 183, step 2 as a colorless foam, MS (ESI$^+$): m/z=465.1 [M+H]$^+$.

Example 185

5-{3-(4-Bromo-phenyl)-1-[(E)-hydroxyimino]-3-o-tolyl-propyl}-1-(2-methoxy-ethyl)-1H-pyridin-2-one

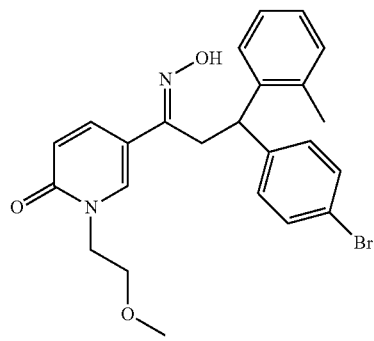

Step 1: 5-[3-(4-Bromo-phenyl)-3-o-tolyl-propionyl]-1-(2-methoxy-ethyl)-1H-pyridin-2-one In analogy to example 161, step 1, 5-[3-(4-bromo-phenyl)-3-otolyl-propionyl]-1-methyl-1H-pyridin-2-one (example 162, step 3) was reacted with 2-bromoethylmethylether in the presence of potassium carbonate to give the title compound as a colorless foam, MS (ESI$^+$): m/z=454.1 [M+H]$^+$.

Step 2: 5-{3-(4-Bromo-phenyl)-1-[(E)-hydroxyimino]-3-o-tolyl-propyl}-1-(2-methoxy-ethyl)-1H-pyridin-2-one In analogy to example 151, step 3, 5-[3-(4-bromo-phenyl)-3-o-tolyl-propionyl]-1-(2-methoxy-ethyl)-1H-pyridin-2-one was reacted with hydroxylamine hydrochloride in the presence of NaHCO$_3$ to give the title compound as a colorless amorphous solid, MS (ESI$^+$): m/z=469.2 [M+H]$^+$.

Example 186

2-(5-{3-(4-Bromo-phenyl)-1-[(E)-hydroxyimino]-3-o-tolyl-propyl}-2-oxo-2H-pyridin-1-yl)-acetamide

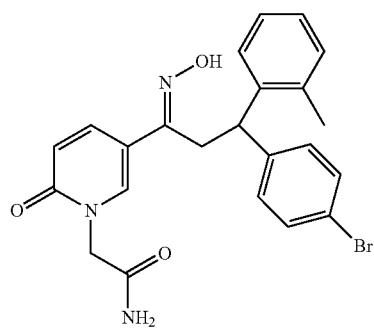

Step 1: 2-{5-[3-(4-Bromo-phenyl)-3-o-tolyl-propionyl]-2-oxo-2H-pyridin-1-yl}-acetamide In analogy to example 161, step 1, 5-[3-(4-bromo-phenyl)-3-o-tolyl-propionyl]-1-methyl-1H-pyridin-2-one (example 162, step 3) was reacted with iodoacetamide in the presence of potassium carbonate to give the title compound as a colorless foam, MS (ESI$^+$): m/z=453.1 [M+H]$^+$.

Step 2: 2-(5-{3-(4-Bromo-phenyl)-1-[(E)-hydroxyimino]-3-o-tolyl-propyl}-2-oxo-2H-pyridin-1-yl)-acetamide In analogy to example 151, step 3, 2-{5-[3-(4-bromo-phenyl)-3-o-tolyl-propionyl]-2-oxo-2H-pyridin-1-yl}-acetamide was reacted with hydroxylamine hydrochloride in the presence of NaHCO$_3$ to give the title compound containing less than 10% of the corresponding Z isomer as a colorless solid, MS (ESI$^-$): m/z=466.1 [M–H]$^-$.

Example 187

5-{3-(4-Bromo-phenyl)-1-[(E)-hydroxyimino]-3-o-tolyl-propyl}-1-cyclobutyl-1H-pyridin-2-one

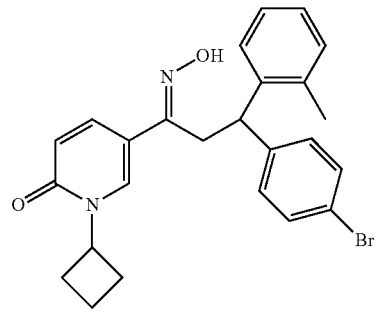

In analogy to example 161, step 1, 5-[3-(4-bromo-phenyl)-3-o-tolyl-propionyl]-1-methyl-1H-pyridin-2-one (example 162, step 3) was reacted with cyclobutylbromide in the presence of potassium carbonate. The product of this reaction was reacted in analogy to example 151, step 3 with hydroxylamine hydrochloride in the presence of NaHCO$_3$ to give the title compound as a colorless solid, MS (ESI$^+$): m/z=465.2 [M+H]$^+$.

Example 188

5-{3-(4-Bromo-phenyl)-1-[(Z)-hydroxyimino]-3-o-tolyl-propyl}-1-cyclobutyl-1H-pyridin-2-one

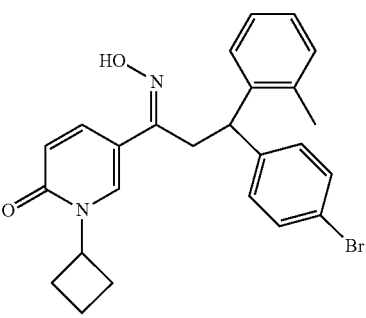

The title compound was obtained as a side product of example 187 as a colorless solid, MS (ESI$^+$): m/z=465.2 [M+H]$^+$.

Example 189

3-(5-{3-(4-Bromo-phenyl)-1-[(E)-hydroxyimino]-3-o-tolyl-propyl}-2-oxo-2H-pyridin-1-yl)-propionic acid

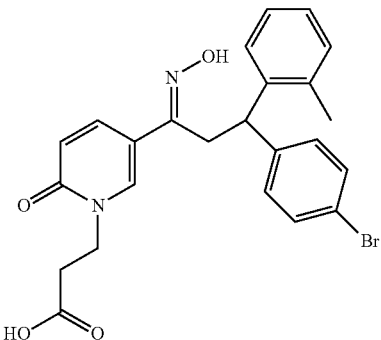

Step 1: 3-{5-[3-(4-Bromo-phenyl)-3-o-tolyl-propionyl]-2-oxo-2H-pyridin-1-yl}-propionic acid methyl ester In analogy to example 161, step 1, 5-[3-(4-bromo-phenyl)-3-o-tolyl-propionyl]-1-methyl-1H-pyridin-2-one (example 162, step 3) was reacted with methyl-3-bromopropionate in the presence of potassium carbonate to give the title compound as a colorless foam, MS (ESI$^+$): m/z=482.2 [M+H]$^+$.

Step 2: 3-{5-[3-(4-Bromo-phenyl)-3-o-tolyl-propionyl]-2-oxo-2H-pyridin-1-yl}-propionic acid In analogy to example 169, step 2, 3-{5-[3-(4-bromo-phenyl)-3-o-tolyl-propionyl]-2-oxo-2H-pyridin-1-yl}-propionic acid methyl ester was hydrolyzed to give the title compound as a colorless solid, MS (ESI$^-$): m/z=466.0 [M–H]$^-$.

Step 3: 3-(5-{3-(4-Bromo-phenyl)-1-[(E)-hydroxyimino]-3-o-tolyl-propyl}-2-oxo-2H-pyridin-1-yl)-propionic acid In analogy to example 151, step 3, 3-{5-[3-(4-bromo-phenyl)-3-o-tolyl-propionyl]-2-oxo-2H-pyridin-1-yl}-propionic acid was reacted with hydroxylamine hydrochloride in the presence of NaHCO$_3$ to give the title compound as a colorless solid, MS (ESI$^-$): m/z=481.0 [M–H]$^-$.

Example 190

4-(5-{3-(4-Bromo-phenyl)-1-[(E)-hydroxyimino]-3-o-tolyl-propyl}-2-oxo-2H-pyridin-1-yl)-butyric acid

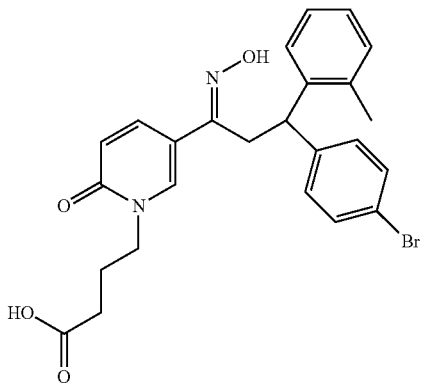

Step 1: 4-{5-[3-(4-Bromo-phenyl)-3-o-tolyl-propionyl]-2-oxo-2H-pyridin-1-yl}-butyric acid methyl ester In analogy to example 161, step 1, 5-[3-(4-bromo-phenyl)-3-o-tolyl-propionyl]-1-methyl-1H-pyridin-2-one (example 162, step 3) was reacted with methyl-4-bromobutyrate in the presence of potassium carbonate to give the title compound as a colorless foam, MS (ESI$^+$): m/z=496.2 [M+H]$^+$.

Step 2: 4-{5-[3-(4-Bromo-phenyl)-3-o-tolyl-propionyl]-2-oxo-2H-pyridin-1-yl}-butyric acid In analogy to example 169, step 2, 4-{5-[3-(4-bromo-phenyl)-3-o-tolyl-propionyl]-2-oxo-2H-pyridin-1-yl}-butyric acid methyl ester was hydrolyzed to give the title compound as a colorless solid, MS (ESI$^-$): m/z=480.1 [M–H]$^-$.

Step 3: 4-(5-{3-(4-Bromo-phenyl)-1-[(E)-hydroxyimino]-3-o-tolyl-propyl}-2-oxo-2H-pyridin-1-yl)-butyric acid In analogy to example 151, step 3, 4-{5-[3-(4-bromo-phenyl)-3-o-tolyl-propionyl]-2-oxo-2H-pyridin-1-yl}-butyric acid was reacted with hydroxylamine hydrochloride in the presence of NaHCO$_3$ to give the title compound as a colorless solid, MS (ESI$^-$): m/z=495.1 [M–H]$^-$.

Example 191

5-{3-(4-Bromo-2-fluoro-phenyl)-1-[(E)-hydroxyimino]-hexyl}-1-methyl-1H-pyridin-2-one

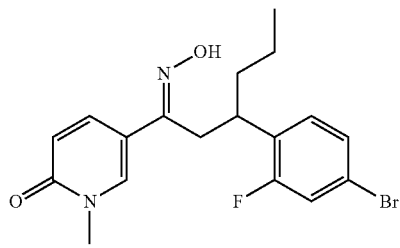 [SMILES: CCCC(C/C(=N\O)c1ccc(=O)n(C)c1)c1ccc(Br)cc1F]

Step 1: (E)-3-(4-Bromo-2-fluoro-phenyl)-1-(6-methoxy-pyridin-3-yl)-propenone In analogy to example 170, step 1, 5-acetyl-2-methoxypyridine was reacted with 4-bromo-2-fluorobenzaldehyde in the presence of potassium hydroxide to give the title compound as a colorless solid. MS (ESI$^+$): m/z=336.2 [M+H]$^+$.

Step 2: 3-(4-Bromo-2-fluoro-phenyl)-1-(6-methoxy-pyridin-3-yl)-hexan-1-one

In analogy to example 170, step 2, (E)-3-(4-bromo-2-fluoro-phenyl)-1-(6-methoxy-pyridin-3-yl)-propenone was reacted with n-propylmagnesium bromide in the presence of CuI to give the title compound as a light yellow oil, MS (ESI$^+$): m/z=380.0 [M+H]$^+$.

Step 3: 5-[3-(4-Bromo-2-fluoro-phenyl)-hexanoyl]-1H-pyridin-2-one

In analogy to example 162, step 2, 3-(4-bromo-2-fluoro-phenyl)-1-(6-methoxy-pyridin-3-yl)-hexan-1-one was reacted with concentrated aqueous HCl in 1,4-dioxane to give the title compound as a colorless foam, MS (ESI+): m/z=366.0 [M+H]+.

Step 4: 5-[3-(4-Bromo-2-fluoro-phenyl)-hexanoyl]-1-methyl-1H-pyridin-2-one

In analogy to example 161, step 1, 5-[3-(4-bromo-2-fluoro-phenyl)-hexanoyl]-1H-pyridin-2-one was reacted with iodomethane in the presence of potassium carbonate to give the title compound as a colorless oil, MS (ESI+): m/z=380.2 [M+H]+.

Step 5: 5-{3-(4-Bromo-2-fluoro-phenyl)-1-[(E)-hydroxyimino]-hexyl}-1-methyl-1H-pyridin-2-one In analogy to example 151, step 3, 5-[3-(4-bromo-2-fluoro-phenyl)-hexanoyl]-1-methyl-1H-pyridin-2-one was reacted with hydroxylamine hydrochloride in the presence of NaHCO₃ to give the title compound as a colorless solid, MS (ESI+): m/z=395.1 [M+H]+.

Example 192

5-{3-(4-Bromo-2-fluoro-phenyl)-3-cyclopentyl-1-[(E)-hydroxyimino]-propyl}-1-methyl-1H-pyridin-2-one

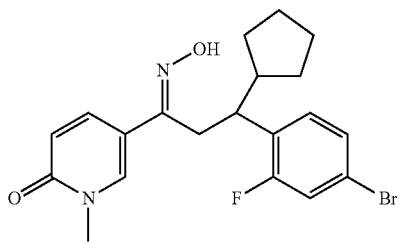 [SMILES: Cn1cc(/C(CC(c2ccc(Br)cc2F)C2CCCC2)=N/O)ccc1=O]

Step 1: 3-(4-Bromo-2-fluoro-phenyl)-3-cyclopentyl-1-(6-methoxy-pyridin-3-yl)-propan-1-one In analogy to example 170, step 2, (E)-3-(4-bromo-2-fluoro-phenyl)-1-(6-methoxy-pyridin-3-yl)-propenone (example 191, step 1) was reacted with cyclopentylmagnesium bromide in the presence of CuI to give the title compound as a light yellow oil, MS (ESI+): m/z=406.2 [M+H]+.

Step 2: 5-[3-(4-Bromo-2-fluoro-phenyl)-3-cyclopentyl-propionyl]-1H-pyridin-2-one In analogy to example 162, step 2, 3-(4-bromo-2-fluoro-phenyl)-3-cyclopentyl-1-(6-methoxy-pyridin-3-yl)-propan-1-one was reacted with concentrated aqueous HCl in 1,4-dioxane to give the title compound as a light yellow foam, MS (ESI+): m/z=392.2 [M+H]+.

Step 3: 5-[3-(4-Bromo-2-fluoro-phenyl)-3-cyclopentyl-propionyl]-1-methyl-1H-pyridin-2-one In analogy to example 161, step 1, 5-[3-(4-bromo-2-fluoro-phenyl)-3-cyclopentyl-propionyl]-1H-pyridin-2-one was reacted with iodomethane in the presence of potassium carbonate to give the title compound as a colorless oil, MS (ESI+): m/z=406.3 [M+H]+.

Step 4: 5-{3-(4-Bromo-2-fluoro-phenyl)-3-cyclopentyl-1-[(E)-hydroxyimino]-propyl}-1-methyl-1H-pyridin-2-one In analogy to example 151, step 3, 5-[3-(4-bromo-2-fluoro-phenyl)-3-cyclopentyl-propionyl]-1-methyl-1H-pyridin-2-one was reacted with hydroxylamine hydrochloride in the presence of NaHCO₃ to give the title compound as a colorless solid, MS (ESI+): m/z=421.1 [M+H]+.

Example 193

5-{3-(4-Bromo-2-fluoro-phenyl)-1-[(E)-hydroxyimino]-3-o-tolyl-propyl}-1-methyl-1H-pyridin-2-one

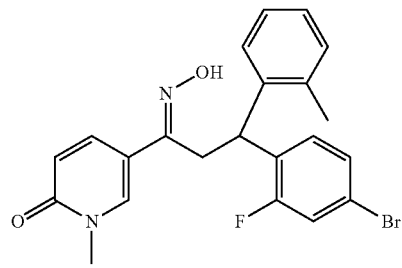 [SMILES: Cc1ccccc1C(C/C(=N\O)c1ccc(=O)n(C)c1)c1ccc(Br)cc1F]

Step 1: 3-(4-Bromo-2-fluoro-phenyl)-1-(6-methoxy-pyridin-3-yl)-3-o-tolyl-propan-1-one To a solution of o-tolylboronic acid (506 mg) in toluene (32 ml) was added diethylzinc (11.2 ml, 1 M solution in hexane) at 0° C. The mixture was warmed to room temperature and then stirred at 60° C. overnight. After cooling in an ice bath, a solution of (E)-3-(4-bromo-2-fluoro-phenyl)-1-(6-methoxy-pyridin-3-yl)-propenone (500 mg, example 191, step 1) in toluene (21 ml) was added. The reaction mixture was stirred at room temperature for 6 h. A saturated aqueous ammonium chloride solution was added and the mixture was extracted with ethyl acetate. The organic phase was dried (MgSO₄), filtered and concentrated to dryness. The product was purified by chromatography (SiO₂, cyclohexane/ethyl acetate 1:0 to 1:1) to give the title compound (392 mg) as a colorless oil, MS (ESI+): m/z=428.0 [M+H]+.

Step 2: 5-[3-(4-Bromo-2-fluoro-phenyl)-3-o-tolyl-propionyl]-1H-pyridin-2-one In analogy to example 162, step 2, 3-(4-bromo-2-fluoro-phenyl)-1-(6-methoxy-pyridin-3-yl)-3-o-tolyl-propan-1-one was reacted with concentrated aqueous HCl in 1,4-dioxane to give the title compound as a colorless foam, MS (ESI+): m/z=414.1 [M+H]+.

Step 3: 5-[3-(4-Bromo-2-fluoro-phenyl)-3-o-tolyl-propionyl]-1-methyl-1H-pyridin-2-one In analogy to example 161, step 1, 5-[3-(4-bromo-2-fluoro-phenyl)-3-o-tolyl-propionyl]-1H-pyridin-2-one was reacted with iodomethane in the presence of potassium carbonate to give the title compound as a colorless solid, MS (ESI+): m/z=428.0 [M+H]+.

Step 4: 5-{3-(4-Bromo-2-fluoro-phenyl)-1-[(E)-hydroxyimino]-3-o-tolyl-propyl}-1-methyl-1H-pyridin-2-one In analogy to example 151, step 3, 5-[3-(4-bromo-2-fluoro-phenyl)-3-o-tolyl-propionyl]-1-methyl-1H-pyridin-2-one was reacted with hydroxylamine hydrochloride in the presence of NaHCO$_3$ to give the title compound as a colorless solid, MS (ESI$^+$): m/z=443.1 [M+H]$^+$.

Example 194

3'-Fluoro-4'-[3-[(E)-hydroxyimino]-3-(1-methyl-6-oxo-1,6-dihydro-pyridin-3-yl)-1-o-tolyl-propyl]-biphenyl-4-carboxylic acid

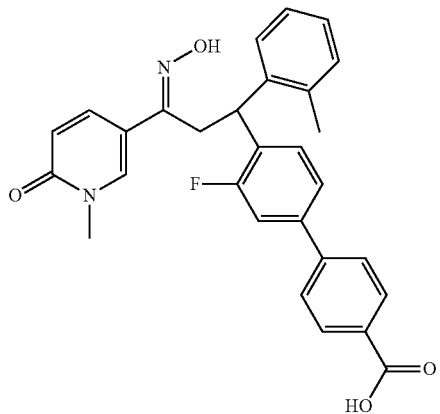

In analogy to example 166, step 1, 5-{3-(4-bromo-2-fluoro-phenyl)-1-[(E)-hydroxyimino]-3-o-tolyl-propyl}-1-methyl-1H-pyridin-2-one (example 193, step 4) was reacted with 4-carboxyphenylboronic acid in the presence of dichloro(1,1'-bis(diphenylphosphino)ferrocene)-palladium(II) dichloromethane adduct in a mixture of 1,4-dioxane, water and 2 M aqueous sodium carbonate solution to give the title compound as a light brown solid, MS (ESI$^+$): m/z=485.2 [M+H]$^+$.

Example 195

3,3'-Difluoro-4'-[3-[(E)-hydroxyimino]-3-(1-methyl-6-oxo-1,6-dihydro-pyridin-3-yl)-1-o-tolyl-propyl]-biphenyl-4-carboxylic acid methyl ester

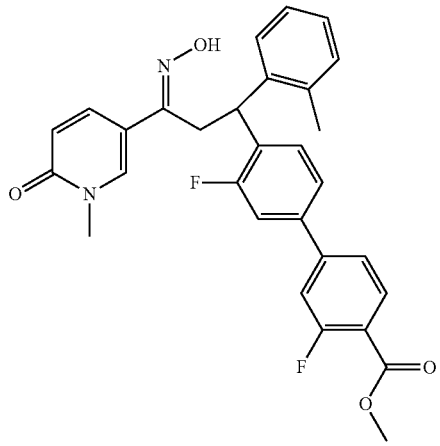

In analogy to example 166, step 1, 5-{3-(4-bromo-2-fluoro-phenyl)-1-[(E)-hydroxyimino]-3-o-tolyl-propyl}-1-methyl-1H-pyridin-2-one (example 193, step 4) was reacted with 3-fluoro-4-methoxycarbonylphenylboronic acid in the presence of dichloro(1,1'-bis(diphenylphosphino)-ferrocene) palladium(II) dichloromethane adduct in a mixture of 1,4-dioxane, water and 2 M aqueous sodium carbonate solution to give the title compound as a light brown solid, MS (ESI$^+$): m/z=517.4 [M+H]$^+$.

Example 196

3,3'-Difluoro-4'-[3-[(E)-hydroxyimino]-3-(1-methyl-6-oxo-1,6-dihydro-pyridin-3-yl)-1-o-tolyl-propyl]-biphenyl-4-carboxylic acid

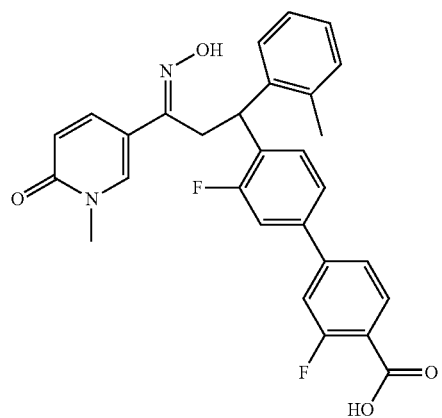

In analogy to example 169, step 2, 3,3'-difluoro-4'-[3-[(E)-hydroxyimino]-3-(1-methyl-6-oxo-1,6-dihydro-pyridin-3-yl)-1-o-tolyl-propyl]-biphenyl-4-carboxylic acid methyl ester was hydrolyzed to give the title compound as a light brown solid, MS (ESI$^-$): m/z=501.1 [M−H]$^-$.

Example 197

5-{3-(2-Chloro-phenyl)-3-cyclopentyl-1-[(E)-hydroxyimino]-propyl}-1-methyl-1H-pyridin-2-one

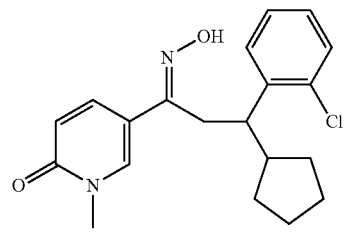 [SMILES: Cn1cc(/C(CC(c2ccccc2Cl)C2CCCC2)=N/O)ccc1=O]

Step 1: (E)-3-(2-Chloro-phenyl)-1-(6-methoxy-pyridin-3-yl)-propenone

In analogy to example 170, step 1, 5-acetyl-2-methoxypyridine was reacted with 2-chlorobenzaldehyde in the presence of potassium hydroxide to give the title compound as a light yellow solid, MS (ESI$^+$): m/z=274.2 [M+H]$^+$.

Step 2: 3-(2-Chloro-phenyl)-3-cyclopentyl-1-(6-methoxy-pyridin-3-yl)-propan-1-one In analogy to example 170, step 2, (E)-3-(2-chloro-phenyl)-1-(6-methoxy-pyridin-3-yl)-propenone was reacted with cyclopentylmagnesium bromide in the presence of CuI to give the title compound as a light yellow oil, MS (ESI$^+$): m/z=344.2 [M+H]$^+$.

Step 3: 5-[3-(2-Chloro-phenyl)-3-cyclopentyl-propionyl]-1H-pyridin-2-one

In analogy to example 162, step 2, 3-(2-chloro-phenyl)-3-cyclopentyl-1-(6-methoxy-pyridin-3-yl)-propan-1-one was reacted with concentrated aqueous HCl in 1,4-dioxane to give the title compound as a light yellow oil, MS (ESI$^+$): m/z=330.2 [M+H]$^+$.

Step 4: 5-[3-(2-Chloro-phenyl)-3-cyclopentyl-propionyl]-1-methyl-1H-pyridin-2-one In analogy to example 161, step 1, 5-[3-(2-chloro-phenyl)-3-cyclopentyl-propionyl]-1H-pyridin-2-one was reacted with iodomethane in the presence of potassium carbonate to give the title compound as a light yellow oil, MS (ESI$^+$): m/z=344.2 [M+H]$^+$.

Step 5: 5-{3-(2-Chloro-phenyl)-3-cyclopentyl-1-[(E)-hydroxyimino]-propyl}-1-methyl-1H-pyridin-2-one In analogy to example 151, step 3, 5-[3-(2-chloro-phenyl)-3-cyclopentyl-propionyl]-1-methyl-1H-pyridin-2-one was reacted with hydroxylamine hydrochloride in the presence of NaHCO$_3$ to give the title compound as a colorless solid, MS (ESI$^+$): m/z=359.2 [M+H]$^+$.

Example 198

4-[1-(2-Chloro-phenyl)-3-[(E)-hydroxyimino]-3-(1-methyl-6-oxo-1,6-dihydro-pyridin-3-yl)-propyl]-1,1-dimethyl-piperidinium iodide

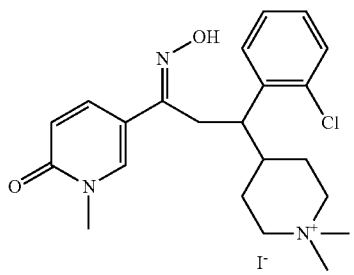 [SMILES: Cn1cc(/C(CC(c2ccccc2Cl)C2CC[N+](C)(C)CC2)=N/O)ccc1=O ; [I-]]

Step 1: 3-(2-Chloro-phenyl)-1-(6-methoxy-pyridin-3-yl)-3-(1-methyl-piperidin-4-yl)-propan-1-one In analogy to example 170, step 2, (E)-3-(2-chloro-phenyl)-1-(6-methoxy-pyridin-3-yl)-propenone (example 197, step 1) was reacted with the Grignard reagent prepared from 4-chloro-1-methyl-piperidine in the presence of CuI to give the title compound as a light yellow oil, MS (ESI$^+$): m/z=373.1 [M+H]$^+$.

Step 2: 5-[3-(2-Chloro-phenyl)-3-(1-methyl-piperidin-4-yl)-propionyl]-1H-pyridin-2-one In analogy to example 162, step 2, 3-(2-chloro-phenyl)-1-(6-methoxy-pyridin-3-yl)-3-(1-methyl-piperidin-4-yl)-propan-1-one was reacted with concentrated aqueous HCl in 1,4-dioxane to give the title compound as a colorless foam, MS (ESI$^+$): m/z=359.2 [M+H]$^+$.

Steps 3 and 4: 4-[1-(2-Chloro-phenyl)-3-[(E)-hydroxyimino]-3-(1-methyl-6-oxo-1,6-dihydro-pyridin-3-yl)-propyl]-1,1-dimethyl-piperidinium iodide In analogy to example 161, step 1, 5-[3-(2-chloro-phenyl)-3-(1-methyl-piperidin-4-yl)-propionyl]-1H-pyridin-2-one was reacted with iodomethane in the presence of potassium carbonate. The product of this reaction was reacted in analogy to example 151, step 3 with hydroxylamine hydrochloride in the presence of NaHCO$_3$ to give the title compound as a light yellow solid, MS (ESI$^-$): m/z=402.4 [M−I$^-$]$^+$.

Example 199

5-{3-(4-Bromo-phenyl)-1-[(E)-hydroxyimino]-3-o-tolyl-propyl}-1,4-dimethyl-1H-pyridin-2-one

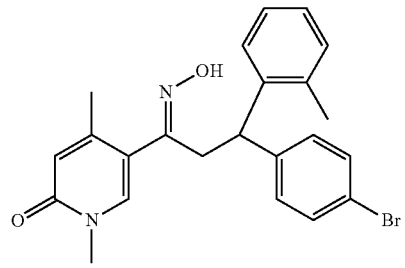 [SMILES: Cc1cc(=O)n(C)cc1/C(CC(c1ccc(Br)cc1)c1ccccc1C)=N/O]

Steps 1 and 2: 5-[3-(4-Bromo-phenyl)-3-o-tolyl-propionyl]-4-methyl-1H-pyridin-2-one In analogy to example 151, step 1, 5-bromo-2-methoxy-4-methylpyridine was reacted first with n-butyllithium and later with 3-(4-bromo-phenyl)-N-methoxy-N-methyl-3-o-tolyl-propionamide (example 74, step 4). The product of this reaction was reacted with concentrated aqueous HCl in 1,4-dioxane in analogy to example 162, step 2 to give the title compound as a colorless foam, MS (ESI$^+$): m/z=410.2 [M+H]$^+$.

Step 3: 5-[3-(4-Bromo-phenyl)-3-o-tolyl-propionyl]-1,4-dimethyl-1H-pyridin-2-one In analogy to example 161, step 1, 5-[3-(4-bromo-phenyl)-3-o-tolyl-propionyl]-4-methyl-1H-pyridin-2-one was reacted with iodomethane in the presence of potassium carbonate to give the title compound as a colorless foam, MS (ESI$^+$): m/z=424.2 [M+H]$^+$.

Step 4: 5-{3-(4-Bromo-phenyl)-1-[(E)-hydroxyimino]-3-o-tolyl-propyl}-1,4-dimethyl-1H-pyridin-2-one In analogy to example 151, step 3, 5-[3-(4-bromo-phenyl)-3-o-tolyl-propionyl]-1,4-dimethyl-1H-pyridin-2-one was reacted with hydroxylamine hydrochloride in the presence of NaHCO₃ to give the title compound as a colorless solid, MS (ESI⁺): m/z=439.2 [M+H]⁺.

Example 200

5-{3-(4-Bromo-phenyl)-1-[(Z)-hydroxyimino]-3-o-tolyl-propyl}-1,4-dimethyl-1H-pyridin-2-one

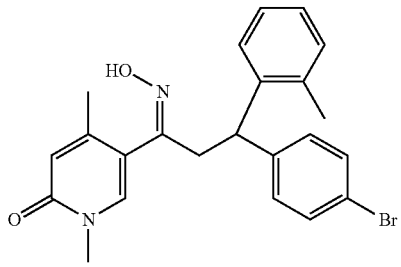 [SMILES: Cc1cc(=O)n(C)cc1/C(CC(c1ccc(Br)cc1)c1ccccc1C)=N\O]

The title compound was obtained as a side product of example 199, step 4 as a colorless solid, MS (ESI⁺): m/z=439.3 [M+H]⁺.

Example 201

4'-[3-[(E)-Hydroxyimino]-3-(1-methyl-6-oxo-1,6-dihydro-pyridin-3-yl)-1-o-tolyl-propyl]-biphenyl-3-carboxylic acid

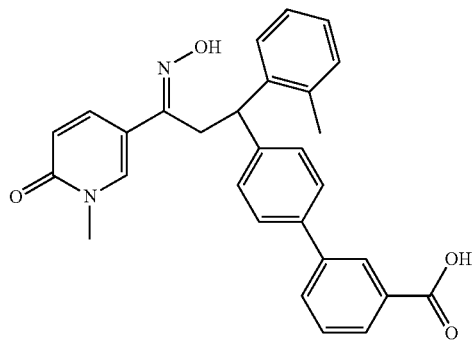

In analogy to example 166, step 1, 5-{3-(4-bromo-phenyl)-1-[(E)-hydroxyimino]-3-o-tolyl-propyl}-1-methyl-1H-pyridin-2-one (example 162, step 4) was reacted with 3-carboxyphenylboronic acid in the presence of dichloro(1,1'-bis(diphenylphosphino)ferrocene)-palladium(II) dichloromethane adduct in a mixture of 1,4-dioxane, water and 2 M aqueous sodium carbonate solution to give the title compound as a light yellow foam, MS (ESI⁻): m/z=465.1 [M−H]⁻.

Example 202

3-{4'-[3-[(E)-Hydroxyimino]-3-(1-methyl-6-oxo-1,6-dihydro-pyridin-3-yl)-1-o-tolyl-propyl]-biphenyl-4-yl}-propionic acid

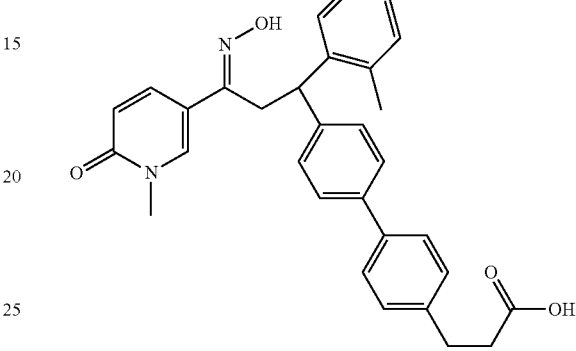

In analogy to example 166, step 1, 5-{3-(4-bromo-phenyl)-1-[(E)-hydroxyimino]-3-o-tolyl-propyl}-1-methyl-1H-pyridin-2-one (example 162, step 4) was reacted with 4-(2-carboxyethyl)benzeneboronic acid in the presence of dichloro(1,1'-bis(diphenylphosphino)-ferrocene)palladium(II) dichloromethane adduct in a mixture of 1,4-dioxane, water and 2 M aqueous sodium carbonate solution to give the title compound as a light yellow solid, MS (ESI⁺): m/z=493.2 [M−H]⁻.

Example 203

5-{3-(4-Bromo-phenyl)-3-(2-chloro-phenyl)-1-[(E)-hydroxyimino]-propyl}-1-methyl-1H-pyridin-2-one

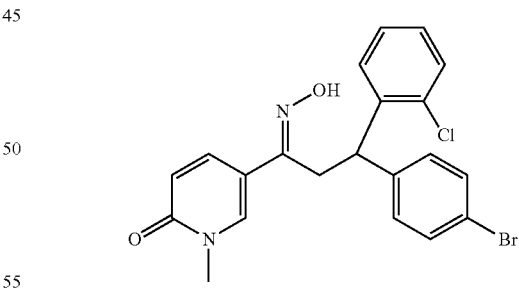

Step 1: 3-(4-Bromo-phenyl)-3-(2-chloro-phenyl)-1-(6-methoxy-pyridin-3-yl)-propan-1-one 4-Bromoboronic acid (220 mg) and chloro(1,5-cyclooctadiene)rhodium(I) dimer (29 mg) were placed in a flask under argon. Dioxane (1.9 ml), water (0.21 ml), (E)-3-(2-chloro-phenyl)-1-(6-methoxy-pyridin-3-yl)-propenone (200 mg, example 197, step 1) and NaHCO₃ (6.1 mg) were added and the mixture was stirred at 60° C. for 4.5 h. After cooling to room temperature, water was added and the mixture was extracted with ethyl acetate. The organic phase was dried (MgSO₄), filtered and concentrated to dryness. The product was purified by chromatography (SiO₂, cyclohexane/ethyl acetate 1:0 to 3:2) to give the title compound (331 mg, not totally pure) as a light yellow oil, MS (ESI⁺): m/z=430.1 [M+H]⁺.

Step 2: 5-[3-(4-Bromo-phenyl)-3-(2-chloro-phenyl)-propionyl]-1H-pyridin-2-one

In analogy to example 162, step 2, 3-(4-bromo-phenyl)-3-(2-chloro-phenyl)-1-(6-methoxy-pyridin-3-yl)-propan-1-one was reacted with concentrated aqueous HCl in 1,4-dioxane to give the title compound as an off-white foam, MS (ESI⁺): m/z=413.9 [M−H]⁻.

Step 3: 5-[3-(4-Bromo-phenyl)-3-(2-chloro-phenyl)-propionyl]-1-methyl-1H-pyridin-2-one In analogy to example 161, step 1, 5-[3-(4-bromo-phenyl)-3-(2-chloro-phenyl)-propionyl]-1H-pyridin-2-one was reacted with iodomethane in the presence of potassium carbonate to give the title compound as a colorless solid, MS (ESI⁻): m/z=429.9 [M−H]⁻.

Step 4: 5-{3-(4-Bromo-phenyl)-3-(2-chloro-phenyl)-1-[(E)-hydroxyimino]-propyl}-1-methyl-1H-pyridin-2-one In analogy to example 151, step 3, 5-[3-(4-bromo-phenyl)-3-(2-chloro-phenyl)-propionyl]-1-methyl-1H-pyridin-2-one was reacted with hydroxylamine hydrochloride in the presence of NaHCO₃ to give the title compound as a colorless foam, MS (ESI⁺): m/z=445.1 [M+H]⁺.

Example 204

4'-[1-(2-Chloro-phenyl)-3-[(E)-hydroxyimino]-3-(1-methyl-6-oxo-1,6-dihydro-pyridin-3-yl)-propyl]-biphenyl-4-carboxylic acid

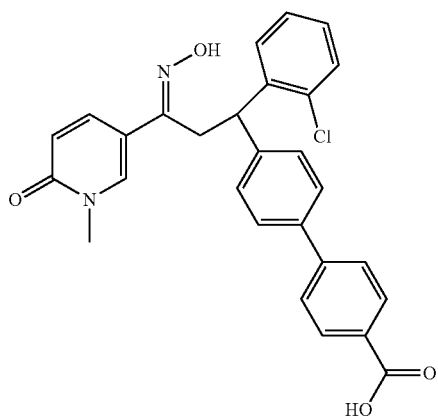

In analogy to example 166, step 1, 5-{3-(4-bromo-phenyl)-3-(2-chloro-phenyl)-1-[(E)-hydroxyimino]-propyl}-1-methyl-1H-pyridin-2-one (example 203, step 4) was reacted with 4-carboxyphenylboronic acid in the presence of dichloro (1,1'-bis(diphenylphosphino)ferrocene)-palladium(II) dichloromethane adduct in a mixture of 1,4-dioxane, water and 2 M aqueous sodium carbonate solution to give the title compound as an off-white solid, MS (ESI⁻): m/z=485.2 [M−H]⁻.

Example 205

4'-[1-(2-Chloro-phenyl)-3-[(E)-hydroxyimino]-3-(1-methyl-6-oxo-1,6-dihydro-pyridin-3-yl)-propyl]-3-fluoro-biphenyl-4-carboxylic acid methyl ester

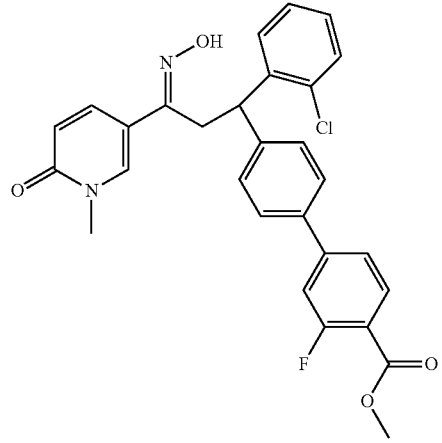

In analogy to example 166, step 1, 5-{3-(4-bromo-phenyl)-3-(2-chloro-phenyl)-1-[(E)-hydroxyimino]-propyl}-1-methyl-1H-pyridin-2-one (example 203, step 4) was reacted with 3-fluoro-4-methoxycarbonylphenylboronic acid in the presence of dichloro(1,1'-bis(diphenylphosphino)ferrocene) palladium(II) dichloromethane adduct in a mixture of 1,4-dioxane, water and 2 M aqueous sodium carbonate solution to give the title compound as a colorless foam, MS (ESI⁺): m/z=519.2 [M+H]⁺.

Example 206

4'-[1-(2-Chloro-phenyl)-3-[(E)-hydroxyimino]-3-(1-methyl-6-oxo-1,6-dihydro-pyridin-3-yl)-propyl]-3-fluoro-biphenyl-4-carboxylic acid

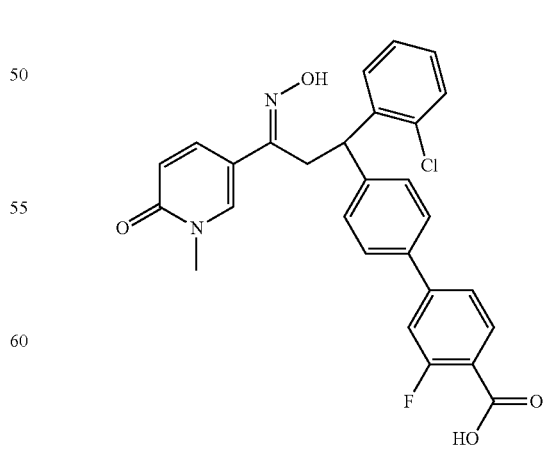

In analogy to example 169, step 2, 4'-[1-(2-chloro-phenyl)-3-[(E)-hydroxyimino]-3-(1-methyl-6-oxo-1,6-dihydro-pyridin-3-yl)-propyl]-3-fluoro-biphenyl-4-carboxylic acid methyl ester (example 205) was hydrolyzed to give the title compound as an off-white solid, MS (ESI−): m/z=503.0 [M−H]−.

Example 207

5-{1-[(E)-Hydroxyimino]-3-[4-(morpholine-4-carbonyl)-phenyl]-3-o-tolyl-propyl}-1-methyl-1H-pyridin-2-one

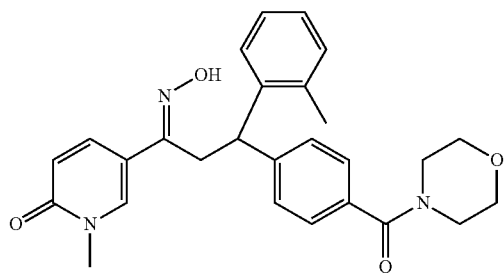 [SMILES: Cc1ccccc1C(C/C(=N\O)c1ccc(=O)n(C)c1)c1ccc(C(=O)N2CCOCC2)cc1]

Step 1: 4-[3-(1-Methyl-6-oxo-1,6-dihydro-pyridin-3-yl)-3-oxo-1-o-tolyl-propyl]-benzoic acid A mixture of 5-[3-(4-bromo-phenyl)-3-o-tolyl-propionyl]-1-methyl-1H-pyridin-2-one (150 mg, example 162, step 3), dichloro(1,1'-bis(diphenylphosphino)ferrocene)palladium (II) dichloromethane adduct (30 mg), NaHCO₃ (77 mg), ethyl acetate (4.5 ml) and water (1.5 ml) was treated with carbon monoxide at 150° C./80 bar for 20 h. After cooling to room temperature, the mixture was filtered. The filter cake was washed with ethyl acetate and with aqueous KHSO₄ solution. The combined filtrate was extracted with ethyl acetate. The organic phase was washed with brine, dried (MgSO₄), filtered and concentrated to dryness. The residue was taken up in 1 M aqueous NaOH solution and washed with diethyl ether. The aqueous phase was acidified using concentrated aqueous HCl and extracted with ethyl acetate. The organic phase was washed with brine, dried (MgSO₄), filtered and concentrated to dryness to give the title compound (129 mg) as a light brown solid, MS (ESI−): m/z=374.1 [M−H]−.

Step 2: 1-Methyl-5-{3-[4-(morpholine-4-carbonyl)-phenyl]-3-o-tolyl-propionyl}-1H-pyridin-2-one A mixture 4-[3-(1-methyl-6-oxo-1,6-dihydro-pyridin-3-yl)-3-oxo-1-o-tolyl-propyl]-benzoic acid (60 mg), morpholine (17 mg), benzotriazol-1-yloxytris(dimethylamino)phosphonium hexafluorophosphate (108 mg, BOP reagent) and N-ethyldiisopropylamine (62 mg) in tetrahydrofuran (0.6 ml) was stirred overnight at room temperature. The mixture was concentrated to dryness. The product was purified by chromatography (SiO₂, dichloromethane/methanol 1:0 to 9:1) to give the title compound (75 mg) as a colorless foam, MS (ESI+): m/z=445.4 [M+H]+.

Step 3: 5-{1-[(E)-Hydroxyimino]-3-[4-(morpholine-4-carbonyl)-phenyl]-3-o-tolyl-propyl}-1-methyl-1H-pyridin-2-one In analogy to example 151, step 3, 1-methyl-5-{3-[4-(morpholine-4-carbonyl)-phenyl]-3-o-tolyl-propionyl}-1H-pyridin-2-one was reacted with hydroxylamine hydrochloride in the presence of NaHCO₃ to give the title compound as a colorless solid, MS (ESI+): m/z=460.4 [M+H]+.

Example 208

N-(2-Hydroxy-ethyl)-4-[3-[(E)-hydroxyimino]-3-(1-methyl-6-oxo-1,6-dihydro-pyridin-3-yl)-1-o-tolyl-propyl]-benzamide

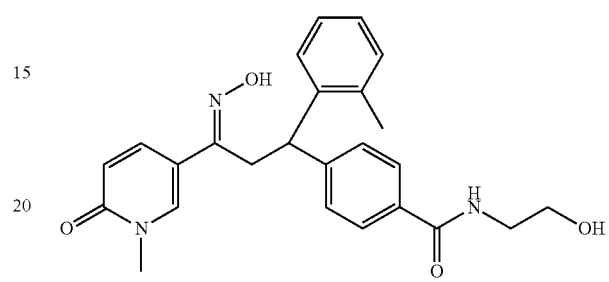

Step 1: N-(2-Hydroxy-ethyl)-4-[3-(1-methyl-6-oxo-1,6-dihydro-pyridin-3-yl)-3-oxo-1-o-tolyl-propyl]-benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with ethanolamine using BOP reagent in tetrahydrofuran to give the title compound as a colorless foam, MS (ESI+): m/z=419.3 [M+H]+.

Step 2: N-(2-Hydroxy-ethyl)-4-[3-[(E)-hydroxyimino]-3-(1-methyl-6-oxo-1,6-dihydro-pyridin-3-yl)-1-o-tolyl-propyl]-benzamide In analogy to example 151, step 3, N-(2-hydroxy-ethyl)-4-[3-(1-methyl-6-oxo-1,6-dihydro-pyridin-3-yl)-3-oxo-1-o-tolyl-propyl]-benzamide was reacted with hydroxylamine hydrochloride in the presence of NaHCO₃ to give the title compound as a colorless solid, MS (ESI+): m/z=434.4 [M+H]+.

Example 209

N-(2-Hydroxy-ethyl)-4-[3-[(E)-hydroxyimino]-3-(1-methyl-6-oxo-1,6-dihydro-pyridin-3-yl)-1-o-tolyl-propyl]-N-methyl-benzamide

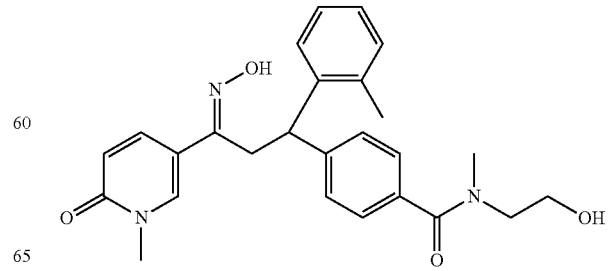

Step 1: N-(2-Hydroxy-ethyl)-N-methyl-4-[3-(1-methyl-6-oxo-1,6-dihydro-pyridin-3-yl)-3-oxo-1-o-tolyl-propyl]-benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with 2-(methylamino)ethanol using BOP reagent in tetrahydrofuran to give the title compound as an off-white foam, MS (ESI$^+$): m/z=433.4 [M+H]$^+$.

Step 2: N-(2-Hydroxy-ethyl)-4-[3-[(E)-hydroxyimino]-3-(1-methyl-6-oxo-1,6-dihydro-pyridin-3-yl)-1-o-tolyl-propyl]-N-methyl-benzamide In analogy to example 151, step 3, N-(2-hydroxy-ethyl)-N-methyl-4-[3-(1-methyl-6-oxo-1,6-dihydro-pyridin-3-yl)-3-oxo-1-o-tolyl-propyl]-benzamide was reacted with hydroxylamine hydrochloride in the presence of NaHCO$_3$ to give the title compound as a colorless solid, MS (ESI$^+$): m/z=448.2 [M+H]$^+$.

Example 210

(1-{4-[3-[(E)-Hydroxyimino]-3-(1-methyl-6-oxo-1,6-dihydro-pyridin-3-yl)-1-o-tolyl-propyl]-benzoyl}-piperidin-4-yl)-acetic acid

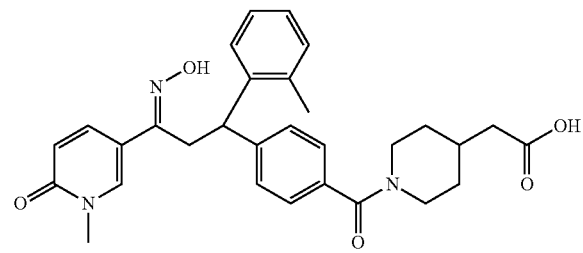 [SMILES: Cc1ccccc1C(C/C(=N\O)c1ccc(=O)n(C)c1)c1ccc(C(=O)N2CCC(CC(=O)O)CC2)cc1]

Step 1: (1-{4-[3-(1-Methyl-6-oxo-1,6-dihydro-pyridin-3-yl)-3-oxo-1-o-tolyl-propyl]-benzoyl}-piperidin-4-yl)-acetic acid ethyl ester In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with 2-(piperidin-4-yl)-acetic acid ethyl ester using BOP reagent in tetrahydrofuran to give the title compound as a light brown foam, MS (ESI$^+$): m/z=529.3 [M+H]$^+$.

Step 2: (1-{4-[3-(1-Methyl-6-oxo-1,6-dihydro-pyridin-3-yl)-3-oxo-1-o-tolyl-propyl]-benzoyl}-piperidin-4-yl)-acetic acid In analogy to example 169, step 2, (1-{4-[3-(1-methyl-6-oxo-1,6-dihydro-pyridin-3-yl)-3-oxo-1-o-tolyl-propyl]-benzoyl}-piperidin-4-yl)-acetic acid ethyl ester was hydrolyzed to give the title compound as a light brown foam, MS (ESI$^-$): m/z=499.3 [M–H]$^-$.

Step 3: (1-{4-[3-[(E)-Hydroxyimino]-3-(1-methyl-6-oxo-1,6-dihydro-pyridin-3-yl)-1-o-tolyl-propyl]-benzoyl}-piperidin-4-yl)-acetic acid In analogy to example 151, step 3, (1-{4-[3-(1-methyl-6-oxo-1,6-dihydro-pyridin-3-yl)-3-oxo-1-o-tolyl-propyl]-benzoyl}-piperidin-4-yl)-acetic acid was reacted with hydroxylamine hydrochloride in the presence of NaHCO$_3$ to give the title compound containing less than 10% of the corresponding Z isomer as a colorless solid, MS (ESI$^-$): m/z=514.4 [M–H]$^-$.

Example 211

({4-[3-[(E)-Hydroxyimino]-3-(1-methyl-6-oxo-1,6-dihydro-pyridin-3-yl)-1-o-tolyl-propyl]-benzoyl}-methyl-amino)-acetic acid

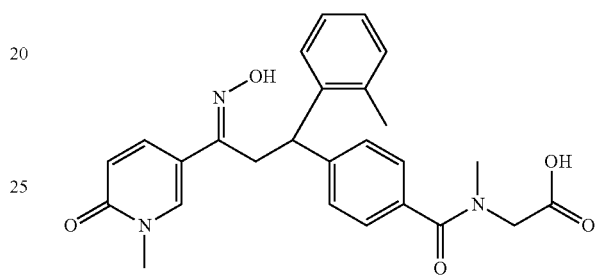

Step 1: (Methyl-{4-[3-(1-methyl-6-oxo-1,6-dihydro-pyridin-3-yl)-3-oxo-1-o-tolyl-propyl]-benzoyl}-amino)-acetic acid methyl ester In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with sarcosine methyl ester hydrochloride using BOP reagent in tetrahydrofuran to give the title compound as a colorless solid, MS (ESI$^+$): m/z=461.3 [M+H]$^+$ Step 2: (Methyl-{4-[3-(1-methyl-6-oxo-1,6-dihydro-pyridin-3-yl)-3-oxo-1-o-tolyl-propyl]-benzoyl}-amino)-acetic acid In analogy to example 169, step 2, (methyl-{4-[3-(1-methyl-6-oxo-1,6-dihydro-pyridin-3-yl)-3-oxo-1-o-tolyl-propyl]-benzoyl}-amino)-acetic acid methyl ester was hydrolyzed to give the title compound as a colorless solid, MS (ESI$^-$): m/z=445.3 [M–H]$^-$.

Step 3: ({4-[3-[(E)-Hydroxyimino]-3-(1-methyl-6-oxo-1,6-dihydro-pyridin-3-yl)-1-o-tolyl-propyl]-benzoyl}-methyl-amino)-acetic acid In analogy to example 151, step 3, (methyl-{4-[3-(1-methyl-6-oxo-1,6-dihydro-pyridin-3-yl)-3-oxo-1-o-tolyl-propyl]-benzoyl}-amino)-acetic acid was reacted with hydroxylamine hydrochloride in the presence of NaHCO$_3$ to give the title compound as a colorless solid, MS (ESI$^-$): m/z=460.3 [M–H]$^-$.

Example 212

4-{4-[3-[(E)-Hydroxyimino]-3-(1-methyl-6-oxo-1,6-dihydro-pyridin-3-yl)-1-o-tolyl-propyl]-benzoylamino}-butyric acid ethyl ester

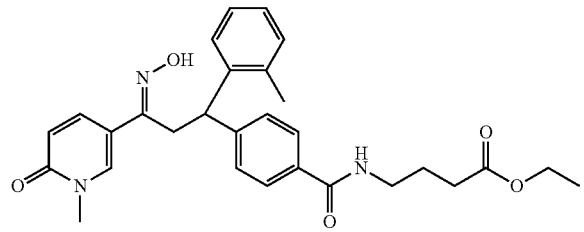 [SMILES: CCOC(=O)CCCNC(=O)c1ccc(C(C/C(=N\O)c2ccc(=O)n(C)c2)c2ccccc2C)cc1]

Step 1: 4-{4-[3-(1-Methyl-6-oxo-1,6-dihydro-pyridin-3-yl)-3-oxo-1-o-tolyl-propyl]-benzoylamino}-butyric acid methyl ester In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with methyl-4-aminobutyrate hydrochloride using BOP reagent in tetrahydrofuran to give the title compound as a colorless foam, MS (ESI$^+$): m/z=475.1 [M+H]$^+$.

Step 2: 4-{4-[3-(1-Methyl-6-oxo-1,6-dihydro-pyridin-3-yl)-3-oxo-1-o-tolyl-propyl]-benzoylamino}-butyric acid In analogy to example 169, step 2, 4-{4-[3-(1-methyl-6-oxo-1,6-dihydro-pyridin-3-yl)-3-oxo-1-o-tolyl-propyl]-benzoylamino}-butyric acid methyl ester was hydrolyzed to give the title compound as a light brown foam, MS (ESI$^-$): m/z=449.3 [M−H]$^-$.

Step 3: 4-{4-[3-[(E)-Hydroxyimino]-3-(1-methyl-6-oxo-1,6-dihydro-pyridin-3-yl)-1-o-tolyl-propyl]-benzoylamino}-butyric acid ethyl ester In analogy to example 151, step 3, 4-{4-[3-(1-methyl-6-oxo-1,6-dihydro-pyridin-3-yl)-3-oxo-1-o-tolyl-propyl]-benzoylamino}-butyric acid was reacted with hydroxylamine hydrochloride in ethanol and water in the presence of NaHCO$_3$ to give the title compound as a colorless solid, MS (ESI$^+$): m/z=504.3 [M+H]$^+$.

Example 213

4-{4-[3-[(E)-Hydroxyimino]-3-(1-methyl-6-oxo-1,6-dihydro-pyridin-3-yl)-1-o-tolyl-propyl]-benzoylamino}-butyric acid

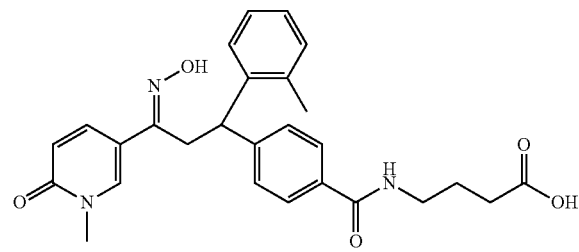 [SMILES: Cc1ccccc1C(C/C(=N\O)c1ccc(=O)n(C)c1)c1ccc(C(=O)NCCCC(=O)O)cc1]

In analogy to example 169, step 2, 4-{4-[3-[(E)-hydroxyimino]-3-(1-methyl-6-oxo-1,6-dihydro-pyridin-3-yl)-1-o-tolyl-propyl]-benzoylamino}-butyric acid ethyl ester (example 212, step 3) was hydrolyzed to give the title compound as a colorless solid, MS (ESI$^+$): m/z=474.3 [M+H]$^+$.

Example 214

3-{4-[3-[(E)-Hydroxyimino]-3-(1-methyl-6-oxo-1,6-dihydro-pyridin-3-yl)-1-o-tolyl-propyl]-benzoylamino}-propionic acid

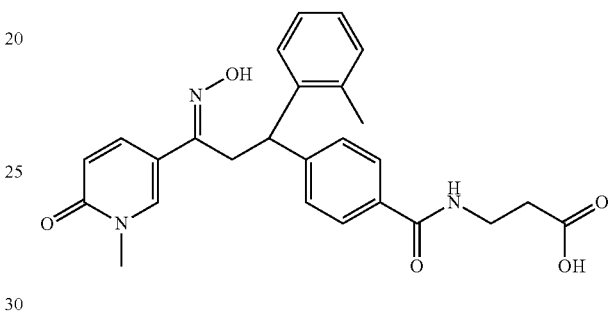

Step 1: 3-{4-[3-(1-Methyl-6-oxo-1,6-dihydro-pyridin-3-yl)-3-oxo-1-o-tolyl-propyl]-benzoylamino}-propionic acid ethyl ester In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with beta-alanine ethyl ester hydrochloride using BOP reagent in tetrahydrofuran to give the title compound as a light brown solid, MS (ESI$^+$): m/z=475.2 [M+H]$^+$.

Step 2: 3-{4-[3-(1-Methyl-6-oxo-1,6-dihydro-pyridin-3-yl)-3-oxo-1-o-tolyl-propyl]-benzoylamino}-propionic acid In analogy to example 169, step 2, 3-{4-[3-(1-methyl-6-oxo-1,6-dihydro-pyridin-3-yl)-3-oxo-1-o-tolyl-propyl]-benzoylamino}-propionic acid ethyl ester was hydrolyzed to give the title compound as a colorless solid, MS (ESI$^-$): m/z=445.3 [M−H]$^-$.

Step 3: 3-{4-[3-[(E)-Hydroxyimino]-3-(1-methyl-6-oxo-1,6-dihydro-pyridin-3-yl)-1-o-tolyl-propyl]-benzoylamino}-propionic acid In analogy to example 151, step 3, 3-{4-[3-(1-methyl-6-oxo-1,6-dihydro-pyridin-3-yl)-3-oxo-1-o-tolyl-propyl]-benzoylamino}-propionic acid was reacted with hydroxylamine hydrochloride in the presence of NaHCO$_3$ to give the title compound containing less than 10% of the corresponding Z isomer as a colorless solid, MS (ESI$^-$): m/z=460.3 [M−H]$^-$.

Example 215

{4-[3-[(E)-Hydroxyimino]-3-(1-methyl-6-oxo-1,6-dihydro-pyridin-3-yl)-1-o-tolyl-propyl]-benzoylamino}-acetic acid

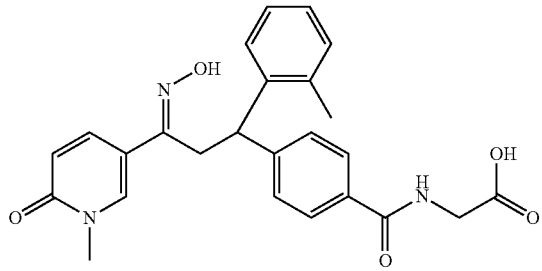 [SMILES: Cc1ccccc1C(C/C(=N\O)c1ccc(=O)n(C)c1)c1ccc(C(=O)NCC(=O)O)cc1]

Step 1: {4-[3-(1-Methyl-6-oxo-1,6-dihydro-pyridin-3-yl)-3-oxo-1-o-tolyl-propyl]-benzoylamino}-acetic acid methyl ester In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with glycine methyl ester hydrochloride using BOP reagent in tetrahydrofuran to give the title compound as a light yellow foam, MS (ESI$^+$): m/z=447.3 [M+H]$^+$.

Step 2: {4-[3-(1-Methyl-6-oxo-1,6-dihydro-pyridin-3-yl)-3-oxo-1-o-tolyl-propyl]-benzoylamino}-acetic acid In analogy to example 169, step 2, {4-[3-(1-methyl-6-oxo-1,6-dihydro-pyridin-3-yl)-3-oxo-1-o-tolyl-propyl]-benzoylamino}-acetic acid methyl ester was hydrolyzed to give the title compound as a colorless solid, MS (ESI$^-$): m/z=431.2 [M−H]$^-$.

Step 3: {4-[3-[(E)-Hydroxyimino]-3-(1-methyl-6-oxo-1,6-dihydro-pyridin-3-yl)-1-o-tolyl-propyl]-benzoylamino}-acetic acid In analogy to example 151, step 3, {4-[3-(1-methyl-6-oxo-1,6-dihydro-pyridin-3-yl)-3-oxo-1-o-tolyl-propyl]-benzoylamino}-acetic acid was reacted with hydroxylamine hydrochloride in the presence of NaHCO$_3$ to give the title compound containing less than 10% of the corresponding Z isomer as a colorless solid, MS (ESI$^-$): m/z=446.3 [M−H]$^-$.

Example 216

(E/Z)-4-(1-(2-Chlorophenyl)-3-(hydroxyimino)-3-(1-methyl-6-oxo-1,6-dihydropyridin-3-yl)propyl)-2-fluoro-N-(2-hydroxyethyl)benzamide

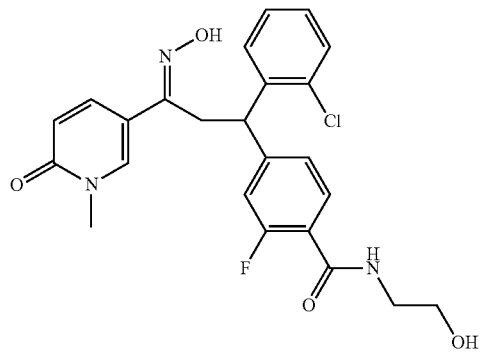 [SMILES: Cn1cc(/C(CC(c2ccc(C(=O)NCCO)c(F)c2)c2ccccc2Cl)=N/O)ccc1=O]

Step 1: Methyl 4-(1-(2-chlorophenyl)-3-(6-methoxypyridin-3-yl)-3-oxopropyl)-2-fluorobenzoate In analogy to example 203, step 1, (E)-3-(2-chloro-phenyl)-1-(6-methoxy-pyridin-3-yl)-propenone (example 197, step 1) was reacted with 3-fluoro-4-(methoxycarbonyl)phenylboronic acid in the presence of chloro(1,5-cyclooctadiene)rhodium(I) dimer and NaHCO$_3$ in dioxane and water at 60° C. to give the title compound as a colorless oil, MS (ESI$^+$): m/z=428.2 [M+H]$^+$.

Step 2: Methyl 4-(1-(2-chlorophenyl)-3-oxo-3-(6-oxo-1,6-dihydropyridin-3-yl)propyl)-2-fluorobenzoate In analogy to example 162, step 2, methyl 4-(1-(2-chlorophenyl)-3-(6-methoxypyridin-3-yl)-3-oxopropyl)-2-fluorobenzoate was reacted with concentrated aqueous HCl in 1,4-dioxane to give the title compound as a colorless foam, MS (ESI$^+$): m/z=414.2 [M+H]$^+$.

Step 3: Methyl 4-(1-(2-chlorophenyl)-3-(1-methyl-6-oxo-1,6-dihydropyridin-3-yl)-3-oxopropyl)-2-fluorobenzoate In analogy to example 161, step 1, methyl 4-(1-(2-chlorophenyl)-3-oxo-3-(6-oxo-1,6-dihydropyridin-3-yl)propyl)-2-fluorobenzoate was reacted with iodomethane in the presence of potassium carbonate to give the title compound as an off-white foam, MS (ESI$^+$): m/z=428.2 [M+H]$^+$.

Step 4: 4-(1-(2-Chlorophenyl)-3-(1-methyl-6-oxo-1,6-dihydropyridin-3-yl)-3-oxopropyl)-2-fluorobenzoic acid In analogy to example 169, step 2, methyl 4-(1-(2-chlorophenyl)-3-(1-methyl-6-oxo-1,6-dihydropyridin-3-yl)-3-oxopropyl)-2-fluorobenzoate was hydrolyzed to give the title compound as a colorless solid, MS (ESI$^-$): m/z=412.0 [M−H]$^-$.

Step 5: 4-(1-(2-Chlorophenyl)-3-(1-methyl-6-oxo-1,6-dihydropyridin-3-yl)-3-oxopropyl)-2-fluoro-N-(2-hydroxyethyl)benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid was coupled with 2-aminoethanol using BOP reagent in tetrahydrofuran to give the title compound as a colorless foam, MS (ESI$^+$): m/z=457.2 [M+H]$^+$.

Step 6: (E/Z)-4-(1-(2-Chlorophenyl)-3-(hydroxyimino)-3-(1-methyl-6-oxo-1,6-dihydropyridin-3-yl)propyl)-2-fluoro-N-(2-hydroxyethyl)benzamide In analogy to example 151, step 3, 4-(1-(2-chlorophenyl)-3-(1-methyl-6-oxo-1,6-dihydropyridin-3-yl)-3-oxopropyl)-2-fluoro-N-(2-hydroxyethyl)benzamide was reacted with hydroxylamine hydrochloride in the presence of NaHCO$_3$ to give the title compound as a colorless foam. The ratio of E/Z isomers was 4:1, MS (ESI$^+$): m/z=472.2 [M+H]$^+$.

Example 217

Trans-4-[1-(2-Chloro-phenyl)-3-[(E)-hydroxyimino]-3-(1-methyl-6-oxo-1,6-dihydro-pyridin-3-yl)-propyl]-2-fluoro-N-(4-hydroxy-cyclohexyl)-benzamide

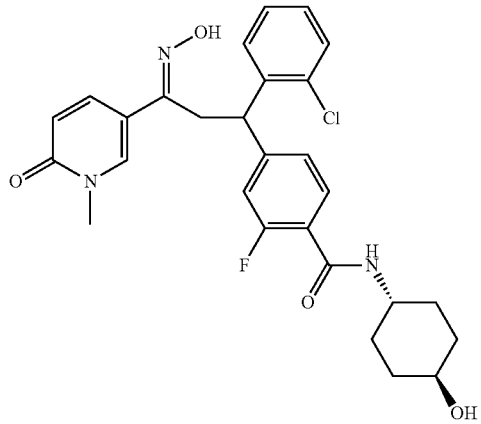 [SMILES: Cn1cc(/C(CC(c2ccc(C(=O)N[C@H]3CC[C@H](O)CC3)c(F)c2)c2ccccc2Cl)=N/O)ccc1=O]

Step 1: trans-4-[1-(2-Chloro-phenyl)-3-(1-methyl-6-oxo-1,6-dihydro-pyridin-3-yl)-3-oxo-propyl]-2-fluoro-N-(4-hydroxy-cyclohexyl)-benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with trans-4-aminocyclohexanol using BOP reagent in tetrahydrofuran to give the title compound as a colorless foam, MS (ESI+): m/z=511.3 [M+H]+.

Step 2: trans-4-[1-(2-Chloro-phenyl)-3-[(E)-hydroxyimino]-3-(1-methyl-6-oxo-1,6-dihydro-pyridin-3-yl)-propyl]-2-fluoro-N-(4-hydroxy-cyclohexyl)-benzamide In analogy to example 151, step 3, trans-4-[1-(2-chloro-phenyl)-3-(1-methyl-6-oxo-1,6-dihydro-pyridin-3-yl)-3-oxo-propyl]-2-fluoro-N-(4-hydroxy-cyclohexyl)-benzamide was reacted with hydroxylamine hydrochloride in the presence of NaHCO₃ to give the title compound as a colorless foam. The ratio of E/Z isomers was 87:13, MS (ESI+): m/z=526.4 [M+H]+.

Example 218

(E)-4-(1-(2-Chlorophenyl)-3-(hydroxyimino)-3-(1-methyl-6-oxo-1,6-dihydropyridin-3-yl)propyl)-2-fluoro-N-methyl-N-(1-methylpiperidin-4-yl)benzamide

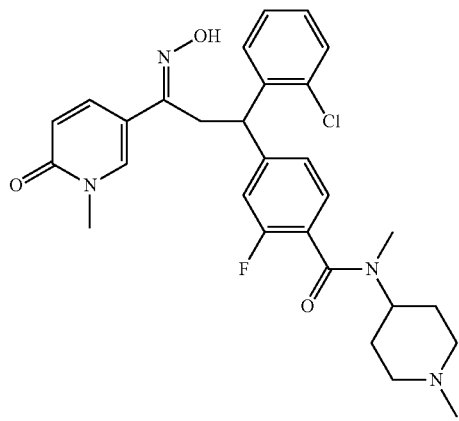 [SMILES: CN1CCC(N(C)C(=O)c2ccc(C(C/C(=N\O)c3ccc(=O)n(C)c3)c3ccccc3Cl)cc2F)CC1]

Step 1: 4-(1-(2-Chlorophenyl)-3-(1-methyl-6-oxo-1,6-dihydropyridin-3-yl)-3-oxopropyl)-2-fluoro-N-methyl-N-(1-methylpiperidin-4-yl)benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with 1-methyl-4-(methylamino)piperidine using BOP reagent in tetrahydrofuran to give the title compound as a colorless foam, MS (ESI+): m/z=524.3 [M+H]+.

Step 2: (E)-4-(1-(2-Chlorophenyl)-3-(hydroxyimino)-3-(1-methyl-6-oxo-1,6-dihydropyridin-3-yl)propyl)-2-fluoro-N-methyl-N-(1-methylpiperidin-4-yl)benzamide In analogy to example 151, step 3, 4-(1-(2-chlorophenyl)-3-(1-methyl-6-oxo-1,6-dihydropyridin-3-yl)-3-oxopropyl)-2-fluoro-N-methyl-N-(1-methylpiperidin-4-yl)benzamide was reacted with hydroxylamine hydrochloride in the presence of NaHCO₃ to give the title compound containing 10% of the corresponding Z isomer as a colorless foam, MS (ESI+): m/z=539.3 [M+H]+.

Example 219

(E)-4-(1-(2-Chlorophenyl)-3-(hydroxyimino)-3-(1-methyl-6-oxo-1,6-dihydropyridin-3-yl)propyl)-2-fluoro-N-(tetrahydro-2H-pyran-4-yl)benzamide

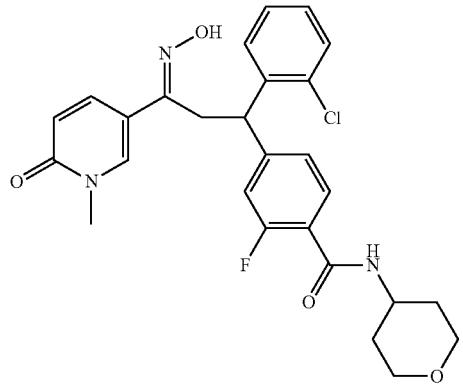 [SMILES: Cn1cc(/C(CC(c2ccc(C(=O)NC3CCOCC3)c(F)c2)c2ccccc2Cl)=N/O)ccc1=O]

Step 1: 4-(1-(2-Chlorophenyl)-3-(1-methyl-6-oxo-1,6-dihydropyridin-3-yl)-3-oxopropyl)-2-fluoro-N-(tetrahydro-2H-pyran-4-yl)benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with tetrahydro-2H-pyran-4-amine using BOP reagent in tetrahydrofuran to give the title compound as a colorless foam, MS (ESI+): m/z=497.2 [M+H]+.

Step 2: (E)-4-(1-(2-Chlorophenyl)-3-(hydroxyimino)-3-(1-methyl-6-oxo-1,6-dihydropyridin-3-yl)propyl)-2-fluoro-N-(tetrahydro-2H-pyran-4-yl)benzamide In analogy to example 151, step 3, 4-(1-(2-chlorophenyl)-3-(1-methyl-6-oxo-1,6-dihydropyridin-3-yl)-3-oxopropyl)-2-fluoro-N-(tetrahydro-2H-pyran-4-yl)benzamide was reacted with hydroxylamine hydrochloride in the presence of NaHCO₃ to give the title compound containing 4% of the corresponding Z isomer as a colorless foam, MS (ESI+): m/z=512.3 [M+H]+.

Example 220

(E)-4-(1-(2-Chlorophenyl)-3-(hydroxyimino)-3-(1-methyl-6-oxo-1,6-dihydropyridin-3-yl)propyl)-2-fluoro-N-(oxetan-3-yl)benzamide

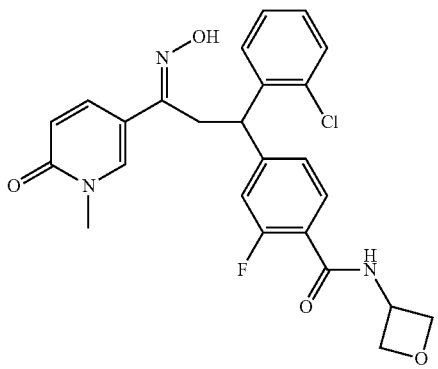 [SMILES: Cn1cc(/C(CC(c2ccc(C(=O)NC3COC3)c(F)c2)c2ccccc2Cl)=N/O)ccc1=O]

Step 1: 4-(1-(2-Chlorophenyl)-3-(1-methyl-6-oxo-1,6-dihydropyridin-3-yl)-3-oxopropyl)-2-fluoro-N-(oxetan-3-yl)benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with oxetan-3-amine using BOP reagent in tetrahydrofuran to give the title compound as a colorless foam, MS (ESI$^+$): m/z=469.2 [M+H]$^+$.

Step 2: (E)-4-(1-(2-Chlorophenyl)-3-(hydroxyimino)-3-(1-methyl-6-oxo-1,6-dihydropyridin-3-yl)propyl)-2-fluoro-N-oxetan-3-yl)-benzamide In analogy to example 151, step 3, 4-(1-(2-chlorophenyl)-3-(1-methyl-6-oxo-1,6-dihydropyridin-3-yl)-3-oxopropyl)-2-fluoro-N-(oxetan-3-yl)benzamide was reacted with hydroxylamine hydrochloride in the presence of NaHCO$_3$ to give the title compound containing 7% of the corresponding Z isomer as a colorless foam, MS (ESI$^+$): m/z=484.2 [M+H]$^+$.

Example 221

{3-Fluoro-4-[3-[(E)-hydroxyimino]-3-(1-methyl-6-oxo-1,6-dihydro-pyridin-3-yl)-1-o-tolyl-propyl]-phenoxy}-acetic acid

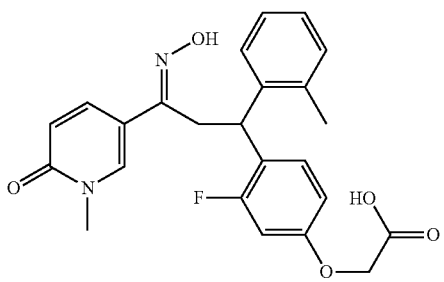 [SMILES: Cc1ccccc1C(C/C(=N\O)c1ccc(=O)n(C)c1)c1ccc(OCC(=O)O)cc1F]

Step 1: (E)-3-(2-Fluoro-4-methoxy-phenyl)-1-(6-methoxy-pyridin-3-yl)-propenone In analogy to example 170, step 1, 5-acetyl-2-methoxypyridine was reacted with 2-fluoro-4-methoxybenzaldehyde in the presence of potassium hydroxide to give the title compound as a yellow solid, MS (ESI$^+$): m/z=288.1 [M+H]$^+$.

Step 2: 3-(2-Fluoro-4-methoxy-phenyl)-1-(6-methoxy-pyridin-3-yl)-3-o-tolyl-propan-1-one In analogy to example 203, step 1, (E)-3-(2-fluoro-4-methoxy-phenyl)-1-(6-methoxy-pyridin-3-yl)-propenone was reacted with o-tolylboronic acid in the presence of chloro(1,5-cyclooctadiene)rhodium(I) dimer and NaHCO$_3$ in dioxane and water at 60° C. to give the title compound as a light yellow foam, MS (ESI$^+$): m/z=380.3 [M+H]$^+$.

Step 3: 5-[3-(2-Fluoro-4-methoxy-phenyl)-3-o-tolyl-propionyl]-1H-pyridin-2-one In analogy to example 162, step 2, 3-(2-fluoro-4-methoxy-phenyl)-1-(6-methoxy-pyridin-3-yl)-3-otolyl-propan-1-one was reacted with concentrated aqueous HCl in 1,4-dioxane to give the title compound as a colorless foam, MS (ESI$^+$): m/z=366.2 [M+H]$^+$.

Step 4: 5-[3-(2-Fluoro-4-methoxy-phenyl)-3-o-tolyl-propionyl]-1-methyl-1H-pyridin-2-one In analogy to example 161, step 1, 5-[3-(2-fluoro-4-methoxy-phenyl)-3-o-tolyl-propionyl]-1H-pyridin-2-one was reacted with iodomethane in the presence of potassium carbonate to give the title compound as a colorless solid, MS (ESI$^+$): m/z=380.3 [M+H]$^+$.

Step 5: 5-[3-(2-Fluoro-4-hydroxy-phenyl)-3-tolyl-propionyl]-1-methyl-1H-pyridin-2-one To a stirred solution of 5-[3-(2-fluoro-4-methoxy-phenyl)-3-o-tolyl-propionyl]-1-methyl-1H-pyridin-2-one (200 mg) in dichloromethane (5 ml) was added a 1 M solution of boron tribromide in dichloromethane (4.22 ml) at −78° C. The mixture was stirred at −78° C. for 30 min and at 0° C. for 30 min. An aqueous solution of NaHCO$_3$ was carefully added and the mixture was extracted with dichloromethane. The organic phase was dried (MgSO$_4$), filtered and concentrated to dryness. The product was purified by chromatography (SiO$_2$, dichloromethane/methanol 1:0 to 4:1) to give the title compound (157 mg) as a light brown foam, MS (ESI$^+$): m/z=366.2 [M+H]$^+$.

Step 6: {3-Fluoro-4-[3-(1-methyl-6-oxo-1,6-dihydro-pyridin-3-yl)-3-oxo-1-o-tolyl-propyl]-phenoxy}-acetic acid ethyl ester To a stirred solution of 5-[3-(2-fluoro-4-hydroxy-phenyl)-3-o-tolyl-propionyl]-1-methyl-1H-pyridin-2-one (71 mg) in N,N-dimethylacetamide (1.5 ml) were added ethylbromoacetate (36 mg) and cesium carbonate (69 mg). The mixture was stirred for 3.5 h at room temperature. Water was added and the mixture was extracted with diethyl ether. The organic phase was dried (MgSO$_4$), filtered and concentrated to dryness. The product was purified by chromatography (SiO$_2$, cyclohexane/ethyl acetate 1:0 to 0:1) to give the title compound (77 mg) as a light brown oil, MS (ESI$^+$): m/z=452.2 [M+H]$^+$.

Step 7: {3-Fluoro-4-[3-(1-methyl-6-oxo-1,6-dihydro-pyridin-3-yl)-3-oxo-1-o-tolyl-propyl]-phenoxy}-acetic acid In analogy to example 169, step 2, {3-fluoro-4-[3-(1-methyl-6-oxo-1,6-dihydro-pyridin-3-yl)-3-oxo-1-o-tolyl-propyl]-phenoxy}-acetic acid ethyl ester was hydrolyzed to give the title compound as a colorless foam, MS (ESI⁺): m/z=424.2 [M+H]⁺.

Step 8: {3-Fluoro-4-[3-[(E)-hydroxyimino]-3-(1-methyl-6-oxo-1,6-dihydro-pyridin-3-yl)-1-o-tolyl-propyl]-phenoxy}-acetic acid In analogy to example 151, step 3, {3-fluoro-4-[3-(1-methyl-6-oxo-1,6-dihydro-pyridin-3-yl)-3-oxo-1-o-tolyl-propyl]-phenoxy}-acetic acid was reacted with hydroxylamine hydrochloride in the presence of NaHCO₃ to give the title compound containing less than 10% of the corresponding Z isomer as a light brown solid, MS (ESI⁺): m/z=439.2 [M+H]⁺.

Example 222

2-Fluoro-4-{3-fluoro-4-[3-[(E)-hydroxyimino]-3-(1-methyl-6-oxo-1,6-dihydro-pyridin-3-yl)-1-o-tolyl-propyl]-phenoxy}-benzoic acid

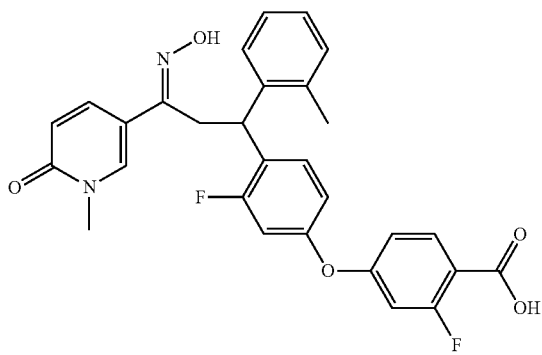 [SMILES: Cc1ccccc1C(C/C(=N\O)c1ccc(=O)n(C)c1)c1ccc(Oc2ccc(C(=O)O)c(F)c2)cc1F]

Step 1: 2-Fluoro-4-{3-fluoro-4-[3-(1-methyl-6-oxo-1,6-dihydro-pyridin-3-yl)-3-oxo-1-o-tolyl-propyl]-phenoxy}-benzoic acid methyl ester To a solution of 5-[3-(2-fluoro-4-hydroxy-phenyl)-3-o-tolyl-propionyl]-1-methyl-1H-pyridin-2-one (50 mg, example 221, step 5) in dichloromethane (1.2 ml) were added 3-fluoro-4-methoxycarbonylphenylboronic acid (83 mg), copper (II) acetate (75 mg), pyridine (54 mg) and molecular sieve. The mixture was stirred under an air atmosphere with exclusion of moisture overnight. The mixture was filtered and the filtrate was washed with 1 M HCl. The organic phase was dried (MgSO₄), filtered and concentrated to dryness. The product was purified by chromatography (SiO₂, cyclohexane/ethyl acetate 1:0 to 1:1) to give the title compound (35 mg) as a colorless foam, MS (ESI⁺): m/z=518.3 [M+H]⁺.

Step 2: 2-Fluoro-4-{3-fluoro-4-[3-(1-methyl-6-oxo-1,6-dihydro-pyridin-3-yl)-3-oxo-1-o-tolyl-propyl]-phenoxy}-benzoic acid In analogy to example 169, step 2, 2-fluoro-4-{3-fluoro-4-[3-(1-methyl-6-oxo-1,6-dihydro-pyridin-3-yl)-3-oxo-1-o-tolyl-propyl]-phenoxy}-benzoic acid methyl ester was hydrolyzed to give the title compound as a colorless solid, MS (ESI⁺): m/z=504.2 [M+H]⁺.

Step 3: 2-Fluoro-4-{3-fluoro-4-[3-[(E)-hydroxyimino]-3-(1-methyl-6-oxo-1,6-dihydro-pyridin-3-yl)-1-o-tolyl-propyl]-phenoxy}-benzoic acid In analogy to example 151, step 3, 2-fluoro-4-{3-fluoro-4-[3-(1-methyl-6-oxo-1,6-dihydro-pyridin-3-yl)-3-oxo-1-o-tolyl-propyl]-phenoxy}-benzoic acid was reacted with hydroxylamine hydrochloride in the presence of NaHCO₃ to give the title compound as a colorless solid, MS (ESI⁺): m/z=519.2 [M+H]⁺.

Example 223

5-{(R)-3-(4-Bromo-phenyl)-1-[(E)-hydroxyimino]-3-o-tolyl-propyl}-1-methyl-1H-pyridin-2-one

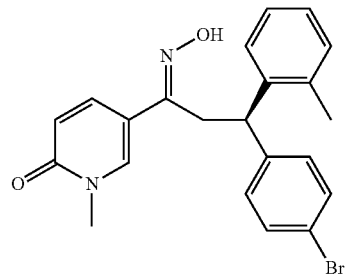 [SMILES: Cc1ccccc1[C@H](C/C(=N\O)c1ccc(=O)n(C)c1)c1ccc(Br)cc1]

Step 1: (R)-3-(4-Bromophenyl)-1-(6-methoxypyridin-3-yl)-3-o-tolylpropan-1-one

In analogy to example 151, step 1, 5-bromo-2-methoxypyridine was reacted first with n-butyllithium and later with (R)-3-(4-bromo-phenyl)-N-methoxy-N-methyl-3-o-tolyl-propionamide (example 142, step 1) to give the title compound as a colorless oil, MS (ESI⁺): m/z=410.1 [M+H]⁺.

Step 2: 5-[(R)-3-(4-Bromo-phenyl)-3-o-tolyl-propionyl]-1H-pyridin-2-one

In analogy to example 162, step 2, (R)-3-(4-bromophenyl)-1-(6-methoxypyridin-3-yl)-3-o-tolyl-propan-1-one was reacted with concentrated aqueous HCl in 1,4-dioxane to give the title compound as a colorless solid, MS (ESI⁺): m/z=396.0 [M+H]⁺.

Step 3: 5-[(R)-3-(4-Bromo-phenyl)-3-o-tolyl-propionyl]-1-methyl-1H-pyridin-2-one In analogy to example 161, step 1, 5-[(R)-3-(4-bromophenyl)-3-o-tolyl-propionyl]-1H-pyridin-2-one was reacted with iodomethane in the presence of potassium carbonate to give the title compound as a colorless solid, MS (ESI⁺): m/z=410.2 [M+H]⁺.

Step 4: 5-{(R)-3-(4-Bromo-phenyl)-1-[(E)-hydroxyimino]-3-o-tolyl-propyl}-1-methyl-1H-pyridin-2-one In analogy to example 151, step 3, 5-[(R)-3-(4-bromophenyl)-3-o-tolyl-propionyl]-1-methyl-1H-pyridin-2-one was reacted with hydroxylamine hydrochloride in the pres-

Example 224

(E)-5-(3-(4-Bromophenyl)-3-(4-fluoro-2-methylphenyl)-1-(hydroxyimino)propyl)-1-methylpyridin-2(1H)-one

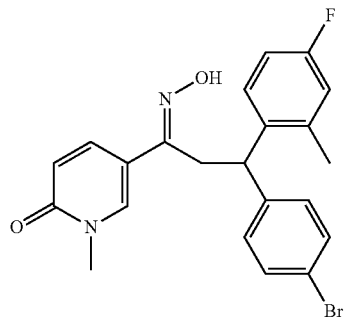 [SMILES: Cc1cc(F)ccc1C(C/C(=N\O)c1ccc(=O)n(C)c1)c1ccc(Br)cc1]

Step 1: 3-(4-Bromophenyl)-3-(4-fluoro-2-methylphenyl)-1-(6-methoxypyridin-3-yl)propan-1-one In analogy to example 151, step 1, 5-bromo-2-methoxypyridine was reacted first with n-butyllithium and later with 3-(4-bromophenyl)-3-(4-fluoro-2-methylphenyl)-N-methoxy-N-methylpropanamide (example 141, step 3) to give the title compound as a light yellow oil, MS (ESI$^+$): m/z=430.06 [M+H]$^+$.

Step 2: 5-(3-(4-Bromophenyl)-3-(4-fluoro-2-methylphenyl)propanoyl)pyridin-2(1H)-one In analogy to example 162, step 2, 3-(4-bromophenyl)-3-(4-fluoro-2-methylphenyl)-1-(6-methoxypyridin-3-yl)propan-1-one was reacted with concentrated aqueous HCl in 1,4-dioxane to give the title compound as a colorless solid, MS (ESI$^+$): m/z=416.05 [M+H]$^+$.

Step 3: 5-(3-(4-Bromophenyl)-3-(4-fluoro-2-methylphenyl)propanoyl)-1-methylpyridin-2(1H)-one In analogy to example 161, step 1, 5-(3-(4-bomophenyl)-3-(4-fluoro-2-methylphenyl)propanoyl)pyridin-2(1H)-one was reacted with iodomethane in the presence of potassium carbonate to give the title compound as a colorless solid, MS (ESI$^+$): m/z=428.07 [M+H]$^+$.

Step 4: (E)-5-(3-(4-Bromophenyl)-3-(4-fluoro-2-methylphenyl)-1-(hydroxyimino)propyl)-1-methylpyridin-2(1H)-one In analogy to example 151, step 3, 5-(3-(4-bromophenyl)-3-(4-fluoro-2-methylphenyl)propanoyl)-1-methylpyridin-2(1H)-one was reacted with hydroxylamine hydrochloride in the presence of NaHCO$_3$ to give the title compound containing 10% of the corresponding Z isomer as a colorless foam, MS (ESI$^+$): m/z=443.08 [M+H]$^+$.

Example 225

(E)-4'-(1-(4-Fluoro-2-methylphenyl)-3-(hydroxyimino)-3-(1-methyl-6-oxo-1,6-dihydropyridin-3-yl)propyl)biphenyl-4-carboxylic acid

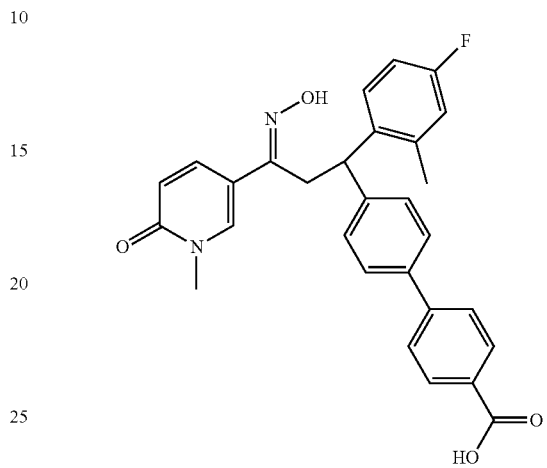

In analogy to example 166, step 1, (E)-5-(3-(4-bromophenyl)-3-(4-fluoro-2-methylphenyl)-1-(hydroxyimino)propyl)-1-methylpyridin-2(1H)-one (example 224, step 4) was reacted with 4-carboxyphenylboronic acid in the presence of dichloro(1,1'-bis(diphenylphosphino)ferrocene) palladium(II) dichloromethane adduct in a mixture of 1,4-dioxane, water and 2 M aqueous sodium carbonate solution to give the title compound containing 10% of the corresponding Z isomer as a colorless solid, MS (ESI$^+$): m/z=485.19 [M+H]$^+$.

Example 226

5-{3-(4-Bromo-phenyl)-3-(4-chloro-2-methyl-phenyl)-1-[(E)-hydroxyimino]-propyl}-1-methyl-1H-pyridin-2-one

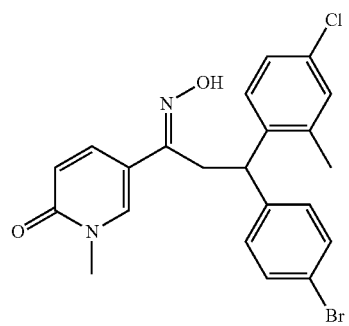 [SMILES: Cc1cc(Cl)ccc1C(C/C(=N\O)c1ccc(=O)n(C)c1)c1ccc(Br)cc1]

Step 1: 3-(4-Bromophenyl)-3-(4-chloro-2-methylphenyl)-1-(6-methoxypyridin-3-yl)propan-1-one In analogy to example 151, step 1, 5-bromo-2-methoxypyridine was reacted first with n-butyllithium and later with 3-(4-bromophenyl)-3-(4-chloro-2-methylphenyl)-N-methoxy-N-methylpropanamide (example 138, step 3) to give the title compound as a light yellow oil, MS (ESI$^+$): m/z=446.03 [M+H]$^+$.

Step 2: 5-(3-(4-Bromophenyl)-3-(4-chloro-2-methylphenyl)propanoyl)pyridin-2(1H)-one In analogy to example 162, step 2, 3-(4-bromophenyl)-3-(4-chloro-2-methylphenyl)-1-(6-methoxypyridin-3-yl)propan-1-one was reacted with concentrated aqueous HCl in 1,4-dioxane to give the title compound as a colorless solid, MS (ESI⁺)=432,019 [M+H]⁺.

Step 3: 5-(3-(4-Bromophenyl)-3-(4-chloro-2-methylphenyl)propanoyl)-1-methylpyridin-2(1H)-one In analogy to example 161, step 1, 5-(3-(4-bromophenyl)-3-(4-chloro-2-methylphenyl)propanoyl)pyridin-2(1H)-one was reacted with iodomethane in the presence of potassium carbonate to give the title compound as a colorless solid, MS (ESI⁺): m/z=446.03 [M+H]⁺.

Step 4: 5-{3-(4-Bromo-phenyl)-3-(4-chloro-2-methyl-phenyl)-1-[(E)-hydroxyimino]-propyl}-1-methyl-1H-pyridin-2-one In analogy to example 151, step 3, 5-(3-(4-bromophenyl)-3-(4-chloro-2-methylphenyl)propanoyl)-1-methylpyridin-2(1H)-one was reacted with hydroxylamine hydrochloride in the presence of NaHCO₃ to give the title compound containing 10% of the corresponding Z isomer as a colorless foam, MS (ESI⁺): m/z=461.05 [M+H]⁺.

Example 227

(E)-4'-(1-(4-Chloro-2-methylphenyl)-3-(hydroxyimino)-3-(1-methyl-6-oxo-1,6-dihydropyridin-3-yl)propyl)biphenyl-4-carboxylic acid

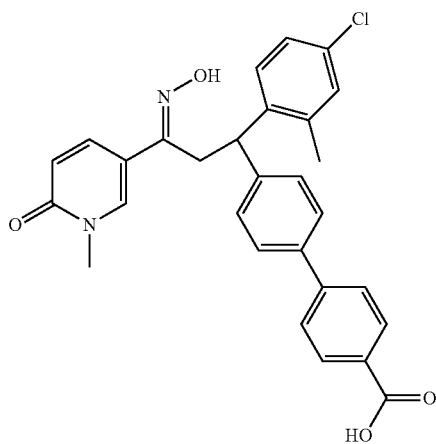 [SMILES: Cc1cc(Cl)ccc1C(C/C(=N\O)c1ccc(=O)n(C)c1)c1ccc(-c2ccc(C(=O)O)cc2)cc1]

In analogy to example 166, step 1, 5-{3-(4-bromo-phenyl)-3-(4-chloro-2-methyl-phenyl)-1-[(E)-hydroxyimino]-propyl}-1-methyl-1H-pyridin-2-one (example 226, step 4) was reacted with 4-carboxyphenylboronic acid in the presence of dichloro(1,1'-bis(diphenylphosphino) ferrocene)palladium (II) dichloromethane adduct in a mixture of 1,4-dioxane, water and 2 M aqueous sodium carbonate solution to give the title compound containing 10% of the corresponding Z isomer as a light brown solid, MS (ESI⁺): m/z=501.16 [M+H]⁺.

Example 228

(E)-methyl 2-(4'-(1-(4-chloro-2-methylphenyl)-3-(hydroxyimino)-3-(1-methyl-6-oxo-1,6-dihydropyridin-3-yl)propyl)biphenyl-4-ylcarboxamido)acetate

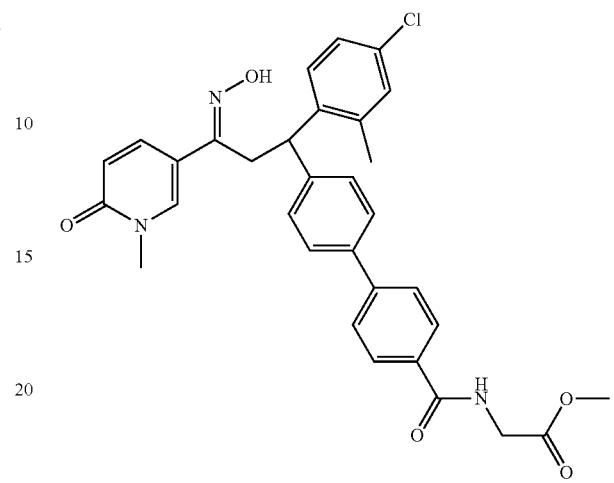

To a solution of (E)-4'-(1-(4-chloro-2-methylphenyl)-3-(hydroxyimino)-3-(1-methyl-6-oxo-1,6-dihydropyridin-3-yl)propyl)biphenyl-4-carboxylic acid (0.15 g, example 227) in dimethylformamide (2 ml) were added HATU (125 mg), diisopropylethylamine (155 mg) and glycine-methylester hydrochloride (41.4 mg) and the reaction mixture was stirred for 3.5 h at room temperature. The reaction mixture was poured on water and ethyl acetate and the layers were separated. The aqeos layer was extracted with 2 times with ethyl acetate. The organic layers were washed 2× with water and once with brine, dried over MgSO₄, filtered, treated with silica gel and evaporated. The compound was purified by two silica gel chromatographies on a 20 g and on a 10 g column using a MPLC system eluting with a gradient of dichloromethane:methanol (100:0 to 90:10) to give the title compound (0.122 g) as a light brown foam, MS (ESI⁺): m/z=572.19 [M+H]⁺.

Example 229

(E)-2-(4'-(1-(4-chloro-2-methylphenyl)-3-(hydroxyimino)-3-(1-methyl-6-oxo-1,6-dihydropyridin-3-yl)propyl)biphenyl-4-ylcarboxamido)acetic acid

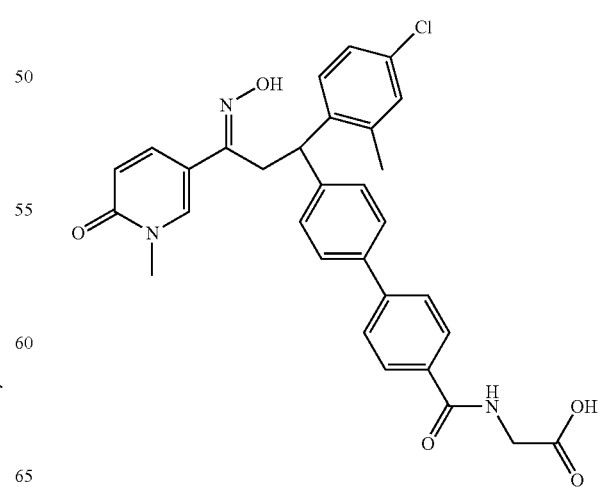

To a solution of (E)-methyl 2-(4'-(1-(4-chloro-2-methylphenyl)-3-(hydroxyimino)-3-(1-methyl-6-oxo-1,6-dihydropyridin-3-yl)propyl)biphenyl-4-ylcarboxamido)acetate (0.1 g, example 228) in dioxane (1 ml) and water (1 ml) was added lithium hydroxide monohydrate (9.17 mg) and the clear solution was stirred at room temperature for 3.5 h. The solution was then evaporated and diluted with 2 ml water. The clear solution was treated with a few drops of HCl 1M. The precipitate was filtered, washed with water and dried to give the title compound (62 mg) as an off-white solid, MS (ESI$^+$): m/z=556.16 [M+H]$^+$.

Example 230

(E)-N-((1H-tetrazol-5-yl)methyl)-4'-(1-(4-chloro-2-methylphenyl)-3-(hydroxyimino)-3-(1-methyl-6-oxo-1,6-dihydropyridin-3-yl)propyl)biphenyl-4-carboxamide

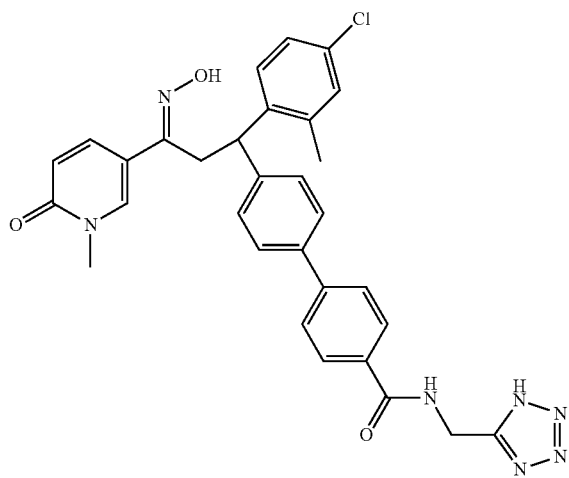 [SMILES: Cc1cc(Cl)ccc1C(C/C(=N\O)c1ccc(=O)n(C)c1)c1ccc(-c2ccc(C(=O)NCc3nnn[nH]3)cc2)cc1]

In analogy to example 228, (E)-4'-(1-(4-chloro-2-methylphenyl)-3-(hydroxyimino)-3-(1-methyl-6-oxo-1,6-dihydropyridin-3-yl)propyl)biphenyl-4-carboxylic acid (example 227) was reacted with 5-aminomethyltetrazole in the presence of HATU to give the title compound as a light yellow foam, MS (ESI$^+$): m/z=582.2 [M+H]$^+$.

Example 231

Trans-4-{4-[1-(2-Chloro-phenyl)-3-[(E)-hydroxyimino]-3-(1-methyl-6-oxo-1,6-dihydro-pyridin-3-yl)-propyl]-2-fluoro-benzoylamino}-cyclohexanecarboxylic acid

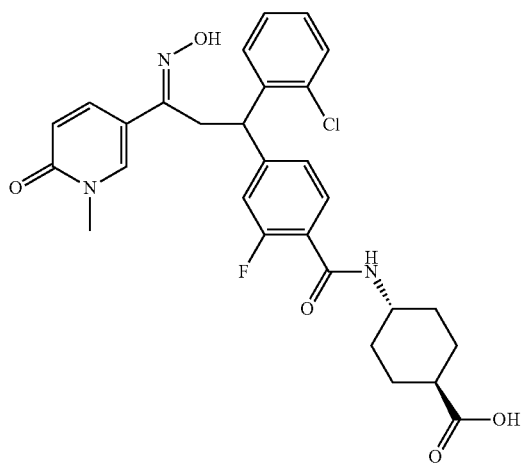 [SMILES: Cn1cc(/C(CC(c2ccc(C(=O)N[C@H]3CC[C@H](C(=O)O)CC3)c(F)c2)c2ccccc2Cl)=N/O)ccc1=O]

Step 1: trans-4-{4-[1-(2-Chloro-phenyl)-3-(1-methyl-6-oxo-1,6-dihydro-pyridin-3-yl)-3-oxo-propyl]-2-fluoro-benzoylamino}-cyclohexanecarboxylic acid methyl ester In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with trans-4-amino-cyclohexylcarboxylic acid methyl ester hydrochloride using BOP reagent in tetrahydrofuran to give the title compound as a light yellow foam, MS (ESI$^+$): m/z=553.3 [M+H]$^+$.

Step 2: trans-4-{4-[1-(2-Chloro-phenyl)-3-(1-methyl-6-oxo-1,6-dihydro-pyridin-3-yl)-3-oxo-propyl]-2-fluoro-benzoylamino}-cyclohexanecarboxylic acid In analogy to example 169, step 2, trans-4-{4-[1-(2-chlorophenyl)-3-(1-methyl-6-oxo-1,6-dihydro-pyridin-3-yl)-3-oxo-propyl]-2-fluoro-benzoylamino}-cyclohexanecarboxylic acid methyl ester was hydrolyzed to give the title compound as a colorless solid, MS (ESI$^-$): m/z=537.3 [M−H]$^-$.

Step 3: trans-4-{4-[1-(2-Chloro-phenyl)-3-[(E)-hydroxyimino]-3-(1-methyl-6-oxo-1,6-dihydro-pyridin-3-yl)-propyl]-2-fluoro-benzoylamino}-cyclohexanecarboxylic acid In analogy to example 151, step 3, trans-4-{4-[1-(2-chlorophenyl)-3-(1-methyl-6-oxo-1,6-dihydro-pyridin-3-yl)-3-oxo-propyl]-2-fluoro-benzoylamino}-cyclohexanecarboxylic acid was reacted with hydroxylamine hydrochloride in the presence of NaHCO$_3$ to give the title compound containing 13% of the corresponding Z isomer as a colorless solid, MS (ESI$^+$): m/z=552.3 [M+H]$^+$.

Example 232

(E)-4-(1-(2-Chlorophenyl)-3-(hydroxyimino)-3-(1-methyl-6-oxo-1,6-dihydropyridin-3-yl)propyl)-2-fluoro-N-(2-methoxyethyl)benzamide

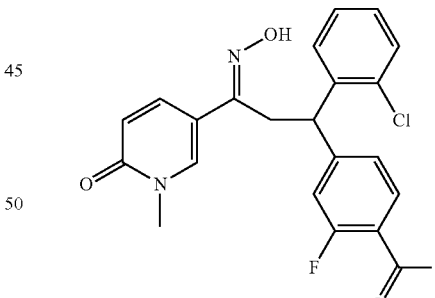

Step 1: 4-(1-(2-Chlorophenyl)-3-(1-methyl-6-oxo-1,6-dihydropyridin-3-yl)-3-oxopropyl)-2-fluoro-N-(2-methoxyethyl)benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with 2-methoxyethylamine using BOP reagent in tetrahydrofuran to give the title compound as a colorless foam, MS (ESI$^+$): m/z=471.1 [M+H]$^+$.

Step 2: (E)-4-(1-(2-Chlorophenyl)-3-(hydroxy-imino)-3-(1-methyl-6-oxo-1,6-dihydropyridin-3-yl)propyl)-2-fluoro-N-(2-methoxyethyl)benzamide In analogy to example 151, step 3, 4-(1-(2-chlorophenyl)-3-(1-methyl-6-oxo-1,6-dihydropyridin-3-yl)-3-oxopropyl)-2-fluoro-N-(2-methoxyethyl)benzamide was reacted with hydroxylamine hydrochloride in the presence of NaHCO₃ to give the title compound as a colorless foam, MS (ESI⁺): m/z=486.2 [M+H]⁺.

Example 233

(E)-4-(1-(2-Chlorophenyl)-3-(hydroxyimino)-3-(1-methyl-6-oxo-1,6-dihydropyridin-3-yl)propyl)-N-cyclopropyl-2-fluorobenzamide

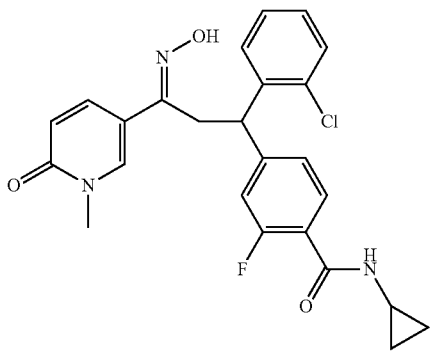 [SMILES: Cn1cc(/C(CC(c2ccc(C(=O)NC3CC3)c(F)c2)c2ccccc2Cl)=N/O)ccc1=O]

Step 1: 4-(1-(2-Chlorophenyl)-3-(1-methyl-6-oxo-1,6-dihydropyridin-3-yl)-3-oxopropyl)-N-cyclopropyl-2-fluorobenzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with cyclopropylamine using BOP reagent in tetrahydrofuran to give the title compound as a colorless foam, MS (ESI⁺): m/z=453.1 [M+H]⁺.

Step 2: (E)-4-(1-(2-Chlorophenyl)-3-(hydroxy-imino)-3-(1-methyl-6-oxo-1,6-dihydropyridin-3-yl)propyl)-N-cyclopropyl-2-fluorobenzamide In analogy to example 151, step 3, 4-(1-(2-chlorophenyl)-3-(1-methyl-6-oxo-1,6-dihydropyridin-3-yl)-3-oxopropyl)-N-cyclopropyl-2-fluorobenzamide was reacted with hydroxylamine hydrochloride in the presence of NaHCO₃ to give the title compound containing 4% of the corresponding Z isomer as a colorless waxy solid, MS (ESI⁺): m/z=468.2 [M+H]⁺.

Example 234

(E)-4-(1-(2-Chlorophenyl)-3-(hydroxyimino)-3-(1-methyl-6-oxo-1,6-dihydropyridin-3-yl)propyl)-2-fluoro-N-(2,2,2-trifluoroethyl)benzamide

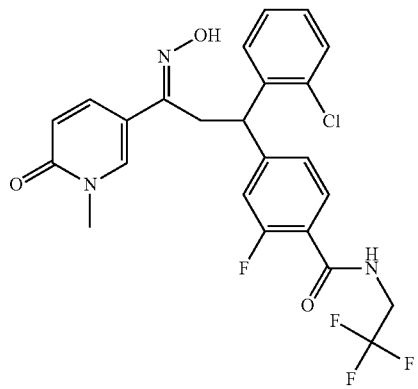 [SMILES: Cn1cc(/C(CC(c2ccc(C(=O)NCC(F)(F)F)c(F)c2)c2ccccc2Cl)=N/O)ccc1=O]

Step 1: 4-(1-(2-Chlorophenyl)-3-(1-methyl-6-oxo-1,6-dihydropyridin-3-yl)-3-oxopropyl)-2-fluoro-N-(2,2,2-trifluoroethyl)benzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with 2,2,2-trifluoro-ethylamine using BOP reagent in tetrahydrofuran to give the title compound as a colorless foam, MS (ESI⁺): m/z=495.1 [M+H]⁺.

Step 2: (E)-4-(1-(2-Chlorophenyl)-3-(hydroxy-imino)-3-(1-methyl-6-oxo-1,6-dihydropyridin-3-yl)propyl)-2-fluoro-N-(2,2,2-trifluoroethyl)benzamide In analogy to example 151, step 3, 4-(1-(2-chlorophenyl)-3-(1-methyl-6-oxo-1,6-dihydropyridin-3-yl)-3-oxopropyl)-2-fluoro-N-(2,2,2-trifluoroethyl)benzamide was reacted with hydroxylamine hydrochloride in the presence of NaHCO₃ to give the title compound containing 8% of the corresponding Z isomer as a colorless waxy solid, MS (ESI⁺): m/z=510.2 [M+H]⁺.

Example 235

3-{3-Fluoro-4-[3-[(E)-hydroxyimino]-3-(1-methyl-6-oxo-1,6-dihydro-pyridin-3-yl)-1-o-tolyl-propyl]-phenoxy}-benzoic acid

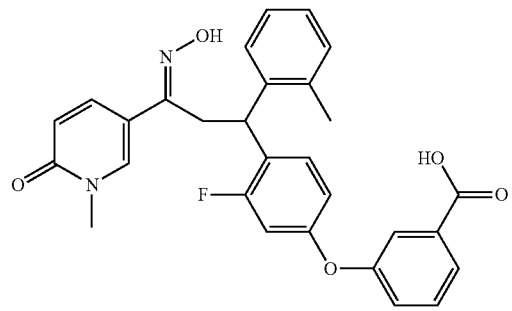 [SMILES: Cc1ccccc1C(C/C(=N\O)c1ccc(=O)n(C)c1)c1ccc(Oc2cccc(C(=O)O)c2)cc1F]

Step 1: 3-{3-Fluoro-4-[3-(1-methyl-6-oxo-1,6-dihydro-pyridin-3-yl)-3-oxo-1-o-tolyl-propyl]-phenoxy}-benzoic acid methyl ester In analogy to example 222, step 1, 5-[3-(2-fluoro-4-hydroxy-phenyl)-3-o-tolyl-propionyl]-1-methyl-1H-pyridin-2-one (example 221, step 5) was reacted with 3-methoxycarbonylphenylboronic acid in dichloromethane in the presence of copper (II) acetate, pyridine and air to give the title compound as a colorless solid, MS (ESI$^+$): m/z=500.3 [M+H]$^+$.

Step 2: 3-{3-Fluoro-4-[3-(1-methyl-6-oxo-1,6-dihydro-pyridin-3-yl)-3-oxo-1-o-tolyl-propyl]-phenoxy}-benzoic acid In analogy to example 169, step 2, 3-{3-fluoro-4-[3-(1-methyl-6-oxo-1,6-dihydro-pyridin-3-yl)-3-oxo-1-o-tolyl-propyl]-phenoxy}-benzoic acid methyl ester was hydrolyzed to give the title compound as a colorless solid, MS (ESI$^+$): m/z=486.3 [M+H]$^+$.

Step 3: 3-{3-Fluoro-4-[3-[(E)-hydroxyimino]-3-(1-methyl-6-oxo-1,6-dihydro-pyridin-3-yl)-1-o-tolyl-propyl]-phenoxy}-benzoic acid In analogy to example 151, step 3, 3-{3-fluoro-4-[3-(1-methyl-6-oxo-1,6-dihydro-pyridin-3-yl)-3-oxo-1-o-tolyl-propyl]-phenoxy}-benzoic acid was reacted with hydroxylamine hydrochloride in the presence of NaHCO$_3$ to give the title compound containing less than 10% of the corresponding Z isomer as a colorless solid, MS (ESI$^+$): m/z=501.2.2 [M+H]$^+$.

Example 236

3'-Fluoro-4'-[3-[(E)-hydroxyimino]-3-(1-methyl-6-oxo-1,6-dihydro-pyridin-3-yl)-1-o-tolyl-propyl]-biphenyl-2-carboxylic acid

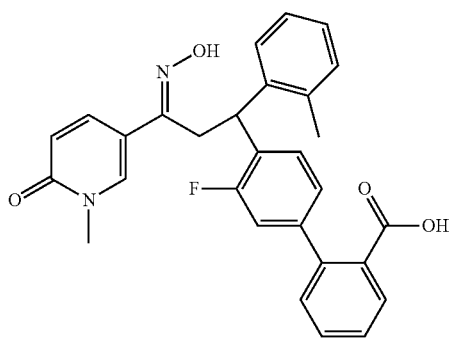 [SMILES: Cc1ccccc1C(C/C(=N\O)c1ccc(=O)n(C)c1)c1ccc(-c2ccccc2C(=O)O)cc1F]

In analogy to example 166, step 1, 5-{3-(4-bromo-2-fluoro-phenyl)-1-[(E)-hydroxyimino]-3-o-tolyl-propyl}-1-methyl-1H-pyridin-2-one (example 193, step 4) was reacted with 2-carboxyphenylboronic acid in the presence of dichloro (1,1'-bis(diphenylphosphino)-ferrocene)palladium(II) dichloromethane adduct in a mixture of 1,4-dioxane, water and 2 M aqueous sodium carbonate solution to give the title compound containing 10% of the corresponding Z isomer as a light brown solid, MS (ESI$^-$): m/z=483.1 [M−H]$^-$.

Example 237

5-{3-(4-Bromo-phenyl)-3-(4-chloro-2-fluoro-phenyl)-1-[(E)-hydroxyimino]-propyl}-1-methyl-1H-pyridin-2-one

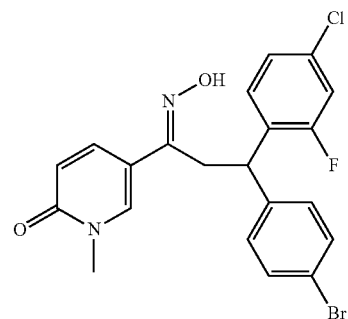

Step 1: (E)-3-(4-Chloro-2-fluoro-phenyl)-1-(6-methoxy-pyridin-3-yl)-propenone In analogy to example 170, step 1, 5-acetyl-2-methoxypyridine was reacted with 4-chloro-2-fluorobenzaldehyde in the presence of potassium hydroxide to give the title compound as a colorless solid. MS (ESI$^+$): m/z=292.1 [M+H]$^+$.

Step 2: 3-(4-Bromo-phenyl)-3-(4-chloro-2-fluoro-phenyl)-1-(6-methoxy-pyridin-3-yl)-propan-1-one In analogy to Exmple 193, step 1, 4-bromobenzeneboronic acid was first reacted with diethylzinc. The product of this reaction was treated with (E)-3-(4-chloro-2-fluoro-phenyl)-1-(6-methoxy-pyridin-3-yl)-propenone to give the title compound as a colorless oil, MS (ESI$^+$): m/z=449.9 [M+H]$^+$.

Step 3: 5-[3-(4-Bromo-phenyl)-3-(4-chloro-2-fluoro-phenyl)-propionyl]-1H-pyridin-2-one In analogy to example 162, step 2, 3-(4-bromo-phenyl)-3-(4-chloro-2-fluoro-phenyl)-1-(6-methoxy-pyridin-3-yl)-propan-1-one was reacted with concentrated aqueous HCl in 1,4-dioxane to give the title compound as an off-white powder, MS (ESI$^+$): m/z=435.8 [M+H]$^+$.

Step 4: 5-[3-(4-Bromo-phenyl)-3-(4-chloro-2-fluoro-phenyl)-propionyl]-1-methyl-1H-pyridin-2-one In analogy to example 161, step 1, 5-[3-(4-bromo-phenyl)-3-(4-chloro-2-fluoro-phenyl)-propionyl]-1H-pyridin-2-one was reacted with iodomethane in the presence of potassium carbonate to give the title compound as a colorless solid, MS (ESI$^+$): m/z=450.0 [M+H]$^+$.

Step 5: 5-{3-(4-Bromo-phenyl)-3-(4-chloro-2-fluoro-phenyl)-1-[(E)-hydroxyimino]-propyl}-1-methyl-1H-pyridin-2-one In analogy to example 151, step 3, 5-[3-(4-bromo-phenyl)-3-(4-chloro-2-fluoro-phenyl)-propionyl]-1-methyl-1H-pyridin-2-one was reacted with hydroxylamine hydrochloride in

Example 238

4'-[1-(4-Chloro-2-fluoro-phenyl)-3-[(E)-hydroxyimino]-3-(1-methyl-6-oxo-1,6-dihydro-pyridin-3-yl)-propyl]-biphenyl-4-carboxylic acid

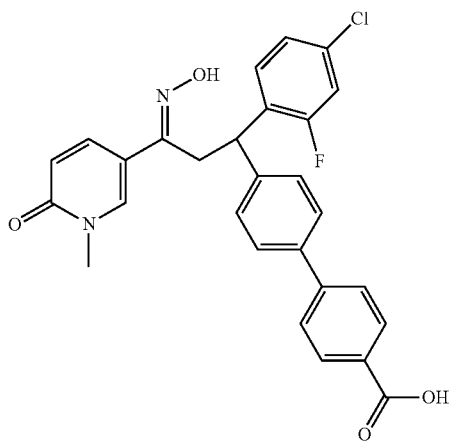 [SMILES: Cn1cc(/C(CC(c2ccc(-c3ccc(C(=O)O)cc3)cc2)c2ccc(Cl)cc2F)=N/O)ccc1=O]

In analogy to example 166, step 1, 5-{3-(4-bromo-phenyl)-3-(4-chloro-2-fluoro-phenyl)-1-[(E)-hydroxyimino]-propyl}-1-methyl-1H-pyridin-2-one (example 237, step 5) was reacted with 4-carboxyphenylboronic acid in the presence of dichloro(1,1'-bis(diphenylphosphino)-ferrocene)palladium (II) dichloromethane adduct in a mixture of 1,4-dioxane, water and 2 M aqueous sodium carbonate solution to give the title compound containing 12% of the corresponding Z isomer as an off-white solid, MS (ESI$^+$): m/z=502.8 [M–H]$^-$.

Example 239 and 240

(+)-5-{3-(4-Bromo-phenyl)-3-(4-chloro-2-fluoro-phenyl)-1-[(E)-hydroxyimino]-propyl}-1-methyl-1H-pyridin-2-one and (−)-5-{3-(4-Bromo-phenyl)-3-(4-chloro-2-fluoro-phenyl)-1-[(E)-hydroxyimino]-propyl}-1-methyl-1H-pyridin-2-one

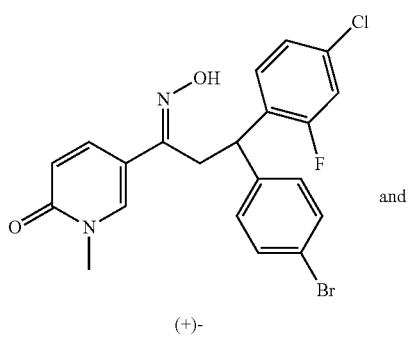

(+)- and

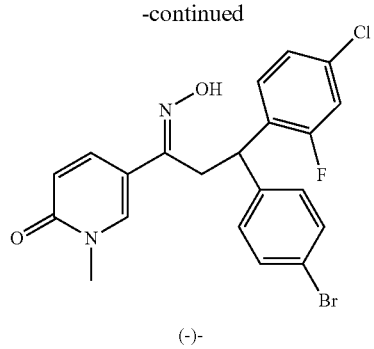

(−)-

Separation of 5-{3-(4-bromo-phenyl)-3-(4-chloro-2-fluoro-phenyl)-1-[(E)-hydroxyimino]-propyl}-1-methyl-1H-pyridin-2-one (example 237) by chiral HPLC on a Chiralpak-AD column using a solvent mixture of n-heptane/ethanol (7/3 v/v) gave (+)-5-{3-(4-bromo-phenyl)-3-(4-chloro-2-fluoro-phenyl)-1-[(E)-hydroxyimino]-propyl}-1-methyl-1H-pyridin-2-one, MS (ESI$^+$): m/z=463.02 [M+H]$^+$ as a white solid and (−)-5-{3-(4-bromo-phenyl)-3-(4-chloro-2-fluoro-phenyl)-1-[(E)-hydroxyimino]-propyl}-1-methyl-1H-pyridin-2-one, MS (ESI$^+$): m/z=463.02 [M+H]$^+$ as a white solid.

Example 241

(+)-4'-[1-(4-Chloro-2-fluoro-phenyl)-3-[(E)-hydroxyimino]-3-(1-methyl-6-oxo-1,6-dihydro-pyridin-3-yl)-propyl]-biphenyl-4-carboxylic acid

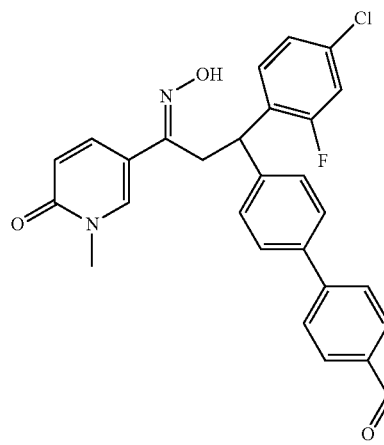

(+)-

In analogy to example 166, step 1, (+)-5-{3-(4-bromo-phenyl)-3-(4-chloro-2-fluoro-phenyl)-1-[(E)-hydroxyimino]-propyl}-1-methyl-1H-pyridin-2-one (example 239) were reacted with 4-carboxyphenylboronic acid in the presence of dichloro(1,1'-bis(diphenylphosphino)-ferrocene)palladium(II) dichloromethane adduct in a mixture of 1,4-dioxane, water and 2 M aqueous sodium carbonate solution to give the title compound as off-white solids, MS (ESI+): m/z=505.3 [M+H]+.

Example 242

(−)-4'-[1-(4-Chloro-2-fluoro-phenyl)-3-[(E)-hydroxyimino]-3-(1-methyl-6-oxo-1,6-dihydro-pyridin-3-yl)-propyl]-biphenyl-4-carboxylic acid

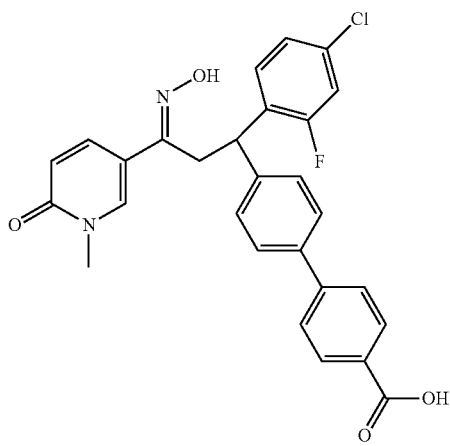

(-)-

In analogy to example 166, step 1, (−)-5-{3-(4-bromo-phenyl)-3-(4-chloro-2-fluoro-phenyl)-1-[(E)-hydroxy-imino]-propyl}-1-methyl-1H-pyridin-2-one (example 240) were reacted with 4-carboxyphenylboronic acid in the presence of dichloro(1,1'-bis(diphenylphosphino)-ferrocene)palladium(II) dichloromethane adduct in a mixture of 1,4-dioxane, water and 2 M aqueous sodium carbonate solution to give the title compound as off-white solids, MS (ESI+): m/z=505.1 [M+H]+.

Example 243

(E)-5-(3-(4-Bromophenyl)-3-(2-fluorophenyl)-1-(hydroxyimino)propyl)-1-methylpyridin-2(1H)-one

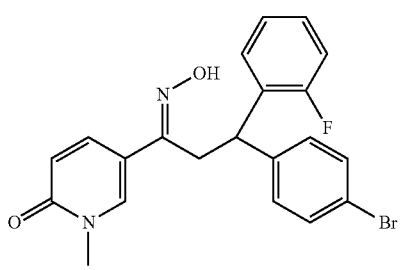 [SMILES: Cn1cc(/C(CC(c2ccc(Br)cc2)c2ccccc2F)=N/O)ccc1=O]

Step 1: (E)-3-(2-Fluoro-phenyl)-1-(6-methoxy-pyridin-3-yl)-propenone

In analogy to example 170, step 1, 5-acetyl-2-methoxypyridine was reacted with 2-fluorobenzaldehyde in the presence of potassium hydroxide to give the title compound as an off-white solid. MS (ESI+): m/z=258.2 [M+H]+.

Step 2: 3-(4-Bromo-phenyl)-3-(2-fluoro-phenyl)-1-(6-methoxy-pyridin-3-yl)-propan-1-one In analogy to example 203, step 1, (E)-3-(2-fluoro-phenyl)-1-(6-methoxy-pyridin-3-yl)-propenone was reacted with 4-bromophenylboronic acid in the presence of chloro(1,5-cyclooctadiene)rhodium(I) dimer and NaHCO3 in dioxane and water at 60° C. to give the title compound as a light yellow oil, MS (ESI+): m/z=414.1 [M+H]+.

Step 3: 5-(3-(4-Bromophenyl)-3-(2-fluorophenyl) propanoyl)pyridin-2(1H)-one

In analogy to example 162, step 2, 3-(4-bromo-phenyl)-3-(2-fluoro-phenyl)-1-(6-methoxy-pyridin-3-yl)-propan-1-one was reacted with concentrated aqueous HCl in 1,4-dioxane to give the title compound as a colorless solid, MS (ESI+): m/z=400.0 [M+H]+.

Step 4: 5-[3-(4-Bromo-phenyl)-3-(2-fluoro-phenyl)-propionyl]-1-methyl-1H-pyridin-2-one In analogy to example 161, step 1, 5-(3-(4-bromophenyl)-3-(2-fluorophenyl)propanoyl)-pyridin-2(1H)-one was reacted with iodomethane in the presence of potassium carbonate to give the title compound as a colorless solid, MS (ESI+): m/z=414.0 [M+H]+.

Step 5: (E)-5-(3-(4-Bromophenyl)-3-(2-fluorophenyl)-1-(hydroxyimino)propyl)-1-methylpyridin-2(1H)-one In analogy to example 151, step 3, 5-[3-(4-bromo-phenyl)-3-(2-fluoro-phenyl)-propionyl]-1-methyl-1H-pyridin-2-one was reacted with hydroxylamine hydrochloride in the presence of NaHCO3 to give the title compound as a colorless foam, MS (ESI+): m/z=429.0 [M+H]+.

Example 244

(E)-4'-(1-(2-Fluorophenyl)-3-(hydroxyimino)-3-(1-methyl-6-oxo-1,6-dihydropyridin-3-yl)propyl)biphenyl-4-carboxylic acid

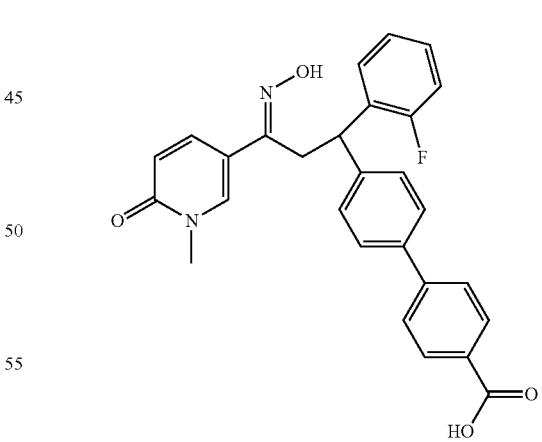

In analogy to example 166, step 1, (E)-5-(3-(4-bromophenyl)-3-(2-fluorophenyl)-1-(hydroxyimino)propyl)-1-methylpyridin-2(1H)-one (example 243, step 5) was reacted with 4-carboxyphenylboronic acid in the presence of dichloro(1,1'-bis(diphenylphosphino)-ferrocene)palladium(II) dichloromethane adduct in a mixture of 1,4-dioxane, water and 2 M aqueous sodium carbonate solution to give the title compound as a light brown solid, MS (ESI−): m/z=469.1 [M−H]−.

Example 245

(E)-4-(1-(2-Chlorophenyl)-3-(hydroxyimino)-3-(1-methyl-6-oxo-1,6-dihydropyridin-3-yl)propyl)-N-ethyl-2-fluorobenzamide

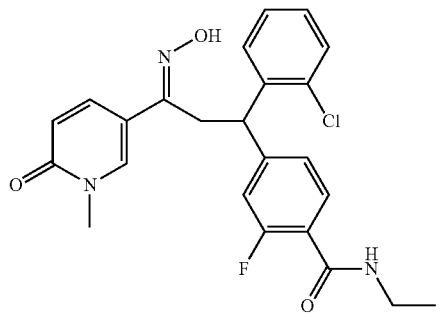 [SMILES: CCNC(=O)c1ccc(C(C/C(=N\O)c2ccc(=O)n(C)c2)c2ccccc2Cl)cc1F]

Step 1: 4-(1-(2-Chlorophenyl)-3-(1-methyl-6-oxo-1,6-dihydropyridin-3-yl)-3-oxopropyl)-N-ethyl-2-fluorobenzamide In analogy to example 207, step 2, 4-(1-(2-chlorophenyl)-3-(1-methyl-6-oxo-1,6-dihydropyridin-3-yl)-3-oxopropyl)-2-fluorobenzoic acid (example 216, step 4) was coupled with ethylamine hydrochloride using BOP reagent in tetrahydrofuran to give the title compound as a colorless foam, MS (ESI$^+$): m/z=441.3 [M+H]$^+$.

Step 2: (E)-4-(1-(2-Chlorophenyl)-3-(hydroxyimino)-3-(1-methyl-6-oxo-1,6-dihydropyridin-3-yl)propyl)-N-ethyl-2-fluorobenzamide In analogy to example 151, step 3, 4-(1-(2-chlorophenyl)-3-(1-methyl-6-oxo-1,6-dihydropyridin-3-yl)-3-oxopropyl)-N-ethyl-2-fluorobenzamide was reacted with hydroxylamine hydrochloride in the presence of NaHCO$_3$ to give the title compound containing 4% of the corresponding Z isomer as a colorless waxy solid, MS (ESI$^+$): m/z=456.2 [M+H]$^+$.

Example 246

(E)-N-(2-Acetamidoethyl)-4-(3-(hydroxyimino)-3-(1-methyl-6-oxo-1,6-dihydropyridin-3-yl)-1-o-tolylpropyl)benzamide

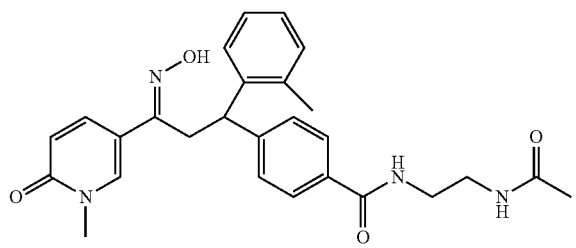 [SMILES: CC(=O)NCCNC(=O)c1ccc(C(C/C(=N\O)c2ccc(=O)n(C)c2)c2ccccc2C)cc1]

Step 1: N-(2-Acetylamino-ethyl)-4-[3-(1-methyl-6-oxo-1,6-dihydro-pyridin-3-yl)-3-oxo-1-o-tolyl-propyl]-benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with N acetylethylenediamine using BOP reagent in tetrahydrofuran to give the title compound as an off-white solid, MS (ESI$^+$): m/z=460.4 [M+H]$^+$.

Step 2: (E)-N-(2-Acetamidoethyl)-4-(3-(hydroxyimino)-3-(1-methyl-6-oxo-1,6-dihydropyridin-3-yl)-1-o-tolylpropyl)benzamide In analogy to example 151, step 3, N-(2-acetylamino-ethyl)-4-[3-(1-methyl-6-oxo-1,6-dihydro-pyridin-3-yl)-3-oxo-1-o-tolyl-propyl]-benzamide was reacted with hydroxylamine hydrochloride in the presence of NaHCO$_3$ to give the title compound containing less than 10% of the corresponding Z isomer as a colorless solid, MS (ESI$^+$): m/z=475.2 [M+H]$^+$.

Example 247

4-((E)-3-(Hydroxyimino)-3-(1-methyl-6-oxo-1,6-dihydropyridin-3-yl)-1-o-tolylpropyl)-N-((S)-2-hydroxypropyl)benzamide

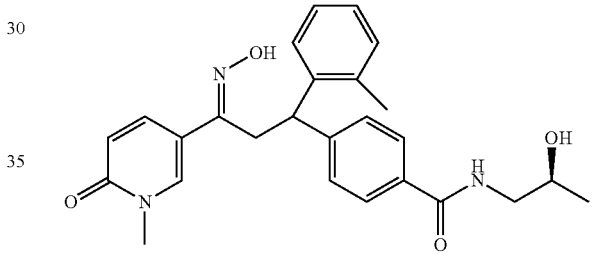

In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (R)-(−)-1-amino-2-propanol using BOP reagent in tetrahydrofuran. The product of this reaction was reacted in analogy to example 151, step 3, with hydroxylamine hydrochloride in the presence of NaHCO$_3$ to give the title compound containing 5% of the corresponding Z isomer as a colorless solid, MS (ESI$^+$): m/z=448.2 [M+H]$^+$.

Example 248

4-((E)-3-(Hydroxyimino)-3-(1-methyl-6-oxo-1,6-dihydropyridin-3-yl)-1-o-tolylpropyl)-N-((R)-2-hydroxypropyl)benzamide

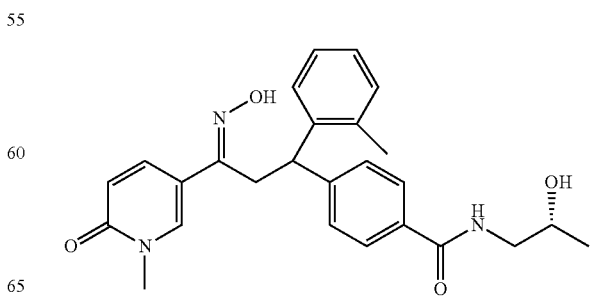

In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (S)-(+)-1-amino-2-propanol using BOP reagent in tetrahydrofuran. The product of this reaction was reacted in analogy to example 151, step 3, with hydroxylamine hydrochloride in the presence of NaHCO₃ to give the title compound containing 5% of the corresponding Z isomer as a colorless solid, MS (ESI⁺): m/z=448.2 [M+H]⁺.

Example 249

(E)-5-(3-(2-Chlorophenyl)-1-(hydroxyimino)-3-(4-(methylsulfonyl)phenyl)propyl)-1-methylpyridin-2(1H)-one

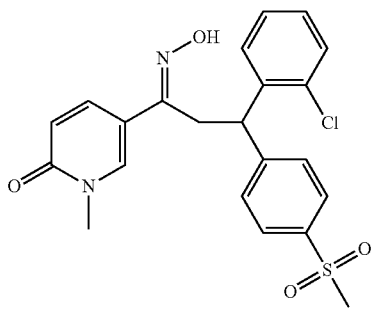 [SMILES: Cn1cc(/C(CC(c2ccc(S(C)(=O)=O)cc2)c2ccccc2Cl)=N/O)ccc1=O]

Step 1: 3-(2-Chloro-phenyl)-3-(4-methanesulfonyl-phenyl)-1-(6-methoxy-pyridin-3-yl)-propan-1-one In analogy to example 203, step 1, (E)-3-(2-chloro-phenyl)-1-(6-methoxy-pyridin-3-yl)-propenone (example 197, step 1) was reacted with 4-(methylsulfonyl)phenylboronic acid in the presence of chloro(1,5-cyclooctadiene)rhodium(I) dimer and NaHCO₃ in dioxane and water at 60° C. to give the title compound as a colorless solid, MS (ESI⁺): m/z=430.1 [M+H]⁺.

Step 2: 5-[3-(2-Chloro-phenyl)-3-(4-methanesulfonyl-phenyl)-propionyl]-1H-pyridin-2-one In analogy to example 162, step 2, 3-(2-chloro-phenyl)-3-(4-methanesulfonyl-phenyl)-1-(6-methoxy-pyridin-3-yl)-propan-1-one was reacted with concentrated aqueous HCl in 1,4-dioxane to give the title compound as a colorless solid, MS (ESI⁺): m/z=416.0 [M+H]⁺.

Step 3: 5-[3-(2-Chloro-phenyl)-3-(4-methanesulfonyl-phenyl)-propionyl]-1-methyl-1H-pyridin-2-one In analogy to example 161, step 1, 5-[3-(2-chloro-phenyl)-3-(4-methanesulfonyl-phenyl)-propionyl]-1H-pyridin-2-one was reacted with iodomethane in the presence of potassium carbonate to give the title compound as a colorless solid, MS (ESI⁺): m/z=430.1 [M+H]⁺.

Step 4: (E)-5-(3-(2-Chlorophenyl)-1-(hydroxyimino)-3-(4-(methylsulfonyl)phenyl)propyl)-1-methylpyridin-2(1H)-one In analogy to example 151, step 3, 5-[3-(2-chloro-phenyl)-3-(4-methanesulfonyl-phenyl)-propionyl]-1-methyl-1H-pyridin-2-one was reacted with hydroxylamine hydrochloride in the presence of NaHCO₃ to give the title compound as a colorless solid, MS (ESI⁺): m/z=445.2 [M+H]⁺.

Example 250

(E)-5,5'-(1-(2-Chlorophenyl)-3-(hydroxyimino)propane-1,3-diyl)bis(1-methylpyridin-2(1H)-one)

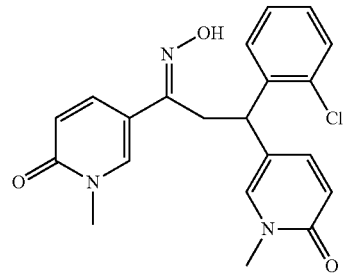 [SMILES: Cn1cc(/C(CC(c2ccc(=O)n(C)c2)c2ccccc2Cl)=N/O)ccc1=O]

Step 1: 3-(2-Chloro-phenyl)-1,3-bis-(6-methoxy-pyridin-3-yl)-propan-1-one

In analogy to example 203, step 1, (E)-3-(2-chloro-phenyl)-1-(6-methoxy-pyridin-3-yl)-propenone (example 197, step 1) was reacted with 2-methoxy-5-pyridineboronic acid in the presence of chloro(1,5-cyclooctadiene)rhodium(I) dimer and NaHCO₃ in dioxane and water at 60° C. to give the title compound as a light yellow solid, MS (ESI⁺): m/z=381.1 [M+H]⁺.

Step 2: 5,5'-[1-(2-Chlorophenyl)-3-oxopropane-1,3-diyl]dipyridin-2(1H)-one

In analogy to example 162, step 2, 3-(2-chloro-phenyl)-1,3-bis-(6-methoxy-pyridin-3-yl)-propan-1-one was reacted with concentrated aqueous HCl in 1,4-dioxane to give the title compound as an off-white solid, MS (ESI⁺): m/z=355.1 [M+H]⁺.

Step 3: 5,5'-[1-(2-Chlorophenyl)-3-oxopropane-1,3-diyl]bis(1-methylpyridin-2(1H)-one)

In analogy to example 161, step 1, 5,5'-[1-(2-chlorophenyl)-3-oxopropane-1,3-diyl]dipyridin-2(1H)-one was reacted with iodomethane in the presence of potassium carbonate to give the title compound as a colorless solid, MS (ESI⁺): m/z=383.1 [M+H]⁺.

Step 4: (E)-5,5'-(1-(2-Chlorophenyl)-3-(hydroxyimino)propane-1,3-diyl)bis(1-methylpyridin-2(1H)-one)

In analogy to example 151, step 3, 5,5'-[1-(2-chlorophenyl)-3-oxopropane-1,3-diyl]bis(1-methylpyridin-2(1H)-one) was reacted with hydroxylamine hydrochloride in the presence of NaHCO₃ to give the title compound containing less than 10% of the corresponding Z isomer as an off-white solid, MS (ESI⁺): m/z=398.1 [M+H]⁺.

Example 251

(E)-4'-(1-(4-Chloro-2-methylphenyl)-3-(hydroxy-imino)-3-(1-methyl-6-oxo-1,6-dihydropyridin-3-yl)propyl)biphenyl-4-carbonitrile

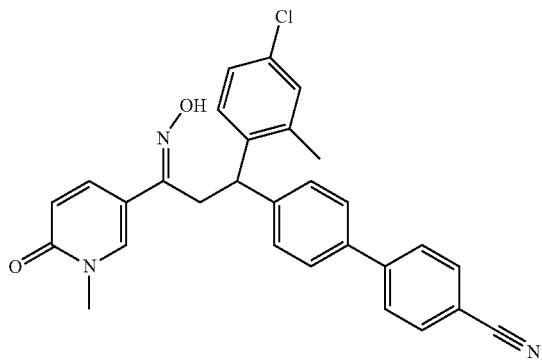 [SMILES: Cc1cc(Cl)ccc1C(C/C(=N\O)c1ccc(=O)n(C)c1)c1ccc(-c2ccc(C#N)cc2)cc1]

In analogy to example 166, step 1, 5-{3-(4-bromo-phenyl)-3-(4-chloro-2-methyl-phenyl)-1-[(E)-hydroxyimino]-propyl}-1-methyl-1H-pyridin-2-one (example 226, step 4) was reacted with 4-cyanophenylboronic acid (CAS RN: [126747-14-6]) in the presence of dichloro(1,1'-bis(diphenylphosphino)ferrocene)palladium(II) dichloromethane adduct in a mixture of 1,4-dioxane, water and 2 M aqueous sodium carbonate solution to give the title compound containing 10% of the corresponding Z isomer as a white solid, MS (ESI⁺): m/z=482.16 [M+H]⁺.

Example 252

3-Bromo-5-{(R)-3-(4-bromo-phenyl)-1-[(E)-hydroxyimino]-3-o-tolyl-propyl}-1-methyl-1H-pyridin-2-one

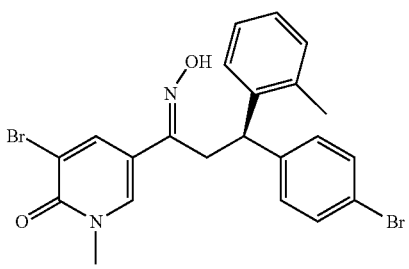 [SMILES: Cc1ccccc1[C@H](C/C(=N\O)c1cc(Br)c(=O)n(C)c1)c1ccc(Br)cc1]

Step 1: (R)-3-Bromo-5-(3-(4-bromophenyl)-3-o-tolylpropanoyl)-1-methylpyridin-2(1H)-one To a solution of (R)-5-(3-(4-bromophenyl)-3-o-tolylpropanoyl)-1-methylpyridin-2(1H)-one (0.1 g, example 223) in DMF (1 mL) were added pyridine (217 μL) and then bromine (12.6 μL) dropwise. The resulting solution was stirred at rt for 2.25 h. The reaction mixture was poured on water and ethyl acetate and the layers were separated. The aqueous layer was extracted with 2× ethyl acetate. The organic layers were washed with water and once with brine, dried over MgSO₄, filtered, treated with silica gel and evaporated. The compound was purified by chromatography (SiO₂, n-heptane/ethyl acetate 100:0 to 50:50) to give the title compound as a light brown solid (0.093 g; 78%), MS (ESI⁺): m/z=489.0 [M+H]⁺.

Step 2: 3-Bromo-5-{(R)-3-(4-bromo-phenyl)-1-[(E)-hydroxyimino]-3-o-tolyl-propyl}-1-methyl-1H-pyridin-2-one To a suspension of (R)-3-bromo-5-(3-(4-bromophenyl)-3-o-tolylpropanoyl)-1-methylpyridin-2(1H)-one in ethanol (2.5 mL) and water (0.1 mL) were added sodium bicarbonate (30.9 mg) and hydroxylamine hydrochloride (32.0 mg) and the reaction mixture was stirred at reflux (100° C. oil bath temperature) for 2 hours. The reaction mixture was poured on water and dichloromethane and the layers were separated. The aqueous layer was extracted twice with dichloromethane. The combined organic layers were washed with brine, dried over magnesium sulfate, filtered, treated with silica gel and evaporated. The compound was purified by silica gel chromatography using a MPLC system (10 g silica gel column, CombiFlash Companion, Isco Inc.) eluting with a gradient of n-heptane/ethyl acetate (100:0 to 50:50) to give the title compound as a white solid, MS (ESI⁺): m/z=504.99 [M+H]⁺.

Examples 253 and 254

(−)-({4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester and (+)-({4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester

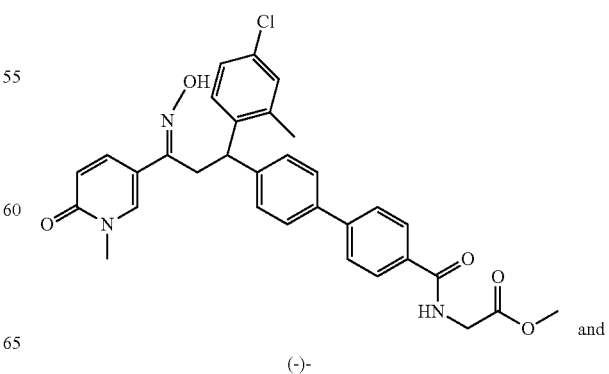

(−)- and

-continued

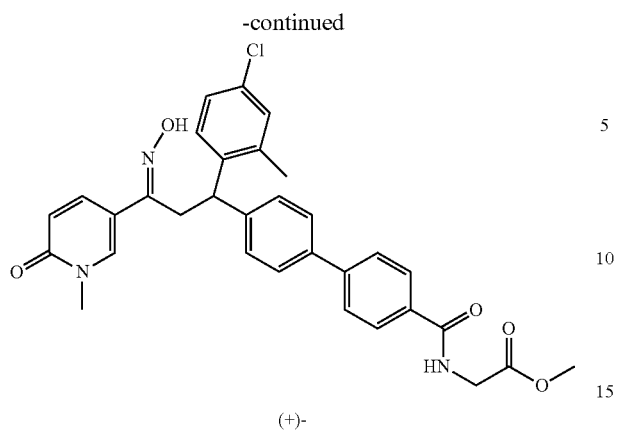

(+)-

Separation of (E)-methyl 2-(4'-(1-(4-chloro-2-methylphenyl)-3-(hydroxyimino)-3-(1-methyl-6-oxo-1,6-dihydropyridin-3-yl)propyl)biphenyl-4-ylcarboxamido)acetate (example 228) by chiral HPLC on a Chiralpak-AD column using a solvent mixture of n-heptane:2-propanol (3:2 v/v) gave (−)-({4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester as a light brown solid, MS (ESI$^+$): m/z=572.19 [M+H]$^+$ and (+)-({4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester as a light brown solid, MS (ESI$^+$): m/z=572.19 [M+H]$^+$.

Example 255

(−)-({4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid

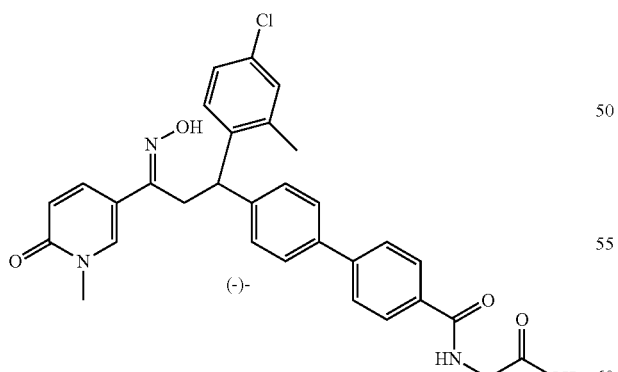

(-)-

In analogy to example 229, from (−)-({4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester was prepared the title compound as a white solid, MS (ESI$^+$): m/z=558.18 [M+H]$^+$.

Example 256

(+)-({4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid

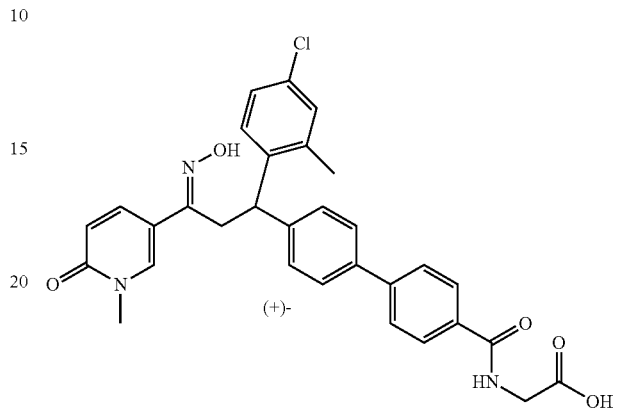

(+)-

In analogy to example 229, from (+)-({4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester was prepared the title compound as a white solid, MS (ESI$^+$): m/z=558.18 [M+H]$^+$.

Example 257

({4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester

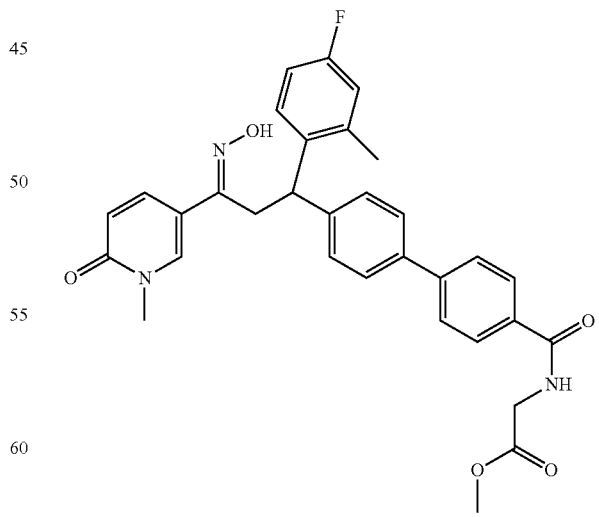

In analogy to example 228, from (E)-4'-(1-(4-fluoro-2-methylphenyl)-3-(hydroxyimino)-3-(1-methyl-6-oxo-1,6-dihydropyridin-3-yl)propyl)biphenyl-4-carboxylic acid (example 225) and glycine-methylester hydrochloride was prepared the title compound as a light brown foam, MS (ESI⁺): m/z=556.22 [M+H]⁺.

Example 258

({4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid

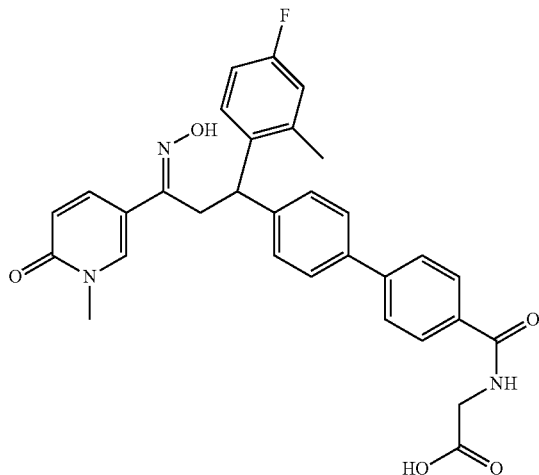 [SMILES: Cc1cc(F)ccc1C(C/C(=N\O)c1ccc(=O)n(C)c1)c1ccc(-c2ccc(C(=O)NCC(=O)O)cc2)cc1]

In analogy to example 229, from ({4'-[1-(4-fluoro-2-methyl-phenyl)-3-[(E)-hydroxyimino]-3-(1-methyl-6-oxo-1,6-dihydro-pyridin-3-yl)-propyl]-biphenyl-4-carbonyl}-amino)-acetic acid methyl ester (example 225) was prepared the title compound as an off-white solid, MS (ESI⁺): m/z=542.21 [M+H]⁺.

Example 259

5-{3-(4'-Amino-biphenyl-4-yl)-3-(4-fluoro-2-methyl-phenyl)-1-[(E)-hydroxyimino]-propyl}-1-methyl-1H-pyridin-2-one

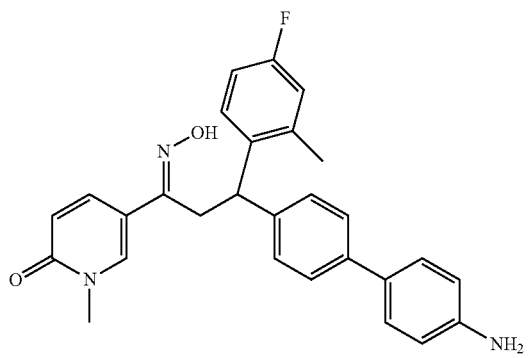 [SMILES: Cc1cc(F)ccc1C(C/C(=N\O)c1ccc(=O)n(C)c1)c1ccc(-c2ccc(N)cc2)cc1]

In analogy to example 166, from (E)-5-(3-(4-bromophenyl)-3-(4-fluoro-2-methylphenyl)-1-(hydroxyimino)propyl)-1-methylpyridin-2(1H)-one (example 224) and 4-aminophenylboronic acid pinacol ester (CAS RN: [214360-73-3]) was prepared the title compound as a light brown foam, MS (ESI⁺): m/z=456.21 [M+H]⁺.

Example 260

5-{3-(4-Fluoro-2-methyl-phenyl)-1-[(E)-hydroxyimino]-3-[4'-(1H-tetrazol-5-yl)-biphenyl-4-yl]-propyl}-1-methyl-1H-pyridin-2-one

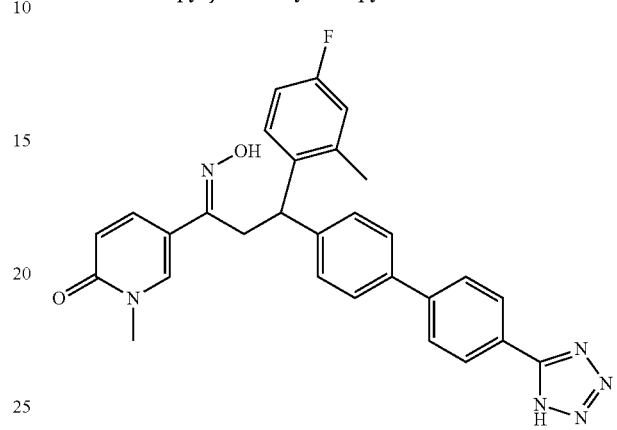

To a solution of (E)-5-(3-(4-bromophenyl)-3-(4-fluoro-2-methylphenyl)-1-(hydroxyimino)propyl)-1-methylpyridin-2 (1H)-one (0.1 g, example 224) in dioxane (1 mL) was added [1,1'-bis(diphenylphosphino)ferrocene]dichloropalladium dichloromethane adduct (CAS RN: [95464-05-4]) (9.21 mg), 4-(1H-tetrazol-5-yl)phenylboronic acid (64.3 mg, CAS RN: [179942-55-3]), water (0.65 mL) and aqueous 2M sodium carbonate solution (338 µL) and the reaction mixture was heated for 23 hours at 80° C. The reaction mixture was poured on 10% aqueous citric acid solution and ethyl acetate and the layers were separated. The aqueous layer was extracted twice with ethyl acetate. The combined organic layers were dried over magnesium sulfate, filtered, treated with silica gel and evaporated. The compound was purified by silica gel chromatography using a MPLC system (20 g silica gel column, CombiFlash Companion, Isco Inc.) eluting with a gradient of dichloromethane:methanol (100:0 to 75:25). The product was purified a second time by preparative HPLC (phenomenex gemini column) with a gradient of acetonitrile:water (containing 0.5% formic acid) (10:90 to 98:2) to yield the title compound containing 10% of the corresponding Z isomer as as a white foam, MS (ESI⁺): m/z=509.21 [M+H]⁺.

Example 261 and 262

(E,R)-4-(4-bromophenyl)-1-(pyridin-4-yl)-4-o-tolylbutan-2-one oxime and (Z,R)-4-(4-bromophenyl)-1-(pyridin-4-yl)-4-o-tolylbutan-2-one oxime

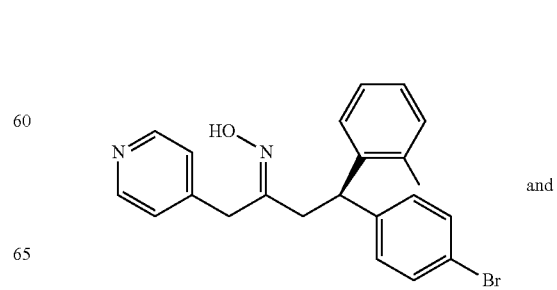

and

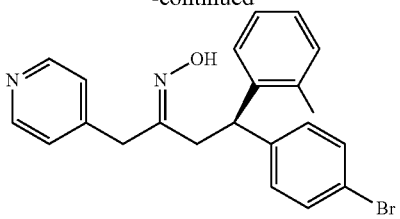

Step 1: (R)-4-(4-bromophenyl)-1-(pyridin-4-yl)-4-o-tolylbutan-2-one

At −78° C., to a solution of 4-methylpyridine (308 mg) in THF (7 mL) n-butyllithium (1.6M in hexane, 2.07 ml) was added. The reaction mixture was warmed slowly to rt, stirred for 1 h at that temperature, and cooled down again to −78° C. (R)-3-(4-Bromophenyl)-N-methoxy-N-methyl-3-o-tolyl-propanamide (example 142, step 1; 400 mg) in THF (3 mL) was added slowly and the reaction mixture was warmed to rt and stirred for 3 h. The mixture was poured into a saturated aqueous solution of NaHCO$_3$ (10 mL), the phases were separated, and the inorganic one was extracted with EtOAc (2×10 mL). The organic layers were combined, washed with brine, dried over Na$_2$SO$_4$ and concentrated in vacuo. The crude material was purified by flash chromatography on silica gel (30% to 60% EtOAc in n-heptane to CH$_2$Cl$_2$/MeOH 9:1) to yield the title compound as a yellow oil (220 mg, 51%), MS (ESI$^+$): m/z=394.0 ([M+H]$^+$, 1Br).

Step 2: (E,R)-4-(4-bromophenyl)-1-(pyridin-4-yl)-4-o-tolylbutan-2-one oxime and (Z,R)-4-(4-bromophenyl)-1-(pyridin-4-yl)-4-o-tolylbutan-2-one oxime In analogy to example 74, step 7, from (R)-4-(4-bromophenyl)-1-(pyridin-4-yl)-4-o-tolylbutan-2-one and hydroxylamine hydrochloride in the presence of NaHCO$_3$ was prepared (E,R)-4-(4-bromophenyl)-1-(pyridin-4-yl)-4-o-tolylbutan-2-one oxime as a colorless oil, MS (ESI$^+$): m/z=409.0908 ([M+H]$^+$, 1Br) and (Z,R)-4-(4-bromophenyl)-1-(pyridin-4-yl)-4-o-tolylbutan-2-one oxime as a colorless oil, MS (ESI$^+$): m/z=409.0909 ([M+H]$^+$, 1Br).

Example 263

(E,R)-4-(4-bromophenyl)-1-(pyridin-2-yl)-4-o-tolylbutan-2-one oxime

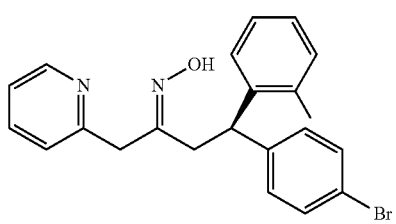 [SMILES: Cc1ccccc1[C@H](C/C(Cc1ccccn1)=N\O)c1ccc(Br)cc1]

Step 1: (R)-4-(4-Bromophenyl)-1-(pyridin-2-yl)-4-o-tolylbutan-2-one

In analogy to example 261, step 1, from (R)-3-(4-bromophenyl)-N-methoxy-N-methyl-3-o-tolylpropanamide (example 142, step 1) and 2-methyl-pyridine was prepared the title compound as a yellow oil, MS (ESI$^+$): m/z=394.0 ([M+H]$^+$, 1Br).

Step 2: (E,R)-4-(4-Bromophenyl)-1-(pyridin-2-yl)-4-o-tolylbutan-2-one oxime

In analogy to example 74, step 7, from (R)-4-(4-bromophenyl)-1-(pyridin-2-yl)-4-o-tolylbutan-2-one and hydroxylamine hydrochloride in the presence of NaHCO$_3$ was prepared the title compound as a colorless oil, MS (ESI$^+$): m/z=409.0904 ([M+H]$^+$, 1Br).

Example 264

(E,R)-1-(2-Methyl-pyridin-4-yl)-3-(4-morpholin-4-yl-phenyl)-3-o-tolyl-propan-1-one oxime

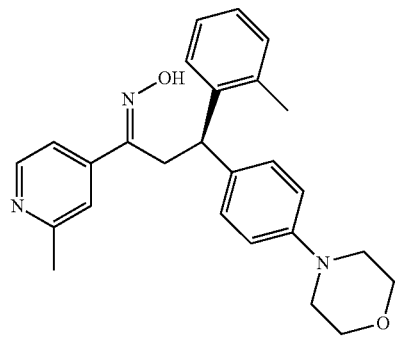 [SMILES: Cc1cc(/C(C[C@H](c2ccc(N3CCOCC3)cc2)c2ccccc2C)=N/O)ccn1]

In analogy to example 39, from (E,R)-3-(4-bromo-phenyl)-1-(2-methyl-pyridin-4-yl)-3-o-tolyl-propan-1-one oxime (example 142) and morpholine was prepared (E,R)-1-(2-methyl-pyridin-4-yl)-3-(4-morpholin-4-yl-phenyl)-3-o-tolyl-propan-1-one oxime as a light yellow semisolid, MS (ESI$^+$): m/z=416.3 ([M+H]$^+$).

Example 265

1-{4-[(R)-3-[(E)-Hydroxyimino]-3-(2-methyl-pyridin-4-yl)-1-o-tolyl-propyl]-phenyl}-piperidine-4-carboxylic acid ethyl ester

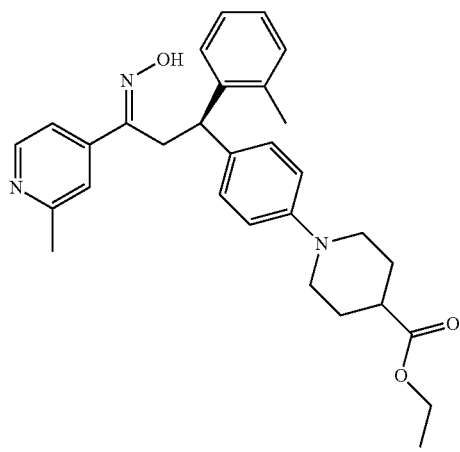 [SMILES: CCOC(=O)C1CCN(c2ccc([C@@H](C/C(=N\O)c3ccnc(C)c3)c3ccccc3C)cc2)CC1]

251

In analogy to example 39, from (E,R)-3-(4-bromophenyl)-1-(2-methylpyridin-4-yl)-3-o-tolylpropan-1-one oxime (example 142) and ethyl piperidine-4-carboxylate using cesium carbonate instead of sodium tert-butylate as base in dioxane instead of toluene was prepared 1-{4-[(R)-3-[(E)-hydroxyimino]-3-(2-methyl-pyridin-4-yl)-1-o-tolyl-propyl]-phenyl}-piperidine-4-carboxylic acid ethyl ester as a yellow semisolid, MS (ESI⁺): m/z=486.5 ([M+H]⁺).

Example 266

1-{4-[(R)-3-[(E)-Hydroxyimino]-3-(2-methyl-pyridin-4-yl)-1-o-tolyl-propyl]-phenyl}-piperidine-4-carboxylic acid

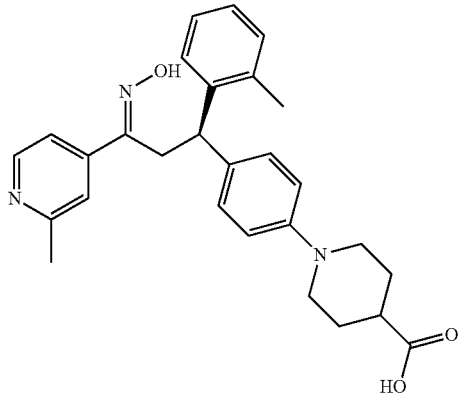 [SMILES: Cc1cc(/C(C[C@H](c2ccc(N3CCC(C(=O)O)CC3)cc2)c2ccccc2C)=N/O)ccn1]

In analogy to example 75, from 1-{4-[(R)-3-[(E)-hydroxyimino]-3-(2-methyl-pyridin-4-yl)-1-o-tolyl-propyl]-phenyl}-piperidine-4-carboxylic acid ethyl ester was prepared 1-{4-[(R)-3-[(E)-hydroxyimino]-3-(2-methyl-pyridin-4-yl)-1-o-tolyl-propyl]-phenyl}-piperidine-4-carboxylic acid as light yellow foam, MS (ESI⁻): m/z=456.2 ([M−H]⁻).

Example 267

(E,R)-3-{4-[(2-Methoxy-ethyl)-methyl-amino]-phenyl}-1-(2-methyl-pyridin-4-yl)-3-o-tolyl-propan-1-one oxime

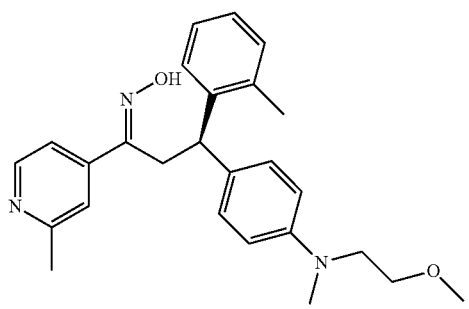 [SMILES: COCCN(C)c1ccc([C@@H](C/C(=N\O)c2ccnc(C)c2)c2ccccc2C)cc1]

In analogy to example 39, from (E,R)-3-(4-bromo-phenyl)-1-(2-methyl-pyridin-4-yl)-3-o-tolyl-propan-1-one oxime (example 142) and 2-methoxy-N-methylethanamine was prepared (E,R)-3-{4-[(2-methoxy-ethyl)-methyl-amino]-phenyl}-1-(2-methyl-pyridin-4-yl)-3-o-tolyl-propan-1-one oxime as a yellow foam, MS (ESI⁺): m/z=418.4 ([M+H]⁺).

Example 268

(E,R)-3-{4-[(2-Hydroxy-ethyl)-methyl-amino]-phenyl}-1-(2-methyl-pyridin-4-yl)-3-o-tolyl-propan-1-one oxime

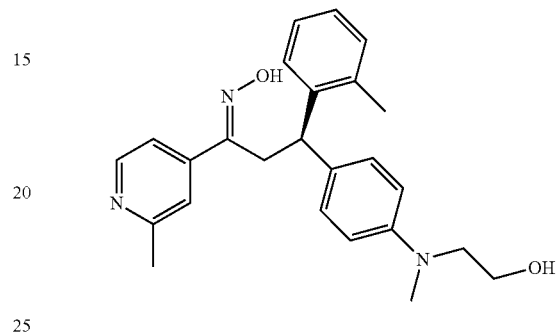

In analogy to example 39, from (E,R)-3-(4-bromo-phenyl)-1-(2-methyl-pyridin-4-yl)-3-o-tolyl-propan-1-one oxime (example 142) and 2-(methylamino)ethanol was prepared (E,R)-3-{4-[(2-hydroxy-ethyl)-methyl-amino]-phenyl}-1-(2-methyl-pyridin-4-yl)-3-o-tolyl-propan-1-one oxime as a yellow oil, MS (ESI⁺): m/z=404.3 ([M+H]⁺).

Example 269

(E,R)-3-[4-(4-Hydroxymethyl-piperidin-1-yl)-phenyl]-1-(2-methyl-pyridin-4-yl)-3-o-tolyl-propan-1-one oxime

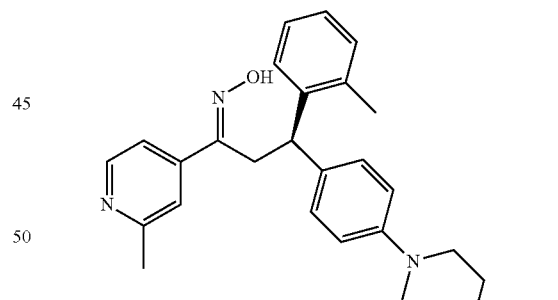

Step 1: (R)-3-[4-(4-Hydroxymethyl-piperidin-1-yl)-phenyl]-1-(2-methyl-pyridin-4-yl)-3-o-tolyl-propan-1-one In analogy to example 39, from (R)-3-(4-bromo-phenyl)-1-(2-methyl-pyridin-4-yl)-3-o-tolyl-propan-1-one (example 142, step 2) and piperidin-4-yl-methanol was prepared (R)-3-[4-(4-hydroxymethyl-piperidin-1-yl)-phenyl]-1-(2-methyl-pyridin-4-yl)-3-o-tolyl-propan-1-one as a light yellow foam, MS (ESI⁺): m/z=429.3 ([M+H]⁺).

Step 2: (E,R)-3-[4-(4-Hydroxymethyl-piperidin-1-yl)-phenyl]-1-(2-methyl-pyridin-4-yl)-3-o-tolyl-propan-1-one oxime In analogy to example 132, step 6, from (R)-3-[4-(4-hydroxymethyl-piperidin-1-yl)-phenyl]-1-(2-methyl-pyridin-4-yl)-3-o-tolyl-propan-1-one and hydroxylamine hydrochloride in the presence of NaHCO$_3$ was prepared the title compound as a colorless oil, MS (ESI$^+$): m/z=444.4 ([M+H]$^+$).

Example 270

(E,R)-3-[4-(3-Methoxy-azetidin-1-yl)-phenyl]-1-(2-methyl-pyridin-4-yl)-3-o-tolyl-propan-1-one oxime

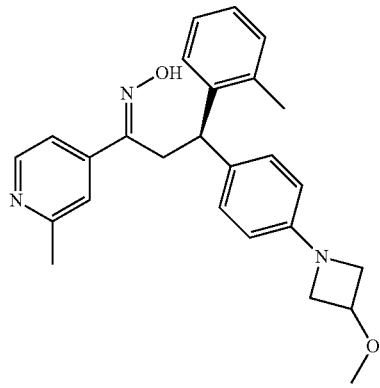 [SMILES: COC1CN(c2ccc([C@@H](C/C(=N\O)c3ccnc(C)c3)c3ccccc3C)cc2)C1]

Step 1: (R)-3-[4-(3-Methoxy-azetidin-1-yl)-phenyl]-1-(2-methyl-pyridin-4-yl)-3-o-tolyl-propan-1-one In analogy to example 39, from (R)-3-(4-bromo-phenyl)-1-(2-methyl-pyridin-4-yl)-3-o-tolyl-propan-1-one (example 142, step 2) and 3-methoxyazetidine hydrochloride in the presence of tris(dibenzylideneacetone) dipalladium (0) chloroform adduct, 2-dicyclohexylphosphino-2',4',6'-triisopropylbiphenyl (X-PHOS) and cesium carbonate in tert-butanol was prepared (R)-3-[4-(3-methoxy-azetidin-1-yl)-phenyl]-1-(2-methyl-pyridin-4-yl)-3-o-tolyl-propan-1-one as a yellow oil, MS (ESI$^+$): m/z=401.3 ([M+H]$^+$).

Step 2: (E,R)-3-[4-(3-Methoxy-azetidin-1-yl)-phenyl]-1-(2-methyl-pyridin-4-yl)-3-o-tolyl-propan-1-one oxime In analogy to example 1, step 2, from (R)-3-[4-(3-methoxy-azetidin-1-yl)-phenyl]-1-(2-methyl-pyridin-4-yl)-3-o-tolyl-propan-1-one and hydroxylamine hydrochloride in the presence of NaHCO$_3$ was prepared the title compound as a white foam, MS (ESI$^+$): m/z=416.3 ([M+H]$^+$).

Example 271

(E,R)-3-[4-(1,1-Dioxo-1λ6-thiomorpholin-4-yl)-phenyl]-1-(2-methyl-pyridin-4-yl)-3-o-tolyl-propan-1-one oxime

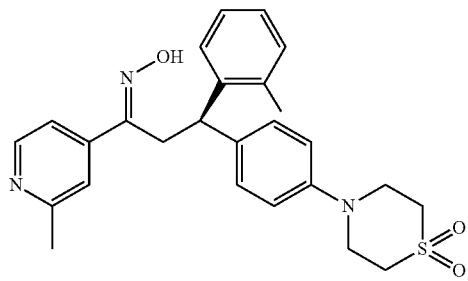 [SMILES: Cc1cc(/C(C[C@H](c2ccc(N3CCS(=O)(=O)CC3)cc2)c2ccccc2C)=N/O)ccn1]

Step 1: (R)-3-[4-(1,1-Dioxo-1λ6-thiomorpholin-4-yl)-phenyl]-1-(2-methyl-pyridin-4-yl)-3-o-tolyl-propan-1-one In analogy to example 39, from (R)-3-(4-bromo-phenyl)-1-(2-methyl-pyridin-4-yl)-3-o-tolyl-propan-1-one (example 142, step 2) and thiomorpholine 1,1-dioxide in the presence of tris(dibenzylideneacetone) dipalladium (0) chloroform adduct, 2-dicyclohexylphosphino-2',4',6'-triisopropylbiphenyl (X-PHOS) and cesium carbonate in tert-butanol was prepared (R)-3-[4-(1,1-dioxo-1lambda6-thiomorpholin-4-yl)-phenyl]-1-(2-methyl-pyridin-4-yl)-3-o-tolyl-propan-1-one as a yellow oil, MS (ESI$^+$): m/z=449.2 ([M+H]$^+$).

Step 2: (E,R)-3-[4-(1,1-Dioxo-1λ6-thiomorpholin-4-yl)-phenyl]-1-(2-methyl-pyridin-4-yl)-3-o-tolyl-propan-1-one oxime In analogy to example 132, step 6, from (R)-3-[4-(1,1-dioxo-1lambda6-thiomorpholin-4-yl)-phenyl]-1-(2-methyl-pyridin-4-yl)-3-o-tolyl-propan-1-one and hydroxylamine hydrochloride in the presence of NaHCO$_3$ was prepared the title compound as a light yellow foam, MS (ESI$^+$): m/z=464.2 ([M+H]$^+$).

Example 272

4-[(R)-3-[(E)-Hydroxyimino]-3-(2-methyl-pyridin-4-yl)-1-o-tolyl-propyl]-benzoic acid

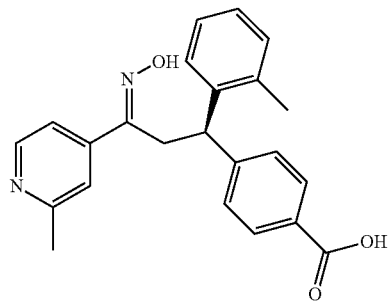 [SMILES: Cc1cc(/C(C[C@H](c2ccc(C(=O)O)cc2)c2ccccc2C)=N/O)ccn1]

Step 1: 4-[(R)-3-(2-Methyl-pyridin-4-yl)-3-oxo-1-o-tolyl-propyl]-benzoic acid methyl ester To a solution of (R)-3-(4-bromo-phenyl)-1-(2-methyl-pyridin-4-yl)-3-o-tolyl-propan-1-one (example 142, step 2, 100 mg) in methanol (1.5 mL) and ethyl acetate (1.5 mL) were added [1,1'-bis(diphenylphosphino)ferrocene]dichloropalladium(II) dichloromethane adduct (10 mg), triethylamine (53.3 µL) at room temperature. The reaction mixture was stirred at 130° C. for 20 h under a carbon monoxide atmosphere (70 bar). A saturated aq. solution of ammonium chloride was added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (ethyl acetate/n-heptane 0:1 to 1:0) to yield the title compound as a colourless oil (95 mg, 87%), MS (ESI$^+$): m/z=374.1 ([M+H]$^+$).

Step 2: 4-[(R)-3-[(E)-Hydroxyimino]-3-(2-methyl-pyridin-4-yl)-1-o-tolyl-propyl]-benzoic acid To a solution of 4-[(R)-3-(2-methyl-pyridin-4-yl)-3-oxo-1-o-tolyl-propyl]-benzoic acid methyl ester (98 mg) in tetrahydrofuran (3 mL) was added 1 M aq. lithium hydroxide solution (2.62 mL). The reaction mixture was stirred at room temperature for 4 h. A saturated aq. solution of ammonium chloride and ethyl acetate were added, the phases were separated and the inorganic one was extracted with ethyl acetate (2×). The combined organic layers were washed with brine, dried over sodium sulfate, filtered and concentrated in vacuo to yield 4-[(R)-3-(2-methyl-pyridin-4-yl)-3-oxo-1-o-tolyl-propyl]-benzoic acid as a white solid. This was reacted in analogy to example 132, step 6 with hydroxylamine hydrochloride in the presence of sodium hydrogencarbonate to afford the title compound as a white solid (98 mg, 60%), MS (ESI$^-$): m/z=372.9 ([M−H]$^-$).

Example 273

N-(2-Hydroxy-ethyl)-4-[(R)-3-[(E)-hydroxyimino]-3-(2-methyl-pyridin-4-yl)-1-o-tolyl-propyl]-benzamide

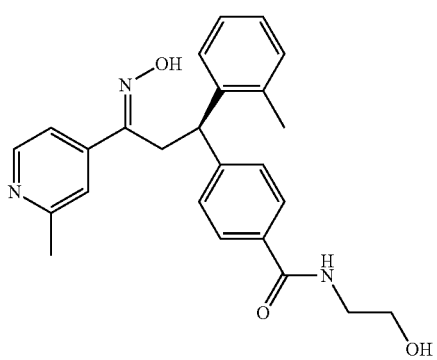 [SMILES: Cc1cc(/C(C[C@H](c2ccc(C(=O)NCCO)cc2)c2ccccc2C)=N/O)ccn1]

In analogy to example 207, step 2, 4-[(R)-3-[(E)-hydroxyimino]-3-(2-methyl-pyridin-4-yl)-1-o-tolyl-propyl]-benzoic acid (example 272) was coupled with 2-aminoethanol using benzotriazol-1-yloxytris(dimethylamino)phosphonium hexafluorophosphate in tetrahydrofuran to give the title compound as a light yellow solid, MS (ESI$^+$): m/z=418.3 [M+H]$^+$.

Example 274

N-(2-Hydroxy-ethyl)-4-[(R)-3-[(E)-hydroxyimino]-3-(2-methyl-pyridin-4-yl)-1-o-tolyl-propyl]-N-methyl-benzamide

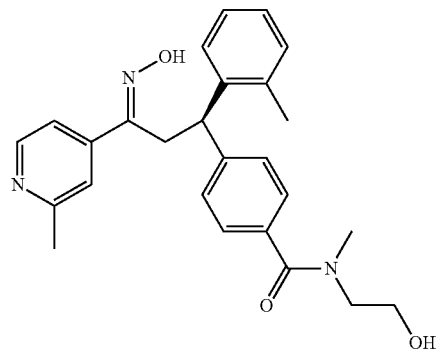 [SMILES: Cc1cc(/C(C[C@H](c2ccc(C(=O)N(C)CCO)cc2)c2ccccc2C)=N/O)ccn1]

In analogy to example 207, step 2, 4-[(R)-3-[(E)-hydroxyimino]-3-(2-methyl-pyridin-4-yl)-1-o-tolyl-propyl]-benzoic acid (example 272) was coupled with 2-(methylamino)ethanol using benzotriazol-1-yloxytris(dimethylamino)phosphonium hexafluorophosphate in tetrahydrofuran to give the title compound as a light yellow solid, MS (ESI$^+$): m/z=432.4 [M+H]$^+$.

Example 275

4-[(R)-3-[(E)-Hydroxyimino]-3-(2-methyl-pyridin-4-yl)-1-o-tolyl-propyl]-N—((S)-2-hydroxy-propyl)-benzamide

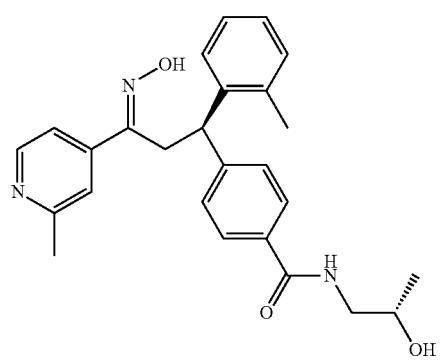 [SMILES: Cc1cc(/C(C[C@H](c2ccc(C(=O)NC[C@H](C)O)cc2)c2ccccc2C)=N/O)ccn1]

In analogy to example 207, step 2, 4-[(R)-3-[(E)-hydroxyimino]-3-(2-methyl-pyridin-4-yl)-1-o-tolyl-propyl]-benzoic acid (example 272) was coupled with (S)-1-aminopropan-2-ol using benzotriazol-1-yloxytris(dimethylamino)phosphonium hexafluorophosphate in tetrahydrofuran to give the title compound as a yellow solid, MS (ESI$^+$): m/z=432.4 [M+H]$^+$.

Example 276

Trans-4-{4-[(R)-3-[(E)-Hydroxyimino]-3-(2-methyl-pyridin-4-yl)-1-o-tolyl-propyl]-benzoylamino}-cyclohexanecarboxylic acid

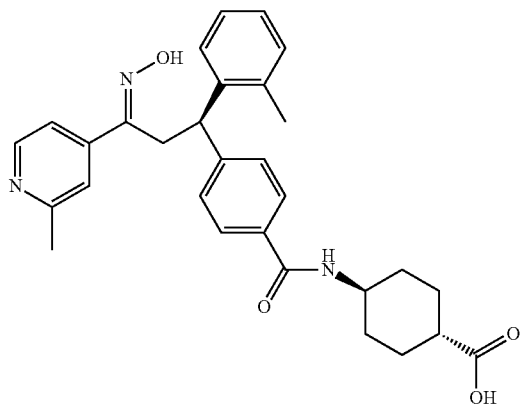 [SMILES: Cc1cc(/C(C[C@H](c2ccc(C(=O)N[C@H]3CC[C@H](C(=O)O)CC3)cc2)c2ccccc2C)=N/O)ccn1]

Step 1: 4-{4-[(R)-3-[(E)-Hydroxyimino]-3-(2-methyl-pyridin-4-yl)-1-o-tolyl-propyl]-benzoylamino}-cyclohexanecarboxylic acid methyl ester In analogy to example 207, step 2, 4-[(R)-3-[(E)-hydroxyimino]-3-(2-methyl-pyridin-4-yl)-1-o-tolyl-propyl]-benzoic acid (example 272) was coupled with trans-methyl 4-aminocyclohexanecarboxylate hydrochloride using benzotriazol-1-yloxytris(dimethylamino)-phosphonium hexafluorophosphate in tetrahydrofuran to give the title compound as a light yellow viscous oil.

Step 2: trans-4-{4-[(R)-3-[(E)-Hydroxyimino]-3-(2-methyl-pyridin-4-yl)-1-o-tolyl-propyl]-benzoylamino}-cyclohexanecarboxylic acid In analogy to example 169, step 2, 4-{4-[(R)-3-[(E)-hydroxyimino]-3-(2-methyl-pyridin-4-yl)-1-o-tolyl-propyl]-benzoylamino}-cyclohexanecarboxylic acid methyl ester was hydrolyzed to give the title compound as a white solid, MS (ESI$^-$): m/z=498.2 [M−H]$^-$.

Example 277

4-[(R)-3-[(E)-Hydroxyimino]-3-(2-methyl-pyridin-4-yl)-1-o-tolyl-propyl]-N,N-dimethyl-benzamide

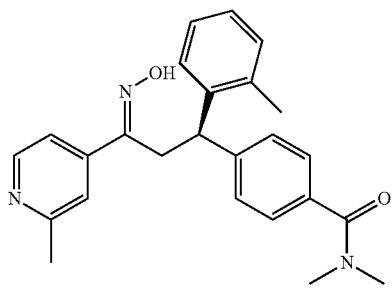 [SMILES: Cc1cc(/C(C[C@H](c2ccc(C(=O)N(C)C)cc2)c2ccccc2C)=N/O)ccn1]

Step 1: N,N-Dimethyl-4-[(R)-3-(2-methyl-pyridin-4-yl)-3-oxo-1-o-tolyl-propyl]-benzamide In analogy to example 207, step 2, 4-[(R)-3-(2-methyl-pyridin-4-yl)-3-oxo-1-o-tolyl-propyl]-benzoic acid (intermediate of example 272, step 2) was coupled with dimethylamine hydrochloride using benzotriazol-1-yloxytris(dimethylamino)phosphonium hexafluorophosphate in tetrahydrofuran to give the title compound as an off-white foam, MS (ESI$^+$): m/z=387.2 [M+H]$^+$.

Step 2: 4-[(R)-3-[(E)-Hydroxyimino]-3-(2-methyl-pyridin-4-yl)-1-o-tolyl-propyl]-N,N-dimethyl-benzamide In analogy to example 132, step 6, from N,N-dimethyl-4-[(R)-3-(2-methyl-pyridin-4-yl)-3-oxo-1-o-tolyl-propyl]-benzamide and hydroxylamine hydrochloride in the presence of sodium hydrogencarbonate was prepared the title compound as a white foam, MS (ESI$^+$): m/z=402.4 ([M+H]$^+$).

Example 278

4-[(R)-3-[(E)-Hydroxyimino]-3-(2-methyl-pyridin-4-yl)-1-o-tolyl-propyl]-N-methyl-benzamide

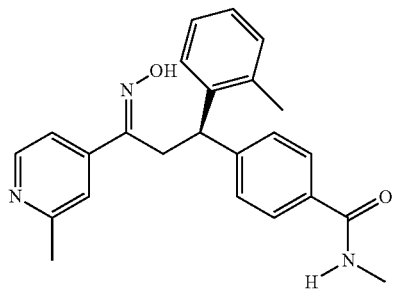 [SMILES: CNC(=O)c1ccc([C@@H](C/C(=N\O)c2ccnc(C)c2)c2ccccc2C)cc1]

Step 1: N-Methyl-4-[(R)-3-(2-methyl-pyridin-4-yl)-3-oxo-1-o-tolyl-propyl]-benzamide In analogy to example 207, step 2, 4-[(R)-3-(2-methyl-pyridin-4-yl)-3-oxo-1-o-tolyl-propyl]-benzoic acid (intermediate of example 272, step 2) was coupled with methylamine using benzotriazol-1-yloxytris(dimethylamino)phosphonium hexafluorophosphate in tetrahydrofuran to give the title compound as a white foam, MS (ESI$^+$): m/z=373.1 [M+H]$^+$.

Step 2: 4-[(R)-3-[(E)-Hydroxyimino]-3-(2-methyl-pyridin-4-yl)-1-o-tolyl-propyl]-N-methyl-benzamide In analogy to example 132, step 6, from N-methyl-4-[(R)-3-(2-methyl-pyridin-4-yl)-3-oxo-1-o-tolyl-propyl]-benzamide and hydroxylamine hydrochloride in the presence of sodium hydrogencarbonate was prepared the title compound as a colourless oil, MS (ESI$^+$): m/z=388.2 ([M+H]$^+$).

Example 279

1-{4-[(R)-3-[(E)-Hydroxyimino]-3-(2-methyl-pyridin-4-yl)-1-o-tolyl-propyl]-phenyl}-azetidine-3-carboxylic acid

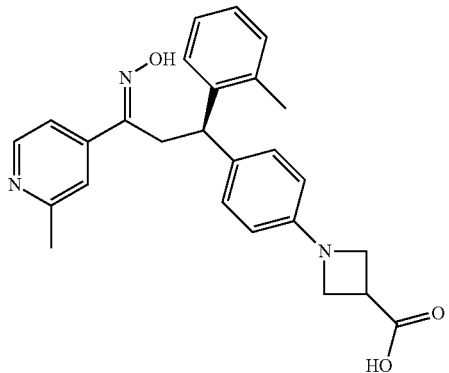 [SMILES: Cc1cc(/C(C[C@H](c2ccc(N3CC(C(=O)O)C3)cc2)c2ccccc2C)=N/O)ccn1]

Step 1: 1-{4-[(R)-3-(2-Methyl-pyridin-4-yl)-3-oxo-1-o-tolyl-propyl]-phenyl}-azetidine-3-carboxylic acid In analogy to example 39, from (R)-3-(4-bromo-phenyl)-1-(2-methyl-pyridin-4-yl)-3-o-tolyl-propan-1-one (example 142, step 2) and methyl azetidine-3-carboxylate hydrochloride in the presence of tris(dibenzylideneacetone)dipalladium(0) chloroform adduct, 2-dicyclohexyl-phosphino-2',4',6'-triisopropylbiphenyl and cesium carbonate in tert-butanol was prepared 1-{4-[(R)-3-(2-methyl-pyridin-4-yl)-3-oxo-1-o-tolyl-propyl]-phenyl}-azetidine-3-carboxylic acid methyl ester.

In analogy to example 169, step 2, 1-{4-[(R)-3-(2-methyl-pyridin-4-yl)-3-oxo-1-o-tolyl-propyl]-phenyl}-azetidine-3-carboxylic acid methyl ester was hydrolyzed to give the title compound as a yellow foam.

Step 2: 1-{4-[(R)-3-[(E)-Hydroxyimino]-3-(2-methyl-pyridin-4-yl)-1-o-tolyl-propyl]-phenyl}-azetidine-3-carboxylicacid In analogy to example 1, step 2, from 1-{4-[(R)-3-(2-methyl-pyridin-4-yl)-3-oxo-1-o-tolyl-propyl]-phenyl}-azetidine-3-carboxylic acid and hydroxylamine hydrochloride in presence of sodium hydrogencarbonate was prepared the title compound as a light yellow foam, MS (ESI+): m/z=430.3 ([M+H]+).

Example 280

2-Chloromethyl-3-{4-[(R)-3-[(E)-hydroxyimino]-3-(2-methyl-pyridin-4-yl)-1-o-tolyl-propyl]-phenylamino}-propionic acid

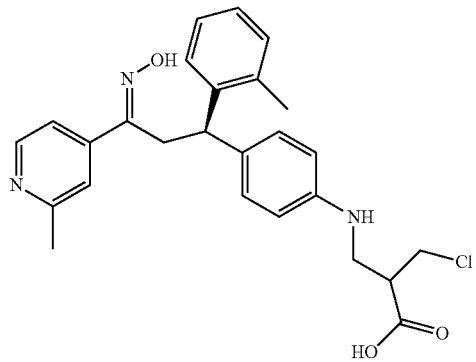 [SMILES: Cc1cc(/C(C[C@H](c2ccc(NCC(CCl)C(=O)O)cc2)c2ccccc2C)=N/O)ccn1]

In analogy to example 132, step 6, from 1-{4-[(R)-3-(2-methyl-pyridin-4-yl)-3-oxo-1-o-tolyl-propyl]-phenyl}-azetidine-3-carboxylic acid (example 279, step 1) and hydroxylamine hydrochloride in the presence of sodium hydrogencarbonate was prepared the title compound as a yellow foam, MS (ESI+): m/z=466.2 ([M+H]+).

Example 281

1-{4-[(S)-3-[(E)-Hydroxyimino]-3-(2-methyl-pyridin-4-yl)-1-o-tolyl-propyl]-phenyl}-piperidine-4-carboxylic acid

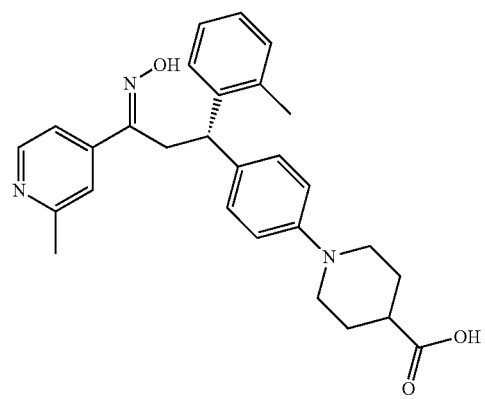 [SMILES: Cc1cc(/C(C[C@@H](c2ccc(N3CCC(C(=O)O)CC3)cc2)c2ccccc2C)=N/O)ccn1]

Step 1: 1-{4-[(S)-3-(2-Methyl-pyridin-4-yl)-3-oxo-1-o-tolyl-propyl]-phenyl}-piperidine-4-carboxylic acid In analogy to example 39, from (S)-3-(4-bromo-phenyl)-1-(2-methyl-pyridin-4-yl)-3-o-tolyl-propan-1-one and ethyl piperidine-4-carboxylate in the presence of tris(dibenzylidene-acetone)dipalladium(0), 2-dicyclohexylphosphino-2',4',6'-triisopropylbiphenyl and sodium tert-butoxide in toluene was prepared 1-{4-[(S)-3-(2-methyl-pyridin-4-yl)-3-oxo-1-o-tolyl-propyl]-phenyl}-piperidine-4-carboxylic acid ethyl ester.

In analogy to example 169, step 2, from 1-{4-[(S)-3-(2-methyl-pyridin-4-yl)-3-oxo-1-o-tolyl-propyl]-phenyl}-piperidine-4-carboxylic acid ethyl ester in presence of 1 M aq. lithium hydroxide solution in tetrahydrofuran was prepared 1-{4-[(S)-3-(2-methyl-pyridin-4-yl)-3-oxo-1-o-tolyl-propyl]-phenyl}-piperidine-4-carboxylic acid as a light yellow solid, MS (ESI−): m/z=441.3 ([M−H]−).

Step 2: 1-{4-[(S)-3-[(E)-Hydroxyimino]-3-(2-methyl-pyridin-4-yl)-1-o-tolyl-propyl]-phenyl}-piperidine-4-carboxylic acid In analogy to example 132, step 6, from 1-{4-[(S)-3-(2-methyl-pyridin-4-yl)-3-oxo-1-o-tolyl-propyl]-phenyl}-piperidine-4-carboxylic acid and hydroxylamine hydrochloride in the presence of sodium hydrogencarbonate was prepared the title compound as a yellow foam, MS (ESI−): m/z=456.3 ([M−H]−).

Example 282

4-[(S)-1-(4-Chloro-2-methyl-phenyl)-3-[(E)-hydroxyimino]-3-(2-methyl-pyridin-4-yl)-propyl]-benzoic acid

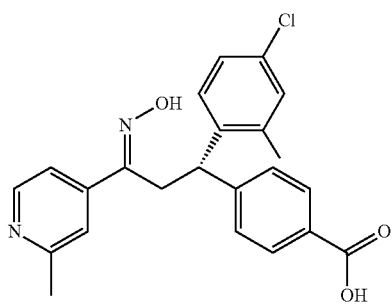 [SMILES: Cc1cc(/C(C[C@@H](c2ccc(C(=O)O)cc2)c2ccc(Cl)cc2C)=N/O)ccn1]

Step 1: (S)-3-(4-Bromo-phenyl)-3-(4-chloro-2-methyl-phenyl)-1-(2-methyl-pyridin-4-yl)-propan-1-one Separation of 3-(4-bromo-phenyl)-3-(4-chloro-2-methyl-phenyl)-1-(2-methyl-pyridin-4-yl)-propan-1-one (example 138, step 4) by chiral HPLC (Chiralcel OD, heptane/isopropanol 3:1) produced (S)-3-(4-bromo-phenyl)-3-(4-chloro-2-methyl-phenyl)-1-(2-methyl-pyridin-4-yl)-propan-1-one (light yellow oil, MS (ESI$^+$): m/z=428.0 ([M+H]$^+$)). and (R)-3-(4-bromo-phenyl)-3-(4-chloro-2-methyl-phenyl)-1-(2-methyl-pyridin-4-yl)-propan-1-one (light yellow oil, MS (ESI$^+$): m/z=428.0 ([M+H]$^+$)).

Step 2: 4-[(S)-1-(4-Chloro-2-methyl-phenyl)-3-(2-methyl-pyridin-4-yl)-3-oxo-propyl]-benzoic acid methyl ester In analogy to example 272, step 1, from (S)-3-(4-bromo-phenyl)-3-(4-chloro-2-methyl-phenyl)-1-(2-methyl-pyridin-4-yl)-propan-1-one and [1,1'-bis(diphenylphosphino)ferrocene]-dichloropalladium(II) dichloromethane adduct in the presence of triethylamine and carbon monoxide gas was prepared the title compound as a light red foam, MS (ESI$^+$): m/z=408.3 ([M+H]$^+$).

Step 3: 4-[(S)-1-(4-Chloro-2-methyl-phenyl)-3-(2-methyl-pyridin-4-yl)-3-oxo-propyl]-benzoic acid In analogy to example 272, step 2, from 4-[(S)-1-(4-chloro-2-methyl-phenyl)-3-(2-methyl-pyridin-4-yl)-3-oxo-propyl]-benzoic acid methyl ester in presence of 1 M aq. lithium hydroxide solution was prepared the title compound as an off-white solid, MS (ESI$^-$): m/z=392.0 ([M−H]$^-$).

Step 4: 4-[(S)-1-(4-Chloro-2-methyl-phenyl)-3-[(E)-hydroxyimino]-3-(2-methyl-pyridin-4-yl)-propyl]-benzoic acid In analogy to example 132, step 6, from 4-[(S)-1-(4-chloro-2-methyl-phenyl)-3-(2-methyl-pyridin-4-yl)-3-oxo-propyl]-benzoic acid and hydroxylamine hydrochloride in the presence of sodium hydrogencarbonate was prepared the title compound as a light yellow solid, MS (ESI$^+$): m/z=409.3 ([M+H]$^+$).

Example 283

4-[(S)-1-(4-Chloro-2-methyl-phenyl)-3-[(E)-hydroxyimino]-3-(2-methyl-pyridin-4-yl)-propyl]-N,N-dimethyl-benzamide

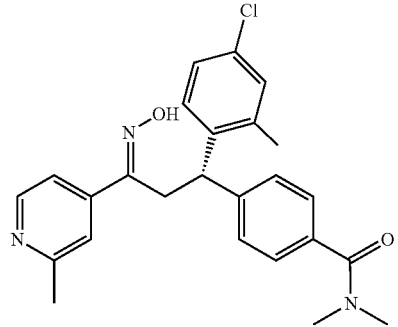 [SMILES: Cc1cc(/C(C[C@@H](c2ccc(C(=O)N(C)C)cc2)c2ccc(Cl)cc2C)=N/O)ccn1]

Step 1: 4-[(S)-1-(4-Chloro-2-methyl-phenyl)-3-(2-methyl-pyridin-4-yl)-3-oxo-propyl]-N,N-dimethyl-benzamide In analogy to example 207, step 2, 4-[(S)-1-(4-chloro-2-methyl-phenyl)-3-(2-methyl-pyridin-4-yl)-3-oxo-propyl]-benzoic acid (example 282, step 3) was coupled with dimethylamine hydrochloride using benzotriazol-1-yloxytris(dimethylamino)phosphonium hexafluorophosphate in tetrahydrofuran to give the title compound as an off-white foam, MS (ESI$^+$): m/z=421.1 [M+H]$^+$.

Step 2: 4-[(S)-1-(4-Chloro-2-methyl-phenyl)-3-[(E)-hydroxyimino]-3-(2-methyl-pyridin-4-yl)-propyl]-N,N-dimethyl-benzamide In analogy to example 132, step 6, from 4-[(S)-1-(4-chloro-2-methyl-phenyl)-3-(2-methyl-pyridin-4-yl)-3-oxo-propyl]-N,N-dimethyl-benzamide and hydroxylamine hydrochloride in the presence of sodium hydrogencarbonate was prepared the title compound as a white foam, MS (ESI$^+$): m/z=436.3 ([M+H]$^+$).

Example 284

1-{4-[(R)-1-(4-Chloro-2-methyl-phenyl)-3-[(E)-hydroxyimino]-3-(2-methyl-pyridin-4-yl)-propyl]-phenyl}-piperidine-4-carboxylic acid

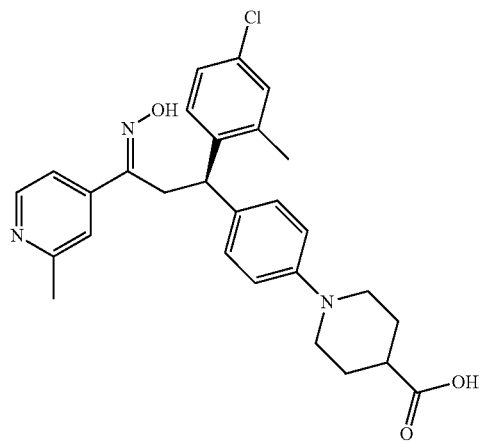 [SMILES: Cc1cc(/C(C[C@H](c2ccc(N3CCC(C(=O)O)CC3)cc2)c2ccc(Cl)cc2C)=N/O)ccn1]

Step 1: 1-{4-[(R)-1-(4-Chloro-2-methyl-phenyl)-3-(2-methyl-pyridin-4-yl)-3-oxo-propyl]-phenyl}-piperidine-4-carboxylic acid In analogy to example 39, from (R)-3-(4-bromo-phenyl)-3-(4-chloro-2-methyl-phenyl)-1-(2-methyl-pyridin-4-yl)-propan-1-one (example 282, step 1) and ethyl piperidine-4-carboxylate in the presence of tris(dibenzylideneacetone)dipalladium(0), 2-dicyclohexylphosphino-2',4',6'-triisopropylbiphenyl and sodium tert-butoxide in toluene was prepared 1-{4-[(R)-1-(4-chloro-2-methyl-phenyl)-3-(2-methyl-pyridin-4-yl)-3-oxo-propyl]-phenyl}-piperidine-4-carboxylic acid ethyl ester.

In analogy to example 169, step 2, from 1-{4-[(R)-1-(4-chloro-2-methyl-phenyl)-3-(2-methyl-pyridin-4-yl)-3-oxo-propyl]-phenyl}-piperidine-4-carboxylic acid ethyl ester in presence of 1 M aq. lithium hydroxide solution in tetrahydrofuran was prepared 1-{4-[(R)-1-(4-chloro-2-methyl-phenyl)-3-(2-methyl-pyridin-4-yl)-3-oxo-propyl]-phenyl}-piperidine-4-carboxylic acid as a yellow solid, MS (ESI$^-$): m/z=475.1 ([M−H]$^-$).

Step 2: 1-{4-[(R)-1-(4-Chloro-2-methyl-phenyl)-3-[(E)-hydroxyimino]-3-(2-methyl-pyridin-4-yl)-propyl]-phenyl}-piperidine-4-carboxylic acid In analogy to example 132, step 6, from 1-{4-[(R)-1-(4-chloro-2-methyl-phenyl)-3-(2-methyl-pyridin-4-yl)-3-oxo-propyl]-phenyl}-piperidine-4-carboxylic acid and hydroxylamine hydrochloride in the presence of sodium hydrogencarbonate was prepared the title compound as a yellow semisolid, MS (ESI$^-$): m/z=490.3 ([M−H]$^-$).

Example 285

1-{4-[(S)-1-(4-Chloro-2-methyl-phenyl)-3-[(E)-hydroxyimino]-3-(2-methyl-pyridin-4-yl)-propyl]-phenyl}-piperidine-4-carboxylic acid

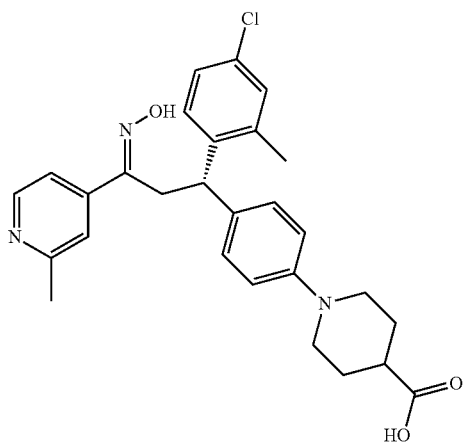 [SMILES: Cc1cc(/C(C[C@@H](c2ccc(N3CCC(C(=O)O)CC3)cc2)c2ccc(Cl)cc2C)=N/O)ccn1]

Step 1: 1-{4-[(S)-1-(4-Chloro-2-methyl-phenyl)-3-(2-methyl-pyridin-4-yl)-3-oxo-propyl]-phenyl}-piperidine-4-carboxylic acid In analogy to example 39, from (S)-3-(4-bromo-phenyl)-3-(4-chloro-2-methyl-phenyl)-1-(2-methyl-pyridin-4-yl)-propan-1-one (example 282, step 1) and ethyl piperidine-4-carboxylate in the presence of tris(dibenzylideneacetone)dipalladium(0), 2-dicyclohexylphosphino-2',4',6'-triisopropylbiphenyl and sodium tert-butoxide in toluene was prepared 1-{4-[(S)-1-(4-chloro-2-methyl-phenyl)-3-(2-methyl-pyridin-4-yl)-3-oxo-propyl]-phenyl}-piperidine-4-carboxylic acid ethyl ester.

In analogy to example 169, step 2, from 1-{4-[(S)-1-(4-chloro-2-methyl-phenyl)-3-(2-methyl-pyridin-4-yl)-3-oxo-propyl]-phenyl}-piperidine-4-carboxylic acid ethyl ester in presence of 1 M aq. lithium hydroxide solution in tetrahydrofuran was prepared 1-{4-[(S)-1-(4-chloro-2-methyl-phenyl)-3-(2-methyl-pyridin-4-yl)-3-oxo-propyl]-phenyl}-piperidine-4-carboxylic acid as a yellow foam, MS (ESI$^+$): m/z=477.2 ([M+H]$^+$).

Step 2: 1-{4-[(S)-1-(4-Chloro-2-methyl-phenyl)-3-[(E)-hydroxyimino]-3-(2-methyl-pyridin-4-yl)-propyl]-phenyl}-piperidine-4-carboxylic acid In analogy to example 132, step 6, from 1-{4-[(S)-1-(4-chloro-2-methyl-phenyl)-3-(2-methyl-pyridin-4-yl)-3-oxo-propyl]-phenyl}-piperidine-4-carboxylic acid and hydroxylamine hydrochloride in the presence of sodium hydrogencarbonate was prepared the title compound as a light yellow foam, MS (ESI$^-$): m/z=490.3 ([M−H]$^-$).

Example 286

2-{4-[(S)-3-[(E)-Hydroxyimino]-3-(2-methyl-pyridin-4-yl)-1-o-tolyl-propyl]-phenyl}-malonic acid diethyl ester

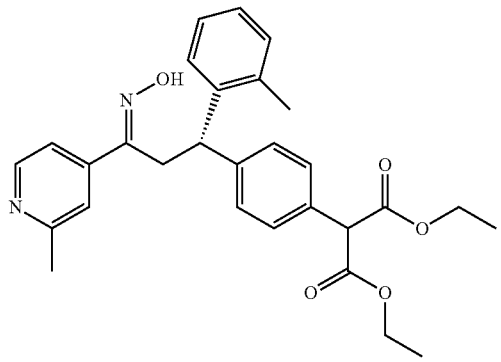 [SMILES: CCOC(=O)C(C(=O)OCC)c1ccc([C@H](C/C(=N\O)c2ccnc(C)c2)c2ccccc2C)cc1]

Step 1: (S)-3-(4-Bromo-phenyl)-1-(2-methyl-pyridin-4-yl)-3-o-tolyl-propan-1-one In analogy to example 74, step 5, from (S)-3-(4-bromo-phenyl)-N-methoxy-N-methyl-3-o-tolyl-propionamide (example 142, step 1) and 4-bromo-2-methylpyridine was prepared the title compound as white solid, MS (ESI$^+$): m/z=394.0 ([M+H]$^+$, 1Br).

Step 2: 2-{4-[(S)-3-(2-Methyl-pyridin-4-yl)-3-oxo-1-o-tolyl-propyl]-phenyl}-malonic acid diethyl ester To a solution of (S)-3-(4-bromo-phenyl)-1-(2-methyl-pyridin-4-yl)-3-o-tolyl-propan-1-one (600 mg) in diethyl malonate (11 mL) were added sodium hydride (124 mg), tris(dibenzylideneacetone)dipalladium(0) (81.4 mg) and 2-(di-tert-butylphosphino)biphenyl (26.5 mg) at room temperature.

The reaction mixture was stirred at 135° C. for 1½ h. A saturated aq. solution of ammonium chloride and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (10% to 70% ethyl acetate in n-heptane) to yield the title compound as a light yellow oil (514 mg, 71%), MS (ESI$^+$): m/z=474.3 ([M+H]$^+$).

Step 3: 2-{4-[(S)-3-[(E)-Hydroxyimino]-3-(2-methyl-pyridin-4-yl)-1-o-tolyl-propyl]-phenyl}-malonic acid diethyl ester In analogy to example 1, step 2, from 2-{4-[(S)-3-(2-methyl-pyridin-4-yl)-3-oxo-1-o-tolyl-propyl]-phenyl}-malonic acid diethyl ester and hydroxylamine hydrochloride in the presence of sodium hydrogencarbonate was prepared the title compound as a mixture of E and Z isomers (2.7:1) as a white oil, MS (ESI$^+$): m/z=489.3 ([M+H]$^+$.

Example 287

(R)-3-(4-Ethynyl-phenyl)-1-(2-methyl-pyridin-4-yl)-3-o-tolyl-propan-1-one oxime

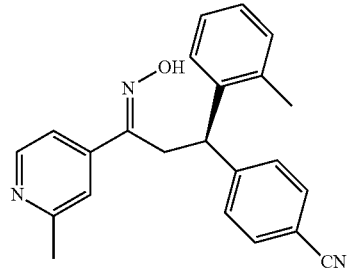 [SMILES: Cc1cc(/C(C[C@H](c2ccc(C#N)cc2)c2ccccc2C)=N/O)ccn1]

Step 1: (R)-1-(2-Methyl-pyridin-4-yl)-3-o-tolyl-3-(4-trimethylsilanylethynyl-phenyl)-propan-1-one To a solution of (R)-3-(4-bromo-phenyl)-1-(2-methyl-pyridin-4-yl)-3-o-tolyl-propan-1-one (example 142, step 2, 150 mg) in piperidine (3 mL) were added under argon copper(I) iodide (3.6 mg) and tetrakis-triphenylphosphine palladium (0) (22 mg). The reaction mixture was heated at 50° C. and ethynyltrimethylsilane (480 µL) was added. The reaction mixture was stirred at 50° C. overnight. water and tert-butyl methyl ether were added, the phases were separated and the inorganic one was extracted with tert-butyl methyl ether (2×). The combined organic layers were washed with brine, dried over sodium sulfate, filtered and concentrated in vacuo. The crude product was purified by flash chromatography on silica gel (15% to 50% ethyl acetate in n-heptane) to yield the title compound as a light yellow oil (105 mg, 61%), MS (ESI$^+$): m/z=412.4 ([M+H]$^+$).

Step 2: (R)-3-(4-Ethynyl-phenyl)-1-(2-methyl-pyridin-4-yl)-3-o-tolyl-propan-1-one To a solution of (R)-1-(2-methyl-pyridin-4-yl)-3-o-tolyl-3-(4-trimethylsilanylethynyl-phenyl)-propan-1-one (100 mg) in methanol (5 mL) was added at 0° C. potassium carbonate (3.4 mg). The reaction mixture was stirred at room temperature for 20 h. A saturated aq. solution of ammonium chloride and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (15% to 50% ethyl acetate in n-heptane) to yield the title compound as a colourless oil (60 mg, 95%), MS (ESI$^+$): m/z=340.2 ([M+H]$^+$).

Step 3: (R)-3-(4-Ethynyl-phenyl)-1-(2-methyl-pyridin-4-yl)-3-o-tolyl-propan-1-one oxime In analogy to example 132, step 6, from (R)-3-(4-ethynyl-phenyl)-1-(2-methyl-pyridin-4-yl)-3-o-tolyl-propan-1-one and hydroxylamine hydrochloride in the presence of sodium hydrogencarbonate was prepared the title compound as a white foam, MS (ESI$^+$): m/z=355.4 ([M+H]$^+$).

Example 288

{4-[(R)-3-[(E)-Hydroxyimino]-3-(2-methyl-pyridin-4-yl)-1-o-tolyl-propyl]-phenyl}-acetic acid

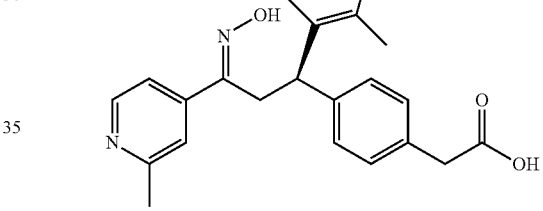

Step 1: (R)-2-(4-(3-(2-methylpyridin-4-yl)-3-oxo-1-o-tolylpropyl)phenyl)acetic acid A mixture of (R)-3-(4-bromophenyl)-1-(2-methylpyridin-4-yl)-3-o-tolylpropan-1-one (example 142, step 2; 3.5 g, 8.88 mmol), diethyl malonate (67.5 g, 421 mmol) sodium hydride (724 mg, 18.1 mmol), tris(dibenzylideneacetone)dipalladium(0) (475 mg, 518 µmol) and 2-(di-tert-butylphosphino)biphenyl (155 mg, 518 µmol) in was heated at 135° C. for 90 min. After cooling the reaction mixture was partitioned between sat. aq. ammonium chloride solution and ethyl acetate. The organic layer was washed with brine, dried over magnesium sulfate, filtered, and concentrated. The residue was dissolved in water (13 mL) and acetic acid (19 mL, 19.8 mmol) then under cooling conc. sulfuric acid (11.9 g, 116 mmol) was added dropwise at a temperature below 30° C. The reaction mixture was heated at 120° C. for 16 h, then partitioned between 2 M aq. sodium hydroxide solution and ethyl acetate. The organic layer was washed with brine, dried over sodium sulfate, filtered, and concentrated in vacuo. The residue was dissolved in tetrahydrofuran (110 mL), then after addition of 1 M aq. lithium hydroxide solution (350 mL, 350 mmol) and methanol (110 mL) the reaction mixture was stirred for 3 h at room temperature. After addition of 1 M aq. potassium hydrogensulfate solution (60 mL) and sat. aq. ammonium chloride solution (100 mL) the reaction mixture was extracted with ethyl acetate. The organic layer was washed with brine, dried over sodium sulfate, filtered, and concentrated. Chromatography (SiO$_2$) produced the title compound (1.96 g, 59%). White foam, MS (ESI$^+$): m/z=374.3 ([M+H]$^+$).

Step 2: {4-[(R)-3-[(E)-Hydroxyimino]-3-(2-methyl-pyridin-4-yl)-1-o-tolyl-propyl]-phenyl}-acetic acid In analogy to example 132, step 6, from {4-[(R)-3-(2-methyl-pyridin-4-yl)-3-oxo-1-o-tolyl-propyl]-phenyl}-acetic acid and hydroxylamine hydrochloride in the presence of sodium hydrogencarbonate was prepared the title compound as a white foam, MS (ESI$^+$): m/z=389.4 ([M+H]$^+$).

Example 289

N-(2-Hydroxy-ethyl)-2-{4-[(R)-3-[(E)-hydroxyimino]-3-(2-methyl-pyridin-4-yl)-1-o-tolyl-propyl]-phenyl}-acetamide

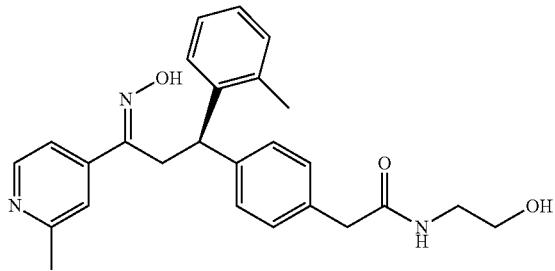 [SMILES: Cc1cc(/C(C[C@H](c2ccc(CC(=O)NCCO)cc2)c2ccccc2C)=N/O)ccn1]

In analogy to example 207, step 2, {4-[(R)-3-[(E)-hydroxyimino]-3-(2-methyl-pyridin-4-yl)-1-o-tolyl-propyl]-phenyl}-acetic acid (example 288) was coupled with 2-aminoethanol using benzotriazol-1-yloxytris(dimethylamino)phosphonium hexafluorophosphate in tetrahydrofuran to give the title compound as a colourless oil, MS (ESI$^+$): m/z=432.3 [M+H]$^+$.

Example 290

4'-{(R)-3-(2-Chloro-pyridin-4-yl)-3-[(E)-hydroxyimino]-1-o-tolyl-propyl}-biphenyl-4-carboxylic acid

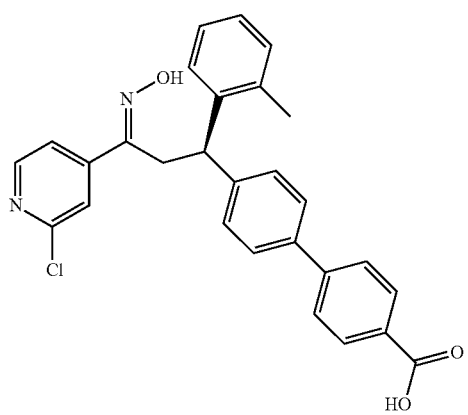 [SMILES: Cc1ccccc1[C@H](C/C(=N\O)c1ccnc(Cl)c1)c1ccc(-c2ccc(C(=O)O)cc2)cc1]

Step 1: 4'-[(R)-2-(Methoxy-methyl-carbamoyl)-1-o-tolyl-ethyl]-biphenyl-4-carboxylic acid In analogy to example 74, step 6, from (R)-3-(4-bromo-phenyl)-N-methoxy-N-methyl-3-o-tolyl-propionamide (example 142, step 1) and 4-boronobenzoic acid was prepared the title compound as a light brown foam, MS (ESI$^+$): m/z=404.2 [M+H]$^+$.

Step 2: 4'-[(R)-2-(Methoxy-methyl-carbamoyl)-1-o-tolyl-ethyl]-biphenyl-4-carboxylic acid, lithium salt To a solution of 4'-[(R)-2-(methoxy-methyl-carbamoyl)-1-o-tolyl-ethyl]-biphenyl-4-carboxylic acid (1.59 g) in 1,4-dioxane (10 mL) was added lithium hydroxide solution (0.067 M in 1,4-dioxane/water, 52.9 mL), then the reaction mixture was stirred for 10 min and concentrated in vacuo to give the title compound.

Step 3: 4'-[(R)-3-(2-Chloro-pyridin-4-yl)-3-oxo-1-o-tolyl-propyl]-biphenyl-4-carboxylic acid In analogy to example 74, step 5, from 4'-[(R)-2-(methoxy-methyl-carbamoyl)-1-o-tolyl-ethyl]-biphenyl-4-carboxylic acid lithium salt, 2-chloro-4-iodopyridine and N,N-diisopropyl-ethylamine was prepared the title compound as a brown foam, MS (ESI$^-$): m/z=454.1 [M−H]$^-$.

Step 4: 4'-{(R)-3-(2-Chloro-pyridin-4-yl)-3-[(E)-hydroxyimino]-1-o-tolyl-propyl}-biphenyl-4-carboxylic acid In analogy to example 132, step 6, from 4'-[(R)-3-(2-chloro-pyridin-4-yl)-3-oxo-1-o-tolyl-propyl]-biphenyl-4-carboxylic acid and hydroxylamine hydrochloride in the presence of sodium hydrogencarbonate was prepared the title compound as an off-white foam, MS (ESI$^-$): m/z=469.1 ([M−H]$^-$).

Example 291

4'-[(R)-3-[(E)-Hydroxyimino]-1-o-tolyl-3-(2-trifluoromethyl-pyridin-4-yl)-propyl]-biphenyl-4-carboxylic acid

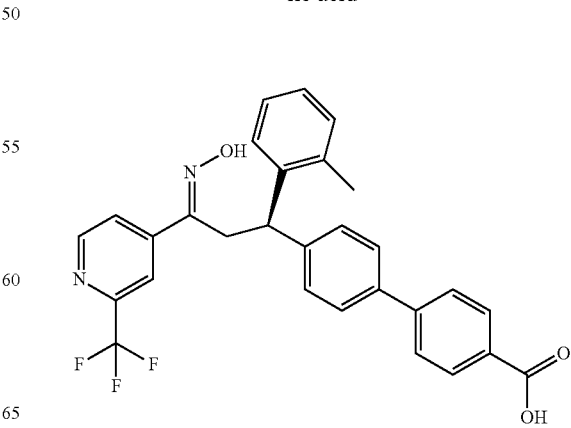

Step 1: 4'-[(R)-3-oxo-1-o-tolyl-3-(2-trifluoromethyl-pyridin-4-yl)-propyl]-biphenyl-4-carboxylic acid In analogy to example 74, step 5, from 4'-[(R)-2-(methoxy-methyl-carbamoyl)-1-o-tolyl-ethyl]-biphenyl-4-carboxylic acid lithium salt (example 290, step 2), 4-iodo-2-(trifluoromethyl)-pyridine and N,N-diisopropylethylamine was prepared the title compound as a brown foam, MS (ESI$^-$): m/z=488.3 [M–H]$^-$.

Step 2: 4'-[(R)-3-[(E)-Hydroxyimino]-1-o-tolyl-3-(2-trifluoromethyl-pyridin-4-yl)-propyl]-biphenyl-4-carboxylic acid In analogy to example 132, step 6, from 4'-[(R)-3-oxo-1-o-tolyl-3-(2-trifluoromethyl-pyridin-4-yl)-propyl]-biphenyl-4-carboxylic acid and hydroxylamine hydrochloride in the presence of sodium hydrogencarbonate was prepared the title compound as a light brown foam, MS (ESI$^-$): m/z=503.0 ([M–H]$^-$).

Example 292

4'-{(R)-3-(2-Chloro-5-fluoro-pyridin-4-yl)-3-[(E)-hydroxyimino]-1-o-tolyl-propyl}-biphenyl-4-carboxylic acid

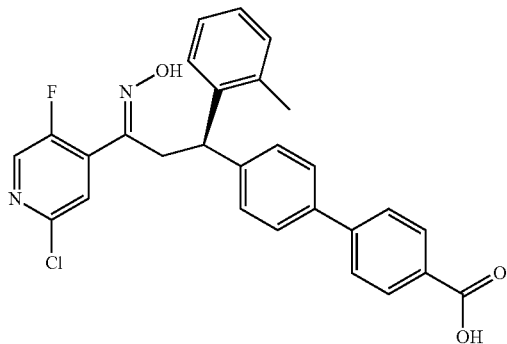 [SMILES: Cc1ccccc1[C@H](C/C(=N\O)c1cc(Cl)ncc1F)c1ccc(-c2ccc(C(=O)O)cc2)cc1]

Step 1: 4'-[(R)-3-(2-Chloro-5-fluoro-pyridin-4-yl)-3-oxo-1-o-tolyl-propyl]-biphenyl-4-carboxylic acid In analogy to example 74, step 5, from 4'-[(R)-2-(methoxy-methyl-carbamoyl)-1-o-tolyl-ethyl]-biphenyl-4-carboxylic acid lithium salt (example 290, step 2), 2-chloro-5-fluoro-4-iodopyridine and N,N-diisopropylethylamine was prepared the title compound as an off-white foam, MS (ESI$^-$): m/z=472.1 [M–H]$^-$.

Step 2: 4'-{(R)-3-(2-Chloro-5-fluoro-pyridin-4-yl)-3-[(E)-hydroxyimino]-1-o-tolyl-propyl}-biphenyl-4-carboxylic acid In analogy to example 132, step 6, from 4'-[(R)-3-(2-chloro-5-fluoro-pyridin-4-yl)-3-oxo-1-o-tolyl-propyl]-biphenyl-4-carboxylic acid and hydroxylamine hydrochloride in the presence of sodium hydrogencarbonate was prepared the title compound as an off-white foam, MS (ESI$^-$): m/z=487.2 ([M–H]$^-$).

Example 293

4'-{(R)-3-(5-Chloro-2-fluoro-pyridin-4-yl)-3-[(E)-hydroxyimino]-1-o-tolyl-propyl}-biphenyl-4-carboxylic acid

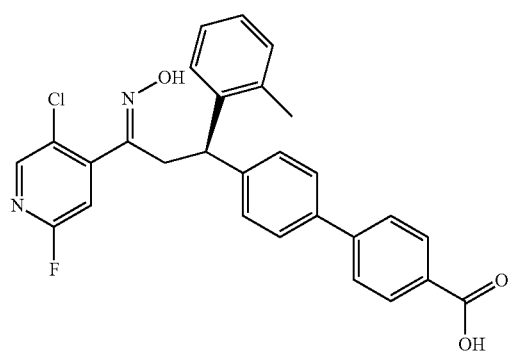 [SMILES: Cc1ccccc1[C@H](C/C(=N\O)c1cc(F)ncc1Cl)c1ccc(-c2ccc(C(=O)O)cc2)cc1]

Step 1: 4'-[(R)-3-(5-Chloro-2-fluoro-pyridin-4-yl)-3-oxo-1-o-tolyl-propyl]-biphenyl-4-carboxylic acid In analogy to example 74, step 5, from 4'-[(R)-2-(methoxy-methyl-carbamoyl)-1-o-tolyl-ethyl]-biphenyl-4-carboxylic acid lithium salt (example 290, step 2) and 5-chloro-2-fluoro-4-iodopyridine at –90° C. was prepared the title compound as an off-white foam, MS (ESI$^-$): m/z=472.0 [M–H]$^-$.

Step 2: 4'-{(R)-3-(5-Chloro-2-fluoro-pyridin-4-yl)-3-[(E)-hydroxyimino]-1-o-tolyl-propyl}-biphenyl-4-carboxylic acid In analogy to example 132, step 6, from 4'-[(R)-3-(5-chloro-2-fluoro-pyridin-4-yl)-3-oxo-1-o-tolyl-propyl]-biphenyl-4-carboxylic acid and hydroxylamine hydrochloride in the presence of sodium hydrogencarbonate was prepared the title compound as a light yellow oil, MS (ESI$^-$): m/z=487.3 ([M–H]$^-$).

Example 294

4'-{(R)-3-(2,6-Dimethyl-pyridin-4-yl)-3-[(E)-hydroxyimino]-1-o-tolyl-propyl}-biphenyl-4-carboxylic acid

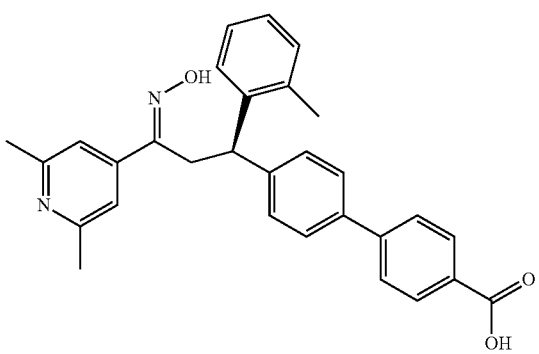 [SMILES: Cc1cc(/C(C[C@H](c2ccc(-c3ccc(C(=O)O)cc3)cc2)c2ccccc2C)=N/O)cc(C)n1]

Step 1: 4'-[(R)-3-(2,6-Dimethyl-pyridin-4-yl)-3-oxo-1-o-tolyl-propyl]-biphenyl-4-carboxylic acid In analogy to example 74, step 5, from 4'-[(R)-2-(methoxy-methyl-carbamoyl)-1-o-tolyl-ethyl]-biphenyl-4-carboxylic acid lithium salt (example 290, step 2) and 4-bromo-2,6-dimethylpyridine at −90° C. was prepared the title compound as a light yellow foam, MS (ESI⁻): m/z=448.1 [M−H]⁻.

Step 2: 4'-{(R)-3-(2,6-Dimethyl-pyridin-4-yl)-3-[(E)-hydroxyimino]-1-o-tolyl-propyl}-biphenyl-4-carboxylic acid In analogy to example 132, step 6, from 4'-[(R)-3-(2,6-dimethyl-pyridin-4-yl)-3-oxo-1-o-tolyl-propyl]-biphenyl-4-carboxylic acid and hydroxylamine hydrochloride in the presence of sodium hydrogencarbonate was prepared the title compound as a white semisolid, MS (ESI⁻): m/z=463.3 ([M−H]⁻).

Example 295

3-(4-Bromo-phenyl)-1-pyridin-4-yl-3-o-tolyl-propan-1-one oxime

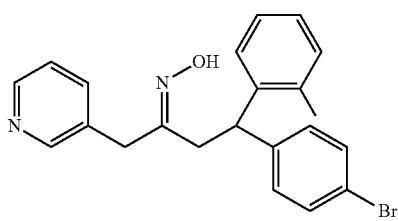 [SMILES: Cc1ccccc1C(C/C(Cc1cccnc1)=N\O)c1ccc(Br)cc1]

Step 1: 3-(4-Bromo-phenyl)-1-pyridin-4-yl-propenone

In analogy to example 11, step 1, from 4-bromobenzaldehyde and 4-acetylpyridine in the presence of sodium hydroxide pellets was prepared the title compound as a yellow solid.

Step 2: 3-(4-Bromo-phenyl)-1-pyridin-4-yl-3-o-tolyl-propan-1-one

In analogy to example 1, step 1, from (E)-3-(4-bromo-phenyl)-1-pyridin-4-yl-propenone and o-tolylboronic acid was prepared the title compound as a yellow foam, MS (ESI⁺): m/z=380.1 ([M+H]⁺, 1Br).

Step 3: 3-(4-Bromo-phenyl)-1-pyridin-4-yl-3-o-tolyl-propan-1-one oxime

In analogy to example 132, step 6, from 3-(4-bromo-phenyl)-1-pyridin-4-yl-3-o-tolyl-propan-1-one and hydroxylamine hydrochloride in the presence of sodium hydrogencarbonate was prepared the title compound as a white foam, MS (ESI⁺): m/z=395.1 ([M+H]⁺, 1Br).

Example 296

4'-[(S)-1-(4-Chloro-2-methyl-phenyl)-3-[(E)-hydroxyimino]-3-(2-methyl-pyridin-4-yl)-propyl]-biphenyl-4-carboxylic acid

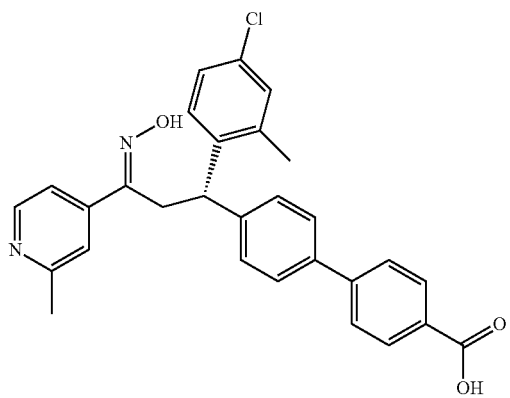 [SMILES: Cc1cc(/C(C[C@@H](c2ccc(-c3ccc(C(=O)O)cc3)cc2)c2ccc(Cl)cc2C)=N/O)ccn1]

Step 1: 4'-[(S)-1-(4-Chloro-2-methyl-phenyl)-3-(2-methyl-pyridin-4-yl)-3-oxo-propyl]-biphenyl-4-carboxylic acid In analogy to example 74, step 6, from (S)-3-(4-bromo-phenyl)-3-(4-chloro-2-methyl-phenyl)-1-(2-methyl-pyridin-4-yl)-propan-1-one (example 282, step 1) and 4-boronobenzoic acid was prepared the title compound as an yellow foam.

Step 2: 4'-[(S)-1-(4-Chloro-2-methyl-phenyl)-3-[(E)-hydroxyimino]-3-(2-methyl-pyridin-4-yl)-propyl]-biphenyl-4-carboxylic acid In analogy to example 132, step 6, from 4'-[(S)-1-(4-chloro-2-methyl-phenyl)-3-(2-methyl-pyridin-4-yl)-3-oxo-propyl]-biphenyl-4-carboxylic acid and hydroxylamine hydrochloride in the presence of sodium hydrogencarbonate was prepared the title compound as a white solid, MS (ESI⁻): m/z=483.1 ([M−H]⁻).

Example 297

4'-[(R)-1-(4-Chloro-2-methyl-phenyl)-3-[(E)-hydroxyimino]-3-(2-methyl-pyridin-4-yl)-propyl]-biphenyl-4-carboxylic acid

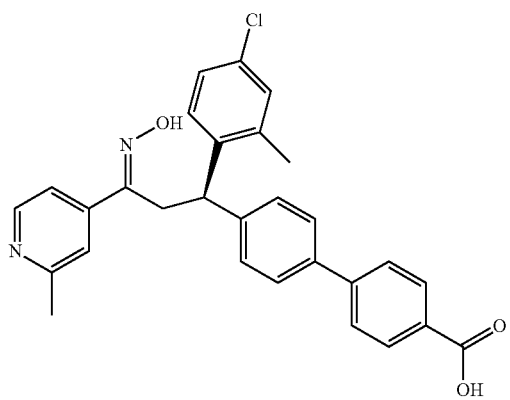 [SMILES: Cc1cc(/C(C[C@H](c2ccc(-c3ccc(C(=O)O)cc3)cc2)c2ccc(Cl)cc2C)=N/O)ccn1]

Step 1: 4'-[(R)-1-(4-Chloro-2-methyl-phenyl)-3-(2-methyl-pyridin-4-yl)-3-oxo-propyl]-biphenyl-4-carboxylic acid In analogy to example 74, step 6, from (R)-3-(4-bromo-phenyl)-3-(4-chloro-2-methyl-phenyl)-1-(2-methyl-pyridin-4-yl)-propan-1-one (example 282, step 1) and 4-boronobenzoic acid was prepared the title compound a brown foam, MS (ESI$^+$): m/z=470.1 ([M+H]$^+$).

Step 2: 4'-[(R)-1-(4-Chloro-2-methyl-phenyl)-3-[(E)-hydroxyimino]-3-(2-methyl-pyridin-4-yl)-propyl]-biphenyl-4-carboxylic acid In analogy to example 132, step 6, from 4'-[(R)-1-(4-chloro-2-methyl-phenyl)-3-(2-methyl-pyridin-4-yl)-3-oxo-propyl]-biphenyl-4-carboxylic acid and hydroxylamine hydrochloride in the presence of sodium hydrogencarbonate was prepared the title compound as a light yellow solid, MS (ESI$^+$): m/z=485.3 ([M+H]$^+$).

Example 298

4'-{(R)-3-[(E)-Hydroxyimino]-4-pyridin-4-yl-1-o-tolyl-butyl}-biphenyl-4-carboxylic acid

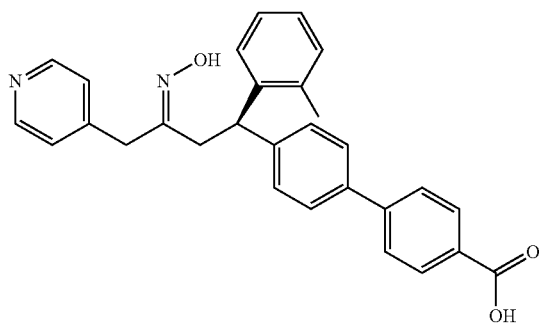 [SMILES: Cc1ccccc1[C@H](C/C(Cc1ccncc1)=N\O)c1ccc(-c2ccc(C(=O)O)cc2)cc1]

Step 1: (R)-4-(4-Bromo-phenyl)-1-pyridin-4-yl-4-o-tolyl-butan-2-one

To a solution of 4-methylpyridine (308 mg, 3.31 mmol) in tetrahydrofuran at −78° C. was added dropwise n-butyllithium solution (1.6 M in hexane, 2.07 mL, 3.31 mmol). The reaction mixture was stirred for 1 hour at room temperature and cooled down again to −78° C. (R)-3-(4-bromo-phenyl)-N-methoxy-N-methyl-3-o-tolyl-propionamide (example 142, step 1; 400 mg, 1.1 mmol) was added and the reaction mixture was stirred at room temperature for 3 hours. A saturated solution of sodium hydrogencarbonate and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (10% methanol in dichloromethane) to yield the title compound as a yellow oil (51%), MS (ESI$^+$): m/z=394.0 ([M+H]$^+$).

Step 2: (R,Z)-4-(4-Bromo-phenyl)-1-pyridin-4-yl-4-o-tolyl-butan-2-one oxime

In analogy to example 1, step 2, from (R)-4-(4-bromo-phenyl)-1-pyridin-4-yl-4-o-tolyl-butan-2-one and hydroxylamine hydrochloride in the presence of sodium hydrogencarbonate was prepared the title compound as a colourless oil, MS (ESI$^+$): m/z=409.1 ([M+H]$^+$, 1Br).

Step 3: 4'-{(R)-3-[(E)-Hydroxyimino]-4-pyridin-4-yl-1-o-tolyl-butyl}-biphenyl-4-carboxylic acid In analogy to example 74, step 6, from (R,Z)-4-(4-bromo-phenyl)-1-pyridin-4-yl-4-o-tolyl-butan-2-one oxime and 4-boronobenzoic acid was prepared 4'-{(R)-3-[(Z)-hydroxyimino]-4-pyridin-4-yl-1-o-tolyl-butyl}-biphenyl-4-carboxylic acid.

The crude was dissolved in 1,2-dimethoxyethane and hydrogen chloride solution (4 M in 1,4-dioxane) was added. The reaction mixture was stirred at 50° C. for 16 hours. A saturated aq. solution of ammonium chloride and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (0% to 10% methanol in dichloromethane) to yield the title compound as a yellow solid (68%), MS (ESI$^+$): m/z=451.2 ([M+H]$^+$).

Example 299

1-{4-[(R)-3-[(E)-Hydroxyimino]-3-(2-methyl-pyridin-4-yl)-1-o-tolyl-propyl]-phenyl}-pyrrolidin-2-one

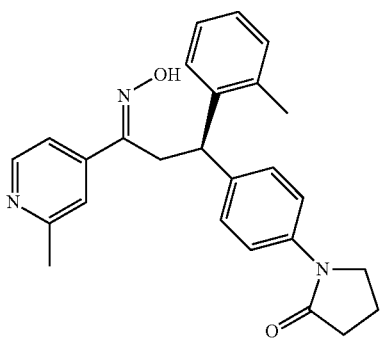 [SMILES: Cc1cc(/C(C[C@H](c2ccc(N3CCCC3=O)cc2)c2ccccc2C)=N/O)ccn1]

Step 1: 1-{4-[(R)-3-(2-Methyl-pyridin-4-yl)-3-oxo-1-o-tolyl-propyl]-phenyl}-pyrrolidin-2-one In analogy to example 39, from (R)-3-(4-bromo-phenyl)-1-(2-methyl-pyridin-4-yl)-3-o-tolyl-propan-1-one (example 142, step 2) and pyrrolidin-2-one in the presence of tris(dibenzylideneacetone)dipalladium(0), 4,5-bis(diphenylphosphino)-9,9-dimethylxanthene and cesium carbonate in 1,4-dioxane was prepared the title compound as a white semisolid, MS (ESI$^+$): m/z=399.1 ([M+H]$^+$).

Step 2: 1-{4-[(R)-3-[(E)-Hydroxyimino]-3-(2-methyl-pyridin-4-yl)-1-o-tolyl-propyl]-phenyl}-pyrrolidin-2-one In analogy to example 132, step 6, from 1-{4-[(R)-3-(2-methyl-pyridin-4-yl)-3-oxo-1-o-tolyl-propyl]-phenyl}-pyrrolidin-2-one and hydroxylamine hydrochloride in the presence of sodium hydrogencarbonate was prepared the title compound as a white foam, MS (ESI$^+$): m/z=414.3 ([M+H]$^+$).

Example 300

3-{4-[(R)-3-[(E)-Hydroxyimino]-3-(2-methyl-pyridin-4-yl)-1-o-tolyl-propyl]-phenylamino}-cyclobutanecarboxylic acid

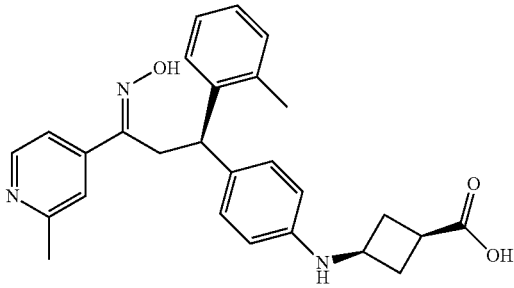 [SMILES: Cc1cc(/C(C[C@H](c2ccc(N[C@H]3C[C@@H](C(=O)O)C3)cc2)c2ccccc2C)=N/O)ccn1]

Step 1: 3-{4-[(R)-3-(2-Methyl-pyridin-4-yl)-3-oxo-1-o-tolyl-propyl]-phenylamino}-cyclobutanecarboxylic acid In analogy to example 39, from (R)-3-(4-bromo-phenyl)-1-(2-methyl-pyridin-4-yl)-3-O— tolyl-propan-1-one (example 142, step 2) and cis-ethyl 3-aminocyclobutanecarboxylate hydrochloride in the presence of tris(dibenzylideneacetone)dipalladium(0), 4,5-bis(diphenylphosphino)-9,9-dimethylxanthene and cesium carbonate in 1,4-dioxane was prepared 3-{4-[(R)-3-(2-methyl-pyridin-4-yl)-3-oxo-1-o-tolyl-propyl]-phenylamino}-cyclobutanecarboxylic acid ethyl ester. In analogy to example 169, step 2, from 3-{4-[(R)-3-(2-methyl-pyridin-4-yl)-3-oxo-1-o-tolyl-propyl]-phenylamino}-cyclobutanecarboxylic acid ethyl ester in presence of 1 M aq. lithium hydroxide solution in tetrahydrofuran was prepared 3-{4-[(R)-3-(2-methyl-pyridin-4-yl)-3-oxo-1-o-tolyl-propyl]-phenylamino}-cyclobutanecarboxylic acid as a yellow foam, MS (ESI$^+$): m/z=429.2 ([M+H]$^+$).

Step 2: 3-{4-[(R)-3-[(E)-Hydroxyimino]-3-(2-methyl-pyridin-4-yl)-1-o-tolyl-propyl]-phenylamino}-cyclobutanecarboxylic acid In analogy to example 132, step 6, from 3-{4-[(R)-3-(2-methyl-pyridin-4-yl)-3-oxo-1-o-tolyl-propyl]-phenylamino}-cyclobutanecarboxylic acid in the presence of sodium hydrogen-carbonate was prepared the title compound as a light yellow foam, MS (ESI$^+$): m/z=444.2 ([M+H]$^+$).

Example 301

4-((E)-3-(Hydroxyimino)-3-(1-methyl-6-oxo-1,6-dihydropyridin-3-yl)-1-o-tolylpropyl)-N-((R)-1-hydroxypropan-2-yl)benzamide

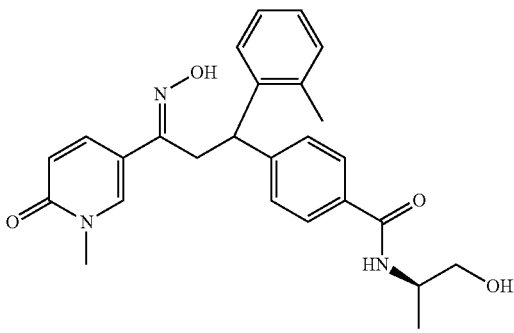 [SMILES: Cc1ccccc1C(C/C(=N\O)c1ccc(=O)n(C)c1)c1ccc(C(=O)N[C@H](C)CO)cc1]

Step 1: N—((R)-1-Hydroxypropan-2-yl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (R)-2-aminopropan-1-ol using benzotriazol-1-yloxytris(dimethylamino)phosphonium hexafluorophosphate in tetrahydrofuran to give the title compound as an off-white solid, MS (ESI$^+$): m/z=433.3 [M+H]$^+$.

Step 2: 4-((E)-3-(Hydroxyimino)-3-(1-methyl-6-oxo-1,6-dihydropyridin-3-yl)-1-o-tolylpropyl)-N—((R)-1-hydroxypropan-2-yl)benzamide In analogy to example 151, step 3, N—((R)-1-hydroxypropan-2-yl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid, MS (ESI$^+$): m/z=448.2 [M+H]$^+$.

Example 302

4-((E)-3-(Hydroxyimino)-3-(1-methyl-6-oxo-1,6-dihydropyridin-3-yl)-1-o-tolylpropyl)-N-((S)-1-hydroxypropan-2-yl)benzamide

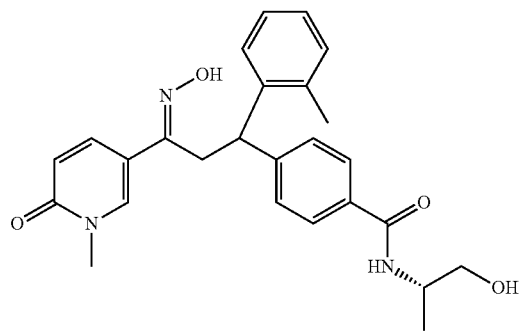 [SMILES: Cc1ccccc1C(C/C(=N\O)c1ccc(=O)n(C)c1)c1ccc(C(=O)N[C@@H](C)CO)cc1]

Step 1: N—((S)-1-Hydroxypropan-2-yl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (S)-2-aminopropan-1-ol using benzotriazol-1-yloxytris(dimethylamino)phosphonium hexafluorophosphate in tetrahydrofuran to give the title compound as an off-white solid, MS (ESI$^+$): m/z=433.3 [M+H]$^+$.

Step 2: 4-((E)-3-(Hydroxyimino)-3-(1-methyl-6-oxo-1,6-dihydropyridin-3-yl)-1-o-tolylpropyl)-N—((S)-1-hydroxypropan-2-yl)benzamide In analogy to example 151, step 3, N—((S)-1-hydroxypropan-2-yl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid, MS (ESI$^+$): m/z=448.2 [M+H]$^+$.

Example 303

(E)-N-(1-Hydroxy-2-methylpropan-2-yl)-4-(3-(hydroxyimino)-3-(1-methyl-6-oxo-1,6-dihydropyridin-3-yl)-1-o-tolylpropyl)benzamide

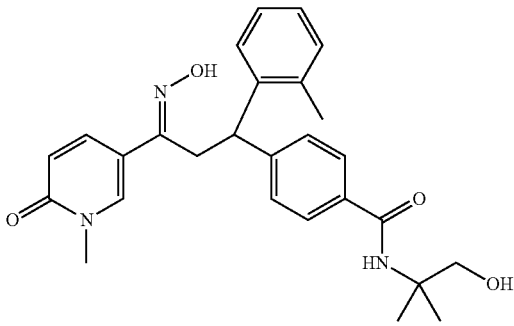 [SMILES: Cc1ccccc1C(C/C(=N\O)c1ccc(=O)n(C)c1)c1ccc(C(=O)NC(C)(C)CO)cc1]

Step 1: N-(1-Hydroxy-2-methylpropan-2-yl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with 2-amino-2-methylpropan-1-ol using benzotriazol-1-yloxytris(dimethylamino)phosphonium hexafluorophosphate in tetrahydrofuran to give the title compound as an off-white solid, MS (ESI$^+$): m/z=447.3 [M+H]$^+$.

Step 2: (E)-N-(1-Hydroxy-2-methylpropan-2-yl)-4-(3-(hydroxyimino)-3-(1-methyl-6-oxo-1,6-dihydro-pyridin-3-yl)-1-o-tolylpropyl)benzamide In analogy to example 151, step 3, N-(1-hydroxy-2-methylpropan-2-yl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid containing <10% of the corresponding Z isomer, MS (ESI$^+$): m/z=462.3 [M+H]$^+$.

Example 304

(E)-N-(1,3-Dihydroxypropan-2-yl)-4-(3-(hydroxyimino)-3-(1-methyl-6-oxo-1,6-dihydropyridin-3-yl)-1-o-tolylpropyl)benzamide

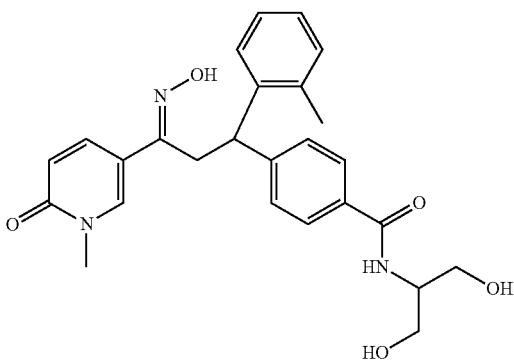 [SMILES: Cc1ccccc1C(C/C(=N\O)c1ccc(=O)n(C)c1)c1ccc(C(=O)NC(CO)CO)cc1]

Step 1: N-(1,3-Dihydroxypropan-2-yl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with 2-aminopropane-1,3-diol using benzotriazol-1-yloxytris(dimethylamino)phosphonium hexafluorophosphate in tetrahydrofuran to give the title compound as an off-white solid, MS (ESI$^+$): m/z=449.2 [M+H]$^+$.

Step 2: (E)-N-(1,3-Dihydroxypropan-2-yl)-4-(3-(hydroxyimino)-3-(1-methyl-6-oxo-1,6-dihydropyridin-3-yl)-1-o-tolylpropyl)benzamide In analogy to example 151, step 3, N-(1,3-dihydroxypropan-2-yl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid containing <10% of the corresponding Z isomer, MS (ESI$^+$): m/z=464.2 [M+H]$^+$.

Example 305

N—((R)-1-hydroxy-3-methylbutan-2-yl)-4-((E)-3-(hydroxyimino)-3-(1-methyl-6-oxo-1,6-dihydropyridin-3-yl)-1-o-tolylpropyl)benzamide

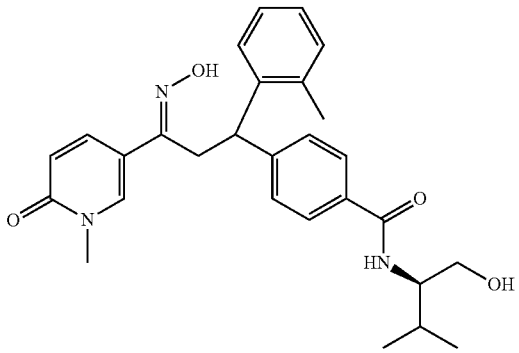 [SMILES: Cc1ccccc1C(C/C(=N\O)c1ccc(=O)n(C)c1)c1ccc(C(=O)N[C@@H](CO)C(C)C)cc1]

Step 1: N—((R)-1-Hydroxy-3-methylbutan-2-yl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (R)-2-amino-3-methylbutan-1-ol using benzotriazol-1-yloxytris(dimethylamino)phosphonium hexafluorophosphate in tetrahydrofuran to give the title compound as an off-white solid, MS (ESI$^+$): m/z=461.3 [M+H]$^+$.

Step 2: N—((R)-1-Hydroxy-3-methylbutan-2-yl)-4-((E)-3-(hydroxyimino)-3-(1-methyl-6-oxo-1,6-dihydropyridin-3-yl)-1-o-tolylpropyl)benzamide In analogy to example 151, step 3, N—((R)-1-hydroxy-3-methylbutan-2-yl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid containing <10% of the corresponding Z isomer, MS (ESI$^+$): m/z=476.2 [M+H]$^+$.

Example 306

N—((R)-1-Hydroxy-3-methylbutan-2-yl)-4-((E)-3-(hydroxyimino)-3-(1-methyl-6-oxo-1,6-dihydropyridin-3-yl)-1-o-tolylpropyl)benzamide

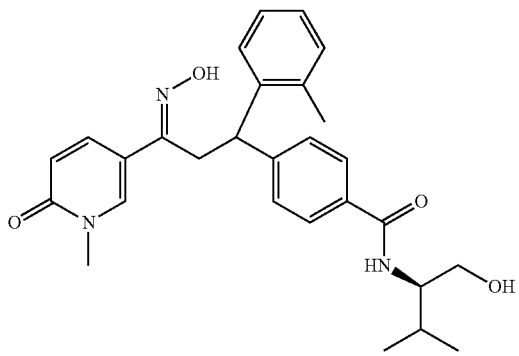 [SMILES: Cc1ccccc1C(C/C(=N\O)c1ccc(=O)n(C)c1)c1ccc(C(=O)N[C@@H](CO)C(C)C)cc1]

Step 1: N—((S)-1-Hydroxy-3-methylbutan-2-yl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (S)-2-amino-3-methylbutan-1-ol using benzotriazol-1-yloxytris(dimethylamino)phosphonium hexafluorophosphate in tetrahydrofuran to give the title compound as an off-white solid, MS (ESI$^+$): m/z=461.3 [M+H]$^+$.

Step 2: N—((S)-1-Hydroxy-3-methylbutan-2-yl)-4-((E)-3-(hydroxyimino)-3-(1-methyl-6-oxo-1,6-dihydropyridin-3-yl)-1-o-tolylpropyl)benzamide In analogy to example 151, step 3, N—((S)-1-hydroxy-3-methylbutan-2-yl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid containing <10% of the corresponding Z isomer, MS (ESI$^+$): m/z=476.2 [M+H]$^+$.

Example 307

N—((R)-2,3-Dihydroxypropyl)-4-((E)-3-(hydroxyimino)-3-(1-methyl-6-oxo-1,6-dihydro-pyridin-3-yl)-1-o-tolylpropyl)benzamide

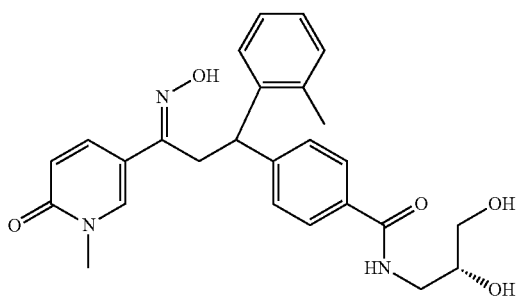 [SMILES: Cc1ccccc1C(C/C(=N\O)c1ccc(=O)n(C)c1)c1ccc(C(=O)NC[C@@H](O)CO)cc1]

Step 1: N—((R)-2,3-Dihydroxypropyl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (R)-3-aminopropane-1,2-diol using benzotriazol-1-yloxytris(dimethylamino)phosphonium hexafluorophosphate in tetrahydrofuran to give the title compound as an off-white solid, MS (ESI$^+$): m/z=449.3 [M+H]$^+$.

Step 2: N—((R)-2,3-Dihydroxypropyl)-4-((E)-3-(hydroxyimino)-3-(1-methyl-6-oxo-1,6-dihydropyridin-3-yl)-1-o-tolylpropyl)benzamide In analogy to example 151, step 3, N—((R)-2,3-dihydroxypropyl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid containing <10% of the corresponding Z isomer, MS (ESI$^+$): m/z=464.3 [M+H]$^+$.

Example 308

(E)-4-(3-(Hydroxyimino)-3-(1-methyl-6-oxo-1,6-dihydropyridin-3-yl)-1-o-tolylpropyl)-N-(1-(hydroxymethyl)cyclopropyl)benzamide

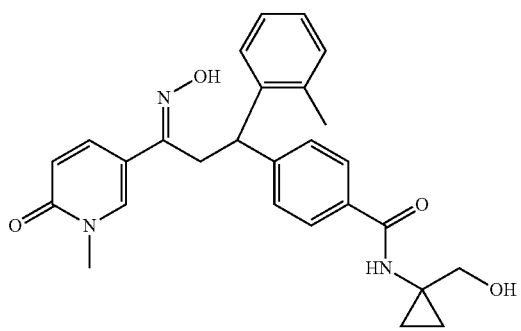 [SMILES: Cc1ccccc1C(C/C(=N\O)c1ccc(=O)n(C)c1)c1ccc(C(=O)NC2(CO)CC2)cc1]

Step 1: N-(1-(Hydroxymethyl)cyclopropyl)-4-(3-(1-methyl-6-oxo-1,6-dihydropyridin-3-yl)-3-oxo-1-o-tolylpropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with (1-aminocyclopropyl)methanol hydrochloride using benzotriazol-1-yloxytris(dimethylamino)phosphonium hexafluorophosphate in tetrahydrofuran to give the title compound as an off-white solid, MS (ESI$^+$): m/z=445.4 [M+H]$^+$.

Step 2: (E)-4-(3-(Hydroxyimino)-3-(1-methyl-6-oxo-1,6-dihydropyridin-3-yl)-1-o-tolylpropyl)-N-(1-(hydroxymethyl)cyclopropyl)benzamide In analogy to example 151, step 3, N-(1-(hydroxymethyl)cyclopropyl)-4-(3-(1-methyl-6-oxo-1,6-dihydropyridin-3-yl)-3-oxo-1-o-tolylpropyl)benzamide was reacted with hydroxylamine hydrochloride in the presence of sodium hydrogencarbonate to give the title compound as an off-white solid containing <10% of the corresponding Z isomer, MS (ESI$^+$): m/z=460.4 [M+H]$^+$.

Example 309

(E)-4-(3-(Hydroxyimino)-3-(1-methyl-6-oxo-1,6-dihydropyridin-3-yl)-1-o-tolylpropyl)-N-(3,3,3-trifluoro-2-hydroxypropyl)benzamide

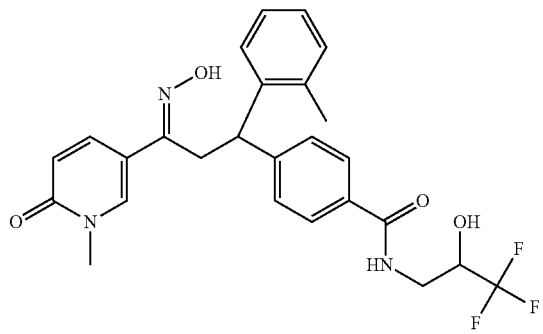 [SMILES: Cc1ccccc1C(C/C(=N\O)c1ccc(=O)n(C)c1)c1ccc(C(=O)NCC(O)C(F)(F)F)cc1]

Step 1: 4-(3-(1-Methyl-6-oxo-1,6-dihydropyridin-3-yl)-3-oxo-1-o-tolylpropyl)-N-(3,3,3-trifluoro-2-hydroxypropyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with 3-amino-1,1,1-trifluoropropan-2-ol using benzotriazol-1-yloxytris(dimethylamino)phosphonium hexafluoro-phosphate in tetrahydrofuran to give the title compound as an off-white solid, MS (ESI$^+$): m/z=487.4 [M+H]$^+$.

Step 2: (E)-4-(3-(Hydroxyimino)-3-(1-methyl-6-oxo-1,6-dihydropyridin-3-yl)-1-o-tolylpropyl)-N-(3,3,3-trifluoro-2-hydroxypropyl)benzamide In analogy to example 151, step 3, 4-(3-(1-methyl-6-oxo-1,6-dihydropyridin-3-yl)-3-oxo-1-o-tolylpropyl)-N-(3,3,3-trifluoro-2-hydroxypropyl)benzamide was reacted with hydroxylamine hydrochloride in the presence of sodium hydrogencarbonate to give the title compound as an off-white solid containing <10% of the corresponding Z isomer, MS (ESI$^+$): m/z=502.2 [M+H]$^+$.

Example 310

(E)-4-(3-(Hydroxyimino)-3-(1-methyl-6-oxo-1,6-dihydropyridin-3-yl)-1-o-tolylpropyl)-N-(2-(methylsulfonyl)ethyl)benzamide

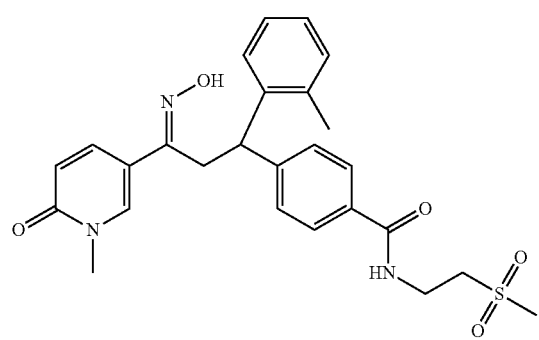 [SMILES: Cc1ccccc1C(C/C(=N\O)c1ccc(=O)n(C)c1)c1ccc(C(=O)NCCS(C)(=O)=O)cc1]

Step 1: 4-(3-(1-Methyl-6-oxo-1,6-dihydropyridin-3-yl)-3-oxo-1-o-tolylpropyl)-N-(2-(methyl-sulfonyl)ethyl)benzamide In analogy to example 207, step 2, 4-[3-(1-methyl-6-oxo-1,6-dihydro-pyridin-3-yl)-3-oxo-1-o-tolyl-propyl]-benzoic acid (example 207, step 1) was coupled with 2-(methylsulfonyl)ethanamine using benzotriazol-1-yloxytris(dimethylamino)phosphonium hexafluorophosphate in tetrahydrofuran to give the title compound as a light brown semisolid, MS (ESI$^-$): m/z=479.1 [M−H]$^-$.

Step 2: (E)-4-(3-(Hydroxyimino)-3-(1-methyl-6-oxo-1,6-dihydropyridin-3-yl)-1-o-tolylpropyl)-N-(2-(methylsulfonyl)ethyl)benzamide In analogy to example 151, step 3, 4-(3-(1-methyl-6-oxo-1,6-dihydropyridin-3-yl)-3-oxo-1-o-tolylpropyl)-N-(2-(methylsulfonyl)ethyl)benzamide was reacted with hydroxylamine hydrochloride in the presence of sodium hydrogencarbonate to give the title compound as an off-white solid containing <10% of the corresponding Z isomer, MS (ESI$^+$): m/z=496.2 [M+H]$^+$.

Example 311

4-[1-(4-Chloro-2-fluoro-phenyl)-3-[(E)-hydroxyimino]-3-(1-methyl-6-oxo-1,6-dihydro-pyridin-3-yl)-propyl]-N-(2-hydroxy-ethyl)-benzamide

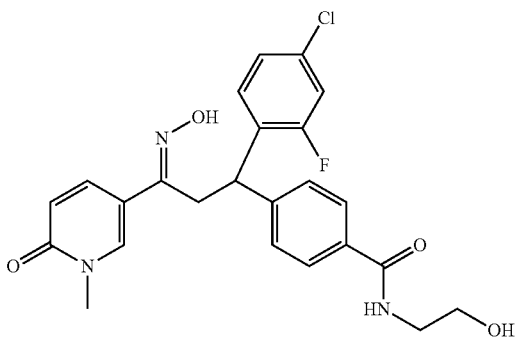 [SMILES: Cn1cc(/C(CC(c2ccc(C(=O)NCCO)cc2)c2ccc(Cl)cc2F)=N/O)ccc1=O]

Steps 1-4: 4-[1-(4-Chloro-2-fluoro-phenyl)-3-(1-methyl-6-oxo-1,6-dihydro-pyridin-3-yl)-3-oxo-propyl]-benzoic acid In analogy to example 203, step 1, (E)-3-(4-chloro-2-fluorophenyl)-1-(6-methoxypyridin-3-yl)prop-2-en-1-one (example 237, step 1) was reacted with 4-methoxycarbonylphenylboronic acid in the presence of chloro(1,5-cyclooctadiene)rhodium(I) dimer and sodium hydrogen-carbonate in 1,4-dioxane and water at 60° C. The product of this reaction could not be obtained pure and was reacted in analogy to example 162, step 2 with concentrated aqueous HCl in 1,4-dioxane to give a light yellow solid which was used in the next step without purification. In analogy to example 161, step 1, the compound was reacted with iodomethane in the presence of potassium carbonate. In analogy to example 169, step 2, the methyl ester was hydrolyzed to give the title compound as an off-white solid, which was purified by extraction. MS (ESI$^-$): m/z=412.0 [M−H]$^-$.

Step 5: 4-[1-(4-Chloro-2-fluoro-phenyl)-3-(1-methyl-6-oxo-1,6-dihydro-pyridin-3-yl)-3-oxo-propyl]-N-(2-hydroxy-ethyl)-benzamide In analogy to example 207, step 2, 4-[1-(4-chloro-2-fluoro-phenyl)-3-(1-methyl-6-oxo-1,6-dihydro-pyridin-3-yl)-3-oxo-propyl]-benzoic acid was coupled with ethanolamine using benzotriazol-1-yloxytris(dimethylamino)phosphonium hexafluorophosphate in tetrahydrofuran to give the title compound as a colourless foam, MS (ESI$^+$): m/z=457.1 [M+H]$^+$.

Step 2: 4-[1-(4-Chloro-2-fluoro-phenyl)-3-[(E)-hydroxyimino]-3-(1-methyl-6-oxo-1,6-dihydro-pyridin-3-yl)-propyl]-N-(2-hydroxy-ethyl)-benzamide In analogy to example 151, step 3, 4-[1-(4-chloro-2-fluoro-phenyl)-3-(1-methyl-6-oxo-1,6-dihydro-pyridin-3-yl)-3-oxo-propyl]-N-(2-hydroxy-ethyl)-benzamide was reacted with hydroxylamine hydrochloride in the presence of sodium hydrogencarbonate to give the title compound as a colourless foam containing 7% of the corresponding Z isomer, MS (ESI$^+$): m/z=472.2 [M+H]$^+$.

Example 312

4-((E)-1-(4-Chloro-2-fluorophenyl)-3-(hydroxyimino)-3-(1-methyl-6-oxo-1,6-dihydropyridin-3-yl)propyl)-N—((R)-2,3-dihydroxypropyl)benzamide

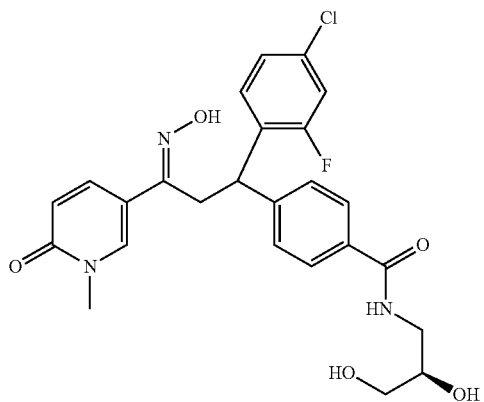 [SMILES: Cn1cc(/C(CC(c2ccc(C(=O)NC[C@@H](O)CO)cc2)c2ccc(Cl)cc2F)=N/O)ccc1=O]

Step 1: 4-(1-(4-Chloro-2-fluorophenyl)-3-(1-methyl-6-oxo-1,6-dihydropyridin-3-yl)-3-oxopropyl)-N—((R)-2,3-dihydroxypropyl)benzamide In analogy to example 207, step 2, 4-[1-(4-chloro-2-fluoro-phenyl)-3-(1-methyl-6-oxo-1,6-dihydro-pyridin-3-yl)-3-oxo-propyl]-benzoic acid (example 311, step 4) was coupled with (R)-3-amino-1,2-propanediol using benzotriazol-1-yloxytris(dimethylamino)phosphonium hexafluorophosphate in tetrahydrofuran to give the title compound as a colourless foam, MS (ESI$^+$): m/z=487.3 [M+H]$^+$.

Step 2: 4-((E)-1-(4-Chloro-2-fluorophenyl)-3-(hydroxyimino)-3-(1-methyl-6-oxo-1,6-dihydropyridin-3-yl)propyl)-N-((R)-2,3-dihydroxypropyl)benzamide In analogy to example 151, step 3, 4-(1-(4-chloro-2-fluorophenyl)-3-(1-methyl-6-oxo-1,6-dihydropyridin-3-yl)-3-oxopropyl)-N—((R)-2,3-dihydroxypropyl)benzamide was reacted with hydroxylamine hydrochloride in the presence of sodium hydrogencarbonate to give the title compound as a colourless solid containing <10% of the corresponding Z isomer, MS (ESI$^+$): m/z=502.1 [M+H]$^+$.

Example 313

4-[1-(4-Chloro-2-fluoro-phenyl)-3-[(E)-hydroxyimino]-3-(1-methyl-6-oxo-1,6-dihydro-pyridin-3-yl)-propyl]-N-(2-methanesulfonyl-ethyl)-benzamide

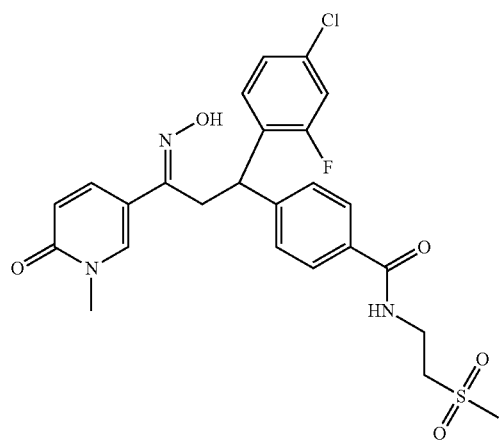 [SMILES: Cn1cc(/C(CC(c2ccc(C(=O)NCCS(C)(=O)=O)cc2)c2ccc(Cl)cc2F)=N/O)ccc1=O]

Step 1: 4-[1-(4-Chloro-2-fluoro-phenyl)-3-(1-methyl-6-oxo-1,6-dihydro-pyridin-3-yl)-3-oxo-propyl]-N-(2-methanesulfonyl-ethyl)-benzamide In analogy to example 207, step 2, 4-[1-(4-chloro-2-fluoro-phenyl)-3-(1-methyl-6-oxo-1,6-dihydro-pyridin-3-yl)-3-oxo-propyl]-benzoic acid (example 311, step 4) was coupled with 2-methanesulfonyl-ethylamine using benzotriazol-1-yloxytris(dimethylamino)phosphonium hexafluorophosphate in tetrahydrofuran to give the title compound as a colourless foam, MS (ESI$^+$): m/z=519.2 [M+H]$^+$.

Step 2: 4-[1-(4-Chloro-2-fluoro-phenyl)-3-[(E)-hydroxyimino]-3-(1-methyl-6-oxo-1,6-dihydro-pyridin-3-yl)-propyl]-N-(2-methanesulfonyl-ethyl)-benzamide In analogy to example 151, step 3, 4-[1-(4-chloro-2-fluoro-phenyl)-3-(1-methyl-6-oxo-1,6-dihydro-pyridin-3-yl)-3-oxo-propyl]-N-(2-methanesulfonyl-ethyl)-benzamide was reacted with hydroxylamine hydrochloride in the presence of sodium hydrogencarbonate to give the title compound as a colourless foam containing 3% of the corresponding Z isomer, MS (ESI$^+$): m/z=534.1 [M+H]$^+$.

Example 314

(E)-5-(3-(4-chloro-2-fluorophenyl)-1-(hydroxyimino)-3-(4-(methylsulfonyl)phenyl)propyl)-1-methylpyridin-2(1H)-one

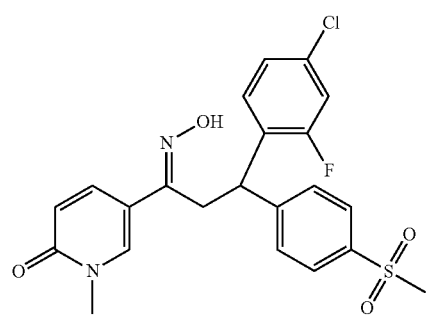 [SMILES: Cn1cc(/C(CC(c2ccc(S(C)(=O)=O)cc2)c2ccc(Cl)cc2F)=N/O)ccc1=O]

285

Step 1: (E)-5-(3-(4-Chloro-2-fluorophenyl)acryloyl) pyridin-2(1H)-one

In analogy to example 162, step 2, (E)-3-(4-chloro-2-fluorophenyl)-1-(6-methoxypyridin-3-yl)prop-2-en-1-one (example 237, step 1) was reacted with concentrated aqueous HCl in 1,4-dioxane to give the title compound as an colourless solid, MS (ESI$^+$): m/z=278.0 [M+H]$^+$.

Step 2: (E)-5-(3-(4-Chloro-2-fluorophenyl)acryloyl)-1-methylpyridin-2(1H)-one

In analogy to example 161, step 1, (E)-5-(3-(4-chloro-2-fluorophenyl)acryloyl)pyridin-2(1H)-one was reacted with iodomethane in the presence of potassium carbonate to give the title compound as a yellow solid, MS (ESI$^+$): m/z=292.0 [M+H]$^+$.

Step 3: 5-(3-(4-Chloro-2-fluorophenyl)-3-(4-(methylsulfonyl)phenyl)propanoyl)-1-methylpyridin-2(1H)-one

In analogy to example 203, step 1, (E)-5-(3-(4-chloro-2-fluorophenyl)acryloyl)-1-methylpyridin-2(1H)-one (example 314, step 2) was reacted with 4-(methylsulfonyl)phenyl-boronic acid in the presence of chloro(1,5-cyclooctadiene)rhodium(I) dimer and sodium hydrogencarbonate in 1,4-dioxane and water at 60° C. to give the title compound as a colourless solid, MS (ESI$^+$): m/z=448.0 [M+H]$^+$.

Step 4: (E)-5-(3-(4-Chloro-2-fluorophenyl)-1-(hydroxyimino)-3-(4-(methylsulfonyl)phenyl)propyl)-1-methylpyridin-2(1H)-one

In analogy to example 151, step 3, 5-(3-(4-chloro-2-fluorophenyl)-3-(4-(methylsulfonyl)-phenyl)propanoyl)-1-methylpyridin-2(1H)-one was reacted with hydroxylamine hydrochloride in the presence of sodium hydrogencarbonate to give the title compound as a colourless solid, MS (ESI$^+$): m/z=463.1 [M+H]$^+$.

Example 315

(E)-5-(3-(4-Chloro-2-fluorophenyl)-1-(hydroxyimino)-3-(3-(methylsulfonyl)phenyl)propyl)-1-methylpyridin-2(1H)-one

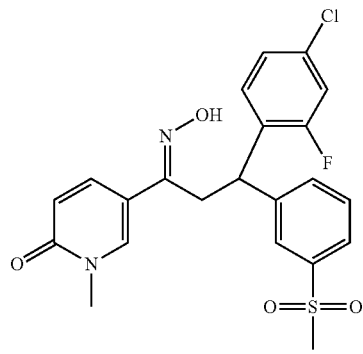 [SMILES: Cn1cc(/C(CC(c2cccc(S(C)(=O)=O)c2)c2ccc(Cl)cc2F)=N/O)ccc1=O]

Step 1: 5-(3-(4-Chloro-2-fluorophenyl)-3-(3-(methylsulfonyl)phenyl)propanoyl)-1-methylpyridin-2(1H)-one

In analogy to example 203, step 1, (E)-5-(3-(4-chloro-2-fluorophenyl)acryloyl)-1-methylpyridin-2(1H)-one (example 314, step 2) was reacted with 3-(methylsulfonyl)phenyl-boronic acid in the presence of chloro(1,5-cyclooctadiene)rhodium(I) dimer and sodium hydrogencarbonate in 1,4-dioxane and water at 60° C. to give the title compound as a yellow solid, MS (ESI$^+$): m/z=448.0 [M+H]$^+$.

Step 2: (E)-5-(3-(4-Chloro-2-fluorophenyl)-1-(hydroxyimino)-3-(3-(methylsulfonyl)phenyl)-propyl)-1-methylpyridin-2(1H)-one

In analogy to example 151, step 3, 5-(3-(4-chloro-2-fluorophenyl)-3-(3-(methylsulfonyl)-phenyl)propanoyl)-1-methylpyridin-2(1H)-one was reacted with hydroxylamine hydrochloride in the presence of sodium hydrogencarbonate to give the title compound as a colourless solid, MS (ESI$^+$): m/z=463.1 [M+H]$^+$.

Example 316

(E)-5-(3-(4-Chloro-2-fluorophenyl)-3-(4-(ethylsulfonyl)phenyl)-1-(hydroxyimino)propyl)-1-methylpyridin-2(1H)-one

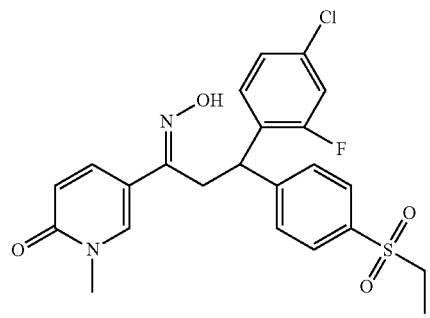 [SMILES: CCS(=O)(=O)c1ccc(C(C/C(=N\O)c2ccc(=O)n(C)c2)c2ccc(Cl)cc2F)cc1]

Step 1: 5-(3-(4-Chloro-2-fluorophenyl)-3-(4-(ethylsulfonyl)phenyl)propanoyl)-1-methylpyridin-2(1H)-one

In analogy to example 203, step 1, (E)-5-(3-(4-chloro-2-fluorophenyl)acryloyl)-1-methyl-pyridin-2(1H)-one (example 314, step 2) was reacted with 4-(ethylsulfonyl)phenyl-boronic acid in the presence of chloro(1,5-cyclooctadiene)rhodium(I) dimer and sodium hydrogencarbonate in 1,4-dioxane and water at 60° C. to give the title compound as a yellow foam, MS (ESI$^+$): m/z=462.2 [M+H]$^+$.

Step 2: (E)-5-(3-(4-Chloro-2-fluorophenyl)-3-(4-(ethylsulfonyl)phenyl)-1-(hydroxyimino)-propyl)-1-methylpyridin-2(1H)-one

In analogy to example 151, step 3, 5-(3-(4-chloro-2-fluorophenyl)-3-(4-(ethylsulfonyl)-phenyl)propanoyl)-1-methylpyridin-2(1H)-one was reacted with hydroxylamine hydrochloride in the presence of sodium hydrogencarbonate to give the title compound as a colourless solid, MS (ESI$^+$): m/z=477.0 [M+H]$^+$.

Example 317

(E)-5-(3-(4-chloro-2-fluorophenyl)-1-(hydroxyimino)-3-(4-(hydroxymethyl)phenyl)propyl)-1-methylpyridin-2(1H)-one

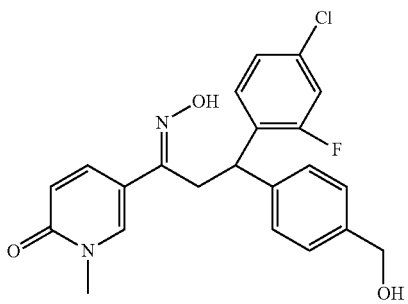 [SMILES: Cn1cc(/C(CC(c2ccc(CO)cc2)c2ccc(Cl)cc2F)=N/O)ccc1=O]

Step 1: 5-(3-(4-Chloro-2-fluorophenyl)-3-(4-(hydroxymethyl)phenyl)propanoyl)-1-methylpyridin-2(1H)-one In analogy to example 203, step 1, (E)-5-(3-(4-chloro-2-fluorophenyl)acryloyl)-1-methylpyridin-2(1H)-one (example 314, step 2) was reacted with 4-(hydroxymethyl)phenyl-boronic acid in the presence of chloro(1,5-cyclooctadiene)rhodium (I) dimer and sodium hydrogencarbonate in 1,4-dioxane and water at 60° C. to give the title compound as a colourless foam, MS (ESI$^+$): m/z=400.2 [M+H]$^+$.

Step 2: (E)-5-(3-(4-Chloro-2-fluorophenyl)-1-(hydroxyimino)-3-(4-(hydroxymethyl)phenyl)-propyl)-1-methylpyridin-2(1H)-one In analogy to example 151, step 3, 5-(3-(4-Chloro-2-fluorophenyl)-3-(4-(hydroxymethyl)-phenyl)propanoyl)-1-methylpyridin-2(1H)-one was reacted with hydroxylamine hydrochloride in the presence of sodium hydrogencarbonate to give the title compound as a colourless solid containing 15% of the corresponding Z isomer, MS (ESI$^+$): m/z=415.2 [M+H]$^+$.

Example 318

(E)-5-(3-(4-Chloro-2-fluorophenyl)-1-(hydroxyimino)-3-(4-hydroxyphenyl)propyl)-1-methylpyridin-2(1H)-one

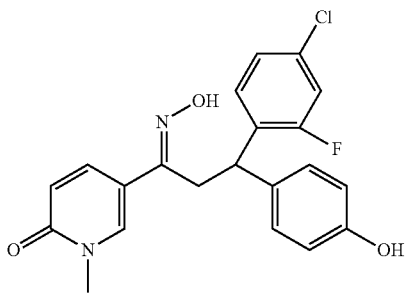 [SMILES: Cn1cc(/C(CC(c2ccc(O)cc2)c2ccc(Cl)cc2F)=N/O)ccc1=O]

Step 1: 5-(3-(4-Chloro-2-fluorophenyl)-3-(4-hydroxyphenyl)propanoyl)-1-methylpyridin-2(1H)-one In analogy to example 203, step 1, (E)-5-(3-(4-chloro-2-fluorophenyl)acryloyl)-1-methyl-pyridin-2(1H)-one (example 314, step 2) was reacted with 4-hydroxyphenylboronic acid in the presence of chloro(1,5-cyclooctadiene)rhodium(I) dimer and sodium hydrogencarbonate in 1,4-dioxane and water at 60° C. to give the title compound as a colourless foam, MS (ESI$^+$): m/z=386.0 [M+H]$^+$.

Step 2: (E)-5-(3-(4-Chloro-2-fluorophenyl)-1-(hydroxyimino)-3-(4-hydroxyphenyl)propyl)-1-methylpyridin-2(1H)-one In analogy to example 151, step 3, (E)-5-(3-(4-chloro-2-fluorophenyl)-1-(hydroxyimino)-3-(4-hydroxyphenyl)propyl)-1-methylpyridin-2(1H)-one was reacted with hydroxylamine hydrochloride in the presence of sodium hydrogencarbonate to give the title compound as a colourless solid, MS (ESI$^+$): m/z=401.1 [M+H]$^+$.

Example 319

(E)-N-(3-(1-(4-Chloro-2-fluorophenyl)-3-(hydroxyimino)-3-(1-methyl-6-oxo-1,6-dihydropyridin-3-yl)propyl)phenyl)acetamide

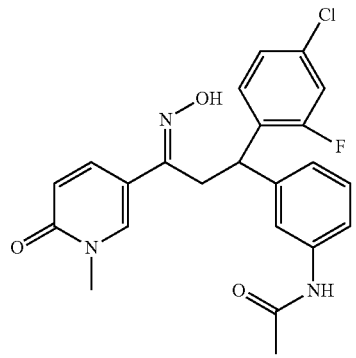 [SMILES: CC(=O)Nc1cccc(C(C/C(=N\O)c2ccc(=O)n(C)c2)c2ccc(Cl)cc2F)c1]

Step 1: N-(3-(1-(4-Chloro-2-fluorophenyl)-3-(1-methyl-6-oxo-1,6-dihydropyridin-3-yl)-3-oxopropyl)phenyl)acetamide In analogy to example 203, step 1, (E)-5-(3-(4-chloro-2-fluorophenyl)acryloyl)-1-methylpyridin-2(1H)-one (example 319, step 2) was reacted with 3-acetamidophenylboronic acid in the presence of chloro(1,5-cyclooctadiene)rhodium(I) dimer and sodium hydrogencarbonate in 1,4-dioxane and water at 60° C. to give the title compound as a brown solid, MS (ESI$^+$): m/z=427.1 [M+H]$^+$.

Step 2: (E)-N-(3-(1-(4-Chloro-2-fluorophenyl)-3-(hydroxyimino)-3-(1-methyl-6-oxo-1,6-dihydropyridin-3-yl)propyl)phenyl)acetamide In analogy to example 151, step 3, N-(3-(1-(4-chloro-2-fluorophenyl)-3-(1-methyl-6-oxo-1,6-dihydropyridin-3-yl)-3-oxopropyl)phenyl)acetamide was reacted with hydroxylamine hydrochloride in the presence of sodium

Example 320

(E)-3-(1-(4-Chloro-2-fluorophenyl)-3-(hydroxy-imino)-3-(1-methyl-6-oxo-1,6-dihydro-pyridin-3-yl)propyl)-N-(2-hydroxyethyl)benzamide

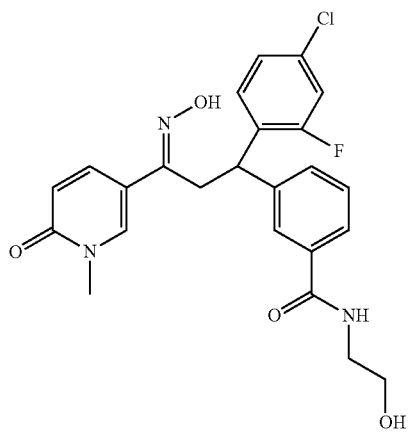 [SMILES: Cn1cc(/C(CC(c2cccc(C(=O)NCCO)c2)c2ccc(Cl)cc2F)=N/O)ccc1=O]

Step 1: Ethyl 3-(1-(4-chloro-2-fluorophenyl)-3-(6-methoxypyridin-3-yl)-3-oxopropyl)benzoate In analogy to example 203, step 1, (E)-3-(4-chloro-2-fluoro-phenyl)-1-(6-methoxy-pyridin-3-yl)-propenone (example 237, step 1) was reacted with 3-(ethoxycarbonyl)phenylboronic acid in the presence of chloro(1,5-cyclooctadiene)rhodium(I) dimer and sodium hydrogencarbonate in 1,4-dioxane and water at 60° C. to give the title compound as a light yellow solid, MS (ESI$^+$): m/z=442.2 [M+H]$^+$.

Step 2: Ethyl 3-(1-(4-chloro-2-fluorophenyl)-3-oxo-3-(6-oxo-1,6-dihydropyridin-3-yl)propyl)benzoate In analogy to example 162, step 2, ethyl 3-(1-(4-chloro-2-fluorophenyl)-3-(6-methoxy-pyridin-3-yl)-3-oxopropyl)benzoate was reacted with concentrated aqueous HCl in 1,4-dioxane to give the title compound as an colourless solid, MS (ESI$^+$): m/z=426.0 [M+H]$^+$.

Step 3: Ethyl 3-(1-(4-chloro-2-fluorophenyl)-3-(1-methyl-6-oxo-1,6-dihydropyridin-3-yl)-3-oxopropyl)benzoate In analogy to example 161, step 1, ethyl 3-(1-(4-chloro-2-fluorophenyl)-3-oxo-3-(6-oxo-1,6-dihydropyridin-3-yl)propyl)benzoate was reacted with iodomethane in the presence of potassium carbonate to give the title compound as a colourless foam, MS (ESI$^+$): m/z=442.2 [M+H]$^+$.

Step 4: 3-(1-(4-Chloro-2-fluorophenyl)-3-(1-methyl-6-oxo-1,6-dihydropyridin-3-yl)-3-oxopropyl)benzoic acid In analogy to example 169, step 2, ethyl 3-(1-(4-chloro-2-fluorophenyl)-3-(1-methyl-6-oxo-1,6-dihydropyridin-3-yl)-3-oxopropyl)benzoate was hydrolyzed to give the title compound as a colourless solid, MS (ESI$^-$): m/z=412.0 [M−H]$^-$.

Step 5: 3-(1-(4-Chloro-2-fluorophenyl)-3-(1-methyl-6-oxo-1,6-dihydropyridin-3-yl)-3-oxopropyl)-N-(2-hydroxyethyl)benzamide In analogy to example 207, step 2, 3-(1-(4-chloro-2-fluorophenyl)-3-(1-methyl-6-oxo-1,6-dihydropyridin-3-yl)-3-oxopropyl)benzoic acid (example 320, step 4) was coupled with 2-aminoethanol using benzotriazol-1-yloxytris(dimethylamino)phosphonium hexafluorophosphate in tetrahydrofuran to give the title compound as a colourless foam, MS (ESI$^+$): m/z=457.3 [M+H]$^+$.

Step 6: (E)-3-(1-(4-Chloro-2-fluorophenyl)-3-(hydroxyimino)-3-(1-methyl-6-oxo-1,6-dihydropyridin-3-yl)propyl)-N-(2-hydroxyethyl)benzamide In analogy to example 151, step 3, 3-(1-(4-chloro-2-fluorophenyl)-3-(1-methyl-6-oxo-1,6-dihydropyridin-3-yl)-3-oxopropyl)-N-(2-hydroxyethyl)benzamide was reacted with hydroxylamine hydrochloride in the presence of sodium hydrogencarbonate to give the title compound as a colourless solid containing 8% of the corresponding Z isomer, MS (ESI$^+$): m/z=472.1 [M+H]$^+$.

Example 321

(E)-3-(1-(4-Chloro-2-fluorophenyl)-3-(hydroxy-imino)-3-(1-methyl-6-oxo-1,6-dihydropyridin-3-yl)propyl)-N-(2-hydroxyethyl)-N-methylbenzamide

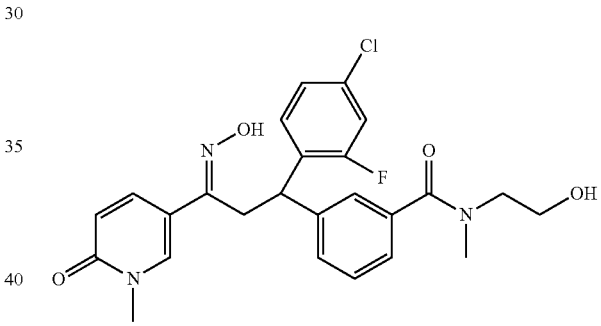

Step 1: 3-(1-(4-Chloro-2-fluorophenyl)-3-(1-methyl-6-oxo-1,6-dihydropyridin-3-yl)-3-oxopropyl)-N-(2-hydroxyethyl)-N-methylbenzamide In analogy to example 207, step 2, 3-(1-(4-chloro-2-fluorophenyl)-3-(1-methyl-6-oxo-1,6-dihydropyridin-3-yl)-3-oxopropyl)benzoic acid (example 320, step 4) was coupled with 2-(methylamino)ethanol using benzotriazol-1-yloxytris(dimethylamino)phosphonium hexafluoro-phosphate in tetrahydrofuran to give the title compound as a colourless foam, MS (ESI$^+$): m/z=471.4 [M+H]$^+$.

Step 2: (E)-3-(1-(4-Chloro-2-fluorophenyl)-3-(hydroxyimino)-3-(1-methyl-6-oxo-1,6-dihydropyridin-3-yl)propyl)-N-(2-hydroxyethyl)-N-methylbenzamide In analogy to example 151, step 3, 3-(1-(4-chloro-2-fluorophenyl)-3-(1-methyl-6-oxo-1,6-dihydropyridin-3-yl)-3-oxopropyl)-N-(2-hydroxyethyl)-N-methylbenzamide was reacted with hydroxylamine hydrochloride in the presence of sodium hydrogencarbonate to give the title compound as a colourless solid containing 7% of the corresponding Z isomer, MS (ESI$^+$): m/z=486.4 [M+H]$^+$.

Example 322

(E)-5-(3-(4-Chloro-2-fluorophenyl)-1-(hydroxy-imino)-3-(3-(morpholine-4-carbonyl)phenyl)propyl)-1-methylpyridin-2(1H)-one

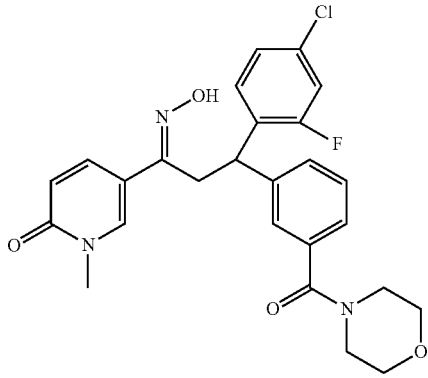 [SMILES: Cn1cc(/C(CC(c2cccc(C(=O)N3CCOCC3)c2)c2ccc(Cl)cc2F)=N/O)ccc1=O]

Step 1: 5-(3-(4-Chloro-2-fluorophenyl)-3-(3-(morpholine-4-carbonyl)phenyl)propanoyl)-1-methylpyridin-2(1H)-one In analogy to example 207, step 2, 3-(1-(4-chloro-2-fluorophenyl)-3-(1-methyl-6-oxo-1,6-dihydropyridin-3-yl)-3-oxopropyl)benzoic acid (example 320, step 4) was coupled with morpholine using benzotriazol-1-yloxytris(dimethylamino)phosphonium hexafluorophosphate in tetrahydrofuran to give the title compound as a colourless foam, MS (ESI⁺): m/z=483.2 [M+H]⁺.

Step 2: (E)-5-(3-(4-Chloro-2-fluorophenyl)-1-(hydroxyimino)-3-(3-(morpholine-4-carbonyl)-phenyl)propyl)-1-methylpyridin-2(1H)-one In analogy to example 151, step 3, 5-(3-(4-chloro-2-fluorophenyl)-3-(3-(morpholine-4-carbonyl)phenyl)propanoyl)-1-methylpyridin-2(1H)-one was reacted with hydroxylamine hydrochloride in the presence of sodium hydrogencarbonate to give the title compound as a colourless solid containing 7% of the corresponding Z isomer, MS (ESI⁺): m/z=498.2 [M+H]⁺.

Example 323

5-{3-(4-Chloro-2-methyl-phenyl)-3-(3-fluoro-4-isopropoxy-phenyl)-1-[(E)-hydroxyimino]-propyl}-1-methyl-1H-pyridin-2-one

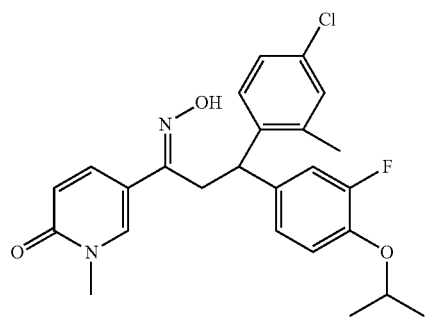 [SMILES: Cc1cc(Cl)ccc1C(C/C(=N\O)c1ccc(=O)n(C)c1)c1ccc(OC(C)C)c(F)c1]

Step 1: (E)-3-(4-Chloro-2-methyl-phenyl)-1-(6-methoxy-pyridin-3-yl)-propenone In analogy to example 170, step 1, 5-acetyl-2-methoxypyridine was reacted with 4-chloro-2-methylbenzaldehyde in the presence of potassium hydroxide to give the title compound as a light yellow solid. MS (ESI⁺): m/z=288.1 [M+H]⁺.

Step 2: 5-[(E)-3-(4-Chloro-2-methyl-phenyl)-acryloyl]-1H-pyridin-2-one

In analogy to example 162, step 2, (E)-3-(4-chloro-2-methyl-phenyl)-1-(6-methoxy-pyridin-3-yl)-propenone was reacted with concentrated aqueous HCl in 1,4-dioxane to give the title compound as an light yellow solid, MS (ESI⁺): m/z=274.2 [M+H]⁺.

Step 3: 5-[(E)-3-(4-Chloro-2-methyl-phenyl)-acryloyl]-1-methyl-1H-pyridin-2-one In analogy to example 161, step 1, 5-[(E)-3-(4-chloro-2-methyl-phenyl)-acryloyl]-1H-pyridin-2-one was reacted with iodomethane in the presence of potassium carbonate to give the title compound as a light yellow solid, MS (ESI⁺): m/z=288.0 [M+H]⁺.

Step 4: 5-[3-(4-Chloro-2-methyl-phenyl)-3-(3-fluoro-4-isopropoxy-phenyl)-propionyl]-1-methyl-1H-pyridin-2-one In analogy to example 203, step 1, 5-[(E)-3-(4-chloro-2-methyl-phenyl)-acryloyl]-1-methyl-1H-pyridin-2-one was reacted with 3-fluoro-4-isopropoxyphenylboronic acid in the presence of chloro(1,5-cyclooctadiene)rhodium(I) dimer and sodium hydrogencarbonate in 1,4-dioxane and water at 60° C. to give the title compound as a colourless solid, MS (ESI⁺): m/z=442.2 [M+H]⁺.

Step 5: 5-{3-(4-Chloro-2-methyl-phenyl)-3-(3-fluoro-4-isopropoxy-phenyl)-1-[(E)-hydroxyimino]-propyl}-1-methyl-1H-pyridin-2-one In analogy to example 151, step 3, 5-[3-(4-chloro-2-methyl-phenyl)-3-(3-fluoro-4-isopropoxy-phenyl)-propionyl]-1-methyl-1H-pyridin-2-one was reacted with hydroxylamine hydrochloride in the presence of sodium hydrogencarbonate to give the title compound as a colourless solid, MS (ESI⁺): m/z=457.2 [M+H]⁺.

Example 324

5-{3-(4-Chloro-2-methyl-phenyl)-3-(3-fluoro-4-hydroxy-phenyl)-1-[(E)-hydroxyimino]-propyl}-1-methyl-1H-pyridin-2-one

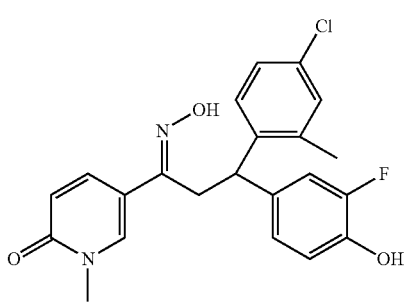 [SMILES: Cc1cc(Cl)ccc1C(C/C(=N\O)c1ccc(=O)n(C)c1)c1ccc(O)c(F)c1]

Step 1: 5-[3-(4-Chloro-2-methyl-phenyl)-3-(3-fluoro-4-hydroxy-phenyl)-propionyl]-1-methyl-1H-pyridin-2-one A solution of 5-[3-(4-Chloro-2-methyl-phenyl)-3-(3-fluoro-4-isopropoxy-phenyl)-propionyl]-1-methyl-1H-pyridin-2-one (example 323, step 4, 1.969 g) in dichloromethane (32.5 mL) was cooled to −10° C. At this temperature boron trichloride solution (1 M in dichloromethane, 13.4 mL) was slowly added. The reaction mixture was stirred at −10° C. for 1 h. The crude reaction mixture was poured into water/sat. sodium hydrogencarbonate-solution, extracted 3× with ethyl acetate, the organic layers were washed 2× with water, dried over magnesium sulfate and concentrated in vacuo to give the title compound as a light yellow solid, MS (ESI$^-$): m/z=397.9 [M−H]$^-$.

Step 2: 5-{3-(4-Chloro-2-methyl-phenyl)-3-(3-fluoro-4-hydroxy-phenyl)-1-[(E)-hydroxyimino]-propyl}-1-methyl-1H-pyridin-2-one In analogy to example 151, step 3, 5-[3-(4-chloro-2-methyl-phenyl)-3-(3-fluoro-4-hydroxy-phenyl)-propionyl]-1-methyl-1H-pyridin-2-one was reacted with hydroxylamine hydrochloride in the presence of sodium hydrogencarbonate to give the title compound containing <5% of the corresponding Z isomer as a colourless solid, MS (ESI$^-$): m/z=413.0 [M−H]$^-$.

Example 325

3-{4-[1-(4-Chloro-2-methyl-phenyl)-3-[(E)-hydroxyimino]-3-(1-methyl-6-oxo-1,6-dihydro-pyridin-3-yl)-propyl]-2-fluoro-phenoxy}-benzoic acid

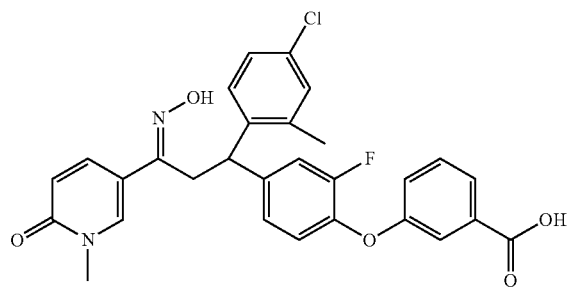 [SMILES: Cc1cc(Cl)ccc1C(C/C(=N\O)c1ccc(=O)n(C)c1)c1ccc(Oc2cccc(C(=O)O)c2)c(F)c1]

Step 1: 3-{4-[1-(4-Chloro-2-methyl-phenyl)-3-(1-methyl-6-oxo-1,6-dihydro-pyridin-3-yl)-3-oxo-propyl]-2-fluoro-phenoxy}-benzoic acid methyl ester In analogy to example 222, step 1, 5-[3-(4-chloro-2-methyl-phenyl)-3-(3-fluoro-4-hydroxy-phenyl)-propionyl]-1-methyl-1H-pyridin-2-one (example 324, step 1) was reacted with 3-methoxycarbonylphenylboronic acid in dichloromethane in the presence of copper(II) acetate, pyridine and air to give the title compound as a colourless solid, MS (ESI$^+$): m/z=534.1 [M+H]$^+$.

Step 2: 3-{4-[1-(4-Chloro-2-methyl-phenyl)-3-(1-methyl-6-oxo-1,6-dihydro-pyridin-3-yl)-3-oxo-propyl]-2-fluoro-phenoxy}-benzoic acid In analogy to example 169, step 2, 3-{4-[1-(4-chloro-2-methyl-phenyl)-3-(1-methyl-6-oxo-1,6-dihydro-pyridin-3-yl)-3-oxo-propyl]-2-fluoro-phenoxy}-benzoic acid methyl ester was hydrolyzed to give the title compound as a colourless solid, MS (ESI$^-$): m/z=518.2 [M−H]$^-$.

Step 3: 3-{4-[1-(4-Chloro-2-methyl-phenyl)-3-[(E)-hydroxyimino]-3-(1-methyl-6-oxo-1,6-dihydro-pyridin-3-yl)-propyl]-2-fluoro-phenoxy}-benzoic acid In analogy to example 151, step 3, 3-{4-[1-(4-chloro-2-methyl-phenyl)-3-(1-methyl-6-oxo-1,6-dihydro-pyridin-3-yl)-3-oxo-propyl]-2-fluoro-phenoxy}-benzoic acid was reacted with hydroxylamine hydrochloride in the presence of sodium hydrogencarbonate to give the title compound containing less than 10% of the corresponding Z isomer as a colourless solid, MS (ESI$^-$): m/z=532.9 [M−H]$^-$.

Example 326

2-Chloro-5-{4-[1-(4-chloro-2-methyl-phenyl)-3-[(E)-hydroxyimino]-3-(1-methyl-6-oxo-1,6-dihydro-pyridin-3-yl)-propyl]-2-fluoro-phenoxy}-benzoic acid

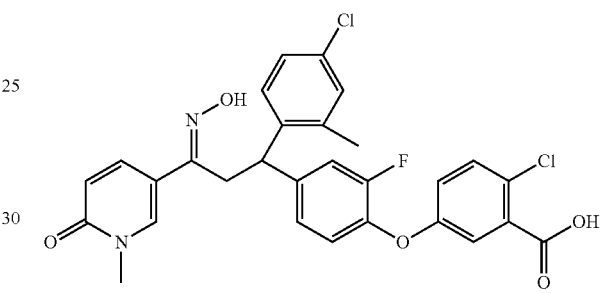

Step 1: 2-Chloro-5-{4-[1-(4-chloro-2-methyl-phenyl)-3-(1-methyl-6-oxo-1,6-dihydro-pyridin-3-yl)-3-oxo-propyl]-2-fluoro-phenoxy}-benzoic acid ethyl ester In analogy to example 222, step 1, 5-[3-(4-chloro-2-methyl-phenyl)-3-(3-fluoro-4-hydroxy-phenyl)-propionyl]-1-methyl-1H-pyridin-2-one (example 324, step 1) was reacted with 4-chloro-3-ethoxycarbonylphenylboronic acid in dichloromethane in the presence of copper(II) acetate, pyridine and air to give the title compound as a colourless solid, MS (ESI$^+$): m/z=582.2 [M+H]$^+$.

Step 2: 2-Chloro-5-{4-[1-(4-chloro-2-methyl-phenyl)-3-(1-methyl-6-oxo-1,6-dihydro-pyridin-3-yl)-3-oxo-propyl]-2-fluoro-phenoxy}-benzoic acid In analogy to example 169, step 2, 2-chloro-5-{4-[1-(4-chloro-2-methyl-phenyl)-3-(1-methyl-6-oxo-1,6-dihydro-pyridin-3-yl)-3-oxo-propyl]-2-fluoro-phenoxy}-benzoic acid ethyl ester was hydrolyzed to give the title compound as a colourless solid, MS (ESI$^-$): m/z=552.2 [M−H]$^-$.

Step 3: 2-Chloro-5-{4-[1-(4-chloro-2-methyl-phenyl)-3-[(E)-hydroxyimino]-3-(1-methyl-6-oxo-1,6-dihydro-pyridin-3-yl)-propyl]-2-fluoro-phenoxy}-benzoic acid In analogy to example 151, step 3, 2-chloro-5-{4-[1-(4-chloro-2-methyl-phenyl)-3-(1-methyl-6-oxo-1,6-dihydro-pyridin-3-yl)-3-oxo-propyl]-2-fluoro-phenoxy}-benzoic acid was reacted with hydroxylamine hydrochloride in the presence of sodium hydrogencarbonate to give the title compound containing less than 10% of the corresponding Z isomer as a colourless solid, MS (ESI⁻): m/z=567.2 [M–H]⁻.

Example 327

4-{4-[1-(4-Chloro-2-methyl-phenyl)-3-[(E)-hydroxyimino]-3-(1-methyl-6-oxo-1,6-dihydro-pyridin-3-yl)-propyl]-2-fluoro-phenoxy}-butyric acid

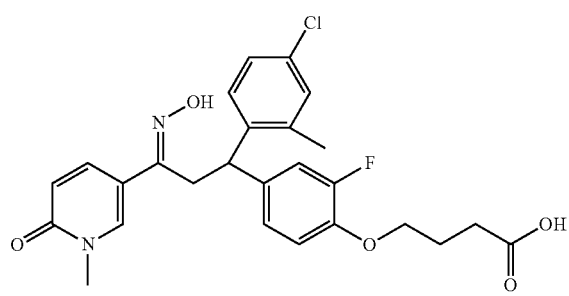 [SMILES: Cc1cc(Cl)ccc1C(C/C(=N\O)c1ccc(=O)n(C)c1)c1ccc(OCCCC(=O)O)c(F)c1]

Step 1: 4-{4-[1-(4-Chloro-2-methyl-phenyl)-3-(1-methyl-6-oxo-1,6-dihydro-pyridin-3-yl)-3-oxo-propyl]-2-fluoro-phenoxy}-butyric acid methyl ester In analogy to example 221, step 6, 5-[3-(4-chloro-2-methyl-phenyl)-3-(3-fluoro-4-hydroxy-phenyl)-propionyl]-1-methyl-1H-pyridin-2-one (example 324, step 1) was reacted with methyl 4-bromobutyrate in N,N-dimethylacetamide in the presence of cesium carbonate to give the title compound as a colourless foam, MS (ESI⁺): m/z=500.3 [M+H]⁺.

Step 2: 4-{4-[1-(4-Chloro-2-methyl-phenyl)-3-(1-methyl-6-oxo-1,6-dihydro-pyridin-3-yl)-3-oxo-propyl]-2-fluoro-phenoxy}-butyric acid In analogy to example 169, step 2, 4-{4-[1-(4-chloro-2-methyl-phenyl)-3-(1-methyl-6-oxo-1,6-dihydro-pyridin-3-yl)-3-oxo-propyl]-2-fluoro-phenoxy}-butyric acid methyl ester was hydrolyzed to give the title compound as a colourless foam, MS (ESI⁻): m/z=484.1 [M–H]⁻.

Step 3: 4-{4-[1-(4-Chloro-2-methyl-phenyl)-3-[(E)-hydroxyimino]-3-(1-methyl-6-oxo-1,6-dihydro-pyridin-3-yl)-propyl]-2-fluoro-phenoxy}-butyric acid In analogy to example 151, step 3, 4-{4-[1-(4-chloro-2-methyl-phenyl)-3-(1-methyl-6-oxo-1,6-dihydro-pyridin-3-yl)-3-oxo-propyl]-2-fluoro-phenoxy}-butyric acid was reacted with hydroxylamine hydrochloride in the presence of sodium hydrogencarbonate to give the title compound containing less than 10% of the corresponding Z isomer as a colourless solid, MS (ESI⁻): m/z=499.2 [M–H]⁻.

Example 328

5-{3-(4-Chloro-2-methyl-phenyl)-3-[3-fluoro-4-(2-hydroxy-ethoxy)-phenyl]-1-[(E)-hydroxyimino]-propyl}-1-methyl-1H-pyridin-2-one

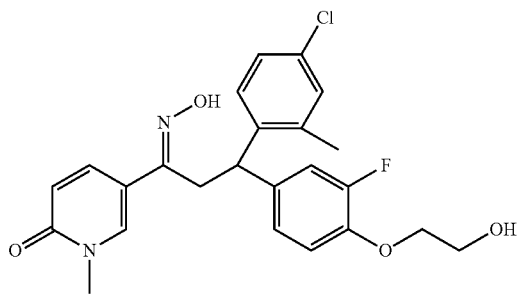 [SMILES: Cc1cc(Cl)ccc1C(C/C(=N\O)c1ccc(=O)n(C)c1)c1ccc(OCCO)c(F)c1]

Step 1: 5-{3-(4-Chloro-2-methyl-phenyl)-3-[3-fluoro-4-(2-hydroxy-ethoxy)-phenyl]-propionyl}-1-methyl-1H-pyridin-2-one In analogy to example 221, step 6, 5-[3-(4-chloro-2-methyl-phenyl)-3-(3-fluoro-4-hydroxy-phenyl)-propionyl]-1-methyl-1H-pyridin-2-one (example 324, step 1) was reacted with 2-bromoethanol in N,N-dimethylacetamide in the presence of cesium carbonate to give the title compound as a colourless foam, MS (ESI⁺): m/z=444.2 [M+H]⁺.

Step 2: 5-{3-(4-Chloro-2-methyl-phenyl)-3-[3-fluoro-4-(2-hydroxy-ethoxy)-phenyl]-1-[(E)-hydroxyimino]-propyl}-1-methyl-1H-pyridin-2-one In analogy to example 151, step 3, 5-{3-(4-chloro-2-methyl-phenyl)-3-[3-fluoro-4-(2-hydroxy-ethoxy)-phenyl]-propionyl}-1-methyl-1H-pyridin-2-one was reacted with hydroxylamine hydrochloride in the presence of sodium hydrogencarbonate to give the title compound as a colourless solid, MS (ESI⁺): m/z=459.3 [M+H]⁺.

Example 329

Methanesulfonic acid 4-[1-(4-chloro-2-methyl-phenyl)-3-[(E)-hydroxyimino]-3-(1-methyl-6-oxo-1,6-dihydro-pyridin-3-yl)-propyl]-2-fluoro-phenyl ester

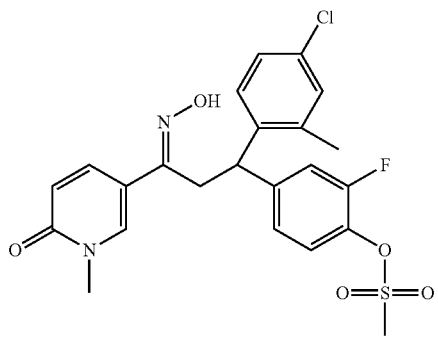 [SMILES: Cc1cc(Cl)ccc1C(C/C(=N\O)c1ccc(=O)n(C)c1)c1ccc(OS(C)(=O)=O)c(F)c1]

Step 1: Methanesulfonic acid 4-[1-(4-chloro-2-methyl-phenyl)-3-(1-methyl-6-oxo-1,6-dihydro-pyridin-3-yl)-3-oxo-propyl]-2-fluoro-phenyl ester In analogy to example 221, step 6, 5-[3-(4-chloro-2-methyl-phenyl)-3-(3-fluoro-4-hydroxy-phenyl)-propionyl]-1-methyl-1H-pyridin-2-one (example 324, step 1) was reacted with 2-(methylsulfonyl)ethyl methanesulfonate in acetone in the presence of cesium carbonate to give the title compound as a colourless foam, MS (ESI⁺): m/z=478.1 [M+H]⁺.

Step 2: Methanesulfonic acid 4-[1-(4-chloro-2-methyl-phenyl)-3-[(E)-hydroxyimino]-3-(1-methyl-6-oxo-1,6-dihydro-pyridin-3-yl)-propyl]-2-fluoro-phenyl ester In analogy to example 151, step 3, methanesulfonic acid 4-[1-(4-chloro-2-methyl-phenyl)-3-(1-methyl-6-oxo-1,6-dihydro-pyridin-3-yl)-3-oxo-propyl]-2-fluoro-phenyl ester was reacted with hydroxylamine hydrochloride in the presence of sodium hydrogencarbonate to give the title compound as a colourless solid, MS (ESI⁺): m/z=493.1 [M+H]⁺.

Example 330

(E)-5-(3-(4-Bromophenyl)-1-(hydroxyimino)-3-(4-methylthiazol-5-yl)propyl)-1-methylpyridin-2(1H)-one

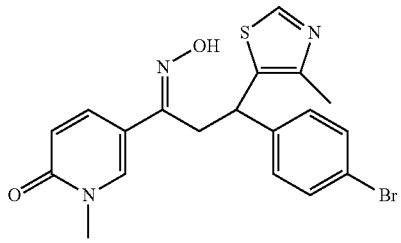 [SMILES: Cc1ncsc1C(C/C(=N\O)c1ccc(=O)n(C)c1)c1ccc(Br)cc1]

Step 1: (E)-1-(6-Methoxypyridin-3-yl)-3-(4-methylthiazol-5-yl)prop-2-en-1-one

In analogy to example 170, step 1, 5-acetyl-2-methoxypyridine was reacted with 4-methylthiazole-5-carbaldehyde in the presence of potassium hydroxide to give the title compound as an off-white solid. MS (ESI⁺): m/z=261.1 [M+H]⁺.

Step 2: 3-(4-Bromophenyl)-1-(6-methoxypyridin-3-yl)-3-(4-methylthiazol-5-yl)propan-1-one In analogy to example 203, step 1, (E)-1-(6-methoxypyridin-3-yl)-3-(4-methylthiazol-5-yl)prop-2-en-1-one was reacted with 4-bromophenylboronic acid in the presence of chloro(1,5-cyclooctadiene)rhodium(I) dimer and sodium hydrogencarbonate in 1,4-dioxane and water at 60° C. to give the title compound as a yellow solid, MS (ESI⁺): m/z=419.1 [M+H]⁺.

Step 3: 5-(3-(4-Bromophenyl)-3-(4-methylthiazol-5-yl)propanoyl)pyridin-2(1H)-one In analogy to example 162, step 2, 3-(4-bromophenyl)-1-(6-methoxypyridin-3-yl)-3-(4-methylthiazol-5-yl)propan-1-one was reacted with concentrated aqueous HCl in 1,4-dioxane to give the title compound as an yellow solid, MS (ESI⁺): m/z=405.2 [M+H]⁺.

Steps 4 and 5: (E)-5-(3-(4-Bromophenyl)-1-(hydroxyimino)-3-(4-methylthiazol-5-yl)propyl)-1-methylpyridin-2(1H)-one In analogy to example 161, step 1, 5-(3-(4-bromophenyl)-3-(4-methylthiazol-5-yl)propanoyl)pyridin-2(1H)-one was reacted with iodomethane in the presence of potassium carbonate. The product of this reaction was reacted in analogy to example 151, step 3 with hydroxylamine hydrochloride in the presence of sodium hydrogencarbonate to give the title compound containing less than 10% of the corresponding Z isomer as an off-white solid, MS (ESI⁺): m/z=432.1 [M+H]⁺.

Example 331

(E)-5-(3-(4-chloro-2-methylphenyl)-1-(hydroxyimino)-3-(4-(methylsulfonyl)phenyl)propyl)-1-methylpyridin-2(1H)-one

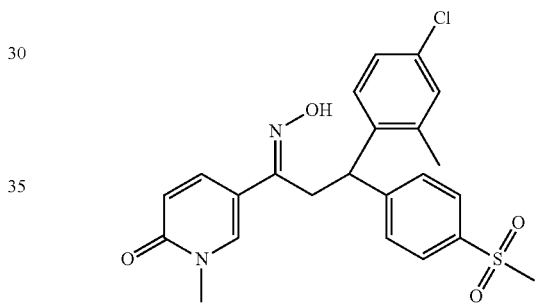

Step 1: 5-(3-(4-Chloro-2-methylphenyl)-3-(4-(methylsulfonyl)phenyl)propanoyl)-1-methylpyridin-2(1H)-one In analogy to example 203, step 1, 5-[(E)-3-(4-chloro-2-methyl-phenyl)-acryloyl]-1-methyl-1H-pyridin-2-one (example 323, step 3) was reacted with 4-(methylsulfonyl)phenyl-boronic acid in the presence of chloro(1,5-cyclooctadiene)rhodium(I) dimer and sodium hydrogencarbonate in 1,4-dioxane and water at 60° C. to give the title compound as a colourless solid, MS (ESI⁺): m/z=444.2 [M+H]⁺.

Step 2: (E)-5-(3-(4-Chloro-2-methylphenyl)-1-(hydroxyimino)-3-(4-(methylsulfonyl)phenyl)propyl)-1-methylpyridin-2(1H)-one In analogy to example 151, step 3, 5-(3-(4-chloro-2-methylphenyl)-3-(4-(methylsulfonyl)phenyl)propanoyl)-1-methylpyridin-2(1H)-one was reacted with hydroxylamine hydrochloride in the presence of sodium hydrogencarbonate to give the title compound as a colourless foam, MS (ESI⁺): m/z=459.2 [M+H]⁺.

Example 332

(E)-4-(1-(4-Chloro-2-methylphenyl)-3-(hydroxyimino)-3-(1-methyl-6-oxo-1,6-dihydropyridin-3-yl)propyl)-N-(2-hydroxyethyl)benzamide

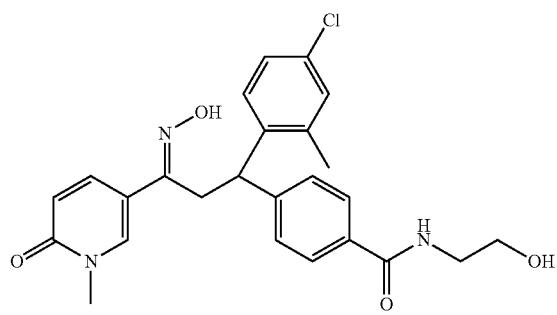 [SMILES: Cc1cc(Cl)ccc1C(C/C(=N\O)c1ccc(=O)n(C)c1)c1ccc(C(=O)NCCO)cc1]

Step 1: Methyl 4-(1-(4-chloro-2-methylphenyl)-3-(1-methyl-6-oxo-1,6-dihydropyridin-3-yl)-3-oxopropyl)benzoate In analogy to example 203, step 1, 5-[(E)-3-(4-chloro-2-methyl-phenyl)-acryloyl]-1-methyl-1H-pyridin-2-one (example 323, step 3) was reacted with 4-(methoxycarbonyl)phenyl-boronic acid in the presence of chloro(1,5-cyclooctadiene)rhodium(I) dimer and sodium hydrogencarbonate in 1,4-dioxane and water at 60° C. to give the title compound as a orange solid, MS (ESI$^+$): m/z=424.1 [M+H]$^+$.

Step 2: 4-(1-(4-Chloro-2-methylphenyl)-3-(1-methyl-6-oxo-1,6-dihydropyridin-3-yl)-3-oxopropyl)benzoic acid In analogy to example 169, step 2, methyl 4-(1-(4-chloro-2-methylphenyl)-3-(1-methyl-6-oxo-1,6-dihydropyridin-3-yl)-3-oxopropyl)benzoate was hydrolyzed to give the title compound as an off-white solid, MS (ESI$^-$): m/z=408.1 [M−H]$^-$.

Step 3: 4-(1-(4-Chloro-2-methylphenyl)-3-(1-methyl-6-oxo-1,6-dihydropyridin-3-yl)-3-oxopropyl)-N-(2-hydroxyethyl)benzamide In analogy to example 207, step 2, 4-(1-(4-chloro-2-methylphenyl)-3-(1-methyl-6-oxo-1,6-dihydropyridin-3-yl)-3-oxopropyl)benzoic acid was coupled with 2-aminoethanol using benzotriazol-1-yloxytris(dimethylamino)phosphonium hexafluorophosphate in tetrahydrofuran to give the title compound as an off-white solid, MS (ESI$^+$): m/z=453.2 [M+H]$^+$.

Step 4: (E)-4-(1-(4-Chloro-2-methylphenyl)-3-(hydroxyimino)-3-(1-methyl-6-oxo-1,6-dihydro-pyridin-3-yl)propyl)-N-(2-hydroxyethyl)benzamide In analogy to example 151, step 3, 4-(1-(4-chloro-2-methylphenyl)-3-(1-methyl-6-oxo-1,6-dihydropyridin-3-yl)-3-oxopropyl)-N-(2-hydroxyethyl)benzamide was reacted with hydroxylamine hydrochloride in the presence of sodium hydrogencarbonate to give the title compound containing less than 10% of the corresponding Z isomer as an off-white solid, MS (ESI$^+$): m/z=468.2 [M+H]$^+$.

Examples 333 and 334

(−)-(E)-5-(3-(4-Chloro-2-methylphenyl)-1-(hydroxyimino)-3-(4-(methylsulfonyl)phenyl)-propyl)-1-methylpyridin-2(1H)-one and (+)-(E)-5-(3-(4-chloro-2-methylphenyl)-1-(hydroxyimino)-3-(4-(methylsulfonyl)phenyl)-propyl)-1-methylpyridin-2(1H)-one

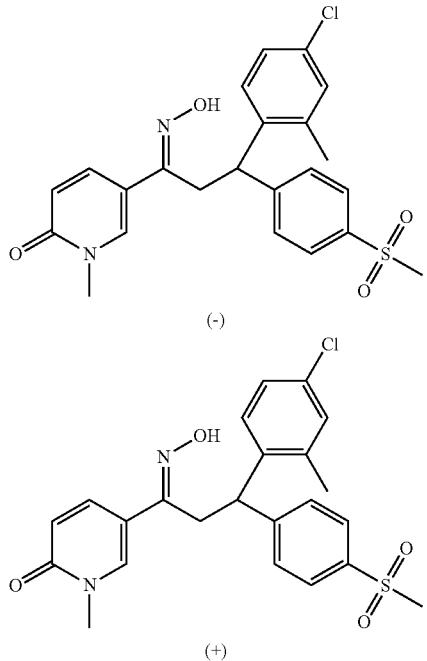

Separation of (E)-5-(3-(4-chloro-2-methylphenyl)-1-(hydroxyimino)-3-(4-(methyl-sulfonyl)phenyl)propyl)-1-methylpyridin-2(1H)-one (example 331) by chiral HPLC on a Chiralpak-AD column using a solvent mixture of n-heptane/isopropanol (65:35 v/v) gave (−)-(E)-5-(3-(4-chloro-2-methylphenyl)-1-(hydroxyimino)-3-(4-(methylsulfonyl)phenyl)propyl)-1-methylpyridin-2(1H)-one, MS (ESI$^+$): m/z=459.0 [M+H]$^+$ as a colourless solid and (+)-(E)-5-(3-(4-chloro-2-methylphenyl)-1-(hydroxyimino)-3-(4-(methylsulfonyl)phenyl)propyl)-1-methylpyridin-2(1H)-one, MS (ESI$^+$): m/z=459.0 [M+H]$^+$ as a colourless solid.

Example 335

4-((E)-1-(4-Chloro-2-methylphenyl)-3-(hydroxyimino)-3-(1-methyl-6-oxo-1,6-dihydropyridin-3-yl)propyl)-N—((R)-2,3-dihydroxypropyl)benzamide

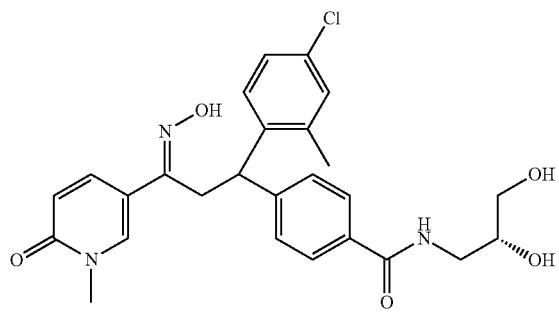 [SMILES: Cc1cc(Cl)ccc1C(C/C(=N\O)c1ccc(=O)n(C)c1)c1ccc(C(=O)NC[C@@H](O)CO)cc1]

Step 1: 4-(1-(4-Chloro-2-methylphenyl)-3-(1-methyl-6-oxo-1,6-dihydropyridin-3-yl)-3-oxopropyl)-N—((R)-2,3-dihydroxypropyl)benzamide In analogy to example 207, step 2, 4-(1-(4-chloro-2-methylphenyl)-3-(1-methyl-6-oxo-1,6-dihydropyridin-3-yl)-3-oxopropyl)benzoic acid (example 332, step 2) was coupled with (R)-3-aminopropane-1,2-diol using benzotriazol-1-yloxytris(dimethylamino)phosphonium hexafluorophosphate in tetrahydrofuran to give the title compound as an off-white solid, MS (ESI$^+$): m/z=483.2 [M+H]$^+$.

Step 2: 4-((E)-1-(4-Chloro-2-methylphenyl)-3-(hydroxyimino)-3-(1-methyl-6-oxo-1,6-dihydropyridin-3-yl)propyl)-N-((R)-2,3-dihydroxypropyl)benzamide In analogy to example 151, step 3, 4-(1-(4-chloro-2-methylphenyl)-3-(1-methyl-6-oxo-1,6-dihydropyridin-3-yl)-3-oxopropyl)-N—((R)-2,3-dihydroxypropyl)benzamide was reacted with hydroxylamine hydrochloride in the presence of sodium hydrogencarbonate to give the title compound containing less than 10% of the corresponding Z isomer as an off-white solid, MS (ESI$^+$): m/z=498.2 [M+H]$^+$.

Example 336

(E)-4-(1-(4-Chloro-2-methylphenyl)-3-(hydroxyimino)-3-(1-methyl-6-oxo-1,6-dihydropyridin-3-yl)propyl)-N-(2-(methylsulfonyl)ethyl)benzamide

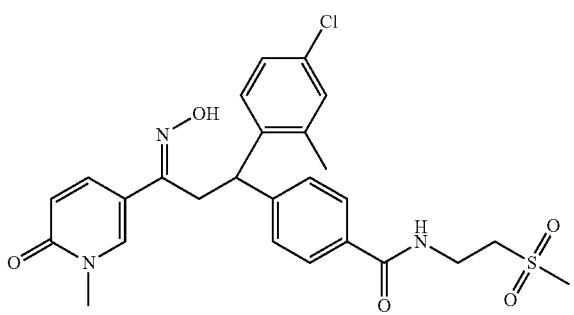 [SMILES: Cc1cc(Cl)ccc1C(C/C(=N\O)c1ccc(=O)n(C)c1)c1ccc(C(=O)NCCS(C)(=O)=O)cc1]

Step 1: 4-(1-(4-Chloro-2-methylphenyl)-3-(1-methyl-6-oxo-1,6-dihydropyridin-3-yl)-3-oxopropyl)-N-(2-(methylsulfonyl)ethyl)benzamide In analogy to example 207, step 2, 4-(1-(4-chloro-2-methylphenyl)-3-(1-methyl-6-oxo-1,6-dihydropyridin-3-yl)-3-oxopropyl)benzoic acid (example 332, step 2) was coupled with 2-(methylsulfonyl)ethanamine using benzotriazol-1-yloxytris(dimethylamino)phosphonium hexafluorophosphate in tetrahydrofuran to give the title compound as an off-white solid, MS (ESI$^+$): m/z=515.3 [M+H]$^+$.

Step 2: (E)-4-(1-(4-Chloro-2-methylphenyl)-3-(hydroxyimino)-3-(1-methyl-6-oxo-1,6-dihydropyridin-3-yl)propyl)-N-(2-(methylsulfonyl)ethyl)benzamide In analogy to example 151, step 3, 4-(1-(4-chloro-2-methylphenyl)-3-(1-methyl-6-oxo-1,6-dihydropyridin-3-yl)-3-oxopropyl)-N-(2-(methylsulfonyl)ethyl)benzamide was reacted with hydroxylamine hydrochloride in the presence of sodium hydrogencarbonate to give the title compound as a colourless solid, MS (ESI$^+$): m/z=530.1 [M+H]$^+$.

Example 337

(E)-5-(3-(4-Chloro-2-methylphenyl)-1-(hydroxyimino)-3-(4-(hydroxymethyl)phenyl)-propyl)-1-methylpyridin-2(1H)-one

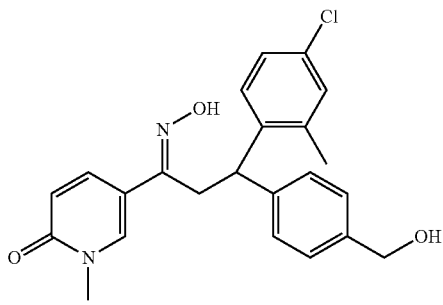 [SMILES: Cc1cc(Cl)ccc1C(C/C(=N\O)c1ccc(=O)n(C)c1)c1ccc(CO)cc1]

Step 1: 5-(3-(4-chloro-2-methylphenyl)-3-(4-(hydroxymethyl)phenyl)propanoyl)-1-methylpyridin-2(1H)-one In analogy to example 203, step 1, 5-[(E)-3-(4-chloro-2-methyl-phenyl)-acryloyl]-1-methyl-1H-pyridin-2-one (example 323, step 3) was reacted with 4-(hydroxymethyl)phenyl-boronic acid in the presence of chloro(1,5-cyclooctadiene)rhodium(I) dimer and sodium hydrogencarbonate in 1,4-dioxane and water at 60° C. to give the title compound as a yellow foam, MS (ESI$^+$): m/z=396.1 [M+H]$^+$.

Step 2: (E)-5-(3-(4-chloro-2-methylphenyl)-1-(hydroxyimino)-3-(4-(hydroxymethyl)phenyl)-propyl)-1-methylpyridin-2(1H)-one In analogy to example 151, step 3, 5-(3-(4-chloro-2-methylphenyl)-3-(4-(hydroxymethyl)phenyl)propanoyl)-1-methylpyridin-2(1H)-one was reacted with hydroxylamine hydrochloride in the presence of sodium hydrogencarbonate to give the title compound as a colourless solid, MS (ESI$^+$): m/z=411.2 [M+H]$^+$.

Example 338

(E)-4-(1-(4-chloro-2-methylphenyl)-3-(hydroxyimino)-3-(1-methyl-6-oxo-1,6-dihydropyridin-3-yl)propyl)benzenesulfonamide

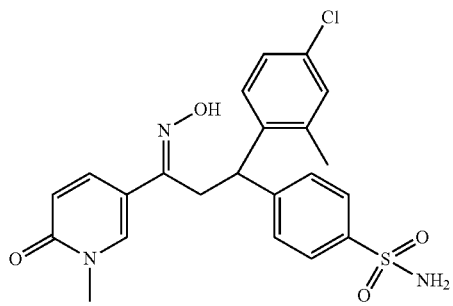 [SMILES: Cc1cc(Cl)ccc1C(C/C(=N\O)c1ccc(=O)n(C)c1)c1ccc(S(N)(=O)=O)cc1]

Step 1: 4-(1-(4-Chloro-2-methylphenyl)-3-(1-methyl-6-oxo-1,6-dihydropyridin-3-yl)-3-oxopropyl)benzenesulfonamide In analogy to example 203, step 1, 5-[(E)-3-(4-chloro-2-methyl-phenyl)-acryloyl]-1-methyl-1H-pyridin-2-one (example 323, step 3) was reacted with 4-(4,4,5,5-tetramethyl-1,3,2-dioxaborolan-2-yl)benzenesulfonamide in the presence of chloro(1,5-cyclooctadiene)rhodium(I) dimer and sodium hydrogencarbonate in 1,4-dioxane and water at 60° C. to give the title compound as a colourless solid, MS (ESI$^+$): m/z=445.3 [M+H]$^+$.

Step 2: (E)-4-(1-(4-Chloro-2-methylphenyl)-3-(hydroxyimino)-3-(1-methyl-6-oxo-1,6-dihydropyridin-3-yl)propyl)benzenesulfonamide In analogy to example 151, step 3, 4-(1-(4-chloro-2-methylphenyl)-3-(1-methyl-6-oxo-1,6-dihydropyridin-3-yl)-3-oxopropyl)benzenesulfonamide was reacted with hydroxylamine hydrochloride in the presence of sodium hydrogencarbonate to give the title compound as a colourless solid, MS (ESI$^+$): m/z=460.2 [M+H]$^+$.

Example 339

(E)-5-(3-(4-chloro-2-methylphenyl)-1-(hydroxyimino)-3-(4-(methylsulfonyl)phenyl)propyl)-1-(2-(2-methoxyethoxy)ethyl)pyridin-2(1H)-one

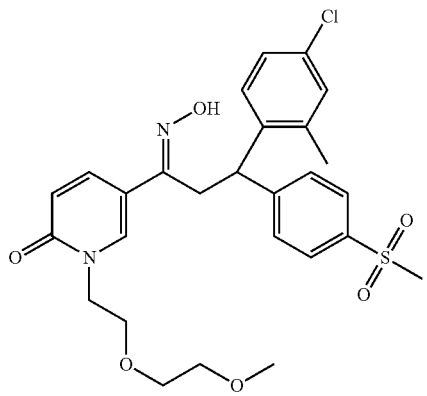 [SMILES: COCCOCCn1cc(/C(CC(c2ccc(S(C)(=O)=O)cc2)c2ccc(Cl)cc2C)=N/O)ccc1=O]

Step 1: 3-(4-Chloro-2-methylphenyl)-1-(6-methoxy-pyridin-3-yl)-3-(4-(methylsulfonyl)phenyl)-propan-1-one In analogy to example 203, step 1, (E)-3-(4-Chloro-2-methyl-phenyl)-1-(6-methoxy-pyridin-3-yl)-propenone (example 323, step 1) was reacted with 4-(methylsulfonyl)phenyl-boronic acid in the presence of chloro(1,5-cyclooctadiene)rhodium(I) dimer and sodium hydrogencarbonate in 1,4-dioxane and water at 60° C. to give the title compound as an off-white solid, MS (ESI$^+$): m/z=444.2 [M+H]$^+$.

Step 2: 5-(3-(4-Chloro-2-methylphenyl)-3-(4-(methylsulfonyl)phenyl)propanoyl)pyridin-2(1H)-one In analogy to example 162, step 2, 3-(4-chloro-2-methylphenyl)-1-(6-methoxypyridin-3-yl)-3-(4-(methylsulfonyl)phenyl)propan-1-one was reacted with concentrated aqueous HCl in 1,4-dioxane to give the title compound as an off-white solid, MS (ESI$^+$): m/z=430.2 [M+H]$^+$.

Step 3: 5-(3-(4-Chloro-2-methylphenyl)-3-(4-(methylsulfonyl)phenyl)propanoyl)-1-(2-(2-methoxyethoxy)ethyl)pyridin-2(1H)-one In analogy to example 161, step 1, 5-(3-(4-chloro-2-methylphenyl)-3-(4-(methylsulfonyl)phenyl)propanoyl)pyridin-2(1H)-one was reacted with 1-bromo-2-(2-methoxyethoxy)ethane in the presence of potassium carbonate and a catalytic amount of tetrabutylammonium iodide to give the title compound as a light brown oil, MS (ESI$^+$): m/z=532.2 [M+H]$^+$.

Step 4: (E)-5-(3-(4-Chloro-2-methylphenyl)-1-(hydroxyimino)-3-(4-(methylsulfonyl)-phenyl)propyl)-1-(2-(2-methoxyethoxy)ethyl)pyridin-2(1H)-one In analogy to example 151, step 3, 5-(3-(4-chloro-2-methylphenyl)-3-(4-(methylsulfonyl)phenyl)propanoyl)-1-(2-(2-methoxyethoxy)ethyl)pyridin-2(1H)-one was reacted with hydroxylamine hydrochloride in the presence of sodium hydrogencarbonate to give the title compound containing 12% of the corresponding Z isomer as a light yellow solid, MS (ESI$^+$): m/z=547.3 [M+H]$^+$.

Example 340

(E)-5-(3-(4-Chloro-2-methylphenyl)-1-(hydroxyimino)-3-(4-(methylsulfonyl)phenyl)-propyl)-1-(2-ethoxyethyl)pyridin-2(1H)-one

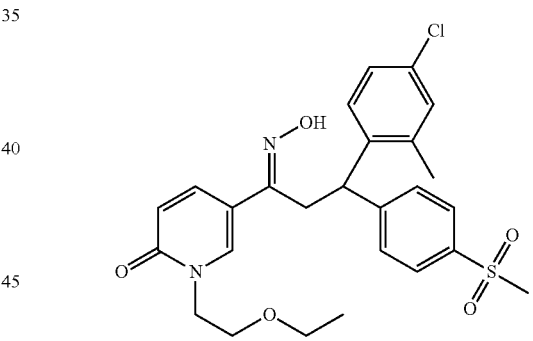

Step 1: 5-(3-(4-Chloro-2-methylphenyl)-3-(4-(methylsulfonyl)phenyl)propanoyl)-1-(2-ethoxyethyl)pyridin-2(1H)-one In analogy to example 161, step 1, 5-(3-(4-chloro-2-methylphenyl)-3-(4-(methylsulfonyl)phenyl)propanoyl)pyridin-2(1H)-one (example 339, step 2) was reacted with 1-bromo-2-ethoxyethane in the presence of potassium carbonate and a catalytic amount of tetrabutylammonium iodide to give the title compound as a light brown solid, MS (ESI$^+$): m/z=502.2 [M+H]$^+$.

Step 2: (E)-5-(3-(4-Chloro-2-methylphenyl)-1-(hydroxyimino)-3-(4-(methylsulfonyl)phenyl)-propyl)-1-(2-ethoxyethyl)pyridin-2(1H)-one In analogy to example 151, step 3, 5-(3-(4-chloro-2-methylphenyl)-3-(4-(methylsulfonyl)phenyl)propanoyl)-1-(2- ethoxyethyl)pyridin-2(1H)-one was reacted with hydroxylamine hydrochloride in the presence of sodium hydrogencarbonate to give the title compound as a colourless foam, MS (ESI$^+$): m/z=517.1 [M+H]$^+$.

Example 341

(E)-5-(3-(4-Chloro-2-methylphenyl)-1-(hydroxyimino)-3-(4-(methylsulfonyl)phenyl)-propyl)-1-(2-methoxyethyl)pyridin-2(1H)-one

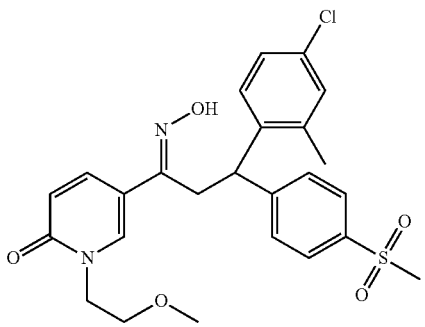 [SMILES: COCCn1cc(/C(CC(c2ccc(S(C)(=O)=O)cc2)c2ccc(Cl)cc2C)=N/O)ccc1=O]

In analogy to example 161, step 1, 5-(3-(4-chloro-2-methylphenyl)-3-(4-(methylsulfonyl)phenyl)propanoyl)pyridin-2(1H)-one (example 339, step 2) was reacted with 1-bromo-2-methoxyethane in the presence of potassium carbonate and a catalytic amount of tetrabutylammonium iodide. The product of this reaction was reacted in analogy to example 151, step 3, with hydroxylamine hydrochloride in the presence of sodium hydrogencarbonate to give the title compound as a colourless solid containing less than 10% of the corresponding Z isomer, MS (ESI$^+$): m/z=503.2 [M+H]$^+$.

Example 342

(E)-5-(3-(4-Chloro-2-methylphenyl)-1-(hydroxyimino)-3-(4-(methylsulfonyl)phenyl)-propyl)-1-(2-hydroxyethyl)pyridin-2(1H)-one

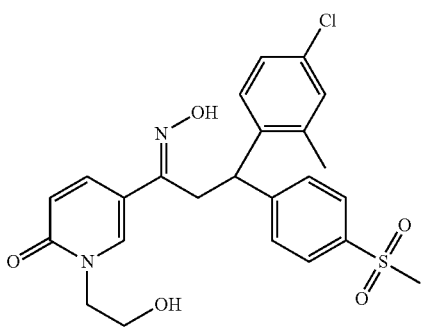 [SMILES: Cc1cc(Cl)ccc1C(C/C(=N\O)c1ccc(=O)n(CCO)c1)c1ccc(S(C)(=O)=O)cc1]

Step 1: 5-(3-(4-Chloro-2-methylphenyl)-3-(4-(methylsulfonyl)phenyl)propanoyl)-1-(2-hydroxyethyl)pyridin-2(1H)-one In analogy to example 161, step 1, 5-(3-(4-chloro-2-methylphenyl)-3-(4-(methylsulfonyl)phenyl)propanoyl)pyridin-2(1H)-one (example 339, step 2) was reacted with 2-bromoethanol in the presence of potassium carbonate and a catalytic amount of tetrabutylammonium iodide to give the title compound as a light yellow solid, MS (ESI$^+$): m/z=474.2 [M+H]$^+$.

Step 2: (E)-5-(3-(4-Chloro-2-methylphenyl)-1-(hydroxyimino)-3-(4-(methylsulfonyl)-phenyl)propyl)-1-(2-hydroxyethyl)pyridin-2(1H)-one In analogy to example 151, step 3, 5-(3-(4-chloro-2-methylphenyl)-3-(4-(methylsulfonyl)phenyl)propanoyl)-1-(2-hydroxyethyl)pyridin-2(1H)-one was reacted with hydroxylamine hydrochloride in the presence of sodium hydrogencarbonate to give the title compound containing less than 10% of the corresponding Z isomer as an off-white solid, MS (ESI$^+$): m/z=489.3 [M+H]$^+$.

Example 343

(E)-2-(5-(3-(4-Chloro-2-methylphenyl)-1-(hydroxyimino)-3-(4-(methylsulfonyl)-phenyl)propyl)-2-oxopyridin-1(2H)-yl)acetamide

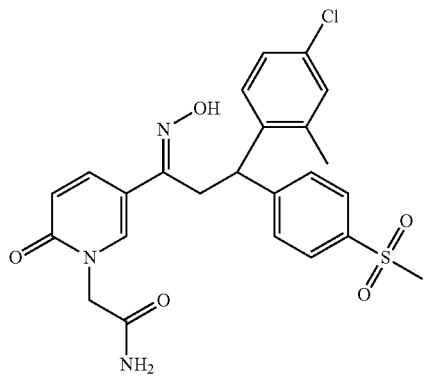 [SMILES: Cc1cc(Cl)ccc1C(C/C(=N\O)c1ccc(=O)n(CC(N)=O)c1)c1ccc(S(C)(=O)=O)cc1]

Step 1: 2-(5-(3-(4-Chloro-2-methylphenyl)-3-(4-(methylsulfonyl)phenyl)propanoyl)-2-oxopyridin-1(2H)-yl)acetamide In analogy to example 161, step 1, 5-(3-(4-chloro-2-methylphenyl)-3-(4-(methylsulfonyl)phenyl)propanoyl)pyridin-2(1H)-one (example 339, step 2) was reacted with 2-iodoacetamide in the presence of potassium carbonate to give the title compound as a light yellow solid, MS (ESI$^+$): m/z=487.3 [M+H]$^+$.

Step 2: (E)-2-(5-(3-(4-Chloro-2-methylphenyl)-1-(hydroxyimino)-3-(4-(methylsulfonyl)phenyl)-propyl)-2-oxopyridin-1(2H)-yl)acetamide In analogy to example 151, step 3, 2-(5-(3-(4-chloro-2-methylphenyl)-3-(4-(methylsulfonyl)phenyl)propanoyl)-2-oxopyridin-1(2H)-yl)acetamide was reacted with hydroxylamine hydrochloride in the presence of sodium hydrogencarbonate to give the title compound as an off-white solid, MS (ESI$^-$): m/z=500.1 [M−H]$^-$.

Example 344

(E)-3-(5-(3-(4-Chloro-2-methylphenyl)-1-(hydroxy-imino)-3-(4-(methylsulfonyl)phenyl)-propyl)-2-ox-opyridin-1(2H)-yl)propanamide

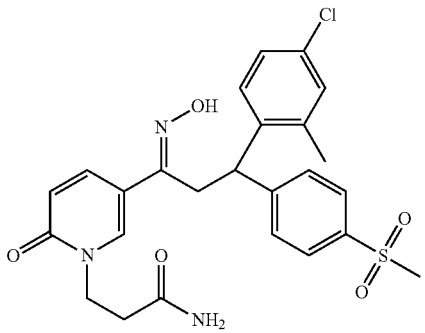 [SMILES: Cc1cc(Cl)ccc1C(C/C(=N\O)c1ccc(=O)n(CCC(N)=O)c1)c1ccc(S(C)(=O)=O)cc1]

Step 1: 3-(5-(3-(4-Chloro-2-methylphenyl)-3-(4-(methylsulfonyl)phenyl)propanoyl)-2-oxopyridin-1(2H)-yl)propanamide In analogy to example 161, step 1, 5-(3-(4-chloro-2-methylphenyl)-3-(4-(methylsulfonyl)phenyl)propanoyl)pyridin-2(1H)-one (example 339, step 2) was reacted with 3-bromopropanamide in the presence of potassium carbonate and a catalytic amount of tetrabutylammonium iodide to give the title compound as a light yellow solid, MS (ESI⁻): m/z=499.1 [M−H]⁻.

Step 2: (E)-3-(5-(3-(4-Chloro-2-methylphenyl)-1-(hydroxyimino)-3-(4-(methylsulfonyl)phenyl)-pro-pyl)-2-oxopyridin-1(2H)-yl)propanamide In analogy to example 151, step 3, 3-(5-(3-(4-chloro-2-methylphenyl)-3-(4-(methylsulfonyl)phenyl)propanoyl)-2-oxopyridin-1(2H)-yl)propanamide was reacted with hydroxylamine hydrochloride in the presence of sodium hydrogencarbonate to give the title compound containing less than 10% of the corresponding Z isomer as an off-white solid, MS (ESI⁺): m/z=516.4 [M+H]⁺.

Example 345

(E)-3-(5-(3-(4-Chloro-2-methylphenyl)-1-(hydroxy-imino)-3-(4-(methylsulfonyl)phenyl)-propyl)-2-ox-opyridin-1(2H)-yl)propanoic acid

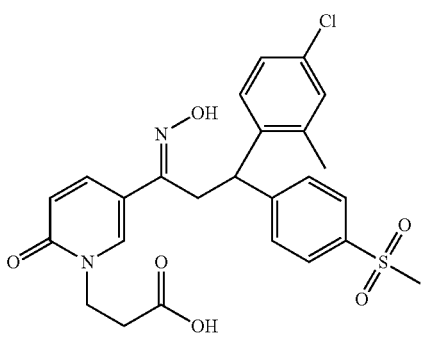 [SMILES: Cc1cc(Cl)ccc1C(C/C(=N\O)c1ccc(=O)n(CCC(=O)O)c1)c1ccc(S(C)(=O)=O)cc1]

Step 1: Methyl 3-(5-(3-(4-chloro-2-methylphenyl)-3-(4-(methylsulfonyl)phenyl)propanoyl)-2-oxopyridin-1(2H)-yl)propanoate In analogy to example 161, step 1, 5-(3-(4-chloro-2-methylphenyl)-3-(4-(methylsulfonyl)phenyl)propanoyl)pyridin-2(1H)-one (example 339, step 2) was reacted with methyl 3-bromopropanoate in the presence of potassium carbonate and a catalytic amount of tetrabutylammonium iodide to give the title compound as a light yellow solid, MS (ESI⁺): m/z=518.4 [M+H]⁺.

Step 2: 3-(5-(3-(4-chloro-2-methylphenyl)-3-(4-(methylsulfonyl)phenyl)propanoyl)-2-oxopyridin-1(2H)-yl)propanoic acid In analogy to example 169, step 2, methyl 3-(5-(3-(4-chloro-2-methylphenyl)-3-(4-(methylsulfonyl)phenyl)propanoyl)-2-oxopyridin-1(2H)-yl)propanoate was hydrolyzed to give the title compound as a light yellow solid, MS (ESI⁻): m/z=500.2 [M−H]⁻.

Step 3: (E)-3-(5-(3-(4-chloro-2-methylphenyl)-1-(hydroxyimino)-3-(4-(methylsulfonyl)phenyl)pro-pyl)-2-oxopyridin-1(2H)-yl)propanoic acid In analogy to example 151, step 3, 3-(5-(3-(4-chloro-2-methylphenyl)-3-(4-(methylsulfonyl)phenyl)propanoyl)-2-oxopyridin-1(2H)-yl)propanoic acid was reacted with hydroxylamine hydrochloride in the presence of sodium hydrogencarbonate to give the title compound containing less than 10% of the corresponding Z isomer as an off-white solid, MS (ESI⁻): m/z=515.3 [M−H]⁻.

Example 346

3-{4-[1-(4-Chloro-2-methyl-phenyl)-3-[(E)-hydroxy-imino]-3-(1-methyl-6-oxo-1,6-dihydro-pyridin-3-yl)-propyl]-phenoxy}-benzoic acid

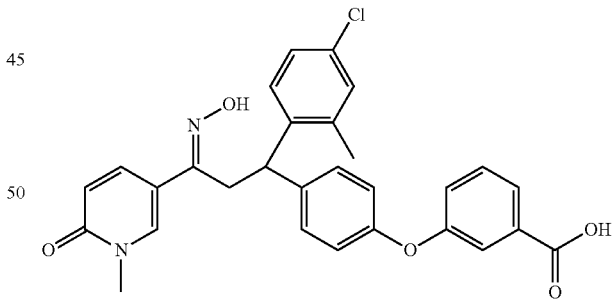

Step 1: 5-[3-(4-Chloro-2-methyl-phenyl)-3-(4-hydroxy-phenyl)-propionyl]-1-methyl-1H-pyridin-2-one In analogy to example 203, step 1, 5-[(E)-3-(4-chloro-2-methyl-phenyl)-acryloyl]-1-methyl-1H-pyridin-2-one (example 323, step 3) was reacted with 4-hydroxyphenylboronic acid in the presence of chloro(1,5-cyclooctadiene)rhodium(I) dimer and sodium hydrogencarbonate in 1,4-dioxane and water at 60° C. to give the title compound as a colourless solid, MS (ESI⁻): m/z=380.1 [M−H]⁻.

Step 2: 3-{4-[1-(4-Chloro-2-methyl-phenyl)-3-(1-methyl-6-oxo-1,6-dihydro-pyridin-3-yl)-3-oxo-propyl]-phenoxy}-benzoic acid methyl ester In analogy to example 222, step 1, 5-[3-(4-chloro-2-methyl-phenyl)-3-(4-hydroxy-phenyl)-propionyl]-1-methyl-1H-pyridin-2-one (example 346, step 1) was reacted with 3-methoxycarbonylphenylboronic acid in dichloromethane in the presence of copper(II) acetate, pyridine and air to give the title compound as a colourless solid, MS (ESI$^+$): m/z=516.4 [M+H]$^+$.

Step 3: 3-{4-[1-(4-Chloro-2-methyl-phenyl)-3-(1-methyl-6-oxo-1,6-dihydro-pyridin-3-yl)-3-oxo-propyl]-phenoxy}-benzoic acid In analogy to example 169, step 2, 3-{4-[1-(4-chloro-2-methyl-phenyl)-3-(1-methyl-6-oxo-1,6-dihydro-pyridin-3-yl)-3-oxo-propyl]-phenoxy}-benzoic acid methyl ester was hydrolyzed to give the title compound as a colourless solid, MS (ESI$^-$): m/z=500.1 [M−H]$^-$.

Step 4: 3-{4-[1-(4-Chloro-2-methyl-phenyl)-3-[(E)-hydroxyimino]-3-(1-methyl-6-oxo-1,6-dihydro-pyridin-3-yl)-propyl]-phenoxy}-benzoic acid In analogy to example 151, step 3, 3-{4-[1-(4-chloro-2-methyl-phenyl)-3-(1-methyl-6-oxo-1,6-dihydro-pyridin-3-yl)-3-oxo-propyl]-phenoxy}-benzoic acid was reacted with hydroxylamine hydrochloride in the presence of sodium hydrogencarbonate to give the title compound containing 9% of the corresponding Z isomer as a colourless solid, MS (ESI$^-$): m/z=515.3 [M−H]$^-$.

Example 347

2-Chloro-5-{4-[1-(4-chloro-2-methyl-phenyl)-3-[(E)-hydroxyimino]-3-(1-methyl-6-oxo-1,6-dihydro-pyridin-3-yl)-propyl]-phenoxy}-benzoic acid

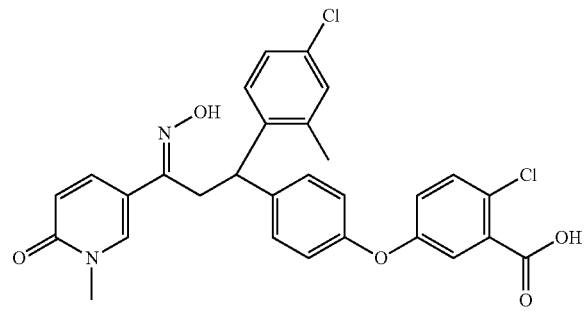 [SMILES: Cc1cc(Cl)ccc1C(C/C(=N\O)c1ccc(=O)n(C)c1)c1ccc(Oc2ccc(F)c(C(=O)O)c2)cc1]

Step 1: 2-Chloro-5-{4-[1-(4-Chloro-2-methyl-phenyl)-3-(1-methyl-6-oxo-1,6-dihydro-pyridin-3-yl)-3-oxo-propyl]-phenoxy}-benzoic acid ethyl ester In analogy to example 222, step 1, 5-[3-(4-chloro-2-methyl-phenyl)-3-(4-hydroxy-phenyl)-propionyl]-1-methyl-1H-pyridin-2-one (example 346, step 1) was reacted with 4-chloro-3-ethoxycarbonylphenylboronic acid in dichloromethane in the presence of copper(II) acetate, pyridine and air to give the title compound as a colourless solid, MS (ESI$^+$): m/z=564.2 [M+H]$^+$.

Step 2: 2-Chloro-5-{4-[1-(4-chloro-2-methyl-phenyl)-3-(1-methyl-6-oxo-1,6-dihydro-pyridin-3-yl)-3-oxo-propyl]-phenoxy}-benzoic acid In analogy to example 169, step 2, 2-chloro-5-{4-[1-(4-chloro-2-methyl-phenyl)-3-(1-methyl-6-oxo-1,6-dihydro-pyridin-3-yl)-3-oxo-propyl]-phenoxy}-benzoic acid ethyl ester was hydrolyzed to give the title compound as a colourless solid, MS (ESI$^-$): m/z=534.1 [M−H]$^-$.

Step 3: 2-Chloro-5-{4-[1-(4-chloro-2-methyl-phenyl)-3-[(E)-hydroxyimino]-3-(1-methyl-6-oxo-1,6-dihydro-pyridin-3-yl)-propyl]-phenoxy}-benzoic acid In analogy to example 151, step 3, 2-chloro-5-{4-[1-(4-chloro-2-methyl-phenyl)-3-(1-methyl-6-oxo-1,6-dihydro-pyridin-3-yl)-3-oxo-propyl]-phenoxy}-benzoic acid was reacted with hydroxylamine hydrochloride in the presence of sodium hydrogencarbonate to give the title compound containing less than 10% of the corresponding Z isomer as a colourless solid, MS (ESI$^-$): m/z=549.2 [M−H]$^-$.

Example 348

5-{4-[1-(4-Chloro-2-methyl-phenyl)-3-[(E)-hydroxyimino]-3-(1-methyl-6-oxo-1,6-dihydro-pyridin-3-yl)-propyl]-phenoxy}-2-fluoro-benzoic acid

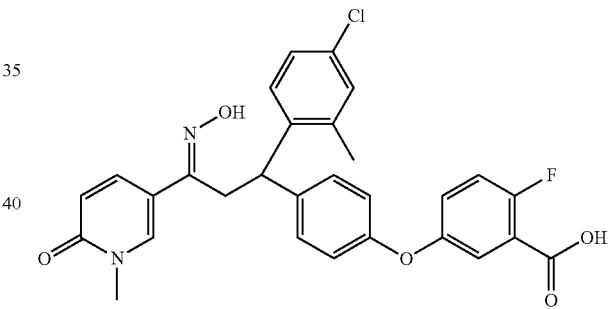

Step 1: 5-{4-[1-(4-Chloro-2-methyl-phenyl)-3-(1-methyl-6-oxo-1,6-dihydro-pyridin-3-yl)-3-oxo-propyl]-phenoxy}-2-fluoro-benzoic acid methyl ester In analogy to example 222, step 1, 5-[3-(4-chloro-2-methyl-phenyl)-3-(4-hydroxy-phenyl)-propionyl]-1-methyl-1H-pyridin-2-one (example 346, step 1) was reacted with 4-fluoro-3-methoxycarbonylphenylboronic acid in dichloromethane in the presence of copper(II) acetate, pyridine and air to give the title compound as a colourless solid, MS (ESI$^+$): m/z=534.2 [M+H]$^+$.

Step 2: 5-{4-[1-(4-Chloro-2-methyl-phenyl)-3-(1-methyl-6-oxo-1,6-dihydro-pyridin-3-yl)-3-oxo-propyl]-phenoxy}-2-fluoro-benzoic acid In analogy to example 169, step 2, 5-{4-[1-(4-chloro-2-methyl-phenyl)-3-(1-methyl-6-oxo-1,6-dihydro-pyridin-3-yl)-3-oxo-propyl]-phenoxy}-2-fluoro-benzoic acid methyl ester was hydrolyzed to give the title compound as a colourless solid, MS (ESI$^-$): m/z=518.1 [M−H]$^-$.

Step 3: 5-{4-[1-(4-Chloro-2-methyl-phenyl)-3-[(E)-hydroxyimino]-3-(1-methyl-6-oxo-1,6-dihydro-pyridin-3-yl)-propyl]-phenoxy}-2-fluoro-benzoic acid In analogy to example 151, step 3, 5-{4-[1-(4-chloro-2-methyl-phenyl)-3-(1-methyl-6-oxo-1,6-dihydro-pyridin-3-yl)-3-oxo-propyl]-phenoxy}-2-fluoro-benzoic acid was reacted with hydroxylamine hydrochloride in the presence of sodium hydrogencarbonate to give the title compound as a colourless solid, MS (ESI⁻): m/z=533.1 [M−H]⁻.

Example 349

4-{4-[1-(4-Chloro-2-methyl-phenyl)-3-[(E)-hydroxyimino]-3-(1-methyl-6-oxo-1,6-dihydro-pyridin-3-yl)-propyl]-phenoxy}-butyric acid

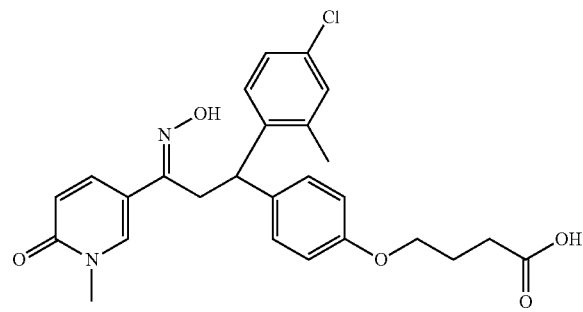 [SMILES: Cc1cc(Cl)ccc1C(C/C(=N\O)c1ccc(=O)n(C)c1)c1ccc(OCCCC(=O)O)cc1]

Step 1: 4-{4-[1-(4-Chloro-2-methyl-phenyl)-3-(1-methyl-6-oxo-1,6-dihydro-pyridin-3-yl)-3-oxo-propyl]-phenoxy}-butyric acid methyl ester In analogy to example 221, step 6, 5-[3-(4-chloro-2-methyl-phenyl)-3-(4-hydroxy-phenyl)-propionyl]-1-methyl-1H-pyridin-2-one (example 346, step 1) was reacted with methyl 4-bromobutyrate in N,N-dimethylacetamide in the presence of cesium carbonate to give the title compound as a colourless foam, MS (ESI⁺): m/z=482.2 [M+H]⁺.

Step 2: 4-{4-[1-(4-Chloro-2-methyl-phenyl)-3-(1-methyl-6-oxo-1,6-dihydro-pyridin-3-yl)-3-oxo-propyl]-phenoxy}-butyric acid In analogy to example 169, step 2, 4-{4-[1-(4-chloro-2-methyl-phenyl)-3-(1-methyl-6-oxo-1,6-dihydro-pyridin-3-yl)-3-oxo-propyl]-phenoxy}-butyric acid methyl ester was hydrolyzed to give the title compound as a colourless solid, MS (ESI⁻): m/z=466.1 [M−H]⁻.

Step 3: 4-{4-[1-(4-Chloro-2-methyl-phenyl)-3-[(E)-hydroxyimino]-3-(1-methyl-6-oxo-1,6-dihydro-pyridin-3-yl)-propyl]-phenoxy}-butyric acid In analogy to example 151, step 3, 4-{4-[1-(4-chloro-2-methyl-phenyl)-3-(1-methyl-6-oxo-1,6-dihydro-pyridin-3-yl)-3-oxo-propyl]-phenoxy}-butyric acid was reacted with hydroxylamine hydrochloride in the presence of sodium hydrogencarbonate to give the title compound containing less than 10% of the corresponding Z isomer as a colourless solid, MS (ESI⁻): m/z=481.1 [M−H]⁻.

Example 350

(E)-5-(3-(2,5-Dichlorophenyl)-1-(hydroxyimino)-3-(4-(methylsulfonyl)phenyl)propyl)-1-methylpyridin-2(1H)-one

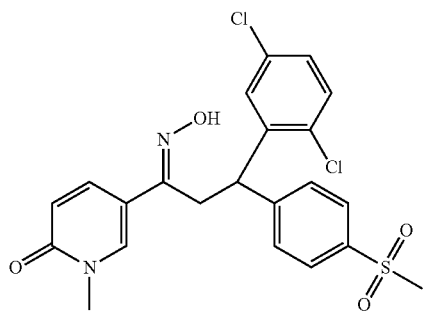 [SMILES: Cn1cc(/C(CC(c2ccc(S(C)(=O)=O)cc2)c2cc(Cl)ccc2Cl)=N/O)ccc1=O]

Step 1: (E)-3-(2,5-Dichlorophenyl)-1-(6-methoxypyridin-3-yl)prop-2-en-1-one

In analogy to example 170, step 1, 5-acetyl-2-methoxypyridine was reacted with 2,5-dichlorobenzaldehyde in the presence of potassium hydroxide to give the title compound as a colourless solid. MS (ESI⁺): m/z=308.1 [M+H]⁺.

Step 2: (E)-5-(3-(2,5-Dichlorophenyl)acryloyl)pyridin-2(1H)-one

In analogy to example 162, step 2, (E)-3-(2,5-dichlorophenyl)-1-(6-methoxypyridin-3-yl)prop-2-en-1-one was reacted with concentrated aqueous HCl in 1,4-dioxane to give the title compound as a light yellow solid, MS (ESI⁺): m/z=294.0 [M+H]⁺.

Step 3: (E)-5-(3-(2,5-Dichlorophenyl)acryloyl)-1-methylpyridin-2(1H)-one

In analogy to example 161, step 1, (E)-5-(3-(2,5-dichlorophenyl)acryloyl)pyridin-2(1H)-one was reacted with iodomethane in the presence of potassium carbonate to give the title compound as a light yellow solid.

Step 4: 5-(3-(2,5-Dichlorophenyl)-3-(4-(methylsulfonyl)phenyl)propanoyl)-1-methylpyridin-2(1H)-one In analogy to example 203, step 1, (E)-5-(3-(2,5-dichlorophenyl)acryloyl)-1-methylpyridin-2(1H)-one was reacted with 4-(methylsulfonyl)phenylboronic acid in the presence of chloro(1,5-cyclooctadiene)rhodium(I) dimer and sodium hydrogencarbonate in 1,4-dioxane and water at 60° C. to give the title compound as a colourless solid, MS (ESI⁺): m/z=464.1 [M+H]⁺.

Step 5: (E)-5-(3-(2,5-Dichlorophenyl)-1-(hydroxyimino)-3-(4-(methylsulfonyl)phenyl)propyl)-1-methylpyridin-2(1H)-one In analogy to example 151, step 3, 5-(3-(2,5-dichlorophenyl)-3-(4-(methylsulfonyl)-phenyl)propanoyl)-1-methylpyridin-2(1H)-one was reacted with hydroxylamine hydrochloride in the presence of sodium hydrogencarbonate to give the title compound containing 3% of the corresponding Z isomer as a colourless solid, MS (ESI+): m/z=479.1 [M+H]+.

Example 351

(E)-5-(3-(3,5-Difluorophenyl)-1-(hydroxyimino)-3-(4-(methylsulfonyl)phenyl)propyl)-1-methylpyridin-2(1H)-one

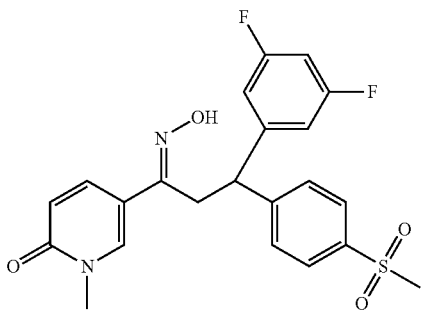 [SMILES: Cn1cc(/C(CC(c2ccc(S(C)(=O)=O)cc2)c2cc(F)cc(F)c2)=N/O)ccc1=O]

Step 1: (E)-3-(3,5-Difluorophenyl)-1-(6-methoxypyridin-3-yl)prop-2-en-1-one

In analogy to example 170, step 1, 5-acetyl-2-methoxypyridine was reacted with 3,5-difluorobenzaldehyde in the presence of potassium hydroxide to give the title compound as a colourless solid. MS (ESI+): m/z=276.2 [M+H]+.

Step 2: (E)-5-(3-(3,5-Difluorophenyl)acryloyl)pyridin-2(1H)-one

In analogy to example 162, step 2, (E)-3-(3,5-difluorophenyl)-1-(6-methoxypyridin-3-yl)prop-2-en-1-one was reacted with concentrated aqueous HCl in 1,4-dioxane to give the title compound as a colourless solid, MS (ESI+): m/z=262.1 [M+H]+.

Step 3: (E)-5-(3-(3,5-Difluorophenyl)acryloyl)-1-methylpyridin-2(1H)-one

In analogy to example 161, step 1, (E)-5-(3-(3,5-difluorophenyl)acryloyl)pyridin-2(1H)-one was reacted with iodomethane in the presence of potassium carbonate to give the title compound as a light yellow solid. MS (ESI+): m/z=276.1 [M+H]+.

Step 4: 5-(3-(3,5-Difluorophenyl)-3-(4-(methylsulfonyl)phenyl)propanoyl)-1-methylpyridin-2(1H)-one In analogy to example 203, step 1, (E)-5-(3-(3,5-difluorophenyl)acryloyl)-1-methylpyridin-2(1H)-one was reacted with 4-(methylsulfonyl)phenylboronic acid in the presence of chloro(1,5-cyclooctadiene)rhodium(I) dimer and sodium hydrogencarbonate in 1,4-dioxane and water at 60° C. to give the title compound as a yellow solid, MS (ESI+): m/z=432.3 [M+H]+.

Step 5: (E)-5-(3-(3,5-Difluorophenyl)-1-(hydroxyimino)-3-(4-(methylsulfonyl)phenyl)propyl)-1-methylpyridin-2(1H)-one In analogy to example 151, step 3, 5-(3-(3,5-difluorophenyl)-3-(4-(methylsulfonyl)phenyl)propanoyl)-1-methylpyridin-2(1H)-one was reacted with hydroxylamine hydrochloride in the presence of sodium hydrogencarbonate to give the title compound containing less than 10% of the corresponding Z isomer as a colourless solid, MS (ESI+): m/z=447.2 [M+H]+.

Example 352

(E)-5-(3-(3,5-Dichlorophenyl)-1-(hydroxyimino)-3-(4-(methylsulfonyl)phenyl)propyl)-1-methylpyridin-2(1H)-one

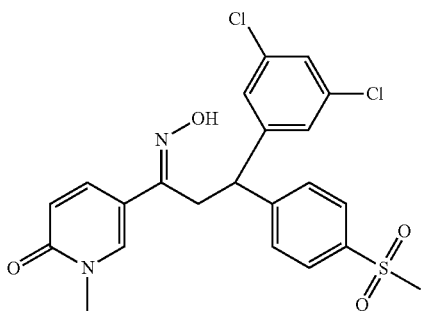 [SMILES: Cn1cc(/C(CC(c2ccc(S(C)(=O)=O)cc2)c2cc(Cl)cc(Cl)c2)=N/O)ccc1=O]

Step 1: (E)-3-(3,5-Dichlorophenyl)-1-(6-methoxypyridin-3-yl)prop-2-en-1-one

In analogy to example 170, step 1, 5-acetyl-2-methoxypyridine was reacted with 3,5-dichlorobenzaldehyde in the presence of potassium hydroxide to give the title compound as a colourless solid.

Step 2: (E)-5-(3-(3,5-Dichlorophenyl)acryloyl)pyridin-2(1H)-one

In analogy to example 162, step 2, (E)-3-(3,5-dichlorophenyl)-1-(6-methoxypyridin-3-yl)prop-2-en-1-one was reacted with concentrated aqueous HCl in 1,4-dioxane to give the title compound as a colourless solid.

Steps 3-5: (E)-5-(3-(3,5-Dichlorophenyl)-1-(hydroxyimino)-3-(4-(methylsulfonyl)phenyl)-propyl)-1-methylpyridin-2(1H)-one In analogy to example 161, step 1, (E)-5-(3-(3,5-dichlorophenyl)acryloyl)pyridin-2(1H)-one was reacted with iodomethane in the presence of potassium carbonate. The product of this reaction was treated in analogy to example 203, step 1, with 4-(methylsulfonyl)phenylboronic acid in the presence of chloro(1,5-cyclooctadiene)rhodium(I) dimer and sodium hydrogen-carbonate in 1,4-dioxane and water at 60° C. The product of this reaction was reacted with hydroxylamine hydrochloride in the presence of sodium hydrogencarbonate to give the title compound containing less than 10% of the corresponding Z isomer as an off-white solid, MS (ESI⁺): m/z=479.1 [M+H]⁺.

Example 353

N-{4-[1-(4-Chloro-2-methyl-phenyl)-3-[(E)-hydroxyimino]-3-(1-methyl-6-oxo-1,6-dihydro-pyridin-3-yl)-propyl]phenyl}-methanesulfonamide

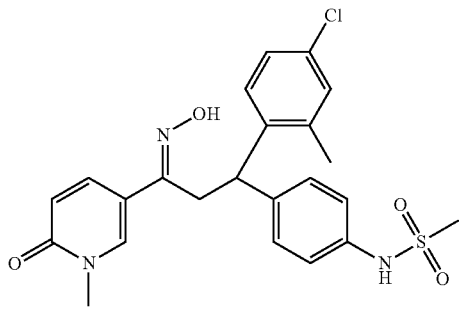 [SMILES: Cc1cc(Cl)ccc1C(C/C(=N\O)c1ccc(=O)n(C)c1)c1ccc(NS(C)(=O)=O)cc1]

Step 1: 5-[3-(4-Amino-phenyl)-3-(4-chloro-2-methyl-phenyl)-propionyl]-1-methyl-1H-pyridin-2-one In analogy to example 203, step 1, 5-[(E)-3-(4-chloro-2-methyl-phenyl)-acryloyl]-1-methyl-1H-pyridin-2-one (example 323, step 3) was reacted with 4-(4,4,5,5-tetramethyl-1,3,2-dioxaborolan-2-yl)aniline in the presence of chloro(1,5-cyclooctadiene)rhodium(I) dimer and sodium hydrogencarbonate in 1,4-dioxane and water at 60° C. to give the title compound as a light brown solid, MS (ESI⁺): m/z=381.3 [M+H]⁺.

Step 2: N-{4-[1-(4-Chloro-2-methyl-phenyl)-3-(1-methyl-6-oxo-1,6-dihydro-pyridin-3-yl)-3-oxo-propyl]-phenyl}-methanesulfonamide In a 10 mL round-bottomed flask 5-[3-(4-amino-phenyl)-3-(4-chloro-2-methyl-phenyl)-propionyl]-1-methyl-1H-pyridin-2-one (88 mg) and methanesulfonyl chloride (40.1 mg) were combined with pyridine (0.87 mL) to give a brown solution. The reaction mixture was stirred at room temperature for 3 h. The crude reaction mixture was concentrated in vacuo. The reaction mixture was extracted 3× with ethyl acetate, the organic layers were washed 3× with water and dried over magnesium sulfate and concentrated in vacuo. The crude material was purified by flash chromatography (silica gel, 20 g, 0% to 10% methanol in dichloromethane) to give the title compound (68 mg) as a colourless foam, MS (ESI⁺): m/z=459.3 [M+H]⁺.

Step 3: N-{4-[1-(4-Chloro-2-methyl-phenyl)-3-[(E)-hydroxyimino]-3-(1-methyl-6-oxo-1,6-dihydro-pyridin-3-yl)-propyl]-phenyl}-methanesulfonamide In analogy to example 151, step 3, N-{4-[1-(4-chloro-2-methyl-phenyl)-3-(1-methyl-6-oxo-1,6-dihydro-pyridin-3-yl)-3-oxo-propyl]-phenyl}-methanesulfonamide was reacted with hydroxylamine hydrochloride in the presence of sodium hydrogencarbonate to give the title compound containing 4% of the corresponding Z isomer as a colourless solid, MS (ESI⁺): m/z=474.2 [M+H]⁺.

Example 354

Cyclopropanesulfonic acid {4-[1-(4-chloro-2-methyl-phenyl)-3-[(E)-hydroxyimino]-3-(1-methyl-6-oxo-1,6-dihydro-pyridin-3-yl)-propyl]-phenyl}-amide

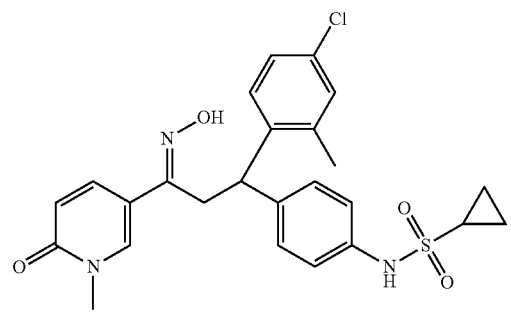 [SMILES: Cc1cc(Cl)ccc1C(C/C(=N\O)c1ccc(=O)n(C)c1)c1ccc(NS(=O)(=O)C2CC2)cc1]

Step 1: Cyclopropanesulfonic acid {4-[1-(4-chloro-2-methyl-phenyl)-3-(1-methyl-6-oxo-1,6-dihydro-pyridin-3-yl)-3-oxo-propyl]-phenyl}-amide In analogy to example 353, step 2, 5-[3-(4-amino-phenyl)-3-(4-chloro-2-methyl-phenyl)-propionyl]-1-methyl-1H-pyridin-2-one (example 353, step 1) was reacted with cyclopropane-sulfonyl chloride in pyridine to give the title compound as an off-white solid, MS (ESI⁺): m/z=485.2 [M+H]⁺.

Step 2: Cyclopropanesulfonic acid {4-[1-(4-chloro-2-methyl-phenyl)-3-[(E)-hydroxyimino]-3-[1-methyl-6-oxo-1,6-dihydro-pyridin-3-yl)-propyl]-phenyl}-amide In analogy to example 151, step 3, cyclopropanesulfonic acid {4-[1-(4-chloro-2-methyl-phenyl)-3-(1-methyl-6-oxo-1,6-dihydro-pyridin-3-yl)-3-oxo-propyl]-phenyl}-amide was reacted with hydroxylamine hydrochloride in the presence of sodium hydrogencarbonate to give the title compound containing 7% of the corresponding Z isomer as a colourless solid, MS (ESI⁺): m/z=500.3 [M+H]⁺.

Example 355

5-{3-(4-Chloro-2-methyl-phenyl)-1-[(E)-hydroxyimino]-3-[4-(2-oxo-pyrrolidin-1-yl)-phenyl]-propyl}-1-methyl-1H-pyridin-2-one

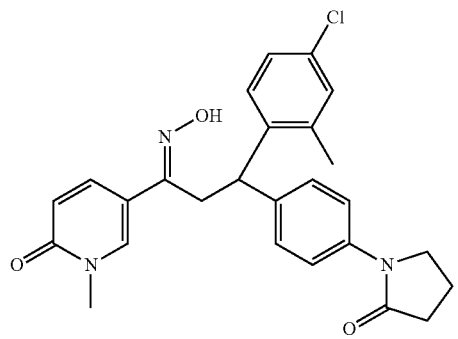 [SMILES: Cc1cc(Cl)ccc1C(C/C(=N\O)c1ccc(=O)n(C)c1)c1ccc(N2CCCC2=O)cc1]

Step 1: 4-Chloro-N-{4-[1-(4-chloro-2-methyl-phenyl)-3-(1-methyl-6-oxo-1,6-dihydro-pyridin-3-yl)-3-oxo-propyl]-phenyl}-butyramide In a 10 mL round-bottomed flask 5-[3-(4-amino-phenyl)-3-(4-chloro-2-methyl-phenyl)-propionyl]-1-methyl-1H-pyridin-2-one (example 353, step 1, 100 mg) was dissolved in dichloromethane (1.3 mL) and pyridine (41 mg). Then the reaction mixture was cooled in an icebath and 4-chlorobutyryl chloride (41.6 mg) was added slowly. The icebath was removed and the reaction mixture was stirred at room temperature for 3 h. The reaction mixture was diluted with ethyl acetate. The organic layer was washed 1× with 1 M HCl and 2× with water. The aqueous layers were extracted 2× with ethyl acetate, the combined organic layers were dried over magnesium sulfate and concentrated in vacuo. The crude material was purified by flash chromatography (silica gel, 20 g, 0% to 10% methanol in dichloromethane) to give the title compound as a light yellow foam, MS (ESI$^+$): m/z=485.3 [M+H]$^+$.

Step 2: 5-{3-(4-Chloro-2-methyl-phenyl)-3-[4-(2-oxo-pyrrolidin-1-yl)-phenyl]-propionyl}-1-methyl-1H-pyridin-2-one In a 5 mL round-bottomed flask 4-chloro-N-{4-[1-(4-chloro-2-methyl-phenyl)-3-(1-methyl-6-oxo-1,6-dihydro-pyridin-3-yl)-3-oxo-propyl]-phenyl}-butyramide (87 mg) was combined with tetrahydrofuran (1.15 mL) to give a colourless solution. The reaction mixture was cooled in an ice bath and potassium tert-butoxide (20.1 mg) was added to give a yellow solution, which was stirred for 2 h at 0° C. and for 1½ h at room temperature The reaction mixture was poured on water, then extracted 3× with ethyl acetate, the organic phases were washed 2× with water, dried over magnesium sulfate and concentrated in vacuo. The crude material was purified by flash chromatography (silica gel, 20 g, 0% to 10% methanol in dichloromethane) to give the title compound (58 mg) as an off-white solid, MS (ESI$^+$): m/z=449.2 [M+H]$^+$.

Step 3: 5-{3-(4-Chloro-2-methyl-phenyl)-1-[(E)-hydroxyimino]-3-[4-(2-oxo-pyrrolidin-1-yl)-phenyl]-propyl}-1-methyl-1H-pyridin-2-one In analogy to example 151, step 3, 5-{3-(4-chloro-2-methyl-phenyl)-3-[4-(2-oxo-pyrrolidin-1-yl)-phenyl]-propionyl}-1-methyl-1H-pyridin-2-one was reacted with hydroxylamine hydrochloride in the presence of sodium hydrogencarbonate to give the title compound containing less than 10% of the corresponding Z isomer as a colourless solid, MS (ESI$^+$): m/z=464.2 [M+H]$^+$.

Example 356

3-{4-[(R)-3-[(E)-Hydroxyimino]-3-(2-methyl-pyridin-4-yl)-1-o-tolyl-propyl]-phenylamino}-cyclobutanecarboxylic acid

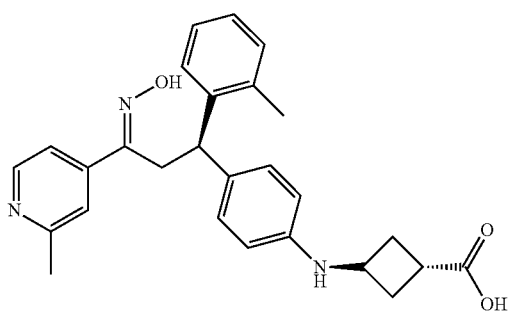

Step 1: 3-{4-[(R)-3-(2-Methyl-pyridin-4-yl)-3-oxo-1-o-tolyl-propyl]-phenylamino}-cyclobutanecarboxylic acid In analogy to example 39, from (R)-3-(4-bromo-phenyl)-1-(2-methyl-pyridin-4-yl)-3-o-tolyl-propan-1-one (example 142, step 2) and trans-ethyl 3-aminocyclobutanecarboxylate hydrochloride in the presence of tris(dibenzylideneacetone)dipalladium(0), 4,5-bis(diphenyl-phosphino)-9,9-dimethylxanthene and cesium carbonate in 1,4-dioxane was prepared 3-{4-[(R)-3-(2-methyl-pyridin-4-yl)-3-oxo-1-o-tolyl-propyl]-phenylamino}-cyclobutanecarboxylic acid ethyl ester.

In analogy to example 169, step 2, from 3-{4-[(R)-3-(2-methyl-pyridin-4-yl)-3-oxo-1-o-tolyl-propyl]-phenylamino}-cyclobutanecarboxylic acid ethyl ester in presence of 1 M aq. lithium hydroxide solution in tetrahydrofuran was prepared 3-{4-[(R)-3-(2-methyl-pyridin-4-yl)-3-oxo-1-o-tolyl-propyl]-phenylamino}-cyclobutanecarboxylic acid as a yellow foam, MS (ESI$^+$): m/z=429.2 ([M+H]$^+$).

Step 2: 3-{4-[(R)-3-[(E)-Hydroxyimino]-3-(2-methyl-pyridin-4-yl)-1-o-tolyl-propyl]-phenylamino}-cyclobutanecarboxylic acid In analogy to example 132, step 6, from 3-{4-[(R)-3-(2-methyl-pyridin-4-yl)-3-oxo-1-o-tolyl-propyl]-phenylamino}-cyclobutanecarboxylic acid in the presence of sodium hydrogen-carbonate was prepared the title compound as a yellow foam, MS (ESI$^+$): m/z=444.4 ([M+H]$^+$).

Example 357

(R)-3-[4-(3-Chloro-2-methoxy-propylamino)-phenyl]-1-(2-methyl-pyridin-4-yl)-3-o-tolyl-propan-1-one oxime

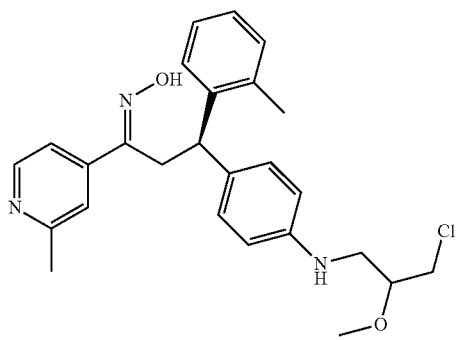 [SMILES: COC(CCl)CNc1ccc([C@@H](C/C(=N\O)c2ccnc(C)c2)c2ccccc2C)cc1]

To a solution of (R)-3-[4-(3-methoxy-azetidin-1-yl)-phenyl]-1-(2-methyl-pyridin-4-yl)-3-o-tolyl-propan-1-one oxime (example 270, 31 mg) in 1,4-dioxane (2 mL) was added at room temperature hydrochloric acid 4 M in 1,4-dioxane (187 µL). The reaction mixture was heated at 50° C. and stirred for 4 hours. A saturated solution of sodium hydrogencarbonate (2 mL) was added to neutralized the crude solution followed by a saturated aq. ammonium chloride solution. Ethyl acetate was added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (25% to 100% ethyl acetate in n-heptane) to yield the title compound as a light yellow foam (89%), MS (ESI$^+$): m/z=452.3 ([M+H]$^+$).

Example 358

(R)-3-(4-Methanesulfonyl-phenyl)-1-(2-methyl-pyridin-4-yl)-3-o-tolyl-propan-1-one oxime

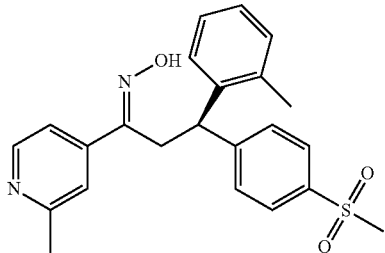 [SMILES: Cc1cc(/C(C[C@H](c2ccc(S(C)(=O)=O)cc2)c2ccccc2C)=N/O)ccn1]

Step 1: (R)-3-(4-Methanesulfonyl-phenyl)-1-(2-methyl-pyridin-4-yl)-3-o-tolyl-propan-1-one To a solution of L-proline (35 mg) in dimethyl sulfoxide (4 mL) was added at room temperature sodium hydroxide (12 mg). The reaction mixture was stirred at room temperature for 30 min. (R)-3-(4-Bromo-phenyl)-1-(2-methyl-pyridin-4-yl)-3-o-tolyl-propan-1-one (example 142, step 2, 150 mg), sodium methanesulfinate (311 mg) and copper(I) iodide (58 mg) were added. The reaction mixture was heated at 110° C. and stirred for 4 hours. Water and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (50% to 100% ethyl acetate in n-heptane) to yield the title compound as an yellow oil (57%), MS (ESI$^+$): m/z=394.0 ([M+H]$^+$).

Step 2: (R)-3-(4-Methanesulfonyl-phenyl)-1-(2-methyl-pyridin-4-yl)-3-o-tolyl-propan-1-one oxime In analogy to example 132, step 6, from (R)-3-(4-methanesulfonyl-phenyl)-1-(2-methyl-pyridin-4-yl)-3-o-tolyl-propan-1-one in the presence of sodium hydrogencarbonate was prepared the title compound as a white foam, MS (ESI$^+$): m/z=409.2 ([M+H]$^+$).

Example 359

(R)-3-(4-Chloro-2-methyl-phenyl)-3-(4-methanesulfonyl-phenyl)-1-(2-methyl-pyridin-4-yl)-propan-1-one oxime

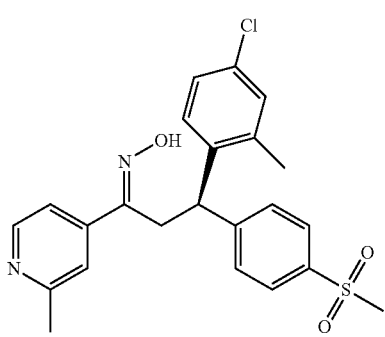 [SMILES: Cc1cc(/C(C[C@H](c2ccc(S(C)(=O)=O)cc2)c2ccc(Cl)cc2C)=N/O)ccn1]

Step 1: (R)-3-(4-Chloro-2-methyl-phenyl)-3-(4-methanesulfonyl-phenyl)-1-(2-methyl-pyridin-4-yl)-propan-1-one In analogy to example 358, step 1, from (R)-3-(4-bromo-phenyl)-3-(4-chloro-2-methyl-phenyl)-1-(2-methyl-pyridin-4-yl)-propan-1-one (example 282, step 1) in the presence of sodium methanesulfinate, L-proline, sodium hydroxide and copper(I) iodide in 1,4-dioxane was prepared the title compound as an yellow oil, MS (ESI$^+$): m/z=428.1 ([M+H]$^+$).

Step 2: (R)-3-(4-Chloro-2-methyl-phenyl)-3-(4-methanesulfonyl-phenyl)-1-(2-methyl-pyridin-4-yl)-propan-1-one oxime In analogy to example 132, step 6, from (R)-3-(4-chloro-2-methyl-phenyl)-3-(4-methanesulfonyl-phenyl)-1-(2-methyl-pyridin-4-yl)-propan-1-one in the presence of sodium hydrogencarbonate was prepared the title compound as a white foam, MS (ESI$^+$): m/z=443.2 ([M+H]$^+$).

Example 360

4-[3-[(E)-Hydroxyimino]-3-(1-methyl-6-oxo-1,6-dihydro-pyridin-3-yl)-1-o-tolyl-propyl]-benzoic acid

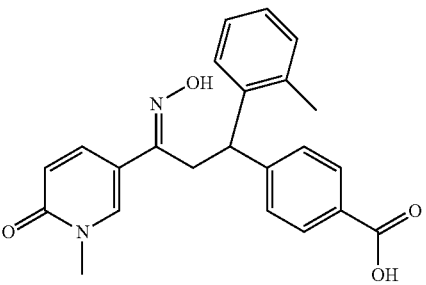 [SMILES: Cc1ccccc1C(C/C(=N\O)c1ccc(=O)n(C)c1)c1ccc(C(=O)O)cc1]

In analogy to example 1, step 2, from 4-[3-(1-methyl-6-oxo-1,6-dihydro-pyridin-3-yl)-3-oxo-1-o-tolyl-propyl]-benzoic acid (example 207, step 1) and hydroxylamine hydrochloride in the presence of sodium hydrogencarbonate was prepared the title compound as a colourless oil, MS (ESI$^+$): m/z=391.3 ([M+H]$^+$).

Example 361

4-[1-(4-Chloro-2-methyl-phenyl)-3-[(E)-hydroxyimino]-3-(1-methyl-6-oxo-1,6-dihydro-pyridin-3-yl)-propyl]-benzoic acid

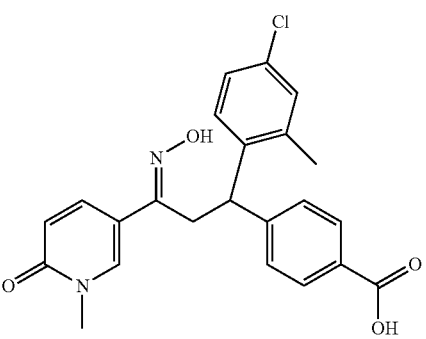 [SMILES: Cc1cc(Cl)ccc1C(C/C(=N\O)c1ccc(=O)n(C)c1)c1ccc(C(=O)O)cc1]

In analogy to example 1, step 2, from 4-[1-(4-chloro-2-methyl-phenyl)-3-(1-methyl-6-oxo-1,6-dihydro-pyridin-3-yl)-3-oxo-propyl]-benzoic acid (example 332, step 2) and hydroxylamine hydrochloride in the presence of sodium hydrogencarbonate was prepared the title compound as a light yellow oil, MS (ESI⁺): m/z=425.1 ([M+H]⁺).

Example 362

(E,R)-4-(4-bromo-phenyl)-4-(4-chloro-2-methyl-phenyl)-1-pyridin-2-yl-butan-2-one oxime

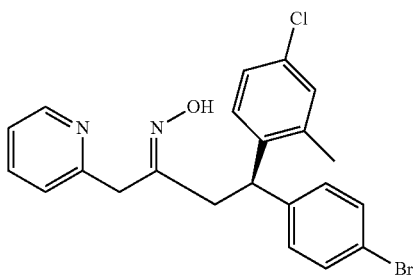 [SMILES: Cc1cc(Cl)ccc1[C@H](C/C(Cc1ccccn1)=N\O)c1ccc(Br)cc1]

Step 1: (R)-4-(4-Bromo-phenyl)-4-(4-chloro-2-methyl-phenyl)-1-pyridin-2-yl-butan-2-one In analogy to example 261, step 1, from (R)-3-(4-bromo-phenyl)-3-(4-chloro-2-methyl-phenyl)-N-methoxy-N-methyl-propionamide and 2-methyl-pyridine was prepared the title compound as a yellow oil, MS (ESI⁺): m/z=430.0 ([M+H]⁺, 1Br).

Step 2: (E,R)-4-(4-bromo-phenyl)-4-(4-chloro-2-methyl-phenyl)-1-pyridin-2-yl-butan-2-one oxime In analogy to example 74, step 7, from (R)-4-(4-bromo-phenyl)-4-(4-chloro-2-methyl-phenyl)-1-pyridin-2-yl-butan-2-one and hydroxylamine hydrochloride in the presence of sodium hydrogencarbonate was prepared (E,R)-4-(4-bromo-phenyl)-4-(4-chloro-2-methyl-phenyl)-1-pyridin-2-yl-butan-2-one oxime as a white foam, MS (ESI⁺): m/z=445.1 ([M+H]⁺, 1Br).

Example 363

(R)-3-(4-Hydroxy-phenyl)-1-(2-methyl-pyridin-4-yl)-3-o-tolyl-propan-1-one oxime

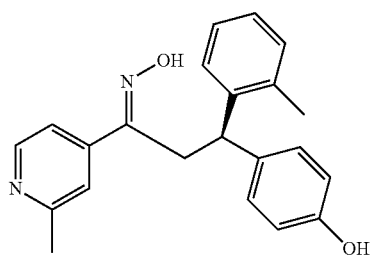 [SMILES: Cc1cc(/C(C[C@H](c2ccc(O)cc2)c2ccccc2C)=N/O)ccn1]

Step 1: (R)-3-(4-Hydroxy-phenyl)-1-(2-methyl-pyridin-4-yl)-3-o-tolyl-propan-1-one To a white suspension of (R)-3-(4-bromo-phenyl)-1-(2-methyl-pyridin-4-yl)-3-o-tolyl-propan-1-one (example 142, step 2, 200 mg) and potassium hydroxide (62.6 mg) in 1,4-dioxane (1 mL) and water (0.6 mL) under argon were added 2-di-tert-butylphosphino-2',4',6'-triisopropyl-biphenyl (17.2 mg) and tris(dibenzylideneacetone)dipalladium(0) (9.3 mg). The reaction mixture was heated to 100° C. and stirred for 3 hours. A saturated aq. solution of ammonium chloride and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (30% to 100% ethyl acetate in heptane) to yield the title compound as a light yellow semisolid (77%), MS (ESI⁺): m/z=332.1 ([M+H]⁺).

Step 2: (R)-3-(4-Hydroxy-phenyl)-1-(2-methyl-pyridin-4-yl)-3-o-tolyl-propan-1-one oxime In analogy to example 132, step 6, from (R)-3-(4-hydroxy-phenyl)-1-(2-methyl-pyridin-4-yl)-3-o-tolyl-propan-1-one and hydroxylamine hydrochloride in the presence of sodium hydrogencarbonate was prepared the title compound as a white solid, MS (ESI⁺): m/z=347.2 ([M+H]⁺).

Example 364

(R)-3-(4-Ethoxy-phenyl)-1-(2-methyl-pyridin-4-yl)-3-o-tolyl-propan-1-one oxime

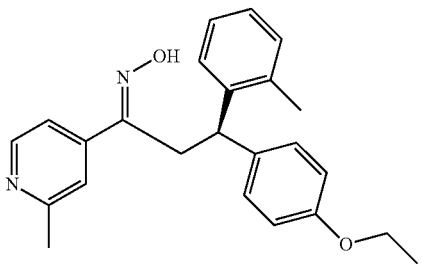 [SMILES: CCOc1ccc([C@@H](C/C(=N\O)c2ccnc(C)c2)c2ccccc2C)cc1]

Step 1: (R)-3-(4-Ethoxy-phenyl)-1-(2-methyl-pyridin-4-yl)-3-o-tolyl-propan-1-one To a white suspension of (R)-3-(4-bromo-phenyl)-1-(2-methyl-pyridin-4-yl)-3-o-tolyl-propan-1-one (example 142, step 2, 200 mg) and potassium hydroxide (171 mg) in 1,4-dioxane (1 mL) and water (2 mL) under argon were added 2-di-tert-butylphosphino-2',4',6'-triisopropyl-biphenyl (17.2 mg) and tris(dibenzylideneacetone)dipalladium(0) (9.3 mg). The reaction mixture was heated to 100° C. and stirred for 3 hours. After cooling at room temperature, cetyl trimethyl-ammonium bromide (18.5 mg) and iodoethane (158 mg) were added. The reaction mixture was heated to 100° C. for 1 hour. A saturated aq. solution of ammonium chloride and ethyl acetate were added, the phases were separated and the inorganic one was extracted with ethyl acetate (2×). The combined organic layers were washed with brine, dried over sodium sulfate, filtered and concentrated in vacuo. The crude product was purified by flash chromatography on silica gel (0% to 50% ethyl acetate in heptane) to yield the title compound as a colourless liquid (90%), MS (ESI⁺): m/z=360.2 ([M+H]⁺).

Step 2: (R)-3-(4-Ethoxy-phenyl)-1-(2-methyl-pyridin-4-yl)-3-o-tolyl-propan-1-one oxime In analogy to example 132, step 6, from (R)-3-(4-ethoxy-phenyl)-1-(2-methyl-pyridin-4-yl)-3-o-tolyl-propan-1-one and hydroxylamine hydrochloride in the presence of sodium hydrogencarbonate was prepared the title compound as a white foam, MS (ESI⁺): m/z=375.2 ([M+H]⁺).

Example 365

(S)-3-(4-Chloro-2-methyl-phenyl)-3-(4-hydroxy-phenyl)-1-(2-methyl-pyridin-4-yl)-propan-1-one oxime

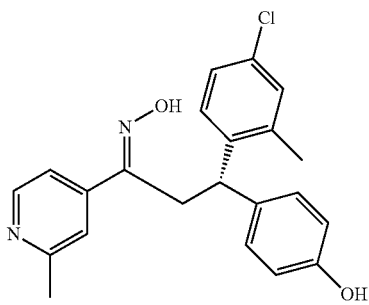 [SMILES: Cc1cc(/C(C[C@@H](c2ccc(O)cc2)c2ccc(Cl)cc2C)=N/O)ccn1]

Step 1: (S)-3-(4-Chloro-2-methyl-phenyl)-3-(4-hydroxy-phenyl)-1-(2-methyl-pyridin-4-yl)-propan-1-one In analogy to example 363, step 1, from (S)-3-(4-bromo-phenyl)-3-(4-chloro-2-methyl-phenyl)-1-(2-methyl-pyridin-4-yl)-propan-1-one (example 282, step 1) in presence of potassium hydroxide, 2-di-tert-butylphosphino-2',4',6'-tri-isopropylbiphenyl and tris(dibenzylidene-acetone)dipalladium(0) was prepared the title compound as a light yellow foam, MS (ESI$^+$): m/z=366.1 ([M+H]$^+$).

Step 2: (S)-3-(4-Chloro-2-methyl-phenyl)-3-(4-hydroxy-phenyl)-1-(2-methyl-pyridin-4-yl)-propan-1-one oxime In analogy to example 132, step 6, from (S)-3-(4-chloro-2-methyl-phenyl)-3-(4-hydroxy-phenyl)-1-(2-methyl-pyridin-4-yl)-propan-1-one and hydroxylamine hydrochloride in the presence of sodium hydrogencarbonate was prepared the title compound as a light yellow foam, MS (ESI$^+$): m/z=381.2 ([M+H]$^+$).

Example 366

(S)-3-(4-Chloro-2-methyl-phenyl)-3-(4-ethoxy-phenyl)-1-(2-methyl-pyridin-4-yl)-propan-1-one oxime

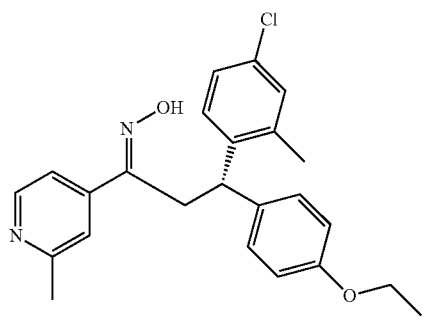 [SMILES: CCOc1ccc([C@H](C/C(=N\O)c2ccnc(C)c2)c2ccc(Cl)cc2C)cc1]

Step 1: (S)-3-(4-Chloro-2-methyl-phenyl)-3-(4-ethoxy-phenyl)-1-(2-methyl-pyridin-4-yl)-propan-1-one In analogy to example 364, step 1, from (S)-3-(4-bromo-phenyl)-3-(4-chloro-2-methyl-phenyl)-1-(2-methyl-pyridin-4-yl)-propan-1-one in presence of potassium hydroxide, 2-di-tert-butylphosphino-2',4',6'-triisopropylbiphenyl, tris(dibenzylideneacetone)dipalladium(0), cetyl trimethylammonium bromide and iodoethane was prepared the title compound as a yellow foam, MS (ESI$^+$): m/z=394.0 ([M+H]$^+$).

Step 2: (S)-3-(4-Chloro-2-methyl-phenyl)-3-(4-ethoxy-phenyl)-1-(2-methyl-pyridin-4-yl)-propan-1-one oxime In analogy to example 132, step 6, from (S)-3-(4-chloro-2-methyl-phenyl)-3-(4-ethoxy-phenyl)-1-(2-methyl-pyridin-4-yl)-propan-1-one and hydroxylamine hydrochloride in the presence of sodium hydrogencarbonate was prepared the title compound as an off-white foam, MS (ESI$^+$): m/z=409.4 ([M+H]$^+$).

Example 367

(R,E)-1-(4-(3-(Hydroxyimino)-3-(2-methylpyridin-4-yl)-1-o-tolylpropyl)phenyl)piperidine-4-carboxamide

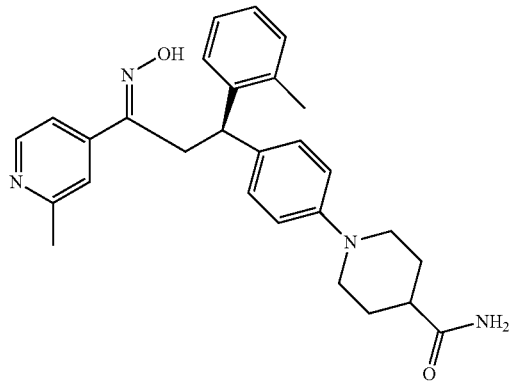 [SMILES: Cc1cc(/C(C[C@H](c2ccc(N3CCC(C(N)=O)CC3)cc2)c2ccccc2C)=N/O)ccn1]

Step 1: (R)-1-(4-(3-(2-Methylpyridin-4-yl)-3-oxo-1-o-tolylpropyl)phenyl)piperidine-4-carboxylic acid A mixture of (R)-3-(4-bromophenyl)-1-(2-methylpyridin-4-yl)-3-o-tolylpropan-1-one (example 142, step 2; 2.00 g, 5.07 mmol), ethyl piperidine-4-carboxylate (1.2 g, 7.61 mmol), sodium tert-butoxide (975 mg, 10.1 mmol), 2-dicyclohexylphosphino-2',4',6'-triisopropyl-biphenyl (484 mg, 1.01 mmol) and tris(dibenzylideneacetone)dipalladium(0) (464 mg, 507 µmol) in toluene (100 mL) was heated at 85° C. for 4 h and at room temperature for 17 h, then filtered through diatomaceous earth. After evaporation of volatile material, the residue was dissolved in tetrahydrofuran (50 mL), 1 M aq. lithium hydroxide solution (50 mL, 50 mmol) and methanol (15 mL), then after 2 h treated with 1 M aq. potassium hydrogensulfate solution (40 mL) and sat. aq. ammonium chloride solution (50 mL). The mixture was extracted with ethyl acetate, the organic layer washed with brine, dried over sodium sulfate, filtered, and evaporated. Chromatography (SiO₂; dichloromethane-methanol gradient) produced the title compound (2.24 g, 66%). Light yellow solid, MS (ESI⁻): m/z=441.3 ([M−H]⁻).

Step 2: (R)-1-(4-(3-(2-Methylpyridin-4-yl)-3-oxo-1-o-tolylpropyl)phenyl)piperidine-4-carboxamide A mixture of (R)-1-(4-(3-(2-methylpyridin-4-yl)-3-oxo-1-o-tolylpropyl)phenyl)-piperidine-4-carboxylic acid (100 mg, 226 µmol), triethylamine (229 mg, 2.26 mmol) and 0-(benzotriazol-1-yl)-N,N,N',N'-tetramethyluronium tetrafluoroborate (218 mg, 678 µmol) in tetrahydrofuran (5 mL) was stirred at room temperature for 15 min, then treated with ammonium chloride (96.7 mg, 1.81 mmol), then after 20 h partitioned between sat. aq. ammonium chloride solution and ethyl acetate. The organic layer was washed with brine, dried over sodium sulfate, filtered, and evaporated to produce the crude title compound (131 mg), which was directly used in the next step. Yellow oil, MS (ESI⁺): m/z=442.4 ([M+H]⁺).

Step 3: (R,E)-1-(4-(3-(hydroxyimino)-3-(2-methylpyridin-4-yl)-1-o-tolylpropyl)phenyl)-piperidine-4-carboxamide In analogy to example 132, step 6, from (R)-1-(4-(3-(2-methylpyridin-4-yl)-3-oxo-1-o-tolylpropyl)phenyl)piperidine-4-carboxamide and hydroxylamine hydrochloride in the presence of sodium hydrogencarbonate was prepared the title compound as a light yellow foam, MS (ESI⁺): m/z=457.5 ([M+H]⁺).

Example 368

(R,E)-1-(2-Methylpyridin-4-yl)-3-phenyl-3-o-tolylpropan-1-one oxime

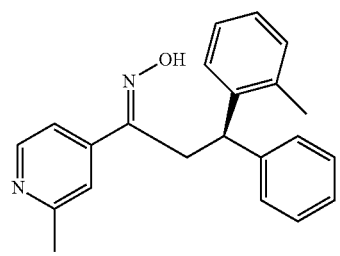 [SMILES: Cc1cc(/C(C[C@H](c2ccccc2)c2ccccc2C)=N/O)ccn1]

Step 1: (R)-1-(2-Methylpyridin-4-yl)-3-phenyl-3-o-tolylpropan-1-ol

The title compound was obtained as a side product of example 367, step 1. Light yellow foam, MS (ESI⁺): m/z=318.2 ([M+H]⁺).

Step 2: (R)-1-(2-Methylpyridin-4-yl)-3-phenyl-3-o-tolylpropan-1-one

A mixture of (R)-1-(2-methylpyridin-4-yl)-3-phenyl-3-o-tolylpropan-1-ol (110 mg, 347 mmol), and manganese dioxide (121 mg, 1.39 mmol) in toluene (2 mL) was heated at 90° C. for 3 h, then filtered through diatomaceous earth and concentrated in vacuo. Chromatography (silica gel, 10 g, 10% to 50% ethyl acetate in heptane) produced the title compound (60 mg, 55%). White semisolid, MS (ESI⁺): m/z=316.3 ([M+H]⁺).

Step 3: (R,E)-1-(2-Methylpyridin-4-yl)-3-phenyl-3-o-tolylpropan-1-one oxime

In analogy to example 132, step 6, from (R)-1-(2-methylpyridin-4-yl)-3-phenyl-3-o-tolylpropan-1-one and hydroxylamine hydrochloride in the presence of sodium hydrogencarbonate was prepared the title compound as a colourless oil, MS (ESI⁺): m/z=331.2 ([M+H]⁺).

Example 369

(R,E)-2-(1-(4-(3-(Hydroxyimino)-3-(2-methylpyridin-4-yl)-1-o-tolylpropyl)phenyl)-piperidine-4-carboxamido)acetic acid

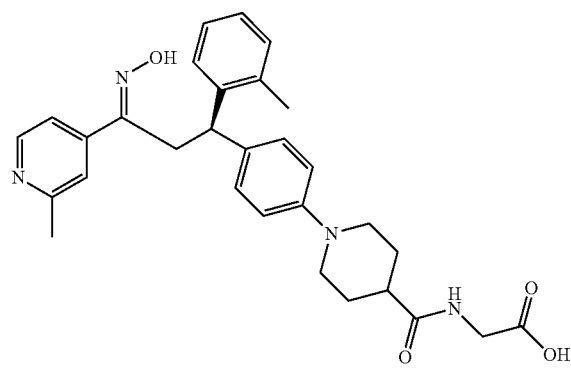 [SMILES: Cc1cc(/C(C[C@H](c2ccc(N3CCC(C(=O)NCC(=O)O)CC3)cc2)c2ccccc2C)=N/O)ccn1]

Step 1: (R)-Methyl 2-(1-(4-(3-(2-methylpyridin-4-yl)-3-oxo-1-o-tolylpropyl)phenyl)piperidine-4-carboxamido)acetate A mixture of (R)-1-(4-(3-(2-methylpyridin-4-yl)-3-oxo-1-o-tolylpropyl)phenyl)-piperidine-4-carboxylic acid (example 367, step 1; 100 mg, 226 µmol) triethylamine (68.6 mg, 94.5 µl, 678 µmol) and O-(benzotriazol-1-yl)-N,N,N',N'-tetramethyluronium tetrafluoroborate (79.8 mg, 249 µmol) in tetrahydrofuran (5 mL) was stirred at room temperature for 15 min, then treated with methyl 2-aminoacetate hydrochloride (42.6 mg, 339 µmol). The reaction mixture was stirred for 20 h at room temperature, then partitioned between sat. aq. ammonium chloride solution and ethyl acetate. The organic layer was washed with brine, dried over sodium sulfate, filtered, and evaporated to afford the crude title compound (130 mg), which was directly used in the next step. Yellow oil, MS (ESI⁺): m/z=514.6 ([M+H]⁺).

Step 2: (R,E)-2-(1-(4-(3-(Hydroxyimino)-3-(2-methylpyridin-4-yl)-1-o-tolylpropyl)phenyl)-piperidine-4-carboxamido)acetic acid A solution of (R)-methyl 2-(1-(4-(3-(2-methylpyridin-4-yl)-3-oxo-1-o-tolylpropyl)-phenyl)piperidine-4-carboxamido)acetate (116 mg, 226 µmol) in tetrahydrofuran (3 mL), 1 M aq. lithium hydroxide solution (2.26 mL, 2.26 mmol) and methanol (1 mL) was stirred for 2 h at room temperature, then after addition of 1 M aq. potassium hydrogensulfate solution (2.5 mL) and sat. aq. ammonium chloride solution (5 mL) the reaction mixture was extracted with ethyl acetate. The organic layer was dried over sodium sulfate, filtered, and concentrated in vacuo to produce [(1-{4-[(R)-3-(2-methyl-pyridin-4-yl)-3-oxo-1-o-tolyl-propyl]-phenyl}-piperidine-4-carbonyl)-amino]-acetic acid. This was reacted in analogy to example 132, step 6 with hydroxylamine hydrochloride in the presence of sodium hydrogencarbonate to produce the title compound (42 mg, 36%). Yellow semisolid, MS (ESI$^+$): m/z=515.6 ([M+H]$^+$).

Example 370

(R,E)-2-(1-(4-(3-(hydroxyimino)-3-(2-methylpyridin-4-yl)-1-o-tolylpropyl)phenyl)-piperidine-4-carboxamido)ethanesulfonic acid

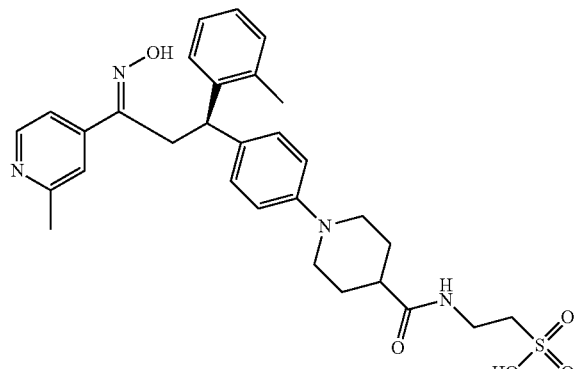

A mixture of (R)-1-(4-(3-(2-methylpyridin-4-yl)-3-oxo-1-o-tolylpropyl)phenyl)-piperidine-4-carboxylic acid (100 mg, 226 µmol), triethylamine (68.6 mg, 678 µmol) and O-(benzotriazol-1-yl)-N,N,N',N'-tetramethyluronium tetrafluoroborate (79.8 mg, 249 µmol) in tetrahydrofuran (5 mL) was stirred for 15 min at room temperature, then treated with 2-aminoethanesulfonic acid (42.4 mg, 339 µmol), then after 20 h volatile material was removed under vacuum to afford the crude title compound (303 mg, yellow oil, MS (ESI$^+$): m/z=550.4 ([M+H]$^+$)). This was taken up in ethanol (5 mL), water (1 mL) and treated with sodium hydrogencarbonate (57 mg, 0.68 mmol) and hydroxylamine hydrochloride (47 mg, 0.68 mmol). The reaction mixture was heated at 90° C. for 2 h, then treated with sat. aq. ammonium chloride solution (10 mL) and concentrated in vacuo. The residue was suspended in 1,4-dioxane (5 mL), then after addition of hydrogen chloride solution (4 M in 1,4-dioxane; 0.56 mL, 2.3 mmol) the reaction mixture was heated at 50° C. for 4 h. After cooling sat. aq. sodium hydrogencarbonate solution (4 mL) and sat. aq. ammonium chloride solution (10 mL) were added and the mixture was evaporated to dryness. The residue was chromatographed (reverse phase [C$_{18}$] SiO$_2$; water-methanol gradient) to produce the title compound (92 mg, 72%) Yellow semisolid, MS (ESI$^+$): m/z=565.3 ([M+H]$^+$).

Example 371

(3R,E)-3-(4-(2-thia-6-azaspiro[3.3]heptan-6-yl)phenyl)-1-(2-methylpyridin-4-yl)-3-o-tolylpropan-1-one oxime

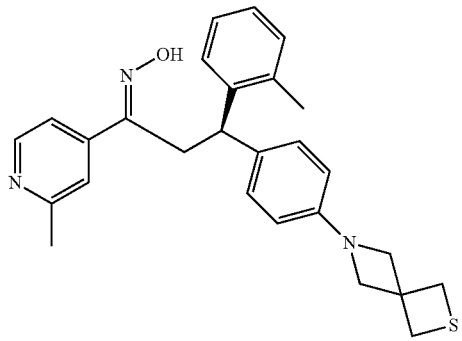 [SMILES: Cc1cc(/C(C[C@H](c2ccc(N3CC4(CSC4)C3)cc2)c2ccccc2C)=N/O)ccn1]

Step 1: (3R)-3-(4-(2-thia-6-azaspiro[3.3]heptan-6-yl)phenyl)-1-(2-methylpyridin-4-yl)-3-o-tolylpropan-1-one The title compound was produced in analogy to example 270, step 1 from (R)-3-(4-bromophenyl)-1-(2-methylpyridin-4-yl)-3-o-tolylpropan-1-one (example 142, step 2) and 2-thia-6-azaspiro[3.3]heptane hemioxalate (*Angew. Chem. Int. Ed.* 2010, 49, 3524). Yellow oil, MS (ESI$^+$): m/z=429.3 ([M+H]$^+$).

Step 2: (3R,E)-3-(4-(2-thia-6-azaspiro[3.3]heptan-6-yl)phenyl)-1-(2-methylpyridin-4-yl)-3-o-tolylpropan-1-one oxime The title compound was produced in analogy to example 1, step 2 from (3R)-3-(4-(2-thia-6-azaspiro[3.3]heptan-6-yl)phenyl)-1-(2-methylpyridin-4-yl)-3-o-tolylpropan-1-one. White semisolid, MS (ESI$^+$): m/z=444.5 ([M+H]$^+$).

Example 372

(R)-tert-Butyl 4-(4-(3-(hydroxyimino)-3-(2-methylpyridin-4-yl)-1-o-tolylpropyl)phenyl)-5,6-dihydropyridine-1(2H)-carboxylate

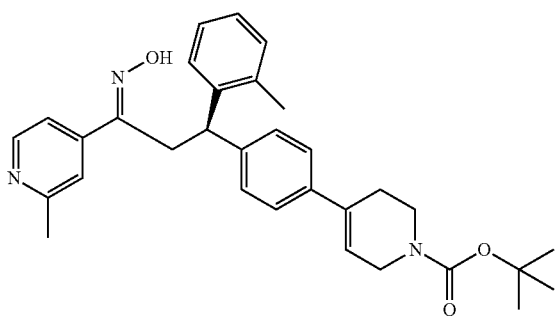 [SMILES: Cc1cc(/C(C[C@H](c2ccc(C3=CCN(C(=O)OC(C)(C)C)CC3)cc2)c2ccccc2C)=N/O)ccn1]

Step 1: (R)-tert-Butyl 4-(4-(3-(2-methylpyridin-4-yl)-3-oxo-1-o-tolylpropyl)phenyl)-5,6-dihydropyridine-1(2H)-carboxylate A mixture of (R)-3-(4-bromophenyl)-1-(2-methylpyridin-4-yl)-3-o-tolylpropan-1-one (example 142, step 2; 300 mg, 761 μmol), tert-butyl 4-(4,4,5,5-tetramethyl-1,3,2-dioxaborolan-2-yl)-5,6-dihydropyridine-1(2H)-carboxylate (353 mg, 1.14 mmol), [1,1'-bis(diphenyl-phosphino)ferrocene] dichloropalladium(II) dichloromethane adduct (27.8 mg, 38.0 μmol) in 1,4-dioxane (7.5 mL), water (5 mL) and 2 M aq. sodium carbonate solution (1.14 mL, 2.28 mmol) was heated at 85° C. for 4 h, then after cooling partitioned between sat. aq. ammonium chloride solution and ethyl acetate. The organic layer was washed with brine, dried over sodium sulfate, filtered, and evaporated. Chromatography (SiO$_2$; heptane-ethyl acetate gradient) produced the title compound (365 mg, 97%). White foam, MS (ESI$^+$): m/z=497.4 ([M+H]$^+$).

Step 2: (R)-tert-Butyl 4-(4-(3-(hydroxyimino)-3-(2-methylpyridin-4-yl)-1-o-tolylpropyl)phenyl)-5,6-dihydropyridine-1(2H)-carboxylate The title compound was produced in analogy to example 1, step 2 from (R)-tert-butyl 4-(4-(3-(2-methylpyridin-4-yl)-3-oxo-1-o-tolylpropyl)phenyl)-5,6-dihydropyridine-1(2H)-carboxylate. Colourless foam, MS (ESI$^+$): m/z=512.5 ([M+H]$^+$).

Example 373

(R,E)-4-(3-(4-(4-Carboxypiperidin-1-yl)phenyl)-1-(hydroxyimino)-3-o-tolylpropyl)-2-methylpyridine 1-oxide

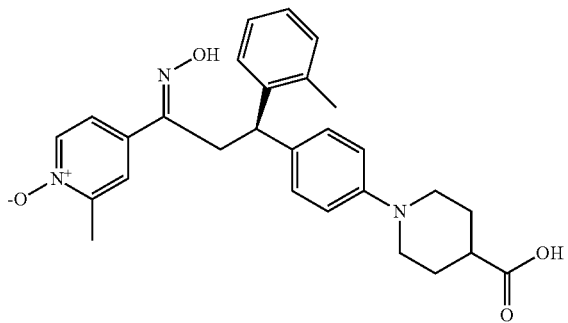

A solution of (R,E)-1-(4-(3-(hydroxyimino)-3-(2-methylpyridin-4-yl)-1-o-tolylpropyl)-phenyl)piperidine-4-carboxylic acid (example 266; 95 mg, 208 μmol) in dichloromethane (3 mL) and methanol (0.75 mL) was treated with 3-chloroperbenzoic acid (42 mg, 241 μmol) at 0° C. The reaction mixture was allowed to reach room temperature over 3 h, then after addition of sat. aq. sodium hydrogencarbonate solution (3 drops) and sat. aq. ammonium chloride solution (5 drops) concentrated under vacuum. The residue was purified by preparative HPLC to afford the title compound (49 mg, 50%). White foam, MS (ESI$^+$): m/z=474.1 ([M+H]$^+$).

Example 374

(R,E)-1-(4-(3-(Hydroxyimino)-3-(2-(hydroxymethyl)pyridin-4-yl)-1-o-tolylpropyl)phenyl)-piperidine-4-carboxylic acid

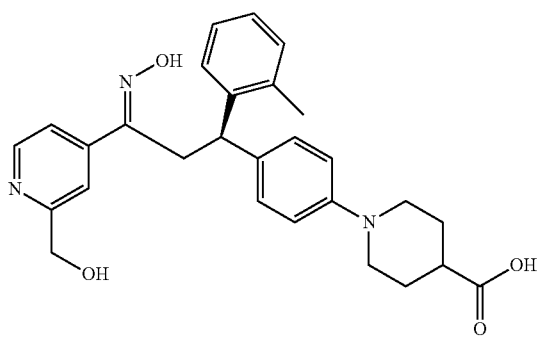 [SMILES: Cc1ccccc1[C@H](C/C(=N\O)c1ccnc(CO)c1)c1ccc(N2CCC(C(=O)O)CC2)cc1]

Trifluoroacetic anhydride (421 mg, 2.01 mmol) was added at 0° C. to a suspension of (R,E)-4-(3-(4-(4-carboxypiperidin-1-yl)phenyl)-1-(hydroxyimino)-3-o-tolylpropyl)-2-methyl-pyridine 1-oxide (95 mg, 201 μmol) in dichloromethane (3 mL) to give a white suspension, then after 1 h another portion of trifluoroacetic anhydride (421 mg, 2.01 mmol) was added. The reaction mixture was allowed to reach room temperature over 1 h, then treated with 1 M aq. sodium hydroxide solution and stirred for another 90 min. After extraction with dichloromethane, the organic layer was washed with brine, dried over sodium sulfate, filtered, and evaporated. The residue was purified by preparative HPLC to produce the title compound (13 mg, 14%). Light yellow oil, MS (ESI$^+$): m/z=474.4 ([M+H]$^+$).

Example 375

(R,E)-1-(2-Methylpyridin-4-yl)-3-(4-(1,2,3,6-tetrahydropyridin-4-yl)phenyl)-3-o-tolylpropan-1-one oxime

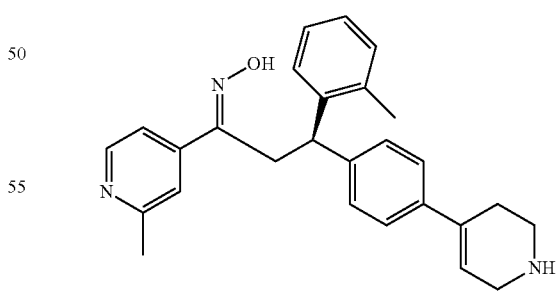

Hydrogen chloride solution (4 M in 1,4-dioxane, 0.22 mL, 0.88 mmol) was added to a solution of (R,E)-tert-butyl 4-(4-(3-(hydroxyimino)-3-(2-methylpyridin-4-yl)-1-o-tolylpropyl)-phenyl)-5,6-dihydropyridine-1(2H)-carboxylate (45 mg, 87.9 μmol) in 1,4-dioxane (4 mL). The reaction mixture was heated for 17 h at 50° C., then treated with sat. aq. sodium hydrogen-carbonate solution (4 mL) and partitioned between sat. aq. ammonium chloride solution and ethyl acetate. The organic layer was washed with brine, dried over sodium sulfate, filtered, and evaporated. The crude material was triturated with ethyl acetate to afford the title compound (20 mg, 55%). Off-white solid, MS (ESI$^+$): m/z=412.4 ([M+H]$^+$).

Example 376

(R,E)-1-(2-Methylpyridin-4-yl)-3-(4-(1-(methylsulfonyl)-1,2,3,6-tetrahydropyridin-4-yl)phenyl)-3-o-tolylpropan-1-one oxime

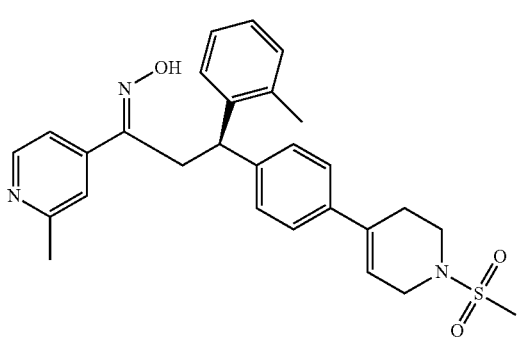 [SMILES: Cc1cc(/C(C[C@H](c2ccc(C3=CCN(S(C)(=O)=O)CC3)cc2)c2ccccc2C)=N/O)ccn1]

Step 1: (R)-1-(2-Methylpyridin-4-yl)-3-(4-(1-(methylsulfonyl)-1,2,3,6-tetrahydropyridin-4-yl)phenyl)-3-o-tolylpropan-1-one Hydrogen chloride solution (4 M in 1,4-dioxane, 2 mL) was added to a solution of (R)-tert-butyl 4-(4-(3-(2-methylpyridin-4-yl)-3-oxo-1-o-tolylpropyl)phenyl)-5,6-dihydropyridine-1(2H)-carboxylate (example 372, step 1; 100 mg, 201 µmol). The reaction mixture was heated at 50° C. for 17 h, then partitioned between sat. aq. sodium hydrogencarbonate solution and ethyl acetate. The organic layer was washed with brine, dried over sodium sulfate, filtered, and evaporated. The residue was dissolved in dichloromethane (5 mL), then cooled to 0° C. and treated with N,N-diisopropylethylamine (78 mg, 604 µmol) and methanesulfonyl chloride (34.6 mg, 302 µmol). The ice bath was removed, then after 3 h the reaction mixture was partitioned between sat. aq. ammonium chloride solution and dichloromethane. The organic layer was washed with brine, dried over sodium sulfate, filtered, and evaporated. Chromatography (SiO$_2$; heptane-ethyl acetate gradient) produced the title compound (24 mg, 25%). White foam, MS (ESI$^+$): m/z=475.1 ([M+H]$^+$).

Step 2: (R,E)-1-(2-Methylpyridin-4-yl)-3-(4-(1-(methylsulfonyl)-1,2,3,6-tetrahydropyridin-4-yl)phenyl)-3-o-tolylpropan-1-one oxime In analogy to example 132, step 6, from (R)-1-(2-methylpyridin-4-yl)-3-(4-(1-(methylsulfonyl)-1,2,3,6-tetrahydropyridin-4-yl)phenyl)-3-o-tolylpropan-1-one and hydroxylamine hydrochloride in the presence of sodium hydrogencarbonate was prepared the title compound as a colourless foam, MS (ESI$^+$): m/z=490.4 ([M+H]$^+$).

Example 377

(R,E)-4-(4-(3-(Hydroxyimino)-3-(2-methylpyridin-4-yl)-1-o-tolylpropyl)phenyl)-5,6-dihydropyridin-2(1H)-one

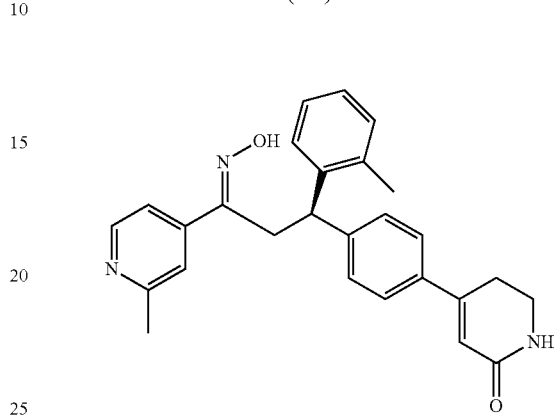

Step 1: (R)-4-(4-(3-(2-Methylpyridin-4-yl)-3-oxo-1-o-tolylpropyl)phenyl)-5,6-dihydropyridin-2(1H)-one Hydrogen chloride solution (4 M in 1,4-dioxane, 1.5 mL, 6.0 mmol) was added at room temperature to a solution of (R)-tert-butyl 4-(4-(3-(2-methylpyridin-4-yl)-3-oxo-1-o-tolyl-propyl)phenyl)-5,6-dihydropyridine-1(2H)-carboxylate (example 372, step 1; 200 mg, 403 µmol) in 1,4-dioxane (4 mL), then after 2 h the reaction mixture was evaporated. The residue was suspended in dichloromethane (8 mL), then treated with N,N-diisopropylethylamine (312 mg, 2.42 mmol) and methanesulfonyl chloride (92 mg, 805 µmol) at 0° C. The ice bath was removed, then after 16 h the reaction mixture was partitioned between sat. aq. ammonium chloride solution and dichloromethane. The organic layer was dried over sodium sulfate, filtered, and evaporated. Chromatography (SiO$_2$; heptane-ethyl acetate gradient, then dichloromethane-methanol 9:1) gave the title compound (27 mg, 16%; light brown foam, MS (ESI$^+$): m/z=411.2 ([M+H]$^+$)) and (R)-3-[4-(1-methane sulfonyl-1,2,3,6-tetrahydro-pyridin-4-yl)-phenyl]-1-(2-methyl-pyridin-4-yl)-3-o-tolyl-propan-1-one (66 mg, 35%).

Step 2: (R,E)-4-(4-(3-(hydroxyimino)-3-(2-methylpyridin-4-yl)-1-o-tolylpropyl)phenyl)-5,6-dihydropyridin-2(1H)-one In analogy to example 132, step 6, from (R)-4-(4-(3-(2-methylpyridin-4-yl)-3-oxo-1-o-tolylpropyl)phenyl)-5,6-dihydropyridin-2(1H)-one and hydroxylamine hydrochloride in the presence of sodium hydrogencarbonate was prepared the title compound as a light yellow foam, MS (ESI$^+$): m/z=426.1 ([M+H]$^+$).

Example 378

(R,E)-1-(2-Methylpyridin-4-yl)-3-(4-(piperidin-4-yl)phenyl)-3-o-tolylpropan-1-one oxime

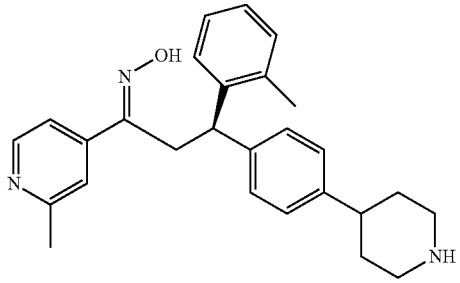 [SMILES: Cc1cc(/C(C[C@H](c2ccc(C3CCNCC3)cc2)c2ccccc2C)=N/O)ccn1]

Step 1: (R)-tert-Butyl 4-(4-(3-(2-methylpyridin-4-yl)-3-oxo-1-o-tolylpropyl)phenyl)piperidine-1-carboxylate (1-(tert-Butoxycarbonyl)piperidin-4-yl) zinc(II) iodide solution (0.5 M in N,N-dimethylacetamide, 2.0 mL, 1.0 mmol; preparation according to *J. Org. Chem.* 2004, 69, 5120) was added at room temperature under argon to a mixture of (R)-3-(4-bromophenyl)-1-(2-methylpyridin-4-yl)-3-o-tolylpropan-1-one (example 142, step 2; 200 mg, 507 µmol), copper(I) iodide (9.7 mg, 51 µmol) and [1,1'-bis(diphenylphosphino)ferrocene]dichloropalladium(II) dichloromethane adduct (18.6 mg, 25.4 µmol) in N,N-dimethylacetamide (3 mL). The reaction mixture was heated at 85° C., then after 4 h partitioned between sat. aq. ammonium chloride solution and ethyl acetate. The organic layer was washed with brine, dried over sodium sulfate, filtered, and evaporated. Chromatography (SiO$_2$; heptane-ethyl acetate gradient) produced the title compound (144 mg, 57%). Off-white foam, MS (ESI$^+$): m/z=499.3 ([M+H]$^+$).

Step 2: (R,E)-1-(2-Methylpyridin-4-yl)-3-(4-(piperidin-4-yl)phenyl)-3-o-tolylpropan-1-one oxime In analogy to example 132, step 6, from (R)-tert-butyl 4-(4-(3-(2-methylpyridin-4-yl)-3-oxo-1-o-tolylpropyl)phenyl)piperidine-1-carboxylate and hydroxylamine hydrochloride in the presence of sodium hydrogencarbonate was prepared the title compound as a white foam, MS (ESI$^+$): m/z=414.4 ([M+H]$^+$).

Example 379

(R,E)-1-(2-methylpyridin-4-yl)-3-(4-(1-(methylsulfonyl)piperidin-4-yl)phenyl)-3-o-tolylpropan-1-one oxime

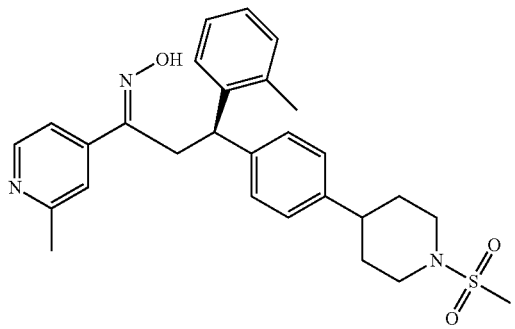 [SMILES: Cc1cc(/C(C[C@H](c2ccc(C3CCN(S(C)(=O)=O)CC3)cc2)c2ccccc2C)=N/O)ccn1]

Step 1: (R)-1-(2-Methylpyridin-4-yl)-3-(4-(1-(methylsulfonyl)piperidin-4-yl)phenyl)-3-o-tolylpropan-1-one The title compound was produced in analogy to example 376, step 1 from (R)-tert-butyl 4-(4-(3-(2-methylpyridin-4-yl)-3-oxo-1-o-tolylpropyl)phenyl)piperidine-1-carboxylate (example 378, step 1) and methanesulfonyl chloride. White foam, MS (ESI$^+$): m/z=477.2 ([M+H]$^+$).

Step 2: (R,E)-1-(2-Methylpyridin-4-yl)-3-(4-(1-(methylsulfonyl)piperidin-4-yl)phenyl)-3-o-tolylpropan-1-one oxime In analogy to example 132, step 6, from (R)-tert-butyl 4-(4-(3-(2-methylpyridin-4-yl)-3-oxo-1-o-tolylpropyl)phenyl)piperidine-1-carboxylate and hydroxylamine hydrochloride in the presence of sodium hydrogencarbonate was prepared the title compound as a white foam, MS (ESI$^+$): m/z=492.3 ([M+H]$^+$).

Example 380

(S,E)-2-(4-(3-(Hydroxyimino)-3-(2-methylpyridin-4-yl)-1-o-tolylpropyl)phenyl)acetic acid

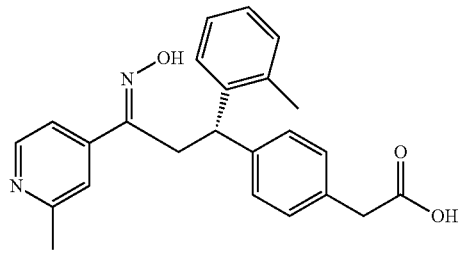 [SMILES: Cc1cc(/C(C[C@@H](c2ccc(CC(=O)O)cc2)c2ccccc2C)=N/O)ccn1]

Step 1: (S)-2-(4-(3-(2-Methylpyridin-4-yl)-3-oxo-1-o-tolylpropyl)phenyl)acetic acid The title compound was produced in analogy to example 288, step 1 from (R)-3-(4-bromophenyl)-1-(2-methylpyridin-4-yl)-3-o-tolylpropan-1-one (example 286, step 1) and diethyl malonate. White foam, MS (ESI$^-$): m/z=372.3 ([M−H]$^-$).

Step 2: (S,E)-2-(4-(3-(Hydroxyimino)-3-(2-methylpyridin-4-yl)-1-o-tolylpropyl)phenyl)acetic acid In analogy to example 132, step 6, from (S)-2-(4-(3-(2-methylpyridin-4-yl)-3-oxo-1-o-tolylpropyl)phenyl)acetic acid and hydroxylamine hydrochloride in the presence of

Example 381

(S,E)-1-(2-Methylpyridin-4-yl)-3-(4-morpholinophenyl)-3-o-tolylpropan-1-one oxime

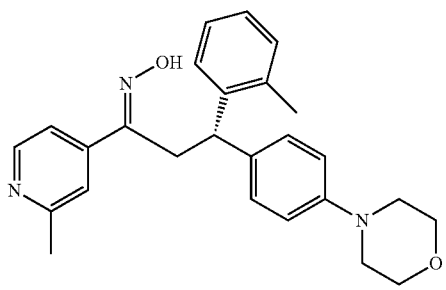 [SMILES: Cc1cc(/C(C[C@@H](c2ccc(N3CCOCC3)cc2)c2ccccc2C)=N/O)ccn1]

Step 1: (S)-1-(2-methylpyridin-4-yl)-3-(4-morpholinophenyl)-3-o-tolylpropan-1-one The title compound was produced in analogy to example 271, step 1 from (S)-3-(4-bromophenyl)-1-(2-methylpyridin-4-yl)-3-o-tolylpropan-1-one (example 286, step 1) and morpholine. Yellow foam, MS (ESI$^+$): m/z=401.4 ([M+H]$^+$).

Step 2: (S,E)-1-(2-Methylpyridin-4-yl)-3-(4-morpholinophenyl)-3-o-tolylpropan-1-one oxime In analogy to example 132, step 6, from (S)-1-(2-methylpyridin-4-yl)-3-(4-morpholino-phenyl)-3-o-tolylpropan-1-one and hydroxylamine hydrochloride in the presence of sodium hydrogencarbonate was prepared the title compound as an off-white solid, MS (ESI$^+$): m/z=416.5 ([M+H]$^+$).

Example 382

{4-[(R)-1-(4-Chloro-2-methyl-phenyl)-3-[(E)-hydroxyimino]-3-(2-methyl-pyridin-4-yl)-propyl]-phenyl}-acetic acid

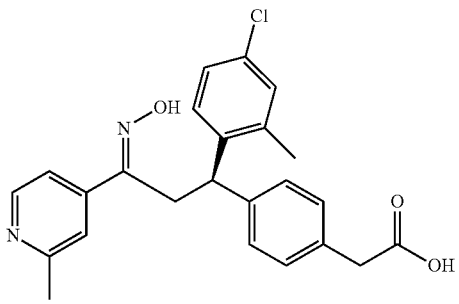 [SMILES: Cc1cc(/C(C[C@H](c2ccc(CC(=O)O)cc2)c2ccc(Cl)cc2C)=N/O)ccn1]

Step 1: (R)-2-(4-(1-(4-Chloro-2-methylphenyl)-3-(2-methylpyridin-4-yl)-3-oxopropyl)phenyl)-acetic acid The title compound was produced in analogy to example 288, step 1 from (S)-3-(4-bromo-phenyl)-3-(4-chloro-2-methyl-phenyl)-1-(2-methyl-pyridin-4-yl)-propan-1-one (example 282, step 1) and ethyl cyanoacetate. Light yellow solid.

Step 2: {4-[(R)-1-(4-Chloro-2-methyl-phenyl)-3-[(E)-hydroxyimino]-3-(2-methyl-pyridin-4-yl)-propyl]-phenyl}-acetic acid In analogy to example 132, step 6, from (R)-2-(4-(1-(4-chloro-2-methylphenyl)-3-(2-methylpyridin-4-yl)-3-oxopropyl)phenyl)acetic acid and hydroxylamine hydrochloride in the presence of sodium hydrogencarbonate was prepared the title compound as a white solid, MS (ESI$^+$): m/z=423.2 ([M+H]$^+$).

Example 383

(R,E)-3-(4-Bromophenyl)-3-(4-chloro-2-methylphenyl)-1-(2-(hydroxymethyl)pyridin-4-yl)propan-1-one oxime

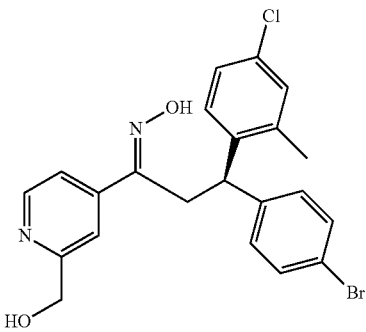 [SMILES: Cc1cc(Cl)ccc1[C@H](C/C(=N\O)c1ccnc(CO)c1)c1ccc(Br)cc1]

Step 1: (R)-4-(3-(4-Bromophenyl)-3-(4-chloro-2-methylphenyl)propanoyl)-2-methylpyridine 1-oxide The title compound was produced in analogy to example 373 from (S)-3-(4-bromo-phenyl)-3-(4-chloro-2-methyl-phenyl)-1-(2-methyl-pyridin-4-yl)-propan-1-one (example 282, step 1). White solid, MS (ESI$^+$): m/z=444.2 ([M+H]$^+$).

Step 2: (R)-3-(4-Bromophenyl)-3-(4-chloro-2-methylphenyl)-1-(2-(hydroxymethyl)pyridin-4-yl)propan-1-one The title compound was produced in analogy to example 374 from (R)-4-(3-(4-bromophenyl)-3-(4-chloro-2-methylphenyl)propanoyl)-2-methylpyridine 1-oxide. White foam, MS (ESI$^+$): m/z=444.2 ([M+H]$^+$).

Step 3: (R,E)-3-(4-Bromophenyl)-3-(4-chloro-2-methylphenyl)-1-(2-(hydroxymethyl)pyridin-4-yl)propan-1-one oxime In analogy to example 132, step 6, from (R)-3-(4-bromophenyl)-3-(4-chloro-2-methyl-phenyl)-1-(2-(hydroxymethyl)pyridin-4-yl)propan-1-one (example 282, step 1) and hydroxyl-amine hydrochloride in the presence of sodium

Example 384

(R,E)-4-(3-(4-Bromophenyl)-3-(4-chloro-2-methylphenyl)-1-(hydroxyimino)propyl)-2-methylpyridine 1-oxide

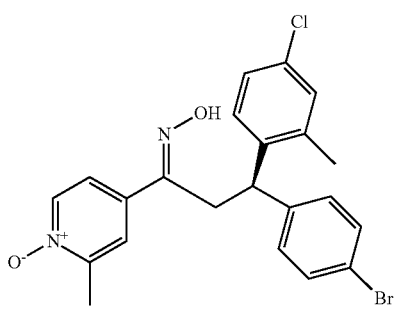 [SMILES: Cc1cc(Cl)ccc1[C@H](C/C(=N\O)c1cc[n+]([O-])c(C)c1)c1ccc(Br)cc1]

In analogy to example 132, step 6, from (R)-4-(3-(4-bromophenyl)-3-(4-chloro-2-methyl-phenyl)propanoyl)-2-methylpyridine 1-oxide (example 383, step 1) and hydroxylamine hydrochloride in the presence of sodium hydrogencarbonate was prepared the title compound as a white foam, MS (ESI$^+$): m/z=459.1 ([M+H]$^+$).

Example 385

(3R,E)-3-(4-bromophenyl)-3-(4-chloro-2-methylphenyl)-2-methyl-1-(2-methylpyridin-4-yl)propan-1-one oxime

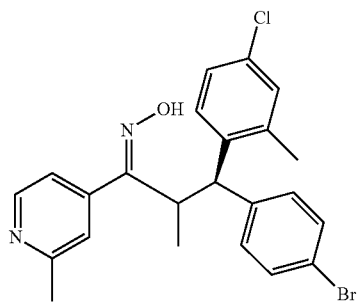 [SMILES: Cc1cc(/C(=N/O)C(C)[C@H](c2ccc(Br)cc2)c2ccc(Cl)cc2C)ccn1]

Step 1: (3R)-3-(4-bromophenyl)-3-(4-chloro-2-methylphenyl)-2-methyl-1-(2-methylpyridin-4-yl)propan-1-one Sodium hydride (60% dispersion in mineral oil, 23 mg, 0.54 mmol) was added to a solution of (R)-3-(4-bromophenyl)-3-(4-chloro-2-methylphenyl)-1-(2-methylpyridin-4-yl)propan-1-one (example 282, step 1; 208 mg, 0.49 mmol) in tetrahydrofuran (7 mL), then after 90 min the reaction mixture was cooled to 0° C. and treated with iodomethane (73 mg, 0.54 mmol). The ice bath was removed, then after 2 h the reaction mixture was partitioned between sat. aq. ammonium chloride solution and ethyl acetate. The organic layer was washed with brine, dried over sodium sulfate, filtered, and evaporated. Chromatography (SiO$_2$; heptane-ethyl acetate 1:1) produced the title compound (149 mg, 70%). Light yellow oil, MS (ESI$^+$): m/z=442.3 ([M+H]$^+$).

Step 2: (3R,E)-3-(4-bromophenyl)-3-(4-chloro-2-methylphenyl)-2-methyl-1-(2-methylpyridin-4-yl)propan-1-one oxime In analogy to example 132, step 6, from (3R)-3-(4-bromophenyl)-3-(4-chloro-2-methyl-phenyl)-2-methyl-1-(2-methylpyridin-4-yl)propan-1-one and hydroxylamine hydrochloride in the presence of sodium hydrogencarbonate was prepared the title compound as a white foam, MS (ESI$^+$): m/z=457.0 ([M+H]$^+$).

Example 386

(R,E)-3-(4-bromophenyl)-3-(4-chloro-2-methylphenyl)-1-(2-methylpyridin-4-yl)propan-1-one oxime

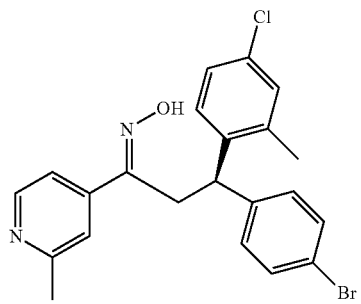 [SMILES: Cc1cc(/C(C[C@H](c2ccc(Br)cc2)c2ccc(Cl)cc2C)=N/O)ccn1]

In analogy to example 132, step 6, from (R)-3-(4-bromophenyl)-3-(4-chloro-2-methyl-phenyl)-1-(2-methylpyridin-4-yl)propan-1-one (example 282, step 1) and hydroxylamine hydrochloride in the presence of sodium hydrogencarbonate was prepared the title compound as a white foam, MS (ESI$^+$): m/z=443.0 ([M+H]$^+$).

Example 387

(R,E)-tert-Butyl 4-(4-(1-(4-chloro-2-methylphenyl)-3-(hydroxyimino)-3-(2-methylpyridin-4-yl)propyl)phenyl)piperidine-1-carboxylate

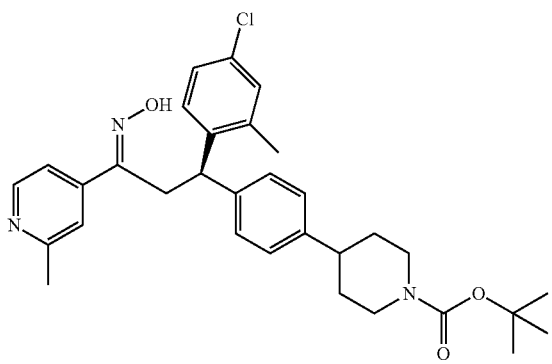 [SMILES: Cc1cc(/C(C[C@H](c2ccc(C3CCN(C(=O)OC(C)(C)C)CC3)cc2)c2ccc(Cl)cc2C)=N/O)ccn1]

339

Step 1: (R)-tert-butyl 4-(4-(1-(4-chloro-2-methylphenyl)-3-(2-methylpyridin-4-yl)-3-oxopropyl)phenyl)piperidine-1-carboxylate The title compound was produced in analogy to example 378, step 1 from (R)-3-(4-bromophenyl)-3-(4-chloro-2-methylphenyl)-1-(2-methylpyridin-4-yl)propan-1-one (example 282, step 1) and (1-(tert-butoxycarbonyl)piperidin-4-yl)zinc(II) iodide. Off-white foam, MS (ESI⁺): m/z=533.2 ([M+H]⁺).

Step 2: (R,E)-tert-Butyl 4-(4-(1-(4-chloro-2-methylphenyl)-3-(hydroxyimino)-3-(2-methylpyridin-4-yl)propyl)phenyl)piperidine-1-carboxylate In analogy to example 1, step 2, from (R)-tert-butyl 4-(4-(1-(4-chloro-2-methylphenyl)-3-(2-methylpyridin-4-yl)-3-oxopropyl)phenyl)piperidine-1-carboxylate and hydroxylamine hydrochloride in the presence of sodium hydrogencarbonate was prepared the title compound as a white foam, MS (ESI⁺): m/z=548.0 ([M+H]⁺).

Example 388

(R,E)-3-(4-chloro-2-methylphenyl)-1-(2-methylpyridin-4-yl)-3-(4-(piperidin-4-yl)phenyl)propan-1-one oxime

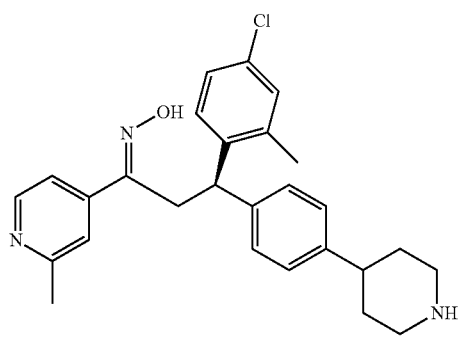 [SMILES: Cc1cc(/C(C[C@H](c2ccc(C3CCNCC3)cc2)c2ccc(Cl)cc2C)=N/O)ccn1]

Hydrogen chloride solution (4 M in 1,4-dioxane, 0.4 mL, 1.6 mmol) was added at room temperature to a solution of (R,E)-tert-butyl 4-(4-(1-(4-chloro-2-methylphenyl)-3-(hydroxy-imino)-3-(2-methylpyridin-4-yl)propyl)phenyl)piperidine-1-carboxylate (example 387; 90 mg, 164 µmol) in 1,4-dioxane (5 mL). The reaction mixture was heated at 50° C. for 17 h, then partitioned between sat. aq. sodium hydrogencarbonate solution and ethyl acetate. The organic layer was dried over sodium sulfate, filtered, and evaporated to produce the title compound (33 mg, 45%). White solid, MS (ESI⁺): m/z=448.0 ([M+H]⁺).

Example 389

(R,E)-3-(4-Chloro-2-methylphenyl)-1-(2-methylpyridin-4-yl)-3-(4-(1-(methylsulfonyl)-piperidin-4-yl)phenyl)propan-1-one oxime

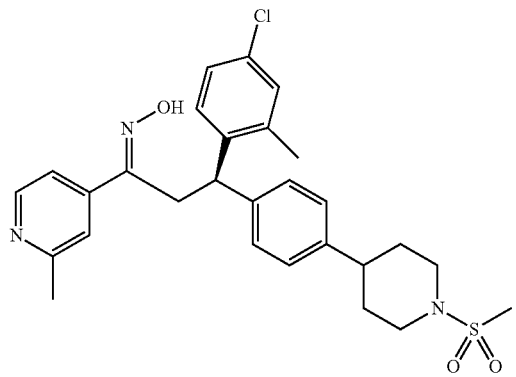 [SMILES: Cc1cc(/C(C[C@H](c2ccc(C3CCN(S(C)(=O)=O)CC3)cc2)c2ccc(Cl)cc2C)=N/O)ccn1]

Step 1: (R)-3-(4-Chloro-2-methylphenyl)-1-(2-methylpyridin-4-yl)-3-(4-(1-(methylsulfonyl)-piperidin-4-yl)phenyl)propan-1-one The title compound was produced in analogy to example 376, step 1 from (R)-tert-butyl 4-(4-(1-(4-chloro-2-methylphenyl)-3-(2-methylpyridin-4-yl)-3-oxopropyl)phenyl)piperidine-1-carboxylate (example 387, step 1) and methanesulfonyl chloride. White foam, MS (ESI⁺): m/z=511.3 ([M+H]⁺).

Step 2: (R,E)-3-(4-chloro-2-methylphenyl)-1-(2-methylpyridin-4-yl)-3-(4-(1-(methylsulfonyl)piperidin-4-yl)phenyl)propan-1-one oxime In analogy to example 132, step 6, from (R)-3-(4-chloro-2-methylphenyl)-1-(2-methyl-pyridin-4-yl)-3-(4-(1-(methylsulfonyl)piperidin-4-yl)phenyl)propan-1-one and hydroxylamine hydrochloride in the presence of sodium hydrogencarbonate was prepared the title compound as a white solid, MS (ESI⁺): m/z=526.3 ([M+H]⁺).

Example 390

(S)-3-(4-Chloro-2-methyl-phenyl)-1-(2-methyl-pyridin-4-yl)-3-phenyl-propan-1-one oxime

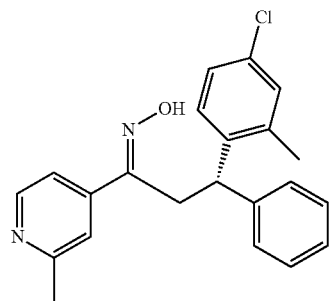 [SMILES: Cc1cc(/C(C[C@@H](c2ccccc2)c2ccc(Cl)cc2C)=N/O)ccn1]

Step 1: (S)-3-(4-chloro-2-methylphenyl)-1-(2-methylpyridin-4-yl)-3-phenylpropan-1-one A mixture of (S)-3-(4-bromophenyl)-3-(4-chloro-2-methylphenyl)-1-(2-methylpyridin-4-yl)propan-1-one (example 282, step 1; 200 mg, 466 μmol) diethyl malonate (112 mg, 700 μmol), [1,1'-bis(diphenylphosphino)ferrocene]dichloropalladium(II) dichloromethane adduct (19 mg, 23 mmol) and potassium tert-butoxide (157 mg, 1.4 mmol) in 1,4-dioxane (4 mL) was heated at 80° C. for 5 h, then partitioned between sat. aq. ammonium chloride solution and ethyl acetate. The organic layer was washed with brine, dried over sodium sulfate, filtered, and evaporated. Chromatography (SiO$_2$; heptane-ethyl acetate gradient) produced the title compound (129 mg, 79%). Light yellow oil, MS (ESI$^+$): m/z=350.2 ([M+H]$^+$).

Step 2: (S)-3-(4-Chloro-2-methyl-phenyl)-1-(2-methyl-pyridin-4-yl)-3-phenyl-propan-1-one oxime In analogy to example 132, step 6, from (S)-3-(4-chloro-2-methylphenyl)-1-(2-methyl-pyridin-4-yl)-3-phenylpropan-1-one and hydroxylamine hydrochloride in the presence of sodium hydrogencarbonate was prepared the title compound as a white solid, MS (ESI$^+$): m/z=365.1 ([M+H]$^+$).

Example 391

(E)-1-(2-methylpyridin-4-yl)-3-(3-(methylsulfonyl)phenyl)-3-o-tolylpropan-1-one oxime

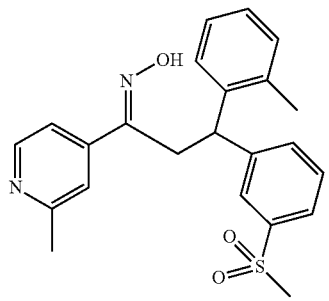 [SMILES: Cc1cc(/C(CC(c2cccc(S(C)(=O)=O)c2)c2ccccc2C)=N/O)ccn1]

Step 1: 1-(2-Methylpyridin-4-yl)-3-(3-(methylsulfonyl)phenyl)-3-o-tolylpropan-1-one The title compound was produced in analogy to example 358, step 1 from 3-(3-bromo-phenyl)-1-(2-methylpyridin-4-yl)-3-o-tolylpropan-1-one (example 98, step 5) and sodium methanesulfinate. Yellow oil, MS (ESI$^+$): m/z=394.3 ([M+H]$^+$).

Step 2: (E)-1-(2-Methylpyridin-4-yl)-3-(3-(methylsulfonyl)phenyl)-3-o-tolylpropan-1-one oxime In analogy to example 132, step 6, from 1-(2-methylpyridin-4-yl)-3-(3-(methylsulfonyl)-phenyl)-3-o-tolylpropan-1-one and hydroxylamine hydrochloride in the presence of sodium hydrogencarbonate was prepared the title compound as a colourless oil, MS (ESI$^+$): m/z=409.3 ([M+H]$^+$).

Example 392

N-{4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-yl}-succinamic acid

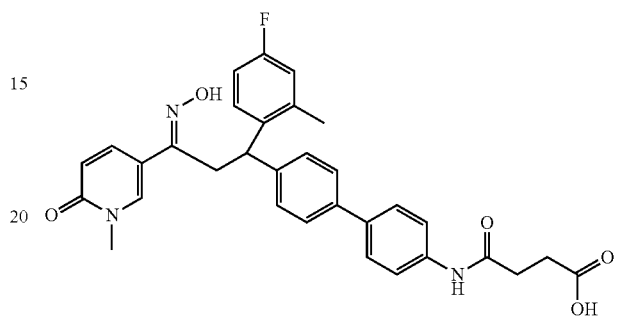

To a solution of (E)-5-(3-(4'-aminobiphenyl-4-yl)-3-(4-fluoro-2-methylphenyl)-1-(hydroxyimino)propyl)-1-methylpyridin-2(1H)-one (0.05 g, 110 μmol, example 259) in N,N-dimethylformamide was added at room temperature succinic anhydride (12.1 mg, 121 μmol) and the resulting solution was stirred at room temperature for 26 hours. The reaction mixture was poured on water and ethyl acetate and the layers were separated. The aqueous layer was extracted twice with ethyl acetate and the organic layers were washed twice with water and once with brine, dried over magnesium sulfate, filtered, treated with silica gel and evaporated. The compound was purified by silica gel chromatography on a 10 g column using a MPLC system eluting with a gradient of dichloromethane:methanol (100:0 to 90:10). Light brown foam (0.043 g, 70%). MS (ESI$^+$): m/z=556.2 ([M+H]$^+$).

Examples 393 and 394

(+)-4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-carboxylic acid; compound with triethylamine 1:0.9

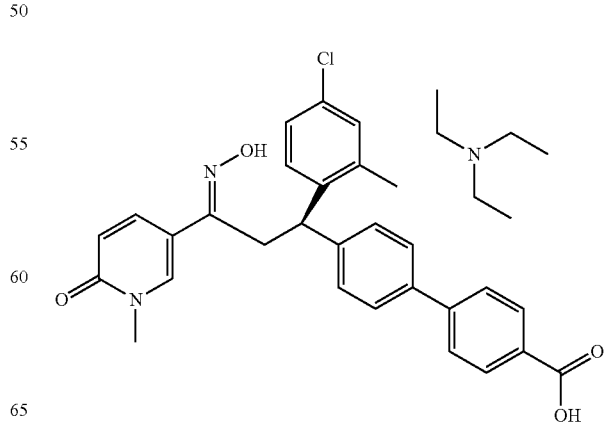

343

And (−)-4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-carboxylic acid; compound with triethylamine 1:0.85

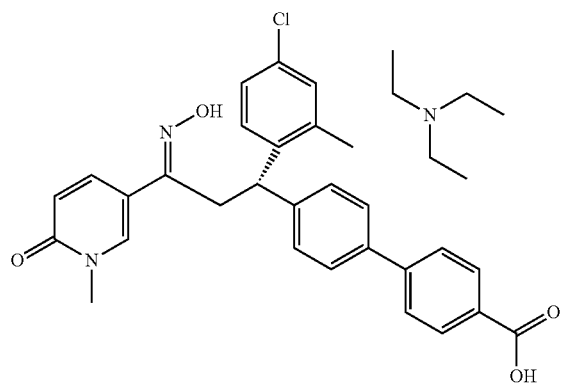

Separation of (E)-4'-(1-(4-chloro-2-methylphenyl)-3-(hydroxyimino)-3-(1-methyl-6-oxo-1,6-dihydropyridin-3-yl)propyl)biphenyl-4-carboxylic acid (example 227) on a SFC (supercritical fluid chromatography) system using a Daicel AD column eluting with 50% methanol (containing 0.2% triethylamine)/CO$_2$ gave (+)-4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carboxylic acid; compound with triethyl-amine 1:0.9 as a light brown solid, MS (ESI$^+$): m/z=501.16 ([M+H]$^+$) and (−)-4'-[1-(4-chloro-2-methyl-phenyl)-3-[(E)-hydroxyimino]-3-(1-methyl-6-oxo-1,6-dihydro-pyridin-3-yl)-propyl]-biphenyl-4-carboxylic acid; compound with triethyl-amine 1:0.85 as a brown solid, MS (ESI$^+$): m/z=501.2 ([M+H]$^+$).

Examples 395 and 396

(+)-4'-[1-(4-Chloro-2-methyl-phenyl)-3-[(E)-hydroxyimino]-3-(2-methyl-pyridin-4-yl)-propyl]-biphenyl-4-carboxylic acid; compound with triethylamine 1:1

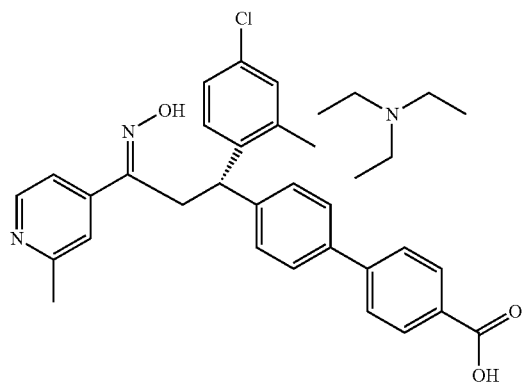

344

And (−)-4'-[1-(4-Chloro-2-methyl-phenyl)-3-[(E)-hydroxyimino]-3-(2-methyl-pyridin-4-yl)-propyl]-biphenyl-4-carboxylic acid; compound with triethylamine 1:0.7

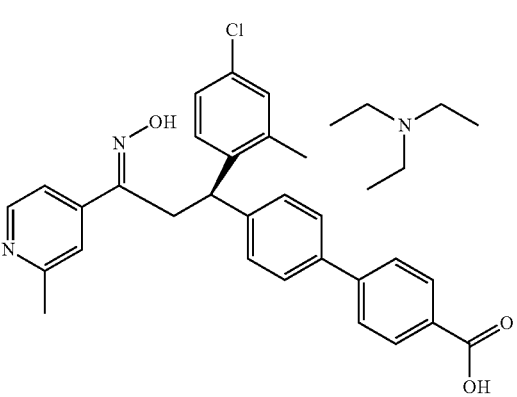

Separation of (E)-4'-(1-(4-chloro-2-methylphenyl)-3-(hydroxyimino)-3-(2-methylpyridin-4-yl)propyl)biphenyl-4-carboxylic acid (example 139) on a SFC system using a Daicel AD column eluting with 40% methanol (containing 0.2% triethylamine)/CO$_2$ gave (+)-4'-[1-(4-chloro-2-methyl-phenyl)-3-[(E)-hydroxyimino]-3-(2-methyl-pyridin-4-yl)-propyl]-biphenyl-4-carboxylic acid; compound with triethyl-amine 1:1 as a light brown solid, MS (ESI$^+$): m/z=485.16 ([M+H]$^+$) and (−)-4'-[1-(4-chloro-2-methyl-phenyl)-3-[(E)-hydroxyimino]-3-(2-methyl-pyridin-4-yl)-propyl]-biphenyl-4-carboxylic acid; compound with triethyl-amine 1:0.7 as a light brown solid, MS (ESI$^+$): m/z=485.2 ([M+H]$^+$).

Examples 397 and 398

(+)-4'-[1-(4-Fluoro-2-methyl-phenyl)-3-[(E)-hydroxyimino]-3-(2-methyl-pyridin-4-yl)-propyl]-biphenyl-4-carboxylic acid; compound with triethylamine 1:0.75

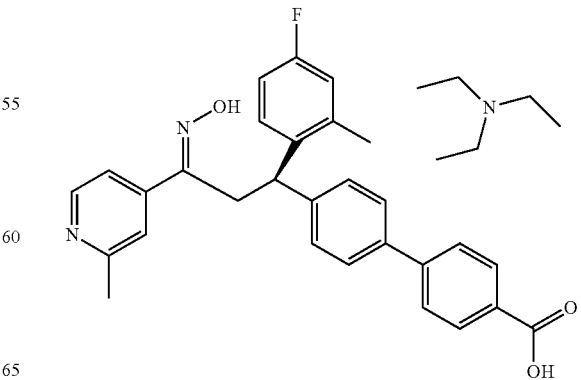

And (−)-4'-[1-(4-Fluoro-2-methyl-phenyl)-3-[(E)-hydroxyimino]-3-(2-methyl-pyridin-4-yl)-propyl]-biphenyl-4-carboxylic acid; compound with triethylamine 1:0.75

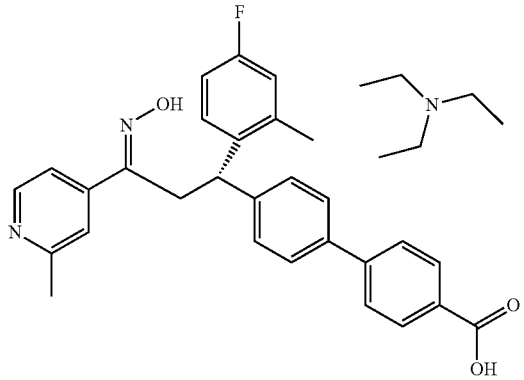

Separation of (E)-4'-(1-(4-fluoro-2-methylphenyl)-3-(hydroxyimino)-3-(2-methylpyridin-4-yl)propyl)biphenyl-4-carboxylic acid (example 141) by chiral HPLC on a SFC system using a Daicel AD column eluting with 40% methanol (containing 0.2% triethylamine)/CO$_2$ gave (+)-4'-[1-(4-fluoro-2-methyl-phenyl)-3-[(E)-hydroxyimino]-3-(2-methyl-pyridin-4-yl)-propyl]-biphenyl-4-carboxylic acid; compound with triethyl-amine 1: 0.75 as a colourless solid, MS (ESI$^+$): m/z=469.19 ([M+H]$^+$) and (−)-4'-[1-(4-fluoro-2-methyl-phenyl)-3-[(E)-hydroxyimino]-3-(2-methyl-pyridin-4-yl)-propyl]-biphenyl-4-carboxylic acid; compound with triethyl-amine 1:0.75 as a colourless solid, MS (ESI$^+$): m/z=469.2 [M+H]$^+$.

Example 399

N-{4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-yl}-malonamic acid methyl ester

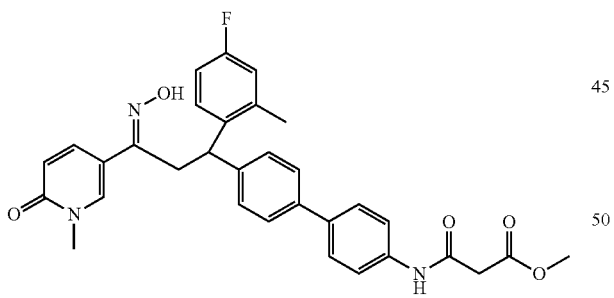

To an ice-cold solution of (E)-5-(3-(4'-aminobiphenyl-4-yl)-3-(4-fluoro-2-methylphenyl)-1-(hydroxyimino)propyl)-1-methylpyridin-2(1H)-one (0.1 g, 220 µmol, example 259) in dichloromethane (2 mL) was added triethylamine (48.9 mg, 67.3 µL, 483 µmol) followed by methyl malonyl chloride (33.0 mg, 25.9 µl, 241 µmol). The brown solution was stirred at 0° C. for 75 min., the cooling bath was removed and stirring was continued for 1.25 hours at room temperature. The solution was cooled down again to 0° C. and another batch of methyl malonyl chloride (33.0 mg, 25.9 µl, 241 µmol) was added. The cooling bath was removed and stirring continued for 20 hours at room temperature. The reaction mixture was poured on water and dichloromethane and the layers were separated. The aqueous layer was extracted twice with dichloromethane. The organic layers were washed with brine, dried over magnesium sulfate, filtered, treated with silica gel and evaporated. The compound was purified by silica gel chromatography on a 20 g column using a MPLC system eluting with a gradient of dichloromethane:methanol (100:0 to 90:10) to give the title compound as a light brown foam (0.045 g; 33%). MS (ESI$^+$): m/z=556.2 ([M+H]$^+$). In addition, (E)-methyl 3-(4'-(1-(4-fluoro-2-methylphenyl)-3-(3-methoxy-3-oxopropanoyloxyimino)-3-(1-methyl-6-oxo-1,6-dihydropyridin-3-yl)propyl)biphenyl-4-ylamino)-3-oxopropanoate (0.044 g, 36%) was isolated as a light brown foam. MS (ESI$^+$): m/z=656.2 ([M+H]$^+$).

Example 400

N-{4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-yl}-malonamic acid

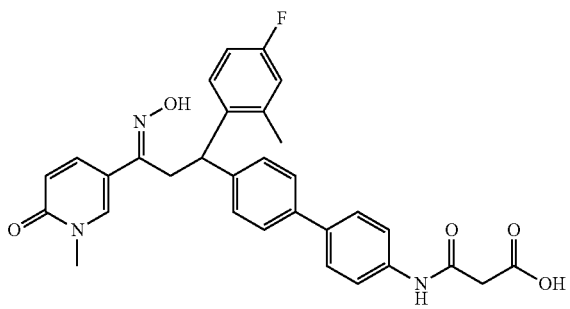 [SMILES: Cc1cc(F)ccc1C(C/C(=N\O)c1ccc(=O)n(C)c1)c1ccc(-c2ccc(NC(=O)CC(=O)O)cc2)cc1]

To a solution of (E)-methyl 3-(4'-(1-(4-fluoro-2-methylphenyl)-3-(3-methoxy-3-oxopropanoyloxyimino)-3-(1-methyl-6-oxo-1,6-dihydropyridin-3-yl)propyl)biphenyl-4-ylamino)-3-oxopropanoate (0.044 g, 67.1 µmol, from example 399) in dioxane (1 mL) and water (1 mL) was added lithium hydroxide monohydrate (7.04 mg, 168 µmol). The resulting clear solution was stirred at room temperature for 2.25 hours, and then the solvents were removed. The residue was dissolved in water (2 mL) and the pH of the solution was adjusted to approximately to pH 3 using 1M aqueous hydrochloric acid. The resulting suspension was filtered, washed with water and the filter cake dried in high vacuum. Colourless solid (0.023 g, 63%). MS (ESI$^+$): m/z=542.2 ([M+H]$^+$).

Example 401

4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-sulfonic acid amide

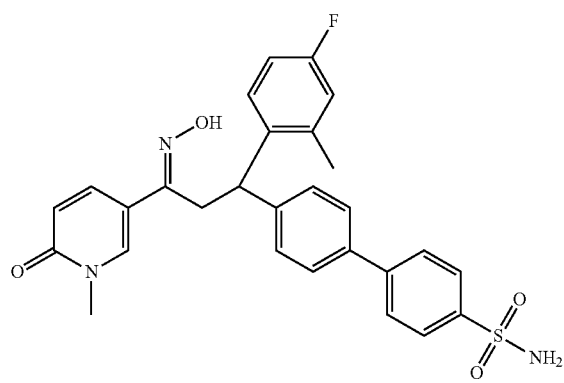 [SMILES: Cc1cc(F)ccc1C(C/C(=N\O)c1ccc(=O)n(C)c1)c1ccc(-c2ccc(S(N)(=O)=O)cc2)cc1]

The title compound was prepared in analogy to example 166, from (E)-5-(3-(4-bromophenyl)-3-(4-fluoro-2-methylphenyl)-1-(hydroxyimino)propyl)-1-methylpyridin-2 (1H)-one (example 224) and 4-(4,4,5,5-tetramethyl-1,3,2-dioxaborolan-2-yl)benzenesulfonamide (CAS RN 214360-51-7). The compound was purified by silica gel chromatography on a 20 g column using a MPLC system eluting with a gradient of dichloromethane:methanol (100:0 to 90:10). Light brown foam. MS (ESI$^+$): m/z=520.2 ([M+H]$^+$).

Example 402

5-{3-(4-Bromo-phenyl)-3-(2,4-difluoro-phenyl)-1-[(E)-hydroxyimino]-propyl}-1-methyl-1H-pyridin-2-one

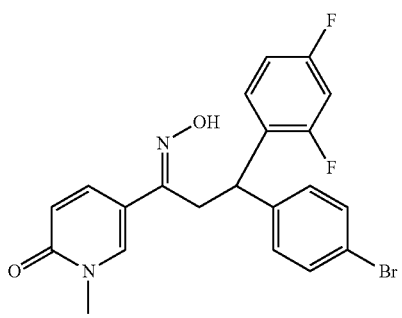 [SMILES: Cn1cc(/C(CC(c2ccc(Br)cc2)c2ccc(F)cc2F)=N/O)ccc1=O]

Step 1: (E)-3-(4-Bromo-phenyl)-1-(6-methoxy-pyridin-3-yl)-propenone

To a solution of 5-acetyl-2-methoxypyridine (5.0 g, 33.1 mmol, CAS RN 213193-32-9) in methanol (100 mL) was added 4-bromobenzaldehyde (6.73 g, 36.4 mmol, CAS RN 1122-91-4). To this solution potassium hydroxide (2.04 g, 36.4 mmol) was added and the resulting slurry was stirred at room temperature for 8 hours. After stirring in an ice-bath for 30 min. the white suspension was filtered and washed with 30 mL ice-cold methanol to give the desired compound as a colourless solid (9.76 g, 92%). MS (ESI$^-$): m/z=318.1 ([M−H]$^-$).

Step 2: 3-(4-Bromophenyl)-3-(2,4-difluorophenyl)-1-(6-methoxypyridin-3-yl)propan-1-one To a suspension of 2,4-difluorophenylboronic acid (620 mg, 3.93 mmol, CAS RN 100124-06-9) in toluene (30 mL) was added dropwise over 10 min. diethylzinc (1M solution in hexanes, 11.8 mL, 11.8 mmol, CAS RN 557-20-0) keeping the temperature below 30° C. The reaction mixture was heated to 60° C. and stirred overnight. After 16 hours heating was stopped and a turbid solution of (E)-3-(4-bromo-phenyl)-1-(6-methoxy-pyridin-3-yl)-propenone (0.5 g, 1.57 mmol) in toluene (30 mL) was added dropwise over 5 min. After stirring at room temperature for 24.5 hours the reaction mixture was poured on saturated aqueous ammonium chloride solution and ethyl acetate and the layers were separated. The aqueous layer was extracted twice with ethyl acetate and the combined organic layers were dried over magnesium sulfate, filtered and evaporated. The compound was purified by silica gel chromatography on a 20 g column using a MPLC system eluting with a gradient of n-heptane:ethyl acetate (100:0 to 70:30). Colourless oil (0.263 g, 38%). MS (ESI$^+$): m/z=432.0 ([M+H]$^+$).

Step 3: 5-[3-(4-Bromo-phenyl)-3-(2,4-difluoro-phenyl)-propionyl]-1H-pyridin-2-one To a solution of 3-(4-bromophenyl)-3-(2,4-difluorophenyl)-1-(6-methoxypyridin-3-yl)propan-1-one (0.245 g, 567 µmol) in dioxane (6 mL) was added 37% hydrochloric acid (1.23 g, 1.04 mL, 12.5 mmol) and the resulting mixture was heated at 100° C. for 1½ h. After cooling to room temperature, the reaction mixture was poured on water and ethyl acetate and the layers were separated. The aqueous layer was extracted twice with ethyl acetate. The organic layers were washed with brine, dried over magnesium sulfate, filtered, and evaporated. Off-white solid (0.227 g, 95%). MS (ESI$^-$): m/z=418.0 ([M−H]$^-$).

Step 4: 5-[3-(4-Bromo-phenyl)-3-(2,4-difluoro-phenyl)-propionyl]-1-methyl-1H-pyridin-2-one To a solution of 5-(3-(4-bromophenyl)-3-(2,4-difluorophenyl)propanoyl)pyridin-2(1H)-one (0.225 g, 538 µmol) in N,N-dimethylacetamide (3 mL) was added potassium carbonate (81.8 mg, 592 µmol) and iodomethane (80.2 mg, 35.3 µL, 565 µmol) and the resulting mixture was stirred at room temperature for 17 hours. The reaction mixture was poured on water and ethyl acetate and the layers were separated. The aqueous layer was extracted twice with ethyl acetate. The organic layers were washed twice with water and once with brine, dried over magnesium sulfate, filtered, treated with silica gel and evaporated. The compound was purified by silica gel chromatography on a 10 g column using a MPLC system eluting with a gradient of n-heptane:ethyl acetate (100:0 to 0:100). Colourless foam (0.20 g, 86%). MS (ESI$^+$): m/z=432.0 ([M+H]$^+$).

Step 5: 5-{3-(4-Bromo-phenyl)-3-(2,4-difluoro-phenyl)-1-[(E)-hydroxyimino]-propyl}-1-methyl-1H-pyridin-2-one To a solution of 5-(3-(4-bromophenyl)-3-(2,4-difluorophenyl)propanoyl)-1-methyl-pyridin-2(1H)-one (0.2 g, 463 µmol) in ethanol (5 mL) and water (0.2 mL) was added hydroxylamine hydrochloride (80.4 mg, 1.16 mmol) and sodium hydrogencarbonate (77.7 mg, 925 µmol) and the resulting colourless suspension was heated at reflux (100° C. oil bath temperature) for 4.5 hours. After cooling down the reaction mixture was poured on water and ethyl acetate and the layers were separated. The aqueous layer was extracted twice with ethyl acetate. The organic layers were washed with brine, dried over magnesium sulfate, filtered, treated with silica gel and evaporated. The compound was purified by silica gel chromatography on a 20 g column using a MPLC system eluting with a gradient of n-heptane:ethyl acetate (100:0 to 0:100). Colourless foam (0.205 g, 99%). MS (ESI+): m/z=449.1 ([M+H]+).

Example 403

4'-[1-(2,4-Difluoro-phenyl)-3-[(E)-hydroxyimino]-3-(1-methyl-6-oxo-1,6-dihydro-pyridin-3-yl)-propyl]-biphenyl-4-carboxylic acid

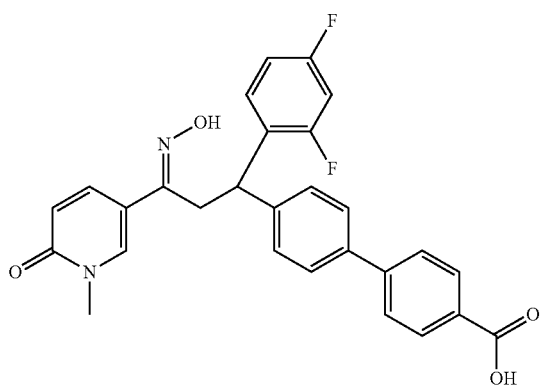 [SMILES: Cn1cc(/C(CC(c2ccc(-c3ccc(C(=O)O)cc3)cc2)c2ccc(F)cc2F)=N/O)ccc1=O]

The title compound was prepared in analogy to example 166, from 5-{3-(4-bromo-phenyl)-3-(2,4-difluoro-phenyl)-1-[(E)-hydroxyimino]-propyl}-1-methyl-1H-pyridin-2-one (example 402) and 4-carboxyphenylboronic acid (CAS RN 14047-29-1). The compound was purified by two silica gel chromatographies using a 20 g column and a MPLC system eluting with a gradient of dichloromethane:methanol (100:0 to 70:30). Light brown foam. MS (ESI+): m/z=489.2 ([M+H]+).

Examples 404 and 405

(−)-5-{3-(4-Bromo-phenyl)-3-(4-fluoro-2-methyl-phenyl)-1-[(E)-hydroxyimino]-propyl}-1-methyl-1H-pyridin-2-one

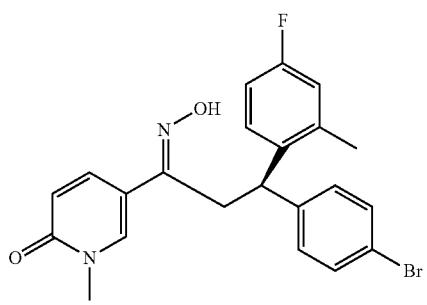 [SMILES: Cc1cc(F)ccc1[C@H](C/C(=N\O)c1ccc(=O)n(C)c1)c1ccc(Br)cc1]

And (+)-5-{3-(4-Bromo-phenyl)-3-(4-fluoro-2-methyl-phenyl)-1-[(E)-hydroxyimino]-propyl}-1-methyl-1H-pyridin-2-one

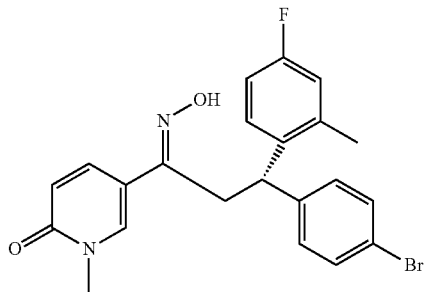 [SMILES: Cc1cc(F)ccc1[C@@H](C/C(=N\O)c1ccc(=O)n(C)c1)c1ccc(Br)cc1]

Separation of (E)-5-(3-(4-bromophenyl)-3-(4-fluoro-2-methylphenyl)-1-(hydroxyimino)-propyl)-1-methylpyridin-2(1H)-one (example 224) by chiral HPLC on a Chiralpak-AD column using an isocratic solvent mixture of 2-propanole (20%) in n-heptane gave (−)-5-{3-(4-bromo-phenyl)-3-(4-fluoro-2-methyl-phenyl)-1-[(E)-hydroxyimino]-propyl}-1-methyl-1H-pyridin-2-one as a light brown foam, MS (ESI+): m/z=443.08 [M+H]+ and (+)-5-{3-(4-bromo-phenyl)-3-(4-fluoro-2-methyl-phenyl)-1-[(E)-hydroxyimino]-propyl}-1-methyl-1H-pyridin-2-one as a light brown foam, MS (ESI+): m/z=443.1 [M+H]+.

Example 406

(−)-4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-sulfonic acid amide

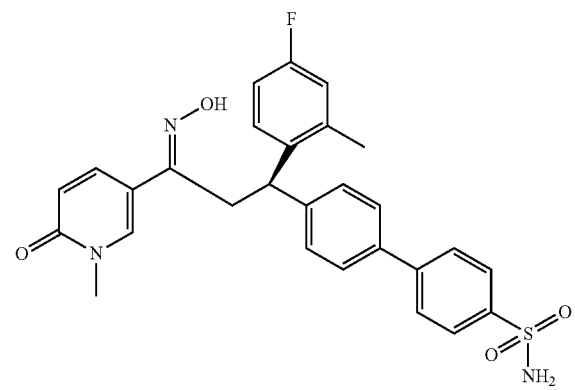 [SMILES: Cc1cc(F)ccc1[C@H](C/C(=N\O)c1ccc(=O)n(C)c1)c1ccc(-c2ccc(S(N)(=O)=O)cc2)cc1]

The title compound was prepared in analogy to example 166, from (−)-5-{3-(4-bromo-phenyl)-3-(4-fluoro-2-methyl-phenyl)-1-[(E)-hydroxyimino]-propyl}-1-methyl-1H-pyridin-2-one (example 404) and 4-(4,4,5,5-tetramethyl-1,3,2-dioxaborolan-2-yl)benzenesulfonamide (CAS RN 214360-51-7). The compound was purified by silica gel chromatography on a 10 g column using a MPLC system eluting with a gradient of dichloromethane:methanol (100:0 to 90:10). Light brown solid. MS (ESI⁺): m/z=520.2 ([M+H]⁺).

Example 407

(+)-4'-[1-(4-Fluoro-2-methyl-phenyl)-3-[(E)-hydroxyimino]-3-(1-methyl-6-oxo-1,6-dihydro-pyridin-3-yl)-propyl]-biphenyl-4-sulfonic acid amide

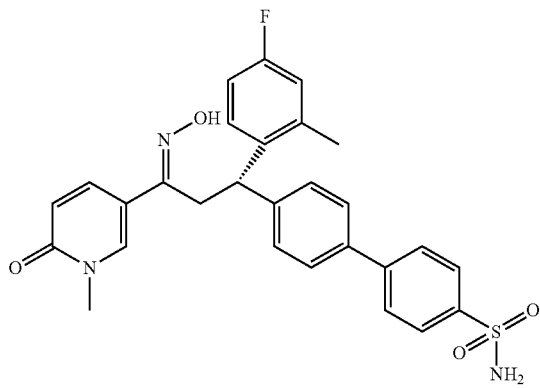

The title compound was prepared in analogy to example 166, from (+)-5-{3-(4-bromo-phenyl)-3-(4-fluoro-2-methyl-phenyl)-1-[(E)-hydroxyimino]-propyl}-1-methyl-1H-pyridin-2-one (example 405) and 4-(4,4,5,5-tetramethyl-1,3,2-dioxaborolan-2-yl)benzenesulfonamide (CAS RN 214360-51-7). The compound was purified by silica gel chromatography on a 10 g column using a MPLC system eluting with a gradient of dichloromethane:methanol (100:0 to 90:10). Light brown solid. MS (ESI⁺): m/z=520.2 ([M+H]⁺).

Example 408

(E)-5-(3-(4-bromophenyl)-3-(2-fluoro-4-methylphenyl)-1-(hydroxyimino)propyl)-1-methylpyridin-2(1H)-one

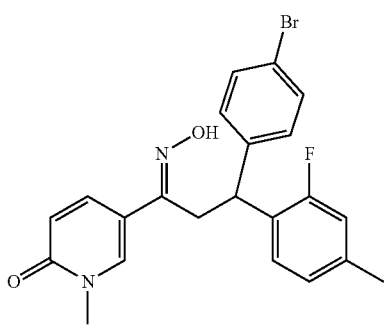 [SMILES: Cc1ccc(C(C/C(=N\O)c2ccc(=O)n(C)c2)c2ccc(Br)cc2)c(F)c1]

Step 1: (E)-3-(2-Fluoro-4-methyl-phenyl)-1-(6-methoxy-pyridin-3-yl)-propenone

The title compound was prepared in analogy to example 402, step 1, from 5-acetyl-2-methoxypyridine and 2-fluoro-4-methylbenzaldehyde (CAS RN 146137-80-6). Off-white solid. MS (ESI⁺): m/z=272.1 ([M+H]⁺).

Step 2: 3-(4-Bromo-phenyl)-3-(2-fluoro-4-methyl-phenyl)-1-(6-methoxy-pyridin-3-yl)-propan-1-one The title compound was prepared in analogy to example 402, step 2, from (E)-3-(2-fluoro-4-methyl-phenyl)-1-(6-methoxy-pyridin-3-yl)-propenone and 4-bromobenzeneboronic acid (CAS RN 5467-74-3). The compound was purified by silica gel chromatography using a MPLC system (CombiFlash Companion, Isco Inc.) eluting with a gradient of n-heptane:ethyl acetate (100:0 to 60:40). Colourless oil. MS (ESI⁺): m/z=430.1 ([M+H]⁺).

Step 3: 5-[3-(4-Bromo-phenyl)-3-(2-fluoro-4-methyl-phenyl)-propionyl]-1-pyridin-2-one The title compound was prepared in analogy to example 402, step 3, from 3-(4-bromo-phenyl)-3-(2-fluoro-4-methyl-phenyl)-1-(6-methoxy-pyridin-3-yl)-propan-1-one. Light brown solid. MS (ESI⁺): m/z=414.0 ([M+H]⁺).

Step 4: 5-[3-(4-Bromo-phenyl)-3-(2-fluoro-4-methyl-phenyl)-propionyl]-1-methyl-1H-pyridin-2-one The title compound was prepared in analogy to example 402, step 4, from 5-[3-(4-bromo-phenyl)-3-(2-fluoro-4-methyl-phenyl)-propionyl]-1H-pyridin-2-one. The compound was purified by silica gel chromatography using a MPLC system (CombiFlash Companion, Isco Inc.) eluting with a gradient of n-heptane:ethyl acetate (100:0 to 0:100). Colourless solid. MS (ESI⁻): m/z=474.1 ([M+HCOO]⁻).

Step 5: (E)-5-{3-(4-Bromo-phenyl)-3-(2-fluoro-4-methyl-phenyl)-1-(hydroxyimino)-propyl}-1-methyl-1H-pyridin-2-one The title compound was prepared in analogy to example 402, step 5, from 5-[3-(4-bromo-phenyl)-3-(2-fluoro-4-methyl-phenyl)-propionyl]-1-methyl-1H-pyridin-2-one. The compound was purified by silica gel chromatography using a MPLC system (CombiFlash Companion, Isco Inc.) eluting with a gradient of n-heptane:ethyl acetate (100:0 to 0:100). Colourless solid. MS (ESI⁺): m/z=445.1 ([M+H]⁺).

Example 409

(E)-5-{3-(4-Bromo-phenyl)-3-(4-fluoro-2-methanesulfonyl-phenyl)-1-(hydroxyimino)-propyl}-1-methyl-1H-pyridin-2-one

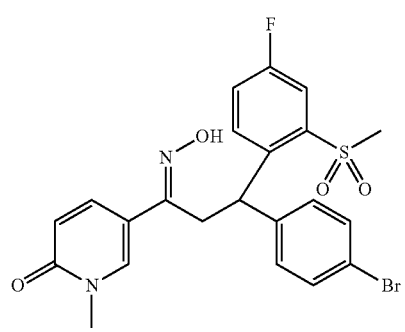 [SMILES: Cn1cc(/C(CC(c2ccc(Br)cc2)c2ccc(F)cc2S(C)(=O)=O)=N/O)ccc1=O]

Step 1: 4-Fluoro-2-methylsulfanyl-benzaldehyde

To a solution of 2,4-difluorobenzaldehyde (3.0 g, 21.1 mmol, CAS RN 1550-35-2) in toluene (29 mL) was added sodium thiomethoxide (2.03 g, 28.9 mmol) and the resulting suspension was stirred at 80° C. for 7 hours. Heating was removed and stirring continued at room temperature for another 18 hours. The reaction mixture was treated with diethyl ether (50 mL) and water (15 mL) and the layers were separated. The aqueous layer was extracted twice with ethyl acetate (50 mL each). The organic layers were washed with saturated aqueous sodium hydrogencarbonate solution and with brine, dried over magnesium sulfate, filtered and evaporated. The residue was dissolved in 50 mL n-heptane and 50 mL diethyl ether and the clear solution was evaporated slowly until a turbid solution formed. The originally oily precipitation turned into a white solid which was filtered, washed with n-heptane and dried under high vacuum to give the compound as a colourless solid (1.35 g, 37%). MS (ESI+): m/z=170.0 ([M+H]+).

Step 2: (E)-3-(4-Fluoro-2-methylsulfanyl-phenyl)-1-(6-methoxy-pyridin-3-yl)-propenone The title compound was prepared in analogy to example 402, step 1, from 1-(6-methoxy-pyridin-3-yl)-ethanone (CAS RN 213193-32-9) and 4-fluoro-2-methylsulfanyl-benzaldehyde. Yellow solid. MS (ESI+): m/z=304.1 ([M+H]+).

Step 3: 3-(4-Bromo-phenyl)-3-(4-fluoro-2-methylsulfanyl-phenyl)-1-(6-methoxy-pyridin-3-yl)-propan-1-one The title compound was prepared in analogy to example 402, step 2, from (E)-3-(4-fluoro-2-methylsulfanyl-phenyl)-1-(6-methoxy-pyridin-3-yl)-propenone and 4-bromophenyl-boronic acid (2.14 g, 10.7 mmol, CAS RN 5467-74-3). The compound was purified by silica gel chromatography on a 50 g column using a MPLC system eluting with a gradient of n-heptane:ethyl acetate (100:0 to 50:50). Light brown foam. MS (ESI+): m/z=462.0 ([M+H]+).

Step 4: 5-[3-(4-Bromo-phenyl)-3-(4-fluoro-2-methylsulfanyl-phenyl)-propionyl]-1H-pyridin-2-one The title compound was prepared in analogy to example 402, step 3, from 3-(4-bromo-phenyl)-3-(4-fluoro-2-methylsulfanyl-phenyl)-1-(6-methoxy-pyridin-3-yl)-propan-1-one. Light brown foam. MS (ESI+): m/z=448.0 ([M+H]+).

Step 5: 5-[3-(4-Bromo-phenyl)-3-(4-fluoro-2-methylsulfanyl-phenyl)-propionyl]-1-methyl-1H-pyridin-2-one The title compound was prepared in analogy to example 402, step 4, from 5-[3-(4-bromo-phenyl)-3-(4-fluoro-2-methylsulfanyl-phenyl)-propionyl]-1H-pyridin-2-one. The compound was purified by silica gel chromatography on a 10 g column using a MPLC system eluting with a gradient of n-heptane:ethyl acetate (100:0 to 0:100). In order to remove final traces of solvent the compound was dissolved in ethyl acetate, washed five times with water, dried over magnesium sulfate, filtered and evaporated. Colourless solid (0.232 g, 84%). MS (ESI+): m/z=462.0 ([M+H]+).

Step 6: 5-[3-(4-Bromo-phenyl)-3-(4-fluoro-2-methanesulfonyl-phenyl)-propionyl]-1-methyl-1H-pyridin-2-one To a solution of 5-[3-(4-bromo-phenyl)-3-(4-fluoro-2-methylsulfanyl-phenyl)-propionyl]-1-methyl-1H-pyridin-2-one (0.222 g, 482 μmol) in dichloromethane (3 mL) was added 3-chloroperoxybenzoic acid (238 mg, 964 μmol) and the resulting clear solution was stirred at room temperature for 2¾ h. After 30 min. a precipitation formed. The reaction mixture was poured on saturated aqueous sodium hydrogencarbonate solution and dichloromethane and the layers were separated. The aqueous layer was extracted twice with dichloromethane. The organic layers were washed twice with saturated aqueous sodium hydrogencarbonate solution and once with brine, dried over magnesium sulfate and basic aluminium oxide, filtered, treated with silica gel and evaporated. The compound was purified by silica gel chromatography on a 20 g column using a MPLC system eluting with a gradient of n-heptane:ethyl acetate (100:0 to 0:100). Colourless foam (0.121 g, 51%). MS (ESI+): m/z=494.0 ([M+H]+).

Step 7: (E)-5-{3-(4-Bromo-phenyl)-3-(4-fluoro-2-methanesulfonyl-phenyl)-1-(hydroxyimino)-propyl}-1-methyl-1H-pyridin-2-one The title compound was prepared in analogy to example 402, step 5, from 5-[3-(4-bromo-phenyl)-3-(4-fluoro-2-methanesulfonyl-phenyl)-propionyl]-1-methyl-1H-pyridin-2-one. The compound was purified by silica gel chromatography on a 20 g column using a MPLC system eluting with a gradient of dichloromethane:methanol (100:0 to 90:10). Colourless foam. MS (ESI+): m/z=509.0 ([M+H]+).

Example 410

(E)-5-(3-(4-bromophenyl)-3-(2-chloro-4-fluorophenyl)-1-(hydroxyimino)propyl)-1-methylpyridin-2 (1H)-one

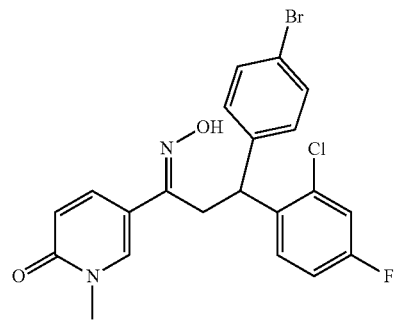 [SMILES: Cn1cc(/C(CC(c2ccc(Br)cc2)c2ccc(F)cc2Cl)=N/O)ccc1=O]

Step 1: (E)-3-(2-Chloro-4-fluoro-phenyl)-1-(6-methoxy-pyridin-3-yl)-propenone The title compound was prepared in analogy to example 402, step 1, from 1-(6-methoxy-pyridin-3-yl)-ethanone (CAS RN 213193-32-9) and 2-chloro-4-fluorobenzaldehyde (CAS RN 84194-36-5). Colourless solid. MS (ESI+): m/z=292.1 ([M+H]+).

Step 2: 3-(4-Bromo-phenyl)-3-(2-chloro-4-fluoro-phenyl)-1-(6-methoxy-pyridin-3-yl)-propan-1-one The title compound was prepared in analogy to example 402, step 2, from (E)-3-(2-chloro-4-fluoro-phenyl)-1-(6-methoxy-pyridin-3-yl)-propenone and 4-bromophenylboronic acid (CAS RN 5467-74-3). The compound was purified by silica gel chromatography using a MPLC system (CombiFlash Companion, Isco Inc.) eluting with a gradient of n-heptane:ethyl acetate (100:0 to 50:50). Colourless viscous oil. MS (ESI$^+$): m/z=450.0 ([M+H]$^+$).

Step 3: 5-[3-(4-Bromo-phenyl)-3-(2-chloro-4-fluoro-phenyl)-propionyl]-1H-pyridin-2-one The title compound was prepared in analogy to example 402, step 3, from 3-(4-bromo-phenyl)-3-(2-chloro-4-fluoro-phenyl)-1-(6-methoxy-pyridin-3-yl)-propan-1-one. Off-white solid. MS (ESI$^+$): m/z=436.0 ([M+H]$^+$).

Step 4: 5-[3-(4-Bromo-phenyl)-3-(2-chloro-4-fluoro-phenyl)-propionyl]-1-methyl-1H-pyridin-2-one The title compound was prepared in analogy to example 402, step 4, from 5-[3-(4-bromo-phenyl)-3-(2-chloro-4-fluoro-phenyl)-propionyl]-1H-pyridin-2-one. The compound was purified by silica gel chromatography using a MPLC system (CombiFlash Companion, Isco Inc.) eluting with a gradient of n-heptane:ethyl acetate (100:0 to 0:100). Colourless solid. MS (ESI$^+$): m/z=450.0 ([M+H$^+$]).

Step 5: (E)-5-{3-(4-Bromo-phenyl)-3-(2-chloro-4-fluoro-phenyl)-1-(hydroxyimino)-propyl}-1-methyl-1H-pyridin-2-one The title compound was prepared in analogy to example 402, step 5, from 5-[3-(4-bromo-phenyl)-3-(2-chloro-4-fluoro-phenyl)-propionyl]-1-methyl-1H-pyridin-2-one. The compound was purified by silica gel chromatography using a MPLC system (CombiFlash Companion, Isco Inc.) eluting with a gradient of n-heptane:ethyl acetate (100:0 to 0:100) to give the desired compound as a colourless solid, MS (ESI$^+$): m/z=465.0 ([M+H]$^+$).

Example 411

(E)-4'-(1-(2-fluoro-4-methylphenyl)-3-(hydroxyimino)-3-(1-methyl-6-oxo-1,6-dihydropyridin-3-yl)propyl)biphenyl-4-carboxylic acid

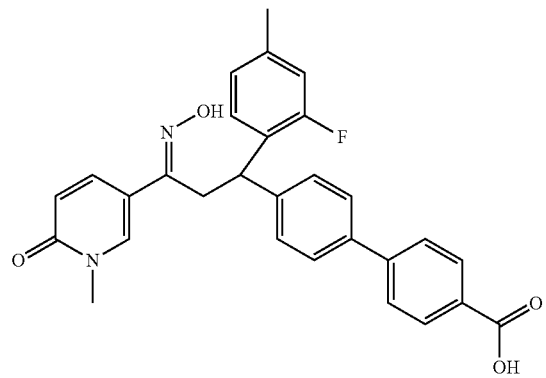 [SMILES: Cc1ccc(C(C/C(=N\O)c2ccc(=O)n(C)c2)c2ccc(-c3ccc(C(=O)O)cc3)cc2)c(F)c1]

The title compound was prepared in analogy to example 166, from (E)-5-(3-(4-bromophenyl)-3-(2-fluoro-4-methylphenyl)-1-(hydroxyimino)propyl)-1-methylpyridin-2(1H)-one and 4-carboxyphenylboronic acid (CAS RN 14047-29-1). The compound was purified by silica gel chromatography using a MPLC system eluting with a gradient of dichloromethane:methanol (100:0 to 90:10). Yellow solid. MS (ESI$^+$): m/z=485.2 ([M+H]$^+$).

Example 412

(E)-4'-(1-(2-chloro-4-fluorophenyl)-3-(hydroxyimino)-3-(1-methyl-6-oxo-1,6-dihydropyridin-3-yl)propyl)biphenyl-4-carboxylic acid

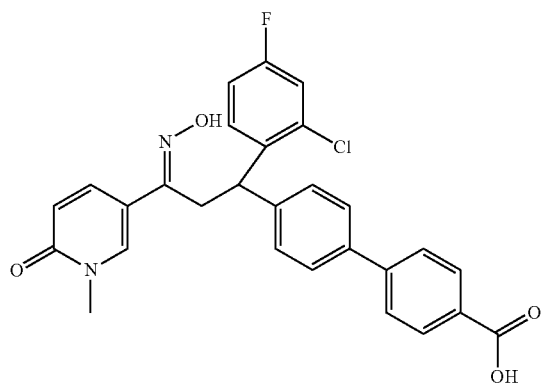 [SMILES: Cn1cc(/C(CC(c2ccc(-c3ccc(C(=O)O)cc3)cc2)c2ccc(F)cc2Cl)=N/O)ccc1=O]

The title compound was prepared in analogy to example 166, from (E)-5-{3-(4-bromo-phenyl)-3-(2-chloro-4-fluoro-phenyl)-1-(hydroxyimino)-propyl}-1-methyl-1H-pyridin-2-one (example 410) and 4-carboxyphenylboronic acid (CAS RN 14047-29-1). The compound was purified by silica gel chromatography using a MPLC system eluting with a gradient of dichlormethane:methanol (100:0 to 90:10). The resulting yellow solid was purified by preparative HPLC (phenomenex gemini column) with a gradient of acetonitrile:water (10:90 to 95:5) followed by another preparative HPLC purification (Reprosil Chiral-NR column) using 80% n-heptane: 20% EtOH (containing 0.5% formic acid) as eluant to give the desired compound as a colourless solid, MS (ESI$^+$): m/z=505.1 ([M+H]$^+$).

Example 413

(−)-4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-sulfonic acid amide

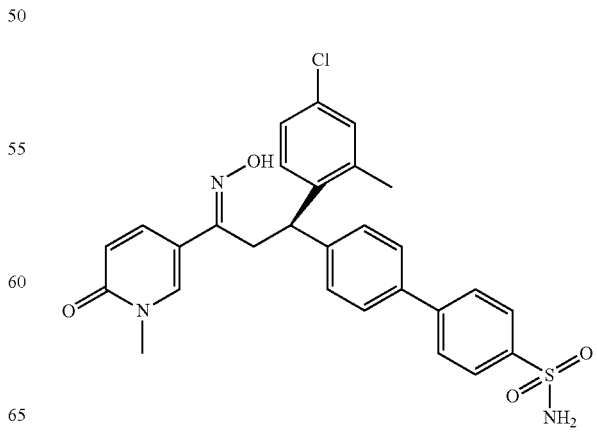

Step 1: (−)-5-[3-(4-Bromo-phenyl)-3-(4-chloro-2-methyl-phenyl)-propionyl]-1-methyl-1H-pyridin-2-one and (+)-5-[3-(4-Bromo-phenyl)-3-(4-chloro-2-methyl-phenyl)-propionyl]-1-methyl-1H-pyridin-2-one Separation of 5-[3-(4-bromo-phenyl)-3-(4-chloro-2-methyl-phenyl)-propionyl]-1-methyl-1H-pyridin-2-one (example 226, step 3) by chiral separation on a Chiralpak-AD column using an isocratic mixture of 30% ethanol in n-heptane gave (−)-5-[3-(4-bromo-phenyl)-3-(4-chloro-2-methyl-phenyl)-propionyl]-1-methyl-1H-pyridin-2-one as a colourless solid, MS (ESI+): m/z=446.03 ([M+H]+) and (+)-5-[3-(4-bromo-phenyl)-3-(4-chloro-2-methyl-phenyl)-propionyl]-1-methyl-1H-pyridin-2-one as a colourless solid, MS (ESI+): m/z=446.0 ([M+H]+).

Step 2: (−)-4'-[1-(4-Chloro-2-methyl-phenyl)-3-(1-methyl-6-oxo-1,6-dihydro-pyridin-3-yl)-3-oxo-propyl]-biphenyl-4-sulfonic acid amide The title compound was prepared in analogy to example 166, from (−)-5-[3-(4-bromo-phenyl)-3-(4-chloro-2-methyl-phenyl)-propionyl]-1-methyl-1H-pyridin-2-one and 4-(4,4,5,5-tetramethyl-1,3,2-dioxaborolan-2-yl)benzenesulfonamide (CAS RN 214360-51-7). The compound was purified by silica gel chromatography on a 10 g column using a MPLC system eluting with a gradient of n-heptane:ethyl acetate (100:0 to 100:0). Light brown solid. MS (ESI+): m/z=521.1 ([M+H]+).

Step 3: (−)-4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-sulfonic acid amide The title was prepared in analogy to example 402, step 5 from (−)-4'-[1-(4-chloro-2-methyl-phenyl)-3-(1-methyl-6-oxo-1,6-dihydro-pyridin-3-yl)-3-oxo-propyl]-biphenyl-4-sulfonic acid amide. The compound was purified by silica gel chromatography on a 20 g column using a MPLC system eluting with a gradient of dichloromethane:methanol (100:0 to 90:10). Colourless solid. MS (ESI+): m/z=536.1 ([M+H]+).

Example 414

(+)-4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-sulfonic acid amide

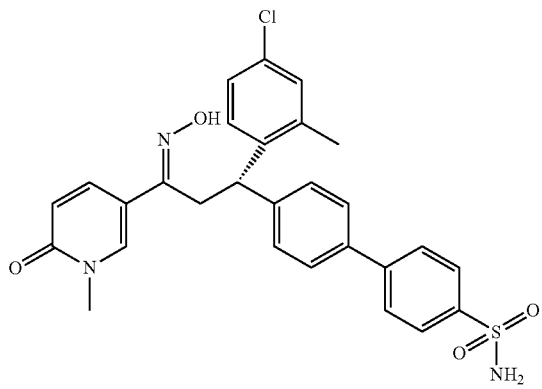 [SMILES: Cc1cc(Cl)ccc1[C@@H](C/C(=N\O)c1ccc(=O)n(C)c1)c1ccc(-c2ccc(S(N)(=O)=O)cc2)cc1]

Step 1: (+)-4'-[1-(4-Chloro-2-methyl-phenyl)-3-(1-methyl-6-oxo-1,6-dihydro-pyridin-3-yl)-3-oxo-propyl]-biphenyl-4-sulfonic acid amide The title compound was prepared in analogy to example 166 from (+)-5-[3-(4-bromo-phenyl)-3-(4-chloro-2-methyl-phenyl)-propionyl]-1-methyl-1H-pyridin-2-one (example 413, step 1) and 4-(4,4,5,5-tetramethyl-1,3,2-dioxaborolan-2-yl)benzenesulfonamide (CAS RN 214360-51-7). The compound was purified by silica gel chromatography on a 10 g column using a MPLC system eluting with a gradient of n-heptane:ethyl acetate (100:0 to 100:0). Light brown solid. MS (ESI+): m/z=521.1 ([M+H]+).

Step 2: (+)-4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-sulfonic acid amide The title was prepared in analogy to example 402, step 5 from (+)-4'-[1-(4-chloro-2-methyl-phenyl)-3-(1-methyl-6-oxo-1,6-dihydro-pyridin-3-yl)-3-oxo-propyl]-biphenyl-4-sulfonic acid amide. The compound was purified by silica gel chromatography on a 20 g column using a MPLC system eluting with a gradient of dichloromethane:methanol (100:0 to 90:10). Colourless solid. MS (ESI+): m/z=536.1 ([M+H]+).

Example 415

(+)-5-{3-(4-Bromo-phenyl)-3-(4-chloro-2-methyl-phenyl)-1-[(E)-hydroxyimino]-propyl}-1-methyl-1H-pyridin-2-one

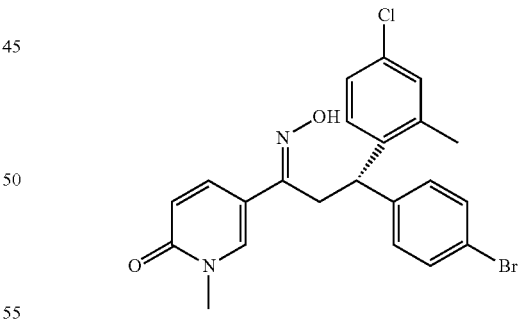

The title compound was prepared in analogy to example 402, step 5, from (+)-5-[3-(4-bromo-phenyl)-3-(4-chloro-2-methyl-phenyl)-propionyl]-1-methyl-1H-pyridin-2-one (example 413, step 1). The compound was purified by silica gel chromatography on a 10 g column using a MPLC system eluting with a gradient of n-heptane:ethyl acetate (100:0 to 0:100). Colourless foam. MS (ESI+): m/z=461.0 ([M+H]+).

Example 416

(+)-N-{4'-[1-(4-Chloro-2-methyl-phenyl)-3-[(E)-hydroxyimino]-3-(1-methyl-6-oxo-1,6-dihydro-pyridin-3-yl)-propyl]-biphenyl-4-yl}-methanesulfonamide

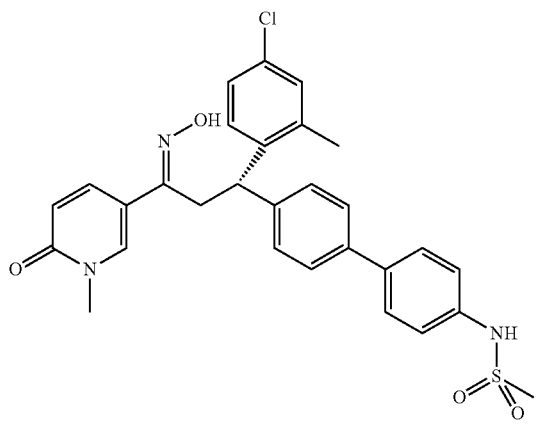 [SMILES: Cc1cc(Cl)ccc1[C@@H](C/C(=N\O)c1ccc(=O)n(C)c1)c1ccc(-c2ccc(NS(C)(=O)=O)cc2)cc1]

The title compound was prepared in analogy to example 166, from (+)-5-{3-(4-bromo-phenyl)-3-(4-chloro-2-methyl-phenyl)-1-[(E)-hydroxyimino]-propyl}-1-methyl-1H-pyridin-2-one (example 415) and 4-(methanesulfonylamino)phenylboronic acid (CAS RN 380430-57-9). The compound was purified by silica gel chromatography on a 20 g column using a MPLC system eluting with a gradient of dichloromethane:methanol (100:0 to 90:10). Light brown foam. MS (ESI⁺): m/z=550.2 ([M+H]⁺).

Example 417

((−), E)-3-[4-(5-Methyl-[1,3,4]oxadiazol-2-yl)-phenyl]-1-(2-methyl-pyridin-4-yl)-3-o-tolyl-propan-1-one oxime

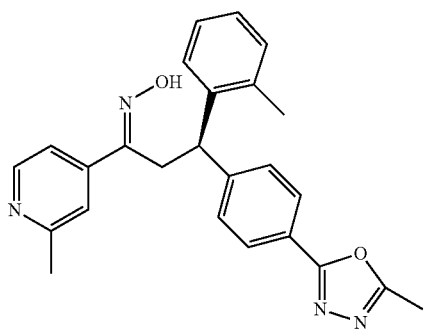 [SMILES: Cc1cc(/C(C[C@H](c2ccc(-c3nnc(C)o3)cc2)c2ccccc2C)=N/O)ccn1]

Step 1: (−)-3-[4-(5-Methyl-[1,3,4]oxadiazol-2-yl)-phenyl]-1-(2-methyl-pyridin-4-yl)-3-o-tolyl-propan-1-one To a solution of 4-[(−)-3-(2-methyl-pyridin-4-yl)-3-oxo-1-o-tolyl-propyl]-benzoic acid (80 mg; example 272, step 2) and diisopropylethylamine (0.078 mL) in N,N-dimethylformamide (2.6 mL) was added O-(7-azabenzotriazol-1-yl)-N,N,N',N'-tetramethyluronium hexafluorophosphate (102 mg) and the reaction mixture stirred at room temperature. After 5 min, acetic acid hydrazide (35 mg; CAS RN 1068-57-1) was added and the reaction mixture heated by microwave irradiation to 100° C. for 10 min. To the reaction mixture was added conc. sulfuric acid (0.24 mL; strongly exothermic!) and heating by microwave irradiation at 140° C. continued for another 10 min. The reaction mixture was extracted over a sat. solution of sodium hydrogencarbonate (50 mL) with ethyl acetate (3×50 mL) and the combined organic phases dried over sodium sulfate. The crude reaction product was purified by silica gel chromatography using a MPLC system (Combi-Flash Companion, Isco Inc.) eluting with a gradient of n-heptane/ethyl acetate (100:0 to 50:50) to give the title compound as a light red oil. MS (ESI⁺): m/z=398.1 ([M+H]⁺).

Step 2: ((−), E)-3-[4-(5-Methyl-[1,3,4]oxadiazol-2-yl)-phenyl]-1-(2-methyl-pyridin-4-yl)-3-o-tolyl-propan-1-one oxime The title compound was prepared in analogy to example 402, step 5, from (−)-3-[4-(5-methyl-[1,3,4]oxadiazol-2-yl)-phenyl]-1-(2-methyl-pyridin-4-yl)-3-o-tolyl-propan-1-one. The compound was purified by silica gel chromatography using a MPLC system (CombiFlash Companion, Isco Inc.) eluting with a gradient of dichloromethane:methanol (100:0 to 98:2). Light pink solid. MS (ESI⁺): m/z=413.1 ([M+H]⁺).

Example 418

((−), E)-3-(4-(5-Cyclopropyl-1,3,4-oxadiazol-2-yl)phenyl)-1-(2-methylpyridin-4-yl)-3-o-tolylpropan-1-one oxime

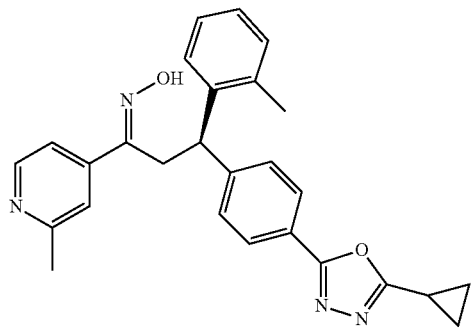 [SMILES: Cc1cc(/C(C[C@H](c2ccc(-c3nnc(C4CC4)o3)cc2)c2ccccc2C)=N/O)ccn1]

Step 1: (−)-3-[4-(5-Cyclopropyl-[1,3,4]oxadiazol-2-yl)-phenyl]-1-(2-methyl-pyridin-4-yl)-3-o-tolyl-propan-1-one The title compound was produced in analogy to example 417, step 1 from 4-[(−)-3-(2-methyl-pyridin-4-yl)-3-oxo-1-o-tolyl-propyl]-benzoic acid (example 272, step 2) and cyclopropanecarboxylic acid hydrazide (CAS RN 6952-93-8). Light yellow oil. MS (ESI⁺): m/z=424.1 ([M+H]⁺).

Step 2: ((−), E)-3-(4-(5-Cyclopropyl-1,3,4-oxadiazol-2-yl)phenyl)-1-(2-methylpyridin-4-yl)-3-o-tolyl-propan-1-one oxime The title compound was produced in analogy to example 417, step 2, from (−)-3-[4-(5-cyclopropyl-[1,3,4]oxadiazol-2-yl)-phenyl]-1-(2-methyl-pyridin-4-yl)-3-o-tolyl-propan-1-one and hydroxylamine hydrochloride in the presence of sodium hydrogencarbonate. White solid. MS (ESI⁺): m/z=439.1 ([M+H]⁺).

Example 419

((−), E)-3-[4-(5-Methoxymethyl-[1,3,4]oxadiazol-2-yl)-phenyl]-1-(2-methyl-pyridin-4-yl)-3-o-tolyl-propan-1-one oxime

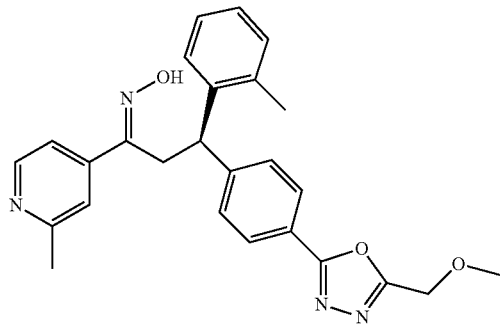 [SMILES: COCc1nnc(-c2ccc([C@@H](C/C(=N\O)c3ccnc(C)c3)c3ccccc3C)cc2)o1]

Step 1: (−)-3-[4-(5-Methoxymethyl-[1,3,4]oxadiazol-2-yl)-phenyl]-1-(2-methyl-pyridin-4-yl)-3-o-tolyl-propan-1-one The title compound was produced in analogy to example 417, step 1 from 4-[(−)-3-(2-methyl-pyridin-4-yl)-3-oxo-1-o-tolyl-propyl]-benzoic acid (example 272, step 2) and methoxy-acetic acid hydrazide (CAS RN 20605-41-8). Light red oil. MS (ESI+): m/z=428.1 ([M+H]+).

Step 2: ((−), E)-3-[4-(5-Methoxymethyl-[1,3,4]oxadiazol-2-yl)-phenyl]-1-(2-methyl-pyridin-4-yl)-3-o-tolyl-propan-1-one oxime The title compound was produced in analogy to example 417, step 2, from (−)-3-[4-(5-methoxymethyl-[1,3,4]oxadiazol-2-yl)-phenyl]-1-(2-methyl-pyridin-4-yl)-3-o-tolyl-propan-1-one and hydroxylamine hydrochloride in the presence of sodium hydrogencarbonate. Light pink solid. MS (ESI+): m/z=443.5 ([M+H]+).

Example 420

((−), E)-3-{4-[5-(2-Methoxy-ethyl)[1,3,4]oxadiazol-2-yl]-phenyl}-1-(2-methyl-pyridin-4-yl)-3-o-tolyl-propan-1-one oxime

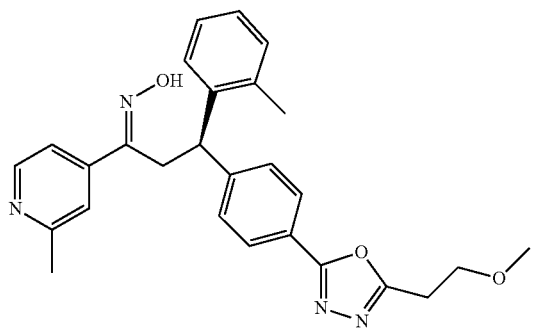 [SMILES: COCCc1nnc(-c2ccc([C@@H](C/C(=N\O)c3ccnc(C)c3)c3ccccc3C)cc2)o1]

Step 1: (−)-3-{4-[5-(2-Methoxy-ethyl)-[1,3,4]oxadiazol-2-yl]-phenyl}-1-(2-methyl-pyridin-4-yl)-3-o-tolyl-propan-1-one The title compound was produced in analogy to example 417, step 1 from 4-[(−)-3-(2-methyl-pyridin-4-yl)-3-oxo-1-o-tolyl-propyl]-benzoic acid (example 272, step 2) and 3-methoxy-propionic acid hydrazide (CAS RN 21920-89-8). Light yellow oil. MS (ESI+): m/z=442.4 ([M+H]+).

Step 2: ((−), E)-3-{4-[5-(2-Methoxy-ethyl)-[1,3,4]oxadiazol-2-yl]-phenyl}-1-(2-methyl-pyridin-4-yl)-3-o-tolyl-propan-1-one oxime The title compound was produced in analogy to example 417, step 2, from (−)-3-{4-[5-(2-methoxy-ethyl)-[1,3,4]oxadiazol-2-yl]-phenyl}-1-(2-methyl-pyridin-4-yl)-3-o-tolyl-propan-1-one and hydroxylamine hydrochloride in the presence of sodium hydrogencarbonate. White solid. MS (ESI+): m/z=457.4 ([M+H]+).

Example 421

((−), E)-1-(2-Methyl-pyridin-4-yl)-3-{4-[5-(tetrahydro-pyran-4-yl)-[1,3,4]oxadiazol-2-yl]-phenyl}-3-o-tolyl-propan-1-one oxime

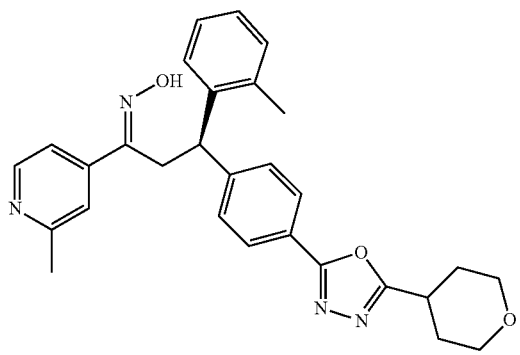 [SMILES: Cc1cc(/C(C[C@H](c2ccc(-c3nnc(C4CCOCC4)o3)cc2)c2ccccc2C)=N/O)ccn1]

Step 1: (−)-1-(2-Methyl-pyridin-4-yl)-3-{4-[5-(tetrahydro-pyran-4-yl)-[1,3,4]oxadiazol-2-yl]-phenyl}-3-o-tolyl-propan-1-one The title compound was produced in analogy to example 417, step 1 from 4-[(−)-3-(2-methyl-pyridin-4-yl)-3-oxo-1-o-tolyl-propyl]-benzoic acid (example 272, step 2) and tetrahydro-pyran-4-carboxylic acid hydrazide (CAS RN 59293-18-4). Light yellow oil. MS (ESI+): m/z=468.4 ([M+H]+).

Step 2: ((−), E)-1-(2-Methyl-pyridin-4-yl)-3-{4-[5-(tetrahydro-pyran-4-yl)-[1,3,4]oxadiazol-2-yl]-phenyl}-3-o-tolyl-propan-1-one oxime The title compound was produced in analogy to example 402, step 5, from (−)-1-(2-methyl-pyridin-4-yl)-3-{4-[5-(tetrahydro-pyran-4-yl)-[1,3,4]oxadiazol-2-yl]-phenyl}-3-o-tolyl-propan-1-one and hydroxylamine hydrochloride in the presence of sodium hydrogencarbonate. White solid. MS (ESI+): m/z=483.3 ([M+H]+).

Example 422

(5-{4-[(−)-3-[(E)-Hydroxyimino]-3-(2-methyl-pyridin-4-yl)-1-o-tolyl-propyl]-phenyl}-[1,3,4]oxadiazol-2-yl)-acetic acid

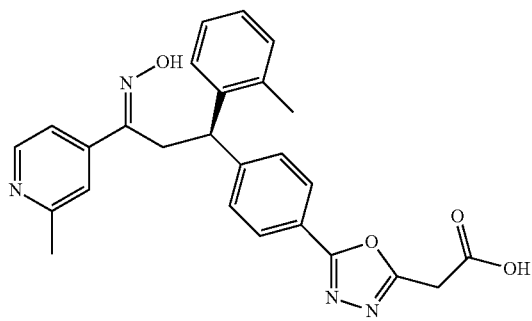 [SMILES: Cc1cc(/C(C[C@H](c2ccc(-c3nnc(CC(=O)O)o3)cc2)c2ccccc2C)=N/O)ccn1]

Step 1: (5-{4-[(−)-3-(2-Methyl-pyridin-4-yl)-3-oxo-1-o-tolyl-propyl]-phenyl}-[1,3,4]oxadiazol-2-yl)-acetic acid ethyl ester The title compound was produced in analogy to example 417, step 1 from 4-[(−)-3-(2-methyl-pyridin-4-yl)-3-oxo-1-o-tolyl-propyl]-benzoic acid (example 272, step 2) and hydrazinocarbonyl-acetic acid ethyl ester (CAS RN 30866-24-1). Light yellow oil. MS (ESI+): m/z=470.4 ([M+H]+).

Step 2: (5-{4-[(−)-3-(2-Methyl-pyridin-4-yl)-3-oxo-1-o-tolyl-propyl]-phenyl}-[1,3,4]oxadiazol-2-yl)-acetic acid To a solution of (5-{4-[(−)-3-(2-methyl-pyridin-4-yl)-3-oxo-1-o-tolyl-propyl]-phenyl}-[1,3,4]oxadiazol-2-yl)-acetic acid ethyl ester (146 mg) in a mixture of ethanol (5 mL) and water (1.25 mL) was added sodium hydrogencarbonate (104 mg) and the reaction mixture stirred at room temperature for 4 h. The solution was adjusted to approximately pH 3 by using 1 M aqueous hydrochloric acid and then extracted over a sat. solution of brine (50 mL) with ethyl acetate (3×50 mL). The combined organic phases were dried over sodium sulfate and the crude reaction product purified by silica gel chromatography using a MPLC system (CombiFlash Companion, Isco Inc.) eluting with a gradient of dichloromethane:methanol (100:0 to 90:10). Light yellow solid. MS (ESI+): m/z=442.4 ([M+H]+).

Step 3: (5-{4-[(−)-3-[(E)-Hydroxyimino]-3-(2-methyl-pyridin-4-yl)-1-o-tolyl-propyl]-phenyl}-[1,3,4]oxadiazol-2-yl)-acetic acid The title compound was produced in analogy to example 417, step 2, from (5-{4-[(−)-3-(2-methyl-pyridin-4-yl)-3-oxo-1-o-tolyl-propyl]-phenyl}-[1,3,4]oxadiazol-2-yl)-acetic acid and hydroxylamine hydrochloride in the presence of sodium hydrogencarbonate. White solid. MS (ESI+): m/z=457.2 ([M+H]+).

Example 423

(5-{4-[(−)-3-[(E)-Hydroxyimino]-3-(2-methyl-pyridin-4-yl)-1-o-tolyl-propyl]-phenyl}-[1,3,4]oxadiazol-2-yl)-acetic acid

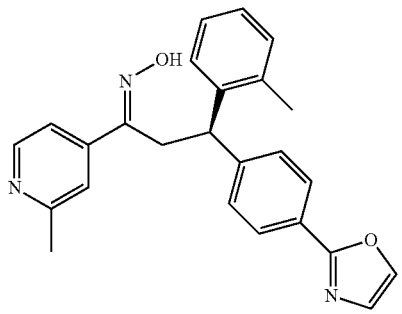 [SMILES: Cc1cc(/C(C[C@H](c2ccc(-c3ncco3)cc2)c2ccccc2C)=N/O)ccn1]

Step 1: (−)-1-(2-Methyl-pyridin-4-yl)-3-(4-oxazol-2-yl-phenyl)-3-o-tolyl-propan-1-one To a solution of (−)-3-(4-bromophenyl)-1-(2-methylpyridin-4-yl)-3-o-tolylpropan-1-one (120 mg; example 142, step 2), oxazole (126 mg) and tetrakis(triphenylphosphine) palladium(0) (68 mg) was added lithium tert-butoxide (141 mg) and the reaction mixture heated by microwave irradiation to 120° C. for 30 min. The reaction mixture was extracted over a sat. solution of sodium hydrogencarbonate (50 mL) with ethyl acetate (3×50 mL) and the combined organic phases dried over sodium sulfate. The crude reaction product was purified by silica gel chromatography using a MPLC system (CombiFlash Companion, Isco Inc.) eluting with a gradient of n-heptane/ethyl acetate (1:1 to 2:1) to give the title compound as a colorless oil. MS (ESI+): m/z=383.0 ([M+H]+).

Step 2: (5-{4-[(−)-3-[(E)-Hydroxyimino]-3-(2-methyl-pyridin-4-yl)-1-o-tolyl-propyl]-phenyl}-[1,3,4]oxadiazol-2-yl)-acetic acid The title compound was produced in analogy to example 402, step 5, from (−)-1-(2-methyl-pyridin-4-yl)-3-(4-oxazol-2-yl-phenyl)-3-o-tolyl-propan-1-one and hydroxylamine hydrochloride in the presence of sodium hydrogencarbonate. White solid. MS (ESI+): m/z=398.1 ([M+H]+)

Example 424

(−)-1-(2-Methyl-pyridin-4-yl)-3-[4-(1-methyl-1H-[1,2,3]triazol-4-yl)-phenyl]-3-o-tolyl-propan-1-one oxime

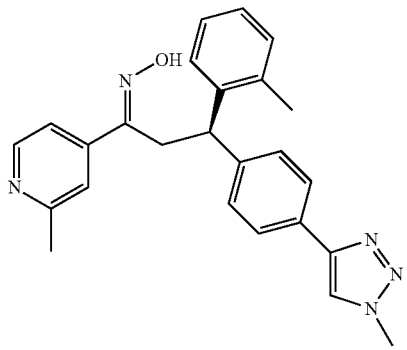 [SMILES: Cc1cc(/C(C[C@H](c2ccc(-c3cn(C)nn3)cc2)c2ccccc2C)=N/O)ccn1]

Step 1: (−)-1-(2-Methyl-pyridin-4-yl)-3-[4-(1-methyl-1H-[1,2,3]triazol-4-yl)-phenyl]-3-o-tolyl-propan-1-one Synthesis conducted in flow using a FlowSyn (Uniqsis) flow system equipped with a home-made copper coil reactor, a standard T-piece mixer and 250 psi back-pressure regulator: A stream of a solution containing (−)-3-(4-ethynyl-phenyl)-1-(2-methyl-pyridin-4-yl)-3-o-tolyl-propan-1-one (150 mg in 5 mL, c=0.088 mol/L; example 287, step 2) and iodomethane (125 mg in 5 mL, c=0.177 mol/L) in ethyl acetate was combined with a second stream of sodium azide (58 mg in 5 mL, c=0.177 mol/L) in water and directed through a copper coil (volume=21 mL) at 150° C. Both channels were running at a flow rate of 0.4 mL/min, which equals to a residence time of 26 min. The product stream was collected in a 25% solution of ammonium hydroxide and extracted with ethyl acetate (3×50 mL). The combined organic phases were dried over sodium sulfate and the crude reaction product purified by silica gel chromatography using a MPLC system (CombiFlash Companion, Isco Inc.) eluting with a gradient of n-heptane/ethyl acetate (1:1 to 2:1) to provide the title compound as a colorless solid. MS (ESI⁺): m/z=397.3 ([M+H]⁺).

Step 2: (−)-1-(2-Methyl-pyridin-4-yl)-3-[4-(1-methyl-1H-[1,2,3]triazol-4-yl)-phenyl]-3-o-tolyl-propan-1-one oxime The title compound was produced in analogy to example 402, step 5, from (−)-1-(2-methyl-pyridin-4-yl)-3-[4-(1-methyl-1H-[1,2,3]triazol-4-yl)-phenyl]-3-o-tolyl-propan-1-one and hydroxylamine hydrochloride in the presence of sodium hydrogencarbonate. The crude reaction product was purified by silica gel chromatography using a MPLC system (NH₂ silica gel column, CombiFlash Companion, Isco Inc.) eluting with a gradient of n-heptane/ethyl acetate (1:4 to 0:1) to provide the title compound as a colorless solid. White solid. MS (ESI⁺): m/z=412.4 ([M+H]⁺).

Example 425

(4-{4-[(−)-3-[(E)-Hydroxyimino]-3-(2-methyl-pyridin-4-yl)-1-o-tolyl-propyl]-phenyl}-[1,2,3]triazol-1-yl)-acetic acid

Step 1: (4-{4-[(−)-3-(2-Methyl-pyridin-4-yl)-3-oxo-1-o-tolyl-propyl]-phenyl}-[1,2,3]triazol-1-yl)-acetic acid ethyl ester The title compound was produced in analogy to example 424, step 1 from (−)-3-(4-ethynyl-phenyl)-1-(2-methyl-pyridin-4-yl)-3-o-tolyl-propan-1-one (example 287, step 2) and bromo-acetic acid ethyl ester (CAS RN 105-36-2) using a flow rate of 0.25 mL/min per channel, which equates to a residence time of 42 min. Light brown solid. MS (ESI⁺): m/z=469.4 ([M+H]⁺).

Step 2: (4-{4-[(−)-3-[(E)-Hydroxyimino]-3-(2-methyl-pyridin-4-yl)-1-o-tolyl-propyl]-phenyl}-[1,2,3]triazol-1-yl)-acetic acid ethyl ester The title compound was produced in analogy to example 402, step 5, from (4-{4-[(−)-3-(2-methyl-pyridin-4-yl)-3-oxo-1-o-tolyl-propyl]-phenyl}-[1,2,3]triazol-1-yl)-acetic acid ethyl ester and hydroxylamine hydrochloride in the presence of sodium hydrogencarbonate. Light yellow solid. MS (ESI⁺): m/z=484.4 ([M+H]⁺).

Step 3: (4-{4-[(−)-3-[(E)-Hydroxyimino]-3-(2-methyl-pyridin-4-yl)-1-o-tolyl-propyl]-phenyl}-[1,2,3]triazol-1-yl)-acetic acid To a solution of (4-{4-[(−)-3-[(E)-hydroxyimino]-3-(2-methyl-pyridin-4-yl)-1-o-tolyl-propyl]-phenyl}-[1,2,3]triazol-1-yl)-acetic acid ethyl ester (35 mg) in a mixture of dioxane (1 mL) and water (1 mL) was added lithium hydroxide (14 mg) and the reaction mixture heated by microwave irradiation to 120° C. for 20 min. The solution was adjusted to approximately pH 3 by using 1 M aqueous hydrochloric acid and then extracted over a sat. solution of brine (50 mL) with ethyl acetate (3×50 mL). The combined organic phases were dried over sodium sulfate and the crude reaction product purified by silica gel chromatography using a MPLC system (CombiFlash Companion, Isco Inc.) eluting with a gradient of dichloromethane/methanol (100:0 to 90:10). Light yellow solid. MS (ESI⁻): m/z=454.1 ([M−H]⁻).

Example 426

(−)-3-(4-Bromo-phenyl)-3-(2,4-difluoro-phenyl)-1-(2-methyl-pyridin-4-yl)-propan-1-one oxime

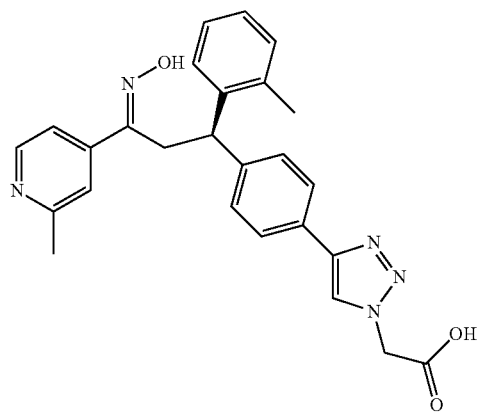 [SMILES: Cc1cc(/C(C[C@H](c2ccc(-c3cn(CC(=O)O)nn3)cc2)c2ccccc2C)=N/O)ccn1]

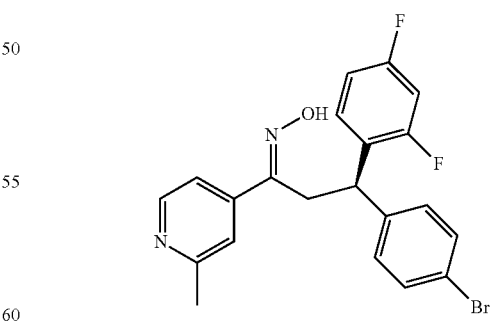

Step 1: 3-(4-Bromo-phenyl)-2-cyano-3-(2,4-difluoro-phenyl)-propionic acid ethyl ester To a solution of 2,4-difluoro-1-iodo-benzene (12.0 g) in anhydrous THF (200 mL) was added a solution of isopropylmagnesium chloride lithium chloride complex (52.9 mL, 14% solution in THF) slowly over 10 min at room temperature. After stirring for 1 h, a solution of 3-(4-bromo-phenyl)-2-cyano-acrylic acid ethyl ester (10.0 g; example 74, step 1) in anhydrous THF (100 mL) was added and stirring continued at room temperature. After 1 h, a saturated aq. solution of ammonium chloride was added (100 mL), the phases separated and the aqueous layer extracted with ethyl acetate (3×100 mL). The combined organic phases were dried over sodium sulfate and the crude reaction product purified by silica gel chromatography using a MPLC system (Combi-Flash Companion, Isco Inc.) eluting with a gradient of n-heptane/ethyl acetate (1:0 to 3:1) to provide the title compound as a light yellow oil. MS (ESI−): m/z=391.9 ([M−H]−).

Step 2: 3-(4-Bromo-phenyl)-3-(2,4-difluoro-phenyl)-propionic acid

To a solution of 3-(4-bromo-phenyl)-2-cyano-3-(2,4-difluoro-phenyl)-propionic acid ethyl ester (2.4 g) in acetic acid (11 mL) was added water (6 mL) and concentrated $H_2SO_4$ (6.83 mL) at 0° C. The reaction mixture was heated to 120° C. overnight, then cooled and poured on ice and extracted with ethyl acetate (3×100 mL). The organic layers were washed with brine, dried over magnesium sulfate, filtered and concentrated in vacuo. The crude reaction product was purified by silica gel chromatography using a MPLC system (CombiFlash Companion, Isco Inc.) eluting with a gradient of n-heptane/ethyl acetate (1:0 to 1:1) to provide the title compound as an off-white solid. MS (ESI−): m/z=339.0 ([M−H]−).

Step 3: 3-(4-Bromo-phenyl)-3-(2,4-difluoro-phenyl)-N-methoxy-N-methyl-propionamide, (−)-3-(4-Bromo-phenyl)-3-(2,4-difluoro-phenyl)-N-methoxy-N-methyl-propionamide and (+)-3-(4-Bromo-phenyl)-3-(2,4-difluoro-phenyl)-N-methoxy-N-methyl-propionamide The title compounds were produced in analogy to example 74, step 4, from 3-(4-bromo-phenyl)-3-(2,4-difluoro-phenyl)-propionic acid and N,O-dimethylhydroxylamine hydrochloride. The crude reaction product was purified by silica gel chromatography using a MPLC system (CombiFlash Companion, Isco Inc.) eluting with a gradient of n-heptane/ethyl acetate (1:0 to 1:1) to provide 3-(4-bromo-phenyl)-3-(2,4-difluoro-phenyl)-N-methoxy-N-methyl-propionamide as a light yellow oil. MS (ESI+): m/z=386.3 ([M+H]+). Separation of 3-(4-bromo-phenyl)-3-(2,4-difluoro-phenyl)-N-methoxy-N-methyl-propionamide by chiral HPLC (Chiralpak-AD, 8% isopropanol in n-heptane) yielded (−)-3-(4-bromo-phenyl)-3-(2,4-difluoro-phenyl)-N-methoxy-N-methyl-propionamide as a light yellow oil, MS (ESI+): m/z=386.1 ([M+H]+) and (+)-3-(4-bromo-phenyl)-3-(2,4-difluoro-phenyl)-N-methoxy-N-methyl-propionamide as a light yellow oil, MS (ESI+): m/z=386.1 ([M+H]+).

Step 4: (−)-3-(4-Bromo-phenyl)-3-(2,4-difluoro-phenyl)-1-(2-methyl-pyridin-4-yl)-propan-1-one The title compound was produced in analogy to example 74, step 5, from (−)-3-(4-bromo-phenyl)-3-(2,4-difluoro-phenyl)-N-methoxy-N-methyl-propionamide and 4-bromo-2-methylpyridine. Light yellow oil. MS (ESI+): m/z=416.3 ([M+H]+).

Step 5: (−)-3-(4-Bromo-phenyl)-3-(2,4-difluoro-phenyl)-1-(2-methyl-pyridin-4-yl)-propan-1-one oxime The title compound was produced in analogy to example 402, step 5, from (−)-3-(4-bromo-phenyl)-3-(2,4-difluoro-phenyl)-1-(2-methyl-pyridin-4-yl)-propan-1-one and hydroxylamine hydrochloride in the presence of sodium hydrogencarbonate. White solid. MS (ESI+): m/z=431.3 ([M+H]+).

Example 427

1-{4-[(−)-1-(2,4-Difluoro-phenyl)-3-[(E)-hydroxyimino]-3-(2-methyl-pyridin-4-yl)-propyl]-phenyl}-piperidine-4-carboxylic acid

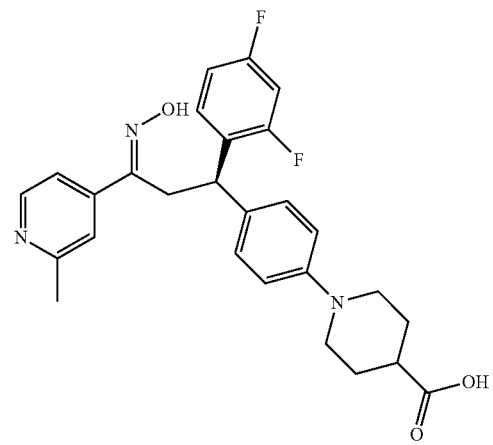 [SMILES: Cc1cc(/C(C[C@H](c2ccc(N3CCC(C(=O)O)CC3)cc2)c2ccc(F)cc2F)=N/O)ccn1]

Step 1: 1-{4-[(−)-1-(2,4-Difluoro-phenyl)-3-(2-methyl-pyridin-4-yl)-3-oxo-propyl]-phenyl}-piperidine-4-carboxylic acid ethyl ester The title compound was produced in analogy to example 39, from (−)-3-(4-bromo-phenyl)-3-(2,4-difluoro-phenyl)-1-(2-methyl-pyridin-4-yl)-propan-1-one (example 426, step 4) and piperidine-4-carboxylic acid ethyl ester (CAS RN 1126-09-6) in the presence of tris(dibenzylideneacetone)dipalladium(0) chloroform adduct, 2-dicyclohexylphosphino-2',4',6'-triisopropylbiphenyl (X-PHOS) and sodium tert-butoxide. The crude reaction product was purified by silica gel chromatography using a MPLC system (CombiFlash Companion, Isco Inc.) eluting with a gradient of n-heptane/ethyl acetate (2:1 to 1:1) to provide the title compound as a light yellow oil. MS (ESI+): m/z=493.5 ([M+H]+).

Step 2: 1-{4-[(−)-1-(2,4-Difluoro-phenyl)-3-[(E)-hydroxyimino]-3-(2-methyl-pyridin-4-yl)-propyl]-phenyl}-piperidine-4-carboxylic acid ethyl ester The title compound was produced in analogy to example 402, step 5, from 1-{4-[(−)-1-(2,4-difluoro-phenyl)-3-(2-methyl-pyridin-4-yl)-3-oxo-propyl]-phenyl}-piperidine-4-carboxylic acid ethyl ester and hydroxylamine hydrochloride in the presence of sodium hydrogencarbonate. The crude reaction product was purified by silica gel chromatography using a MPLC system ($NH_2$ silica gel column, CombiFlash Companion, Isco Inc.) eluting with a gradient of n-heptane/ethyl acetate (1:4 to 0:1) to provide the title compound as a light yellow solid. MS (ESI⁺): m/z=508.5 ([M+H]⁺).

Step 3: 1-{4-[(−)-1-(2,4-Difluoro-phenyl)-3-[(E)-hydroxyimino]-3-(2-methyl-pyridin-4-yl)-propyl]-phenyl}-piperidine-4-carboxylic acid The title compound was produced in analogy to example 425, step 3, from 1-{4-[(−)-1-(2,4-difluoro-phenyl)-3-[(E)-hydroxyimino]-3-(2-methyl-pyridin-4-yl)-propyl]-phenyl}-piperidine-4-carboxylic acid ethyl ester. The crude reaction product was purified by silica gel chromatography using a MPLC system (CombiFlash Companion, Isco Inc.) eluting with a gradient of n-heptane/ethyl acetate (1:4 to 0:1) to provide the title compound as a light yellow solid. MS (ESI⁻): m/z=478.3 ([M−H]⁻).

Example 428

1-{4-[(+)-1-(2,4-Difluoro-phenyl)-3-[(E)-hydroxyimino]-3-(2-methyl-pyridin-4-yl)-propyl]-phenyl}-piperidine-4-carboxylic acid

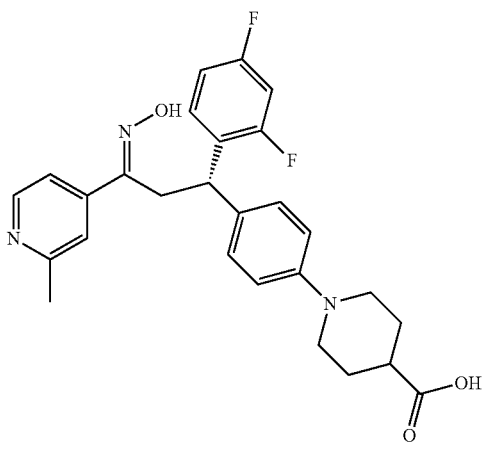 [SMILES: Cc1cc(/C(C[C@@H](c2ccc(N3CCC(C(=O)O)CC3)cc2)c2ccc(F)cc2F)=N/O)ccn1]

Step 1: (+)-3-(4-Bromo-phenyl)-3-(2,4-difluoro-phenyl)-1-(2-methyl-pyridin-4-yl)-propan-1-one The title compound was produced in analogy to example 74, step 5, from (+)-3-(4-bromo-phenyl)-3-(2,4-difluoro-phenyl)-propionic acid (example 426, step 3) and 4-bromo-2-methylpyridine. Light yellow oil. MS (ESI⁺): m/z=416.3 ([M+H]⁺).

Step 2: 1-{4-[(+)-1-(2,4-Difluoro-phenyl)-3-(2-methyl-pyridin-4-yl)-3-oxo-propyl]-phenyl}-piperidine-4-carboxylic acid ethyl ester The title compound was produced in analogy to example 427, step 1, from (+)-3-(4-bromo-phenyl)-3-(2,4-difluoro-phenyl)-1-(2-methyl-pyridin-4-yl)-propan-1-one and piperidine-4-carboxylic acid ethyl ester (CAS RN 1126-09-6). Light yellow solid. MS (ESI⁻): m/z=491.0 ([M−H]⁻).

Step 3: 1-{4-[(+)-1-(2,4-Difluoro-phenyl)-3-[(E)-hydroxyimino]-3-(2-methyl-pyridin-4-yl)-propyl]-phenyl}-piperidine-4-carboxylic acid ethyl ester The title compound was produced in analogy to example 402, step 5, from 1-{4-[(+)-1-(2,4-difluoro-phenyl)-3-(2-methyl-pyridin-4-yl)-3-oxo-propyl]-phenyl}-piperidine-4-carboxylic acid ethyl ester and hydroxylamine hydrochloride in the presence of sodium hydrogencarbonate. The crude reaction product was purified by silica gel chromatography using a MPLC system (NH₂ silica gel column, CombiFlash Companion, Isco Inc.) eluting with a gradient of n-heptane/ethyl acetate (1:4 to 0:1) to provide the title compound as a light yellow solid. MS (ESI⁺): m/z=508.3 ([M+H]⁺).

Step 4: 1-{4-[(+)-1-(2,4-Difluoro-phenyl)-3-[(E)-hydroxyimino]-3-(2-methyl-pyridin-4-yl)-propyl]-phenyl}-piperidine-4-carboxylic acid The title compound was produced in analogy to example 425, step 3, from 1-{4-[(+)-1-(2,4-difluoro-phenyl)-3-[(E)-hydroxyimino]-3-(2-methyl-pyridin-4-yl)-propyl]-phenyl}-piperidine-4-carboxylic acid ethyl ester. The crude reaction product was purified by silica gel chromatography using a MPLC system (CombiFlash Companion, Isco Inc.) eluting with a gradient of dichloromethane/methanol (100:1 to 50:3) to provide the title compound as a light yellow solid. MS (ESI⁺): m/z=480.1 ([M+H]⁺).

Example 429

(1S,5R)-3-{4-[(−)-1-(2,4-Difluoro-phenyl)-3-[(E)-hydroxyimino]-3-(2-methyl-pyridin-4-yl)-propyl]-phenyl}-3-aza-bicyclo[3.1.0]hexane-6-carboxylic acid

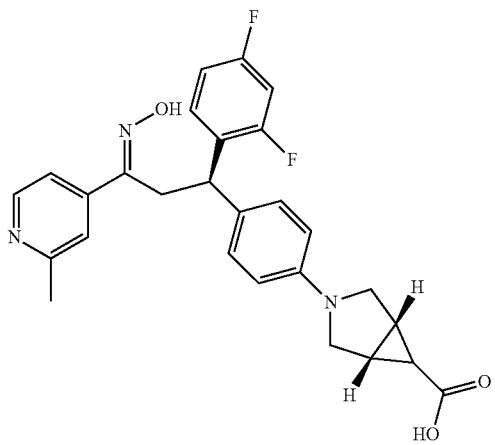 [SMILES: Cc1cc(/C(C[C@H](c2ccc(N3C[C@@H]4C(C(=O)O)[C@@H]4C3)cc2)c2ccc(F)cc2F)=N/O)ccn1]

Step 1: (1S,5R)-3-{4-[(−)-1-(2,4-Difluoro-phenyl)-3-(2-methyl-pyridin-4-yl)-3-oxo-propyl]-phenyl}-3-aza-bicyclo[3.1.0]hexane-6-carboxylic acid ethyl ester The title compound was produced in analogy to example 427, step 1, from (−)-3-(4-bromo-phenyl)-3-(2,4-difluoro-phenyl)-1-(2-methyl-pyridin-4-yl)-propan-1-one (example 426, step 4) and (1S,5R)-3-aza-bicyclo[3.1.0]hexane-6-carboxylic acid ethyl ester (CAS RN 174456-77-0) and directly used in the consecutive reaction step. Light yellow solid.

Step 2: (1S,5R)-3-{4-[(−)-1-(2,4-Difluoro-phenyl)-3-[(E)-hydroxyimino]-3-(2-methyl-pyridin-4-yl)-propyl]-phenyl}-3-aza-bicyclo[3.1.0]hexane-6-carboxylic acid ethyl ester The title compound was produced in analogy to example 402, step 5, from (1S,5R)-3-{4-[(−)-1-(2,4-difluoro-phenyl)-

3-(2-methyl-pyridin-4-yl)-3-oxo-propyl]-phenyl}-3-aza-bicyclo[3.1.0]hexane-6-carboxylic acid ethyl ester and hydroxylamine hydrochloride in the presence of sodium hydrogencarbonate. The crude reaction product was purified by silica gel chromatography using a MPLC system (NH$_2$ silica gel column, CombiFlash Companion, Isco Inc.) eluting with a gradient of n-heptane/ethyl acetate (1:4 to 0:1) to provide the title compound as a light yellow solid. MS (ESI$^+$): m/z=506.5 ([M+H]$^+$).

Step 3: (1S,5R)-3-{4-[(−)-1-(2,4-Difluoro-phenyl)-3-[(E)-hydroxyimino]-3-(2-methyl-pyridin-4-yl)-propyl]-phenyl}-3-aza-bicyclo[3.1.0]hexane-6-carboxylic acid The title compound was produced in analogy to example 425, step 3, from (1S,5R)-3-{4-[(−)-1-(2,4-difluoro-phenyl)-3-[(E)-hydroxyimino]-3-(2-methyl-pyridin-4-yl)-propyl]-phenyl}-3-aza-bicyclo[3.1.0]hexane-6-carboxylic acid ethyl ester. The crude reaction product was purified by silica gel chromatography using a MPLC system (CombiFlash Companion, Isco Inc.) eluting with a gradient of dichloromethane/methanol (100:1 to 50:3) to provide the title compound as a light yellow solid. MS (ESI$^-$): m/z=478.2 ([M−H]$^-$).

Example 430

(1-{4-[(+)-1-(2,4-Difluoro-phenyl)-3-[(E)-hydroxyimino]-3-(2-methyl-pyridin-4-yl)-propyl]-phenyl}-piperidin-4-yl)-acetic acid

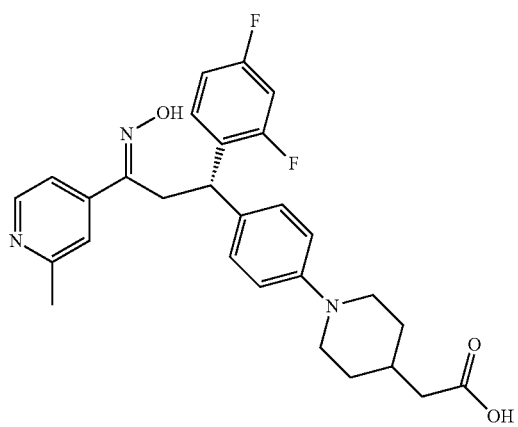 [SMILES: Cc1cc(/C(C[C@@H](c2ccc(N3CCC(CC(=O)O)CC3)cc2)c2ccc(F)cc2F)=N/O)ccn1]

The title compound was produced in analogy to 1-{4-[(+)-1-(2,4-difluoro-phenyl)-3-[(E)-hydroxyimino]-3-(2-methyl-pyridin-4-yl)-propyl]-phenyl}-piperidine-4-carboxylic acid (example 428) replacing in step 2 piperidine-4-carboxylic acid ethyl ester with piperidin-4-yl-acetic acid ethyl ester (CAS RN 59184-90-6). Light yellow solid. MS (ESI$^+$): m/z=494.3 ([M+H]$^+$).

Example 431

4-[1-(2,4-Difluoro-phenyl)-3-[(E)-hydroxyimino]-3-(2-methyl-pyridin-4-yl)-propyl]-benzoic acid

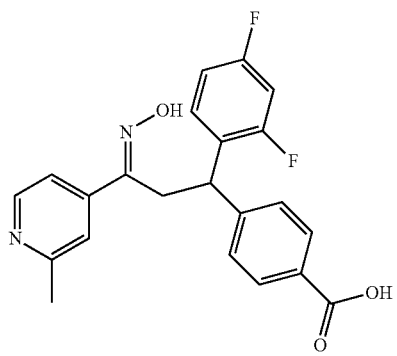 [SMILES: Cc1cc(/C(CC(c2ccc(C(=O)O)cc2)c2ccc(F)cc2F)=N/O)ccn1]

Step 1: 3-(4-Bromo-phenyl)-3-(2,4-difluoro-phenyl)-1-(2-methyl-pyridin-4-yl)-propan-1-one The title compound was produced in analogy to example 74, step 5, from 3-(4-bromo-phenyl)-3-(2,4-difluoro-phenyl)-N-methoxy-N-methyl-propionamide (example 426, step 3) and 4-bromo-2-methylpyridine. Light yellow oil. MS (ESI$^+$): m/z=416.2 ([M+H]$^+$).

Step 2: 4-[1-(2,4-Difluoro-phenyl)-3-(2-methyl-pyridin-4-yl)-3-oxo-propyl]-benzoic acid methyl ester The title compound was produced in analogy to example 272, step 1, from 3-(4-bromo-phenyl)-3-(2,4-difluoro-phenyl)-1-(2-methyl-pyridin-4-yl)-propan-1-one. Light yellow oil. MS (ESI$^+$): m/z=396.0 ([M+H]$^+$).

Step 3: 4-[1-(2,4-Difluoro-phenyl)-3-[(E)-hydroxyimino]-3-(2-methyl-pyridin-4-yl)-propyl]-benzoic acid methyl ester The title compound was produced in analogy to example 402, step 5, from 4-[1-(2,4-difluoro-phenyl)-3-(2-methyl-pyridin-4-yl)-3-oxo-propyl]-benzoic acid methyl ester and hydroxylamine hydrochloride in the presence of sodium hydrogencarbonate. Light yellow solid. MS (ESI$^+$): m/z=411.5 ([M+H]$^+$).

Step 4: 4-[1-(2,4-Difluoro-phenyl)-3-[(E)-hydroxyimino]-3-(2-methyl-pyridin-4-yl)-propyl]-benzoic acid The title compound was produced in analogy to example 425, step 3, from 4-[1-(2,4-difluoro-phenyl)-3-[(E)-hydroxyimino]-3-(2-methyl-pyridin-4-yl)-propyl]-benzoic acid methyl ester. The crude reaction product was purified by silica gel chromatography using a MPLC system (CombiFlash Companion, Isco Inc.) eluting with a gradient of dichloromethane/methanol (98:2 to 85:15) to provide the title compound as a light yellow solid. MS (ESI+): m/z=397.1 ([M+H]+).

Example 432

N-Cyclopropyl-4-[1-(2,4-difluoro-phenyl)-3-[(E)-hydroxyimino]-3-(2-methyl-pyridin-4-yl)-propyl]-benzamide

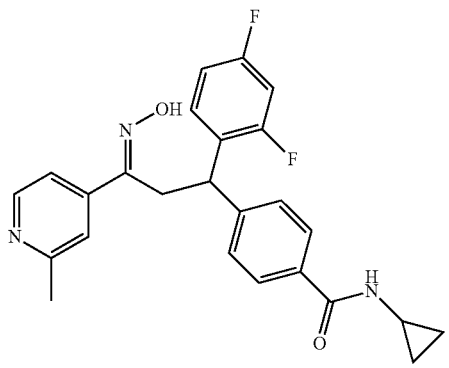 [SMILES: Cc1cc(/C(CC(c2ccc(C(=O)NC3CC3)cc2)c2ccc(F)cc2F)=N/O)ccn1]

Step 1: 4-[1-(2,4-Difluoro-phenyl)-3-(2-methyl-pyridin-4-yl)-3-oxo-propyl]-benzoic acid The title compound was produced in analogy to example 431, step 2, from 4-[1-(2,4-difluoro-phenyl)-3-(2-methyl-pyridin-4-yl)-3-oxo-propyl]-benzoic acid methyl ester (example 431, step 2). The crude reaction product was purified by silica gel chromatography using a MPLC system (CombiFlash Companion, Isco Inc.) eluting with a gradient of dichloro-methane/methanol (98:2 to 85:15) to provide the title compound as a light yellow oil. MS (ESI+): m/z=382.1 ([M+H]+).

Step 2: N-Cyclopropyl-4-[1-(2,4-difluoro-phenyl)-3-(2-methyl-pyridin-4-yl)-3-oxo-propyl]-benzamide To a solution of 4-[1-(2,4-difluoro-phenyl)-3-(2-methyl-pyridin-4-yl)-3-oxo-propyl]-benzoic acid (40 mg) in dichloromethane (1.5 mL) was added O-(7-azabenzotriazol-1-yl)-N,N,N',N'-tetramethyluronium hexafluorophosphate (48 mg) and triethylamine (29 µL) and the reaction mixture stirred at 40° C. After 15 min, cyclopropylamine (157 µL; CAS RN 765-30-0) was added and stirring continued for 2 h at 40° C. A saturated aq. solution of sodium hydrogencarbonate (50 mL) was added, the phases separated and the aqueous layer extracted with ethyl acetate (3×100 mL). The combined organic phases were dried over sodium sulfate and the crude reaction product purified by silica gel chromatography using a MPLC system (CombiFlash Companion, Isco Inc.) eluting with a gradient of n-heptane/ethyl acetate (100:0 to 50:50) to give the title compound as a light yellow solid. MS (ESI+): m/z=421.1 ([M+H]+).

Step 3: N-Cyclopropyl-4-[1-(2,4-difluoro-phenyl)-3-[(E)-hydroxyimino]-3-(2-methyl-pyridin-4-yl)-propyl]-benzamide The title compound was produced in analogy to example 402, step 5, from N-cyclopropyl-4-[1-(2,4-difluoro-phenyl)-3-(2-methyl-pyridin-4-yl)-3-oxo-propyl]-benzamide and hydroxylamine hydrochloride in the presence of sodium hydrogencarbonate. The compound was purified by silica gel chromatography using a MPLC system (CombiFlash Companion, Isco Inc.) eluting with a gradient of dichloromethane/methanol (100:0 to 90:10). Off-white solid. MS (ESI+): m/z=436.3 ([M+H]+).

Example 433

4-[1-(2,4-Difluoro-phenyl)-3-[(E)-hydroxyimino]-3-(2-methyl-pyridin-4-yl)-propyl]-N-(2-hydroxy-ethyl)-benzamide

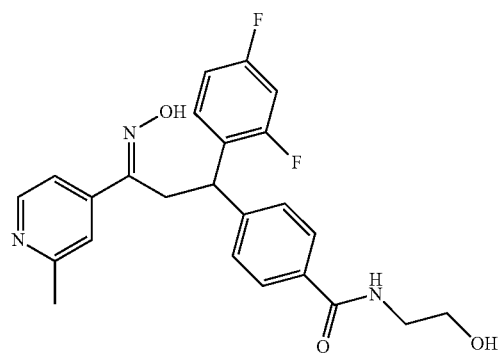 [SMILES: Cc1cc(/C(CC(c2ccc(C(=O)NCCO)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with 2-amino-ethanol (CAS RN 141-43-5). Off-white solid. MS (ESI+): m/z=440.1 ([M+H]+).

Example 434

4-[1-(2,4-Difluoro-phenyl)-3-[(E)-hydroxyimino]-3-(2-methyl-pyridin-4-yl)-propyl]-N—((R)-2-hydroxy-propyl)-benzamide

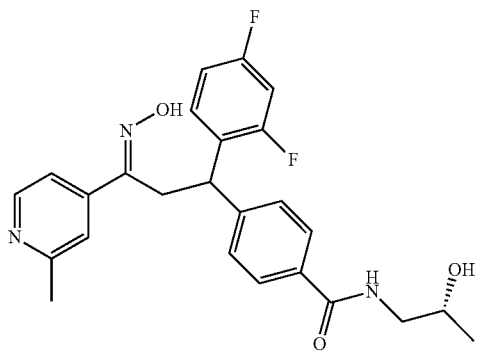 [SMILES: Cc1cc(/C(CC(c2ccc(C(=O)NC[C@@H](C)O)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432)

replacing in step 2 cyclopropylamine with (R)-1-amino-propan-2-ol (CAS RN 2799-16-8). Off-white solid. MS (ESI⁺): m/z=454.3 ([M+H]⁺).

Example 435

4-[1-(2,4-Difluoro-phenyl)-3-[(E)-hydroxyimino]-3-(2-methyl-pyridin-4-yl)-propyl]-N-(2-hydroxy-1,1-dimethyl-ethyl)-benzamide

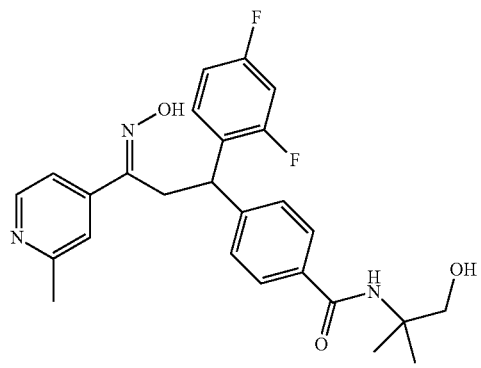 [SMILES: Cc1cc(/C(CC(c2ccc(C(=O)NC(C)(C)CO)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with 2-amino-2-methyl-propan-1-ol (CAS RN 124-68-5). Off-white solid. MS (ESI⁺): m/z=468.4 ([M+H]⁺).

Example 436

N-Cyclohexyl-4-[1-(2,4-difluoro-phenyl)-3-[(E)-hydroxyimino]-3-(2-methyl-pyridin-4-yl)-propyl]-benzamide

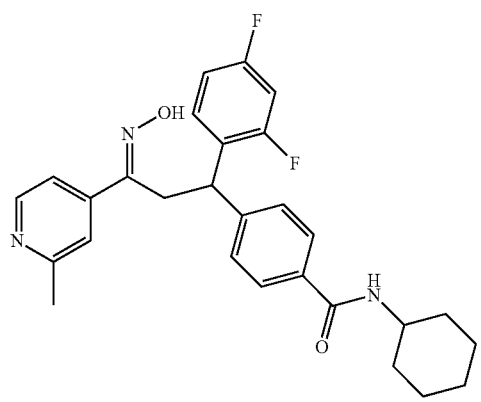 [SMILES: Cc1cc(/C(CC(c2ccc(C(=O)NC3CCCCC3)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with cyclohexylamine (CAS RN 108-91-8). White solid. MS (ESI⁺): m/z=478.1 ([M+H]⁺).

Example 437

3-(2,4-Difluoro-phenyl)-3-[4-(4,4-difluoro-piperidine-1-carbonyl)-phenyl]-1-(2-methyl-pyridin-4-yl)-propan-1-one oxime

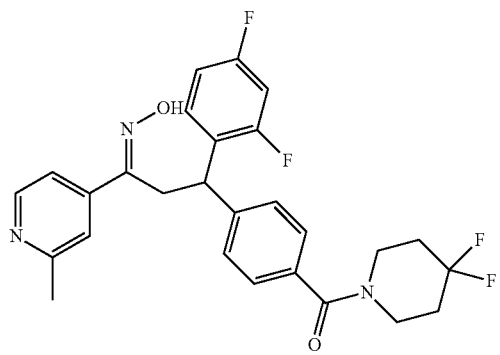 [SMILES: Cc1cc(/C(CC(c2ccc(C(=O)N3CCC(F)(F)CC3)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with 4,4-difluoro-piperidine hydrochloride (CAS RN 144230-52-4). White solid. MS (ESI⁺): m/z=500.3 ([M+H]⁺).

Example 438

3-(2,4-Difluoro-phenyl)-1-(2-methyl-pyridin-4-yl)-3-[4-(morpholine-4-carbonyl)-phenyl]-propan-1-one oxime

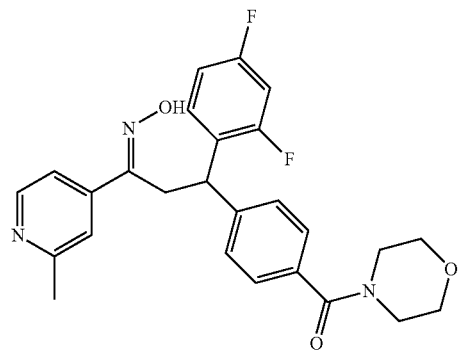 [SMILES: Cc1cc(/C(CC(c2ccc(C(=O)N3CCOCC3)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432)

replacing in step 2 cyclopropylamine with morpholine (CAS RN 110-91-8). Off-white solid. MS (ESI+): m/z=466.1 ([M+H]+).

Example 439

3-(2,4-Difluoro-phenyl)-3-[4-(4-methanesulfonyl-piperazine-1-carbonyl)-phenyl]-1-(2-methyl-pyridin-4-yl)-propan-1-one oxime

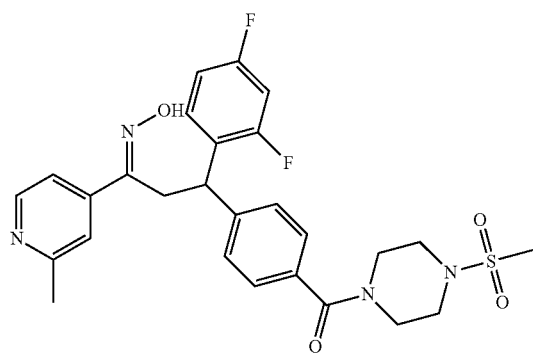 [SMILES: Cc1cc(/C(CC(c2ccc(C(=O)N3CCN(S(C)(=O)=O)CC3)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with 1-methanesulfonyl-piperazine (CAS RN 55276-43-2). Off-white solid. MS (ESI+): m/z=543.3 ([M+H]+).

Example 440

4-[1-(2,4-Difluoro-phenyl)-3-[(E)-hydroxyimino]-3-(2-methyl-pyridin-4-yl)-propyl]-N-(1,1-dioxo-hexahydro-1λ⁶-thiopyran-4-yl)-benzamide

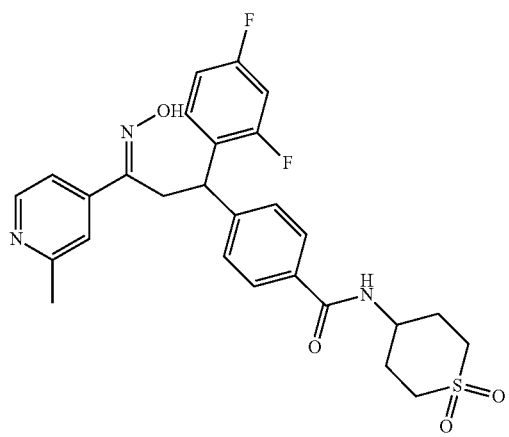 [SMILES: Cc1cc(/C(CC(c2ccc(C(=O)NC3CCS(=O)(=O)CC3)cc2)c2ccc(F)cc2F)=N/O)ccn1]

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with 1,1-dioxo-hexahydro-1λ⁶-thiopyran-4-ylamine (CAS RN 210240-20-3). White solid. MS (ESI+): m/z=528.3 ([M+H]+).

Example 441

4-[1-(2,4-Difluoro-phenyl)-3-[(E)-hydroxyimino]-3-(2-methyl-pyridin-4-yl)-propyl]-N-[2-(1,1-dioxo-1λ⁶-thiomorpholin-4-yl)-ethyl]-benzamide

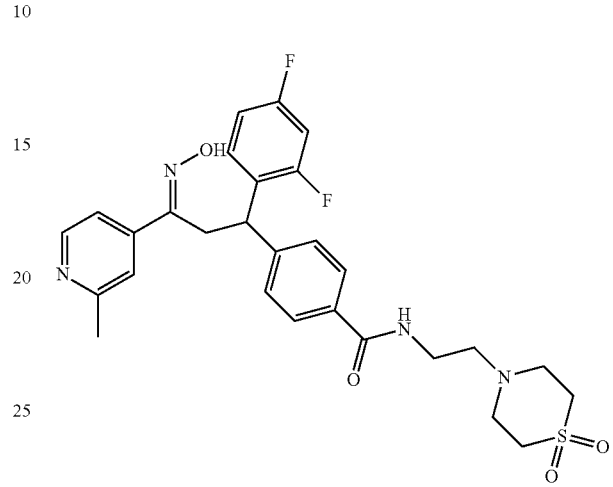

The title compound was produced in analogy to N-cyclopropyl-4-[1-(2,4-difluoro-phenyl)-3-[(E)-hydroxyimino]-3-(2-methyl-pyridin-4-yl)-propyl]-benzamide (example 432) replacing in step 2 cyclopropylamine with 2-(1,1-dioxo-1λ⁶-thiomorpholin-4-yl)-ethylamine (CAS RN 89937-52-0). White solid. MS (ESI+): m/z=528.3 ([M+H]+).

Example 442

3-(2,4-Difluoro-phenyl)-1-(2-methyl-pyridin-4-yl)-3-(4-trifluoromethyl-phenyl)-propan-1-one oxime

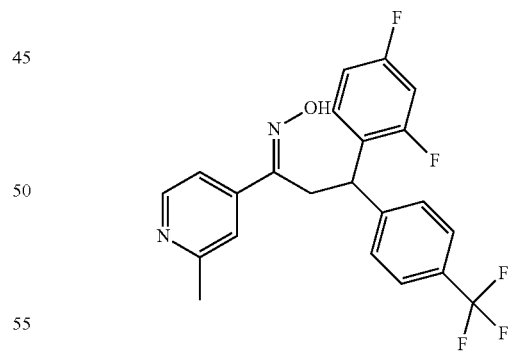

Step 1: (E)-3-(2,4-Difluoro-phenyl)-1-(2-methyl-pyridin-4-yl)-propenone

To a solution of 1-(2-methyl-pyridin-4-yl)-ethanone (2.0 g; CAS RN 2732-28-7) and 2,4-difluoro-benzaldehyde (2.31 g; CAS RN 1550-35-2) in ethanol (16 mL) was added piperidine (0.88 mL). The reaction mixture was heated to reflux overnight. Evaporation of the solvent mixture and purification of the crude reaction product by silica gel chromatography using a MPLC system (CombiFlash Companion, Isco Inc.) eluting with a gradient of n-heptane/ethyl acetate (1:1 to 1:4) to give the title compound as a light yellow solid. MS (ESI⁺): m/z=260.1 ([M+H]⁺).

Step 2: 3-(2,4-Difluoro-phenyl)-1-(2-methyl-pyridin-4-yl)-3-(4-trifluoromethyl-phenyl)-propan-1-one The title compound was produced in analogy to example 402, step 2, from (E)-3-(2,4-difluoro-phenyl)-1-(2-methyl-pyridin-4-yl)-propenone and 4-(trifluoromethyl)phenylboronic acid (CAS RN 128796-39-4). Light yellow oil. MS (ESI⁺): m/z=406.4 ([M+H]⁺).

Step 3: 3-(2,4-Difluoro-phenyl)-1-(2-methyl-pyridin-4-yl)-3-(4-trifluoromethyl-phenyl)-propan-1-one oxime The title compound was produced in analogy to example 402, step 5, from 3-(2,4-difluoro-phenyl)-1-(2-methyl-pyridin-4-yl)-3-(4-trifluoromethyl-phenyl)-propan-1-one and hydroxylamine hydrochloride in the presence of sodium hydrogencarbonate. The compound was purified by silica gel chromatography using a MPLC system (CombiFlash Companion, Isco Inc.) eluting with a gradient of n-heptane/ethyl acetate (1:1 to 1:4) to give the title compound as a white solid. MS (ESI⁺): m/z=421.1 ([M+H]⁺).

Example 443

3-(2,4-Difluoro-phenyl)-1-(2-methyl-pyridin-4-yl)-3-(6-morpholin-4-yl-pyridin-3-yl)-propan-1-one oxime

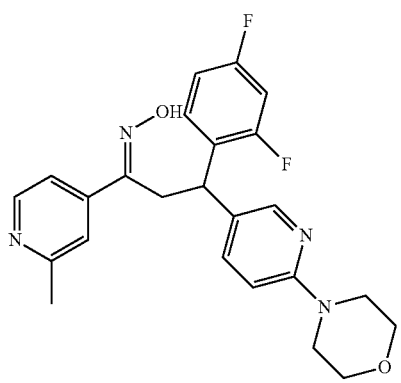 [SMILES: Cc1cc(/C(CC(c2ccc(N3CCOCC3)nc2)c2ccc(F)cc2F)=N/O)ccn1]

The title compound was produced in analogy to 3-(2,4-difluoro-phenyl)-1-(2-methyl-pyridin-4-yl)-3-(4-trifluoromethyl-phenyl)-propan-1-one oxime (example 442) replacing in step 2 4-(trifluoromethyl)phenylboronic acid with 4-[5-(4,4,5,5-tetramethyl-[1,3,2]dioxaborolan-2-yl)-pyridin-2-yl]-morpholine (CAS RN 485799-04-0). Light yellow solid. MS (ESI⁺): m/z=439.1 ([M+H]⁺).

Example 444

3-[6-(4-Acetyl-piperazin-1-yl)-pyridin-3-yl]-3-(2,4-difluoro-phenyl)-1-(2-methyl-pyridin-4-yl)-propan-1-one oxime

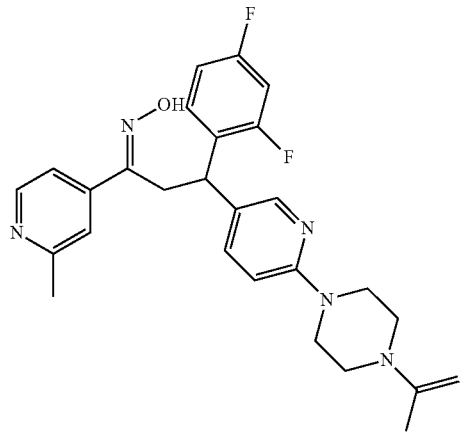 [SMILES: C=C(C)N1CCN(c2ccc(C(C/C(=N\O)c3ccnc(C)c3)c3ccc(F)cc3F)cn2)CC1]

The title compound was produced in analogy to 3-(2,4-difluoro-phenyl)-1-(2-methyl-pyridin-4-yl)-3-(4-trifluoromethyl-phenyl)-propan-1-one oxime (example 442) replacing in step 2 4-(trifluoromethyl)phenylboronic acid with 1-{4-[5-(4,4,5,5-tetramethyl-[1,3,2]dioxaborolan-2-yl)-pyridin-2-yl]-piperazin-1-yl}-ethanone (CAS RN 1073372-01-6). White solid. MS (ESI⁺): m/z=480.3 ([M+H]⁺).

Example 445

3-(4-Bromo-phenyl)-3-(3,5-difluoro-phenyl)-1-(2-methyl-pyridin-4-yl)-propan-1-one oxime

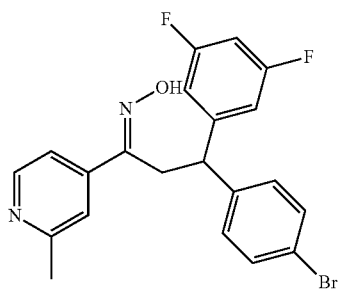 [SMILES: Cc1cc(/C(CC(c2ccc(Br)cc2)c2cc(F)cc(F)c2)=N/O)ccn1]

The title compound was produced in analogy to (−)-3-(4-bromo-phenyl)-3-(2,4-difluoro-phenyl)-1-(2-methyl-pyridin-4-yl)-propan-1-one oxime (example 426) replacing in step 1 2,4-difluoro-1-iodo-benzene with 1,3-difluoro-5-iodo-benzene (CAS RN 2265-91-0). Light yellow solid. MS (ESI⁺): m/z=431.1 ([M+H]⁺).

Example 446

4'-[1-(4-Chloro-2-fluoro-phenyl)-3-[(E)-hydroxy-imino]-3-(2-methyl-pyridin-4-yl)-propyl]-3-fluoro-biphenyl-4-carboxylic acid methyl ester

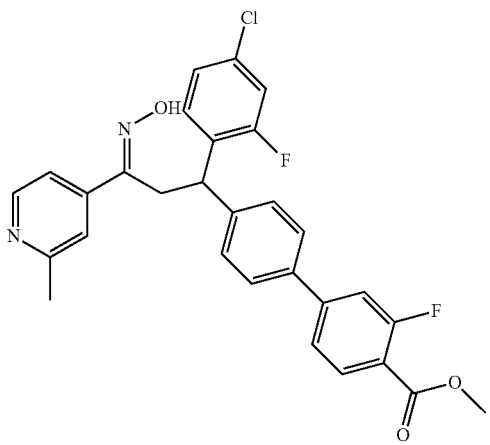 [SMILES: COC(=O)c1ccc(-c2ccc(C(C/C(=N\O)c3ccnc(C)c3)c3ccc(Cl)cc3F)cc2)cc1F]

The title compound was produced in analogy to example 372, step 1, from (E)-3-(4-bromo-phenyl)-3-(4-chloro-2-fluoro-phenyl)-1-(2-methyl-pyridin-4-yl)-propan-1-one oxime (example 147) and 3-fluoro-4-methoxycarbonylphenylboronic acid (CAS RN 505083-04-5). Light yellow solid. MS (ESI⁺): m/z=521.0 ([M+H]⁺).

Example 447

4'-[1-(4-Chloro-2-fluoro-phenyl)-3-[(E)-hydroxy-imino]-3-(2-methyl-pyridin-4-yl)-propyl]-3-fluoro-biphenyl-4-carboxylic acid

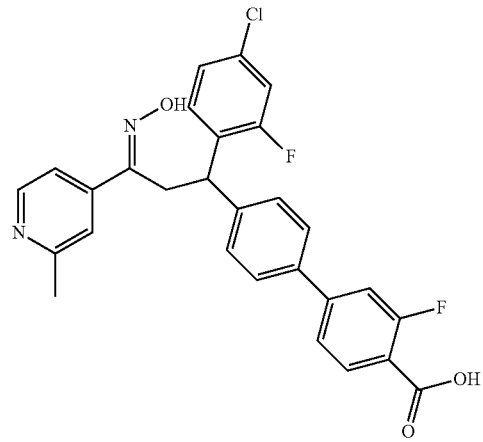 [SMILES: Cc1cc(/C(CC(c2ccc(-c3ccc(C(=O)O)c(F)c3)cc2)c2ccc(Cl)cc2F)=N/O)ccn1]

The title compound was produced in analogy to example 425, step 3, from 4'-[1-(4-chloro-2-fluoro-phenyl)-3-[(E)-hydroxyimino]-3-(2-methyl-pyridin-4-yl)-propyl]-3-fluoro-biphenyl-4-carboxylic acid methyl ester (example 446). The crude reaction product was purified by silica gel chromatography using a MPLC system (CombiFlash Companion, Isco Inc.) eluting with a gradient of n-heptane/ethyl acetate (1:9 to 0:1) to provide the title compound as a light yellow solid. MS (ESI⁺): m/z=507.0 ([M+H]⁺).

Example 448

4'-[(−)-1-(4-Chloro-2-fluoro-phenyl)-3-[(E)-hydroxyimino]-3-(2-methyl-pyridin-4-yl)-propyl]-3-fluoro-biphenyl-4-carboxylic acid

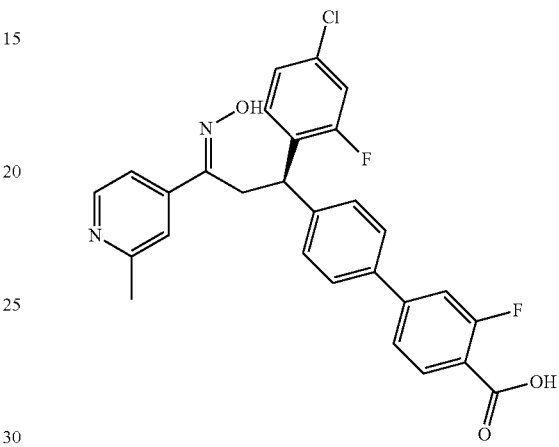

Step 1: (−)-3-(4-Bromo-phenyl)-3-(4-chloro-2-fluoro-phenyl)-1-(2-methyl-pyridin-4-yl)-propan-1-one and (+)-3-(4-Bromo-phenyl)-3-(4-chloro-2-fluoro-phenyl)-1-(2-methyl-pyridin-4-yl)-propan-1-one Separation of 3-(4-bromo-phenyl)-3-(4-chloro-2-fluoro-phenyl)-1-(2-methyl-pyridin-4-yl)-propan-1-one (example 147, step 4) by chiral HPLC (Reprosil Chiral NR, 10% isopropanol in n-heptane) yielded (−)-3-(4-bromo-phenyl)-3-(4-chloro-2-fluoro-phenyl)-1-(2-methyl-pyridin-4-yl)-propan-1-one a colorless oil, MS (ESI⁺): m/z=434.1 ([M+H]⁺) and (+)-3-(4-bromo-phenyl)-3-(4-chloro-2-fluoro-phenyl)-1-(2-methyl-pyridin-4-yl)-propan-1-one as a colorless oil, MS (ESI⁺): m/z=434.0 ([M+H]⁺).

Step 2: (−)-3-(4-Bromo-phenyl)-3-(4-chloro-2-fluoro-phenyl)-1-(2-methyl-pyridin-4-yl)-propan-1-one oxime The title compound was produced in analogy to example 402, step 5, from (−)-3-(4-bromo-phenyl)-3-(4-chloro-2-fluoro-phenyl)-1-(2-methyl-pyridin-4-yl)-propan-1-one and hydroxylamine hydrochloride in the presence of sodium hydrogencarbonate. The compound was purified by silica gel chromatography using a MPLC system (CombiFlash Companion, Isco Inc.) eluting with a gradient of n-heptane/ethyl acetate (1:4 to 0:1) to give the title compound as a white solid. MS (ESI⁺): m/z=449.0 ([M+H]⁺).

Step 3: 4'-[(−)-1-(4-Chloro-2-fluoro-phenyl)-3-[(E)-hydroxyimino]-3-(2-methyl-pyridin-4-yl)-propyl]-3-fluoro-biphenyl-4-carboxylic acid The title compound was produced in analogy to example 372, step 1, from (−)-3-(4-bromo-phenyl)-3-(4-chloro-2- fluoro-phenyl)-1-(2-methyl-pyridin-4-yl)-propan-1-one oxime and (3-fluoro-4-carboxyphenyl)boronic acid (CAS RN 120153-08-4). White solid. MS (ESI−): m/z=505.1 ([M−H]−).

Example 449

4'-[(+)-1-(4-Chloro-2-fluoro-phenyl)-3-[(E)-hydroxyimino]-3-(2-methyl-pyridin-4-yl)-propyl]-3-fluoro-biphenyl-4-carboxylic acid

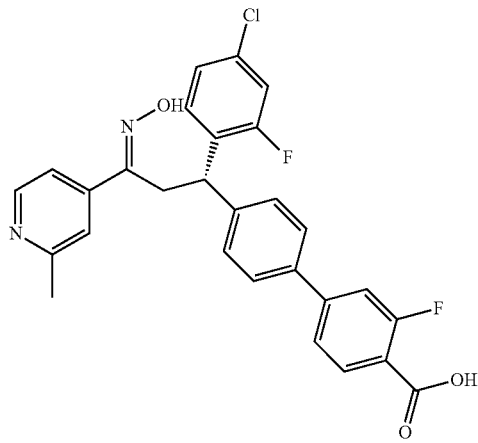 [SMILES: Cc1cc(/C(C[C@@H](c2ccc(-c3ccc(C(=O)O)c(F)c3)cc2)c2ccc(Cl)cc2F)=N/O)ccn1]

Step 1: (+)-3-(4-Bromo-phenyl)-3-(4-chloro-2-fluoro-phenyl)-1-(2-methyl-pyridin-4-yl)-propan-1-one oxime The title compound was produced in analogy to example 402, step 5, from (+)-3-(4-bromo-phenyl)-3-(4-chloro-2-fluoro-phenyl)-1-(2-methyl-pyridin-4-yl)-propan-1-one (example 448, step 1) and hydroxylamine hydrochloride in the presence of sodium hydrogencarbonate. The compound was purified by silica gel chromatography using a MPLC system (CombiFlash Companion, Isco Inc.) eluting with a gradient of n-heptane/ethyl acetate (1:4 to 0:1) to give the title compound as a white solid. MS (ESI+): m/z=449.0 ([M+H]+).

Step 2: 4'-[(+)-1-(4-Chloro-2-fluoro-phenyl)-3-[(E)-hydroxyimino]-3-(2-methyl-pyridin-4-yl)-propyl]-3-fluoro-biphenyl-4-carboxylic acid The title compound was produced in analogy to 4'-[(−)-1-(4-chloro-2-fluoro-phenyl)-3-[(E)-hydroxyimino]-3-(2-methyl-pyridin-4-yl)-propyl]-3-fluoro-biphenyl-4-carboxylic acid (example 448) replacing in step 2 (−)-3-(4-bromo-phenyl)-3-(4-chloro-2-fluoro-phenyl)-1-(2-methyl-pyridin-4-yl)-propan-1-one oxime with (+)-3-(4-bromo-phenyl)-3-(4-chloro-2-fluoro-phenyl)-1-(2-methyl-pyridin-4-yl)-propan-1-one oxime. Light yellow solid. MS (ESI−): m/z=505.3 ([M−H]−).

Example 450

3-Chloro-4'-[1-(4-chloro-2-fluoro-phenyl)-3-[(E)-hydroxyimino]-3-(2-methyl-pyridin-4-yl)-propyl]-biphenyl-4-carboxylic acid methyl ester

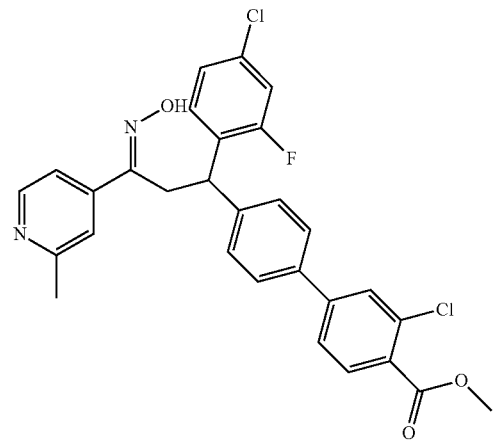 [SMILES: COC(=O)c1ccc(-c2ccc(C(C/C(=N\O)c3ccnc(C)c3)c3ccc(Cl)cc3F)cc2)cc1Cl]

The title compound was produced in analogy to 4'-[1-(4-chloro-2-fluoro-phenyl)-3-[(E)-hydroxyimino]-3-(2-methyl-pyridin-4-yl)-propyl]-3-fluoro-biphenyl-4-carboxylic acid methyl ester (example 446) replacing 3-fluoro-4-methoxycarbonylphenylboronic acid with 3-chloro-4-methoxycarbonylphenylboronic acid (CAS RN 603122-82-3). Light yellow solid. MS (ESI+): m/z=537.2 ([M+H]+).

Example 451

3-Chloro-4'-[1-(4-chloro-2-fluoro-phenyl)-3-[(E)-hydroxyimino]-3-(2-methyl-pyridin-4-yl)-propyl]-biphenyl-4-carboxylic acid

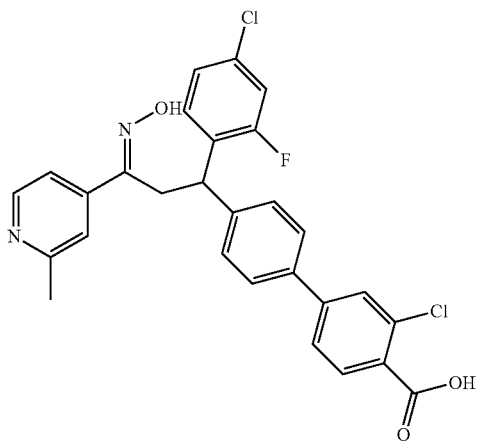

The title compound was produced in analogy to example 425, step 3, from 3-chloro-4'-[1-(4-chloro-2-fluoro-phenyl)-3-[(E)-hydroxyimino]-3-(2-methyl-pyridin-4-yl)-propyl]- biphenyl-4-carboxylic acid methyl ester (example 450). The crude reaction product was purified by silica gel chromatography using a MPLC system (CombiFlash Companion, Isco Inc.) eluting with a gradient of n-heptane/ethyl acetate (1:9 to 0:1) to provide the title compound as an off-white solid. MS (ESI$^+$): m/z=523.0 ([M+H]$^+$).

Example 452

(−)-3-Chloro-4'-[1-(4-chloro-2-fluoro-phenyl)-3-[(E)-hydroxyimino]-3-(2-methyl-pyridin-4-yl)-propyl]-biphenyl-4-carboxylic acid

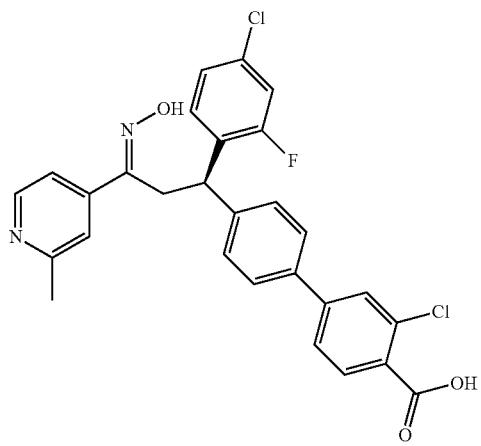 [SMILES: Cc1cc(/C(C[C@H](c2ccc(-c3ccc(C(=O)O)c(Cl)c3)cc2)c2ccc(Cl)cc2F)=N/O)ccn1]

Step 1: 3-Chloro-4'-[(−)-1-(4-chloro-2-fluoro-phenyl)-3-[(E)-hydroxyimino]-3-(2-methyl-pyridin-4-yl)-propyl]-biphenyl-4-carboxylic acid methyl ester The title compound was produced in analogy to example 372, step 1, from (−)-3-(4-bromo-phenyl)-3-(4-chloro-2-fluoro-phenyl)-1-(2-methyl-pyridin-4-yl)-propan-1-one oxime (example 448, step 2) and 3-chloro-4-methoxycarbonylphenylboronic acid (CAS RN 603122-82-3). Off-white solid. MS (ESI$^+$): m/z=537.3 ([M+H]$^+$.

Step 2: (−)-3-Chloro-4'-[1-(4-chloro-2-fluoro-phenyl)-3-[(E)-hydroxyimino]-3-(2-methyl-pyridin-4-yl)-propyl]-biphenyl-4-carboxylic acid The title compound was produced in analogy to example 425, step 3, from 3-chloro-4'-[(−)-1-(4-chloro-2-fluoro-phenyl)-3-[(E)-hydroxyimino]-3-(2-methyl-pyridin-4-yl)-propyl]-biphenyl-4-carboxylic acid methyl ester. Off-white solid. MS (ESI$^−$): m/z=521.2 ([M−H]$^−$).

Example 453

(+)-3-Chloro-4'-[1-(4-chloro-2-fluoro-phenyl)-3-[(E)-hydroxyimino]-3-(2-methyl-pyridin-4-yl)-propyl]-biphenyl-4-carboxylic acid

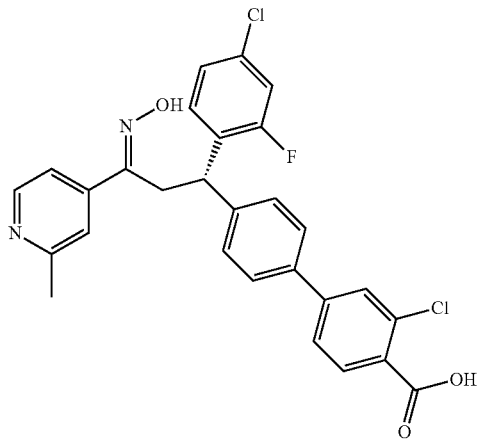 [SMILES: Cc1cc(/C(C[C@@H](c2ccc(-c3ccc(C(=O)O)c(Cl)c3)cc2)c2ccc(Cl)cc2F)=N/O)ccn1]

The title compound was produced in analogy to (−)-3-chloro-4'-[1-(4-chloro-2-fluoro-phenyl)-3-[(E)-hydroxyimino]-3-(2-methyl-pyridin-4-yl)-propyl]-biphenyl-4-carboxylic acid (example 452) replacing in step 1 (−)-3-(4-bromo-phenyl)-3-(4-chloro-2-fluoro-phenyl)-1-(2-methyl-pyridin-4-yl)-propan-1-one oxime with (+)-3-(4-bromo-phenyl)-3-(4-chloro-2-fluoro-phenyl)-1-(2-methyl-pyridin-4-yl)-propan-1-one oxime (example 449, step 1). Off-white solid. MS (ESI$^−$): m/z=521.0 ([M−H]$^−$).

Example 454

4'-[1-(4-Chloro-2-fluoro-phenyl)-3-[(E)-hydroxyimino]-3-(2-methyl-pyridin-4-yl)-propyl]-3-methoxy-biphenyl-4-carboxylic acid methyl ester

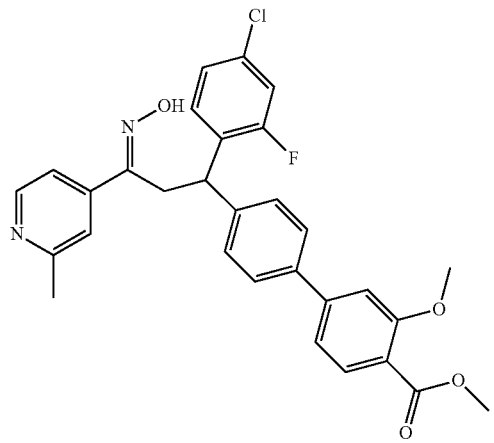 [SMILES: COC(=O)c1ccc(-c2ccc(C(C/C(=N\O)c3ccnc(C)c3)c3ccc(Cl)cc3F)cc2)cc1OC]

The title compound was produced in analogy to 4'-[1-(4-chloro-2-fluoro-phenyl)-3-[(E)-hydroxyimino]-3-(2-methyl-pyridin-4-yl)-propyl]-3-fluoro-biphenyl-4-carboxylic acid methyl ester (example 446) replacing 3-fluoro-4-methoxycarbonylphenylboronic acid with 3-methoxy-4-methoxycarbonylphenylboronic acid (CAS RN 603122-41-4). White solid. MS (ESI$^+$): m/z=533.3 ([M+H]$^+$).

Example 455

4'-[1-(4-Chloro-2-fluoro-phenyl)-3-[(E)-hydroxy-imino]-3-(2-methyl-pyridin-4-yl)-propyl]-3-methoxy-biphenyl-4-carboxylic acid

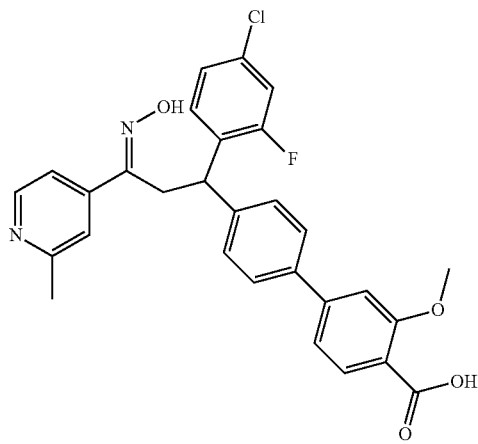 [SMILES: COc1cc(-c2ccc(C(C/C(=N\O)c3ccnc(C)c3)c3ccc(Cl)cc3F)cc2)ccc1C(=O)O]

The title compound was produced in analogy to example 425, step 3, from 4'-[1-(4-chloro-2-fluoro-phenyl)-3-[(E)-hydroxyimino]-3-(2-methyl-pyridin-4-yl)-propyl]-3-methoxy-biphenyl-4-carboxylic acid methyl ester (example 454). The crude reaction product was purified by silica gel chromatography using a MPLC system (CombiFlash Companion, Isco Inc.) eluting with a gradient of n-heptane/ethyl acetate (1:9 to 0:1) to provide the title compound as an off-white solid. MS (ESI$^+$): m/z=519.0 ([M+H]$^+$).

Example 456

4'-[1-(4-Chloro-2-fluoro-phenyl)-3-[(E)-hydroxy-imino]-3-(2-methyl-pyridin-4-yl)-propyl]-2-methyl-biphenyl-4-carboxylic acid

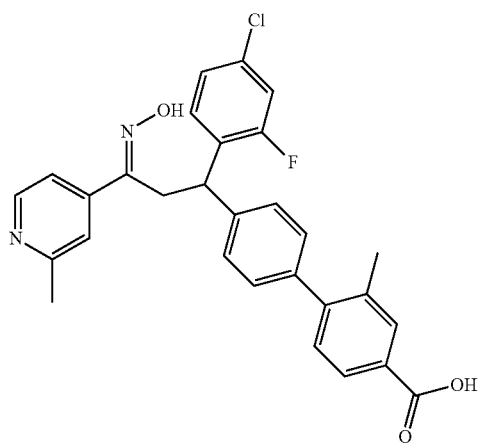 [SMILES: Cc1cc(/C(CC(c2ccc(-c3ccc(C(=O)O)cc3C)cc2)c2ccc(Cl)cc2F)=N/O)ccn1]

The title compound was produced in analogy to example 372, step 1, from (E)-3-(4-bromo-phenyl)-3-(4-chloro-2-fluoro-phenyl)-1-(2-methyl-pyridin-4-yl)-propan-1-one oxime (example 147) and (2-methyl-4-carboxyphenyl)boronic acid (CAS RN 158429-66-4). Light yellow solid. MS (ESI$^+$): m/z=503.3 ([M+H]$^+$).

Example 457

5-{4-[1-(4-Chloro-2-fluoro-phenyl)-3-[(E)-hydroxy-imino]-3-(2-methyl-pyridin-4-yl)-propyl]-phenyl}-thiophene-2-carboxylic acid

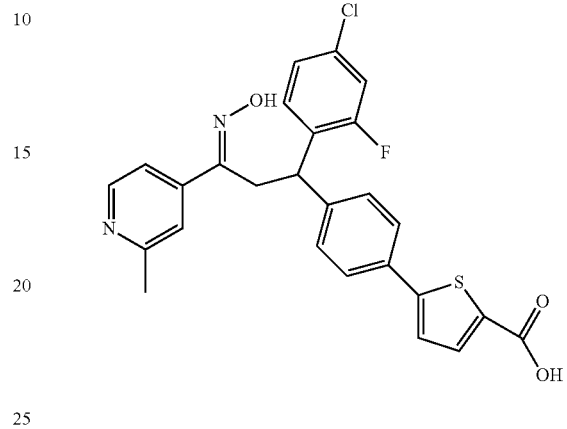

The title compound was produced in analogy to example 372, step 1, from (E)-3-(4-bromo-phenyl)-3-(4-chloro-2-fluoro-phenyl)-1-(2-methyl-pyridin-4-yl)-propan-1-one oxime (example 147) and (5-carboxythien-2-yl)boronic acid (CAS RN 465515-31-5). Off-white solid. MS (ESI$^+$): m/z=495.0 ([M+H]$^+$).

Example 458

5-{4-[1-(4-Chloro-2-fluoro-phenyl)-3-[(E)-hydroxy-imino]-3-(2-methyl-pyridin-4-yl)-propyl]-phenyl}-1H-pyrimidine-2,4-dione

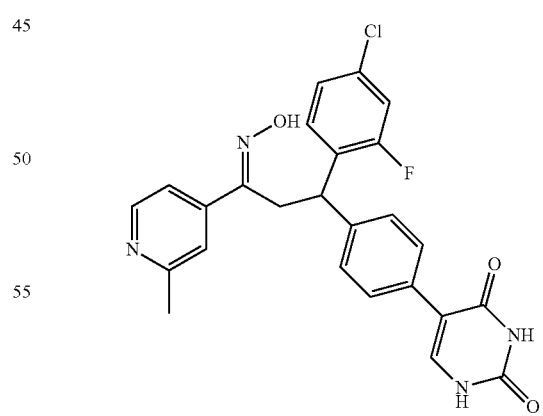

The title compound was produced in analogy to example 372, step 1, from (E)-3-(4-bromo-phenyl)-3-(4-chloro-2-fluoro-phenyl)-1-(2-methyl-pyridin-4-yl)-propan-1-one oxime (example 147) and uracil-5-boronic acid (CAS RN 70523-22-7). Off-white solid. MS (ESI$^+$): m/z=479.0 ([M+H]$^+$).

Example 459

{4'-[1-(4-Chloro-2-fluoro-phenyl)-3-[(E)-hydroxy-imino]-3-(1-methyl-6-oxo-1,6-dihydro-pyridin-3-yl)-propyl]-biphenyl-4-yl}-acetonitrile

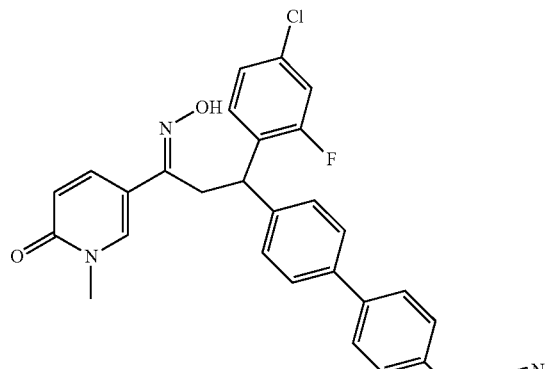

The title compound was produced in analogy to example 372, step 1, from 5-{3-(4-bromo-phenyl)-3-(4-chloro-2-fluoro-phenyl)-1-[(E)-hydroxyimino]-propyl}-1-methyl-1H-pyridin-2-one (example 237) and 4-(cyanomethyl)phenylboronic acid (CAS RN 91983-26-5). Off-white solid. MS (ESI+): m/z=500.1 ([M+H]+).

Example 460

{4'-[1-(4-Chloro-2-fluoro-phenyl)-3-[(E)-hydroxy-imino]-3-(1-methyl-6-oxo-1,6-dihydro-pyridin-3-yl)-propyl]-biphenyl-4-yl}-acetic acid

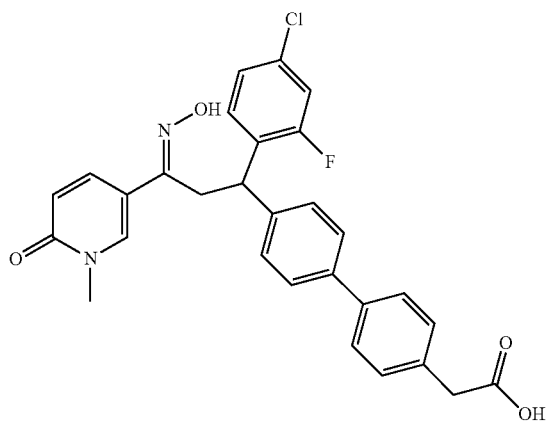 [SMILES: Cn1cc(/C(CC(c2ccc(-c3ccc(CC(=O)O)cc3)cc2)c2ccc(Cl)cc2F)=N/O)ccc1=O]

The title compound was produced in analogy to example 425, step 3, from {4'-[1-(4-chloro-2-fluoro-phenyl)-3-[(E)-hydroxyimino]-3-(1-methyl-6- oxo-1,6-dihydro-pyridin-3-yl)-propyl]-biphenyl-4-yl}-acetonitrile (example 459). Off-white solid. MS (ESI+): m/z=519.3 ([M+H]+).

Examples 461 and 462

{4'-[(−)-1-(4-Chloro-2-fluoro-phenyl)-3-[(E)-hydroxyimino]-3-(1-methyl-6-oxo-1,6-dihydro-pyridin-3-yl)-propyl]-biphenyl-4-yl}-acetic acid and {4'-[(+)-1-(4-chloro-2-fluoro-phenyl)-3-[(E)-hydroxyimino]-3-(1-methyl-6-oxo-1,6-dihydro-pyridin-3-yl)-propyl]-biphenyl-4-yl}-acetic acid

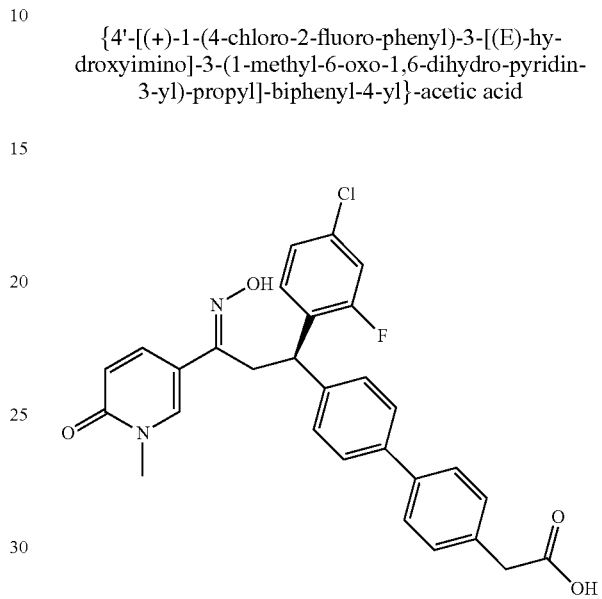

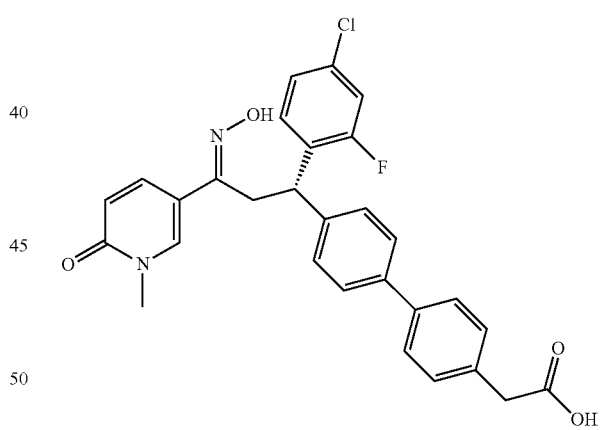

Separation of {4'-[1-(4-chloro-2-fluoro-phenyl)-3-[(E)-hydroxyimino]-3-(1-methyl-6-oxo-1,6-dihydro-pyridin-3-yl)-propyl]-biphenyl-4-yl}-acetic acid (example 460) by chiral HPLC (Chiralpak-AD, 30% ethanol (+0.5% formic acid) in n-heptane) yielded {4'-[(−)-1-(4-chloro-2-fluorophenyl)-3-[(E)-hydroxyimino]-3-(1-methyl-6-oxo-1,6-dihydro-pyridin-3-yl)-propyl]-biphenyl-4-yl}-acetic acid as an off-white solid, MS (ESI+): m/z=519.3 ([M+H]+) and {4'-[(+)-1-(4- chloro-2-fluoro-phenyl)-3-[(E)-hydroxyimino]-3-

(1-methyl-6-oxo-1,6-dihydro-pyridin-3-yl)-propyl]-biphenyl-4-yl}-acetic acid as an off-white solid, MS (ESI⁺): m/z=519.5 ([M+H]⁺).

Example 463

4'-[(−)-1-(4-Chloro-2-fluoro-phenyl)-3-[(E)-hydroxyimino]-3-(1-methyl-6-oxo-1,6-dihydro-pyridin-3-yl)-propyl]-3-fluoro-biphenyl-4-carboxylic acid

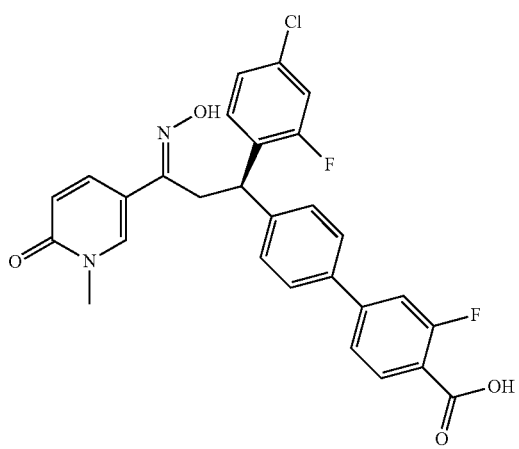 [SMILES: Cn1cc(/C(C[C@H](c2ccc(-c3ccc(C(=O)O)c(F)c3)cc2)c2ccc(Cl)cc2F)=N/O)ccc1=O]

The title compound was produced in analogy to example 372, step 1, from (−)-5-{3-(4-bromo-phenyl)-3-(4-chloro-2-fluoro-phenyl)-1-[(E)-hydroxyimino]-propyl}-1-methyl-1H-pyridin-2-one (example 240) and (3-fluoro-4-carboxyphenyl)boronic acid (CAS RN 120153-08-4). Light yellow solid. MS (ESI⁺): m/z=523.2 ([M+H]⁺).

Example 464

4'-[(+)-1-(4-Chloro-2-fluoro-phenyl)-3-[(E)-hydroxyimino]-3-(1-methyl-6-oxo-1,6-dihydro-pyridin-3-yl)-propyl]-3-fluoro-biphenyl-4-carboxylic acid

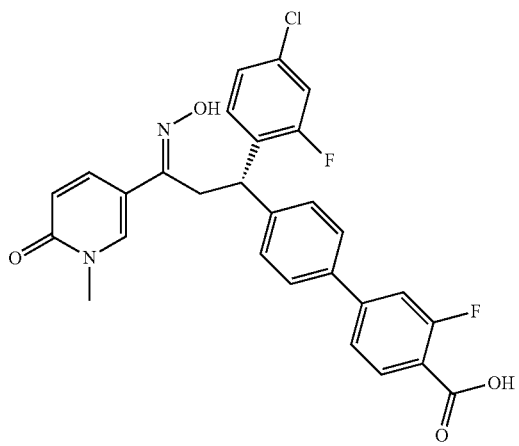 [SMILES: Cn1cc(/C(C[C@@H](c2ccc(-c3ccc(C(=O)O)c(F)c3)cc2)c2ccc(Cl)cc2F)=N/O)ccc1=O]

The title compound was produced in analogy to example 372, step 1, from (+)-5-{3-(4-bromo-phenyl)-3-(4-chloro-2-fluoro-phenyl)-1-[(E)-hydroxyimino]-propyl}-1-methyl-1H-pyridin-2-one (example 239) and (3-fluoro-4-carboxyphenyl)boronic acid (CAS RN 120153-08-4). Off-white solid. MS (ESI⁺): m/z=523.3 ([M+H]⁺).

Example 465

4'-[(−)-1-(4-Chloro-2-fluoro-phenyl)-3-[(E)-hydroxyimino]-3-(1-methyl-6-oxo-1,6-dihydro-pyridin-3-yl)-propyl]-2-methyl-biphenyl-4-carboxylic acid

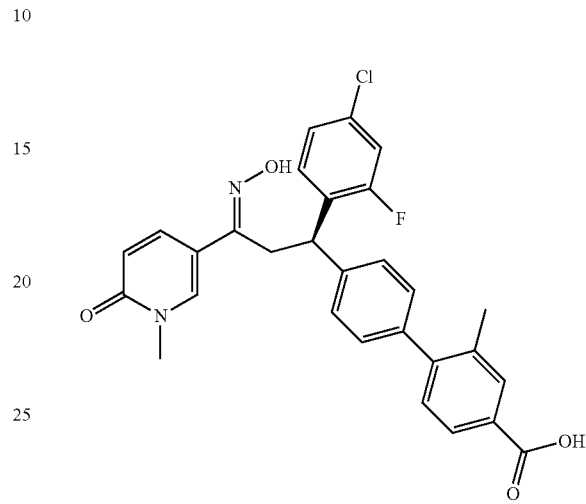

The title compound was produced in analogy to example 372, step 1, from (−)-5-{3-(4-bromo-phenyl)-3-(4-chloro-2-fluoro-phenyl)-1-[(E)-hydroxyimino]-propyl}-1-methyl-1H-pyridin-2-one (example 240) and (2-methyl-4-carboxyphenyl)boronic acid (CAS RN 158429-66-4). Light yellow solid. MS (ESI⁺): m/z=519.5 ([M+H]⁺).

Example 466

4'-[(+)-1-(4-Chloro-2-fluoro-phenyl)-3-[(E)-hydroxyimino]-3-(1-methyl-6-oxo-1,6-dihydro-pyridin-3-yl)-propyl]-2-methyl-biphenyl-4-carboxylic acid

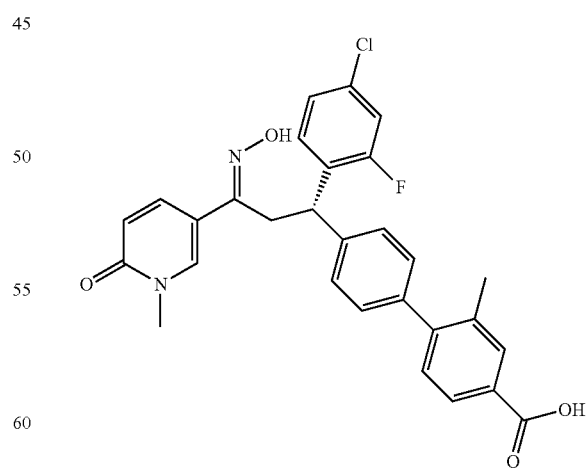

The title compound was produced in analogy to example 372, step 1, from (+)-5-{3-(4-bromo-phenyl)-3-(4-chloro-2-fluoro-phenyl)-1-[(E)-hydroxyimino]-propyl}-1-methyl-1H-pyridin-2-one (example 239) and (2-methyl-4-carbox-

Example 467

5-{4-[(−)-1-(4-Chloro-2-fluoro-phenyl)-3-[(E)-hydroxyimino]-3-(1-methyl-6-oxo-1,6-dihydro-pyridin-3-yl)-propyl]-phenyl}-thiophene-2-carboxylic acid ethyl ester

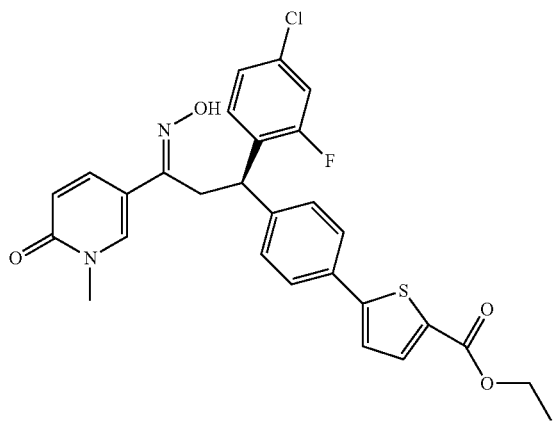 [SMILES: CCOC(=O)c1ccc(-c2ccc([C@@H](C/C(=N\O)c3ccc(=O)n(C)c3)c3ccc(Cl)cc3F)cc2)s1]

The title compound was produced in analogy to example 372, step 1, from (−)-5-{3-(4-bromo-phenyl)-3-(4-chloro-2-fluoro-phenyl)-1-[(E)-hydroxyimino]-propyl}-1-methyl-1H-pyridin-2-one (example 240) and 5-(ethoxycarbonyl)thiophene-3-boronic acid (CAS RN 957121-19-6). Light brown solid. MS (ESI⁺): m/z=539.3 ([M+H]⁺).

Example 468

5-{4-[(−)-1-(4-Chloro-2-fluoro-phenyl)-3-[(E)-hydroxyimino]-3-(1-methyl-6-oxo-1,6-dihydro-pyridin-3-yl)-propyl]-phenyl}-thiophene-2-carboxylic acid

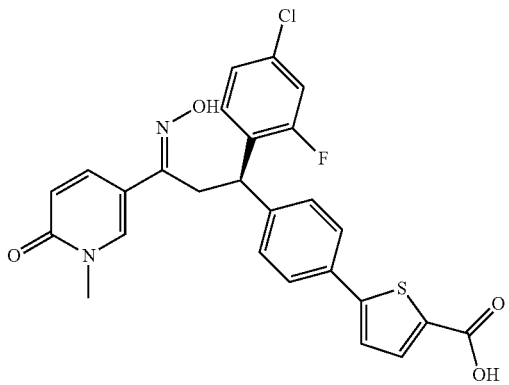 [SMILES: Cn1cc(/C(C[C@H](c2ccc(-c3ccc(C(=O)O)s3)cc2)c2ccc(Cl)cc2F)=N/O)ccc1=O]

The title compound was produced in analogy to example 425, step 3, from 5-{4-[(−)-1-(4-chloro-2-fluoro-phenyl)-3-[(E)-hydroxyimino]-3-(1-methyl-6-oxo-1,6-dihydro-pyridin-3-yl)-propyl]-phenyl}-thiophene-2-carboxylic acid ethyl ester (example 467). Off-white solid. MS (ESI⁺): m/z=511.1 ([M+H]⁺).

Example 469

5-{4-[(+)-1-(4-Chloro-2-fluoro-phenyl)-3-[(E)-hydroxyimino]-3-(1-methyl-6-oxo-1,6-dihydro-pyridin-3-yl)-propyl]-phenyl}-thiophene-2-carboxylic acid ethyl ester

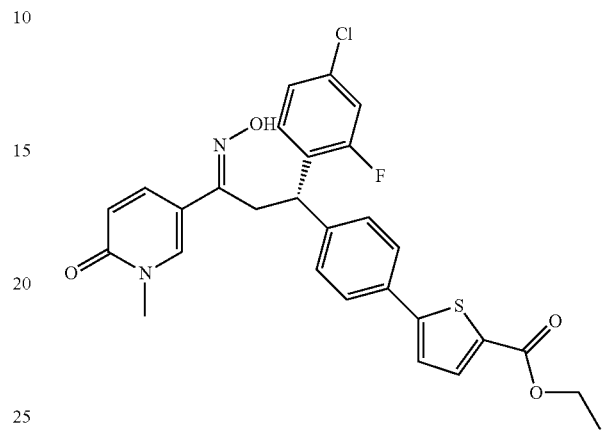

The title compound was produced in analogy to example 372, step 1, from (+)-5-{3-(4-bromo-phenyl)-3-(4-chloro-2-fluoro-phenyl)-1-[(E)-hydroxyimino]-propyl}-1-methyl-1H-pyridin-2-one (example 239) and 5-(ethoxycarbonyl)thiophene-3-boronic acid (CAS RN 957121-19-6). Light brown solid. MS (ESI⁺): m/z=539.3 ([M+H]⁺).

Example 470

5-{4-[(+)-1-(4-Chloro-2-fluoro-phenyl)-3-[(E)-hydroxyimino]-3-(1-methyl-6-oxo-1,6-dihydro-pyridin-3-yl)-propyl]-phenyl}-thiophene-2-carboxylic acid

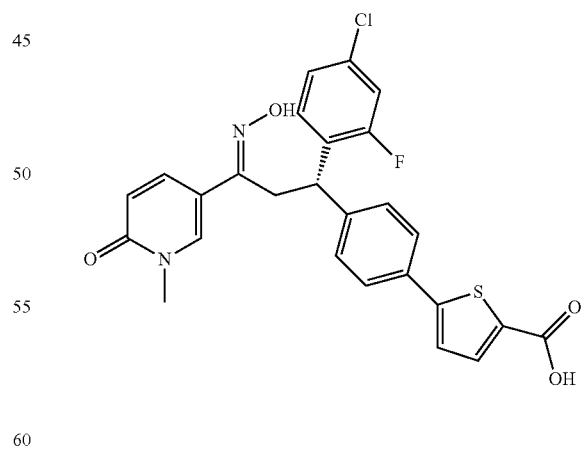

The title compound was produced in analogy to example 425, step 3, from 5-{4-[(+)-1-(4-chloro-2-fluoro-phenyl)-3-[(E)-hydroxyimino]-3-(1-methyl-6-oxo-1,6-dihydro-pyridin-3-yl)-propyl]-phenyl}-thiophene-2-carboxylic acid ethyl ester (example 469). Off-white solid. MS (ESI⁺): m/z=511.0 ([M+H]⁺).

Example 471

5-{4-[1-(4-Chloro-2-fluoro-phenyl)-3-[(E)-hydroxyimino]-3-(1-methyl-6-oxo-1,6-dihydro-pyridin-3-yl)-propyl]-phenyl}-1H-pyrimidine-2,4-dione

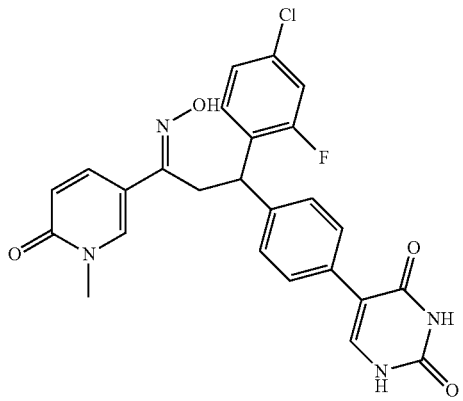 [SMILES: Cn1cc(/C(CC(c2ccc(-c3c[nH]c(=O)[nH]c3=O)cc2)c2ccc(Cl)cc2F)=N/O)ccc1=O]

The title compound was produced in analogy to example 372, step 1, from 5-{3-(4-bromo-phenyl)-3-(4-chloro-2-fluoro-phenyl)-1-[(E)-hydroxyimino]-propyl}-1-methyl-1H-pyridin-2-one (example 237) and uracil-5-boronic acid (CAS RN 70523-22-7). Off-white solid. MS (ESI$^+$): m/z=495.3 ([M+H]$^+$).

Example 472

5-{3-(4-Bromo-phenyl)-3-(2,4-dichloro-phenyl)-1-[(E)-hydroxyimino]-propyl}-1-methyl-1H-pyridin-2-one

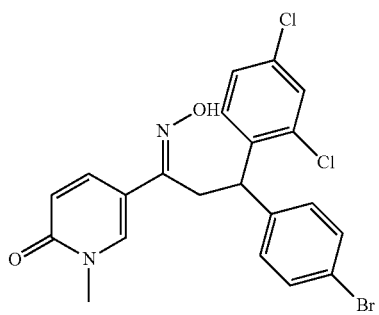 [SMILES: Cn1cc(/C(CC(c2ccc(Br)cc2)c2ccc(Cl)cc2Cl)=N/O)ccc1=O]

The title compound was produced in analogy to (E)-3-(4-bromo-phenyl)-3-(4-chloro-2-fluoro-phenyl)-1-(2-methyl-pyridin-4-yl)-propan-1-one oxime (example 147) replacing in step 3 4-chloro-2-fluorobenzaldehyde with 2,4-dichlorobenzaldehyde (CAS RN 874-42-0). White foam. MS (ESI$^-$): m/z=478.9 ([M−H]$^-$).

Example 473

4'-[1-(2,4-Dichloro-phenyl)-3-[(E)-hydroxyimino]-3-(1-methyl-6-oxo-1,6-dihydro-pyridin-3-yl)-propyl]-3-fluoro-biphenyl-4-carboxylic acid

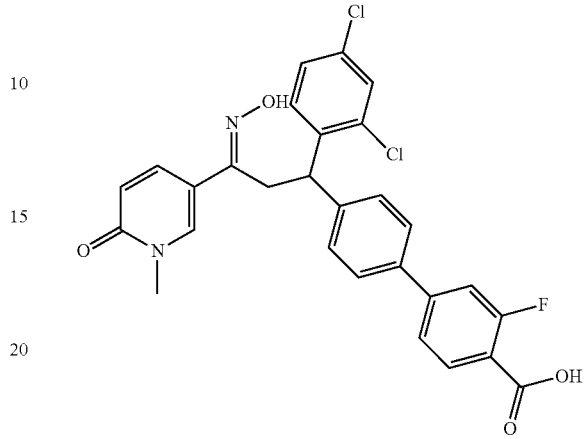

The title compound was produced in analogy to example 372, step 1, from 5-{3-(4-bromo-phenyl)-3-(2,4-dichloro-phenyl)-1-[(E)-hydroxyimino]-propyl}-1-methyl-1H-pyridin-2-one (example 472) and (3-fluoro-4-carboxyphenyl)boronic acid (CAS RN 120153-08-4). The crude reaction product was purified by silica gel chromatography using a MPLC system (CombiFlash Companion, Isco Inc.) eluting with a gradient of dichloromethane (+2% formic acid)/methanol (100:0 to 95:5) to provide the title compound as an off-white solid. MS (ESI$^+$): m/z=539.3 ([M+H]$^+$).

Examples 474 and 475

4'-[(−)-1-(2,4-Dichloro-phenyl)-3-[(E)-hydroxyimino]-3-(1-methyl-6-oxo-1,6-dihydro-pyridin-3-yl)-propyl]-3-fluoro-biphenyl-4-carboxylic acid and 4'-[(+)-1-(2,4-dichloro-phenyl)-3-[(E)-hydroxyimino]-3-(1-methyl-6-oxo-1,6-dihydro-pyridin-3-yl)-propyl]-3-fluoro-biphenyl-4-carboxylic acid

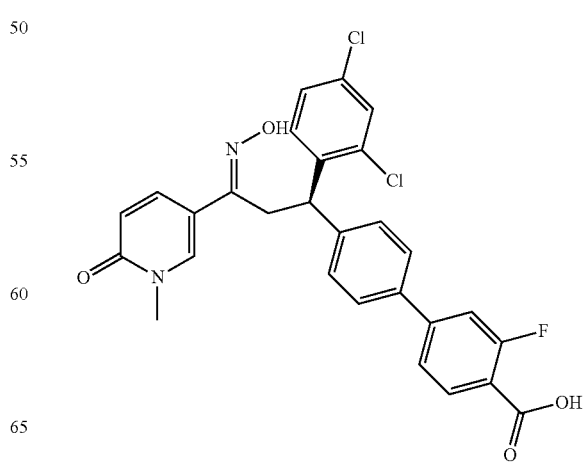

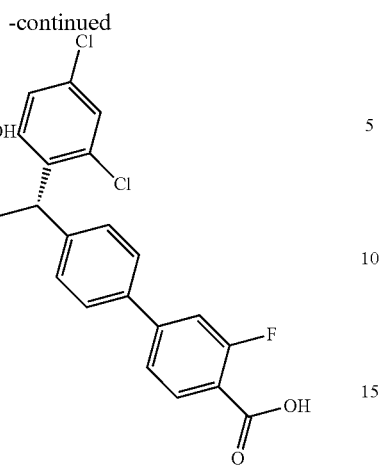

Separation of 4'-[1-(2,4-dichloro-phenyl)-3-[(E)-hydroxyimino]-3-(1-methyl-6-oxo-1,6-dihydro-pyridin-3-yl)-propyl]-3-fluoro-biphenyl-4-carboxylic acid (example 473) by chiral HPLC (Chiralpak-AD, 20% ethanol (+0.5% formic acid) in n-heptane) yielded 4'-[(−)-1-(2,4-dichloro-phenyl)-3-[(E)-hydroxyimino]-3-(1-methyl-6-oxo-1,6-dihydro-pyridin-3-yl)-propyl]-3-fluoro-biphenyl-4-carboxylic acid as a light yellow solid, MS (ESI+): m/z=539.3 ([M+H]+) and 4'-[(+)-1-(2,4-dichloro-phenyl)-3-[(E)-hydroxyimino]-3-(1-methyl-6-oxo-1,6-dihydro-pyridin-3-yl)-propyl]-3-fluoro-biphenyl-4-carboxylic acid as a light yellow solid, MS (ESI+): m/z=539.3 ([M+H]+).

Example 476

4'-[1-(2,4-Dichloro-phenyl)-3-[(E)-hydroxyimino]-3-(1-methyl-6-oxo-1,6-dihydro-pyridin-3-yl)-propyl]-2-methyl-biphenyl-4-carboxylic acid

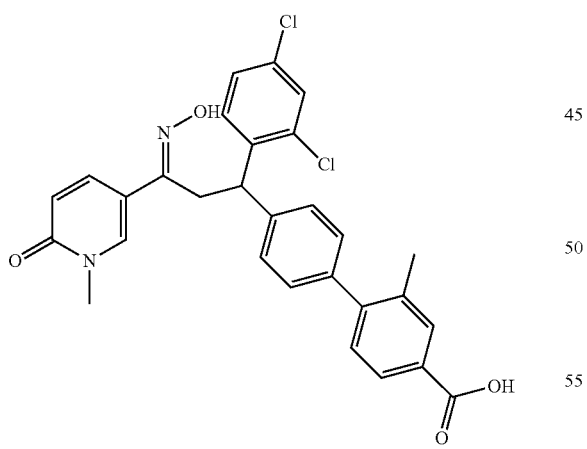

The title compound was produced in analogy to example 372, step 1, from 5-{3-(4-bromo-phenyl)-3-(2,4-dichloro-phenyl)-1-[(E)-hydroxyimino]-propyl}-1-methyl-1H-pyridin-2-one (example 472) and (2-methyl-4-carboxyphenyl)boronic acid (CAS RN 158429-66-4). The crude reaction product was purified by silica gel chromatography using a MPLC system (CombiFlash Companion, Isco Inc.) eluting with a gradient of dichloromethane (+2% formic acid)/methanol (100:0 to 95:5) to provide the title compound as an off-white solid. MS (ESI+): m/z=535.2 ([M+H]+).

Examples 477 and 478

4'-[(−)-1-(2,4-Dichloro-phenyl)-3-[(E)-hydroxyimino]-3-(1-methyl-6-oxo-1,6-dihydro-pyridin-3-yl)-propyl]-2-methyl-biphenyl-4-carboxylic acid and 4'-[(+)-1-(2,4-dichloro-phenyl)-3-[(E)-hydroxyimino]-3-(1-methyl-6-oxo-1,6-dihydro-pyridin-3-yl)-propyl]-2-methyl-biphenyl-4-carboxylic acid

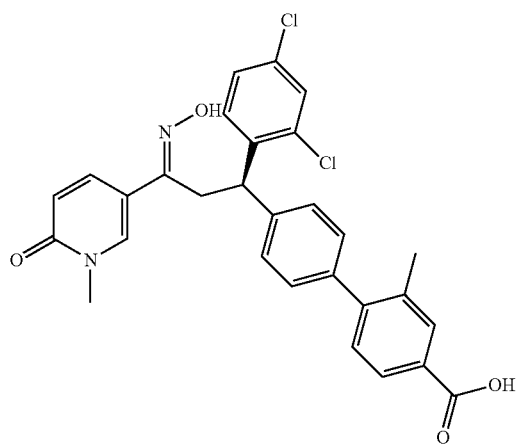

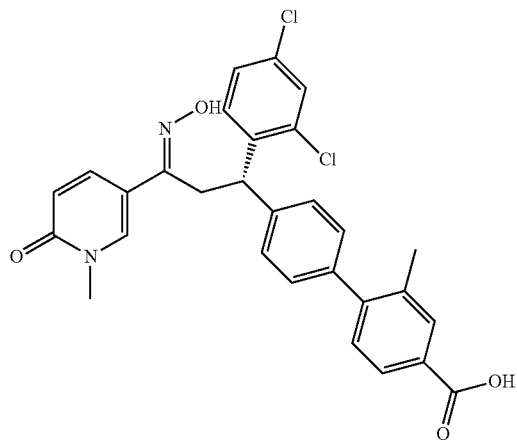 [SMILES: Cc1cc(C(=O)O)ccc1-c1ccc(C(C/C(=N\O)c2ccc(=O)n(C)c2)c2ccc(Cl)cc2Cl)cc1]

Separation of 4'-[1-(2,4-dichloro-phenyl)-3-[(E)-hydroxyimino]-3-(1-methyl-6-oxo-1,6-dihydro-pyridin-3-yl)-propyl]-2-methyl-biphenyl-4-carboxylic acid (example 476) by chiral HPLC (Chiralpak-AD, 20% ethanol (+0.5% formic acid) in n-heptane) yielded 4'-[(−)-1-(2,4-dichloro-phenyl)-3-[(E)-hydroxyimino]-3-(1-methyl-6-oxo-1,6-dihydro-pyridin-3-yl)-propyl]-2-methyl-biphenyl-4-carboxylic acid as a light yellow solid, MS (ESI+): m/z=535.2 ([M+H]+) and 4'-[(+)-1-(2,4-dichloro-phenyl)-3-[(E)-hydroxyimino]-3-(1- methyl-6-oxo-1,6-dihydro-pyridin-3-yl)-propyl]-2-methyl-biphenyl-4-carboxylic acid as a light yellow solid, MS (ESI⁺): m/z=535.2 ([M+H]⁺).

Example 479

5-{3-(4-Bromo-phenyl)-3-(4-fluoro-phenyl)-1-[(E)-hydroxyimino]-propyl}-1-methyl-1H-pyridin-2-one

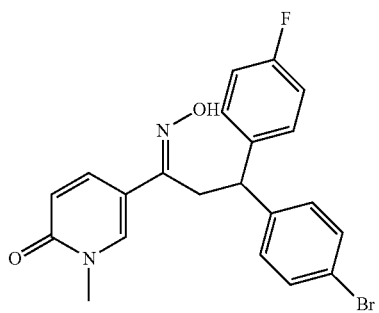 [SMILES: Cn1cc(/C(CC(c2ccc(F)cc2)c2ccc(Br)cc2)=N/O)ccc1=O]

The title compound was produced in analogy to (E)-3-(4-bromo-phenyl)-3-(4-chloro-2-fluoro-phenyl)-1-(2-methyl-pyridin-4-yl)-propan-1-one oxime (example 147) replacing in step 3 4-chloro-2-fluorobenzaldehyde with 4-fluoro-benzaldehyde (CAS RN 459-57-4). Light yellow solid. MS (ESI⁺): m/z=431.1 ([M+H]⁺).

Example 480

(R,E)-4-(4-(1-(4-Chloro-2-methylphenyl)-3-(hydroxyimino)-3-(2-methylpyridin-4-yl)propyl)phenyl)piperidine-1-sulfonamide

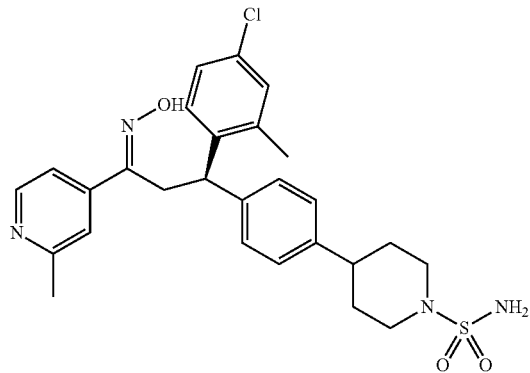 [SMILES: Cc1cc(/C(C[C@H](c2ccc(C3CCN(S(N)(=O)=O)CC3)cc2)c2ccc(Cl)cc2C)=N/O)ccn1]

Step 1: (R)-3-(4-Chloro-2-methylphenyl)-1-(2-methylpyridin-4-yl)-3-(4-(piperidin-4-yl)phenyl)propan-1-one Hydrogen chloride solution (4 M in 1,4-dioxane, 0.66 mL, 2.6 mmol) was added to a solution of (R)-tert-butyl 4-(4-(1-(4-chloro-2-methylphenyl)-3-(2-methylpyridin-4-yl)-3-oxopropyl)phenyl)piperidine-1-carboxylate (example 387, step 1; 140 mg, 263 μmol) in ethanol (4 mL) to give a colourless solution, then after 20 h the reaction mixture was partitioned between sat. aq. sodium hydrogencarbonate solution and ethyl acetate. The organic layer was washed with brine, dried over sodium sulfate, filtered, and evaporated to afford the title compound (123 mg), which was used without further purification. Off-white foam, MS (ESI⁺): m/z=433.1 ([M+H]⁺).

Step 2: (R)-4-(4-(1-(4-Chloro-2-methylphenyl)-3-(2-methylpyridin-4-yl)-3-oxopropyl)phenyl)-piperidine-1-sulfonamide A solution of (R)-3-(4-chloro-2-methylphenyl)-1-(2-methylpyridin-4-yl)-3-(4-(piperidin-4-yl)phenyl)propan-1-one (60 mg, 0.14 mmol) and sulfamide (20 mg, 0.21 mmol) in 1,4-dioxane (5 mL) was stirred for 17 h at 108° C., then partitioned between sat. aq. ammonium chloride solution and ethyl acetate. The organic layer was washed with brine, dried over sodium sulfate, filtered, and evaporated. Flash chromatography (silica gel, 50% to 100% EtOAc in heptane) afforded the title compound (59 mg, 83%). White foam, MS (ESI⁺): m/z=512.3 ([M+H]⁺).

Step 3: (R,E)-4-(4-(1-(4-Chloro-2-methylphenyl)-3-(hydroxyimino)-3-(2-methylpyridin-4-yl)propyl)phenyl)piperidine-1-sulfonamide In analogy to example 1, step 2, from (R)-4-(4-(1-(4-chloro-2-methylphenyl)-3-(2-methylpyridin-4-yl)-3-oxopropyl)phenyl)piperidine-1-sulfonamide and hydroxylamine hydrochloride in the presence of sodium hydrogencarbonate was prepared the title compound as a white foam, MS (ESI⁺): m/z=527.3 ([M+H]⁺).

Example 481

(R,E)-tert-Butyl 3-(4-(3-(hydroxyimino)-3-(2-methylpyridin-4-yl)-1-o-tolylpropyl)phenyl)-azetidine-1-carboxylate

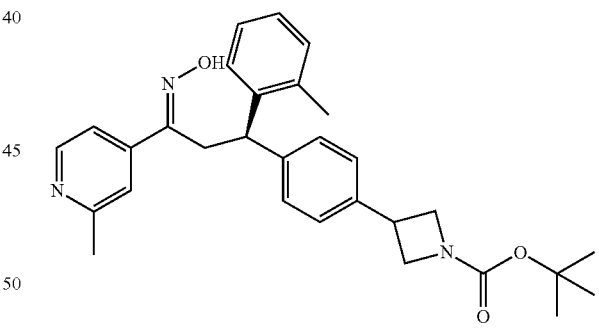

Step 1:
(1-(tert-Butoxycarbonyl)azetidin-3-yl)zinc(II) iodide

To a suspension of zinc dust (390 mg, 5.5 mmol) in N,N-dimethylacetamide (3 mL) was added a solution of chlorotrimethylsilane (70 μL) and 1,2-dibromoethane (48 μL) in N,N-dimethylacetamide (1.5 mL) at a rate to maintain the temperature in the range of 45-65° C. The resulting slurry was aged for 15 min, then a solution of 3-iodo-azetidine-1-carboxylic acid tert-butyl ester (1.42 g, 5.0 mmol) in N,N-dimethylacetaminde (5.5 mL) was slowly added to the mixture described above at a rate to maintain the temperature below 40° C. The resulting reaction mixture was then aged for 30 min at room temperature, then the supernatant was transferred into a flame-dried flask to afford the title compound as a ca. 0.5 M solution.

Step 2: (R)-tert-Butyl 3-(4-(3-(2-methylpyridin-4-yl)-3-oxo-1-o-tolylpropyl)phenyl)azetidine-1-carboxylate The title compound was produced in analogy to example 378, step 1 from (R)-3-(4-bromophenyl)-3-(4-chloro-2-methylphenyl)-1-(2-methylpyridin-4-yl)propan-1-one (example 282, step 1) and (1-(tert-butoxycarbonyl)azetidin-3-yl)zinc(II) iodide. Light brown foam, MS (ESI$^+$): m/z=471.1 ([M+H]$^+$).

Step 3: (R,E)-tert-Butyl 3-(4-(3-(hydroxyimino)-3-(2-methylpyridin-4-yl)-1-o-tolylpropyl)phenyl)azetidine-1-carboxylate In analogy to example 1, step 2, from (R)-tert-butyl 3-(4-(3-(2-methylpyridin-4-yl)-3-oxo-1-o-tolylpropyl)phenyl)azetidine-1-carboxylate and hydroxylamine hydrochloride in the presence of sodium hydrogencarbonate was prepared the title compound as a white foam, MS (ESI$^+$): m/z=486.3 ([M+H]$^+$).

Example 482

(R,E)-3-(4-(Azetidin-3-yl)phenyl)-1-(2-methylpyridin-4-yl)-3-o-tolylpropan-1-one oxime

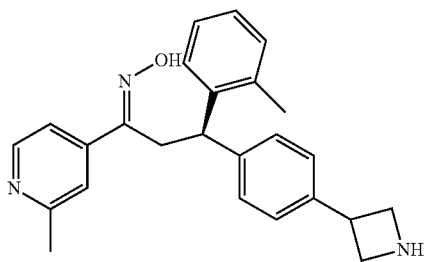 [SMILES: Cc1cc(/C(C[C@H](c2ccc(C3CNC3)cc2)c2ccccc2C)=N/O)ccn1]

Step 1: (R)-3-(4-(Azetidin-3-yl)phenyl)-1-(2-methylpyridin-4-yl)-3-o-tolylpropan-1-one Trifluoroacetic acid (1.37 g, 927 µl, 12.0 mmol) was added at 0° C. to a solution of (R)-tert-butyl 3-(4-(3-(2-methylpyridin-4-yl)-3-oxo-1-o-tolylpropyl)phenyl)azetidine-1-carboxylate (283 mg, 601 µmol, Eq: 1.00) in dichloromethane (2 mL). The ice bath was removed, then after 2 h the reaction mixture was partitioned between sat. aq. sodium hydrogencarbonate solution and dichloromethane. The organic layer was washed with brine, dried over sodium sulfate, filtered, and evaporated to afford the title compound (258 mg, purity ca. 85%), which was used for the next step without purification. Off-white foam, MS (ESI$^+$): m/z=371.0 ([M+H]$^+$).

Step 2: (R,E)-3-(4-(Azetidin-3-yl)phenyl)-1-(2-methylpyridin-4-yl)-3-o-tolylpropan-1-one oxime In analogy to example 1, step 2, from (R)-3-(4-(azetidin-3-yl)phenyl)-1-(2-methylpyridin-4-yl)-3-o-tolylpropan-1-one and hydroxylamine hydrochloride in the presence of sodium hydrogencarbonate was prepared the title compound as a white foam, MS (ESI$^+$): m/z=386.0 ([M+H]$^+$).

Example 483

(R,E)-1-(3-(4-(3-Hydroxyimino)-3-(2-methylpyridin-4-yl)-1-o-tolylpropyl)phenyl)azetidin-1-yl)ethanone

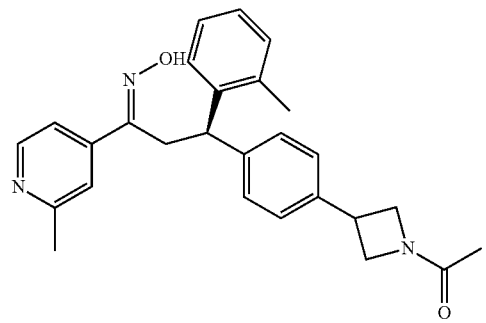 [SMILES: CC(=O)N1CC(c2ccc([C@@H](C/C(=N\O)c3ccnc(C)c3)c3ccccc3C)cc2)C1]

Step 1: (R)-3-(4-(1-Acetylazetidin-3-yl)phenyl)-1-(2-methylpyridin-4-yl)-3-o-tolylpropan-1-one Acetyl chloride (30 mg) was added at room temperature to a solution of (R)-3-(4-(azetidin-3-yl)phenyl)-1-(2-methylpyridin-4-yl)-3-o-tolylpropan-1-one (example 482, step 1; 70 mg) and N,N-diisopropylethylamine (98 mg) in dichloromethane (4 mL), then after 2 h the reaction mixture was partitioned between sat. aq. sodium hydrogencarbonate solution and dichloromethane. The organic layer was washed with brine, dried over sodium sulfate, filtered, and evaporated. Flash chromatography (silica gel, 10 g, 2% to 5% methanol in dichlormethane) produced the title compound (19 mg). Colourless oil, MS (ESI$^+$): m/z=413.0 [M+H]$^+$.

Step 2: (R,E)-1-(3-(4-(3-(Hydroxyimino)-3-(2-methylpyridin-4-yl)-1-o-tolylpropyl)phenyl)-azetidin-1-yl)ethanone In analogy to example 1, step 2, from (R)-3-(4-(1-acetylazetidin-3-yl)phenyl)-1-(2-methylpyridin-4-yl)-3-o-tolylpropan-1-one and hydroxylamine hydrochloride in the presence of sodium hydrogencarbonate was prepared the title compound as a colourless oil, MS (ESI$^+$): m/z=428.1 ([M+H]$^+$).

Example 484

(R,E)-1-(2-Methylpyridin-4-yl)-3-(4-(1-(methylsulfonyl)azetidin-3-yl)phenyl)-3-o-tolylpropan-1-one oxime

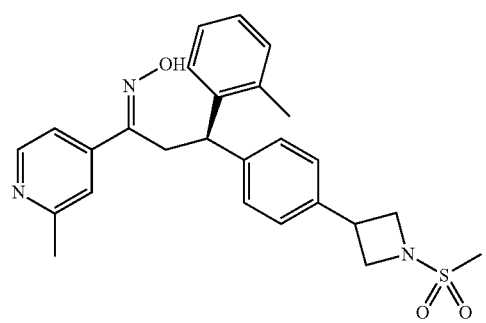 [SMILES: Cc1cc(/C(C[C@H](c2ccc(C3CN(S(C)(=O)=O)C3)cc2)c2ccccc2C)=N/O)ccn1]

Step 1: (R)-1-(2-Methylpyridin-4-yl)-3-(4-(1-methylsulfonyl)azetidin-3-yl)phenyl)-3-o-tolylpropan-1-one The title compound was produced in analogy with example 483, step 1 from (R)-3-(4-(azetidin-3-yl)phenyl)-1-(2-methylpyridin-4-yl)-3-o-tolylpropan-1-one (example 482, step 1) and methanesulfonyl chloride. Light yellow oil, MS (ESI⁺): m/z=449.0 ([M+H]⁺).

Step 2: (R,E)-1-(2-Methylpyridin-4-yl)-3-(4-(1-methylsulfonyl)azetidin-3-yl)phenyl)-3-o-tolylpropan-1-one oxime In analogy to example 1, step 2, from (R)-1-(2-methylpyridin-4-yl)-3-(4-(1-(methyl-sulfonyl)azetidin-3-yl)phenyl)-3-o-tolylpropan-1-one and hydroxylamine hydrochloride in the presence of sodium hydrogencarbonate was prepared the title compound as a colourless oil, MS (ESI⁺): m/z=464.1 ([M+H]⁺).

Example 485

(R,E)-3-(4-(3-(Hydroxyimino)-3-(2-methylpyridin-4-yl)-1-o-tolylpropyl)phenyl)azetidine-1-sulfonamide

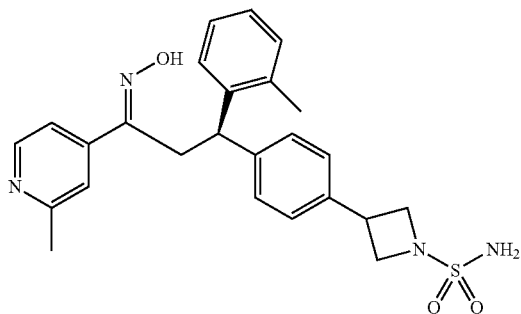 [SMILES: Cc1cc(/C(C[C@H](c2ccc(C3CN(S(N)(=O)=O)C3)cc2)c2ccccc2C)=N/O)ccn1]

Step 1: (R)-3-(4-(3-(2-Methylpyridin-4-yl)-3-oxo-1-o-tolylpropyl)phenyl)azetidine-1-sulfonamide The title compound was produced in analogy with example 480, step 2 from (R)-3-(4-(azetidin-3-yl)phenyl)-1-(2-methylpyridin-4-yl)-3-o-tolylpropan-1-one (example 482, step 1) and sulfamide. White foam, MS (ESI⁺): m/z=450.1 ([M+H]⁺).

Step 2: (R,E)-3-(4-(3-(Hydroxyimino)-3-(2-methylpyridin-4-yl)-1-o-tolylpropyl)phenyl)-azetidine-1-sulfonamide In analogy to example 1, step 2, from (R)-3-(4-(3-(2-methylpyridin-4-yl)-3-oxo-1-o-tolylpropyl)phenyl)azetidine-1-sulfonamide and hydroxylamine hydrochloride in the presence of sodium hydrogencarbonate was prepared the title compound as a white foam, MS (ESI⁺): m/z=465.3 ([M+H]⁺).

Example 486

(S,E)-5-(3-(4-bromophenyl)-1-(hydroxyimino)-3-o-tolylpropyl)-1-methylpyridin-2(1H)-one

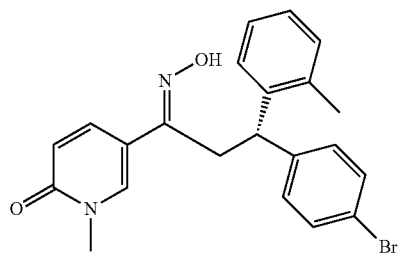 [SMILES: Cc1ccccc1[C@@H](C/C(=N\O)c1ccc(=O)n(C)c1)c1ccc(Br)cc1]

Step 1: (S)-3-(4-Bromophenyl)-1-(6-methoxypyridin-3-yl)-3-o-tolylpropan-1-one In analogy to example 151, step 1, 5-bromo-2-methoxypyridine was reacted first with n-butyllithium and later with (S)-3-(4-bromo-phenyl)-N-methoxy-N-methyl-3-o-tolyl-propionamide (example 142, step 1) to give the title compound as a colourless oil, MS (ESI⁺): m/z=410.1 [M+H]⁺.

Step 2: 5-[(S)-3-(4-Bromo-phenyl)-3-o-tolyl-propionyl]-1H-pyridin-2-one

In analogy to example 162, step 2, (S)-3-(4-bromophenyl)-1-(6-methoxypyridin-3-yl)-3-o-tolyl-propan-1-one was reacted with 37% aqueous hydrochloric acid solution in 1,4-dioxane to give the title compound as a light yellow foam, MS (ESI⁺): m/z=396.0 [M+H]⁺.

Step 3: 5-[(S)-3-(4-Bromo-phenyl)-3-o-tolyl-propionyl]-1-methyl-1H-pyridin-2-one In analogy to example 161, step 1, 5-[(S)-3-(4-bromo-phenyl)-3-o-tolyl-propionyl]-1H-pyridin-2-one was reacted with iodomethane in the presence of potassium carbonate to give the title compound as a white solid, MS (ESI⁺): m/z=410.1 [M+H]⁺.

Step 4: 5-{(S)-3-(4-Bromo-phenyl)-1-[(E)-hydroxyimino]-3-o-tolyl-propyl}-1-methyl-1H-pyridin-2-one In analogy to example 151, step 3, 5-[(S)-3-(4-bromo-phenyl)-3-o-tolyl-propionyl]-1-methyl-1H-pyridin-2-one was reacted with hydroxylamine hydrochloride in the pres-

Example 487

(S,E)-4-(4-(3-(hydroxyimino)-3-(1-methyl-6-oxo-1,6-dihydropyridin-3-yl)-1-o-tolylpropyl)-phenyl)cyclohexanecarboxylic acid

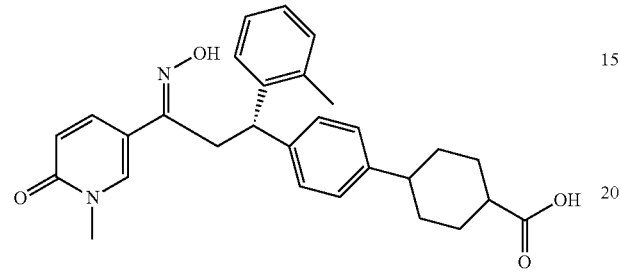

Step 1: 4-(Ethoxycarbonyl)-1-cyclohexylzinc(II) iodide

The title compound was produced as a ca. 0.5 M solution in N,N-dimethylacetamide in analogy with example 481, step 1 from 4-iodo-cyclohexanecarboxylic acid ethyl ester (CAS RN 524734-42-7) and zinc.

Step 2: (S)-Ethyl 4-(4-(3-(1-methyl-6-oxo-1,6-dihydropyridin-3-yl)-3-oxo-1-o-tolylpropyl)-phenyl)cyclohexanecarboxylate The title compound was produced in analogy to example 378, step 1 from 5-[(S)-3-(4-Bromo-phenyl)-3-o-tolyl-propionyl]-1-methyl-1H-pyridin-2-one (example 486, step 3) and 4-(ethoxycarbonyl)-1-cyclohexylzinc(II) iodide. Light brown oil, MS (ESI+): m/z=486.3 [M+H]+.

Step 3: (S)-4-(4-(3-(1-Methyl-6-oxo-1,6-dihydropyridin-3-yl)-3-oxo-1-o-tolylpropyl)phenyl)-cyclohexanecarboxylic acid The title compound was produced in analogy to example 169, step 2 from (S)-ethyl 4-(4-(3-(1-methyl-6-oxo-1,6-dihydropyridin-3-yl)-3-oxo-1-o-tolylpropyl)phenyl)cyclohexane-carboxylate. Light yellow foam, MS (ESI−): m/z=456.1 [M−H]−.

Step 4: (S,E)-4-(4-(3-(Hydroxyimino)-3-(1-methyl-6-oxo-1,6-dihydropyridin-3-yl)-1-o-tolylpropyl)-phenyl)cyclohexanecarboxylic acid In analogy to example 1, step 2, from (S)-4-(4-(3-(1-methyl-6-oxo-1,6-dihydropyridin-3-yl)-3-oxo-1-o-tolylpropyl)phenyl)cyclohexanecarboxylic acid and hydroxylamine hydrochloride in the presence of sodium hydrogencarbonate was prepared the title compound as a white foam, MS (ESI−): m/z=471.4 [M−H]−.

Examples 488 and 489

Trans-4-(4-((S,E)-3-(Hydroxyimino)-3-(1-methyl-6-oxo-1,6-dihydropyridin-3-yl)-1-o-tolylpropyl)phenyl)cyclohexanecarboxylic acid And cis-4-(4-((S,E)-3-(hydroxyimino)-3-(1-methyl-6-oxo-1,6-dihydropyridin-3-yl)-1-o-tolylpropyl)phenyl)cyclohexanecarboxylic acid HPLC separation of (S,E)-4-(4-(3-(hydroxyimino)-3-(1-methyl-6-oxo-1,6-dihydro-pyridin-3-yl)-1-o-tolylpropyl)-phenyl)cyclohexanecarboxylic acid (example 487; 99 mg) on a Chiralpak AD-H column (heptane/ethanol/formic acid 60:40:0.2) produced trans-4-(4-((S,E)-3-(hydroxyimino)-3-(1-methyl-6-oxo-1,6-dihydropyridin-3-yl)-1-o-tolylpropyl)phenyl)-cyclohexanecarboxylic acid (40 mg, 40%; white foam, MS (D) 472.2 (M+)) and cis-4-(4-((S,E)-3-(hydroxyimino)-3-(1-methyl-6-oxo-1,6-dihydropyridin-3-yl)-1-o-tolylpropyl)phenyl)-cyclohexanecarboxylic acid (55 mg, 56%; white foam, MS (D) 472.2 (M+)).

Example 490

(R,E)-4-(4-(3-(Hydroxyimino)-3-(2-methylpyridin-4-yl)-1-o-tolylpropyl)phenyl)-cyclohexanecarboxylic acid Step 1: (R)-Ethyl 4-(4-(3-(2-methylpyridin-4-yl)-3-oxo-1-o-tolylpropyl)phenyl)-cyclohexanecarboxylate The title compound was produced in analogy to example 378, step 1 from (R)-3-(4-bromophenyl)-1-(2-methylpyridin-4-yl)-3-o-tolylpropan-1-one (example 142, step 2) and 4-(ethoxycarbonyl)-1-cyclohexylzinc(II) iodide (example 487, step 1). Orange oil, MS (ESI⁺): m/z=470.1 ([M+H]⁺).

Step 2: (R)-4-(4-(3-(2-Methylpyridin-4-yl)-3-oxo-1-o-tolylpropyl)phenyl)cyclohexanecarboxylic acid The title compound was produced in analogy to example 169, step 2 from (R)-ethyl 4-(4-(3-(2-methylpyridin-4-yl)-3-oxo-1-o-tolylpropyl)phenyl)cyclohexanecarboxylate. Yellow foam, MS (ESI⁺): m/z=442.0 ([M+H]⁺).

Step 3: (R,E)-4-(4-(3-(Hydroxyimino)-3-(2-methylpyridin-4-yl)-1-o-tolylpropyl)-phenyl)cyclohexanecarboxylic acid In analogy to example 132, step 6, from(R)-4-(4-(3-(2-methylpyridin-4-yl)-3-oxo-1-o-tolylpropyl)phenyl)cyclohexanecarboxylic acid and hydroxylamine hydrochloride in the presence of sodium hydrogencarbonate was prepared the title compound as a light yellow foam, MS (ESI⁺): m/z=457.2 ([M+H]⁺).

Examples 491 and 492

Trans-4-{4-[(R)-3-[(E)-Hydroxyimino]-3-(2-methyl-pyridin-4-yl)-1-o-tolyl-propyl]-phenyl}-cyclohexanecarboxylic acid

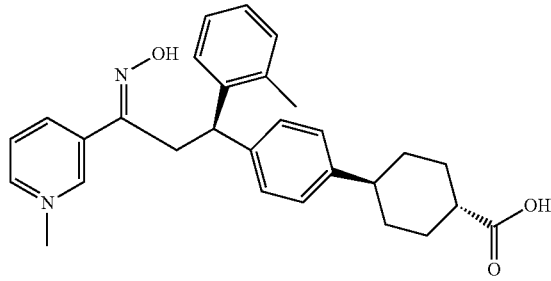

And cis-4-{4-[(R)-3-[(E)-hydroxyimino]-3-(2-methyl-pyridin-4-yl)-1-o-tolyl-propyl]-phenyl}-cyclohexanecarboxylic acid

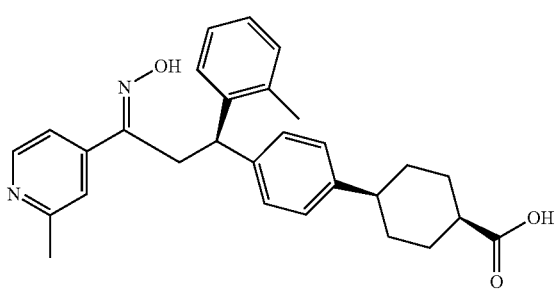 [SMILES: Cc1cc(/C(C[C@H](c2ccc([C@H]3CC[C@@H](C(=O)O)CC3)cc2)c2ccccc2C)=N/O)ccn1]

HPLC separation of (R,E)-4-(4-(3-(hydroxyimino)-3-(2-methylpyridin-4-yl)-1-o-tolylpropyl)phenyl)cyclohexanecarboxylic acid (example 490; 107 mg) on a Chiralpak AD-H column (heptane/ethanol/formic acid 90:10:0.05) produced trans-4-{4-[(R)-3-[(E)-hydroxy-imino]-3-(2-methyl-pyridin-4-yl)-1-o-tolyl-propyl]-phenyl}-cyclohexanecarboxylic acid (32 mg, 29%; white foam, MS (ESI⁺): m/z=457.2 [M+H]⁺) and cis-4-{4-[(R)-3-[(E)-hydroxy-imino]-3-(2-methyl-pyridin-4-yl)-1-o-tolyl-propyl]-phenyl}-cyclohexanecarboxylic acid (32 mg, 29%; white foam, MS (ESI⁺): m/z=457.2 [M+H]⁺).

Example 493

(R,E)-2-(4-(3-(Hydroxyimino)-3-(1-methyl-6-oxo-1,6-dihydropyridin-3-yl)-1-o-tolylpropyl)phenyl)acetic acid

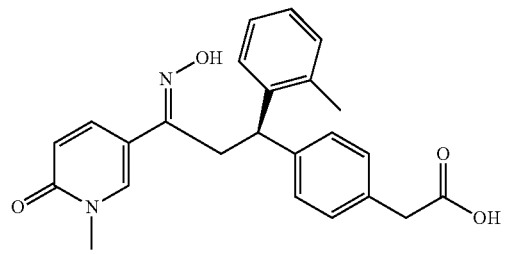 [SMILES: Cc1ccccc1[C@H](C/C(=N\O)c1ccc(=O)n(C)c1)c1ccc(CC(=O)O)cc1]

Step 1: (R)-2-(4-(3-(1-Methyl-6-oxo-1,6-dihydropyridin-3-yl)-3-oxo-1-o-tolylpropyl)phenyl)-acetic acid The title compound was produced in analogy to example 288, step 1 from 5-[(R)-3-(4-bromo-phenyl)-3-o-tolyl-propionyl]-1-methyl-1H-pyridin-2-one (example 223, step 3) and ethyl cyanoacetate. Off-white foam, MS (ESI⁺): m/z=390.3 [M+H]⁺.

Step 2: (R,E)-2-(4-(3-(Hydroxyimino)-3-(1-methyl-6-oxo-1,6-dihydropyridin-3-yl)-1-o-tolylpropyl)phenyl)acetic acid In analogy to example 1, step 2, from and (R)-2-(4-(3-(1-methyl-6-oxo-1,6-dihydropyridin-3-yl)-3-oxo-1-o-tolylpropyl)phenyl)acetic acid hydroxylamine hydrochloride in the presence of sodium hydrogencarbonate was prepared the title compound as an off-white solid, MS (ESI⁺): m/z=405.4 [M+H]⁺.

Examples 494 and 495

(R,E)-5-(1-(Hydroxyimino)-3-(4-(methylsulfonyl)phenyl)-3-o-tolylpropyl)-1-methylpyridin-2(1H)-one

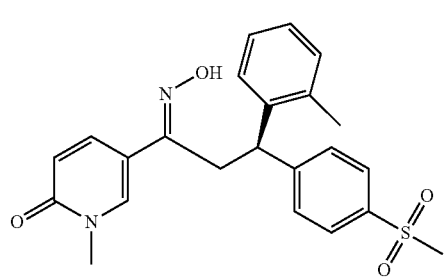 [SMILES: Cc1ccccc1[C@H](C/C(=N\O)c1ccc(=O)n(C)c1)c1ccc(S(C)(=O)=O)cc1]

And (R,Z)-5-(1-(hydroxyimino)-3-(4-(methylsulfonyl)phenyl)-3-o-tolylpropyl)-1-methylpyridin-2(1H)-one

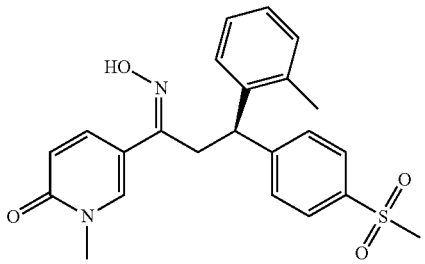 [SMILES: Cc1ccccc1[C@H](C/C(=N/O)c1ccc(=O)n(C)c1)c1ccc(S(C)(=O)=O)cc1]

Step 1: (R)-1-Methyl-5-(3-(4-(methylsulfonyl)phenyl)-3-o-tolylpropanoyl)pyridin-2(1H)-one L-proline (44.9 mg, 390 µmol) was combined with dimethyl sulfoxide (5 mL), then sodium hydroxide (15.6 mg, 390 µmol) was added and the reaction stirred at room temperature for 30 min. Then (R)-5-(3-(4-bromophenyl)-3-o-tolylpropanoyl)-1-methylpyridin-2(1H)-one (example 223, step 3; 200 mg, 487 µmol), sodium methanesulfinate (410 mg, 3.9 mmol) and copper(I) iodide (74.3 mg, 390 µmol) were added. The reaction mixture was heated at 120° C. for 21 h, then partitioned between water and ethyl acetate. The organic layer was washed with brine, dried over magnesium sulfate and evaporated. Chromatography (SiO$_2$; gradient ethyl acetate/heptane 1:1 to ethyl acetate) afforded the title compound (176 mg, 88%). White foam, MS (ESI$^+$): m/z=: 410.2 [M+H]$^+$.

Step 2: (R)-5-(1-(Hydroxyimino)-3-(4-(methylsulfonyl)phenyl)-3-o-tolylpropyl)-1-methylpyridin-2(1H)-one To a microwave vial was added (R)-1-methyl-5-(3-(4-(methylsulfonyl)phenyl)-3-o-tolylpropanoyl)pyridin-2(1H)-one (168 mg, 410 µmol), hydroxylamine hydrochloride (85.5 mg, 1.23 mmol) and sodium hydrogencarbonate (103 mg, 1.23 mmol) in ethanol (3 mL) and water (0.2 mL). The vial was capped and heated in the microwave at 120° C. for 15 min. The reaction mixture was diluted with ethyl acetate and poured onto water. The organic layer was washed with brine, dried over magnesium sulfate and evaporated to afforded the title compound (169 mg, 97%) as a mixture of the E and Z isomers (ratio ca. 85:15). Light yellow foam, MS (ESI$^+$): m/z=425.2 [M+H]$^+$.

Step 3: (R,E)-5-(1-(Hydroxyimino)-3-(4-(methylsulfonyl)phenyl)-3-o-tolylpropyl)-1-methylpyridin-2(1H)-one and (R,Z)-5-(1-(hydroxyimino)-3-(4-(methylsulfonyl)phenyl)-3-o-tolylpropyl)-1-methylpyridin-2(1H)-one HPLC separation of (R)-5-(1-(hydroxyimino)-3-(4-(methylsulfonyl)phenyl)-3-o-tolylpropyl)-1-methylpyridin-2(1H)-one (168 mg) using a Chiralpak AD column (heptane/ethanol 3:2) produced (R,E)-5-(1-(hydroxyimino)-3-(4-(methylsulfonyl)phenyl)-3-o-tolylpropyl)-1-methylpyridin-2(1H)-one (130 mg, 77%; light yellow foam, MS (ESI$^+$): m/z=425.2 [M+H]$^+$) and (R,Z)-5-(1-(hydroxyimino)-3-(4-(methylsulfonyl)phenyl)-3-o-tolylpropyl)-1-methylpyridin-2(1H)-one (18 mg, 11%; light yellow solid, MS (ESI$^+$): m/z=425.2 [M+H]$^+$).

Example 496

5-[(S)-1-[(E)-Hydroxyimino]-3-(4-methanesulfonylphenyl)-3-o-tolyl-propyl]-1-methyl-1H-pyridin-2-one

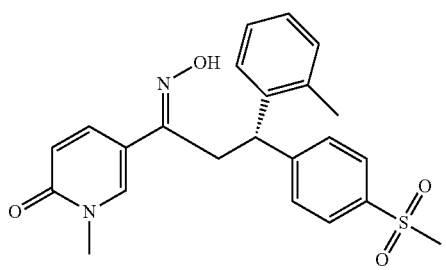 [SMILES: Cc1ccccc1[C@@H](C/C(=N\O)c1ccc(=O)n(C)c1)c1ccc(S(C)(=O)=O)cc1]

Step 1: (S)-1-Methyl-5-(3-(4-(methylsulfonyl)phenyl)-3-o-tolylpropanoyl)pyridin-2(1H)-one The title compound was produced in analogy to example 495, step 1 from (S)-5-(3-(4-bromophenyl)-3-o-tolylpropanoyl)-1-methylpyridin-2(1H)-one (example 486, step 3). White foam, MS (ESI$^+$): m/z=: 410.3 [M+H]$^+$.

Step 2: 5-[(S)-1-[(E)-Hydroxyimino]-3-(4-methanesulfonyl-phenyl)-3-o-tolyl-propyl]-1-methyl-1H-pyridin-2-one To a microwave vial was added (R)-1-methyl-5-(3-(4-(methylsulfonyl)phenyl)-3-o-tolylpropanoyl)pyridin-2(1H)-one (168 mg, 410 µmol), hydroxylamine hydrochloride (85.5 mg, 1.23 mmol) and sodium hydrogencarbonate (103 mg, 1.23 mmol) in ethanol (3 mL) and water (0.2 mL). The vial was capped and heated at 120° C. for 15 min. The reaction mixture was diluted with ethyl acetate and poured onto water. The organic layer was washed with brine, dried over magnesium sulfate and evaporated to afforded the title compound (169 mg, 97%) as a mixture of the E and Z isomers (ratio ca. 85:15). Light yellow foam, MS (ESI$^+$): m/z=425.2 [M+H]$^+$.

Example 497

Sodium (R,E)-1-(4-(3-(Hydroxyimino)-3-(1-methyl-6-oxo-1,6-dihydropyridin-3-yl)-1-o-tolylpropyl)phenyl)piperidine-4-carboxylate

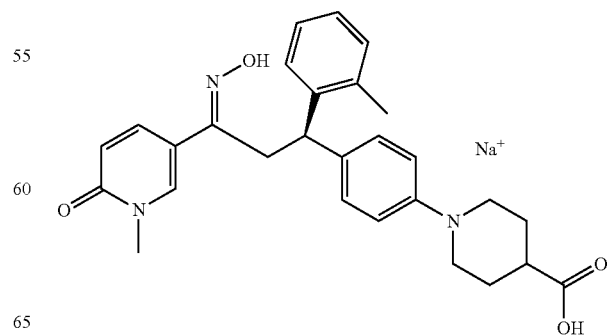

Step 1: (R)-1-(4-(3-(1-Methyl-6-oxo-1,6-dihydropyridin-3-yl)-3-oxo-1-o-tolylpropyl)phenyl)piperidine-4-carboxylic acid To a solution of (R)-5-(3-(4-bromophenyl)-3-o-tolylpropanoyl)-1-methylpyridin-2(1H)-one (example 223, step 3; 500 mg, 1.22 mmol) in toluene (7 mL) was added ethyl piperidine-4-carboxylate (293 mg, 1.83 mmol), sodium tert-butoxide (234 mg, 2.44 mmol), tris(di-benzylideneacetone) dipalladium(0) (22.3 mg, 24.4 μmol) and 2-dicyclohexylphosphino-2',4',6'-triisopropylbiphenyl (23.7 mg, 48.7 μmol) and the reaction mixture was stirred for 1 h at 85° C. The reaction mixture was evaporated and the residue chromatographed to afford the title compound (101 mg, 18%; light yellow foam, MS (ESI⁻): m/z=: 457.4 [M−H]⁻) and (R)-methyl 1-(4-(3-(1-methyl-6-oxo-1,6-dihydropyridin-3-yl)-3-oxo-1-o-tolylpropyl)phenyl)piperidine-4-carboxylate (174 mg, 30%; light yellow foam, MS (ESI⁺): m/z=: 487.4 [M+H]⁺).

Step 2: Sodium (R,E)-1-(4-(3-(hydroxyimino)-3-(1-methyl-6-oxo-1,6-dihydropyridin-3-yl)-1-o-tolylpropyl)phenyl)piperidine-4-carboxylate To a microwave vial was added (R)-1-(4-(3-(1-methyl-6-oxo-1,6-dihydropyridin-3-yl)-3-oxo-1-o-tolylpropyl)phenyl)piperidine-4-carboxylic acid (100 mg, 218 μmol), hydroxylamine hydrochloride (45.5 mg, 654 μmol) and sodium hydrogencarbonate (91.6 mg, 1.09 mmol) in ethanol (2 mL) and water (0.2 mL). The vial was capped and heated at 120° C. for 15 min, then hydroxylamine hydrochloride (45.5 mg, 654 μmol) and sodium hydrogencarbonate (91.6 mg, 1.09 mmol) were added again. The vial was capped and heated at 120° C. for 10 min, then the reaction mixture was evaporated. The residue was washed with dichloromethane, then suspended in dichloromethane/methanol 9:1 and filtered. The filtrate was concentrated and purified by chromatography (SiO₂; gradient dichloromethane/methanol 19:1 to dichloro-methane/methanol 4:1) to afford the title compound (66 mg, 61%). Light brown solid, MS (ESI⁻): m/z=472.4 (M−H)⁻.

Examples 498 and 499

(R,E)-4-(3-(Hydroxyimino)-3-(1-methyl-6-oxo-1,6-dihydropyridin-3-yl)-1-o-tolylpropyl)benzonitrile

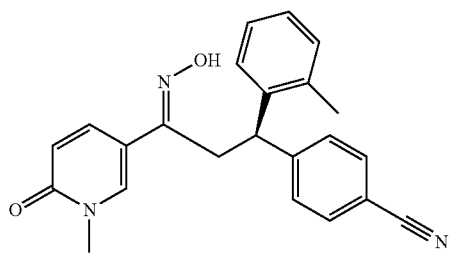 [SMILES: Cc1ccccc1[C@H](C/C(=N\O)c1ccc(=O)n(C)c1)c1ccc(C#N)cc1]

And (R,Z)-4-(3-(hydroxyimino)-3-(1-methyl-6-oxo-1,6-dihydropyridin-3-yl)-1-o-tolylpropyl)benzonitrile

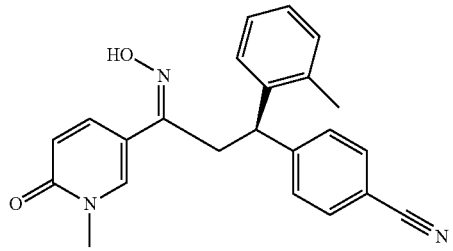 [SMILES: Cc1ccccc1[C@H](C/C(=N/O)c1ccc(=O)n(C)c1)c1ccc(C#N)cc1]

To a microwave vial was added (R)-5-(3-(4-bromophenyl)-1-(hydroxyimino)-3-o-tolylpropyl)-1-methylpyridin-2(1H)-one (example 223; 98 mg, 230 μmol), 1,1'-bis(diphenyl-phosphino)ferrocene (3.83 mg, 6.91 μmol), tris(dibenzylideneacetone)dipalladium(0) (2.11 mg, 2.3 μmol), zinc cyanide (14.9 mg, 127 μmol), zinc (0.6 mg, 9 μmol) and zinc acetate (1.69 mg, 9.22 μmol) in N,N-dimethylformamide (1.5 mL) and water (15 μl). The vial was capped and heated at 180° C. for 35 min, then at 200° C. for 10 min, then the reaction mixture was concentrated in vacuo and the residue purified by chromatography (SiO₂, gradient dichloro-methane to dichloromethane/methanol/25% aq. ammonia solution 95:5:0.25) to produce (R,E)-4-(3-(hydroxyimino)-3-(1-methyl-6-oxo-1,6-dihydropyridin-3-yl)-1-o-tolylpropyl)benzonitrile (8 mg, 9%; dark brown gum, MS (ESI⁺): m/z=: 372.2 [M+H]⁺) and (R,Z)-4-(3-(hydroxyimino)-3-(1-methyl-6-oxo-1,6-dihydropyridin-3-yl)-1-o-tolylpropyl)benzonitrile (6 mg, 6%; dark brown gum, MS (ESI⁺): m/z=: 372.2 [M+H]⁺).

Example 500

(R,E)-5-(3-(4-(1H-Tetrazol-5-yl)phenyl)-1-(hydroxyimino)-3-o-tolylpropyl)-1-methyl-pyridin-2(1H)-one, sodium salt

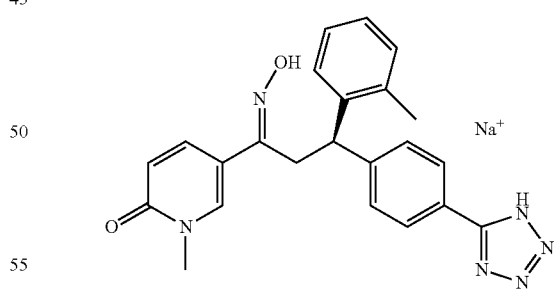

Step 1: (R)-5-(3-(4-(1H-Tetrazol-5-yl)phenyl)-3-o-tolylpropanoyl)-1-methylpyridin-2(1H)-one To a solution of (R)-4-(3-(1-methyl-6-oxo-1,6-dihydropyridin-3-yl)-3-oxo-1-o-tolyl-propyl)benzonitrile (60 mg, 168 μmol) in N,N-dimethylformamide (1 mL) was added sodium azide (54.7 mg, 842 μmol) and ammonium chloride (45.0 mg, 842 μmol). The reaction mixture was heated to 80° C. for 24 h, then another portion of sodium azide (54.7 mg, 842 μmol)

and ammonium chloride (45.0 mg, 842 μmol) was added and the reaction mixture was stirred at 80° C. for another 72 h, then concentrated in vacuo. The residue was suspended in dichloro-methane/methanol 19:1, filtered, and the filtrate was purified by chromatography (SiO₂, gradient dichloromethane to dichloromethane/methanol 9:1) afforded the product as a salt. This was partitioned between ethyl acetate and 1 M aq. hydrochloric acid solution. After removal of the aqueous layer, the organic layer was dried over magnesium sulfate, filtered, evaporated and precipitated with dichloromethane and heptane to produce the title compound (25 mg, 37%). White solid, MS (ESI⁺): m/z=: 400.2 [M+H]⁺.

Step 2: (R,E)-5-(3-(4-(1H-Tetrazol-5-yl)phenyl)-1-(hydroxyimino)-3-o-tolylpropyl)-1-methylpyridin-2(1H)-one, sodium salt To a microwave vial was added (R)-5-(3-(4-(1H-tetrazol-5-yl)phenyl)-3-o-tolyl-propanoyl)-1-methylpyridin-2(1H)-one (22 mg, 55.1 μmol), hydroxylamine hydrochloride (11.5 mg, 165 μmol) and sodium hydrogen (23.1 mg, 275 μmol) in ethanol (0.5 mL) and water (50 μl). The vial was capped and heated at 120° C. for 15 min, then the reaction mixture was evaporated. Chromatography (SiO₂, gradient dichloromethane/methanol 9:1 to dichloromethane/methanol 4:1), followed by precipitation with dichloromethane and heptane afforded the title compound (11 mg, 46%). Off-white solid MS (ESI⁺): m/z=: 415.2 [M+H]⁺.

Example 501

(S,E)-5-(3-(4-Bromophenyl)-1-(hydroxyimino)-3-o-tolylpropyl)-1-methylpyrimidin-2(1H)-one

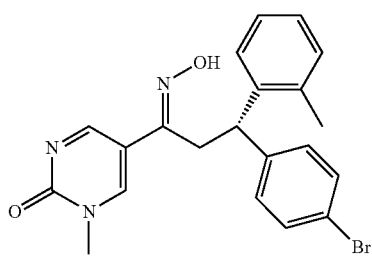 [SMILES: Cc1ccccc1[C@@H](C/C(=N\O)c1cnc(=O)n(C)c1)c1ccc(Br)cc1]

Step 1: (S)-3-(4-Bromophenyl)-1-(2-methoxypyrimidin-5-yl)-3-o-tolylpropan-1-one

A solution of n-butyllithium (1.6 M in hexane, 3.31 mL, 5.3 mmol) in tetrahydrofuran (12 mL) was cooled to −95° C. and added dropwise, under nitrogen, to a stirred, cooled (−95° C.) solution of 5-bromo-2-methoxypyrimidine (1.00 g, 5.3 mmol) in dry tetrahydrofuran (40 mL). To the resulting yellow solution was immediately added a solution of (S)-3-(4-bromophenyl)-N-methoxy-N-methyl-3-o-tolylpropanamide (example 142, step 1; 1.6 g, 4.42 mmol) in dry THF (12 mL), with the temperature of the reaction mixture being kept between −90° C. and −100° C. The solution was stirred and allowed to warm to room temperature over 2 h. The reaction mixture was poured onto sat. aq. ammonium chloride solution and extracted with ethyl acetate. The organic layer was washed with brine dried over magnesium sulfate, filtered, and evaporated. Chromatography (SiO₂; heptane-ethyl acetate gradient) produced the title compound (700 mg, 35%), Colourless gum, MS (ESI⁺): m/z=: 411.2 [M+H]⁺.

Step 2: (5)-5-(3-(4-Bromophenyl)-3-o-tolylpropanoyl)pyrimidin-2(1H)-one

To a solution of (S)-3-(4-bromophenyl)-1-(2-methoxypyrimidin-5-yl)-3-o-tolylpropan-1-one (700 mg, 1.53 mmol, Eq: 1.00) in dioxane (18 mL) was added 37% aq. hydrochloric acid solution (2.56 mL, 30.6 mmol) and the resulting solution was first stirred at ambient temperature for 45 min and then 2½ h at 60° C., then poured onto sat. aq. sodium hydrogencarbonate solution and ethyl acetate. The organic layer was washed with brine, dried over magnesium sulfate, filtered, and evaporated. Chromatography (SiO₂; gradient dichloromethane to dichloro-methane/methanol/25% aq. ammonia solution 90:10:0.25) produced the title compound (592 mg, 97%). White solid, MS (ESI⁺): m/z=: 397.0 [M+H]⁺.

Step 3: (S)-5-(3-(4-Bromophenyl)-3-o-tolylpropanoyl)-1-methylpyrimidin-2(1H)-one The title compound was produced in analogy to example 161, step 1 from (S)-5-(3-(4-bromophenyl)-3-o-tolylpropanoyl)pyrimidin-2(1H)-one and iodomethane. Off-white solid, MS (ESI⁺): m/z=: 411.1 [M+H]⁺.

Step 4: (S,E)-5-(3-(4-Bromophenyl)-1-(hydroxyimino)-3-o-tolylpropyl)-1-methylpyrimidin-2(1H)-one The title compound was produced in analogy to examples 494 and 495, step 2 from (S)-5-(3-(4-bromophenyl)-3-o-tolylpropanoyl)-1-methylpyrimidin-2(1H)-one and hydroxylamine hydrochloride. White solid, MS (ESI⁺): m/z=: 426.0 [M+H]⁺.

Example 502

(S,E)-5-(1-(Hydroxyimino)-3-(4-(methylsulfonyl)phenyl)-3-o-tolylpropyl)-1-methyl-pyrimidin-2(1H)-one

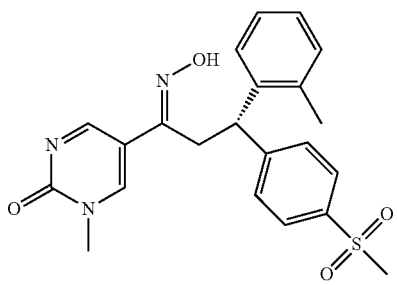 [SMILES: Cc1ccccc1[C@@H](C/C(=N\O)c1cnc(=O)n(C)c1)c1ccc(S(C)(=O)=O)cc1]

Step 1: (S)-1-Methyl-5-(3-(4-(methylsulfonyl)phenyl)-3-o-tolylpropanoyl)pyrimidin-2(1H)-one The title compound was produced in analogy to examples 494 and 495, step 1 from (S)-5-(3-(4-bromophenyl)-3-o-tolylpropanoyl)-1-methylpyrimidin-2(1H)-one (example 501, step 3). Light brown solid, MS (ESI⁺): m/z=: 411.1 [M+H]⁺.

Step 2: (S,E)-5-(1-(Hydroxyimino)-3-(4-(methylsulfonyl)phenyl)-3-o-tolylpropyl)-1-methyl-pyrimidin-2(1H)-one The title compound was produced in analogy to examples 494 and 495, step 2 from (S)-1-methyl-5-(3-(4-(methylsulfonyl)phenyl)-3-o-tolylpropanoyl)pyrimidin-2(1H)-one and hydroxyl-amine hydrochloride. White solid, MS (ESI+): m/z=: 426.0 [M+H]+.

Example 503

(R,E)-4-(4-(1-(4-Chloro-2-methylphenyl)-3-(hydroxyimino)-3-(2-methylpyridin-4-yl)propyl)phenyl)cyclohexanecarboxylic acid

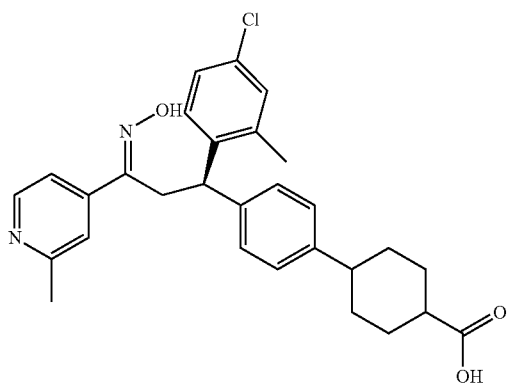 [SMILES: Cc1cc(/C(C[C@H](c2ccc(C3CCC(C(=O)O)CC3)cc2)c2ccc(Cl)cc2C)=N/O)ccn1]

Step 1: (R)-Ethyl 4-(4-(1-(4-chloro-2-methylphenyl)-3-(2-methylpyridin-4-yl)-3-oxopropyl)phenyl)cyclohexanecarboxylate The title compound was produced in analogy to example 378, step 1 from (R)-3-(4-bromo-phenyl)-3-(4-chloro-2-methyl-phenyl)-1-(2-methyl-pyridin-4-yl)-propan-1-one (example 282, step 1) and 4-(ethoxycarbonyl)-1-cyclohexylzinc (II) iodide (example 487, step 1). Brown gum, MS (ESI+): m/z=: 504.3 [M+H]+.

Step 2: (R)-4-(4-(1-(4-Chloro-2-methylphenyl)-3-(2-methylpyridin-4-yl)-3-oxopropyl)phenyl)cyclohexanecarboxylic acid The title compound was produced in analogy to example 169, step 2 from (R)-ethyl 4-(4-(1-(4-chloro-2-methylphenyl)-3-(2-methylpyridin-4-yl)-3-oxopropyl)phenyl)cyclohexane-carboxylate. Yellow gum, MS (ESI+): m/z=: 476.2 [M+H]+.

Step 3: (R,E)-4-(4-(1-(4-Chloro-2-methylphenyl)-3-(hydroxyimino)-3-(2-methylpyridin-4-yl)propyl)phenyl)cyclohexanecarboxylic acid The title compound was produced in analogy to examples 494 and 495, step 2 from (R)-4-(4-(1-(4-chloro-2-methylphenyl)-3-(2-methylpyridin-4-yl)-3-oxopropyl)phenyl)cyclohexane-carboxylic acid and hydroxylamine hydrochloride. Light yellow foam, MS (ESI+): m/z=: 491.2 [M+H]+.

Examples 504 and 505

Trans-4-(4-((R,E)-1-(4-Chloro-2-methylphenyl)-3-(hydroxyimino)-3-(2-methylpyridin-4-yl)propyl)phenyl)cyclohexanecarboxylic acid

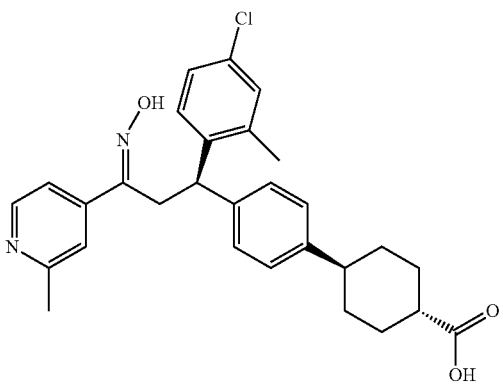 [SMILES: Cc1cc(/C(C[C@H](c2ccc([C@H]3CC[C@H](C(=O)O)CC3)cc2)c2ccc(Cl)cc2C)=N/O)ccn1]

And cis-4-(4-((R,E)-1-(4-chloro-2-methylphenyl)-3-(hydroxyimino)-3-(2-methylpyridin-4-yl)propyl)phenyl)cyclohexanecarboxylic acid

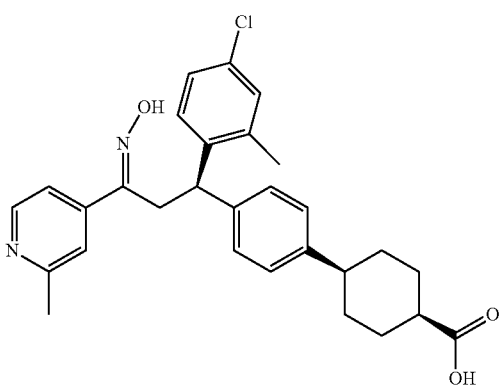 [SMILES: Cc1cc(/C(C[C@H](c2ccc([C@H]3CC[C@@H](C(=O)O)CC3)cc2)c2ccc(Cl)cc2C)=N/O)ccn1]

HPLC separation of (R,E)-4-(4-(1-(4-chloro-2-methylphenyl)-3-(hydroxyimino)-3-(2-methylpyridin-4-yl)propyl)phenyl)cyclohexanecarboxylic acid (185 mg) on a Reprosil Chiral NR column (heptane/ethanol/formic acid 90:10:0.05) produced trans-4-(4-((R,E)-1-(4-chloro-2-methylphenyl)-3-(hydroxyimino)-3-(2-methylpyridin-4-yl)propyl)phenyl)cyclohexanecarboxylic acid (56 mg, 30%; white solid, MS (ESI+): m/z=: 491.2 [M+H]+) and cis-4-(4-((R,E)-1-(4-chloro-2-methylphenyl)-3- (hydroxyimino)-3-(2-methylpyridin-4-yl)propyl)phenyl)cyclohexane-carboxylic acid (75 mg, 39%; white solid, MS (ESI+): m/z=: 491.2 [M+H]+).

Example 506

(R,E)-tert-Butyl 4-(4-(3-(hydroxyimino)-3-(1-methyl-6-oxo-1,6-dihydropyridin-3-yl)-1-o-tolylpropyl) phenyl)piperidine-1-carboxylate

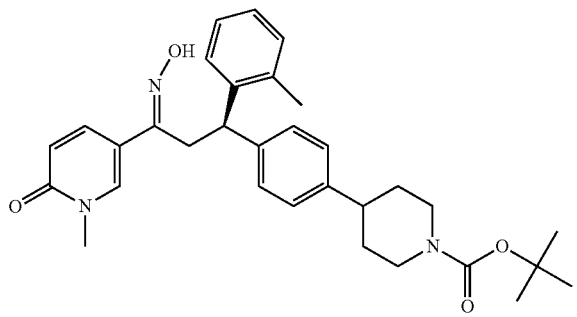 [SMILES: Cc1ccccc1[C@H](C/C(=N\O)c1ccc(=O)n(C)c1)c1ccc(C2CCN(C(=O)OC(C)(C)C)CC2)cc1]

Step 1: (R)-tert-Butyl 4-(4-(3-(methoxy(methyl) amino)-3-oxo-1-o-tolylpropyl)phenyl)-piperidine-1-carboxylate The title compound was produced in analogy to example 378, step 1 from (R)-3-(4-bromophenyl)-N-methoxy-N-methyl-3-o-tolylpropanamide (example 142, step 1) and (1-(tert-butoxycarbonyl)piperidin-4-yl)zinc(II) iodide. Dark brown gum, MS (ESI+): m/z=467.3 ([M+H]+).

Step 2: (R)-tert-Butyl 4-(4-(3-(6-methoxypyridin-3-yl)-3-oxo-1-o-tolylpropyl)phenyl)piperidine-1-carboxylate The title compound was produced in analogy example 151, step 1 from (R)-tert-butyl 4-(4-(3-(methoxy(methyl)amino)-3-oxo-1-o-tolylpropyl)phenyl)piperidine-1-carboxylate and 5-bromo-2-methoxypyridine. Light yellow foam, MS (ESI+): m/z=515.4 ([M+H]+).

Step 3: (R)-tert-Butyl 4-(4-(3-oxo-3-(6-oxo-1,6-dihydropyridin-3-yl)-1-o-tolylpropyl)phenyl)-piperidine-1-carboxylate A solution of (R)-tert-butyl 4-(4-(3-(6-methoxypyridin-3-yl)-3-oxo-1-o-tolylpropyl)-phenyl)piperidine-1-carboxylate (260 mg, 505 µmol), hydrogen chloride solution (4.0 M in 1,4-dioxane, 3.03 mL, 12.1 mmol) and water (0.5 mL) was heated to 100° C., then after 90 min the reaction mixture was purged with argon and concentrated to afford (R)-5-(3-(4-(piperidin-4-yl)phenyl)-3-o-tolylpropanoyl)pyridin-2(1H)-one hydrochloride (272 mg, light yellow foam, MS (ESI+): m/z=: 401.4 [M+H]+). This was taken up in dichloromethane (4 mL) and N,N-dimethylformamide (0.4 mL), then after addition of N,N-diisopropylethylamine (326 mg, 2.53 mmol) and a solution of di-tert-butyl-dicarbonate (121 mg, 0.56 mmol) at 0° C. After 30 min the reaction mixture was partitioned between sat. aq. sodium hydrogencarbonate solution and ethyl acetate. The organic layer was washed with brine, dried over magnesium sulfate, and evaporated. Chromatography (SiO2; gradient ethyl acetate/heptane 1:1 to ethyl acetate) afforded the title compound (204 mg, 81%). Light yellow foam, MS (ESI+): m/z=: 501.1 [M+H]+.

Step 4: (R)-tert-Butyl 4-(4-(3-(1-methyl-6-oxo-1,6-dihydropyridin-3-yl)-3-oxo-1-o-tolylpropyl)phenyl) piperidine-1-carboxylate The title compound was produced in analogy to example 161, step 1 from (R)-tert-butyl 4-(4-(3-oxo-3-(6-oxo-1,6-dihydropyridin-3-yl)-1-o-tolylpropyl)phenyl)piperidine-1-carboxylate. White foam, MS (ESI+): m/z=: 515.4 [M+H]+).

Step 5: (R,E)-tert-Butyl 4-(4-(3-(hydroxyimino)-3-(1-methyl-6-oxo-1,6-dihydropyridin-3-yl)-1-o-tolylpropyl)phenyl)-piperidine-1-carboxylate To a microwave vial was added (R)-tert-butyl 4-(4-(3-(1-methyl-6-oxo-1,6-dihydropyridin-3-yl)-3-oxo-1-o-tolylpropyl)phenyl)piperidine-1-carboxylate (35 mg, 68.0 µmol), sodium hydrogencarbonate (17.1 mg, 204 µmol) and hydroxylamine hydrochloride (14.2 mg, 204 µmol) in ethanol (1 mL) and water (0.02 mL). The vial was capped and heated at 120° C. for 15 min. The reaction mixture was poured onto aq. sat. sodium hydrogen carbonate solution and extracted with ethyl acetate. The combined organic layers were washed with brine, dried over magnesium sulfate, filtered and evaporated to afford the title compound (37 mg), which contained ca. 15% of the (Z)-stereoisomer. White foam; MS (ESI+): m/z=: 530.3 [M+H]+).

Example 507

(R,E)-5-(1-(Hydroxyimino)-3-(4-(piperidin-4-yl) phenyl)-3-o-tolylpropyl)-1-methylpyridin-2(1H)-one

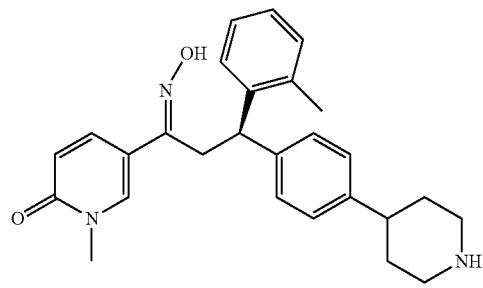 [SMILES: Cc1ccccc1[C@H](C/C(=N\O)c1ccc(=O)n(C)c1)c1ccc(C2CCNCC2)cc1]

(R,E)-tert-Butyl 4-(4-(3-(hydroxyimino)-3-(1-methyl-6-oxo-1,6-dihydropyridin-3-yl)-1-o-tolylpropyl)phenyl)piperidine-1-carboxylate (example 506, 30 mg) was dissolved in ethanol (0.8 mL) and hydrochloric acid solution (4.0 M in 1,4-dioxane (170 µl, 680 µmol) was added, then after 14 h the reaction mixture was poured onto aq. sat. sodium hydrogencarbonate solution and extracted 2 times with dichloromethane. The combined organic layers were washed with brine dried over magnesium sulfate, filtered and evaporated. The residue was triturated with ethyl acetate/heptane to afford the title compound (12 mg, 41%). Light yellow solid; MS (ESI+): m/z=: 430.5 [M+H]+).

Example 508

(R,E)-5-(3-(4-(1-Acetylpiperidin-4-yl)phenyl)-1-(hydroxyimino)-3-o-tolylpropyl)-1-methylpyridin-2(1H)-one

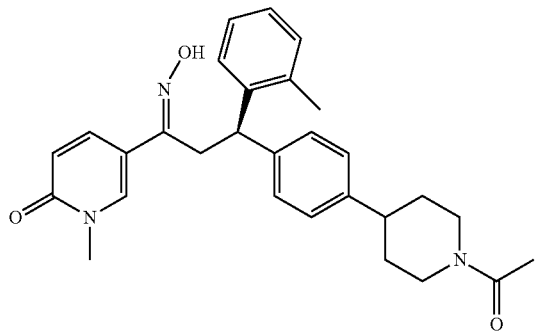 [SMILES: CC(=O)N1CCC(c2ccc([C@@H](C/C(=N\O)c3ccc(=O)n(C)c3)c3ccccc3C)cc2)CC1]

Step 1: (R)-1-Methyl-5-(3-(4-(piperidin-4-yl)phenyl)-3-o-tolylpropanoyl)pyridin-2(1H)-one The title compound was produced in analogy to example 480, step 1 from (R)-tert-butyl 4-(4-(3-(1-methyl-6-oxo-1,6-dihydropyridin-3-yl)-3-oxo-1-o-tolylpropyl)phenyl)piperidine-1-carboxylate (example 506, step 4). Light yellow foam, MS (ESI$^+$): m/z=: 415.4 [M+H]$^+$).

Step 2: (R)-5-(3-(4-(1-Acetylpiperidin-4-yl)phenyl)-3-o-tolylpropanoyl)-1-methylpyridin-2(1H)-one The title compound was produced in analogy to example 483, step 1 from (R)-1-methyl-5-(3-(4-(piperidin-4-yl)phenyl)-3-o-tolylpropanoyl)pyridin-2(1H)-one and acetyl chloride. White foam, MS (ESI$^+$): m/z=: 457.4 [M+H]$^+$.

Step 3: (R,E)-5-(3-(4-(1-Acetylpiperidin-4-yl)phenyl)-1-(hydroxyimino)-3-o-tolylpropyl)-1-methylpyridin-2(1H)-one The title compound was produced in analogy to example 506, step 5 from (R)-5-(3-(4-(1-acetylpiperidin-4-yl)phenyl)-3-o-tolylpropanoyl)-1-methylpyridin-2(1H)-one and hydroxylamine hydrochloride in the presence of sodium hydrogencarbonate. White foam, MS (ESI$^+$): m/z=: 472.3 [M+H]$^+$.

Example 509

(R,E)-5-(1-(Hydroxyimino)-3-(4-(1-(methylsulfonyl)piperidin-4-yl)phenyl)-3-o-tolylpropyl)-1-methylpyridin-2(1H)-one

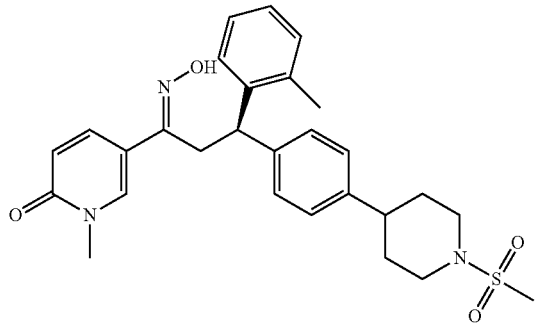 [SMILES: Cc1ccccc1[C@H](C/C(=N\O)c1ccc(=O)n(C)c1)c1ccc(C2CCN(S(C)(=O)=O)CC2)cc1]

Step 1: (R)-1-Methyl-5-(3-(4-(piperidin-4-yl)phenyl)-3-o-tolylpropanoyl)pyridin-2(1H)-one The title compound was produced in analogy to example 483, step 1 from (R)-1-methyl-5-(3-(4-(piperidin-4-yl)phenyl)-3-o-tolylpropanoyl)pyridin-2(1H)-one (example 508, step 1) and methanesulfonyl chloride. White foam, MS (ESI$^+$): m/z=: 493.2 [M+H]$^+$.

Step 2: (R,E)-5-(1-(Hydroxyimino)-3-(4-(1-(methylsulfonyl)piperidin-4-yl)phenyl)-3-o-tolylpropyl)-1-methylpyridin-2(1H)-one The title compound was produced in analogy to example 506, step 5 from (R)-1-methyl-5-(3-(4-(piperidin-4-yl)phenyl)-3-o-tolylpropanoyl)pyridin-2(1H)-one and hydroxylamine hydrochloride in the presence of sodium hydrogencarbonate. White foam, MS (ESI$^+$): m/z=: 508.3 [M+H]$^+$.

Example 510

(R,E)-4-(4-(3-(Hydroxyimino)-3-(1-methyl-6-oxo-1,6-dihydropyridin-3-yl)-1-o-tolylpropyl)phenyl)piperidine-1-sulfonamide

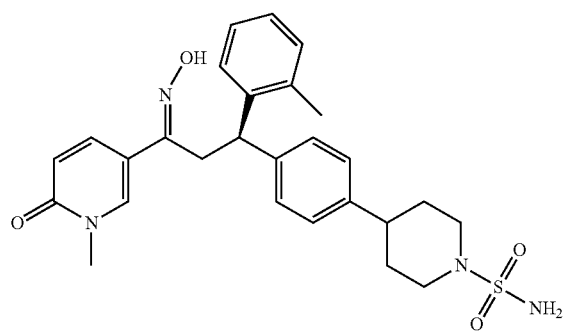 [SMILES: Cc1ccccc1[C@H](C/C(=N\O)c1ccc(=O)n(C)c1)c1ccc(C2CCN(S(N)(=O)=O)CC2)cc1]

Step 1: (R)-4-(4-(3-(1-Methyl-6-oxo-1,6-dihydropyridin-3-yl)-3-oxo-1-o-tolylpropyl)-phenyl)piperidine-1-sulfonamide The title compound was produced in analogy to example 480, step 2 from (R)-1-methyl-5-(3-(4-(piperidin-4-yl)phenyl)-3-o-tolylpropanoyl)pyridin-2(1H)-one (example 508, step 1) and sulfamide. White foam, MS (ESI$^+$): m/z=494.3 ([M+H]$^+$).

Step 2: (R,E)-4-(4-(3-(Hydroxyimino)-3-(1-methyl-6-oxo-1,6-dihydropyridin-3-yl)-1-o-tolylpropyl)phenyl)piperidine-1-sulfonamide The title compound was produced in analogy to example 506, step 5 from (R)-4-(4-(3-(1-methyl-6-oxo-1,6-dihydropyridin-3-yl)-3-oxo-1-o-tolylpropyl)phenyl)piperidine-1-sulfonamide and hydroxylamine hydrochloride in the presence of sodium hydrogencarbonate. Light yellow gum, MS (ESI$^+$): m/z=509.3 ([M+H]$^+$).

Example 511

(R,E)-1-(4-(4-(1-(4-Chloro-2-methylphenyl)-3-(hydroxyimino)-3-(2-methylpyridin-4-yl)propyl)phenyl)piperidin-1-yl)ethanone

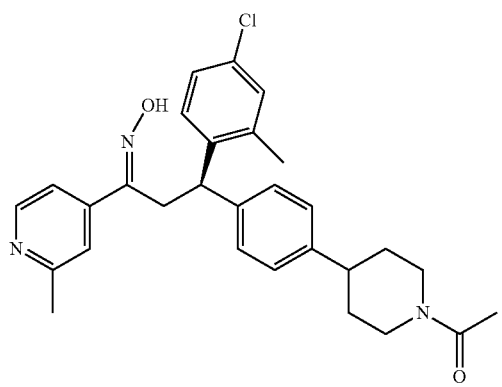 [SMILES: CC(=O)N1CCC(c2ccc([C@@H](C/C(=N\O)c3ccnc(C)c3)c3ccc(Cl)cc3C)cc2)CC1]

Step 1: (R)-3-(4-(1-Acetylpiperidin-4-yl)phenyl)-3-(4-chloro-2-methylphenyl)-1-(2-methylpyridin-4-yl)propan-1-one The title compound was produced in analogy to example 483, step 1 from (R)-3-(4-chloro-2-methylphenyl)-1-(2-methylpyridin-4-yl)-3-(4-(piperidin-4-yl)phenyl)propan-1-one (example 480, step 1) and acetyl chloride. White foam, MS (ESI$^+$): m/z=: 475.0 [M+H]$^+$.

Step 2: (R,E)-1-(4-(4-(1-(4-Chloro-2-methylphenyl)-3-(hydroxyimino)-3-(2-methylpyridin-4-yl)propyl)phenyl)piperidin-1-yl)ethanone In analogy to example 132, step 6, from (R)-3-(4-(1-acetylpiperidin-4-yl)phenyl)-3-(4-chloro-2-methylphenyl)-1-(2-methylpyridin-4-yl)propan-1-one and hydroxylamine hydrochloride in the presence of sodium hydrogencarbonate was prepared the title compound as a white foam, MS (ESI$^+$): m/z=490.0 [M+H]$^+$.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |

-continued

| | |
|---|---|
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

The invention claimed is:
1. A compound according to formula I,

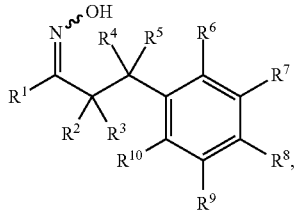

I wherein
$R^1$ is —$(CH_2)_n$-heteroaryl, wherein n is 0 or 1 and said heteroaryl is selected from the group consisting of pyridine, 1H-pyridin-2-one and 1-oxy-pyridine and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl,
$C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl;
$R^2$ is hydrogen or $C_{1-7}$-alkyl,
$R^3$ is hydrogen,
$R^5$ is hydrogen or hydroxy,
or $R^3$ and $R^5$ are replaced by a double bond;
$R^4$ is selected from the group consisting of:
unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl;
phenyl-$C_{1-7}$-alkyl, wherein said phenyl is unsubstituted or substituted by one, two or three groups independently selected from the group consisting of $C_{1-7}$-alkyl, halogen, halogen-$C_{1-7}$-alkyl and halogen-$C_{1-7}$-alkoxy;
heteroaryl, said heteroaryl being unsubstituted or substituted by $C_{1-7}$-alkyl or oxo; and
heterocyclyl, said heterocyclyl being selected from morpholinyl, piperazinyl and piperidinyl and being unsubstituted or substituted by $C_{1-7}$-alkyl, oxo or $C_{1-7}$-alkylcarbonyl;
$R^6$ is selected from the group consisting of hydrogen, halogen and $C_{1-7}$-alkyl;
$R^7$ and $R^9$ are independently selected from the group consisting of:
hydrogen; halogen; halogen-$C_{1-7}$-alkyl, cyano; cyano-$C_{1-7}$-alkyl; $C_{1-7}$-alkyl; $C_{3-7}$-alkenyl; $C_{1-7}$-alkinyl; $C_{1-7}$-alkoxy; $C_{1-7}$-alkoxy-$C_{1-7}$-alkyl; hydroxy; hydroxy-$C_{1-7}$-alkyl; hydroxy-$C_{3-7}$-alkenyl; hydroxy-$C_{3-7}$-alkinyl; hydroxy-$C_{1-7}$-alkoxy; carboxyl; carboxyl-$C_{1-7}$-alkyl; carboxyl-$C_{3-7}$-alkenyl; carboxyl-$C_{1-7}$-alkinyl; carboxyl-$C_{1-7}$-alkoxy; tetrazolyl; $C_{1-7}$-alkoxycarbonyl; $C_{1-7}$-alkylsulfonyl; $C_{1-7}$-alkylsulfonyloxy; $C_{1-7}$-alkylsulfonylamino; $C_{3-7}$-cycloalkylsulfonylamino; aminosulfonyl; ($C_{1-7}$-alkyl)-aminosulfonyl; di-($C_{1-7}$-alkyl)aminosulfonyl; heterocyclylsulfonyl; $C_{1-7}$-alkyl-amino; di-($C_{1-7}$-alkyl)-amino; $C_{1-7}$-alkoxy-$C_{1-7}$-alkyl-amino; $C_{1-7}$-alkoxy-$C_{1-7}$-alkyl-$C_{1-7}$-alkyl-amino; $C_{1-7}$-alkoxy-halogen-$C_{1-7}$-alkyl-amino; hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl; $C_{1-7}$-alkoxycarbonyl-$C_{1-7}$-alkyl-aminocarbonyl; $C_{1-7}$-alkyl-aminocarbonyl; di-($C_{1-7}$-alkyl)-aminocarbonyl; $C_{1-7}$-alkylsulfonyl-$C_{1-7}$-alkyl-aminocarbonyl; halogen-$C_{1-7}$-alkyl-aminocarbonyl; hydroxy-$C_{1-7}$-alkyl-aminocarbonyl; hydroxy-$C_{1-7}$-alkyl-$C_{1-7}$-alkyl-aminocarbonyl; halogen-hydroxy-$C_{1-7}$-alkyl-aminocarbonyl; $C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl; $C_{1-7}$-alkoxycarbonyl-$C_{1-7}$-alkyl; di-($C_{1-7}$-alkoxycarbonyl)-$C_{1-7}$-alkyl; $C_{1-7}$-alkylcarbonylamino-$C_{1-7}$-alkylaminocarbonyl; $C_{1-7}$-alkylcarbonylamino; carboxyl-$C_{1-7}$-alkylcarbonylamino; $C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl; heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;

heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;

phenyloxy, wherein said phenyl is unsubstituted or substituted by one to three groups selected from halogen or carboxyl; and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxycarbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkylsulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;

$R^8$ is selected from the group consisting of:

hydrogen; halogen; halogen-$C_{1-7}$-alkyl; cyano; cyano-$C_{1-7}$-alkyl; $C_{1-7}$-alkyl; $C_{3-7}$-alkenyl; $C_{1-7}$-alkinyl; $C_{1-7}$-alkoxy; $C_{1-7}$-alkoxy-$C_{1-7}$-alkyl; hydroxy; hydroxy-$C_{1-7}$-alkyl; hydroxy-$C_{3-7}$-alkenyl; hydroxy-$C_{3-7}$-alkinyl; hydroxy-$C_{1-7}$-alkoxy; carboxyl; carboxyl-$C_{1-7}$-alkyl; carboxyl-$C_{3-7}$-alkenyl; carboxyl-$C_{1-7}$-alkinyl; carboxyl-$C_{1-7}$-alkoxy; tetrazolyl; $C_{1-7}$-alkoxycarbonyl; $C_{1-7}$-alkylsulfonyl; $C_{1-7}$-alkylsulfonyloxy; $C_{1-7}$-alkylsulfonylamino; $C_{3-7}$-cycloalkylsulfonylamino; aminosulfonyl; ($C_{1-7}$-alkyl)-aminosulfonyl; di-($C_{1-7}$-alkyl)-aminosulfonyl; heterocyclylsulfonyl; $C_{1-7}$-alkyl-amino; di-($C_{1-7}$-alkyl)-amino; $C_{1-7}$-alkoxy-$C_{1-7}$-alkyl-amino; $C_{1-7}$-alkoxy-$C_{1-7}$-alkyl-$C_{1-7}$-alkyl-amino; $C_{1-7}$-alkoxy-halogen-$C_{1-7}$-alkyl-amino; hydroxy-$C_{1-7}$-alkyl-$C_{1-7}$-alkyl-amino; an amino acid attached through the amino group of the amino acid;

$C_{3-7}$-cycloalkyl-amino, wherein said $C_{3-7}$-cycloalkyl is unsubstituted or substituted by hydroxy, hydroxy-$C_{1-7}$-alkyl or carboxyl;

carboxyl-$C_{1-7}$-alkyl-aminocarbonyl; carboxyl-$C_{1-7}$-alkyl-($C_{1-7}$-alkyl)-aminocarbonyl; $C_{1-7}$-alkoxycarbonyl-$C_{1-7}$-alkyl-aminocarbonyl; $C_{1-7}$-alkyl-aminocarbonyl; di-($C_{1-7}$-alkyl)-aminocarbonyl; $C_{1-7}$-alkylsulfonyl-$C_{1-7}$-alkyl-aminocarbonyl; halogen-$C_{1-7}$-alkyl-aminocarbonyl; hydroxy-$C_{1-7}$-alkyl-aminocarbonyl; hydroxy-$C_{1-7}$-alkyl-$C_{1-7}$-alkyl-aminocarbonyl; halogen-hydroxy-$C_{1-7}$-alkyl-aminocarbonyl; $C_{1-7}$-alkoxy-$C_{1-7}$-alkyl-aminocarbonyl;

$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;

heterocyclyl-aminocarbonyl, wherein said heterocyclyl is unsubstituted or substituted by $C_{1-7}$-alkyl or oxo;

heterocyclyl-$C_{1-7}$-alkyl-aminocarbonyl, wherein said heterocyclyl is unsubstituted or substituted by $C_{1-7}$-alkyl or oxo;

hydroxy-$C_{1-7}$-alkyl-aminocarbonyl-$C_{1-7}$-alkyl; $C_{1-7}$-alkoxycarbonyl-$C_{1-7}$-alkyl; di-($C_{1-7}$-alkoxycarbonyl)-$C_{1-7}$-alkyl; $C_{1-7}$-alkylcarbonylamino-$C_{1-7}$-alkylaminocarbonyl; $C_{1-7}$-alkylcarbonylamino; carboxyl-$C_{1-7}$-alkylcarbonylamino; $C_{1-7}$-alkoxycarbonyl-$C_{1-7}$-alkylcarbonylamino;

$C_{3-7}$-cycloalkyl, wherein said $C_{3-7}$-cycloalkyl is unsubstituted or substituted by hydroxy, hydroxy-$C_{1-7}$-alkyl or carboxyl;

$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;

heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;

heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;

heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;

phenyloxy, wherein said phenyl is unsubstituted or substituted by one to three groups selected from halogen or carboxyl; and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxycarbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkylsulfonylamino, aminosulfonyl, $C_{1-7}$-alkylaminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl; and $R^{10}$ is selected from the group consisting of hydrogen, halogen and $C_{1-7}$-alkyl;

or a pharmaceutically acceptable salt thereof.

2. A compound according to claim 1, wherein $R^1$ is —$(CH_2)_n$-heteroaryl, wherein n is 0 or 1 and said heteroaryl is pyridine or 1-oxy-pyridine, and is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl.

3. A compound according to claim 1, wherein $R^1$ is —$(CH_2)_n$-heteroaryl, wherein n is 0 or 1 and said heteroaryl is 1H-pyridin-2-one, which is unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy, $C_{1-7}$-alkoxy-$C_{1-7}$-alkyl, $C_{1-7}$-alkoxy-$C_{1-7}$-alkoxy-$C_{1-7}$-alkyl, $C_{3-7}$-cyloalkyl, $C_{3-7}$-cycloalkyl-$C_{1-7}$-alkyl, carboxyl-$C_{1-7}$-alkyl and aminocarbonyl-$C_{1-7}$-alkyl.

4. A compound according to claim 1, wherein $R^2$ and $R^3$ are hydrogen.

5. A compound according to claim 1, wherein $R^5$ is hydrogen.

6. A compound according to claim 1, wherein $R^4$ is unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl.

7. A compound according to claim 1, wherein
$R^7$ and $R^9$ are hydrogen and
$R^8$ is selected from the group consisting of:
halogen; halogen-$C_{1-7}$-alkyl; cyano; cyano-$C_{1-7}$-alkyl; $C_{1-7}$-alkyl; $C_{3-7}$-alkenyl; $C_{1-7}$-alkinyl; $C_{1-7}$-alkoxy; $C_{1-7}$-alkoxy-$C_{1-7}$-alkyl; hydroxy; hydroxy-$C_{1-7}$-alkyl; hydroxy-$C_{3-7}$-alkenyl; hydroxy-$C_{3-7}$-alkinyl; hydroxy-$C_{1-7}$-alkoxy; carboxyl; carboxyl-$C_{1-7}$-alkyl; carboxyl-$C_{3-7}$-alkenyl; carboxyl-$C_{1-7}$-alkinyl; carboxyl-$C_{1-7}$-alkoxy; tetrazolyl; $C_{1-7}$-alkoxycarbonyl; $C_{1-7}$-alkylsulfonyl; $C_{1-7}$-alkylsulfonyloxy; $C_{1-7}$-alkylsulfonylamino; $C_{3-7}$-cycloalkylsulfonylamino; aminosulfonyl; ($C_{1-7}$-alkyl)-aminosulfonyl; di-($C_{1-7}$-alkyl)-aminosulfonyl; heterocyclylsulfonyl; $C_{1-7}$-alkyl-amino, di-($C_{1-7}$-alkyl)-amino; $C_{1-7}$-alkoxy-$C_{1-7}$-alkyl-amino; $C_{1-7}$-alkoxy-$C_{1-7}$-alkyl-$C_{1-7}$-alkyl-amino; $C_{1-7}$-alkoxy-halogen-$C_{1-7}$-alkyl-amino; hydroxy-$C_{1-7}$-alkyl-$C_{1-7}$-alkyl-amino; an amino acid attached through the amino group of the amino acid;
$C_{3-7}$-cycloalkyl-amino, wherein said $C_{3-7}$-cycloalkyl is unsubstituted or substituted by hydroxy, hydroxy-$C_{1-7}$-alkyl or carboxyl;
carboxyl-$C_{1-7}$-alkyl-aminocarbonyl; carboxyl-$C_{1-7}$-alkyl-($C_{1-7}$-alkyl)-aminocarbonyl; $C_{1-7}$-alkoxycarbonyl-$C_{1-7}$-alkyl-aminocarbonyl; $C_{1-7}$-alkyl-aminocarbonyl; di-($C_{1-7}$-alkyl)-aminocarbonyl; $C_{1-7}$-alkylsulfonyl-$C_{1-7}$-alkyl-aminocarbonyl; halogen-$C_{1-7}$-alkyl-aminocarbonyl; hydroxy-$C_{1-7}$-alkyl-aminocarbonyl; hydroxy-$C_{1-7}$-alkyl-$C_{1-7}$-alkyl-aminocarbonyl; halogen-hydroxy-$C_{1-7}$-alkyl-aminocarbonyl; $C_{1-7}$-alkoxy-$C_{1-7}$-alkyl-aminocarbonyl;
$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;
heterocyclyl-aminocarbonyl, wherein said heterocyclyl is unsubstituted or substituted by $C_{1-7}$-alkyl or oxo;
heterocyclyl-$C_{1-7}$-alkyl-aminocarbonyl, wherein said heterocyclyl is unsubstituted or substituted by $C_{1-7}$-alkyl or oxo;
hydroxy-$C_{1-7}$-alkyl-aminocarbonyl-$C_{1-7}$-alkyl; $C_{1-7}$-alkoxycarbonyl-$C_{1-7}$-alkyl; di-($C_{1-7}$-alkoxycarbonyl)-$C_{1-7}$-alkyl; $C_{1-7}$-alkylcarbonylamino-$C_{1-7}$-alkylaminocarbonyl; $C_{1-7}$-alkylcarbonylamino; carboxyl-$C_{1-7}$-alkylcarbonylamino; $C_{1-7}$-alkoxycarbonyl-$C_{1-7}$-alkylcarbonylamino;
$C_{3-7}$-cycloalkyl, wherein said $C_{3-7}$-cycloalkyl is unsubstituted or substituted by hydroxy, hydroxy-$C_{1-7}$-alkyl or carboxyl;
$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;
heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl; heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;
phenyloxy, wherein said phenyl is unsubstituted or substituted by one to three groups selected from halogen or carboxyl; and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

8. A compound according to claim 1, wherein $R^8$ is phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

9. A compound according to claim 1, wherein $R^8$ is selected from the group consisting of:
halogen; halogen-$C_{1-7}$-alkyl; cyano, cyano-$C_{1-7}$-alkyl; $C_{1-7}$-alkyl; $C_{3-7}$-alkenyl; $C_{1-7}$-alkinyl; $C_{1-7}$-alkoxy; $C_{1-7}$-alkoxy-$C_{1-7}$-alkyl; hydroxy; hydroxy-$C_{1-7}$-alkyl; hydroxy-$C_{3-7}$-alkenyl; hydroxy-$C_{3-7}$-alkinyl; hydroxy-$C_{1-7}$-alkoxy; carboxyl; carboxyl-$C_{1-7}$-alkyl; carboxyl-$C_{3-7}$-alkenyl; carboxyl-$C_{1-7}$-alkinyl; carboxyl-$C_{1-7}$-alkoxy; tetrazolyl; $C_{1-7}$-alkoxycarbonyl; $C_{1-7}$-alkylsulfonyl; $C_{1-7}$-alkylsulfonyloxy; $C_{1-7}$-alkylsulfonylamino; $C_{3-7}$-cycloalkylsulfonylamino; aminosulfonyl; ($C_{1-7}$-alkyl)-aminosulfonyl; di-($C_{1-7}$-alkyl)-aminosulfonyl; heterocyclylsulfonyl; $C_{1-7}$-alkyl-amino, di-($C_{1-7}$-alkyl)-amino; $C_{1-7}$-alkoxy-$C_{1-7}$-alkyl-amino; $C_{1-7}$-alkoxy-$C_{1-7}$-alkyl-$C_{1-7}$-alkyl-amino; $C_{1-7}$-alkoxy-halogen-$C_{1-7}$-alkyl-amino; hydroxy-$C_{1-7}$-alkyl-$C_{1-7}$-alkyl-amino; an amino acid attached through the amino group of the amino acid;

$C_{3-7}$-cycloalkyl-amino, wherein said $C_{3-7}$-cycloalkyl is unsubstituted or substituted by hydroxy, hydroxy-$C_{1-7}$-alkyl or carboxyl;

carboxyl-$C_{1-7}$-alkyl-aminocarbonyl; carboxyl-$C_{1-7}$-alkyl-($C_{1-7}$-alkyl)-aminocarbonyl; $C_{1-7}$-alkoxycarbonyl-$C_{1-7}$-alkyl-aminocarbonyl; $C_{1-7}$-alkyl-aminocarbonyl; di-($C_{1-7}$-alkyl)-aminocarbonyl; $C_{1-7}$-alkylsulfonyl-$C_{1-7}$-alkyl-aminocarbonyl; halogen-$C_{1-7}$-alkyl-aminocarbonyl; hydroxy-$C_{1-7}$-alkyl-aminocarbonyl; hydroxy-$C_{1-7}$-alkyl-$C_{1-7}$-alkyl-aminocarbonyl; halogen-hydroxy-$C_{1-7}$-alkyl-aminocarbonyl; $C_{1-7}$-alkoxy-$C_{1-7}$-alkyl-aminocarbonyl;

$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;

heterocyclyl-aminocarbonyl, wherein said heterocyclyl is unsubstituted or substituted by $C_{1-7}$-alkyl or oxo;

heterocyclyl-$C_{1-7}$-alkyl-aminocarbonyl, wherein said heterocyclyl is unsubstituted or substituted by $C_{1-7}$-alkyl or oxo;

hydroxy-$C_{1-7}$-alkyl-aminocarbonyl-$C_{1-7}$-alkyl; $C_{1-7}$-alkoxycarbonyl-$C_{1-7}$-alkyl; di-($C_{1-7}$-alkoxycarbonyl)-$C_{1-7}$-alkyl; $C_{1-7}$-alkylcarbonylamino-$C_{1-7}$-alkylaminocarbonyl; $C_{1-7}$-alkylcarbonylamino; carboxyl-$C_{1-7}$-alkylcarbonylamino; $C_{1-7}$-alkoxycarbonyl-$C_{1-7}$-alkylcarbonylamino;

$C_{3-7}$-cycloalkyl, wherein said $C_{3-7}$-cycloalkyl is unsubstituted or substituted by hydroxy, hydroxy-$C_{1-7}$-alkyl or carboxyl; and $C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl.

10. A compound according to claim 1, wherein $R^8$ is selected from the group consisting of:

heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;

heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;

heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl; and phenyloxy, wherein phenyl is unsubstituted or substituted by one to three groups selected from halogen or carboxyl.

11. A compound according to claim 1, wherein
$R^7$ and $R^8$ are hydrogen and
$R^9$ is selected from the group consisting of:
halogen; halogen-$C_{1-7}$-alkyl; cyano; cyano-$C_{1-7}$-alky; $C_{1-7}$-alkyl; $C_{3-7}$-alkenyl; $C_{1-7}$-alkinyl; $C_{1-7}$-alkoxy; $C_{1-7}$-alkoxy-$C_{1-7}$-alkyl; hydroxy; hydroxy-$C_{1-7}$-alkyl; hydroxy-$C_{3-7}$-alkenyl; hydroxy-$C_{3-7}$-alkinyl; hydroxy-$C_{1-7}$-alkoxy; carboxyl; carboxyl-$C_{1-7}$-alkyl; carboxyl-$C_{3-7}$-alkenyl; carboxyl-$C_{1-7}$-alkinyl; carboxyl-$C_{1-7}$-alkoxy; tetrazolyl; $C_{1-7}$-alkoxycarbonyl; $C_{1-7}$-alkylsulfonyl; $C_{1-7}$-alkylsulfonyloxy; $C_{1-7}$-alkylsulfonylamino; $C_{3-7}$-cycloalkylsulfonylamino; aminosulfonyl; ($C_{1-7}$-alkyl)-aminosulfonyl; di-($C_{1-7}$-alkyl)-aminosulfonyl; heterocyclylsulfonyl; $C_{1-7}$-alkyl-amino, di-($C_{1-7}$-alkyl)-amino; $C_{1-7}$-alkoxy-$C_{1-7}$-alkyl-amino; $C_{1-7}$-alkoxy-$C_{1-7}$-alkyl-$C_{1-7}$-alkyl-amino; $C_{1-7}$-alkoxy-halogen-$C_{1-7}$-alkyl-amino; hydroxy-$C_{1-7}$-alkyl-$C_{1-7}$-alkyl-amino; an amino acid attached through the amino group of the amino acid;

$C_{3-7}$-cycloalkyl-amino; wherein said $C_{3-7}$-cycloalkyl is unsubstituted or substituted by hydroxy, hydroxy-$C_{1-7}$-alkyl or carboxyl;

carboxyl-$C_{1-7}$-alkyl-aminocarbonyl; carboxyl-$C_{1-7}$-alkyl-($C_{1-7}$-alkyl)-aminocarbonyl; $C_{1-7}$-alkoxycarbonyl-$C_{1-7}$-alkyl-aminocarbonyl; $C_{1-7}$-alkyl-aminocarbonyl, di-($C_{1-7}$-alkyl)-aminocarbonyl; $C_{1-7}$-alkylsulfonyl-$C_{1-7}$-alkyl-aminocarbonyl; halogen-$C_{1-7}$-alkyl-aminocarbonyl; hydroxy-$C_{1-7}$-alkyl-aminocarbonyl; hydroxy-$C_{1-7}$-alkyl-$C_{1-7}$-alkyl-aminocarbonyl; halogen-hydroxy-$C_{1-7}$-alkyl-aminocarbonyl; $C_{1-7}$-alkoxy-$C_{1-7}$-alkyl-aminocarbonyl;

$C_{3-7}$-cycloalkylaminocarbonyl, wherein said $C_{3-7}$-cycloalkyl is unsubstituted or substituted by hydroxy, hydroxy-$C_{1-7}$-alkyl or carboxyl;

heterocyclyl-aminocarbonyl, wherein said heterocyclyl is unsubstituted or substituted by $C_{1-7}$-alkyl or oxo;

heterocyclyl-$C_{1-7}$-alkyl-aminocarbonyl, wherein said heterocyclyl is unsubstituted or substituted by $C_{1-7}$-alkyl or oxo;

hydroxy-$C_{1-7}$-alkyl-aminocarbonyl-$C_{1-7}$-alkyl; $C_{1-7}$-alkoxycarbonyl-$C_{1-7}$-alkyl; di-($C_{1-7}$-alkoxycarbonyl)-$C_{1-7}$-alkyl; $C_{1-7}$-alkylcarbonylamino-$C_{1-7}$-alkylaminocarbonyl; $C_{1-7}$-alkylcarbonylamino; carboxyl-$C_{1-7}$-alkylcarbonylamino; $C_{1-7}$-alkoxycarbonyl-$C_{1-7}$-alkylcarbonylamino;

$C_{3-7}$-cycloalkyl, wherein said $C_{3-7}$-cycloalkyl is unsubstituted or substituted by hydroxy, hydroxy-$C_{1-7}$-alkyl or carboxyl;

$C_{3-7}$-cycloalkyl-$C_{1-7}$-alkyl, wherein said $C_{3-7}$-cycloalkyl is unsubstituted or substituted by hydroxy, hydroxy-$C_{1-7}$-alkyl or carboxyl;

heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl;

heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl;

heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl;

phenyloxy, wherein phenyl is unsubstituted or substituted by one to three groups selected from halogen or carboxyl; and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxycarbonyl, tetrazolyl, carboxyl-$C_{1-7}$-alkyl-carbonylamino, $C_{1-7}$-alkoxy-carbonyl-$C_{1-7}$-alkylcarbonylamino, $C_{1-7}$-alkylsulfonyl, $C_{1-7}$-alkylsulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$- alkoxy, $C_{1-7}$-alkoxycarbonyl-$C_{1-7}$-alkylaminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

12. A compound according to claim 11, wherein $R^9$ is phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl.

13. A compound according to claim 1, selected from the group consisting of
- {4-[3-[hydroxyimino]-3-(2-methyl-pyridin-4-yl)-1-o-tolyl-propyl]-phenyl}-acetic acid,
- 3-[4-(3-hydroxy-propyl)-phenyl]-1-(2-methyl-pyridin-4-yl)-3-o-tolyl-propan-1-one oxime,
- ({4'-[3-[hydroxyimino]-3-(2-methyl-pyridin-4-yl)-1-o-tolyl-propyl]-biphenyl-4-carbonyl}-amino)-acetic acid,
- 4'-[(S)-3-[(E)-hydroxyimino]-3-(2-methyl-pyridin-4-yl)-1-o-tolyl-propyl]-biphenyl-4-carboxylic acid,
- 4'-[(R)-3-[(E)-hydroxyimino]-3-(2-methyl-pyridin-4-yl)-1-o-tolyl-propyl]-biphenyl-4-carboxylic acid,
- (E)-4'-[3-[hydroxyimino]-3-(2-methyl-pyridin-4-yl)-1-(3-methyl-pyridin-2-yl)-propyl]-biphenyl-4-carboxylic acid,
- 3-(4-bromo-phenyl)-1-(2-methyl-pyridin-4-yl)-3-o-tolyl-propan-1-one oxime,
- 3-fluoro-4'-[3-[(E)-hydroxyimino]-3-(2-methyl-pyridin-4-yl)-1-o-tolyl-propyl]-biphenyl-4-carboxylic acid,
- (E,R)-1-(2-methyl-pyridin-4-yl)-3-(4-pyrimidin-5-yl-phenyl)-3-o-tolyl-propan-1-one oxime,
- (E,R)-1-(2-methylpyridin-4-yl)-3-(4-(4-(methylsulfonyl)piperazin-1-yl)phenyl)-3-o-tolylpropan-1-one oxime,
- (E,R)-3-(4-(4-hydroxypiperidin-1-yl)phenyl)-1-(2-methylpyridin-4-yl)-3-o-tolylpropan-1-one oxime,
- 4'-[1-(4-chloro-2-fluoro-phenyl)-3-[(E)-hydroxyimino]-3-(2-methyl-pyridin-4-yl)-propyl]-biphenyl-4-carboxylic acid
- 4'-[(R)-3-[(E)-hydroxyimino]-3-(1-methyl-6-oxo-1,6-dihydro-pyridin-3-yl)-1-o-tolyl-propyl]-biphenyl-4-carboxylic acid,
- 3,3'-difluoro-4'-[3-[(E)-hydroxyimino]-3-(1-methyl-6-oxo-1,6-dihydro-pyridin-3-yl)-1-o-tolyl-propyl]-biphenyl-4-carboxylic acid,
- 4'-[1-(2-chloro-phenyl)-3-[(E)-hydroxyimino]-3-(1-methyl-6-oxo-1,6-dihydro-pyridin-3-yl)-propyl]-biphenyl-4-carboxylic acid,
- N-(2-hydroxy-ethyl)-4-[3-[(E)-hydroxyimino]-3-(1-methyl-6-oxo-1,6-dihydro-pyridin-3-yl)-1-o-tolyl-propyl]-benzamide,
- (E)-4'-(1-(4-chloro-2-methylphenyl)-3-(hydroxyimino)-3-(1-methyl-6-oxo-1,6-dihydropyridin-3-yl)propyl)biphenyl-4-carboxylic acid,
- 3-{3-fluoro-4-[3-[(E)-hydroxyimino]-3-(1-methyl-6-oxo-1,6-dihydro-pyridin-3-yl)-1-o-tolyl-propyl]-phenoxy}-benzoic acid,
- 4'-[1-(4-chloro-2-fluoro-phenyl)-3-[(E)-hydroxyimino]-3-(1-methyl-6-oxo-1,6-dihydro-pyridin-3-yl)-propyl]-biphenyl-4-carboxylic acid,
- (E)-5-(3-(2-chlorophenyl)-1-(hydroxyimino)-3-(4-(methylsulfonyl)phenyl)propyl)-1-methylpyridin-2(1H)-one,
- 1-{4-[(R)-3-[(E)-hydroxyimino]-3-(2-methyl-pyridin-4-yl)-1-o-tolyl-propyl]-phenyl}-piperidine-4-carboxylic acid,
- 1-{4-[(R)-1-(4-chloro-2-methyl-phenyl)-3-[(E)-hydroxyimino]-3-(2-methyl-pyridin-4-yl)-propyl]-phenyl}-piperidine-4-carboxylic acid,
- (R,E)-2-(4-(3-(hydroxyimino)-3-(2-methylpyridin-4-yl)-1-o-tolylpropyl)phenyl)acetic acid,
- (R,E)-2-(1-(4-(3-(hydroxyimino)-3-(2-methylpyridin-4-yl)-1-o-tolylpropyl)phenyl)piperidine-4-carboxamido)acetic acid,
- (R,E)-2-(1-(4-(3-(hydroxyimino)-3-(2-methylpyridin-4-yl)-1-o-tolylpropyl)phenyl)piperidine-4-carboxamido)ethanesulfonic acid,
- 4-{4-[(R)-3-[(E)-hydroxyimino]-3-(2-methyl-pyridin-4-yl)-1-o-tolyl-propyl]-phenyl}-cyclohexanecarboxylic acid,
- (R,E)-5-(1-(hydroxyimino)-3-(4-(methylsulfonyl)phenyl)-3-o-tolylpropyl)-1-methylpyridin-2(1H)-one, and pharmaceutically acceptable salts thereof.

14. A pharmaceutical composition comprising a compound according to claim 1 and a pharmaceutically acceptable carrier and/or adjuvant.

* * * * *